US011602558B2

(12) United States Patent
Lavoie et al.

(10) Patent No.: US 11,602,558 B2
(45) Date of Patent: Mar. 14, 2023

(54) MODIFIED NOROVIRUS VP1 PROTEINS AND VLPS COMPRISING MODIFIED NOROVIRUS VP1 PROTEINS

(71) Applicant: MEDICAGO INC., Québec (CA)

(72) Inventors: Pierre-Olivier Lavoie, Quebec (CA); Marc-Andre D'Aoust, Quebec (CA)

(73) Assignee: MEDICAGO INC., Québec (CA)

( * ) Notice: Subject to any disclaimer, the term of this patent is extended or adjusted under 35 U.S.C. 154(b) by 211 days.

(21) Appl. No.: 16/768,524

(22) PCT Filed: Nov. 30, 2018

(86) PCT No.: PCT/CA2018/051530
§ 371 (c)(1),
(2) Date: May 29, 2020

(87) PCT Pub. No.: WO2019/104439
PCT Pub. Date: Jun. 6, 2019

(65) Prior Publication Data

US 2020/0330583 A1 Oct. 22, 2020

Related U.S. Application Data

(60) Provisional application No. 62/712,744, filed on Jul. 31, 2018, provisional application No. 62/593,006, filed on Nov. 30, 2017.

(51) Int. Cl.

| | |
|---|---|
| ***A61K 39/12*** | (2006.01) |
| ***A61K 39/00*** | (2006.01) |
| ***A61K 39/125*** | (2006.01) |
| ***C12N 7/00*** | (2006.01) |
| ***C07K 14/005*** | (2006.01) |
| ***A61P 31/14*** | (2006.01) |
| ***C12N 15/82*** | (2006.01) |

(52) U.S. Cl.
CPC .............. *A61K 39/12* (2013.01); *A61P 31/14* (2018.01); *C07K 14/005* (2013.01); *C12N 7/00* (2013.01); *C12N 15/8258* (2013.01); *A61K 2039/5258* (2013.01); *C12N 2770/16022* (2013.01); *C12N 2770/16023* (2013.01); *C12N 2770/16034* (2013.01)

(58) Field of Classification Search
CPC .......... A61P 31/14; A61P 31/12; A61K 39/12; A61K 2039/5258; C12N 2770/16034
See application file for complete search history.

(56) References Cited

U.S. PATENT DOCUMENTS

| | | | |
|---|---|---|---|
| 9,518,096 | B2 | 12/2016 | Richardson et al. |
| 2013/0273105 | A1 | 10/2013 | Richardson et al. |
| 2015/0023995 | A1 | 1/2015 | Richardson et al. |

FOREIGN PATENT DOCUMENTS

| | | | |
|---|---|---|---|
| WO | 2011/035422 A1 | | 3/2011 |
| WO | WO2011035422 | * | 3/2011 |
| WO | 2017/191264 A1 | | 11/2017 |
| WO | WO2017191264 | * | 11/2017 |
| WO | 2018/170603 A1 | | 9/2018 |

OTHER PUBLICATIONS

Bertolotti-Ciarlet et al., "The 3' End of Norwalk Virus mRNA Contains Determinants That Regulate the Expression and Stability of the Viral Capsid Protein VP1: a Novel Function for the VP2 Protein", Journal of Virology, Nov. 2003, vol. 77, Issue 21, pp. 11603-11615 (27 pages).
Huo et al., "Chimeric VLPs with GII.3 P2 domain in a backbone of GII.4 VP1 confers novel HBGA binding ability", Virus Research, 2016, vol. 224, pp. 1-5 (5 pages).
Mason et al., "Expression of Norwalk virus capsid protein in transgenic tobacco and potato and its oral immunogenicity in mice", Proc. Natl. Acad. Sci. USA, May 1996, vol. 93, pp. 5335-5340 (6 pages).
Tacket et al., "Human Immune Responses to a Novel Norwalk Virus Vaccine Delivered in Transgenic Potatoes", The Journal of Infectious Diseases, 2000, vol. 182, pp. 302-305 (4 pages).
Huang et al., "A DNA Replicon System for Rapid High-Level Production of Virus-Like Particles in Plants", Biotechnology and Bioengineering, Jul. 1, 2009, vol. 103, No. 4, pp. 706-714 (9 pages).
Ausar et al., "Conformational Stability and Disassembly of Norwalk Virus-like Particles", Journal of Biological Chemistry, Jul. 14, 2006, vol. 281, No. 28, pp. 19478-19488 (11 pages).
Genbank, Accession No. APY24054.1, capsid protein, partial [Norovirus sp.], 2017, 1 page.
Hansman et al., "Genetic and antigenic diversity among noroviruses", Journal of General Virology, 2006, vol. 87, pp. 909-919 (11 pages).
Parra et al., "Identification of a Broadly Cross-Reactive Epitope in the Inner Shell of the Norovirus Capsid", PLOS ONE, Jun. 2013, vol. 8, Issue 6, e67592, pp. 1-7 (7 pages).
Vongpunsawad et al., "Norwalk Virus Minor Capsid Protein VP2 Associates within the VP1 Shell Domain", Journal of Virology, May 2013, vol. 87, No. 9, pp. 4818-4825 (8 pages).

* cited by examiner

*Primary Examiner* — Barry A Chestnut
(74) *Attorney, Agent, or Firm* — Sughrue Mion, PLLC

(57) ABSTRACT

Nucleic acids encoding modified norovirus VP1 proteins, and VLPs comprising one or more of the modified norovirus VP1 proteins are provided. Methods for modified norovirus VP1 protein, and norovirus VLP, production in plants, portions of the plant or a plant cell, are also described.

22 Claims, 140 Drawing Sheets

Specification includes a Sequence Listing.

Figure 2A

| Norovirus VP1 Major Capsid Amino Acid Sequences | | |
|---|---|---|
| **Access (Uniprot)** | **Access (NCBI)** | **Strain Name** |
| Q83884 | NP_056821 | Hu/GI.1/United States/Norwalk/1968 |
| D2DEL3 | ACU56258 | Hu/GI.2/Leuven/2003/BEL |
| H2DG70 | AEY77318 | Hu/GI.3/S29/2008/Lilla Edet/Sweden |
| A0A023NFH0 | AHW99832 | Hu/GI.5/Siklos/HUN5407/2013/HUN |
| A0A1I9WIM4 | APA31979 | Hu/GI.7/GA5043/USA/2014 |
| H6V703 | AFA55174 | Hu/GII.1/Ascension208/2010/USA |
| S5ZGB5 | AGT39206 | Hu/GII.2/CGMH47/2011/TW |
| U3RI89 | AGX01095 | Hu/GII.3/Jingzhou/2013402/CHN |
| K4LM89 | AFV08795 | Hu/GII.4/Sydney/NSW0514/2012/AU |
| A0A1I9WIL4 | APA31970 | Hu/USA/2015/GII.P16_GII.4_Sydney/CA3477 |
| A0A0U3E729 | ALT54485 | Hu/GII.5/AlbertaEI390/2013/CA |
| M9T020 | AGI96397 | Hu/GII.6/Ohio/490/2012/USA |
| F8SRB4 | AEI29586 | Hu/GII.12/HS206/2010/USA |
| H9AWU4 | AFC89656 | Hu/GII.17/Kawasaki323/2014/JP |
| H9AWV4 | AFC89665 | Hu/GII.21/Salisbury150/2011/USA |
| **Norovirus VP2 Minor Capsid Amino Acid Sequence** | | |
| **Access (Uniprot)** | **Access (NCBI)** | **Strain Name** |
| W6APL0 | AHI59155 | Hu/GII.6/HS245/2010/USA |

Figure 2B

| Norovirus VP1 Major Capsid Nucleotide Sequences | |
|---|---|
| **Genome Access (NCBI)** | **Strain Name** |
| M87661 | Hu/GI.1/United States/Norwalk/1968 |
| FJ515294 | Hu/GI.2/Leuven/2003/BEL |
| JN603244 | Hu/GI.3/S29/2008/Lilla Edet/Sweden |
| KJ402295 | Hu/GI.5/Siklos/HUN5407/2013/HUN |
| KX907730 | Hu/GI.7/GA5043/USA/2014 |
| JN797508 | Hu/GII.1/Ascension208/2010/USA |
| KC464505 | Hu/GII.2/CGMH47/2011/TW |
| KF306213 | Hu/GII.3/Jingzhou/2013402/CHN |
| JX459908 | Hu/GII.4/Sydney/NSW0514/2012/AU |
| KU311160 | Hu/GII.5/AlbertaEI390/2013/CA |
| KC464321 | Hu/GII.6/Ohio/490/2012/USA |
| HQ664990 | Hu/GII.12/HS206/2010/USA |
| JN899242 | Hu/GII.17/Kawasaki323/2014/JP |
| JN899245 | Hu/GII.21/Salisbury150/2011/USA |
| **Norovirus VP2 Minor Capsid Nucleotide Sequence** | |
| **Access (NCBI)** | **Strain Name** |
| KJ407072 | Hu/GII.6/HS245/2010/USA |

GI.3/S29/2008/Lila Edet/Sweden

Mag. 15 K, 563-041-1
VP1 (GI.3)

Mag. 15 K, 563-041-3
VP1 (GI.3 S94L)

Mag. 15 K, 563-041-5
VP1 (GI.3 Q84S + S94L)

GI.3/S29/2008/Lila Edet/Sweden

VP1 (GI.3_M57I+S94L)

GI.5/Siklos/HUN54107/2013/HUN

GI.5
100 mM PBS pH 7.2
VP1 (wt)
VP1 (Q84S)
VP1 (A94L)
VP1 (Q84S + A94L)
35%
33%
31%
29%
25%
25%

VP1 GI.7/GA5043/USA/2014

GII.4/Sydney/SW0514/2012/AU

GII.4/Sydney/SW0514/2012/AU

GII.4_A39V+R53I+P80S

GII.12/HS206/2010/USA

Figure 12A

Amino acid sequence of VP1 G1.1 (SEQ ID NO: 1)

MMMASKDATSSVDGASGAGQLVPEVNASDPLAMDPVAGSSTAVATAGQVNPIDPWIINNFVQAPQGEFTISPNNTP
GDVLFDLSLGPHLNPFLLHLSQMYNGWVGNMRVRIMLAGNAFTAGKIIVSCIPPGFGSHNLTIAQATLFPHVIADVRTLD
PIEVPLEDVRNVLFHNNDRNQQTMRLVCMLYTPLRTGGGTGDSFVVAGRVMTCPSPDFNFLFLVPPTVEQKTRPFTLPN
LPLSSLSNSRAPLPISSMGISPDNVQSVQFQNGRCTLDGRLVGTTPVSLSHVAKIRGTSNGTVINLTELDGTPFHPFEGPAPI
GFPDLGGCDWHINMTQFGHSSQTQYDVDTTPDTFVPHLGSIQANGIGSGNYVGVLSWISPPSHPSGSQVDLWKIPNYG
SSITEATHLAPSVYPPGFGEVLVFFMSKMPGPGAYNLPCLLPQEYISHLASEQAPTVGEAALLHYVDPDTGRNLGEFKAYP
DGFLTCVPNGASSGPQQLPINGVFVFVSWVSRFYQLKPVGTASSARGRLGLRR

Figure 12B

Nucleic acid sequence of wild-type VP1 G1.1 (SEQ ID NO: 2)

ATGATGATGGCGTCTAAGGACGCTACATCAAGCGTGGATGGCGCTAGTGGCGCTGGTCAGTTGGTACCGGAGGTTA
ATGCTTCTGACCCTCTTGCAATGGATCCTGTAGCAGGTTCTTCGACAGCAGTCGCGACTGCTGGACAAGTTAATCCTA
TTGATCCCTGGATAATTAATAATTTTGTGCAAGCCCCCCAAGGTGAATTTACTATTTCCCCAAATAATACCCCCGGTG
ATGTTTTGTTTGATTTGAGTTTGGGTCCCCATCTTAATCCTTTCTTGCTCCATCTATCACAAATGTATAATGGTTGGGTT
GGTAACATGAGAGTCAGGATTATGCTAGCTGGTAATGCCTTTACTGCGGGGAAGATAATAGTTTCCTGCATACCCCC
TGGTTTTGGTTCACATAATCTTACTATAGCACAAGCAACTCTCTTTCCACATGTGATTGCTGATGTTAGGACTCTAGAC
CCCATTGAGGTGCCTTTGGAAGATGTTAGGAATGTTCTCTTTCATAATAATGATAGAAATCAACAAACCATGCGCCTT
GTGTGCATGCTGTACACCCCCCTCCGCACTGGTGGTGGTACTGGTGATTCTTTTGTAGTTGCAGGGCGAGTTATGAC
TTGCCCCAGTCCTGATTTTAATTTCTTGTTTTTAGTCCCTCCTACGGTGGAGCAGAAAACCAGGCCCTTCACACTCCCA
AATCTGCCATTGAGTTCTCTGTCTAACTCACGTGCCCCTCTCCCAATCAGTAGTATGGGCATTTCCCCAGACAATGTCC
AGAGTGTGCAGTTCCAAAATGGTCGGTGTACTCTGGATGGCCGCCTGGTTGGCACCACCCCAGTTTCATTGTCACAT
GTTGCCAAGATAAGAGGGACCTCCAATGGCACTGTAATCAACCTTACTGAATTGGATGGCACACCCTTTCACCCTTTT
GAGGGCCCTGCCCCCATTGGGTTTCCAGACCTCGGTGGTTGTGATTGGCATATCAATATGACACAGTTTGGCCATTC
TAGCCAGACCCAGTATGATGTAGACACCACCCCTGACACTTTTGTCCCCCATCTTGGTTCAATTCAGGCAAATGGCAT
TGGCAGTGGTAATTATGTTGGTGTTCTTAGCTGGATTTCCCCCCCATCACACCCGTCTGGCTCCCAAGTTGACCTTTG
GAAGATCCCCAATTATGGGTCAAGTATTACGGAGGCAACACATCTAGCCCCTTCTGTATACCCCCCTGGTTTCGGAG
AGGTATTGGTCTTTTTCATGTCAAAAATGCCAGGTCCTGGTGCTTATAATTTGCCCTGTCTATTACCACAAGAGTACA
TTTCACATCTTGCTAGTGAACAAGCCCCTACTGTAGGTGAGGCTGCCCTGCTCCACTATGTTGACCCTGATACCGGTC
GGAATCTTGGGGAATTCAAAGCATACCCTGATGGTTTCCTCACTTGTGTCCCCAATGGGGCTAGCTCGGGTCCACAA
CAGCTGCCGATCAATGGGGTCTTTGTCTTTGTTTCATGGGTGTCCAGATTTTATCAATTAAAGCCTGTGGGAACTGCC
AGCTCGGCAAGAGGTAGGCTTGGTCTGCGCCGATAA

Figure 12C

Nucleic acid sequence of human codon-optimized VP1 G1.1 (SEQ ID NO: 3)

ATGATGATGGCTAGTAAAGATGCGACCTCCTCTGTGGATGGTGCGTCAGGGGCAGGACAACTCGTACCCGAGGTAA
ACGCCAGCGACCCACTTGCCATGGACCCCGTTGCCGGAAGTTCCACAGCAGTGGCCACAGCCGGTCAAGTGAATCC
AATTGATCCGTGGATTATCAACAATTTCGTCCAGGCACCCCAGGGCGAGTTCACAATTTCACCAAACAATACACCGG
GCGATGTGCTATTCGATCTTTCCTTGGGTCCTCACCTTAACCCTTTTCTACTCCATCTCTCACAGATGTACAATGGTTG
GGTAGGAAACATGAGAGTCCGGATCATGCTGGCTGGCAATGCCTTTACCGCTGGCAAGATCATCGTCAGTTGTATTC
CTCCCGGATTTGGATCTCATAATCTGACCATTGCTCAAGCGACTCTCTTTCCCCATGTCATCGCCGACGTTAGGACCCT
GGACCCCATCGAGGTGCCCCTGGAGGACGTCCGGAATGTTTTGTTCCACAACAACGACAGAAACCAGCAGACGATG
AGACTTGTCTGTATGCTCTATACCCCACTGCGGACTGGAGGCGGGACTGGAGACTCCTTCGTTGTGGCAGGAAGAG
TGATGACATGCCCCTCCCCCGACTTCAACTTTCTTTTTCTGGTCCCACCAACCGTTGAGCAGAAGACGCGGCCCTTTA
CACTGCCCAATCTCCCGCTTTCAAGTCTGAGTAATTCACGGGCCCCATTGCCGATCTCCTCAATGGGAATCTCCCCCG
ACAACGTCCAGTCTGTCCAATTCCAAAATGGGAGATGCACACTGGACGGTCGCCTGGTGGGAACAACTCCGGTGTC
CCTCTCACATGTCGCCAAAATCCGCGGCACATCAAATGGTACCGTAATCAATCTGACAGAACTTGATGGCACGCCCTT
CCATCCCTTTGAAGGACCAGCCCCTATTGGATTTCCTGATCTGGGAGGTTGCGACTGGCACATAAACATGACACAGT
TTGGCCACTCCAGCCAGACACAGTATGATGTCGATACAACCCCAGATACCTTCGTGCCACACCTGGGATCTATTCAA
GCTAACGGTATTGGATCCGGCAACTACGTGGGAGTCTTATCTTGGATCTCACCACCATCCCACCCCTCAGGATCCCAG
GTTGACTTGTGGAAGATACCGAATTATGGATCCTCGATCACTGAAGCCACGCACCTCGCACCTTCCGTCTACCCACCA
GGTTTTGGAGAAGTCTTGGTGTTTTTCATGAGCAAAATGCCCGGCCCTGGAGCCTACAATCTCCCTTGCCTACTCCCT
CAAGAGTATATTAGTCACCTCGCATCTGAGCAGGCCCCGACCGTTGGCGAGGCAGCCCTGCTGCATTATGTGGATCC
GGACACCGGCAGGAACCTGGGTGAGTTCAAAGCTTATCCTGACGGTTTTCTAACATGTGTACCAAATGGCGCTTCCA
GCGGCCCTCAACAGCTCCCAATCAATGGCGTGTTCGTTTTTGTCAGCTGGGTAAGCCGCTTCTACCAGCTGAAGCCC
GTGGGGACAGCTTCTTCTGCCCGCGGACGCCTCGGTCTGCGGAGATAA

Figure 13A

Amino acid sequence of VP1 G1.2_Leuven_2003_D2DEL3 (SEQ ID NO: 4)

MMMASKDAPQSADGASGAGQLVPEVNTADPLPMEPVAGPTTAVATAGQVNMIDPWIVNNFVQSPQGEFTISPNNT
PGDILFDLQLGPHLNPFLSHLSQMYNGWVGNMRVRILLAGNAFSAGKIIVCCVPPGFTSSSLTIAQATLFPHVIADVRTLEP
IEMPLEDVRNVLYHTNDNQPTMRLVCMLYTPLRTGGGSGNSDSFVVAGRVLTAPSSDFSFLFLVPPTIEQKTRAFTVPNIP
LQTLSNSRFPSLIQGMILSPDASQVVQFQNGRCLIDGQLLGTTPATSGQLFRVRGKINQGARTLNLTEVDGKPFMAFDSP
APVGFPDFGKCDWHMRISKTPNNTSSGDPMRSVDVQTDVQGFVPHLGSIQFDEVFNHPTGDYIGTIEWISQPSTPPGT
DINLWEIPDYGSSLSQAANLAPPVFPPGFGEALVYFVSAFPGPNNRSAPNDVPCLLPQEYVTHFVSEQAPTMGDAALLHY
VDPDTNRNLGEFKLYPGGYLTCVPNGVGAGPQQLPLNGVFLFVSWVSRFYQLKPVGTASTARGRLGVRRI

Figure 13B

Nucleic acid sequence of human codon-optimized VP1 G1.2_Leuven_2003_D2DEL3 (SEQ ID NO: 5)

ATGATGATGGCTTCAAAGGATGCTCCCCAAAGCGCGGACGGAGCTAGCGGCGCCGGACAGTTGGTTCCGGAAGTC
AACACTGCCGATCCACTGCCCATGGAACCCGTAGCTGGTCCAACAACCGCTGTTGCCACCGCCGGCCAGGTTAACAT
GATCGATCCATGGATTGTTAATAACTTTGTACAGAGCCCCCAGGGGGAGTTCACAATTTCTCCGAACAATACCCCTG
GGGACATTCTGTTCGATCTGCAACTGGGCCCACACTTGAATCCTTTCCTGAGCCATCTTTCACAGATGTACAACGGAT
GGGTTGGGAACATGCGTGTTCGGATCCTCCTTGCTGGCAACGCCTTCAGTGCTGGCAAGATTATCGTGTGCTGCGTA
CCACCAGGGTTTACCTCGAGTTCATTAACCATTGCTCAGGCCACCCTTTTCCCTCACGTGATCGCAGACGTGCGTACC
TTAGAACCAATCGAAATGCCCCTGGAAGATGTACGGAACGTGCTGTACCATACTAATGATAACCAGCCAACGATGA
GATTAGTGTGCATGCTGTACACCCCCCTGAGAACTGGAGGAGGTTCTGGAAATTCCGACAGTTTTGTGGTGGCTGG
CAGGGTCCTGACCGCTCCCAGTAGCGACTTCAGCTTTTTGTTCCTCGTTCCTCCTACAATCGAACAAAAAACAAGAGC
ATTCACAGTGCCCAACATTCCACTGCAGACTTTAAGCAATTCCAGGTTTCCCAGCTTGATCCAGGGTATGATCCTTTCT
CCCGACGCCTCCCAAGTTGTGCAGTTCCAGAATGGGAGATGTCTTATCGACGGTCAGCTTCTGGGAACAACCCCTGC
CACCTCCGGGCAACTCTTCCGGGTGAGAGGCAAAATCAATCAGGGCGCCAGAACACTGAATCTGACAGAAGTGGAC
GGGAAACCCTTTATGGCGTTCGATAGCCCCGCGCCCGTTGGATTCCCTGACTTCGGCAAGTGTGATTGGCACATGCG
CATCAGTAAGACTCCCAACAACACTTCATCTGGAGACCCCATGAGGAGCGTGGATGTCCAGACCGACGTGCAGGGC
TTCGTGCCGCACTTGGGATCTATCCAGTTCGATGAGGTGTTCAATCACCCTACTGGCGACTACATAGGCACAATTGA
GTGGATAAGTCAACCATCTACACCTCCAGGGACCGACATAAACCTGTGGGAAATTCCTGATTACGGGTCATCCCTGA
GTCAAGCTGCCAATCTTGCACCCCCTGTCTTTCCCCCCGGCTTTGGTGAGGCTCTTGTTTACTTCGTCTCTGCATTTCCT
GGTCCTAACAACCGCTCCGCCCCTAACGATGTTCCGTGTTTGTTACCCCAGGAATATGTGACTCATTTCGTTTCCGAA
CAGGCACCCACCATGGGGGACGCTGCCCTGCTACACTATGTGGACCCCGACACCAATAGAAACCTCGGCGAGTTCA
AACTCTACCCCGGGGGATACCTGACCTGTGTTCCAAATGGAGTGGGAGCAGGCCCACAACAGCTGCCCCTGAATGG
GGTCTTCCTGTTCGTTTCTTGGGTGTCACGCTTTTACCAGCTGAAGCCCGTTGGCACAGCTTCTACGGCACGCGGCAG
GCTAGGGGTCCGCCGAATCTGA

Figure 14A

Amino acid sequence of VP1 GI.3_LillaEdet_2008_H2DG70 (SEQ ID NO: 6)

MMMASKDAPTNMDGTSGAGQLVPEVSTAEPISMEPVAGAATAAATAGQVNMIDPWIMSNYVQAPQGEFTISPNNT
PGDILFDLQLGPHLNPFLSHLAQMYNGWVGNMKVRVLLAGNAFTAGKIIISCVPPGFAAQNVSIAQATMFPHVIADVRV
LEPIEVPLEDVRNVLFHNNDSTPTMRLICMLYTPLRASGSSSGTDPFVIAGRVLTCPSPDFNFLFLVPPNVEQKTKPFSVPNL
PLNVLSNSRVPSLIKSMMVSQDHGQMVQFQNGRVTLDGQLQGTTPTSASQLCKIRGTVYHATGGQGLNLTEIDGTPYH
AFESPAPIGFPDLGECDWHINASPANAFTDGSIIHRIDVAQDSTFAPHLGTIHYTNADYNANVGLICSLEWLSPPSGGAPK
VNPWAIPRYGSTLTEAAQLAPPIYPPGFGEAIVFFMSDFPIANGSDGLSVPCTIPQEFVTHFVNEQAPTRGEAALLHYVDP
DTHRNLGEFKLYPEGFMTCVPNSSGSGPQTLPINGVFTFISWVSRFYQLKPVGTTGPVRRLGIRRS

Figure 14B

Nucleic acid sequence of human codon-optimized VP1 GI.3_LillaEdet_2008_H2DG70 (SEQ ID NO: 7)

ATGATGATGGCTTCCAAGGATGCTCCCACAAACATGGATGGAACAAGCGGCGCGGGGCAACTTGTGCCGGAGGTG
TCCACGGCGGAACCCATTTCCATGGAACCTGTGGCCGGCGCAGCCACTGCTGCCGCCACCGCAGGACAGGTAAACA
TGATCGACCCCTGGATCATGTCAAATTACGTTCAGGCTCCACAGGGGGAGTTTACCATAAGCCCAAACAACACCCCG
GGTGACATCTTGTTTGACCTGCAGCTAGGACCACACTTGAATCCGTTTCTGAGTCACTTGGCTCAGATGTATAATGGA
TGGGTTGGAAACATGAAGGTGCGCGTGCTCCTGGCGGGCAATGCATTCACAGCCGGGAAGATTATTATCTCTTGCG
TGCCACCTGGATTTGCAGCCCAGAACGTGTCTATCGCACAGGCAACCATGTTTCCGCATGTCATCGCAGATGTGCGC
GTGCTAGAGCCCATCGAGGTGCCCCTTGAGGACGTGCGCAACGTCCTATTCCATAACAATGATAGCACCCCCACCAT
GCGCTTGATATGTATGTTATATACTCCCCTCCGCGCCAGTGGGTCCAGCTCCGGGACCGATCCTTTTGTGATTGCTGG
GCGGGTGTTGACTTGTCCTAGCCCTGACTTCAACTTCCTTTTTCTGGTGCCTCCAAATGTAGAACAGAAAACAAAGCC
ATTCAGCGTGCCAAACCTGCCCCTTAACGTGCTGTCGAATTCCCGAGTGCCTTCCCTTATTAAGTCCATGATGGTATC
TCAGGATCACGGTCAAATGGTGCAGTTTCAGAACGGCCGAGTGACGTTAGACGGGCAGCTGCAGGGCACAACCCC
AACCAGTGCCAGTCAGCTGTGTAAGATCAGAGGCACCGTCTACCACGCAACTGGCGGACAGGGGCTGAATCTTACT
GAGATCGATGGTACCCCCTACCATGCATTCGAGTCACCTGCACCTATTGGATTTCCCGATCTTGGGGAGTGTGATTG
GCATATCAATGCTTCACCTGCCAACGCTTTCACAGACGGGTCTATTATTCATCGCATTGACGTAGCACAGGATAGCAC
ATTTGCCCCGCACCTGGGTACCATCCACTATACGAACGCAGATTACAACGCAAACGTGGGTCTTATCTGTAGCCTAG
AGTGGCTATCTCCGCCAAGCGGTGGGGCCCCTAAAGTTAACCCATGGGCTATTCCTCGGTACGGGTCTACGCTGACT
GAGGCCGCTCAGCTGGCACCCCCCATATATCCACCAGGATTCGGGGAAGCCATTGTTTTCTTTATGTCCGATTTTCCG
ATAGCCAACGGTTCAGATGGCCTTAGTGTCCCTTGCACGATTCCACAGGAATTTGTGACACACTTCGTAAACGAGCA
GGCTCCTACTCGGGGCGAGGCTGCCTTGTTGCATTACGTAGACCCCGATACCCATAGAAACCTGGGCGAATTCAAAC
TCTACCCTGAAGGTTTCATGACCTGCGTACCTAACTCCTCCGGCAGTGGCCCTCAAACCTTGCCGATCAACGGCGTGT
TCACGTTTATCAGCTGGGTTTCACGGTTTTACCAACTCAAGCCCGTCGGAACAACTGGGCCAGTTCGGAGGCTCGGG
ATCAGACGGAGCTAG

Figure 15A

Amino acid sequence of VP1 GI.5_Siklos_HUN5407_2013_HUN_AHW99832 (SEQ ID NO: 12)

MMMASKDAPSSADGANGAGQLVPEVNNAEPLPLDPVAGASTALATAGQVNMIDPWIFNNFVQAPQGEFTISPNNTP
GDILFDLQLGPHLNPFLAHLSQMYNGWVGNMRVRVILAGNAFTAGKVIICCVPPGFQSRTLSIAQATLFPHIIADVRTLEPI
EIPLEDVRNTLYHTNDNQPTMRLLCMLYTPLRTGGGSGGTDAFVVAGRVLTCPSSDFNFLFLVPPTVEQKTRPFSVPNIPL
QLLSNSRVPNLIQSMVLSPDQAQNVQFQNGRCTTDGQLLGTTPVSVSQILKFRGKVSAGSKVINLTELDGSPFLAFEAPAP
TGFPDLGTSDWHVEMSLNSNSQSSGNPILLRDIHPNSSEFVPHLGSVCVTAAIEVAGDYTGTIQWTSQPSNVTPVPDVNF
WTIPHYGSNLAEASQLAPVVYPPGFGEAIVYFMSPIPGPNTAHKPNLVPCLLPQEFVTHFVSEQAPSMGEAALVHYVDPD
TNRNLGEFKLYPEGFITCVPNGTGPQQLPLNGVFVFASWVSRFYQLKPVGTASSARGRLGVRR

Figure 15B

Nucleic acid sequence of human codon-optimized VP1 GI.5_Siklos_HUN5407_2013_HUN AHW99832 (SEQ ID NO: 33)

ATGATGATGGCCTCCAAAGACGCTCCTAGCAGTGCTGATGGCGCTAACGGTGCCGGCCAGCTGGTCCCCGAGGTGA
ATAACGCCGAGCCTCTCCCCTTGGACCCAGTAGCCGGAGCTTCAACGGCCCTAGCTACTGCCGGACAGGTTAATATG
ATTGACCCCTGGATTTTCAATAATTTCGTGCAGGCCCCTCAAGGCGAGTTTACTATAAGCCCTAACAACACACCAGGG
GATATTCTGTTCGACCTGCAGTTAGGCCCTCATCTCAACCCCTTCTTGGCCCACCTGAGCCAGATGTACAATGGCTGG
GTGGGCAACATGCGAGTGAGAGTTATCCTCGCAGGGAACGCCTTTACCGCTGGTAAGGTGATCATTTGTTGCGTAC
CACCTGGATTCCAGTCTAGGACATTAAGTATTGCGCAAGCTACCCTCTTTCCTCATATCATCGCCGACGTGCGGACAC
TAGAGCCCATCGAGATCCCACTGGAGGATGTCCGGAATACCCTGTACCATACCAACGATAATCAGCCCACTATGAGG
TTACTGTGCATGCTGTACACGCCACTCCGGACTGGTGGGGGCAGTGGGGGGACCGATGCTTTCGTCGTTGCCGGTA
GGGTGCTCACTTGCCCGTCATCTGACTTTAACTTCCTATTCCTTGTGCCCCCAACGGTGGAACAGAAAACGAGACCTT
TTTCCGTACCTAACATCCCTTTACAGCTCCTAAGCAATAGCAGAGTACCTAACCTGATCCAATCCATGGTTCTTAGCCC
TGATCAAGCGCAGAACGTACAGTTTCAGAACGGGCGGTGCACCACAGATGGCCAGCTGCTTGGTACAACTCCCGTC
TCCGTGTCTCAGATACTTAAGTTTCGCGGCAAGGTCTCCGCTGGATCCAAAGTAATCAACCTCACTGAGCTTGATGG
CTCTCCCTTTCTGGCGTTCGAGGCGCCCGCCCCAACAGGCTTTCCAGACCTGGGAACATCCGATTGGCATGTCGAGA
TGAGTCTGAATAGCAACTCCCAGTCTTCTGGCAATCCAATACTGCTCCGCGATATCCATCCTAATTCTAGCGAGTTCG
TTCCACACCTGGGTTCTGTGTGCGTGACGGCTGCAATAGAGGTGGCTGGCGACTACACGGGTACCATTCAGTGGAC
CTCTCAGCCAAGTAACGTGACCCCTGTGCCAGACGTTAACTTTTGGACAATTCCACACTACGGCTCTAACTTGGCCGA
AGCATCCCAGCTTGCCCCCGTTGTATATCCCCCAGGCTTTGGCGAAGCAATAGTTTATTTTATGTCCCCAATCCCTGG
ACCTAACACAGCACACAAGCCAAACCTCGTCCCATGCCTGCTGCCCCAGGAGTTCGTGACTCATTTCGTTTCGGAACA
AGCCCCATCAATGGGGGAGGCCGCCCTGGTCCACTACGTGGATCCAGATACCAATCGGAATCTGGGAGAATTCAAA
CTCTACCCTGAAGGATTCATTACATGTGTGCCCAATGGAACAGGACCGCAGCAGCTCCCACTGAACGGTGTCTTTGT
ATTCGCATCATGGGTTAGCCGGTTCTATCAACTTAAACCCGTGGGGACAGCTTCATCTGCCCGGGGGCGCCTTGGCG
TGCGGCGCTGA

Figure 16A

Amino acid sequence of VP1_GI.7 (SEQ ID NO:101)

MMMASKDAPSNMDGTSGAGQLVPEVNAAEPLPLEPVVGAATAVATAGQVNMIDPWIMNNFVQAPEGEFTISPNNT
PGDILFDLRLGPHLNPFLLHLSQMYNGWVGNMRVRVMLAGNAFSAGKIIICCVPPGFESQNISIGQATMFPHVIADVRVL
EPIEVPLDDVRNVLFHTNENRPTMRLLCMLYTPLRAGGASSGTDPFVIAGRVLTCPAPDFNFLFLVPPSVEQKTRQLTIPNI
PLNNLANSRVPAMINKMTVSADQNQVVQFQNGRCTLEGQLLGTTPVSANQVARIRGKVFSTNSGTGLNLTEVDGTPYH
AFESPAPLGFPDIGNCDWHVYAFKVNQNTGDPMYRLDITQGNSFAPHLGSIEFSSENHPSGDQLGTLTWISPLNNASRV
DPWKIPTYGSTLTESTNLAPPIFPPGFGEAIVYFMSDFPIVSGNTAQIPCTLPQEFVSSFVEQQAPIRGEAALLHYVDPDTHR
NLGEFKLYPDGFITCVPNTGGGPQNLPSNGVFVFSSWVSRYYQLKPVGTTGPVRRLGVRRV

Figure 16B

Nucleic acid sequence of human codon-optimized VP1 GI.7/GA5043/USA/2014 VP1 (SEQ ID NO:175)

ATGATGATGGCCAGCAAGGACGCTCCGAGTAACATGGACGGCACTTCGGGCGCGGGGCAGCTGGTGCC
CGAGGTCAATGCCGCAGAACCACTTCCTCTTGAGCCCGTCGTTGGCGCCGCCACAGCTGTCGCAACTGCA
GGCCAAGTCAATATGATCGACCCGTGGATAATGAACAATTTCGTTCAGGCACCAGAAGGAGAATTCACC
ATCTCCCCCAATAACACCCCAGGGGATATTCTGTTTGACCTCAGGTTAGGACCCCACTTGAACCCCTTTCT
GCTTCATCTCTCACAAATGTATAATGGCTGGGTCGGGAATATGCGCGTGCGGGTGATGCTAGCCGGCAA
TGCTTTTTCTGCAGGCAAGATTATCATTTGCTGCGTTCCTCCTGGATTCGAATCTCAAAATATCAGCATTG
GTCAAGCAACCATGTTTCCACATGTGATCGCTGATGTTCGCGTCCTGGAACCCATTGAAGTTCCTCTCGAC
GACGTGAGAAATGTTCTCTTCCACACCAACGAGAATAGGCCGACTATGAGACTTCTGTGTATGCTCTACA
CCCCATTAAGAGCCGGGGGAGCATCCTCAGGTACTGACCCATTTGTGATTGCCGGGCGGGTGCTCACAT
GCCCGGCTCCAGACTTTAACTTCCTTTTCTTGGTGCCACCCAGTGTTGAACAGAAAACCAGACAGCTCACC
ATCCCAAATATCCCATTGAACAATCTCGCCAACAGCAGGGTGCCAGCAATGATAAACAAAATGACAGTCA
GTGCTGACCAGAACCAGGTAGTCCAGTTTCAGAACGGCAGATGCACGCTTGAGGGCCAACTGCTTGGGA
CGACCCCAGTCTCCGCGAACCAGGTGGCCCGAATCCGGGGTAAAGTCTTCAGTACAAACTCCGGCACTG
GCCTTAACCTCACAGAGGTTGACGGCACTCCCTATCATGCTTTTGAGTCTCCAGCCCCTCTTGGCTTTCCC
GATATAGGCAACTGTGACTGGCACGTTTATGCGTTTAAAGTAAACCAGAACACCGGCGATCCTATGTATA
GGTTGGATATAACACAAGGTAATTCATTCGCCCCACACTTGGGTAGCATCGAGTTCAGTTCAGAGAACCA
TCCGAGTGGTGATCAGCTAGGCACATTGACGTGGATCAGCCCTCTGAATAACGCATCAAGAGTGGATCC
CTGGAAGATCCCTACCTATGGGTCCACTCTGACAGAGAGCACAAATTTGGCTCCGCCCATTTTCCCACCCG
GATTCGGCGAGGCCATAGTGTACTTTATGTCTGACTTTCCTATCGTCAGCGGGAATACAGCCCAGATTCCT
TGCACACTGCCACAAGAATTCGTCTCATCCTTTGTAGAGCAGCAGGCACCTATTCGAGGTGAGGCCGCCC
TCTTGCACTACGTGGACCCTGACACCCACCGCAATCTTGGCGAGTTTAAGCTGTACCCTGACGGGTTTATT
ACCTGTGTACCCAACACCGGCGGCGGCCCACAAAATTTGCCCAGCAATGGCGTGTTTGTCTTTTCCTCTTG
GGTGTCTCGATACTACCAGCTTAAACCTGTCGGAACTACGGGCCCCGTGCGACGACTCGGCGTGAGGCG
GGTGTGA

Figure 16C

Amino acid sequence of GII.1_Ascension208_2010_USA_AFA55174 native VP1 (SEQ ID NO: 13)

MKMASNDAAPSNDGAAGLVPEVNNETMALEPVAGASIAAPLTGQNNVIDPWIRMNFVQAPNGEFTVSPRNSPGEVLL
NLELGPELNPFLAHLSRMYNGYAGGVEVQVLLAGNAFTAGKLVFAAIPPHFPLENLSPGQITMFPHVIIDVRTLEPVLLPLP
DVRNNFFHYNQQPEPRMRLVAMLYTPLRSNGSGDDVFTVSCRVLTRPSPDFDFNYLVPPTVESKTKPFTLPILTIGELSNS
RFPVPIDELYTSPNEGVVVQPQNGRSTLDGELLGTTQLVPSNICALRGRINAQVPDDHHQWNLQVTNANGTSFDPTEDV
PAPLGTPDFLANIYGVTSQRNPDNTCRAHDGVLATWSPKFTPKLGSVVLGTWEESDLDLNQPTRFTPVGLYDTGHFDQ
WVLPNYSGRLTLNMNLAPSVAPLFPGEQILFFRSHIPLKGGTSNGAIDCLLPQEWIQHFYQESAPSPTDVALIRYTNPDTG
RVLFEAKLHRQGFITVANSGSRPIVVPPNGYFRFDSWVNQFYSLAPMGTGNGRRRVQ

Figure 17A

Amino acid sequence of VP1 GII.2_CGMH47_2011_TW_AGT39206 (SEQ ID NO: 14)

MKMASNDAAPSTDGAAGLVPESNNEVMALEPVAGAALAAPVTGQTNIIDPWIRANFVQAPNGEFTVSPRNSPGEVLL
NLELGPELNPYLAHLARMYNGYAGGMEVQVMLAGNAFTAGKLVFAAVPPHFPVENLSPQQITMFPHVIIDVRTLEPVLL
PLPDVRNNFFHYNQKDDPKMRIVAMLYTPLRSNGSGDDVFTVSCRVLTRPSPDFDFTYLVPPTVESKTKPFTLPILTLGELS
NSRFPVSIDQMYTSPNEVISVQCQNGRCTLDGELQGTTQLQVSGICAFKGEVTAHLHDNDHLYNVTITNLNGSPFDPSED
IPAPLGVPDFQGRVFGVISQRDKHNTPGHNEPANRAHDAVVPTYTAQYTPKLGQIQIGTWQTDDLTVNQPVKFTPVGL
NDTDHFNQWVVPRYAGALNLNTNLAPSVAPVFPGERLLFFRSYIPLKGGYGTPAIDCLLPQEWVQHFYQEAAPSMSEVA
LVRYINPDTGRALFEAKLHRAGFMTVSSNTSAPVVVPANGYFRFDSWVNQFYSLAPMGTGNGRRRIQ

Figure 17B

Nucleic acid sequence of human codon-optimized VP1 GII.2 CGMH47 2011 TW AGT39206 (SEQ ID NO: 40)

ATGAAGATGGCATCCAACGACGCCGCACCCAGCACAGACGGAGCTGCCGGATTGGTACCCGAGTCTAATAACGAG
GTGATGGCCTTGGAGCCTGTTGCAGGGGCTGCCCTCGCAGCTCCTGTGACCGGGCAGACAAATATCATCGATCCTTG
GATTAGAGCTAATTTCGTGCAAGCCCCAAATGGGGAGTTTACGGTCAGCCCTAGAAATAGCCCTGGGGAAGTGCTC
CTCAATCTCGAGCTGGGACCAGAACTTAATCCGTACCTGGCTCACCTGGCCCGGATGTACAATGGATATGCAGGAG
GGATGGAGGTGCAGGTTATGCTGGCTGGCAATGCCTTTACAGCAGGCAAACTCGTTTTCGCAGCCGTCCCTCCCCAC
TTCCCAGTTGAAAATCTTTCCCCTCAGCAGATTACCATGTTTCCCCATGTCATCATCGATGTGCGTACCCTGGAACCTG
TGCTGTTGCCTTTACCAGACGTGCGGAATAATTTCTTTCACTATAATCAGAAGGATGACCCAAAAATGCGGATCGTTG
CGATGCTTTATACTCCCCTGCGTAGCAATGGTAGTGGGGATGACGTTTTTACAGTGAGTTGTCGGGTACTAACTCGC
CCTTCACCAGACTTCGACTTTACGTACTTGGTGCCTCCCACTGTCGAAAGCAAAACTAAGCCATTCACACTTCCCATCC
TCACCCTCGGAGAACTCTCGAACTCCCGCTTCCCTGTTTCAATTGATCAGATGTACACGTCTCCAAATGAAGTCATTTC
TGTGCAGTGTCAGAACGGCAGGTGCACCTTAGACGGTGAACTGCAGGGGACAACGCAGTTGCAGGTCAGTGGAAT
TTGCGCCTTTAAGGGCGAAGTGACAGCTCACCTCCACGACAACGATCATCTCTACAATGTTACTATTACTAATCTCAA
TGGAAGTCCTTTCGACCCCTCGGAAGATATTCCCGCTCCACTCGGAGTACCTGACTTTCAGGGACGCGTCTTCGGCG
TGATATCACAACGAGATAAGCATAACACACCCGGACATAATGAGCCAGCCAATAGAGCCCACGACGCAGTCGTTCC
GACCTATACGGCTCAGTACACCCCAAAGCTCGGCCAGATACAAATCGGGACTTGGCAGACCGATGACCTCACTGTG
AATCAACCTGTGAAATTCACTCCAGTAGGTCTGAATGATACAGACCACTTTAACCAGTGGGTGGTCCCTAGATACGC
CGGAGCCTTGAACCTAAACACTAACCTTGCCCCTTCCGTTGCACCTGTGTTTCCGGGGGAGCGGTTGCTCTTCTTTAG
AAGCTATATTCCTCTGAAGGGCGGGTATGGTACTCCAGCAATCGACTGCCTGCTACCTCAGGAGTGGGTTCAACATT
TCTATCAAGAGGCCGCACCTAGTATGAGCGAGGTGGCTTTGGTCAGATACATCAATCCAGACACAGGAAGAGCACT
GTTCGAGGCCAAGCTGCACAGAGCCGGCTTCATGACCGTCTCATCCAATACATCCGCACCCGTAGTAGTCCCCGCCA
ACGGGTACTTCAGATTCGACAGTTGGGTGAATCAGTTTTACTCGTTGGCCCCCATGGGCACAGGGAACGGTCGCCG
ACGGATCCAGTAA

Figure 18A

Amino acid sequence of VP1 GII.3_Jingzhou_2013402_CHN_AGX01095 (SEQ ID NO: 15)

MKMASNDAAPSNDGAAGLVPEISSEAMALEPVAGAAIAAPLTGQQNIIDPWIMNNFVQAPGGEFTVSPRNSPGEVLLN
LELGPEINPYLAHLARMYNGYAGGFEVQVVLAGNAFTAGKIIFAAIPPNFPIDNLSAAQITMCPHVIVDVRQLEPVNLPMP
DVRNNFFHYNQGSDSRLRLIAMLYTPLRANNSGDDVFTVSCRVLTRPSPDFSFNFLVPPTVESKTKPFSLPILTISEMSNSRF
PVPIDSLHTSPTENIVVQCQNGRVTLDGELMGTTQLLPSQICAFRGTLTRSTSRASDQADTATPRLFNYYWHIQLDNLNG
TPYDPAEDIPAPLGTPDFRGKVFGVASQRNPDATTRAHEAKIDTTSGRFTPKLGSLEISTESGDFDQNQPTRFTPVGIGVD
HEPDFQQWALPDYAGQFTHNMNLAPAVAPNFPGEQLLFFRSQLPSSGGRSNGILDCLVPQEWVQHFYQESAPSQTQV
ALVRYVNPDTGRVLFEAKLHKLRFMTIAKSGDSPITVPPNGYFRFESWVNPFYTLAPMGTGNGRRRIQ

Figure 18B

Nucleic acid sequence of human codon-optimized VP1 GII.3_Jingzhou_2013402_CHN AGX01095 (SEQ ID NO: 45)

ATGAAAATGGCTTCCAACGATGCAGCACCCTCTAATGATGGCGCTGCCGGACTTGTGCCGGAGATTAGCTCTGAGG
CTATGGCCCTAGAACCAGTAGCCGGGGCAGCCATAGCTGCCCCACTGACTGGCCAGCAGAATATCATTGACCCCTG
GATAATGAACAATTTCGTGCAGGCACCGGGGGGAGAATTCACGGTCTCTCCTCGAAACTCCCCCGGGGAGGTTCTCT
TGAATTTGGAACTGGGCCCTGAAATTAATCCTTATCTGGCCCATCTAGCCCGAATGTACAACGGCTACGCCGGAGGT
TTCGAGGTCCAGGTGGTGCTCGCTGGTAACGCCTTCACAGCTGGCAAGATCATTTTTGCAGCAATCCCTCCAAACTTC
CCTATCGATAATCTTAGTGCCGCCCAGATCACAATGTGCCCTCACGTTATCGTAGATGTGAGGCAGCTGGAACCTGT
CAATCTCCCAATGCCCGACGTGCGCAACAACTTCTTTCACTATAACCAGGGATCTGACTCCCGCCTTCGCCTTATCGCT
ATGCTGTACACCCCTCTGAGGGCTAACAATTCCGGAGATGACGTTTTCACTGTGAGTTGTCGAGTCCTGACACGTCC
ATCTCCTGACTTTAGCTTTAATTTCCTCGTGCCCCCCACAGTGGAATCCAAAACTAAGCCATTCTCTCTGCCAATTCTT
ACCATTAGCGAAATGTCGAATAGTAGGTTCCCGGTGCCCATAGATTCACTGCATACCAGTCCAACAGAAAACATCGT
CGTACAGTGTCAGAACGGACGCGTGACTCTCGACGGGGAGCTTATGGGCACTACCCAGCTGCTGCCCAGCCAGATA
TGCGCCTTCCGCGGCACACTGACTAGAAGCACTTCGCGTGCTTCTGACCAGGCAGATACAGCTACACCAAGGCTGTT
CAATTATTATTGGCATATACAACTCGATAATCTGAATGGCACTCCTTATGACCCAGCCGAGGACATCCCCGCCCCACT
TGGCACCCCGGACTTTAGAGGGAAGGTCTTTGGAGTGGCTTCTCAAAGAAATCCCGACGCAACCACCCGGGCCCAC
GAGGCCAAAATCGATACTACATCAGGGCGTTTCACCCCTAAGTTAGGCAGTCTGGAGATATCTACCGAAAGTGGAG
ATTTCGATCAGAACCAGCCAACCCGGTTTACCCCCGTGGGAATCGGGGTTGACCACGAACCGGATTTCCAGCAGTG
GGCTCTGCCTGATTACGCAGGCCAGTTCACACATAACATGAATCTTGCCCCCGCTGTGGCCCCCAACTTCCCGGGAG
AACAACTTCTGTTTTTCAGGAGCCAACTGCCTTCCAGCGGCGGCCGATCTAACGGGATTTTGGACTGTCTCGTGCCCC
AGGAATGGGTGCAGCATTTTTACCAGGAGTCCGCGCCCTCCCAGACGCAGGTGGCTCTGGTTAGATATGTCAATCCC
GACACCGGCAGGGTGCTATTTGAGGCAAAGCTGCACAAGCTTCGCTTTATGACTATCGCTAAGAGCGGTGATTCGCC
TATTACAGTGCCCCCCAACGGATACTTCAGATTTGAGAGTTGGGTGAACCCATTCTATACCCTGGCCCCCATGGGTAC
AGGCAATGGCAGACGGCGGATCCAGTAA

Figure 19A

Amino acid sequence of VP1 GII.4_Sydney_2012_K4LM89 (SEQ ID NO: 16)

MKMASSDANPSDGSAANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 19B

Nucleic acid sequence of human codon-optimized VP1 GII.4_Sydney_2012_K4LM89 (SEQ ID NO:52)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATGTGATTGACCCGT
GGATACGCAACAATTTTGTCCAAGCCCCTGGTGGGGAGTTCACCGTTAGCCCGAGAAATGCGCCAGGAGAAATCCT
GTGGTCGGCCCCATTGGGACCCGATCTGAACCCCTATTTGTCACATCTCGCTCGGATGTACAACGGGTATGCCGGCG
GATTTGAAGTGCAGGTGATTCTGGCTGGGAACGCGTTCACTGCTGGCAAAGTGATCTTTGCAGCGGTGCCTCCCAAC
TTCCCCACTGAAGGACTGTCTCCAAGCCAGGTCACAATGTTTCCACACATCGTGGTGGACGTACGGCAGCTAGAGCC
TGTCCTGATTCCCCTCCCTGATGTACGCAATAATTTCTACCACTACAATCAATCCAATGATCCGACCATTAAACTCATC
GCGATGTTGTACACCCCTCTGCGCGCTAACAATGCTGGAGACGACGTATTCACCGTGTCATGCAGAGTGCTCACCAG
ACCTTCACCAGACTTTGACTTTATCTTCTTAGTGCCCCCCACTGTTGAGAGCCGAACCAAGCCCTTTAGTGTCCCCGTA
CTCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 19C

Amino acid sequence of VP1 US96: GII.4/Dresden174/1997/DE_AY741811 (SEQ ID NO: 27)

MKMASNDANPSDGSTANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKVIFAAVPPNFPTEGLSPSQVTMFPHIIVDVRQLEPVLIP
LPDVRNNFYHYNQSNDSTIKLIAMLYTPLKANNAGDDVFTVSCRVLTRPSPDFDFIFLVPPTVESRTKPFTVPILTVEEMSN
SRFPIPLEKLYTGPSSAFVVQPQNGRCTTDGVLLGTTQLSAVNICTFRGDVTHIAGSHDYTMNLASQNWNNYDPTEEIPA
PLGTPDFVGKIQGMLTQTTREDGSTRAHKATVSTGSVHFTPKLGSVQYTTDTNNDFQTGQNTKFTPVGVIQDGNNHQN
EPQQWVLPNYSGRTGHNVHLAPAVAPTFPGEQLLFFRSTMPGCSGYPNMNLDCLLPQEWVQHFYQEAAPAQSDVALL
RFVNPDTGRVLFECKLHKSGYVTVAHTGPHDLVIPPNGYFRFDSWVNQFYTLAPMGNGAGRRRAL

Figure 19D

Amino acid sequence of VP1 FH02: GII.4/FarmingtonHills/2002/US_AY502023 (SEQ ID NO: 28)

MKMASNDANPSDGSTANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKIIFAAVPPNFPTEGLSPSQVTMFPHIIVDVRQLEPVLIP
LPDVRNNFYHYNQLNDPTIKLIAMLYTPLRANNAGEDVFTVSCRVLTRPSPDFDFIFLVPPTVESRTKPFTVPILTVEEMTN
SRFPIPLEKLFTGPSGAFVVQPQNGRCTTDGVLLGTTQLSPVNICTFRGDVTHIAGTHNYTMNLASQNWNNYDPTEEIPA
PLGTPDFVGRIQGMLTQTTRGDGSTRGHKATVSTGDVHFTPKLGSIQFNTDTNNDFETGQNTKFTPVGVVQDGNGTH
QNEPQQWVLPSYSGRTGHNVHLAPAVAPTFPGEQLLFFRSTMPGCSGYPNMNLDCLLPQEWVQHFYQEAAPAQSDV
ALLRFVNPDTGRVLFECKLHKSGYVTVAHTGQHDLVIPPNGYFRFDSWVNQFYTLAPMGNGTGRRRAL

Figure 19E

Amino acid sequence of VP1 Hnt04:GII.4/Hunter-NSW504D/2004/AU_DQ078814 (SEQ ID NO: 29)

MKMASNDATPSDGSTANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKIIFAAVPPNFPTEVLSPSQVTMFPHIIVDVRQLEPVLIP
LPDVRNNLYHYNQSNDPTIRLIAMLYTPLRANNAGDDVFTVSCRVLTRPSPDFDFIFLVPPTVESRTKPFSVPILTVEEMTN
SRFPIPLEKLFTGPSSAFVVQPQNGRCTTDGVLLGTTQLSPVNICTFRGDVTHIAGTQNYTMNLASQNWNNYDPTEEIPA
PLGTPDFVGRIQGVLTQTTRRDGSTRGHKATVSTGSVHFTPKLGSVQFSTDTSNDFETGQNTRFTPVGVVQDGSTTHQN
EPQQWVLPDYSGRDSHNVHLAPAVAPTFPGEQLLFFRSTMPGCSGYPNMNLDCLLPQEWVQHFYQESAPAQSDVALL
RFVNPDTGRVLFECKLHKSGYVTVAHTGQHDLVIPPNGYFRFDSWVNQFYTLAPMGNGAGRRRAL

Figure 19F

Amino acid sequence of VP1 2006b: GII.4/Shellharbour-NSW696T/2006/AU_EF684915 (SEQ ID NO: 30)

MKMASNDANPSDGSAANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKIIFAAVPPNFPTEGLSPSQVTMFPHIIVDVRQLEPVLIP
LPDVRNNFYHYNQSNDSTIKLIAMLYTPLRANNAGEDVFTVSCRVLTRPSPDFDFIFLVPPTVESRTKPFTVPILTVEEMTNS
RFPIPLEKLFTGPSGAFVVQPQNGRCTTDGVLLGTTQLSPVNICTFRGDVTHIAGSRNYTMNLASLKWNKYDPTEEIPAPL
GTPDFVGKIQGVLTQTTKGDGSTRGHKATIYTGSAPFTPKLGSVQFSTDTENDFETHQNTKFTPVGVTQDGSTTHRNEPQ
QWVLPSYSGRNVHNVHLAPAVAPTFPGEQLLFFRSTMPGCSGYPNMDLDCLLPQEWVQHFYQEAAPAQSDVALLRFV
NPDTGRVLFECKLHKSGYVTVAHTGQHDLVIPPNGYFRFDSWVNQFYTLAPMGNGTGRRRAL

Figure 19G

Amino acid sequence of VP1 NO09: GII.4/Orange-NSW001P/2008/AU_GQ845367 (SEQ ID NO: 31)

MKMASSDANPSDGSTANLVPEVNNEVMALEPVVGAAIAAPVAGQQNVIDPWIRNNFVQAPGGEFTVSPRNAPGEIL
WSAPLGPDMNPYLSHLARMYNGYAGGFEVQVILAGNAFTAGKIIFAAVPPNFPTEGLSPSQVTMFPHIIVDVRQLEPVLI
PLPDVRNNFYHYNQSNDPTIKLIAMLYTPLRANNAGDDVFTVSCRVLTRPSPDFDFIFLVPPTVESRTKPFSVPILTVEEMT
NSRFPIPLEKLFTGPSSAFVVQPQNGRCTTDGVLLGTTQLSPVNICTFRGDVTHIAGSRNYTMNLASQNWNSYDPTEEIPA
PLGTPDFVGKIQGVLTQTTRTDGSTRGHKATVYTGSADFSPKLGRVQFATDTDNDFDANQNTKFTPVGVIQDGNTAHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAL

Figure 20

Amino acid sequence of VP1 GII.5_Alberta_2013_CA_ALT54485 (SEQ ID NO: 17)

MKMASNDATPSNDGAAGLVPESNNEAMALEPVVGASLAAPVTGQTNIIDPWIRTNFVQAPNGEFTVSPRNSPGEILVN
LELGPELNPYLAHLARMYNGYAGGMEVQVLLAGNAFTAGKIIFAAVPPYFPVENLSPSQITMFPHVIIDVRTLEPVLLPMP
DVRSTLFHFNQKDEPKMRLVAMLYTPLRSNGSGDDVFTVSCRILTRPSPEFDFTYLVPPTVESKTKPFTLPVLTLGELSNSRF
PLSIDEMVTSPNESIVVQPQNGRVTLDGELLGTTQLQACNICSIRGKVTGQVPNEQHMWNLEITNLNGTQFDPTDDVPA
PLGVPDFAGEVFGVLSQRNRGESNPANRAHDAVVATYSDKYTPKLGLVQIGTWNTNDVENQPTKFTPIGLNEVANGHR
FEQWTLPRYSGALTLNMNLAPAVAPLFPGERLLFFRSYVPLKGGFGNPAIDCLVPQEWVQHFYQESAPSLGDVALVRYV
NPDTGRVLFEAKLHKGGFLTVSSTSTGPVVVPANGYFRFDSWVNQFYSLAPMGTGNGRRRFQ

Figure 21A

Amino acid sequence of VP1 GII.6_Ohio_2012_M9T020 (SEQ ID NO: 20)

MKMASNDAAPSNDGAANLVPEANNEVMALEPVVGASIAAPVVGQQNIIDPWIRENFVQAPQGEFTVSPRNSPGEMLL
NLELGPELNPYLSHLSRMYNGYAGGMQVQVVLAGNAFTAGKIIFAAVPPHFPVENINAAQITMCPHVIVDVRQLEPVLLP
LPDIRNRFFHYNQENTSRMRLVAMLYTPLRANSGEDVFTVSCRVLTRPAPDFEFTFLVPPTVESKTKPFSLPILTLGELSNSR
FPAPIDMLYTDPNEGIVVQPQNGRCTLDGTLQGTTQLVPTQICAFRGTLIGQTSRSPDSTDSAPRRRDHPLHVQLKNLDG
TQYDPTDEVPAVLGAIDFKGTVFGVASQRDVSGQQVGATRAHEVHINTTDPRYTPKLGSILMYSESDDFVTGQPVRFTPI
GMGDNDWHQWELPDYPGHLTLNMNLAPAVAPAFPGERILFFRSIVPSAGGYGSGQIDCLIPQEWVQHFYQEAAPSQS
AVALIRYVNPDTGRNIFEAKLHREGFITVANSGNNPIVVPPNGYFRFEAWVNQFYTLTPMGTGQGRRRDQ

Figure 21B

Nucleic acid sequence of human codon-optimized VP1 GII.6_Ohio_2012_M9T020 (SEQ ID NO: 21)

ATGAAGATGGCAAGCAACGACGCAGCTCCCTCCAATGATGGTGCCGCCAACCTGGTCCCCGAAGCTAATAATGAGG
TGATGGCGTTAGAGCCGGTGGTTGGCGCATCTATTGCAGCGCCTGTGGTCGGACAGCAGAACATCATTGATCCCTG
GATTCGCGAGAACTTCGTACAAGCTCCACAGGGGGAGTTCACAGTCTCCCCCCGGAACTCCCCGGGCGAGATGCTG
CTCAATCTGGAACTCGGCCCTGAACTAAACCCTTATCTGTCACACCTTTCACGGATGTACAATGGCTACGCAGGAGG
AATGCAAGTTCAGGTGGTCCTGGCCGGCAATGCTTTCACCGCGGGCAAAATCATCTTTGCGGCCGTTCCTCCACACT
TCCCTGTCGAAAATATCAACGCCGCCCAGATTACTATGTGCCCCCACGTGATTGTGGATGTGCGACAGTTAGAGCCA
GTTCTGCTGCCCCTGCCCGACATCAGAAACCGGTTCTTCCATTACAATCAAGAGAATACTTCACGGATGAGACTTGTT
GCGATGCTGTACACCCCTCTTCGTGCAAATTCCGGCGAAGACGTGTTCACTGTGTCTTGTCGAGTACTTACCCGACCC
GCCCCCGATTTCGAATTCACCTTCCTGGTTCCCCCTACTGTGGAGAGCAAGACAAAACCCTTCAGCCTCCCAATCTTA
ACACTCGGGGAGCTGTCTAATTCACGCTTCCCCGCACCTATTGATATGCTGTATACTGACCCCAACGAGGGGATAGT
GGTGCAGCCCCAAAATGGACGGTGTACTCTCGACGGCACGCTCCAGGGCACAACCCAACTGGTGCCAACCCAGATT
TGTGCATTCAGGGGCACTTTGATTGGGCAGACATCGAGATCTCCAGATTCTACTGATTCCGCGCCAAGGAGGAGGG
ACCACCCACTCCACGTTCAGTTAAAAAACCTGGACGGAACCCAGTACGACCCTACAGACGAGGTCCCCGCTGTCCTC
GGAGCCATCGACTTTAAAGGAACTGTATTTGGAGTGGCATCCCAAAGGGATGTCTCGGGGCAGCAGGTGGGAGCT
ACGAGAGCACATGAAGTCCACATTAACACCACAGACCCAAGATATACCCCAAAACTAGGGTCAATTTTAATGTATTC
GGAATCAGACGATTTTGTTACAGGTCAGCCCGTGCGGTTTACCCCGATCGGAATGGGGGACAACGATTGGCACCAG
TGGGAATTGCCCGATTACCCTGGACACCTCACCTTGAATATGAATCTGGCCCCAGCCGTCGCGCCCGCCTTCCCCGGT
GAGCGGATCCTCTTTTTTAGAAGCATAGTGCCCTCCGCAGGTGGGTATGGATCAGGGCAGATTGATTGCCTGATCCC
CCAAGAATGGGTACAGCATTTCTACCAGGAAGCAGCCCCTAGCCAGTCCGCAGTAGCACTGATCAGATATGTTAATC
CTGATACGGGAAGGAACATCTTCGAAGCAAAACTGCACCGTGAGGGCTTCATTACCGTCGCCAACAGTGGTAATAA
CCCTATTGTGGTGCCTCCTAATGGATACTTCAGGTTTGAGGCATGGGTGAATCAGTTTTATACTCTGACTCCCATGGG
GACAGGCCAGGGGCGACGCCGGGATCAGTGA

Figure 22

Amino acid sequence of VP1 GII.7_Musa_2010_AII73774 (SEQ ID NO: 18)

MKMASNDAAPSNDGAAGLVPEINNEVMPLEPVAGASLATPVVGQQNIIDPWIRNNFVQAPAGEFTVSPRNSPGEILLD
LELGPELNPYLAHLARMYNGHAGGMEVQIVLAGNAFTAGKIIFAAIPPGFPYENLSPSQITMCPHVIIDVRQLEPVLLPMP
DIRNNFFHYNQGNDPKLRLIAMLYTPLRANNSGDDVFTVSCRVLTKPSPDFEFTFLVPPTVESKTKQFTLPILKISEMTNSRF
PVPVEMMYTARNENQVVQPQNGRVTLDGELLGTTPLLAVNICKFKGEVIAKNGDVRSYRMDMEITNTDGTPIDPTEDT
PGPIGSPDFQGILFGVASQRNKNEQNPATRAHEANINTGGDQYAPKLAQVKFFSESQDFEVHQPTVFTPVGVAGDTSHP
FRQWVLPRYGGHLTNNTHLAPAVAPLFPGEQILFFRSQIPSSGGHELGYMDCLVPQEWVQHFYQEAATAQSEVALIRFIN
PDTGRVLFEAKLHKQGFITVAHTGDNPIVMPPNGYFRFEAWVNQFYSLAPVGTGNGRRRIQ

Figure 23A

Amino acid sequence of VP1 GII.12_HS206_2010_USA_AEI29586 (SEQ ID NO: 19)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFTLPILTIGELTNS
RFPVPIDELYTSPNESLVVQPQNGRCALDGELQGTTQLLPTAICSFRGRINQKVSGENHVWNMQVTNIDGTPFDPTEDV
PAPLGTPDFSGKLFGVLSQRDHDNACRSHDAVIATNSAKFTPKLGAIQIGTWEQDDVHINQPTKFTPVGLFESEGFNQW
TLPNYSGALTLNMGLAPPVAPTFPGEQILFFRSHIPLKGGVADPVIDCLLPQEWIQHLYQESAPSQTDVALIRFTNPDTGRV
LFEAKLHRSGYITVANTGSRPIVVPANGYFRFDSWVNQFYSLAPMGTGNGRRRVQ

Figure 23B

Human codon-optimized VP1 GII.12_HS206_2010_USA_AEI29586 (SEQ ID NO: 87)

ATGAAGATGGCGTCTAATGATGCTGCTCCTTCCAATGATGGCGCAGCCGGCCTGGTCCCTGAAGTGAATAACGAGA
CTATGGCTCTCGAACCCGTGGCCGGAGCCTCAATTGCCGCCCCCCTCACTGGCCAGAACAACGTGATTGATCCCTGG
ATCAGACTGAACTTCGTTCAGGCTCCTAATGGGGAGTTCACCGTGTCCCCGAGAAACTCCCCCGGCGAAGTGTTATT
GAATTTGGAATTAGGACCAGAACTCAACCCCTATCTGGCACATCTGTCTCGGATGTACAACGGCTATGCGGGCGGA
GTGGAGGTGCAAGTTCTTCTCGCTGGTAATGCATTCACAGCAGGAAAATTAGTATTTGCAGCGGTTCCACCCCATTTT
CCACTTGAAAACATAAGCCCAGGCCAGATCACCATGTTCCCTCACGTGATAATCGACGTGCGGACATTAGAGCCCGT
GCTGCTACCCCTGCCCGACGTGAGGAACAATTTCTTTCACTACAATCAGCAAAATGAACCAAGAATGCGCCTGGTCG
CCATGCTCTATACTCCTTTAAGAAGTAATGGCAGTGGGGATGACGTGTTTACTGTTAGCTGTCGGGTGCTCACCCGA
CCTTCCCCAGATTTCGACTTCAATTATCTGGTCCCCCCCACGGTAGAGTCCAAAACAAAGCCTTTCACTCTTCCAATCC
TTACAATTGGCGAACTGACCAACTCACGCTTTCCAGTGCCTATTGATGAGCTGTACACAAGTCCAAATGAATCCCTTG
TCGTTCAGCCACAGAATGGGCGCTGCGCGCTTGACGGTGAGCTCCAGGGCACAACACAACTGTTGCCAACCGCTAT
ATGCTCTTTCAGGGGGCGTATTAATCAGAAGGTCTCCGGGGAGAACCACGTGTGGAACATGCAAGTGACGAATATC
GACGGGACACCTTTCGATCCAACAGAGGATGTCCCAGCGCCTCTAGGTACCCCTGACTTCTCAGGCAAGTTGTTCGG
CGTCCTTTCCCAGCGCGACCATGATAATGCTTGCCGGAGCCACGATGCCGTCATTGCCACCAACTCAGCCAAATTCAC
CCCAAAACTTGGAGCGATACAGATCGGAACTTGGGAACAAGACGACGTCCATATCAACCAACCAACAAAGTTTACCC
CTGTTGGCCTTTTCGAAAGCGAAGGCTTTAACCAGTGGACACTTCCCAATTACAGCGGGGCTCTCACTCTTAATATGG
GACTCGCACCACCCGTCGCTCCAACGTTTCCTGGTGAGCAGATTTTGTTTTTCCGCAGTCATATTCCACTGAAGGGTG
GAGTTGCTGATCCCGTGATAGACTGCCTCCTCCCTCAGGAATGGATTCAGCACTTGTATCAGGAGTCCGCTCCCTCGC
AGACCGATGTGGCCCTGATACGCTTCACAAACCCCGATACCGGAAGAGTGTTGTTTGAAGCTAAACTTCATCGCTCC

Figure 23B (cont)

GGTTACATCACAGTAGCCAACACGGGTTCCAGGCCAATCGTAGTTCCGGCAAACGGATACTTTCGATTCGACAGTTG
GGTCAATCAGTTCTACAGCCTGGCTCCAATGGGAACAGGAAATGGGAGGAGGCGTGTGCAGTAA

Figure 24A

Amino acid sequence of VP1 GII.13_VA173_2010_H9AWU4 (SEQ ID NO: 22)

MKMASNDAAPSNDGAASLVPEAINETMPLEPVAGASIAAPVAGQTNIIDPWIRTNFVQAPNGEFTVSPRNS
PGEILLNLELGPDLNPYLAHLSRMYNGYAGGVEVQVLLAGNAFTAGKILFAAIPPNFPVDMISPAQITMLPHLI
VDVRTLEPIMIPLPDVRNVFYHFNNQPQPRMRLVAMLYTPLRSNGSGDDVFTVSCRVLTRPTPDFEFIYLVPP
SVESKTKPFTLPILTISELTNSRFPISIEQLYTAPNENNVVQCQNGRCTLDGELQGTTQLLSSAVCSYRGRTVANS
GDNWDQNVLQLTYPSGASYDPTDEVPAPLGTQDFSGILYGVLTQDNVRENTGEAKNAKGVYISTTSGKFTPK
IGSIGLHSITEDVRPNQQSRFTPVGVAQNENTPFQQWVLPHYAGALALNTNLAPAVAPTFPGEQLLFFRSRVP
CVQGLQGQDAFIDCLLPQEWVNHFYQEAAPSQADVALIRYVNPDTGRTLFEAKLHRSGFITVSHTGAYPLVV
PPNGHFRFDSWVNQFYSLAPMGTGNGRRRVQ

Figure 24B

Nucleic acid sequence of human codon-optimized VP1 GII.13_VA173_2010_H9AWU4 (SEQ ID NO: 23)

ATGAAAATGGCTTCTAATGATGCCGCGCCCAGCAATGATGGTGCCGCCAGCCTTGTGCCCGAAGCAATTAACGAGA
CAATGCCCTTGGAGCCAGTCGCCGGGGCTTCTATTGCGGCCCCAGTTGCTGGACAGACGAATATCATCGATCCTTGG
ATACGGACTAATTTTGTTCAAGCTCCTAACGGAGAGTTCACTGTCTCCCCCCGTAATAGTCCTGGCGAGATCCTGTTG
AACCTCGAGTTGGGGCCAGATCTCAATCCTTACCTGGCTCATCTGTCGAGAATGTACAACGGGTACGCGGGGGGGG
TTGAGGTGCAGGTCTTACTGGCAGGTAACGCATTCACAGCAGGCAAGATTCTGTTTGCGGCCATCCCTCCTAATTTTC
CAGTGGATATGATATCTCCAGCACAGATTACAATGCTGCCCCATTTGATAGTGGATGTGCGGACACTTGAACCTATC
ATGATCCCTTTGCCCGATGTCCGAAATGTGTTTTATCATTTCAACAACCAGCCGCAGCCAAGAATGCGTCTCGTCGCG
ATGCTGTACACCCCGTTGCGGTCCAACGGCTCTGGCGATGATGTTTTCACAGTGTCGTGTCGAGTGTTAACCCGCCCT
ACCCCAGATTTTGAGTTTATATATCTAGTTCCCCCTTCTGTGGAAAGCAAGACTAAACCCTTTACTCTTCCCATTCTGA
CTATATCCGAGCTTACCAACTCCCGGTTCCCCATCTCAATCGAGCAACTGTACACTGCACCCAACGAGAACAACGTAG
TCCAGTGCCAGAACGGGAGATGTACCCTGGACGGGGAGCTCCAAGGGACCACGCAACTGTTAAGTTCAGCCGTTTG
CAGTTACAGAGGCAGGACTGTGGCGAACTCTGGTGATAACTGGGATCAAAATGTGTTGCAGCTGACTTACCCATCC
GGCGCAAGCTACGATCCAACAGATGAGGTGCCAGCGCCCCTTGGCACACAGGATTTCTCAGGAATTCTATACGGGG
TGCTTACTCAGGATAATGTGCGAGAAAATACTGGCGAGGCCAAGAATGCTAAAGGAGTGTATATAAGCACGACAAG
CGGTAAGTTTACCCCCAAAATTGGCAGTATTGGGCTCCACAGCATTACTGAGGACGTCCGCCCAAACCAGCAGTCTC
GTTTCACTCCCGTGGGGGTGGCACAGAACGAGAACACACCTTTCCAGCAGTGGGTCTTGCCCCATTATGCAGGTGCT
TTGGCGCTCAATACAAATCTGGCACCCGCCGTAGCGCCGACATTTCCTGGGGAGCAATTGCTGTTCTTTAGAAGCCG
CGTCCCGTGTGTTCAGGGCTTGCAGGGCCAGGACGCGTTCATTGATTGCCTCTTGCCCCAGGAATGGGTCAACCACT
TTTATCAGGAGGCAGCGCCCTCTCAAGCAGATGTGGCCCTGATAAGATATGTGAATCCCGACACAGGACGGACTTT
GTTTGAGGCAAAACTCCACCGGTCAGGATTCATTACTGTGAGTCACACAGGAGCCTATCCCCTTGTGGTTCCACCTAA
TGGCCACTTCAGGTTCGACTCTTGGGTCAATCAGTTTTATTCGCTGGCACCAATGGGTACCGGGAATGGTCGCCGTC
GGGTGCAATGA

Figure 25

Amino acid sequence of VP1 GII.14_Saga_2008_JPN_ADE28701 (SEQ ID NO: 32)

MKMASNDATPSDDGAAGLVPEINNEVMALEPVAGASIAAPVVGQQNIIDPWIRNNFVQAPAGEFTVSPRNSPGELLLD
LELGPELNPYLAHLARMYNGHAGGMEVQIVLAGNAFTAGKILFAAIPPSFPYENLSPAQLTMCPHVIVDVRQLEPVLLPM
PDIRNVFYHYNQNNSPKLRLVAMLYTPLRANNSGDDVFTVSCRVLTRPSPDFQFTFLVPPTVESKTKNFTLPVLRVSEMTN
SRFPVVLDQMYTSRNENIIVQPQNGRCTTDGELLGTTILQSVSICNFKGTMQAKLNEEPRYQLQLTNLDGSPIDPTDDMP
APLGTPDFQAMLYGVASQRSSIDNATRAHDAQIDTAGDTFAPKIGQVRFKSSSNDFDLHDPTKFTPIGVNVDDQHPFRQ
WSLPNYGGHLALNNHLAPAVTPLFPGEQILFFRSYIPSAGGHTDGAMDCLLPQEWVEHFYQEAAPSQSDIALVRFINPDT
GRVLFEAKLHKQGFLTIAASGDHPIVMPTNGYFRFEAWVNPFYTLAPVGTGSGRRRIQ

Figure 26A

Amino acid sequence of VP1 GII.17_Kawa_2014_A0A077KVU6 (SEQ ID NO: 24)

MKMASNDAAPSNDGAAGLVPEGNNETLPLEPVAGAAIAAPVTGQNNIIDPWIRTNFVQAPNGEFTVSPRNS
PGEILLNLELGPDLNPYLAHLSRMYNGYAGGVEVQVLLAGNAFTAGKILFAAVPPNFPVEFLSPAQITMLPHLI
VDVRTLEPIMIPLPDVRNTFFHYNNQPNSRMRLVAMLYTPLRSNGSGDDVFTVSCRVLTRPTPDFEFTYLVPP
SVESKTKPFSLPILTLSELTNSRFPVPIDSLFTAQNNVLQVQCQNGRCTLDGELQGTTQLLPSGICAFRGRVTAE
TDHRDKWHMQLQNLNGTTYDPTDDVPAPLGTPDFKGVVFGVASQRNVGNDAPGSTRAHEAVISTYSPQFV
PKLGSVNFRSNDNDFQLQPTKFTPVGINDDGDHPFRQWELPDYSGLLTLNMNLAPPVAPNFPGEQLLFFRSF
VPCSGGYNQGIVDCLIPQEWIQHFYQESAPSQSDVALIRYVNPDTGRTLFEAKLHRSGYITVAHSGDYPLVVPA
NGYFRFDSWVNQFYSLAPMGTGNGRRRAQ

Figure 26B

Human codon-optimized VP1 GII.17_Kawa_2014_A0A077KVU6 (SEQ ID NO: 25)

ATGAAAATGGCATCTAACGACGCAGCCCCCTCAAACGATGGCGCTGCTGGACTCGTGCCGGAGGGGAATAATGAG
ACACTTCCACTAGAGCCGGTTGCAGGCGCCGCTATAGCTGCCCCAGTGACAGGGCAGAATAATATTATAGACCCTTG
GATTCGGACAAACTTCGTGCAGGCACCCAACGGCGAGTTTACAGTATCCCCCCGGAACTCCCCAGGTGAGATACTCC
TGAATCTTGAGCTCGGCCCTGACCTCAATCCATATCTGGCTCATCTGAGCCGCATGTACAATGGTTACGCTGGGGGG
GTCGAAGTGCAGGTCCTCCTGGCCGGAAACGCCTTTACCGCTGGCAAAATTCTGTTTGCCGCCGTTCCACCAAACTTT
CCAGTCGAATTCCTCTCTCCCGCGCAAATAACCATGCTGCCACATTTGATCGTTGACGTGCGGACCCTGGAGCCAATA
ATGATTCCCCTGCCGGATGTGCGTAACACCTTTTTCCATTATAACAATCAGCCAAACTCTCGGATGAGACTTGTTGCT
ATGCTGTACACCCCCCTGCGGAGCAACGGCAGTGGCGATGATGTGTTTACCGTGAGTTGCAGAGTCCTGACGCGCC
CAACCCCGGACTTCGAGTTCACCTACCTGGTGCCCCCTTCTGTGGAATCTAAGACCAAACCGTTTTCACTGCCAATCT
TAACTCTCTCCGAACTGACTAACAGCCGGTTTCCAGTACCCATAGATTCTCTTTTTACCGCTCAAAACAACGTACTCCA
AGTCCAGTGCCAGAACGGCCGCTGTACGCTTGATGGTGAGTTGCAGGGGACAACACAGCTACTCCCCAGTGGCATC
TGTGCATTCCGGGGCCGCGTGACCGCTGAGACAGACCATCGTGACAAATGGCACATGCAACTCCAAAACTTAAACG
GGACCACCTACGACCCAACCGACGACGTCCCTGCTCCGCTAGGGACTCCTGACTTTAAGGGGGTGGTGTTCGGAGT
GGCCTCTCAGCGGAATGTTGGGAATGACGCCCCCGGCTCTACCCGAGCTCACGAGGCCGTTATCTCAACATATAGCC
CCCAATTTGTGCCCAAGCTCGGATCCGTTAATTTTCGTAGTAACGACAACGACTTCCAACTGCAACCAACGAAGTTTA
CGCCAGTGGGGATTAATGATGATGGAGACCATCCTTTCCGCCAATGGGAACTACCAGATTATTCTGGGCTGCTCACC
CTCAATATGAACCTCGCCCCACCCGTGGCCCCTAATTTCCCCGGTGAGCAGCTGCTGTTTTTTCGGAGCTTTGTGCCA
TGCAGTGGCGGATATAATCAAGGCATCGTAGACTGCTTGATTCCCCAAGAGTGGATACAACATTTTTACCAGGAAAG

Figure 26B (cont)

TGCGCCCTCCCAGTCCGATGTGGCCCTGATACGGTACGTTAACCCCGATACCGGAAGAACATTATTCGAAGCGAAAT
TGCACAGATCAGGGTACATTACCGTTGCACATTCCGGCGATTATCCCCTGGTGGTTCCCGCCAACGGTTACTTTAGGT
TCGATAGTTGGGTCAACCAGTTCTATTCACTAGCCCCAATGGGCACCGGTAACGGCAGACGCCGGGCTCAGTAG

Figure 27

Amino acid sequence of VP1 GII.21_Sali_2011_USA_AFC89665 (SEQ ID NO: 26)

MKMASNDAAPSNDGATGLVPEINTETLPLEPVAGAAIAAPVTGQNNIIDPWIRNNFVQAPNGEFTVSPRNSPGEILMNL
ELGPDLNPYLAHLSRMYNGYAGGVEVQVLLAGNAFTAGKILFAAVPPNFPVDMLSPAQITMLPHLIVDVRTLEPIMIPLP
DVRNVFYHFNNQPAPRMRLVAMLYTPLRSNGSGDDVFTVSCRVLTRPTPDFEFTYLVPPSVESKTKPFTLPILTIGELTNSR
FPAPIDQLYTSPNADVVVQPQNGRCTLDGELQGTTQLLTTAICSYRGMTSNPTSDYWDDHLLHLVHPNGATYDPTEDVP
APFGTQDFRGILYGMLTQNPRTSGDEAANSHGIYISSTSEKFTPKLGTIGLHQVQGDIASNQQSKFTPVGIAVNGNTPFRQ
WELPNYSGALTLNTNLAPAVGPNFPGEQILFFRSNVPSVQGGQPIEIDCLIPQEWVSHFYQESAPSQSDVALVRYVNPDT
GRTIFEAKLHRQGFITIAATGSNPVVVPPNGYFRFDSWVNQFYALAPMGTGNGRRRVQ

Figure 28A

Amino acid sequence of VP1_GI.3_Lil08_Q84S (SEQ ID NO:98)

MMMASKDAPTNMDGTSGAGQLVPEVSTAEPISMEPVAGAATAAATAGQVNMIDPWIMSNYVQAPQGEFTISPNNT
PGDILFDLSLGPHLNPFLSHLAQMYNGWVGNMKVRVLLAGNAFTAGKIIISCVPPGFAAQNVSIAQATMFPHVIADVRV
LEPIEVPLEDVRNVLFHNNDSTPTMRLICMLYTPLRASGSSSGTDPFVIAGRVLTCPSPDFNFLFLVPPNVEQKTKPFSVPNL
PLNVLSNSRVPSLIKSMMVSQDHGQMVQFQNGRVTLDGQLQGTTPTSASQLCKIRGTVYHATGGQGLNLTEIDGTPYH
AFESPAPIGFPDLGECDWHINASPANAFTDGSIIHRIDVAQDSTFAPHLGTIHYTNADYNANVGLICSLEWLSPPSGGAPK
VNPWAIPRYGSTLTEAAQLAPPIYPPGFGEAIVFFMSDFPIANGSDGLSVPCTIPQEFVTHFVNEQAPTRGEAALLHYVDP
DTHRNLGEFKLYPEGFMTCVPNSSGSGPQTLPINGVFTFISWVSRFYQLKPVGTTGPVRRLGIRRS

Figure 28B

Nucleic acid sequence of human codon optimized VP1_GI.3_Lil08_Q84S (SEQ ID NO:167)

ATGATGATGGCTTCCAAGGATGCTCCCACAAACATGGATGGAACAAGCGGCGCGGGGCAACTTGTGCCGGAGGTG
TCCACGGCGGAACCCATTTCCATGGAACCTGTGGCCGGCGCAGCCACTGCTGCCGCCACCGCAGGACAGGTAAACA
TGATCGACCCCTGGATCATGTCAAATTACGTTCAGGCTCCACAGGGGGAGTTTACCATAAGCCCAAACAACACCCCG
GGTGACATCTTGTTTGACCTGAGCCTAGGACCACACTTGAATCCGTTTCTGAGTCACTTGGCTCAGATGTATAATGGA
TGGGTTGGAAACATGAAGGTGCGCGTGCTCCTGGCGGGCAATGCATTCACAGCCGGGAAGATTATTATCTCTTGCG
TGCCACCTGGATTTGCAGCCCAGAACGTGTCTATCGCACAGGCAACCATGTTTCCGCATGTCATCGCAGATGTGCGC
GTGCTAGAGCCCATCGAGGTGCCCCTTGAGGACGTGCGCAACGTCCTATTCCATAACAATGATAGCACCCCCACCAT
GCGCTTGATATGTATGTTATATACTCCCCTCCGCGCCAGTGGGTCCAGCTCCGGGACCGATCCTTTTGTGATTGCTGG
GCGGGTGTTGACTTGTCCTAGCCCTGACTTCAACTTCCTTTTTCTGGTGCCTCCAAATGTAGAACAGAAAACAAAGCC
ATTCAGCGTGCCAAACCTGCCCCTTAACGTGCTGTCGAATTCCCGAGTGCCTTCCCTTATTAAGTCCATGATGGTATC
TCAGGATCACGGTCAAATGGTGCAGTTTCAGAACGGCCGAGTGACGTTAGACGGGCAGCTGCAGGGCACAACCCC
AACCAGTGCCAGTCAGCTGTGTAAGATCAGAGGCACCGTCTACCACGCAACTGGCGGACAGGGGCTGAATCTTACT
GAGATCGATGGTACCCCCTACCATGCATTCGAGTCACCTGCACCTATTGGATTTCCCGATCTTGGGGAGTGTGATTG
GCATATCAATGCTTCACCTGCCAACGCTTTCACAGACGGGTCTATTATTCATCGCATTGACGTAGCACAGGATAGCAC

Figure 28B (cont)

ATTTGCCCCGCACCTGGGTACCATCCACTATACGAACGCAGATTACAACGCAAACGTGGGTCTTATCTGTAGCCTAG
AGTGGCTATCTCCGCCAAGCGGTGGGGCCCCTAAAGTTAACCCATGGGCTATTCCTCGGTACGGGTCTACGCTGACT
GAGGCCGCTCAGCTGGCACCCCCCATATATCCACCAGGATTCGGGGAAGCCATTGTTTTCTTTATGTCCGATTTTCCG
ATAGCCAACGGTTCAGATGGCCTTAGTGTCCCTTGCACGATTCCACAGGAATTTGTGACACACTTCGTAAACGAGCA
GGCTCCTACTCGGGGCGAGGCTGCCTTGTTGCATTACGTAGACCCCGATACCCATAGAAACCTGGGCGAATTCAAAC
TCTACCCTGAAGGTTTCATGACCTGCGTACCTAACTCCTCCGGCAGTGGCCCTCAAACCTTGCCGATCAACGGCGTGT
TCACGTTTATCAGCTGGGTTTCACGGTTTTACCAACTCAAGCCCGTCGGAACAACTGGGCCAGTTCGGAGGCTCGGG
ATCAGACGGAGCTAG

Figure 28C

Amino acid sequence of VP1_GI.3_Lil08_S94L (SEQ ID NO:8)

MMMASKDAPTNMDGTSGAGQLVPEVSTAEPISMEPVAGAATAAATAGQVNMIDPWIMSNYVQAPQGEFTISPNNT
PGDILFDLQLGPHLNPFLLHLAQMYNGWVGNMKVRVLLAGNAFTAGKIIISCVPPGFAAQNVSIAQATMFPHVIADVRV
LEPIEVPLEDVRNVLFHNNDSTPTMRLICMLYTPLRASGSSSGTDPFVIAGRVLTCPSPDFNFLFLVPPNVEQKTKPFSVPNL
PLNVLSNSRVPSLIKSMMVSQDHGQMVQFQNGRVTLDGQLQGTTPTSASQLCKIRGTVYHATGGQGLNLTEIDGTPYH
AFESPAPIGFPDLGECDWHINASPANAFTDGSIIHRIDVAQQDSTFAPHLGTIHYTNADYNANVGLICSLEWLSPPSGGAPK
VNPWAIPRYGSTLTEAAQLAPPIYPPGFGEAIVFFMSDFPIANGSDGLSVPCTIPQEFVTHFVNEQAPTRGEAALLHYVDP
DTHRNLGEFKLYPEGFMTCVPNSSGSGPQTLPINGVFTFISWVSRFYQLKPVGTTGPVRRLGIRRS

Figure 28D

Nucleic acid sequence of human codon optimized VP1_GI.3_Lil08_S94L (SEQ ID NO:9)

ATGATGATGGCTTCCAAGGATGCTCCCACAAACATGGATGGAACAAGCGGCGCGGGGCAACTTGTGCCGGAGGTG
TCCACGGCGGAACCCATTTCCATGGAACCTGTGGCCGGCGCAGCCACTGCTGCCGCCACCGCAGGACAGGTAAACA
TGATCGACCCCTGGATCATGTCAAATTACGTTCAGGCTCCACAGGGGGAGTTTACCATAAGCCCAAACAACACCCCG
GGTGACATCTTGTTTGACCTGCAGCTAGGACCACACTTGAATCCGTTTCTGCTCCACTTGGCTCAGATGTATAATGGA
TGGGTTGGAAACATGAAGGTGCGCGTGCTCCTGGCGGGCAATGCATTCACAGCCGGGAAGATTATTATCTCTTGCG
TGCCACCTGGATTTGCAGCCCAGAACGTGTCTATCGCACAGGCAACCATGTTTCCGCATGTCATCGCAGATGTGCGC
GTGCTAGAGCCCATCGAGGTGCCCCTTGAGGACGTGCGCAACGTCCTATTCCATAACAATGATAGCACCCCCACCAT
GCGCTTGATATGTATGTTATATACTCCCCTCCGCGCCAGTGGGTCCAGCTCCGGGACCGATCCTTTTGTGATTGCTGG
GCGGGTGTTGACTTGTCCTAGCCCTGACTTCAACTTCCTTTTTCTGGTGCCTCCAAATGTAGAACAGAAAACAAAGCC
ATTCAGCGTGCCAAACCTGCCCCTTAACGTGCTGTCGAATTCCCGAGTGCCTTCCCTTATTAAGTCCATGATGGTATC
TCAGGATCACGGTCAAATGGTGCAGTTTCAGAACGGCCGAGTGACGTTAGACGGGCAGCTGCAGGGCACAACCCC
AACCAGTGCCAGTCAGCTGTGTAAGATCAGAGGCACCGTCTACCACGCAACTGGCGGACAGGGGCTGAATCTTACT
GAGATCGATGGTACCCCCTACCATGCATTCGAGTCACCTGCACCTATTGGATTTCCCGATCTTGGGGAGTGTGATTG
GCATATCAATGCTTCACCTGCCAACGCTTTCACAGACGGGTCTATTATTCATCGCATTGACGTAGCACAGGATAGCAC
ATTTGCCCCGCACCTGGGTACCATCCACTATACGAACGCAGATTACAACGCAAACGTGGGTCTTATCTGTAGCCTAG
AGTGGCTATCTCCGCCAAGCGGTGGGGCCCCTAAAGTTAACCCATGGGCTATTCCTCGGTACGGGTCTACGCTGACT
GAGGCCGCTCAGCTGGCACCCCCCATATATCCACCAGGATTCGGGGAAGCCATTGTTTTCTTTATGTCCGATTTTCCG
ATAGCCAACGGTTCAGATGGCCTTAGTGTCCCTTGCACGATTCCACAGGAATTTGTGACACACTTCGTAAACGAGCA
GGCTCCTACTCGGGGCGAGGCTGCCTTGTTGCATTACGTAGACCCCGATACCCATAGAAACCTGGGCGAATTCAAAC
TCTACCCTGAAGGTTTCATGACCTGCGTACCTAACTCCTCCGGCAGTGGCCCTCAAACCTTGCCGATCAACGGCGTGT

Figure 28D (cont)

TCACGTTTATCAGCTGGGTTTCACGGTTTTACCAACTCAAGCCCGTCGGAACAACTGGGCCAGTTCGGAGGCTCGGG
ATCAGACGGAGCTAG

Figure 28E

Amino acid sequence of VP1_GI.3_Lil08_Q84S+S94L (SEQ ID NO:10)

MMMASKDAPTNMDGTSGAGQLVPEVSTAEPISMEPVAGAATAAATAGQVNMIDPWIMSNYVQAPQGEFTISPNNT
PGDILFDLSLGPHLNPFLLHLAQMYNGWVGNMKVRVLLAGNAFTAGKIIISCVPPGFAAQNVSIAQATMFPHVIADVRVL
EPIEVPLEDVRNVLFHNNDSTPTMRLICMLYTPLRASGSSSGTDPFVIAGRVLTCPSPDFNFLFLVPPNVEQKTKPFSVPNL
PLNVLSNSRVPSLIKSMMVSQDHGQMVQFQNGRVTLDGQLQGTTPTSASQLCKIRGTVYHATGGQGLNLTEIDGTPYH
AFESPAPIGFPDLGECDWHINASPANAFTDGSIIHRIDVAQDSTFAPHLGTIHYTNADYNANVGLICSLEWLSPPSGGAPK
VNPWAIPRYGSTLTEAAQLAPPIYPPGFGEAIVFFMSDFPIANGSDGLSVPCTIPQEFVTHFVNEQAPTRGEAALLHYVDP
DTHRNLGEFKLYPEGFMTCVPNSSGSGPQTLPINGVFTFISWVSRFYQLKPVGTTGPVRRLGIRRS

Figure 28F

Nucleic acid sequence of human codon optimized VP1_GI.3_Lil08_Q84S+S94L (SEQ ID NO:11)

ATGATGATGGCTTCCAAGGATGCTCCCACAAACATGGATGGAACAAGCGGCGCGGGGCAACTTGTGCCGGAGGTG
TCCACGGCGGAACCCATTTCCATGGAACCTGTGGCCGGCGCAGCCACTGCTGCCGCCACCGCAGGACAGGTAAACA
TGATCGACCCCTGGATCATGTCAAATTACGTTCAGGCTCCACAGGGGGAGTTTACCATAAGCCCAAACAACACCCCG
GGTGACATCTTGTTTGACCTGAGCCTAGGACCACACTTGAATCCGTTTCTGCTCCACTTGGCTCAGATGTATAATGGA
TGGGTTGGAAACATGAAGGTGCGCGTGCTCCTGGCGGGCAATGCATTCACAGCCGGGAAGATTATTATCTCTTGCG
TGCCACCTGGATTTGCAGCCCAGAACGTGTCTATCGCACAGGCAACCATGTTTCCGCATGTCATCGCAGATGTGCGC
GTGCTAGAGCCCATCGAGGTGCCCCTTGAGGACGTGCGCAACGTCCTATTCCATAACAATGATAGCACCCCCACCAT
GCGCTTGATATGTATGTTATATACTCCCCTCCGCGCCAGTGGGTCCAGCTCCGGGACCGATCCTTTTGTGATTGCTGG
GCGGGTGTTGACTTGTCCTAGCCCTGACTTCAACTTCCTTTTTCTGGTGCCTCCAAATGTAGAACAGAAAACAAAGCC
ATTCAGCGTGCCAAACCTGCCCCTTAACGTGCTGTCGAATTCCCGAGTGCCTTCCCTTATTAAGTCCATGATGGTATC
TCAGGATCACGGTCAAATGGTGCAGTTTCAGAACGGCCGAGTGACGTTAGACGGGCAGCTGCAGGGCACAACCCC
AACCAGTGCCAGTCAGCTGTGTAAGATCAGAGGCACCGTCTACCACGCAACTGGCGGACAGGGGCTGAATCTTACT
GAGATCGATGGTACCCCCTACCATGCATTCGAGTCACCTGCACCTATTGGATTTCCCGATCTTGGGGAGTGTGATTG
GCATATCAATGCTTCACCTGCCAACGCTTTCACAGACGGGTCTATTATTCATCGCATTGACGTAGCACAGGATAGCAC
ATTTGCCCCGCACCTGGGTACCATCCACTATACGAACGCAGATTACAACGCAAACGTGGGTCTTATCTGTAGCCTAG
AGTGGCTATCTCCGCCAAGCGGTGGGGCCCCTAAAGTTAACCCATGGGCTATTCCTCGGTACGGGTCTACGCTGACT
GAGGCCGCTCAGCTGGCACCCCCCATATATCCACCAGGATTCGGGGAAGCCATTGTTTTCTTTATGTCCGATTTTCCG
ATAGCCAACGGTTCAGATGGCCTTAGTGTCCCTTGCACGATTCCACAGGAATTTGTGACACACTTCGTAAACGAGCA
GGCTCCTACTCGGGGCGAGGCTGCCTTGTTGCATTACGTAGACCCCGATACCCATAGAAACCTGGGCGAATTCAAAC
TCTACCCTGAAGGTTTCATGACCTGCGTACCTAACTCCTCCGGCAGTGGCCCTCAAACCTTGCCGATCAACGGCGTGT
TCACGTTTATCAGCTGGGTTTCACGGTTTTACCAACTCAAGCCCGTCGGAACAACTGGGCCAGTTCGGAGGCTCGGG
ATCAGACGGAGCTAG

Figure 28G

Amino acid sequence of VP1_GI.3_Lil08_A43V+S94L (SEQ ID NO:170)

MMMASKDAPTNMDGTSGAGQLVPEVSTAEPISMEPVAGAATAVATAGQVNMIDPWIMSNYVQAPQGE
FTISPNNTPGDILFDLQLGPHLNPFLLHLAQMYNGWVGNMKVRVLLAGNAFTAGKIIISCVPPGFAAQNVSIA
QATMFPHVIADVRVLEPIEVPLEDVRNVLFHNNDSTPTMRLICMLYTPLRASGSSSGTDPFVIAGRVLTCPSPD
FNFLFLVPPNVEQKTKPFSVPNLPLNVLSNSRVPSLIKSMMVSQDHGQMVQFQNGRVTLDGQLQGTTPTSA
SQLCKIRGTVYHATGGQGLNLTEIDGTPYHAFESPAPIGFPDLGECDWHINASPANAFTDGSIIHRIDVAQDST
FAPHLGTIHYTNADYNANVGLICSLEWLSPPSGGAPKVNPWAIPRYGSTLTEAAQLAPPIYPPGFGEAIVFFMS
DFPIANGSDGLSVPCTIPQEFVTHFVNEQAPTRGEAALLHYVDPDTHRNLGEFKLYPEGFMTCVPNSSGSGPQ
TLPINGVFTFISWVSRFYQLKPVGTTGPVRRLGIRRS

Figure 28H

Nucleic acid sequence of human codon optimized VP1_GI.3_Lil08_A43V+S94L (SEQ ID NO:169)

ATGATGATGGCTTCCAAGGATGCTCCCACAAACATGGATGGAACAAGCGGCGCGGGGCAACTTGTGCCG
GAGGTGTCCACGGCGGAACCCATTTCCATGGAACCTGTGGCCGGCGCAGCCACTGCTGTGGCCACCGCA
GGACAGGTAAACATGATCGACCCCTGGATCATGTCAAATTACGTTCAGGCTCCACAGGGGGAGTTTACC
ATAAGCCCAAACAACACCCCGGGTGACATCTTGTTTGACCTGCAGCTAGGACCACACTTGAATCCGTTTCT
GCTCCACTTGGCTCAGATGTATAATGGATGGGTTGGAAACATGAAGGTGCGCGTGCTCCTGGCGGGCAA
TGCATTCACAGCCGGGAAGATTATTATCTCTTGCGTGCCACCTGGATTTGCAGCCCAGAACGTGTCTATC
GCACAGGCAACCATGTTTCCGCATGTCATCGCAGATGTGCGCGTGCTAGAGCCCATCGAGGTGCCCCTTG
AGGACGTGCGCAACGTCCTATTCCATAACAATGATAGCACCCCCACCATGCGCTTGATATGTATGTTATAT
ACTCCCCTCCGCGCCAGTGGGTCCAGCTCCGGGACCGATCCTTTTGTGATTGCTGGGCGGGTGTTGACTT
GTCCTAGCCCTGACTTCAACTTCCTTTTTCTGGTGCCTCCAAATGTAGAACAGAAAACAAAGCCATTCAGC
GTGCCAAACCTGCCCCTTAACGTGCTGTCGAATTCCCGAGTGCCTTCCCTTATTAAGTCCATGATGGTATC
TCAGGATCACGGTCAAATGGTGCAGTTTCAGAACGGCCGAGTGACGTTAGACGGGCAGCTGCAGGGCA
CAACCCCAACCAGTGCCAGTCAGCTGTGTAAGATCAGAGGCACCGTCTACCACGCAACTGGCGGACAGG
GGCTGAATCTTACTGAGATCGATGGTACCCCCTACCATGCATTCGAGTCACCTGCACCTATTGGATTTCCC
GATCTTGGGGAGTGTGATTGGCATATCAATGCTTCACCTGCCAACGCTTTCACAGACGGGTCTATTATTCA
TCGCATTGACGTAGCACAGGATAGCACATTTGCCCCGCACCTGGGTACCATCCACTATACGAACGCAGAT
TACAACGCAAACGTGGGTCTTATCTGTAGCCTAGAGTGGCTATCTCCGCCAAGCGGTGGGGCCCCTAAA
GTTAACCCATGGGCTATTCCTCGGTACGGGTCTACGCTGACTGAGGCCGCTCAGCTGGCACCCCCCATAT
ATCCACCAGGATTCGGGGAAGCCATTGTTTTCTTTATGTCCGATTTTCCGATAGCCAACGGTTCAGATGGC
CTTAGTGTCCCTTGCACGATTCCACAGGAATTTGTGACACACTTCGTAAACGAGCAGGCTCCTACTCGGG
GCGAGGCTGCCTTGTTGCATTACGTAGACCCCGATACCCATAGAAACCTGGGCGAATTCAAACTCTACCC
TGAAGGTTTCATGACCTGCGTACCTAACTCCTCCGGCAGTGGCCCTCAAACCTTGCCGATCAACGGCGTG
TTCACGTTTATCAGCTGGGTTTCACGGTTTTACCAACTCAAGCCCGTCGGAACAACTGGGCCAGTTCGGA
GGCTCGGGATCAGACGGAGCTAG

Figure 28I

Amino acid sequence of VP1_GI.3_Lil08_M57I+S94L (SEQ ID NO:172)

MMMASKDAPTNMDGTSGAGQLVPEVSTAEPISMEPVAGAATAAATAGQVNMIDPWIISNYVQAPQGEFT
ISPNNTPGDILFDLQLGPHLNPFLLHLAQMYNGWVGNMKVRVLLAGNAFTAGKIIISCVPPGFAAQNVSIAQ
ATMFPHVIADVRVLEPIEVPLEDVRNVLFHNNDSTPTMRLICMLYTPLRASGSSSGTDPFVIAGRVLTCPSPDF
NFLFLVPPNVEQKTKPFSVPNLPLNVLSNSRVPSLIKSMMVSQDHGQMVQFQNGRVTLDGQLQGTTPTSAS
QLCKIRGTVYHATGGQGLNLTEIDGTPYHAFESPAPIGFPDLGECDWHINASPANAFTDGSIIHRIDVAQDSTF
APHLGTIHYTNADYNANVGLICSLEWLSPPSGGAPKVNPWAIPRYGSTLTEAAQLAPPIYPPGFGEAIVFFMS
DFPIANGSDGLSVPCTIPQEFVTHFVNEQAPTRGEAALLHYVDPDTHRNLGEFKLYPEGFMTCVPNSSGSGPQ
TLPINGVFTFISWVSRFYQLKPVGTTGPVRRLGIRRS

Figure 28J

Nucleic acid sequence of human codon optimized VP1_GI.3_Lil08_M57I+S94L (SEQ ID NO:171)

ATGATGATGGCTTCCAAGGATGCTCCCACAAACATGGATGGAACAAGCGGCGCGGGGCAACTTGTGCCG
GAGGTGTCCACGGCGGAACCCATTTCCATGGAACCTGTGGCCGGCGCAGCCACTGCTGCCGCCACCGCA
GGACAGGTAAACATGATCGACCCCTGGATCATCTCAAATTACGTTCAGGCTCCACAGGGGGAGTTTACCA
TAAGCCCAAACAACACCCCGGGTGACATCTTGTTTGACCTGCAGCTAGGACCACACTTGAATCCGTTTCTG
CTCCACTTGGCTCAGATGTATAATGGATGGGTTGGAAACATGAAGGTGCGCGTGCTCCTGGCGGGCAAT
GCATTCACAGCCGGGAAGATTATTATCTCTTGCGTGCCACCTGGATTTGCAGCCCAGAACGTGTCTATCG
CACAGGCAACCATGTTTCCGCATGTCATCGCAGATGTGCGCGTGCTAGAGCCCATCGAGGTGCCCCTTGA
GGACGTGCGCAACGTCCTATTCCATAACAATGATAGCACCCCCACCATGCGCTTGATATGTATGTTATATA
CTCCCCTCCGCGCCAGTGGGTCCAGCTCCGGGACCGATCCTTTTGTGATTGCTGGGCGGGTGTTGACTTG
TCCTAGCCCTGACTTCAACTTCCTTTTTCTGGTGCCTCCAAATGTAGAACAGAAAACAAAGCCATTCAGCG
TGCCAAACCTGCCCCTTAACGTGCTGTCGAATTCCCGAGTGCCTTCCCTTATTAAGTCCATGATGGTATCT
CAGGATCACGGTCAAATGGTGCAGTTTCAGAACGGCCGAGTGACGTTAGACGGGCAGCTGCAGGGCAC
AACCCCAACCAGTGCCAGTCAGCTGTGTAAGATCAGAGGCACCGTCTACCACGCAACTGGCGGACAGGG
GCTGAATCTTACTGAGATCGATGGTACCCCCTACCATGCATTCGAGTCACCTGCACCTATTGGATTTCCCG
ATCTTGGGGAGTGTGATTGGCATATCAATGCTTCACCTGCCAACGCTTTCACAGACGGGTCTATTATTCAT
CGCATTGACGTAGCACAGGATAGCACATTTGCCCCGCACCTGGGTACCATCCACTATACGAACGCAGATT
ACAACGCAAACGTGGGTCTTATCTGTAGCCTAGAGTGGCTATCTCCGCCAAGCGGTGGGGCCCCTAAAG
TTAACCCATGGGCTATTCCTCGGTACGGGTCTACGCTGACTGAGGCCGCTCAGCTGGCACCCCCCATATA
TCCACCAGGATTCGGGGAAGCCATTGTTTTCTTTATGTCCGATTTTCCGATAGCCAACGGTTCAGATGGCC
TTAGTGTCCCTTGCACGATTCCACAGGAATTTGTGACACACTTCGTAAACGAGCAGGCTCCTACTCGGGG
CGAGGCTGCCTTGTTGCATTACGTAGACCCCGATACCCATAGAAACCTGGGCGAATTCAAACTCTACCCT
GAAGGTTTCATGACCTGCGTACCTAACTCCTCCGGCAGTGGCCCTCAAACCTTGCCGATCAACGGCGTGT
TCACGTTTATCAGCTGGGTTTCACGGTTTTACCAACTCAAGCCCGTCGGAACAACTGGGCCAGTTCGGAG
GCTCGGGATCAGACGGAGCTAG

Figure 28K

Amino acid sequence of VP1_GI.3_Lil08_A43V+M57I+S94L (SEQ ID NO:174)

MMMASKDAPTNMDGTSGAGQLVPEVSTAEPISMEPVAGAATAVATAGQVNMIDPWIISNYVQAPQGEFT
ISPNNTPGDILFDLQLGPHLNPFLLHLAQMYNGWVGNMKVRVLLAGNAFTAGKIIISCVPPGFAAQNVSIAQ
ATMFPHVIADVRVLEPIEVPLEDVRNVLFHNNDSTPTMRLICMLYTPLRASGSSSGTDPFVIAGRVLTCPSPDF
NFLFLVPPNVEQKTKPFSVPNLPLNVLSNSRVPSLIKSMMVSQDHGQMVQFQNGRVTLDGQLQGTTPTSAS
QLCKIRGTVYHATGGQGLNLTEIDGTPYHAFESPAPIGFPDLGECDWHINASPANAFTDGSIIHRIDVAQDSTF
APHLGTIHYTNADYNANVGLICSLEWLSPPSGGAPKVNPWAIPRYGSTLTEAAQLAPPIYPPGFGEAIVFFMS
DFPIANGSDGLSVPCTIPQEFVTHFVNEQAPTRGEAALLHYVDPDTHRNLGEFKLYPEGFMTCVPNSSGSGPQ
TLPINGVFTFISWVSRFYQLKPVGTTGPVRRLGIRRS

Figure 28L

Nucleic acid sequence of human codon optimized VP1_GI.3_Lil08_A43V+M57I+S94L (SEQ ID NO:173)

ATGATGATGGCTTCCAAGGATGCTCCCACAAACATGGATGGAACAAGCGGCGCGGGGCAACTTGTGCCG
GAGGTGTCCACGGCGGAACCCATTTCCATGGAACCTGTGGCCGGCGCAGCCACTGCTGTGGCCACCGCA
GGACAGGTAAACATGATCGACCCCTGGATCATCTCAAATTACGTTCAGGCTCCACAGGGGGAGTTTACCA
TAAGCCCAAACAACACCCCGGGTGACATCTTGTTTGACCTGCAGCTAGGACCACACTTGAATCCGTTTCTG
CTCCACTTGGCTCAGATGTATAATGGATGGGTTGGAAACATGAAGGTGCGCGTGCTCCTGGCGGGCAAT
GCATTCACAGCCGGGAAGATTATTATCTCTTGCGTGCCACCTGGATTTGCAGCCCAGAACGTGTCTATCG
CACAGGCAACCATGTTTCCGCATGTCATCGCAGATGTGCGCGTGCTAGAGCCCATCGAGGTGCCCCTTGA
GGACGTGCGCAACGTCCTATTCCATAACAATGATAGCACCCCCACCATGCGCTTGATATGTATGTTATATA
CTCCCCTCCGCGCCAGTGGGTCCAGCTCCGGGACCGATCCTTTTGTGATTGCTGGGCGGGTGTTGACTTG
TCCTAGCCCTGACTTCAACTTCCTTTTTCTGGTGCCTCCAAATGTAGAACAGAAAACAAAGCCATTCAGCG
TGCCAAACCTGCCCCTTAACGTGCTGTCGAATTCCCGAGTGCCTTCCCTTATTAAGTCCATGATGGTATCT
CAGGATCACGGTCAAATGGTGCAGTTTCAGAACGGCCGAGTGACGTTAGACGGGCAGCTGCAGGGCAC
AACCCCAACCAGTGCCAGTCAGCTGTGTAAGATCAGAGGCACCGTCTACCACGCAACTGGCGGACAGGG
GCTGAATCTTACTGAGATCGATGGTACCCCCTACCATGCATTCGAGTCACCTGCACCTATTGGATTTCCCG
ATCTTGGGGAGTGTGATTGGCATATCAATGCTTCACCTGCCAACGCTTTCACAGACGGGTCTATTATTCAT
CGCATTGACGTAGCACAGGATAGCACATTTGCCCCGCACCTGGGTACCATCCACTATACGAACGCAGATT
ACAACGCAAACGTGGGTCTTATCTGTAGCCTAGAGTGGCTATCTCCGCCAAGCGGTGGGGCCCCTAAAG
TTAACCCATGGGCTATTCCTCGGTACGGGTCTACGCTGACTGAGGCCGCTCAGCTGGCACCCCCCATATA
TCCACCAGGATTCGGGGAAGCCATTGTTTTCTTTATGTCCGATTTTCCGATAGCCAACGGTTCAGATGGCC
TTAGTGTCCCTTGCACGATTCCACAGGAATTTGTGACACACTTCGTAAACGAGCAGGCTCCTACTCGGGG
CGAGGCTGCCTTGTTGCATTACGTAGACCCCGATACCCATAGAAACCTGGGCGAATTCAAACTCTACCCT
GAAGGTTTCATGACCTGCGTACCTAACTCCTCCGGCAGTGGCCCTCAAACCTTGCCGATCAACGGCGTGT
TCACGTTTATCAGCTGGGTTTCACGGTTTTACCAACTCAAGCCCGTCGGAACAACTGGGCCAGTTCGGAG
GCTCGGGATCAGACGGAGCTAG

Figure 28M (SEQ ID NO:292)

AA sequence of VP1_GI.3_Lil08_S94X; where X = V, I, M, T, E, D, N, Q, K, or H

MMMASKDAPTNMDGTSGAGQLVPEVSTAEPISMEPVAGAATAAATAGQVNMIDPWIMSNYVQAPQGE
FTISPNNTPGDILFDLQLGPHLNPFLXHLAQMYNGWVGNMKVRVLLAGNAFTAGKIIISCVPPGFAAQNVSIA
QATMFPHVIADVRVLEPIEVPLEDVRNVLFHNNDSTPTMRLICMLYTPLRASGSSSGTDPFVIAGRVLTCPSPD
FNFLFLVPPNVEQKTKPFSVPNLPLNVLSNSRVPSLIKSMMVSQDHGQMVQFQNGRVTLDGQLQGTTPTSA
SQLCKIRGTVYHATGGQGLNLTEIDGTPYHAFESPAPIGFPDLGECDWHINASPANAFTDGSIIHRIDVAQDST
FAPHLGTIHYTNADYNANVGLICSLEWLSPPSGGAPKVNPWAIPRYGSTLTEAAQLAPPIYPPGFGEAIVFFMS
DFPIANGSDGLSVPCTIPQEFVTHFVNEQAPTRGEAALLHYVDPDTHRNLGEFKLYPEGFMTCVPNSSGSGPQ
TLPINGVFTFISWVSRFYQLKPVGTTGPVRRLGIRRS*

Figure 28N (SEQ ID NO:293)

hCod optimized VP1_GI.3_Lil08_S94x; 'x' = V (XXX=GTG), I (XXX=ATC), M (XXX=ATG), T (XXX = ACC), E (XXX=GAG), D (XXX=GAC), N (XXX=AAC), Q (XXX=CAG), K (XXX=AAG), or H (XXX=CAC)

ATGATGATGGCTTCCAAGGATGCTCCCACAAACATGGATGGAACAAGCGGCGCGGGGCAACTTGTGCCG
GAGGTGTCCACGGCGGAACCCATTTCCATGGAACCTGTGGCCGGCGCAGCCACTGCTGCCGCCACCGCA
GGACAGGTAAACATGATCGACCCCTGGATCATGTCAAATTACGTTCAGGCTCCACAGGGGGAGTTTACC
ATAAGCCCAAACAACACCCCGGGTGACATCTTGTTTGACCTGCAGCTAGGACCACACTTGAATCCGTTTCT
GXXXCACTTGGCTCAGATGTATAATGGATGGGTTGGAAACATGAAGGTGCGCGTGCTCCTGGCGGGCAA
TGCATTCACAGCCGGGAAGATTATTATCTCTTGCGTGCCACCTGGATTTGCAGCCCAGAACGTGTCTATC
GCACAGGCAACCATGTTTCCGCATGTCATCGCAGATGTGCGCGTGCTAGAGCCCATCGAGGTGCCCCTTG
AGGACGTGCGCAACGTCCTATTCCATAACAATGATAGCACCCCCACCATGCGCTTGATATGTATGTTATAT
ACTCCCCTCCGCGCCAGTGGGTCCAGCTCCGGGACCGATCCTTTTGTGATTGCTGGGCGGGTGTTGACTT
GTCCTAGCCCTGACTTCAACTTCCTTTTTCTGGTGCCTCCAAATGTAGAACAGAAAACAAAGCCATTCAGC
GTGCCAAACCTGCCCCTTAACGTGCTGTCGAATTCCCGAGTGCCTTCCCTTATTAAGTCCATGATGGTATC
TCAGGATCACGGTCAAATGGTGCAGTTTCAGAACGGCCGAGTGACGTTAGACGGGCAGCTGCAGGGCA
CAACCCCAACCAGTGCCAGTCAGCTGTGTAAGATCAGAGGCACCGTCTACCACGCAACTGGCGGACAGG
GGCTGAATCTTACTGAGATCGATGGTACCCCCTACCATGCATTCGAGTCACCTGCACCTATTGGATTTCCC
GATCTTGGGGAGTGTGATTGGCATATCAATGCTTCACCTGCCAACGCTTTCACAGACGGGTCTATTATTCA
TCGCATTGACGTAGCACAGGATAGCACATTTGCCCCGCACCTGGGTACCATCCACTATACGAACGCAGAT
TACAACGCAAACGTGGGTCTTATCTGTAGCCTAGAGTGGCTATCTCCGCCAAGCGGTGGGGCCCCTAAA
GTTAACCCATGGGCTATTCCTCGGTACGGGTCTACGCTGACTGAGGCCGCTCAGCTGGCACCCCCCATAT
ATCCACCAGGATTCGGGGAAGCCATTGTTTTCTTTATGTCCGATTTTCCGATAGCCAACGGTTCAGATGGC
CTTAGTGTCCCTTGCACGATTCCACAGGAATTTGTGACACACTTCGTAAACGAGCAGGCTCCTACTCGGG
GCGAGGCTGCCTTGTTGCATTACGTAGACCCCGATACCCATAGAAACCTGGGCGAATTCAAACTCTACCC
TGAAGGTTTCATGACCTGCGTACCTAACTCCTCCGGCAGTGGCCCTCAAACCTTGCCGATCAACGGCGTG
TTCACGTTTATCAGCTGGGTTTCACGGTTTTACCAACTCAAGCCCGTCGGAACAACTGGGCCAGTTCGGA
GGCTCGGGATCAGACGGAGCTAG

Figure 29A

Amino acid sequence of VP1_GI.5_Siklos_Q84S (SEQ ID NO:34)

MMMASKDAPSSADGANGAGQLVPEVNNAEPLPLDPVAGASTALATAGQVNMIDPWIFNNFVQAPQGEFTISPNNTP
GDILFDLSLGPHLNPFLAHLSQMYNGWVGNMRVRVILAGNAFTAGKVIICCVPPGFQSRTLSIAQATLFPHIIADVRTLEPI
EIPLEDVRNTLYHTNDNQPTMRLLCMLYTPLRTGGGSGGTDAFVVAGRVLTCPSSDFNFLFLVPPTVEQKTRPFSVPNIPL
QLLSNSRVPNLIQSMVLSPDQAQNVQFQNGRCTTDGQLLGTTPVSVSQILKFRGKVSAGSKVINLTELDGSPFLAFEAPAP
TGFPDLGTSDWHVEMSLNSNSQSSGNPILLRDIHPNSSEFVPHLGSVCVTAAIEVAGDYTGTIQWTSQPSNVTPVPDVNF
WTIPHYGSNLAEASQLAPVVYPPGFGEAIVYFMSPIPGPNTAHKPNLVPCLLPQEFVTHFVSEQAPSMGEAALVHYVDPD
TNRNLGEFKLYPEGFITCVPNGTGPQQLPLNGVFVFASWVSRFYQLKPVGTASSARGRLGVRR

Figure 29B

Nucleic acid sequence of human codon optimized VP1_GI.5_Siklos_Q84S (SEQ ID NO:35)

ATGATGATGGCCTCCAAAGACGCTCCTAGCAGTGCTGATGGCGCTAACGGTGCCGGCCAGCTGGTCCCCGAGGTGA
ATAACGCCGAGCCTCTCCCCTTGGACCCAGTAGCCGGAGCTTCAACGGCCCTAGCTACTGCCGGACAGGTTAATATG
ATTGACCCCTGGATTTTCAATAATTTCGTGCAGGCCCCTCAAGGCGAGTTTACTATAAGCCCTAACAACACACCAGGG
GATATTCTGTTCGACCTGAGCTTAGGCCCTCATCTCAACCCCTTCTTGGCCCACCTGAGCCAGATGTACAATGGCTGG
GTGGGCAACATGCGAGTGAGAGTTATCCTCGCAGGGAACGCCTTTACCGCTGGTAAGGTGATCATTTGTTGCGTAC
CACCTGGATTCCAGTCTAGGACATTAAGTATTGCGCAAGCTACCCTCTTTCCTCATATCATCGCCGACGTGCGGACAC
TAGAGCCCATCGAGATCCCACTGGAGGATGTCCGGAATACCCTGTACCATACCAACGATAATCAGCCCACTATGAGG
TTACTGTGCATGCTGTACACGCCACTCCGGACTGGTGGGGGCAGTGGGGGGACCGATGCTTTCGTCGTTGCCGGTA
GGGTGCTCACTTGCCCGTCATCTGACTTTAACTTCCTATTCCTTGTGCCCCCAACGGTGGAACAGAAAACGAGACCTT
TTTCCGTACCTAACATCCCTTTACAGCTCCTAAGCAATAGCAGAGTACCTAACCTGATCCAATCCATGGTTCTTAGCCC
TGATCAAGCGCAGAACGTACAGTTTCAGAACGGGCGGTGCACCACAGATGGCCAGCTGCTTGGTACAACTCCCGTC
TCCGTGTCTCAGATACTTAAGTTTCGCGGCAAGGTCTCCGCTGGATCCAAAGTAATCAACCTCACTGAGCTTGATGG
CTCTCCCTTTCTGGCGTTCGAGGCGCCCGCCCCAACAGGCTTTCCAGACCTGGGAACATCCGATTGGCATGTCGAGA
TGAGTCTGAATAGCAACTCCCAGTCTTCTGGCAATCCAATACTGCTCCGCGATATCCATCCTAATTCTAGCGAGTTCG
TTCCACACCTGGGTTCTGTGTGCGTGACGGCTGCAATAGAGGTGGCTGGCGACTACACGGGTACCATTCAGTGGAC
CTCTCAGCCAAGTAACGTGACCCCTGTGCCAGACGTTAACTTTTGGACAATTCCACACTACGGCTCTAACTTGGCCGA
AGCATCCCAGCTTGCCCCCGTTGTATATCCCCCAGGCTTTGGCGAAGCAATAGTTTATTTTATGTCCCCAATCCCTGG
ACCTAACACAGCACACAAGCCAAACCTCGTCCCATGCCTGCTGCCCCAGGAGTTCGTGACTCATTTCGTTTCGGAACA
AGCCCCATCAATGGGGGAGGCCGCCCTGGTCCACTACGTGGATCCAGATACCAATCGGAATCTGGGAGAATTCAAA
CTCTACCCTGAAGGATTCATTACATGTGTGCCCAATGGAACAGGACCGCAGCAGCTCCCACTGAACGGTGTCTTTGT
ATTCGCATCATGGGTTAGCCGGTTCTATCAACTTAAACCCGTGGGGACAGCTTCATCTGCCCGGGGGCGCCTTGGCG
TGCGGCGCTGA

Figure 29C

Amino acid sequence of VP1_GI.5_Siklos_A94L (SEQ ID NO:36)

MMMASKDAPSSADGANGAGQLVPEVNNAEPLPLDPVAGASTALATAGQVNMIDPWIFNNFVQAPQGEFTISPNNTP
GDILFDLQLGPHLNPFLLHLSQMYNGWVGNMRVRVILAGNAFTAGKVIICCVPPGFQSRTLSIAQATLFPHIIADVRTLEPI
EIPLEDVRNTLYHTNDNQPTMRLLCMLYTPLRTGGGSGGTDAFVVAGRVLTCPSSDFNFLFLVPPTVEQKTRPFSVPNIPL
QLLSNSRVPNLIQSMVLSPDQAQNVQFQNGRCTTDGQLLGTTPVSVSQILKFRGKVSAGSKVINLTELDGSPFLAFEAPAP
TGFPDLGTSDWHVEMSLNSNSQSSGNPILLRDIHPNSSEFVPHLGSVCVTAAIEVAGDYTGTIQWTSQPSNVTPVPDVNF
WTIPHYGSNLAEASQLAPVVYPPGFGEAIVYFMSPIPGPNTAHKPNLVPCLLPQEFVTHFVSEQAPSMGEAALVHYVDPD
TNRNLGEFKLYPEGFITCVPNGTGPQQLPLNGVFVFASWVSRFYQLKPVGTASSARGRLGVRR

Figure 29D

Nucleic acid sequence of human codon optimized VP1_GI.5_siklos_A94L (SEQ ID NO:37)

ATGATGATGGCCTCCAAAGACGCTCCTAGCAGTGCTGATGGCGCTAACGGTGCCGGCCAGCTGGTCCCCGAGGTGA
ATAACGCCGAGCCTCTCCCCTTGGACCCAGTAGCCGGAGCTTCAACGGCCCTAGCTACTGCCGGACAGGTTAATATG
ATTGACCCCTGGATTTTCAATAATTTCGTGCAGGCCCCTCAAGGCGAGTTTACTATAAGCCCTAACAACACACCAGGG
GATATTCTGTTCGACCTGCAGTTAGGCCCTCATCTCAACCCCTTCTTGCTCCACCTGAGCCAGATGTACAATGGCTGG
GTGGGCAACATGCGAGTGAGAGTTATCCTCGCAGGGAACGCCTTTACCGCTGGTAAGGTGATCATTTGTTGCGTAC
CACCTGGATTCCAGTCTAGGACATTAAGTATTGCGCAAGCTACCCTCTTTCCTCATATCATCGCCGACGTGCGGACAC
TAGAGCCCATCGAGATCCCACTGGAGGATGTCCGGAATACCCTGTACCATACCAACGATAATCAGCCCACTATGAGG
TTACTGTGCATGCTGTACACGCCACTCCGGACTGGTGGGGGCAGTGGGGGGACCGATGCTTTCGTCGTTGCCGGTA
GGGTGCTCACTTGCCCGTCATCTGACTTTAACTTCCTATTCCTTGTGCCCCCAACGGTGGAACAGAAAACGAGACCTT
TTTCCGTACCTAACATCCCTTTACAGCTCCTAAGCAATAGCAGAGTACCTAACCTGATCCAATCCATGGTTCTTAGCCC
TGATCAAGCGCAGAACGTACAGTTTCAGAACGGGCGGTGCACCACAGATGGCCAGCTGCTTGGTACAACTCCCGTC
TCCGTGTCTCAGATACTTAAGTTTCGCGGCAAGGTCTCCGCTGGATCCAAAGTAATCAACCTCACTGAGCTTGATGG
CTCTCCCTTTCTGGCGTTCGAGGCGCCCGCCCCAACAGGCTTTCCAGACCTGGGAACATCCGATTGGCATGTCGAGA
TGAGTCTGAATAGCAACTCCCAGTCTTCTGGCAATCCAATACTGCTCCGCGATATCCATCCTAATTCTAGCGAGTTCG
TTCCACACCTGGGTTCTGTGTGCGTGACGGCTGCAATAGAGGTGGCTGGCGACTACACGGGTACCATTCAGTGGAC
CTCTCAGCCAAGTAACGTGACCCCTGTGCCAGACGTTAACTTTTGGACAATTCCACACTACGGCTCTAACTTGGCCGA
AGCATCCCAGCTTGCCCCCGTTGTATATCCCCCAGGCTTTGGCGAAGCAATAGTTTATTTTATGTCCCCAATCCCTGG
ACCTAACACAGCACACAAGCCAAACCTCGTCCCATGCCTGCTGCCCCAGGAGTTCGTGACTCATTTCGTTTCGGAACA
AGCCCCATCAATGGGGGAGGCCGCCCTGGTCCACTACGTGGATCCAGATACCAATCGGAATCTGGGAGAATTCAAA
CTCTACCCTGAAGGATTCATTACATGTGTGCCCAATGGAACAGGACCGCAGCAGCTCCCACTGAACGGTGTCTTTGT
ATTCGCATCATGGGTTAGCCGGTTCTATCAACTTAAACCCGTGGGGACAGCTTCATCTGCCCGGGGGCGCCTTGGCG
TGCGGCGCTGA

Figure 29E

Amino acid sequence of VP1_GI.5_siklos_Q84S+A94L (SEQ ID NO:38)

MMMASKDAPSSADGANGAGQLVPEVNNAEPLPLDPVAGASTALATAGQVNMIDPWIFNNFVQAPQGEFTISPNNTP
GDILFDLSLGPHLNPFLLHLSQMYNGWVGNMRVRVILAGNAFTAGKVIICCVPPGFQSRTLSIAQATLFPHIIADVRTLEPI
EIPLEDVRNTLYHTNDNQPTMRLLCMLYTPLRTGGGSGGTDAFVVAGRVLTCPSSDFNFLFLVPPTVEQKTRPFSVPNIPL
QLLSNSRVPNLIQSMVLSPDQAQNVQFQNGRCTTDGQLLGTTPVSVSQILKFRGKVSAGSKVINLTELDGSPFLAFEAPAP

Figure 29E (cont)

TGFPDLGTSDWHVEMSLNSNSQSSGNPILLRDIHPNSSEFVPHLGSVCVTAAIEVAGDYTGTIQWTSQPSNVTPVPDVNF
WTIPHYGSNLAEASQLAPVVYPPGFGEAIVYFMSPIPGPNTAHKPNLVPCLLPQEFVTHFVSEQAPSMGEAALVHYVDPD
TNRNLGEFKLYPEGFITCVPNGTGPQQLPLNGVFVFASWVSRFYQLKPVGTASSARGRLGVRR

Figure 29F

Nucleic acid sequence of human codon optimized VP1_GI.5_siklos_Q84S+A94L (SEQ ID NO:39)

ATGATGATGGCCTCCAAAGACGCTCCTAGCAGTGCTGATGGCGCTAACGGTGCCGGCCAGCTGGTCCCCGAGGTGA
ATAACGCCGAGCCTCTCCCCTTGGACCCAGTAGCCGGAGCTTCAACGGCCCTAGCTACTGCCGGACAGGTTAATATG
ATTGACCCCTGGATTTTCAATAATTTCGTGCAGGCCCCTCAAGGCGAGTTTACTATAAGCCCTAACAACACACCAGGG
GATATTCTGTTCGACCTGAGCTTAGGCCCTCATCTCAACCCCTTCTTGCTCCACCTGAGCCAGATGTACAATGGCTGG
GTGGGCAACATGCGAGTGAGAGTTATCCTCGCAGGGAACGCCTTTACCGCTGGTAAGGTGATCATTTGTTGCGTAC
CACCTGGATTCCAGTCTAGGACATTAAGTATTGCGCAAGCTACCCTCTTTCCTCATATCATCGCCGACGTGCGGACAC
TAGAGCCCATCGAGATCCCACTGGAGGATGTCCGGAATACCCTGTACCATACCAACGATAATCAGCCCACTATGAGG
TTACTGTGCATGCTGTACACGCCACTCCGGACTGGTGGGGGCAGTGGGGGGACCGATGCTTTCGTCGTTGCCGGTA
GGGTGCTCACTTGCCCGTCATCTGACTTTAACTTCCTATTCCTTGTGCCCCCAACGGTGGAACAGAAAACGAGACCTT
TTTCCGTACCTAACATCCCTTTACAGCTCCTAAGCAATAGCAGAGTACCTAACCTGATCCAATCCATGGTTCTTAGCCC
TGATCAAGCGCAGAACGTACAGTTTCAGAACGGGCGGTGCACCACAGATGGCCAGCTGCTTGGTACAACTCCCGTC
TCCGTGTCTCAGATACTTAAGTTTCGCGGCAAGGTCTCCGCTGGATCCAAAGTAATCAACCTCACTGAGCTTGATGG
CTCTCCCTTTCTGGCGTTCGAGGCGCCCGCCCCAACAGGCTTTCCAGACCTGGGAACATCCGATTGGCATGTCGAGA
TGAGTCTGAATAGCAACTCCCAGTCTTCTGGCAATCCAATACTGCTCCGCGATATCCATCCTAATTCTAGCGAGTTCG
TTCCACACCTGGGTTCTGTGTGCGTGACGGCTGCAATAGAGGTGGCTGGCGACTACACGGGTACCATTCAGTGGAC
CTCTCAGCCAAGTAACGTGACCCCTGTGCCAGACGTTAACTTTTGGACAATTCCACACTACGGCTCTAACTTGGCCGA
AGCATCCCAGCTTGCCCCCGTTGTATATCCCCCAGGCTTTGGCGAAGCAATAGTTTATTTTATGTCCCCAATCCCTGG
ACCTAACACAGCACACAAGCCAAACCTCGTCCCATGCCTGCTGCCCCAGGAGTTCGTGACTCATTTCGTTTCGGAACA
AGCCCCATCAATGGGGGAGGCCGCCCTGGTCCACTACGTGGATCCAGATACCAATCGGAATCTGGGAGAATTCAAA
CTCTACCCTGAAGGATTCATTACATGTGTGCCCAATGGAACAGGACCGCAGCAGCTCCCACTGAACGGTGTCTTTGT
ATTCGCATCATGGGTTAGCCGGTTCTATCAACTTAAACCCGTGGGGACAGCTTCATCTGCCCGGGGGCGCCTTGGCG
TGCGGCGCTGA

Figure 29G

Amino acid sequence of VP1_ GI.7/GA5043/USA/2014_R84S (SEQ ID NO:177)

MMMASKDAPSNMDGTSGAGQLVPEVNAAEPLPLEPVVGAATAVATAGQVNMIDPWIMNNFVQAPEGE
FTISPNNTPGDILFDLSLGPHLNPFLLHLSQMYNGWVGNMRVRVMLAGNAFSAGKIIICCVPPGFESQNISIG
QATMFPHVIADVRVLEPIEVPLDDVRNVLFHTNENRPTMRLLCMLYTPLRAGGASSGTDPFVIAGRVLTCPAP
DFNFLFLVPPSVEQKTRQLTIPNIPLNNLANSRVPAMINKMTVSADQNQVVQFQNGRCTLEGQLLGTTPVSA
NQVARIRGKVFSTNSGTGLNLTEVDGTPYHAFESPAPLGFPDIGNCDWHVYAFKVNQNTGDPMYRLDITQG
NSFAPHLGSIEFSSENHPSGDQLGTLTWISPLNNASRVDPWKIPTYGSTLTESTNLAPPIFPPGFGEAIVYFMSD
FPIVSGNTAQIPCTLPQEFVSSFVEQQAPIRGEAALLHYVDPDTHRNLGEFKLYPDGFITCVPNTGGGPQNLPS
NGVFVFSSWVSRYYQLKPVGTTGPVRRLGVRRV

Figure 29H

Nucleic acid sequence of human codon optimized VP1_ GI.7/GA5043/USA/2014_R84S (SEQ ID NO:176)

ATGATGATGGCCAGCAAGGACGCTCCGAGTAACATGGACGGCACTTCGGGCGCGGGGCAGCTGGTGCC
CGAGGTCAATGCCGCAGAACCACTTCCTCTTGAGCCCGTCGTTGGCGCCGCCACAGCTGTCGCAACTGCA
GGCCAAGTCAATATGATCGACCCGTGGATAATGAACAATTTCGTTCAGGCACCAGAAGGAGAATTCACC
ATCTCCCCCAATAACACCCCAGGGGATATTCTGTTTGACCTCAGCTTAGGACCCCACTTGAACCCCTTTCT
GCTTCATCTCTCACAAATGTATAATGGCTGGGTCGGGAATATGCGCGTGCGGGTGATGCTAGCCGGCAA
TGCTTTTTCTGCAGGCAAGATTATCATTTGCTGCGTTCCTCCTGGATTCGAATCTCAAAATATCAGCATTG
GTCAAGCAACCATGTTTCCACATGTGATCGCTGATGTTCGCGTCCTGGAACCCATTGAAGTTCCTCTCGAC
GACGTGAGAAATGTTCTCTTCCACACCAACGAGAATAGGCCGACTATGAGACTTCTGTGTATGCTCTACA
CCCCATTAAGAGCCGGGGGAGCATCCTCAGGTACTGACCCATTTGTGATTGCCGGGCGGGTGCTCACAT
GCCCGGCTCCAGACTTTAACTTCCTTTTCTTGGTGCCACCCAGTGTTGAACAGAAAACCAGACAGCTCACC
ATCCCAAATATCCCATTGAACAATCTCGCCAACAGCAGGGTGCCAGCAATGATAAACAAAATGACAGTCA
GTGCTGACCAGAACCAGGTAGTCCAGTTTCAGAACGGCAGATGCACGCTTGAGGGCCAACTGCTTGGGA
CGACCCCAGTCTCCGCGAACCAGGTGGCCCGAATCCGGGGTAAAGTCTTCAGTACAAACTCCGGCACTG
GCCTTAACCTCACAGAGGTTGACGGCACTCCCTATCATGCTTTTGAGTCTCCAGCCCCTCTTGGCTTTCCC
GATATAGGCAACTGTGACTGGCACGTTTATGCGTTTAAAGTAAACCAGAACACCGGCGATCCTATGTATA
GGTTGGATATAACACAAGGTAATTCATTCGCCCCACACTTGGGTAGCATCGAGTTCAGTTCAGAGAACCA
TCCGAGTGGTGATCAGCTAGGCACATTGACGTGGATCAGCCCTCTGAATAACGCATCAAGAGTGGATCC
CTGGAAGATCCCTACCTATGGGTCCACTCTGACAGAGAGCACAAATTTGGCTCCGCCCATTTTCCCACCCG
GATTCGGCGAGGCCATAGTGTACTTTATGTCTGACTTTCCTATCGTCAGCGGGAATACAGCCCAGATTCCT
TGCACACTGCCACAAGAATTCGTCTCATCCTTTGTAGAGCAGCAGGCACCTATTCGAGGTGAGGCCGCCC
TCTTGCACTACGTGGACCCTGACACCCACCGCAATCTTGGCGAGTTTAAGCTGTACCCTGACGGGTTTATT
ACCTGTGTACCCAACACCGGCGGCGGCCCACAAAATTTGCCCAGCAATGGCGTGTTTGTCTTTTCCTCTTG
GGTGTCTCGATACTACCAGCTTAAACCTGTCGGAACTACGGGCCCCGTGCGACGACTCGGCGTGAGGCG
GGTGTGA

Figure 29I

Amino acid sequence of VP1_ GI.7/GA5043/USA/2014_M57I (SEQ ID NO:179)

MMMASKDAPSNMDGTSGAGQLVPEVNAAEPLPLEPVVGAATAVATAGQVNMIDPWIINNFVQAPEGEFT
ISPNNTPGDILFDLRLGPHLNPFLLHLSQMYNGWVGNMRVRVMLAGNAFSAGKIIICCVPPGFESQNISIGQA
TMFPHVIADVRVLEPIEVPLDDVRNVLFHTNENRPTMRLLCMLYTPLRAGGASSGTDPFVIAGRVLTCPAPDF
NFLFLVPPSVEQKTRQLTIPNIPLNNLANSRVPAMINKMTVSADQNQVVQFQNGRCTLEGQLLGTTPVSANQ
VARIRGKVFSTNSGTGLNLTEVDGTPYHAFESPAPLGFPDIGNCDWHVYAFKVNQNTGDPMYRLDITQGNSF
APHLGSIEFSSENHPSGDQLGTLTWISPLNNASRVDPWKIPTYGSTLTESTNLAPPIFPPGFGEAIVYFMSDFPI
VSGNTAQIPCTLPQEFVSSFVEQQAPIRGEAALLHYVDPDTHRNLGEFKLYPDGFITCVPNTGGGPQNLPSNG
VFVFSSWVSRYYQLKPVGTTGPVRRLGVRRV

Figure 29J human codon optimized VP1_ GI.7/GA5043/USA/2014_M57I (SEQ ID NO:178)

ATGATGATGGCCAGCAAGGACGCTCCGAGTAACATGGACGGCACTTCGGGCGCGGGGCAGCTGGTGCC
CGAGGTCAATGCCGCAGAACCACTTCCTCTTGAGCCCGTCGTTGGCGCCGCCACAGCTGTCGCAACTGCA
GGCCAAGTCAATATGATCGACCCGTGGATAATCAACAATTTCGTTCAGGCACCAGAAGGAGAATTCACCA
TCTCCCCCAATAACACCCCAGGGGATATTCTGTTTGACCTCAGGTTAGGACCCCACTTGAACCCCTTTCTG
CTTCATCTCTCACAAATGTATAATGGCTGGGTCGGGAATATGCGCGTGCGGGTGATGCTAGCCGGCAAT
GCTTTTTCTGCAGGCAAGATTATCATTTGCTGCGTTCCTCCTGGATTCGAATCTCAAAATATCAGCATTGG
TCAAGCAACCATGTTTCCACATGTGATCGCTGATGTTCGCGTCCTGGAACCCATTGAAGTTCCTCTCGACG
ACGTGAGAAATGTTCTCTTCCACACCAACGAGAATAGGCCGACTATGAGACTTCTGTGTATGCTCTACAC
CCCATTAAGAGCCGGGGGAGCATCCTCAGGTACTGACCCATTTGTGATTGCCGGGCGGGTGCTCACATG
CCCGGCTCCAGACTTTAACTTCCTTTTCTTGGTGCCACCCAGTGTTGAACAGAAAACCAGACAGCTCACCA
TCCCAAATATCCCATTGAACAATCTCGCCAACAGCAGGGTGCCAGCAATGATAAACAAAATGACAGTCAG
TGCTGACCAGAACCAGGTAGTCCAGTTTCAGAACGGCAGATGCACGCTTGAGGGCCAACTGCTTGGGAC
GACCCCAGTCTCCGCGAACCAGGTGGCCCGAATCCGGGGTAAAGTCTTCAGTACAAACTCCGGCACTGG
CCTTAACCTCACAGAGGTTGACGGCACTCCCTATCATGCTTTTGAGTCTCCAGCCCCTCTTGGCTTTCCCGA
TATAGGCAACTGTGACTGGCACGTTTATGCGTTTAAAGTAAACCAGAACACCGGCGATCCTATGTATAGG
TTGGATATAACACAAGGTAATTCATTCGCCCCACACTTGGGTAGCATCGAGTTCAGTTCAGAGAACCATC
CGAGTGGTGATCAGCTAGGCACATTGACGTGGATCAGCCCTCTGAATAACGCATCAAGAGTGGATCCCT
GGAAGATCCCTACCTATGGGTCCACTCTGACAGAGAGCACAAATTTGGCTCCGCCCATTTTCCCACCCGG
ATTCGGCGAGGCCATAGTGTACTTTATGTCTGACTTTCCTATCGTCAGCGGGAATACAGCCCAGATTCCTT
GCACACTGCCACAAGAATTCGTCTCATCCTTTGTAGAGCAGCAGGCACCTATTCGAGGTGAGGCCGCCCT
CTTGCACTACGTGGACCCTGACACCCACCGCAATCTTGGCGAGTTTAAGCTGTACCCTGACGGGTTTATTA
CCTGTGTACCCAACACCGGCGGCGGCCCACAAAATTTGCCCAGCAATGGCGTGTTTGTCTTTTCCTCTTGG
GTGTCTCGATACTACCAGCTTAAACCTGTCGGAACTACGGGCCCCGTGCGACGACTCGGCGTGAGGCGG
GTGTGA

Figure 29K

Amino acid sequence of VP1_ GI.7/GA5043/USA/2014_M57I+R84S (SEQ ID NO:181)

MMMASKDAPSNMDGTSGAGQLVPEVNAAEPLPLEPVVGAATAVATAGQVNMIDPWIINNFVQAPEGEFT
ISPNNTPGDILFDLSLGPHLNPFLLHLSQMYNGWVGNMRVRVMLAGNAFSAGKIIICCVPPGFESQNISIGQA
TMFPHVIADVRVLEPIEVPLDDVRNVLFHTNENRPTMRLLCMLYTPLRAGGASSGTDPFVIAGRVLTCPAPDF
NFLFLVPPSVEQKTRQLTIPNIPLNNLANSRVPAMINKMTVSADQNQVVQFQNGRCTLEGQLLGTTPVSANQ
VARIRGKVFSTNSGTGLNLTEVDGTPYHAFESPAPLGFPDIGNCDWHVYAFKVNQNTGDPMYRLDITQGNSF
APHLGSIEFSSENHPSGDQLGTLTWISPLNNASRVDPWKIPTYGSTLTESTNLAPPIFPPGFGEAIVYFMSDFPI
VSGNTAQIPCTLPQEFVSSFVEQQAPIRGEAALLHYVDPDTHRNLGEFKLYPDGFITCVPNTGGGPQNLPSNG
VFVFSSWVSRYYQLKPVGTTGPVRRLGVRRV

Figure 29L

Human codon optimized VP1_ GI.7/GA5043/USA/2014_M57I+R84S (SEQ ID NO:180)

ATGATGATGGCCAGCAAGGACGCTCCGAGTAACATGGACGGCACTTCGGGCGCGGGGCAGCTGGTGCCCGAGGTC
AATGCCGCAGAACCACTTCCTCTTGAGCCCGTCGTTGGCGCCGCCACAGCTGTCGCAACTGCAGGCCAAGTCAATAT
GATCGACCCGTGGATAATCAACAATTTCGTTCAGGCACCAGAAGGAGAATTCACCATCTCCCCCAATAACACCCCAG
GGGATATTCTGTTTGACCTCAGCTTAGGACCCCACTTGAACCCCTTTCTGCTTCATCTCTCACAAATGTATAATGGCTG
GGTCGGGAATATGCGCGTGCGGGTGATGCTAGCCGGCAATGCTTTTTCTGCAGGCAAGATTATCATTTGCTGCGTTC
CTCCTGGATTCGAATCTCAAAATATCAGCATTGGTCAAGCAACCATGTTTCCACATGTGATCGCTGATGTTCGCGTCC
TGGAACCCATTGAAGTTCCTCTCGACGACGTGAGAAATGTTCTCTTCCACACCAACGAGAATAGGCCGACTATGAGA
CTTCTGTGTATGCTCTACACCCCATTAAGAGCCGGGGGAGCATCCTCAGGTACTGACCCATTTGTGATTGCCGGGCG
GGTGCTCACATGCCCGGCTCCAGACTTTAACTTCCTTTTCTTGGTGCCACCCAGTGTTGAACAGAAAACCAGACAGCT
CACCATCCCAAATATCCCATTGAACAATCTCGCCAACAGCAGGGTGCCAGCAATGATAAACAAAATGACAGTCAGTG
CTGACCAGAACCAGGTAGTCCAGTTTCAGAACGGCAGATGCACGCTTGAGGGCCAACTGCTTGGGACGACCCCAGT
CTCCGCGAACCAGGTGGCCCGAATCCGGGGTAAAGTCTTCAGTACAAACTCCGGCACTGGCCTTAACCTCACAGAG
GTTGACGGCACTCCCTATCATGCTTTTGAGTCTCCAGCCCCTCTTGGCTTTCCCGATATAGGCAACTGTGACTGGCAC
GTTTATGCGTTTAAAGTAAACCAGAACACCGGCGATCCTATGTATAGGTTGGATATAACACAAGGTAATTCATTCGC
CCCACACTTGGGTAGCATCGAGTTCAGTTCAGAGAACCATCCGAGTGGTGATCAGCTAGGCACATTGACGTGGATC
AGCCCTCTGAATAACGCATCAAGAGTGGATCCCTGGAAGATCCCTACCTATGGGTCCACTCTGACAGAGAGCACAAA
TTTGGCTCCGCCCATTTTCCCACCCGGATTCGGCGAGGCCATAGTGTACTTTATGTCTGACTTTCCTATCGTCAGCGG
GAATACAGCCCAGATTCCTTGCACACTGCCACAAGAATTCGTCTCATCCTTTGTAGAGCAGCAGGCACCTATTCGAG
GTGAGGCCGCCCTCTTGCACTACGTGGACCCTGACACCCACCGCAATCTTGGCGAGTTTAAGCTGTACCCTGACGGG
TTTATTACCTGTGTACCCAACACCGGCGGCGGCCCACAAAATTTGCCCAGCAATGGCGTGTTTGTCTTTTCCTCTTGG
GTGTCTCGATACTACCAGCTTAAACCTGTCGGAACTACGGGCCCCGTGCGACGACTCGGCGTGAGGCGGGTGTGA

Figure 29M (SEQ ID NO:290)

AA sequence of VP1_GI.7/GA5043/USA/2014_M57X; where X = L, G, S, T, N, Q, K, or H MMMASKDAPSNMDGTSGAGQLVPEVNAAEPLPLEPVVGAATAVATAGQVNMIDPWIXNNFVQAPEGEF
TISPNNTPGDILFDLRLGPHLNPFLLHLSQMYNGWVGNMRVRVMLAGNAFSAGKIIICCVPPGFESQNISIGQ
ATMFPHVIADVRVLEPIEVPLDDVRNVLFHTNENRPTMRLLCMLYTPLRAGGASSGTDPFVIAGRVLTCPAPD
FNFLFLVPPSVEQKTRQLTIPNIPLNNLANSRVPAMINKMTVSADQNQVVQFQNGRCTLEGQLLGTTPVSAN
QVARIRGKVFSTNSGTGLNLTEVDGTPYHAFESPAPLGFPDIGNCDWHVYAFKVNQNTGDPMYRLDITQGN
SFAPHLGSIEFSSENHPSGDQLGTLTWISPLNNASRVDPWKIPTYGSTLTESTNLAPPIFPPGFGEAIVYFMSDF
PIVSGNTAQIPCTLPQEFVSSFVEQQAPIRGEAALLHYVDPDTHRNLGEFKLYPDGFITCVPNTGGGPQNLPSN
GVFVFSSWVSRYYQLKPVGTTGPVRRLGVRRV*

Figure 29N (SEQ ID NO:291)

Human codon optimized VP1_GI.7/GA5043/USA/2014_M57x; 'x' = L (XXX=CTG), G (XXX=GGC), S (XXX=AGC), T (XXX=ACC), N (XXX=AAC), Q (XXX=CAG), K (XXX=AAG), or H (XXX=CAC)

ATGATGATGGCCAGCAAGGACGCTCCGAGTAACATGGACGGCACTTCGGGCGCGGGGCAGCTGGTGCC
CGAGGTCAATGCCGCAGAACCACTTCCTCTTGAGCCCGTCGTTGGCGCCGCCACAGCTGTCGCAACTGCA
GGCCAAGTCAATATGATCGACCCGTGGATAXXXAACAATTTCGTTCAGGCACCAGAAGGAGAATTCACC
ATCTCCCCCAATAACACCCCAGGGGATATTCTGTTTGACCTCAGGTTAGGACCCCACTTGAACCCCTTTCT
GCTTCATCTCTCACAAATGTATAATGGCTGGGTCGGGAATATGCGCGTGCGGGTGATGCTAGCCGGCAA
TGCTTTTTCTGCAGGCAAGATTATCATTTGCTGCGTTCCTCCTGGATTCGAATCTCAAAATATCAGCATTG
GTCAAGCAACCATGTTTCCACATGTGATCGCTGATGTTCGCGTCCTGGAACCCATTGAAGTTCCTCTCGAC
GACGTGAGAAATGTTCTCTTCCACACCAACGAGAATAGGCCGACTATGAGACTTCTGTGTATGCTCTACA
CCCCATTAAGAGCCGGGGGAGCATCCTCAGGTACTGACCCATTTGTGATTGCCGGGCGGGTGCTCACAT
GCCCGGCTCCAGACTTTAACTTCCTTTTCTTGGTGCCACCCAGTGTTGAACAGAAAACCAGACAGCTCACC
ATCCCAAATATCCCATTGAACAATCTCGCCAACAGCAGGGTGCCAGCAATGATAAACAAAATGACAGTCA
GTGCTGACCAGAACCAGGTAGTCCAGTTTCAGAACGGCAGATGCACGCTTGAGGGCCAACTGCTTGGGA
CGACCCCAGTCTCCGCGAACCAGGTGGCCCGAATCCGGGGTAAAGTCTTCAGTACAAACTCCGGCACTG
GCCTTAACCTCACAGAGGTTGACGGCACTCCCTATCATGCTTTTGAGTCTCCAGCCCCTCTTGGCTTTCCC
GATATAGGCAACTGTGACTGGCACGTTTATGCGTTTAAAGTAAACCAGAACACCGGCGATCCTATGTATA
GGTTGGATATAACACAAGGTAATTCATTCGCCCCACACTTGGGTAGCATCGAGTTCAGTTCAGAGAACCA
TCCGAGTGGTGATCAGCTAGGCACATTGACGTGGATCAGCCCTCTGAATAACGCATCAAGAGTGGATCC
CTGGAAGATCCCTACCTATGGGTCCACTCTGACAGAGAGCACAAATTTGGCTCCGCCCATTTTCCCACCCG
GATTCGGCGAGGCCATAGTGTACTTTATGTCTGACTTTCCTATCGTCAGCGGGAATACAGCCCAGATTCCT
TGCACACTGCCACAAGAATTCGTCTCATCCTTTGTAGAGCAGCAGGCACCTATTCGAGGTGAGGCCGCCC
TCTTGCACTACGTGGACCCTGACACCCACCGCAATCTTGGCGAGTTTAAGCTGTACCCTGACGGGTTTATT
ACCTGTGTACCCAACACCGGCGGCGGCCCACAAAATTTGCCCAGCAATGGCGTGTTTGTCTTTTCCTCTTG
GGTGTCTCGATACTACCAGCTTAAACCTGTCGGAACTACGGGCCCCGTGCGACGACTCGGCGTGAGGCG
GGTGTGA

Figure 30A

Amino acid sequence of VP1_GII.2_CGMH47_E80S (SEQ ID NO:85)

MKMASNDAAPSTDGAAGLVPESNNEVMALEPVAGAALAAPVTGQTNIIDPWIRANFVQAPNGEFTVSPRNSPGEVLL
NLSLGPELNPYLAHLARMYNGYAGGMEVQVMLAGNAFTAGKLVFAAVPPHFPVENLSPQQITMFPHVIIDVRTLEPVLL
PLPDVRNNFFHYNQKDDPKMRIVAMLYTPLRSNGSGDDVFTVSCRVLTRPSPDFDFTYLVPPTVESKTKPFTLPILTLGELS
NSRFPVSIDQMYTSPNEVISVQCQNGRCTLDGELQGTTQLQVSGICAFKGEVTAHLHDNDHLYNVTITNLNGSPFDPSED
IPAPLGVPDFQGRVFGVISQRDKHNTPGHNEPANRAHDAVVPTYTAQYTPKLGQIQIGTWQTDDLTVNQPVKFTPVGL
NDTDHFNQWVVPRYAGALNLNTNLAPSVAPVFPGERLLFFRSYIPLKGGYGTPAIDCLLPQEWVQHFYQEAAPSMSEVA
LVRYINPDTGRALFEAKLHRAGFMTVSSNTSAPVVVPANGYFRFDSWVNQFYSLAPMGTGNGRRRIQ

Figure 30B

Nucleic acid sequence of human codon optimized VP1_GII.2_CGMH47_E80S_ (SEQ ID NO:86)

ATGAAGATGGCATCCAACGACGCCGCACCCAGCACAGACGGAGCTGCCGGATTGGTACCCGAGTCTAATAACGAG
GTGATGGCCTTGGAGCCTGTTGCAGGGGCTGCCCTCGCAGCTCCTGTGACCGGGCAGACAAATATCATCGATCCTTG
GATTAGAGCTAATTTCGTGCAAGCCCCAAATGGGGAGTTTACGGTCAGCCCTAGAAATAGCCCTGGGGAAGTGCTC
CTCAATCTCAGCCTGGGACCAGAACTTAATCCGTACCTGGCTCACCTGGCCCGGATGTACAATGGATATGCAGGAGG
GATGGAGGTGCAGGTTATGCTGGCTGGCAATGCCTTTACAGCAGGCAAACTCGTTTTCGCAGCCGTCCCTCCCCACT
TCCCAGTTGAAAATCTTTCCCCTCAGCAGATTACCATGTTTCCCCATGTCATCATCGATGTGCGTACCCTGGAACCTGT
GCTGTTGCCTTTACCAGACGTGCGGAATAATTTCTTTCACTATAATCAGAAGGATGACCCAAAAATGCGGATCGTTG
CGATGCTTTATACTCCCCTGCGTAGCAATGGTAGTGGGGATGACGTTTTTACAGTGAGTTGTCGGGTACTAACTCGC
CCTTCACCAGACTTCGACTTTACGTACTTGGTGCCTCCCACTGTCGAAAGCAAAACTAAGCCATTCACACTTCCCATCC
TCACCCTCGGAGAACTCTCGAACTCCCGCTTCCCTGTTTCAATTGATCAGATGTACACGTCTCCAAATGAAGTCATTTC
TGTGCAGTGTCAGAACGGCAGGTGCACCTTAGACGGTGAACTGCAGGGGACAACGCAGTTGCAGGTCAGTGGAAT
TTGCGCCTTTAAGGGCGAAGTGACAGCTCACCTCCACGACAACGATCATCTCTACAATGTTACTATTACTAATCTCAA
TGGAAGTCCTTTCGACCCCTCGGAAGATATTCCCGCTCCACTCGGAGTACCTGACTTTCAGGGACGCGTCTTCGGCG
TGATATCACAACGAGATAAGCATAACACACCCGGACATAATGAGCCAGCCAATAGAGCCCACGACGCAGTCGTTCC
GACCTATACGGCTCAGTACACCCCAAAGCTCGGCCAGATACAAATCGGGACTTGGCAGACCGATGACCTCACTGTG
AATCAACCTGTGAAATTCACTCCAGTAGGTCTGAATGATACAGACCACTTTAACCAGTGGGTGGTCCCTAGATACGC
CGGAGCCTTGAACCTAAACACTAACCTTGCCCCTTCCGTTGCACCTGTGTTTCCGGGGGAGCGGTTGCTCTTCTTTAG
AAGCTATATTCCTCTGAAGGGCGGGTATGGTACTCCAGCAATCGACTGCCTGCTACCTCAGGAGTGGGTTCAACATT
TCTATCAAGAGGCCGCACCTAGTATGAGCGAGGTGGCTTTGGTCAGATACATCAATCCAGACACAGGAAGAGCACT
GTTCGAGGCCAAGCTGCACAGAGCCGGCTTCATGACCGTCTCATCCAATACATCCGCACCCGTAGTAGTCCCCGCCA
ACGGGTACTTCAGATTCGACAGTTGGGTGAATCAGTTTTACTCGTTGGCCCCCATGGGCACAGGGAACGGTCGCCG
ACGGATCCAGTAA

Figure 30C

Amino acid sequence of VP1_GII.2_CGMH47_A90L (SEQ ID NO:41)

MKMASNDAAPSTDGAAGLVPESNNEVMALEPVAGAALAAPVTGQTNIIDPWIRANFVQAPNGEFTVSPRNSPGEVLL
NLELGPELNPYLLHLARMYNGYAGGMEVQVMLAGNAFTAGKLVFAAVPPHFPVENLSPQQITMFPHVIIDVRTLEPVLL
PLPDVRNNFFHYNQKDDPKMRIVAMLYTPLRSNGSGDDVFTVSCRVLTRPSPDFDFTYLVPPTVESKTKPFTLPILTLGELS
NSRFPVSIDQMYTSPNEVISVQCQNGRCTLDGELQGTTQLQVSGICAFKGEVTAHLHDNDHLYNVTITNLNGSPFDPSED
IPAPLGVPDFQGRVFGVISQRDKHNTPGHNEPANRAHDAVVPTYTAQYTPKLGQIQIGTWQTDDLTVNQPVKFTPVGL
NDTDHFNQWVVPRYAGALNLNTNLAPSVAPVFPGERLLFFRSYIPLKGGYGTPAIDCLLPQEWVQHFYQEAAPSMSEVA
LVRYINPDTGRALFEAKLHRAGFMTVSSNTSAPVVVPANGYFRFDSWVNQFYSLAPMGTGNGRRRIQ

Figure 30D

Nucleic acid sequence of human codon optimized VP1_GII.2_CGMH47_A90L (SEQ ID NO:42)

ATGAAGATGGCATCCAACGACGCCGCACCCAGCACAGACGGAGCTGCCGGATTGGTACCCGAGTCTAATAACGAG
GTGATGGCCTTGGAGCCTGTTGCAGGGGCTGCCCTCGCAGCTCCTGTGACCGGGCAGACAAATATCATCGATCCTTG
GATTAGAGCTAATTTCGTGCAAGCCCCAAATGGGGAGTTTACGGTCAGCCCTAGAAATAGCCCTGGGGAAGTGCTC
CTCAATCTCGAGCTGGGACCAGAACTTAATCCGTACCTGCTCCACCTGGCCCGGATGTACAATGGATATGCAGGAGG

Figure 30D (cont)

GATGGAGGTGCAGGTTATGCTGGCTGGCAATGCCTTTACAGCAGGCAAACTCGTTTTCGCAGCCGTCCCTCCCCACT
TCCCAGTTGAAAATCTTTCCCCTCAGCAGATTACCATGTTTCCCCATGTCATCATCGATGTGCGTACCCTGGAACCTGT
GCTGTTGCCTTTACCAGACGTGCGGAATAATTTCTTTCACTATAATCAGAAGGATGACCCAAAAATGCGGATCGTTG
CGATGCTTTATACTCCCCTGCGTAGCAATGGTAGTGGGGATGACGTTTTTACAGTGAGTTGTCGGGTACTAACTCGC
CCTTCACCAGACTTCGACTTTACGTACTTGGTGCCTCCCACTGTCGAAAGCAAAACTAAGCCATTCACACTTCCCATCC
TCACCCTCGGAGAACTCTCGAACTCCCGCTTCCCTGTTTCAATTGATCAGATGTACACGTCTCCAAATGAAGTCATTTC
TGTGCAGTGTCAGAACGGCAGGTGCACCTTAGACGGTGAACTGCAGGGGACAACGCAGTTGCAGGTCAGTGGAAT
TTGCGCCTTTAAGGGCGAAGTGACAGCTCACCTCCACGACAACGATCATCTCTACAATGTTACTATTACTAATCTCAA
TGGAAGTCCTTTCGACCCCTCGGAAGATATTCCCGCTCCACTCGGAGTACCTGACTTTCAGGGACGCGTCTTCGGCG
TGATATCACAACGAGATAAGCATAACACACCCGGACATAATGAGCCAGCCAATAGAGCCCACGACGCAGTCGTTCC
GACCTATACGGCTCAGTACACCCCAAAGCTCGGCCAGATACAAATCGGGACTTGGCAGACCGATGACCTCACTGTG
AATCAACCTGTGAAATTCACTCCAGTAGGTCTGAATGATACAGACCACTTTAACCAGTGGGTGGTCCCTAGATACGC
CGGAGCCTTGAACCTAAACACTAACCTTGCCCCTTCCGTTGCACCTGTGTTTCCGGGGGAGCGGTTGCTCTTCTTTAG
AAGCTATATTCCTCTGAAGGGCGGGTATGGTACTCCAGCAATCGACTGCCTGCTACCTCAGGAGTGGGTTCAACATT
TCTATCAAGAGGCCGCACCTAGTATGAGCGAGGTGGCTTTGGTCAGATACATCAATCCAGACACAGGAAGAGCACT
GTTCGAGGCCAAGCTGCACAGAGCCGGCTTCATGACCGTCTCATCCAATACATCCGCACCCGTAGTAGTCCCCGCCA
ACGGGTACTTCAGATTCGACAGTTGGGTGAATCAGTTTTACTCGTTGGCCCCCATGGGCACAGGGAACGGTCGCCG
ACGGATCCAGTAA

Figure 30E

Amino acid sequence of VP1_GII.2_CGMH47_E80S+A90L (SEQ ID NO:43)

MKMASNDAAPSTDGAAGLVPESNNEVMALEPVAGAALAAPVTGQTNIIDPWIRANFVQAPNGEFTVSPRNSPGEVLL
NLSLGPELNPYLLHLARMYNGYAGGMEVQVMLAGNAFTAGKLVFAAVPPHFPVENLSPQQITMFPHVIIDVRTLEPVLL
PLPDVRNNFFHYNQKDDPKMRIVAMLYTPLRSNGSGDDVFTVSCRVLTRPSPDFDFTYLVPPTVESKTKPFTLPILTLGELS
NSRFPVSIDQMYTSPNEVISVQCQNGRCTLDGELQGTTQLQVSGICAFKGEVTAHLHDNDHLYNVTITNLNGSPFDPSED
IPAPLGVPDFQGRVFGVISQRDKHNTPGHNEPANRAHDAVVPTYTAQYTPKLGQIQIGTWQTDDLTVNQPVKFTPVGL
NDTDHFNQWVVPRYAGALNLNTNLAPSVAPVFPGERLLFFRSYIPLKGGYGTPAIDCLLPQEWVQHFYQEAAPSMSEVA
LVRYINPDTGRALFEAKLHRAGFMTVSSNTSAPVVVPANGYFRFDSWVNQFYSLAPMGTGNGRRRIQ

Figure 30F

Nucleic acid sequence of human codon optimized VP1_GII.2_CGMH47_E80S+A90L (SEQ ID NO:44)

ATGAAGATGGCATCCAACGACGCCGCACCCAGCACAGACGGAGCTGCCGGATTGGTACCCGAGTCTAATAACGAG
GTGATGGCCTTGGAGCCTGTTGCAGGGGCTGCCCTCGCAGCTCCTGTGACCGGGCAGACAAATATCATCGATCCTTG
GATTAGAGCTAATTTCGTGCAAGCCCCAAATGGGGAGTTTACGGTCAGCCCTAGAAATAGCCCTGGGGAAGTGCTC
CTCAATCTCAGCCTGGGACCAGAACTTAATCCGTACCTGCTCCACCTGGCCCGGATGTACAATGGATATGCAGGAGG
GATGGAGGTGCAGGTTATGCTGGCTGGCAATGCCTTTACAGCAGGCAAACTCGTTTTCGCAGCCGTCCCTCCCCACT
TCCCAGTTGAAAATCTTTCCCCTCAGCAGATTACCATGTTTCCCCATGTCATCATCGATGTGCGTACCCTGGAACCTGT
GCTGTTGCCTTTACCAGACGTGCGGAATAATTTCTTTCACTATAATCAGAAGGATGACCCAAAAATGCGGATCGTTG
CGATGCTTTATACTCCCCTGCGTAGCAATGGTAGTGGGGATGACGTTTTTACAGTGAGTTGTCGGGTACTAACTCGC
CCTTCACCAGACTTCGACTTTACGTACTTGGTGCCTCCCACTGTCGAAAGCAAAACTAAGCCATTCACACTTCCCATCC

Figure 30F (cont)

TCACCCTCGGAGAACTCTCGAACTCCCGCTTCCCTGTTTCAATTGATCAGATGTACACGTCTCCAAATGAAGTCATTTC
TGTGCAGTGTCAGAACGGCAGGTGCACCTTAGACGGTGAACTGCAGGGGACAACGCAGTTGCAGGTCAGTGGAAT
TTGCGCCTTTAAGGGCGAAGTGACAGCTCACCTCCACGACAACGATCATCTCTACAATGTTACTATTACTAATCTCAA
TGGAAGTCCTTTCGACCCCTCGGAAGATATTCCCGCTCCACTCGGAGTACCTGACTTTCAGGGACGCGTCTTCGGCG
TGATATCACAACGAGATAAGCATAACACACCCGGACATAATGAGCCAGCCAATAGAGCCCACGACGCAGTCGTTCC
GACCTATACGGCTCAGTACACCCCAAAGCTCGGCCAGATACAAATCGGGACTTGGCAGACCGATGACCTCACTGTG
AATCAACCTGTGAAATTCACTCCAGTAGGTCTGAATGATACAGACCACTTTAACCAGTGGGTGGTCCCTAGATACGC
CGGAGCCTTGAACCTAAACACTAACCTTGCCCCTTCCGTTGCACCTGTGTTTCCGGGGGAGCGGTTGCTCTTCTTTAG
AAGCTATATTCCTCTGAAGGGCGGGTATGGTACTCCAGCAATCGACTGCCTGCTACCTCAGGAGTGGGTTCAACATT
TCTATCAAGAGGCCGCACCTAGTATGAGCGAGGTGGCTTTGGTCAGATACATCAATCCAGACACAGGAAGAGCACT
GTTCGAGGCCAAGCTGCACAGAGCCGGCTTCATGACCGTCTCATCCAATACATCCGCACCCGTAGTAGTCCCCGCCA
ACGGGTACTTCAGATTCGACAGTTGGGTGAATCAGTTTTACTCGTTGGCCCCCATGGGCACAGGGAACGGTCGCCG
ACGGATCCAGTAA

FIGURE 30G

Amino acid sequence of VP1_GII.2_CGMH47_A39V+E80S+A90L (SEQ ID NO:182)

MKMASNDAAPSTDGAAGLVPESNNEVMALEPVAGAALAVPVTGQTNIIDPWIRANFVQAPNGEFTVSPRNSPGEVLL
NLSLGPELNPYLLHLARMYNGYAGGMEVQVMLAGNAFTAGKLVFAAVPPHFPVENLSPQQITMFPHVIIDVRTLEPVLL
PLPDVRNNFFHYNQKDDPKMRIVAMLYTPLRSNGSGDDVFTVSCRVLTRPSPDFDFTYLVPPTVESKTKPFTLPILTLGELS
NSRFPVSIDQMYTSPNEVISVQCQNGRCTLDGELQGTTQLQVSGICAFKGEVTAHLHDNDHLYNVTITNLNGSPFDPSED
IPAPLGVPDFQGRVFGVISQRDKHNTPGHNEPANRAHDAVVPTYTAQYTPKLGQIQIGTWQTDDLTVNQPVKFTPVGL
NDTDHFNQWVVPRYAGALNLNTNLAPSVAPVFPGERLLFFRSYIPLKGGYGTPAIDCLLPQEWVQHFYQEAAPSMSEVA
LVRYINPDTGRALFEAKLHRAGFMTVSSNTSAPVVVPANGYFRFDSWVNQFYSLAPMGTGNGRRRIQ

FIGURE 30H

Nucleic acid sequence of human codon optimized VP1_GII.2_CGMH47_A39V+E80S+A90L (SEQ ID NO:183)

ATGAAGATGGCATCCAACGACGCCGCACCCAGCACAGACGGAGCTGCCGGATTGGTACCCGAGTCTAATAACGAG
GTGATGGCCTTGGAGCCTGTTGCAGGGGCTGCCCTCGCAGTGCCTGTGACCGGGCAGACAAATATCATCGATCCTT
GGATTAGAGCTAATTTCGTGCAAGCCCCAAATGGGGAGTTTACGGTCAGCCCTAGAAATAGCCCTGGGGAAGTGCT
CCTCAATCTCAGCCTGGGACCAGAACTTAATCCGTACCTGCTCCACCTGGCCCGGATGTACAATGGATATGCAGGAG
GGATGGAGGTGCAGGTTATGCTGGCTGGCAATGCCTTTACAGCAGGCAAACTCGTTTTCGCAGCCGTCCCTCCCCAC
TTCCCAGTTGAAAATCTTTCCCCTCAGCAGATTACCATGTTTCCCCATGTCATCATCGATGTGCGTACCCTGGAACCTG
TGCTGTTGCCTTTACCAGACGTGCGGAATAATTTCTTTCACTATAATCAGAAGGATGACCCAAAAATGCGGATCGTTG
CGATGCTTTATACTCCCCTGCGTAGCAATGGTAGTGGGGATGACGTTTTTACAGTGAGTTGTCGGGTACTAACTCGC
CCTTCACCAGACTTCGACTTTACGTACTTGGTGCCTCCCACTGTCGAAAGCAAAACTAAGCCATTCACACTTCCCATCC
TCACCCTCGGAGAACTCTCGAACTCCCGCTTCCCTGTTTCAATTGATCAGATGTACACGTCTCCAAATGAAGTCATTTC
TGTGCAGTGTCAGAACGGCAGGTGCACCTTAGACGGTGAACTGCAGGGGACAACGCAGTTGCAGGTCAGTGGAAT
TTGCGCCTTTAAGGGCGAAGTGACAGCTCACCTCCACGACAACGATCATCTCTACAATGTTACTATTACTAATCTCAA
TGGAAGTCCTTTCGACCCCTCGGAAGATATTCCCGCTCCACTCGGAGTACCTGACTTTCAGGGACGCGTCTTCGGCG
TGATATCACAACGAGATAAGCATAACACACCCGGACATAATGAGCCAGCCAATAGAGCCCACGACGCAGTCGTTCC
GACCTATACGGCTCAGTACACCCCAAAGCTCGGCCAGATACAAATCGGGACTTGGCAGACCGATGACCTCACTGTG
AATCAACCTGTGAAATTCACTCCAGTAGGTCTGAATGATACAGACCACTTTAACCAGTGGGTGGTCCCTAGATACGC

Figure 30H (cont)

CGGAGCCTTGAACCTAAACACTAACCTTGCCCCTTCCGTTGCACCTGTGTTTCCGGGGGAGCGGTTGCTCTTCTTTAG
AAGCTATATTCCTCTGAAGGGCGGGTATGGTACTCCAGCAATCGACTGCCTGCTACCTCAGGAGTGGGTTCAACATT
TCTATCAAGAGGCCGCACCTAGTATGAGCGAGGTGGCTTTGGTCAGATACATCAATCCAGACACAGGAAGAGCACT
GTTCGAGGCCAAGCTGCACAGAGCCGGCTTCATGACCGTCTCATCCAATACATCCGCACCCGTAGTAGTCCCCGCCA
ACGGGTACTTCAGATTCGACAGTTGGGTGAATCAGTTTTACTCGTTGGCCCCCATGGGCACAGGGAACGGTCGCCG
ACGGATCCAGTAA

FIGURE 30I

Amino acid sequence of VP1_GII.2_CGMH47_ R53I+E80S+A90L (SEQ ID NO:184)

MKMASNDAAPSTDGAAGLVPESNNEVMALEPVAGAALAAPVTGQTNIIDPWIIANFVQAPNGEFTVSPRNSPGEVLLN
LSLGPELNPYLLHLARMYNGYAGGMEVQVMLAGNAFTAGKLVFAAVPPHFPVENLSPQQITMFPHVIIDVRTLEPVLLPL
PDVRNNFFHYNQKDDPKMRIVAMLYTPLRSNGSGDDVFTVSCRVLTRPSPDFDFTYLVPPTVESKTKPFTLPILTLGELSNS
RFPVSIDQMYTSPNEVISVQCQNGRCTLDGELQGTTQLQVSGICAFKGEVTAHLHDNDHLYNVTITNLNGSPFDPSEDIP
APLGVPDFQGRVFGVISQRDKHNTPGHNEPANRAHDAVVPTYTAQYTPKLGQIQIGTWQTDDLTVNQPVKFTPVGLND
TDHFNQWVVPRYAGALNLNTNLAPSVAPVFPGERLLFFRSYIPLKGGYGTPAIDCLLPQEWVQHFYQEAAPSMSEVALV
RYINPDTGRALFEAKLHRAGFMTVSSNTSAPVVVPANGYFRFDSWVNQFYSLAPMGTGNGRRRIQ

FIGURE 30J

Nucleic acid sequence of human codon optimized VP1_GII.2_CGMH47_ R53I+E80S+A90L (SEQ ID NO:185)

ATGAAGATGGCATCCAACGACGCCGCACCCAGCACAGACGGAGCTGCCGGATTGGTACCCGAGTCTAATAACGAG
GTGATGGCCTTGGAGCCTGTTGCAGGGGCTGCCCTCGCAGCTCCTGTGACCGGGCAGACAAATATCATCGATCCTTG
GATTATCGCTAATTTCGTGCAAGCCCCAAATGGGGAGTTTACGGTCAGCCCTAGAAATAGCCCTGGGGAAGTGCTCC
TCAATCTCAGCCTGGGACCAGAACTTAATCCGTACCTGCTCCACCTGGCCCGGATGTACAATGGATATGCAGGAGGG
ATGGAGGTGCAGGTTATGCTGGCTGGCAATGCCTTTACAGCAGGCAAACTCGTTTTCGCAGCCGTCCCTCCCCACTT
CCCAGTTGAAAATCTTTCCCCTCAGCAGATTACCATGTTTCCCCATGTCATCATCGATGTGCGTACCCTGGAACCTGT
GCTGTTGCCTTTACCAGACGTGCGGAATAATTTCTTTCACTATAATCAGAAGGATGACCCAAAAATGCGGATCGTTG
CGATGCTTTATACTCCCCTGCGTAGCAATGGTAGTGGGGATGACGTTTTTACAGTGAGTTGTCGGGTACTAACTCGC
CCTTCACCAGACTTCGACTTTACGTACTTGGTGCCTCCCACTGTCGAAAGCAAAACTAAGCCATTCACACTTCCCATCC
TCACCCTCGGAGAACTCTCGAACTCCCGCTTCCCTGTTTCAATTGATCAGATGTACACGTCTCCAAATGAAGTCATTTC
TGTGCAGTGTCAGAACGGCAGGTGCACCTTAGACGGTGAACTGCAGGGGACAACGCAGTTGCAGGTCAGTGGAAT
TTGCGCCTTTAAGGGCGAAGTGACAGCTCACCTCCACGACAACGATCATCTCTACAATGTTACTATTACTAATCTCAA
TGGAAGTCCTTTCGACCCCTCGGAAGATATTCCCGCTCCACTCGGAGTACCTGACTTTCAGGGACGCGTCTTCGGCG
TGATATCACAACGAGATAAGCATAACACACCCGGACATAATGAGCCAGCCAATAGAGCCCACGACGCAGTCGTTCC
GACCTATACGGCTCAGTACACCCCAAAGCTCGGCCAGATACAAATCGGGACTTGGCAGACCGATGACCTCACTGTG
AATCAACCTGTGAAATTCACTCCAGTAGGTCTGAATGATACAGACCACTTTAACCAGTGGGTGGTCCCTAGATACGC
CGGAGCCTTGAACCTAAACACTAACCTTGCCCCTTCCGTTGCACCTGTGTTTCCGGGGGAGCGGTTGCTCTTCTTTAG
AAGCTATATTCCTCTGAAGGGCGGGTATGGTACTCCAGCAATCGACTGCCTGCTACCTCAGGAGTGGGTTCAACATT
TCTATCAAGAGGCCGCACCTAGTATGAGCGAGGTGGCTTTGGTCAGATACATCAATCCAGACACAGGAAGAGCACT
GTTCGAGGCCAAGCTGCACAGAGCCGGCTTCATGACCGTCTCATCCAATACATCCGCACCCGTAGTAGTCCCCGCCA
ACGGGTACTTCAGATTCGACAGTTGGGTGAATCAGTTTTACTCGTTGGCCCCCATGGGCACAGGGAACGGTCGCCG
ACGGATCCAGTAA

FIGURE 30K

Amino acid sequence of VP1_GII.2_CGMH47_A39V+ R53I+E80S+A90L (SEQ ID NO:186)

MKMASNDAAPSTDGAAGLVPESNNEVMALEPVAGAALAVPVTGQTNIIDPWIIANFVQAPNGEFTVSPRNSPGEVLLN
LSLGPELNPYLLHLARMYNGYAGGMEVQVMLAGNAFTAGKLVFAAVPPHFPVENLSPQQITMFPHVIIDVRTLEPVLLPL
PDVRNNFFHYNQKDDPKMRIVAMLYTPLRSNGSGDDVFTVSCRVLTRPSPDFDFTYLVPPTVESKTKPFTLPILTLGELSNS
RFPVSIDQMYTSPNEVISVQCQNGRCTLDGELQGTTQLQVSGICAFKGEVTAHLHDNDHLYNVTITNLNGSPFDPSEDIP
APLGVPDFQGRVFGVISQRDKHNTPGHNEPANRAHDAVVPTYTAQYTPKLGQIQIGTWQTDDLTVNQPVKFTPVGLND
TDHFNQWVVPRYAGALNLNTNLAPSVAPVFPGERLLFFRSYIPLKGGYGTPAIDCLLPQEWVQHFYQEAAPSMSEVALV
RYINPDTGRALFEAKLHRAGFMTVSSNTSAPVVVPANGYFRFDSWVNQFYSLAPMGTGNGRRRIQ

FIGURE 30L (SEQ ID NO:187)

Nucleic acid sequence of human codon optimized VP1_GII.2_CGMH47_A39V+ R53I+E80S+A90L ATGAAGATGGCATCCAACGACGCCGCACCCAGCACAGACGGAGCTGCCGGATTGGTACCCGAGTCTAATAACGAG
GTGATGGCCTTGGAGCCTGTTGCAGGGGCTGCCCTCGCAGTGCCTGTGACCGGGCAGACAAATATCATCGATCCTT
GGATTATCGCTAATTTCGTGCAAGCCCCAAATGGGGAGTTTACGGTCAGCCCTAGAAATAGCCCTGGGGAAGTGCT
CCTCAATCTCAGCCTGGGACCAGAACTTAATCCGTACCTGCTCCACCTGGCCCGGATGTACAATGGATATGCAGGAG
GGATGGAGGTGCAGGTTATGCTGGCTGGCAATGCCTTTACAGCAGGCAAACTCGTTTTCGCAGCCGTCCCTCCCCAC
TTCCCAGTTGAAAATCTTTCCCCTCAGCAGATTACCATGTTTCCCCATGTCATCATCGATGTGCGTACCCTGGAACCTG
TGCTGTTGCCTTTACCAGACGTGCGGAATAATTTCTTTCACTATAATCAGAAGGATGACCCAAAAATGCGGATCGTTG
CGATGCTTTATACTCCCCTGCGTAGCAATGGTAGTGGGGATGACGTTTTTACAGTGAGTTGTCGGGTACTAACTCGC
CCTTCACCAGACTTCGACTTTACGTACTTGGTGCCTCCCACTGTCGAAAGCAAAACTAAGCCATTCACACTTCCCATCC
TCACCCTCGGAGAACTCTCGAACTCCCGCTTCCCTGTTTCAATTGATCAGATGTACACGTCTCCAAATGAAGTCATTTC
TGTGCAGTGTCAGAACGGCAGGTGCACCTTAGACGGTGAACTGCAGGGGACAACGCAGTTGCAGGTCAGTGGAAT
TTGCGCCTTTAAGGGCGAAGTGACAGCTCACCTCCACGACAACGATCATCTCTACAATGTTACTATTACTAATCTCAA
TGGAAGTCCTTTCGACCCCTCGGAAGATATTCCCGCTCCACTCGGAGTACCTGACTTTCAGGGACGCGTCTTCGGCG
TGATATCACAACGAGATAAGCATAACACACCCGGACATAATGAGCCAGCCAATAGAGCCCACGACGCAGTCGTTCC
GACCTATACGGCTCAGTACACCCCAAAGCTCGGCCAGATACAAATCGGGACTTGGCAGACCGATGACCTCACTGTG
AATCAACCTGTGAAATTCACTCCAGTAGGTCTGAATGATACAGACCACTTTAACCAGTGGGTGGTCCCTAGATACGC
CGGAGCCTTGAACCTAAACACTAACCTTGCCCCTTCCGTTGCACCTGTGTTTCCGGGGGAGCGGTTGCTCTTCTTTAG
AAGCTATATTCCTCTGAAGGGCGGGTATGGTACTCCAGCAATCGACTGCCTGCTACCTCAGGAGTGGGTTCAACATT
TCTATCAAGAGGCCGCACCTAGTATGAGCGAGGTGGCTTTGGTCAGATACATCAATCCAGACACAGGAAGAGCACT
GTTCGAGGCCAAGCTGCACAGAGCCGGCTTCATGACCGTCTCATCCAATACATCCGCACCCGTAGTAGTCCCCGCCA
ACGGGTACTTCAGATTCGACAGTTGGGTGAATCAGTTTTACTCGTTGGCCCCCATGGGCACAGGGAACGGTCGCCG
ACGGATCCAGTAA

Figure 31A

Amino acid sequence of VP1_GII.3_Jing_E80S (SEQ ID NO:46)

MKMASNDAAPSNDGAAGLVPEISSEAMALEPVAGAAIAAPLTGQQNIIDPWIMNNFVQAPGGEFTVSPRNSPGEVLLN
LSLGPEINPYLAHLARMYNGYAGGFEVQVVLAGNAFTAGKIIFAAIPPNFPIDNLSAAQITMCPHVIVDVRQLEPVNLPMP
DVRNNFFHYNQGSDSRLRLIAMLYTPLRANNSGDDVFTVSCRVLTRPSPDFSFNFLVPPTVESKTKPFSLPILTISEMSNSRF
PVPIDSLHTSPTENIVVQCQNGRVTLDGELMGTTQLLPSQICAFRGTLTRSTSRASDQADTATPRLFNYYWHIQLDNLNG
TPYDPAEDIPAPLGTPDFRGKVFGVASQRNPDATTRAHEAKIDTTSGRFTPKLGSLEISTESGDFDQNQPTRFTPVGIGVD

Figure 31A (cont)

HEPDFQQWALPDYAGQFTHNMNLAPAVAPNFPGEQLLFFRSQLPSSGGRSNGILDCLVPQEWVQHFYQESAPSQTQV
ALVRYVNPDTGRVLFEAKLHKLRFMTIAKSGDSPITVPPNGYFRFESWVNPFYTLAPMGTGNGRRRIQ

Figure 31B

Nucleic acid sequence of human codon optimized VP1_GII.3_Jing_E80S (SEQ ID NO:47)

ATGAAAATGGCTTCCAACGATGCAGCACCCTCTAATGATGGCGCTGCCGGACTTGTGCCGGAGATTAGCTCTGAGG
CTATGGCCCTAGAACCAGTAGCCGGGGCAGCCATAGCTGCCCCACTGACTGGCCAGCAGAATATCATTGACCCCTG
GATAATGAACAATTTCGTGCAGGCACCGGGGGGAGAATTCACGGTCTCTCCTCGAAACTCCCCCGGGGAGGTTCTCT
TGAATTTGAGCCTGGGCCCTGAAATTAATCCTTATCTGGCCCATCTAGCCCGAATGTACAACGGCTACGCCGGAGGT
TTCGAGGTCCAGGTGGTGCTCGCTGGTAACGCCTTCACAGCTGGCAAGATCATTTTTGCAGCAATCCCTCCAAACTTC
CCTATCGATAATCTTAGTGCCGCCCAGATCACAATGTGCCCTCACGTTATCGTAGATGTGAGGCAGCTGGAACCTGT
CAATCTCCCAATGCCCGACGTGCGCAACAACTTCTTTCACTATAACCAGGGATCTGACTCCCGCCTTCGCCTTATCGCT
ATGCTGTACACCCCTCTGAGGGCTAACAATTCCGGAGATGACGTTTTCACTGTGAGTTGTCGAGTCCTGACACGTCC
ATCTCCTGACTTTAGCTTTAATTTCCTCGTGCCCCCCACAGTGGAATCCAAAACTAAGCCATTCTCTCTGCCAATTCTT
ACCATTAGCGAAATGTCGAATAGTAGGTTCCCGGTGCCCATAGATTCACTGCATACCAGTCCAACAGAAAACATCGT
CGTACAGTGTCAGAACGGACGCGTGACTCTCGACGGGGAGCTTATGGGCACTACCCAGCTGCTGCCCAGCCAGATA
TGCGCCTTCCGCGGCACACTGACTAGAAGCACTTCGCGTGCTTCTGACCAGGCAGATACAGCTACACCAAGGCTGTT
CAATTATTATTGGCATATACAACTCGATAATCTGAATGGCACTCCTTATGACCCAGCCGAGGACATCCCCGCCCCACT
TGGCACCCCGGACTTTAGAGGGAAGGTCTTTGGAGTGGCTTCTCAAAGAAATCCCGACGCAACCACCCGGGCCCAC
GAGGCCAAAATCGATACTACATCAGGGCGTTTCACCCCTAAGTTAGGCAGTCTGGAGATATCTACCGAAAGTGGAG
ATTTCGATCAGAACCAGCCAACCCGGTTTACCCCCGTGGGAATCGGGGTTGACCACGAACCGGATTTCCAGCAGTG
GGCTCTGCCTGATTACGCAGGCCAGTTCACACATAACATGAATCTTGCCCCCGCTGTGGCCCCCAACTTCCCGGGAG
AACAACTTCTGTTTTTCAGGAGCCAACTGCCTTCCAGCGGCGGCCGATCTAACGGGATTTTGGACTGTCTCGTGCCCC
AGGAATGGGTGCAGCATTTTTACCAGGAGTCCGCGCCCTCCCAGACGCAGGTGGCTCTGGTTAGATATGTCAATCCC
GACACCGGCAGGGTGCTATTTGAGGCAAAGCTGCACAAGCTTCGCTTTATGACTATCGCTAAGAGCGGTGATTCGCC
TATTACAGTGCCCCCCAACGGATACTTCAGATTTGAGAGTTGGGTGAACCCATTCTATACCCTGGCCCCCATGGGTAC
AGGCAATGGCAGACGGCGGATCCAGTAA

Figure 31C

Amino acid sequence of VP1_GII.3_Jing_A90L (SEQ ID NO:48)

MKMASNDAAPSNDGAAGLVPEISSEAMALEPVAGAAIAAPLTGQQNIIDPWIMNNFVQAPGGEFTVSPRNSPGEVLLN
LELGPEINPYLLHLARMYNGYAGGFEVQVVLAGNAFTAGKIIFAAIPPNFPIDNLSAAQITMCPHVIVDVRQLEPVNLPMP
DVRNNFFHYNQGSDSRLRLIAMLYTPLRANNSGDDVFTVSCRVLTRPSPDFSFNFLVPPTVESKTKPFSLPILTISEMSNSRF
PVPIDSLHTSPTENIVVQCQNGRVTLDGELMGTTQLLPSQICAFRGTLTRSTSRASDQADTATPRLFNYYWHIQLDNLNG
TPYDPAEDIPAPLGTPDFRGKVFGVASQRNPDATTRAHEAKIDTTSGRFTPKLGSLEISTESGDFDQNQPTRFTPVGIGVD
HEPDFQQWALPDYAGQFTHNMNLAPAVAPNFPGEQLLFFRSQLPSSGGRSNGILDCLVPQEWVQHFYQESAPSQTQV
ALVRYVNPDTGRVLFEAKLHKLRFMTIAKSGDSPITVPPNGYFRFESWVNPFYTLAPMGTGNGRRRIQ

Figure 31D

Nucleic acid sequence of human codon optimized VP1_GII.3_Jing_A90L (SEQ ID NO:49)

ATGAAAATGGCTTCCAACGATGCAGCACCCTCTAATGATGGCGCTGCCGGACTTGTGCCGGAGATTAGCTCTGAGG
CTATGGCCCTAGAACCAGTAGCCGGGGCAGCCATAGCTGCCCCACTGACTGGCCAGCAGAATATCATTGACCCCTG
GATAATGAACAATTTCGTGCAGGCACCGGGGGGAGAATTCACGGTCTCTCCTCGAAACTCCCCCGGGGAGGTTCTCT
TGAATTTGGAACTGGGCCCTGAAATTAATCCTTATCTGCTCCATCTAGCCCGAATGTACAACGGCTACGCCGGAGGT
TTCGAGGTCCAGGTGGTGCTCGCTGGTAACGCCTTCACAGCTGGCAAGATCATTTTTGCAGCAATCCCTCCAAACTTC
CCTATCGATAATCTTAGTGCCGCCCAGATCACAATGTGCCCTCACGTTATCGTAGATGTGAGGCAGCTGGAACCTGT
CAATCTCCCAATGCCCGACGTGCGCAACAACTTCTTTCACTATAACCAGGGATCTGACTCCCGCCTTCGCCTTATCGCT
ATGCTGTACACCCCTCTGAGGGCTAACAATTCCGGAGATGACGTTTTCACTGTGAGTTGTCGAGTCCTGACACGTCC
ATCTCCTGACTTTAGCTTTAATTTCCTCGTGCCCCCCACAGTGGAATCCAAAACTAAGCCATTCTCTCTGCCAATTCTT
ACCATTAGCGAAATGTCGAATAGTAGGTTCCCGGTGCCCATAGATTCACTGCATACCAGTCCAACAGAAAACATCGT
CGTACAGTGTCAGAACGGACGCGTGACTCTCGACGGGGAGCTTATGGGCACTACCCAGCTGCTGCCCAGCCAGATA
TGCGCCTTCCGCGGCACACTGACTAGAAGCACTTCGCGTGCTTCTGACCAGGCAGATACAGCTACACCAAGGCTGTT
CAATTATTATTGGCATATACAACTCGATAATCTGAATGGCACTCCTTATGACCCAGCCGAGGACATCCCCGCCCCACT
TGGCACCCCGGACTTTAGAGGGAAGGTCTTTGGAGTGGCTTCTCAAAGAAATCCCGACGCAACCACCCGGGCCCAC
GAGGCCAAAATCGATACTACATCAGGGCGTTTCACCCCTAAGTTAGGCAGTCTGGAGATATCTACCGAAAGTGGAG
ATTTCGATCAGAACCAGCCAACCCGGTTTACCCCCGTGGGAATCGGGGTTGACCACGAACCGGATTTCCAGCAGTG
GGCTCTGCCTGATTACGCAGGCCAGTTCACACATAACATGAATCTTGCCCCCGCTGTGGCCCCCAACTTCCCGGGAG
AACAACTTCTGTTTTTCAGGAGCCAACTGCCTTCCAGCGGCGGCCGATCTAACGGGATTTTGGACTGTCTCGTGCCCC
AGGAATGGGTGCAGCATTTTTACCAGGAGTCCGCGCCCTCCCAGACGCAGGTGGCTCTGGTTAGATATGTCAATCCC
GACACCGGCAGGGTGCTATTTGAGGCAAAGCTGCACAAGCTTCGCTTTATGACTATCGCTAAGAGCGGTGATTCGCC
TATTACAGTGCCCCCCAACGGATACTTCAGATTTGAGAGTTGGGTGAACCCATTCTATACCCTGGCCCCCATGGGTAC
AGGCAATGGCAGACGGCGGATCCAGTAA

Figure 31E

Amino acid sequence of VP1_GII.3_Jing_E80S+A90L (SEQ ID NO:50)

MKMASNDAAPSNDGAAGLVPEISSEAMALEPVAGAAIAAPLTGQQNIIDPWIMNNFVQAPGGEFTVSPRNSPGEVLLN
LSLGPEINPYLLHLARMYNGYAGGFEVQVVLAGNAFTAGKIIFAAIPPNFPIDNLSAAQITMCPHVIVDVRQLEPVNLPMP
DVRNNFFHYNQGSDSRLRLIAMLYTPLRANNSGDDVFTVSCRVLTRPSPDFSFNFLVPPTVESKTKPFSLPILTISEMSNSRF
PVPIDSLHTSPTENIVVQCQNGRVTLDGELMGTTQLLPSQICAFRGTLTRSTSRASDQADTATPRLFNYYWHIQLDNLNG
TPYDPAEDIPAPLGTPDFRGKVFGVASQRNPDATTRAHEAKIDTTSGRFTPKLGSLEISTESGDFDQNQPTRFTPVGIGVD
HEPDFQQWALPDYAGQFTHNMNLAPAVAPNFPGEQLLFFRSQLPSSGGRSNGILDCLVPQEWVQHFYQESAPSQTQV
ALVRYVNPDTGRVLFEAKLHKLRFMTIAKSGDSPITVPPNGYFRFESWVNPFYTLAPMGTGNGRRRIQ

Figure 31F

Nucleic acid sequence of human codon optimized VP1_GII.3_Jing_E80S+A90L (SEQ ID NO:51)

ATGAAAATGGCTTCCAACGATGCAGCACCCTCTAATGATGGCGCTGCCGGACTTGTGCCGGAGATTAGCTCTGAGG
CTATGGCCCTAGAACCAGTAGCCGGGGCAGCCATAGCTGCCCCACTGACTGGCCAGCAGAATATCATTGACCCCTG
GATAATGAACAATTTCGTGCAGGCACCGGGGGGAGAATTCACGGTCTCTCCTCGAAACTCCCCCGGGGAGGTTCTCT
TGAATTTGAGCCTGGGCCCTGAAATTAATCCTTATCTGCTCCATCTAGCCCGAATGTACAACGGCTACGCCGGAGGT

Figure 31F (cont)

TTCGAGGTCCAGGTGGTGCTCGCTGGTAACGCCTTCACAGCTGGCAAGATCATTTTTGCAGCAATCCCTCCAAACTTC
CCTATCGATAATCTTAGTGCCGCCCAGATCACAATGTGCCCTCACGTTATCGTAGATGTGAGGCAGCTGGAACCTGT
CAATCTCCCAATGCCCGACGTGCGCAACAACTTCTTTCACTATAACCAGGGATCTGACTCCCGCCTTCGCCTTATCGCT
ATGCTGTACACCCCTCTGAGGGCTAACAATTCCGGAGATGACGTTTTCACTGTGAGTTGTCGAGTCCTGACACGTCC
ATCTCCTGACTTTAGCTTTAATTTCCTCGTGCCCCCCACAGTGGAATCCAAAACTAAGCCATTCTCTCTGCCAATTCTT
ACCATTAGCGAAATGTCGAATAGTAGGTTCCCGGTGCCCATAGATTCACTGCATACCAGTCCAACAGAAAACATCGT
CGTACAGTGTCAGAACGGACGCGTGACTCTCGACGGGGAGCTTATGGGCACTACCCAGCTGCTGCCCAGCCAGATA
TGCGCCTTCCGCGGCACACTGACTAGAAGCACTTCGCGTGCTTCTGACCAGGCAGATACAGCTACACCAAGGCTGTT
CAATTATTATTGGCATATACAACTCGATAATCTGAATGGCACTCCTTATGACCCAGCCGAGGACATCCCCGCCCCACT
TGGCACCCCGGACTTTAGAGGGAAGGTCTTTGGAGTGGCTTCTCAAAGAAATCCCGACGCAACCACCCGGGCCCAC
GAGGCCAAAATCGATACTACATCAGGGCGTTTCACCCCTAAGTTAGGCAGTCTGGAGATATCTACCGAAAGTGGAG
ATTTCGATCAGAACCAGCCAACCCGGTTTACCCCCGTGGGAATCGGGGTTGACCACGAACCGGATTTCCAGCAGTG
GGCTCTGCCTGATTACGCAGGCCAGTTCACACATAACATGAATCTTGCCCCCGCTGTGGCCCCCAACTTCCCGGGAG
AACAACTTCTGTTTTTCAGGAGCCAACTGCCTTCCAGCGGCGGCCGATCTAACGGGATTTTGGACTGTCTCGTGCCCC
AGGAATGGGTGCAGCATTTTTACCAGGAGTCCGCGCCCTCCCAGACGCAGGTGGCTCTGGTTAGATATGTCAATCCC
GACACCGGCAGGGTGCTATTTGAGGCAAAGCTGCACAAGCTTCGCTTTATGACTATCGCTAAGAGCGGTGATTCGCC
TATTACAGTGCCCCCCAACGGATACTTCAGATTTGAGAGTTGGGTGAACCCATTCTATACCCTGGCCCCCATGGGTAC
AGGCAATGGCAGACGGCGGATCCAGTAA

Figure 32A

Amino acid sequence of VP1_GII.4_Syd12_A39V (SEQ ID NO:53)

MKMASSDANPSDGSAANLVPEVNNEVMALEPVVGAAIAVPVAGQQNVIDPWIRNNFVQAPGGEFTVSPRNAPGEIL
WSAPLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32B

Nucleic acid sequence of human codon optimized VP1_GII.4_Syd12_A39V (SEQ ID NO:54)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGTCCCCGTGGCCGGTCAGCAGAATGTGATTGACCCGTG
GATACGCAACAATTTTGTCCAAGCCCCTGGTGGGGAGTTCACCGTTAGCCCGAGAAATGCGCCAGGAGAAATCCTG
TGGTCGGCCCCATTGGGACCCGATCTGAACCCCTATTTGTCACATCTCGCTCGGATGTACAACGGGTATGCCGGCGG
ATTTGAAGTGCAGGTGATTCTGGCTGGGAACGCGTTCACTGCTGGCAAAGTGATCTTTGCAGCGGTGCCTCCCAACT
TCCCCACTGAAGGACTGTCTCCAAGCCAGGTCACAATGTTTCCACACATCGTGGTGGACGTACGGCAGCTAGAGCCT
GTCCTGATTCCCCTCCCTGATGTACGCAATAATTTCTACCACTACAATCAATCCAATGATCCGACCATTAAACTCATCG
CGATGTTGTACACCCCTCTGCGCGCTAACAATGCTGGAGACGACGTATTCACCGTGTCATGCAGAGTGCTCACCAGA
CCTTCACCAGACTTTGACTTTATCTTCTTAGTGCCCCCCACTGTTGAGAGCCGAACCAAGCCCTTTAGTGTCCCCGTAC
TCACAGTCGAGGAGATGACAAATAGCCGCTTTCCAATCCCCCTTGAGAAACTGTTCACAGGACCTTCCTCGGCATTC

Figure 32B (cont)

GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32C

Amino acid sequence of VP1_GII.4_Syd12_V47P (SEQ ID NO:55)

MKMASSDANPSDGSAANLVPEVNNEVMALEPVVGAAIAAPVAGQQNPIDPWIRNNFVQAPGGEFTVSPRNAPGEIL
WSAPLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32D

Nucleic acid sequence of human codon optimized VP1_GII.4_Syd12_V47P (SEQ ID NO:56)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATCCCATTGACCCGTG
GATACGCAACAATTTTGTCCAAGCCCCTGGTGGGGAGTTCACCGTTAGCCCGAGAAATGCGCCAGGAGAAATCCTG
TGGTCGGCCCCATTGGGACCCGATCTGAACCCCTATTTGTCACATCTCGCTCGGATGTACAACGGGTATGCCGGCGG
ATTTGAAGTGCAGGTGATTCTGGCTGGGAACGCGTTCACTGCTGGCAAAGTGATCTTTGCAGCGGTGCCTCCCAACT
TCCCCACTGAAGGACTGTCTCCAAGCCAGGTCACAATGTTTCCACACATCGTGGTGGACGTACGGCAGCTAGAGCCT
GTCCTGATTCCCCTCCCTGATGTACGCAATAATTTCTACCACTACAATCAATCCAATGATCCGACCATTAAACTCATCG
CGATGTTGTACACCCCTCTGCGCGCTAACAATGCTGGAGACGACGTATTCACCGTGTCATGCAGAGTGCTCACCAGA
CCTTCACCAGACTTTGACTTTATCTTCTTAGTGCCCCCCACTGTTGAGAGCCGAACCAAGCCCTTTAGTGTCCCCGTAC
TCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG

Figure 32D (cont)

AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32E

Amino acid sequence of VP1_GII.4_Syd12_R53I (SEQ ID NO:57)

MKMASSDANPSDGSAANLVPEVNNEVMALEPVVGAAIAAPVAGQQNVIDPWIINNFVQAPGGEFTVSPRNAPGEILW
SAPLGPDLNPYLSHLARMYNGYAGGFEVQVILAGNAFTAGKVIFAAVPPNFPTEGLSPSQVTMFPHIVVDVRQLEPVLIPL
PDVRNNFYHYNQSNDPTIKLIAMLYTPLRANNAGDDVFTVSCRVLTRPSPDFDFIFLVPPTVESRTKPFSVPVLTVEEMTN
SRFPIPLEKLFTGPSSAFVVQPQNGRCTTDGVLLGTTQLSPVNICTFRGDVTHITGSRNYTMNLASQNWNDYDPTEEIPAP
LGTPDFVGKIQGVLTQTTRTDGSTRGHKATVYTGSADFAPKLGRVQFETDTDRDFEANQNTKFTPVGVIQDGGTTHRNE
PQQWVLPSYSGRNTHNVHLAPAVAPTFPGEQLLFFRSTMPGCSGYPNMDLDCLLPQEWVQYFYQEAAPAQSDVALLR
FVNPDTGRVLFECKLHKSGYVTVAHTGQHDLVIPPNGYFRFDSWVNQFYTLAPMGNGTGRRRAV

Figure 32F

Nucleic acid sequence of human codon optimized VP1_GII.4_Syd12_R53I (SEQ ID NO:58)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATGTGATTGACCCGT
GGATAATCAACAATTTTGTCCAAGCCCCTGGTGGGGAGTTCACCGTTAGCCCGAGAAATGCGCCAGGAGAAATCCT
GTGGTCGGCCCCATTGGGACCCGATCTGAACCCCTATTTGTCACATCTCGCTCGGATGTACAACGGGTATGCCGGCG
GATTTGAAGTGCAGGTGATTCTGGCTGGGAACGCGTTCACTGCTGGCAAAGTGATCTTTGCAGCGGTGCCTCCCAAC
TTCCCCACTGAAGGACTGTCTCCAAGCCAGGTCACAATGTTTCCACACATCGTGGTGGACGTACGGCAGCTAGAGCC
TGTCCTGATTCCCCTCCCTGATGTACGCAATAATTTCTACCACTACAATCAATCCAATGATCCGACCATTAAACTCATC
GCGATGTTGTACACCCCTCTGCGCGCTAACAATGCTGGAGACGACGTATTCACCGTGTCATGCAGAGTGCTCACCAG
ACCTTCACCAGACTTTGACTTTATCTTCTTAGTGCCCCCCACTGTTGAGAGCCGAACCAAGCCCTTTAGTGTCCCCGTA
CTCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32G

Amino acid sequence of VP1_GII.4_Syd12_P80S (SEQ ID NO:59)

MKMASSDANPSDGSAANLVPEVNNEVMALEPVVGAAIAAPVAGQQNVIDPWIRNNFVQAPGGEFTVSPRNAPGEIL
WSASLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32H

Nucleic acid sequence of human codon optimized VP1_GII.4_Syd12_P80S (SEQ IDNO:60)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATGTGATTGACCCGT
GGATACGCAACAATTTTGTCCAAGCCCCTGGTGGGGAGTTCACCGTTAGCCCGAGAAATGCGCCAGGAGAAATCCT
GTGGTCGGCCAGCTTGGGACCCGATCTGAACCCCTATTTGTCACATCTCGCTCGGATGTACAACGGGTATGCCGGCG
GATTTGAAGTGCAGGTGATTCTGGCTGGGAACGCGTTCACTGCTGGCAAAGTGATCTTTGCAGCGGTGCCTCCCAAC
TTCCCCACTGAAGGACTGTCTCCAAGCCAGGTCACAATGTTTCCACACATCGTGGTGGACGTACGGCAGCTAGAGCC
TGTCCTGATTCCCCTCCCTGATGTACGCAATAATTTCTACCACTACAATCAATCCAATGATCCGACCATTAAACTCATC
GCGATGTTGTACACCCCTCTGCGCGCTAACAATGCTGGAGACGACGTATTCACCGTGTCATGCAGAGTGCTCACCAG
ACCTTCACCAGACTTTGACTTTATCTTCTTAGTGCCCCCCACTGTTGAGAGCCGAACCAAGCCCTTTAGTGTCCCCGTA
CTCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32I

Amino acid sequence of VP1_GII.4_Syd12_S90L (SEQ ID NO:61)

MKMASSDANPSDGSAANLVPEVNNEVMALEPVVGAAIAAPVAGQQNVIDPWIRNNFVQAPGGEFTVSPRNAPGEIL
WSAPLGPDLNPYLLHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP

Figure 32I (cont)

APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32J

Nucleic acid sequence of human codon optimized VP1_GII.4_Syd12_S90L (SEQ IDNO:62)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATGTGATTGACCCGT
GGATACGCAACAATTTTGTCCAAGCCCCTGGTGGGGAGTTCACCGTTAGCCCGAGAAATGCGCCAGGAGAAATCCT
GTGGTCGGCCCCATTGGGACCCGATCTGAACCCCTATTTGCTGCATCTCGCTCGGATGTACAACGGGTATGCCGGCG
GATTTGAAGTGCAGGTGATTCTGGCTGGGAACGCGTTCACTGCTGGCAAAGTGATCTTTGCAGCGGTGCCTCCCAAC
TTCCCCACTGAAGGACTGTCTCCAAGCCAGGTCACAATGTTTCCACACATCGTGGTGGACGTACGGCAGCTAGAGCC
TGTCCTGATTCCCCTCCCTGATGTACGCAATAATTTCTACCACTACAATCAATCCAATGATCCGACCATTAAACTCATC
GCGATGTTGTACACCCCTCTGCGCGCTAACAATGCTGGAGACGACGTATTCACCGTGTCATGCAGAGTGCTCACCAG
ACCTTCACCAGACTTTGACTTTATCTTCTTAGTGCCCCCCACTGTTGAGAGCCGAACCAAGCCCTTTAGTGTCCCCGTA
CTCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32K

Amino acid sequence of VP1_GII.4_Syd12_Δ35-42 (SEQ ID NO:63)

MKMASSDANPSDGSAANLVPEVNNEVMALEPVVGGQQNVIDPWIRNNFVQAPGGEFTVSPRNAPGEILWSAPLGPD
LNPYLSHLARMYNGYAGGFEVQVILAGNAFTAGKVIFAAVPPNFPTEGLSPSQVTMFPHIVVDVRQLEPVLIPLPDVRNN
FYHYNQSNDPTIKLIAMLYTPLRANNAGDDVFTVSCRVLTRPSPDFDFIFLVPPTVESRTKPFSVPVLTVEEMTNSRFPIPLE
KLFTGPSSAFVVQPQNGRCTTDGVLLGTTQLSPVNICTFRGDVTHITGSRNYTMNLASQNWNDYDPTEEIPAPLGTPDFV
GKIQGVLTQTTRTDGSTRGHKATVYTGSADFAPKLGRVQFETDTDRDFEANQNTKFTPVGVIQDGGTTHRNEPQQWVL
PSYSGRNTHNVHLAPAVAPTFPGEQLLFFRSTMPGCSGYPNMDLDCLLPQEWVQYFYQEAAPAQSDVALLRFVNPDTG
RVLFECKLHKSGYVTVAHTGQHDLVIPPNGYFRFDSWVNQFYTLAPMGNGTGRRRAV

Figure 32L

Nucleic acid sequence of human codon optimized VP1_GII.4_Syd12_Δ35-42 (SEQ IDNO:64)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGGTCAGCAGAATGTGATTGACCCGTGGATACGCAACAATTTTGTCCAAGC
CCCTGGTGGGGAGTTCACCGTTAGCCCGAGAAATGCGCCAGGAGAAATCCTGTGGTCGGCCCCATTGGGACCCGAT
CTGAACCCCTATTTGTCACATCTCGCTCGGATGTACAACGGGTATGCCGGCGGATTTGAAGTGCAGGTGATTCTGGC
TGGGAACGCGTTCACTGCTGGCAAAGTGATCTTTGCAGCGGTGCCTCCCAACTTCCCCACTGAAGGACTGTCTCCAA
GCCAGGTCACAATGTTTCCACACATCGTGGTGGACGTACGGCAGCTAGAGCCTGTCCTGATTCCCCTCCCTGATGTA
CGCAATAATTTCTACCACTACAATCAATCCAATGATCCGACCATTAAACTCATCGCGATGTTGTACACCCCTCTGCGC
GCTAACAATGCTGGAGACGACGTATTCACCGTGTCATGCAGAGTGCTCACCAGACCTTCACCAGACTTTGACTTTATC
TTCTTAGTGCCCCCCACTGTTGAGAGCCGAACCAAGCCCTTTAGTGTCCCCGTACTCACAGTCGAGGAGATGACAAA
TAGCCGCTTTCCAATCCCCCTTGAGAAACTGTTCACAGGACCTTCCTCGGCATTCGTGGTTCAGCCACAGAACGGACG
CTGCACAACTGACGGCGTGCTGCTCGGAACCACCCAGCTTAGCCCTGTTAATATCTGTACGTTTAGAGGCGACGTAA
CTCACATAACTGGCTCACGGAACTATACCATGAATCTGGCATCACAGAATTGGAATGACTACGACCCAACCGAAGAG
ATTCCCGCACCTCTTGGAACCCCCGACTTTGTGGGAAAAATACAGGGCGTCCTGACACAAACCACCAGAACCGATGG
CTCCACACGGGGACACAAGGCAACCGTCTACACTGGCTCTGCCGATTTTGCCCCGAAACTGGGTAGAGTGCAGTTTG
AGACCGACACTGACCGGGACTTTGAAGCCAATCAGAATACTAAGTTCACACCTGTAGGAGTGATTCAGGACGGGGG
CACCACTCACCGGAACGAGCCGCAACAATGGGTCCTGCCCTCTTATAGCGGGAGGAATACTCATAATGTGCATTTGG
CTCCTGCAGTGGCTCCCACGTTTCCCGGGGAACAACTGCTCTTTTTTCGTTCAACCATGCCTGGATGCTCCGGATATC
CCAATATGGATCTCGATTGCCTGCTCCCACAGGAATGGGTGCAGTATTTTTATCAAGAGGCCGCACCAGCCCAATCC
GACGTCGCACTTCTGCGGTTCGTGAATCCAGACACAGGCCGCGTGTTGTTTGAGTGCAAATTGCACAAATCAGGATA
CGTTACAGTGGCTCATACTGGACAGCATGACCTGGTGATCCCACCCAACGGATATTTTAGGTTCGACTCCTGGGTGA
ATCAGTTTTATACATTAGCCCCCATGGGGAATGGGACTGGCAGACGCAGGGCTGTCTGA

Figure 32M

Amino acid sequence of VP1_GII.4_Syd12_SSTAVATA (SEQ ID NO:65)

MKMASSDANPSDGSAANLVPEVNNEVMALEPVVGSSTAVATAGQQNVIDPWIRNNFVQAPGGEFTVSPRNAPGEIL
WSAPLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32N

Nucleic acid sequence of human codon optimized VP1_GII.4_Syd12_SSTAVATA (SEQ ID NO:66)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCAGCTCCACCGCCGTCGCTACAGCCGGTCAGCAGAATGTGATTGACCCGTG
GATACGCAACAATTTTGTCCAAGCCCCTGGTGGGGAGTTCACCGTTAGCCCGAGAAATGCGCCAGGAGAAATCCTG
TGGTCGGCCCCATTGGGACCCGATCTGAACCCCTATTTGTCACATCTCGCTCGGATGTACAACGGGTATGCCGGCGG
ATTTGAAGTGCAGGTGATTCTGGCTGGGAACGCGTTCACTGCTGGCAAAGTGATCTTTGCAGCGGTGCCTCCCAACT

Figure 32N (cont)

TCCCCACTGAAGGACTGTCTCCAAGCCAGGTCACAATGTTTCCACACATCGTGGTGGACGTACGGCAGCTAGAGCCT
GTCCTGATTCCCCTCCCTGATGTACGCAATAATTTCTACCACTACAATCAATCCAATGATCCGACCATTAAACTCATCG
CGATGTTGTACACCCCTCTGCGCGCTAACAATGCTGGAGACGACGTATTCACCGTGTCATGCAGAGTGCTCACCAGA
CCTTCACCAGACTTTGACTTTATCTTCTTAGTGCCCCCCACTGTTGAGAGCCGAACCAAGCCCTTTAGTGTCCCCGTAC
TCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32O

Amino acid sequence of VP1_GII.4_Syd12_P80S+A39V (SEQ ID NO:67)

MKMASSDANPSDGSAANLVPEVNNEVMALEPVVGAAIAVPVAGQQNVIDPWIRNNFVQAPGGEFTVSPRNAPGEIL
WSASLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32P

Nucleic acid sequence of human codon optimized VP1_GII.4_Syd12_P80S+A39V (SEQ ID NO:68)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGTCCCCGTGGCCGGTCAGCAGAATGTGATTGACCCGTG
GATACGCAACAATTTTGTCCAAGCCCCTGGTGGGGAGTTCACCGTTAGCCCGAGAAATGCGCCAGGAGAAATCCTG
TGGTCGGCCAGCTTGGGACCCGATCTGAACCCCTATTTGTCACATCTCGCTCGGATGTACAACGGGTATGCCGGCGG
ATTTGAAGTGCAGGTGATTCTGGCTGGGAACGCGTTCACTGCTGGCAAAGTGATCTTTGCAGCGGTGCCTCCCAACT
TCCCCACTGAAGGACTGTCTCCAAGCCAGGTCACAATGTTTCCACACATCGTGGTGGACGTACGGCAGCTAGAGCCT
GTCCTGATTCCCCTCCCTGATGTACGCAATAATTTCTACCACTACAATCAATCCAATGATCCGACCATTAAACTCATCG
CGATGTTGTACACCCCTCTGCGCGCTAACAATGCTGGAGACGACGTATTCACCGTGTCATGCAGAGTGCTCACCAGA
CCTTCACCAGACTTTGACTTTATCTTCTTAGTGCCCCCCACTGTTGAGAGCCGAACCAAGCCCTTTAGTGTCCCCGTAC
TCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT

Figure 32P (cont)

CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32Q

Amino acid sequence of VP1_GII.4_Syd12_P80S+V47P (SEQ ID NO:69)

MKMASSDANPSDGSAANLVPEVNNEVMALEPVVGAAIAAPVAGQQNPIDPWIRNNFVQAPGGEFTVSPRNAPGEIL
WSASLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32R

Nucleic acid sequence of human codon optimized VP1_GII.4_Syd12_P80S+V47P (SEQ ID NO:70)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATCCCATTGACCCGTG
GATACGCAACAATTTTGTCCAAGCCCCTGGTGGGGAGTTCACCGTTAGCCCGAGAAATGCGCCAGGAGAAATCCTG
TGGTCGGCCAGCTTGGGACCCGATCTGAACCCCTATTTGTCACATCTCGCTCGGATGTACAACGGGTATGCCGGCGG
ATTTGAAGTGCAGGTGATTCTGGCTGGGAACGCGTTCACTGCTGGCAAAGTGATCTTTGCAGCGGTGCCTCCCAACT
TCCCCACTGAAGGACTGTCTCCAAGCCAGGTCACAATGTTTCCACACATCGTGGTGGACGTACGGCAGCTAGAGCCT
GTCCTGATTCCCCTCCCTGATGTACGCAATAATTTCTACCACTACAATCAATCCAATGATCCGACCATTAAACTCATCG
CGATGTTGTACACCCCTCTGCGCGCTAACAATGCTGGAGACGACGTATTCACCGTGTCATGCAGAGTGCTCACCAGA
CCTTCACCAGACTTTGACTTTATCTTCTTAGTGCCCCCCACTGTTGAGAGCCGAACCAAGCCCTTTAGTGTCCCCGTAC
TCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA

Figure 32R (cont)

ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32S

Amino acid sequence of VP1_GII.4_Syd12_P80S+R53I (SEQID NO:71)

MKMASSDANPSDGSAANLVPEVNNEVMALEPVVGAAIAAPVAGQQNVIDPWIINNFVQAPGGEFTVSPR
NAPGEILWSASLGPDLNPYLSHLARMYNGYAGGFEVQVILAGNAFTAGKVIFAAVPPNFPTEGLSPSQVTMF
PHIVVDVRQLEPVLIPLPDVRNNFYHYNQSNDPTIKLIAMLYTPLRANNAGDDVFTVSCRVLTRPSPDFDFIFLV
PPTVESRTKPFSVPVLTVEEMTNSRFPIPLEKLFTGPSSAFVVQPQNGRCTTDGVLLGTTQLSPVNICTFRGDVT
HITGSRNYTMNLASQNWNDYDPTEEIPAPLGTPDFVGKIQGVLTQTTRTDGSTRGHKATVYTGSADFAPKLG
RVQFETDTDRDFEANQNTKFTPVGVIQDGGTTHRNEPQQWVLPSYSGRNTHNVHLAPAVAPTFPGEQLLFF
RSTMPGCSGYPNMDLDCLLPQEWVQYFYQEAAPAQSDVALLRFVNPDTGRVLFECKLHKSGYVTVAHTGQ
HDLVIPPNGYFRFDSWVNQFYTLAPMGNGTGRRRAV

Figure 32T

Nucleic acid sequence of human codon optimized VP1_GII.4_Syd12_P80S+R53I (SEQ ID NO:72)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATGTGATTGACCCGT
GGATAATCAACAATTTTGTCCAAGCCCCTGGTGGGGAGTTCACCGTTAGCCCGAGAAATGCGCCAGGAGAAATCCT
GTGGTCGGCCAGCTTGGGACCCGATCTGAACCCCTATTTGTCACATCTCGCTCGGATGTACAACGGGTATGCCGGCG
GATTTGAAGTGCAGGTGATTCTGGCTGGGAACGCGTTCACTGCTGGCAAAGTGATCTTTGCAGCGGTGCCTCCCAAC
TTCCCCACTGAAGGACTGTCTCCAAGCCAGGTCACAATGTTTCCACACATCGTGGTGGACGTACGGCAGCTAGAGCC
TGTCCTGATTCCCCTCCCTGATGTACGCAATAATTTCTACCACTACAATCAATCCAATGATCCGACCATTAAACTCATC
GCGATGTTGTACACCCCTCTGCGCGCTAACAATGCTGGAGACGACGTATTCACCGTGTCATGCAGAGTGCTCACCAG
ACCTTCACCAGACTTTGACTTTATCTTCTTAGTGCCCCCCACTGTTGAGAGCCGAACCAAGCCCTTTAGTGTCCCCGTA
CTCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32U

Amino acid sequence of VP1_GII.4_Syd12_P80S+S90L (SEQ ID NO:73)

MKMASSDANPSDGSAANLVPEVNNEVMALEPVVGAAIAAPVAGQQNVIDPWIRNNFVQAPGGEFTVSPRNAPGEIL
WSASLGPDLNPYLLHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32V

Nucleic acid sequence of human codon optimized VP1_GII.4_Syd12_P80S+S90L (SEQ ID NO:74)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATGTGATTGACCCGT
GGATACGCAACAATTTTGTCCAAGCCCCTGGTGGGGAGTTCACCGTTAGCCCGAGAAATGCGCCAGGAGAAATCCT
GTGGTCGGCCAGCTTGGGACCCGATCTGAACCCCTATTTGCTGCATCTCGCTCGGATGTACAACGGGTATGCCGGCG
GATTTGAAGTGCAGGTGATTCTGGCTGGGAACGCGTTCACTGCTGGCAAAGTGATCTTTGCAGCGGTGCCTCCCAAC
TTCCCCACTGAAGGACTGTCTCCAAGCCAGGTCACAATGTTTCCACACATCGTGGTGGACGTACGGCAGCTAGAGCC
TGTCCTGATTCCCCTCCCTGATGTACGCAATAATTTCTACCACTACAATCAATCCAATGATCCGACCATTAAACTCATC
GCGATGTTGTACACCCCTCTGCGCGCTAACAATGCTGGAGACGACGTATTCACCGTGTCATGCAGAGTGCTCACCAG
ACCTTCACCAGACTTTGACTTTATCTTCTTAGTGCCCCCCACTGTTGAGAGCCGAACCAAGCCCTTTAGTGTCCCCGTA
CTCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 32W

Amino acid sequence of VP1_GII.4_Syd12_P80S+Δ35-42 (SEQ ID NO:75)

MKMASSDANPSDGSAANLVPEVNNEVMALEPVVGGQQNVIDPWIRNNFVQAPGGEFTVSPRNAPGEILWSASLGPD
LNPYLSHLARMYNGYAGGFEVQVILAGNAFTAGKVIFAAVPPNFPTEGLSPSQVTMFPHIVVDVRQLEPVLIPLPDVRNN
FYHYNQSNDPTIKLIAMLYTPLRANNAGDDVFTVSCRVLTRPSPDFDFIFLVPPTVESRTKPFSVPVLTVEEMTNSRFPIPLE
KLFTGPSSAFVVQPQNGRCTTDGVLLGTTQLSPVNICTFRGDVTHITGSRNYTMNLASQNWNDYDPTEEIPAPLGTPDFV

Figure 32W (cont)

GKIQGVLTQTTRTDGSTRGHKATVYTGSADFAPKLGRVQFETDTDRDFEANQNTKFTPVGVIQDGGTTHRNEPQQWVL
PSYSGRNTHNVHLAPAVAPTFPGEQLLFFRSTMPGCSGYPNMDLDCLLPQEWVQYFYQEAAPAQSDVALLRFVNPDTG
RVLFECKLHKSGYVTVAHTGQHDLVIPPNGYFRFDSWVNQFYTLAPMGNGTGRRRAV

Figure 32X

Nucleic acid sequence of human codon optimized VP1_GII.4_Syd12_P80S+Δ35-42 (SEQ ID NO:76)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGGTCAGCAGAATGTGATTGACCCGTGGATACGCAACAATTTTGTCCAAGC
CCCTGGTGGGGAGTTCACCGTTAGCCCGAGAAATGCGCCAGGAGAAATCCTGTGGTCGGCCAGCTTGGGACCCGAT
CTGAACCCCTATTTGTCACATCTCGCTCGGATGTACAACGGGTATGCCGGCGGATTTGAAGTGCAGGTGATTCTGGC
TGGGAACGCGTTCACTGCTGGCAAAGTGATCTTTGCAGCGGTGCCTCCCAACTTCCCCACTGAAGGACTGTCTCCAA
GCCAGGTCACAATGTTTCCACACATCGTGGTGGACGTACGGCAGCTAGAGCCTGTCCTGATTCCCCTCCCTGATGTA
CGCAATAATTTCTACCACTACAATCAATCCAATGATCCGACCATTAAACTCATCGCGATGTTGTACACCCCTCTGCGC
GCTAACAATGCTGGAGACGACGTATTCACCGTGTCATGCAGAGTGCTCACCAGACCTTCACCAGACTTTGACTTTATC
TTCTTAGTGCCCCCCACTGTTGAGAGCCGAACCAAGCCCTTTAGTGTCCCCGTACTCACAGTCGAGGAGATGACAAA
TAGCCGCTTTCCAATCCCCCTTGAGAAACTGTTCACAGGACCTTCCTCGGCATTCGTGGTTCAGCCACAGAACGGACG
CTGCACAACTGACGGCGTGCTGCTCGGAACCACCCAGCTTAGCCCTGTTAATATCTGTACGTTTAGAGGCGACGTAA
CTCACATAACTGGCTCACGGAACTATACCATGAATCTGGCATCACAGAATTGGAATGACTACGACCCAACCGAAGAG
ATTCCCGCACCTCTTGGAACCCCCGACTTTGTGGGAAAAATACAGGGCGTCCTGACACAAACCACCAGAACCGATGG
CTCCACACGGGGACACAAGGCAACCGTCTACACTGGCTCTGCCGATTTTGCCCCGAAACTGGGTAGAGTGCAGTTTG
AGACCGACACTGACCGGGACTTTGAAGCCAATCAGAATACTAAGTTCACACCTGTAGGAGTGATTCAGGACGGGGG
CACCACTCACCGGAACGAGCCGCAACAATGGGTCCTGCCCTCTTATAGCGGGAGGAATACTCATAATGTGCATTTGG
CTCCTGCAGTGGCTCCCACGTTTCCCGGGGAACAACTGCTCTTTTTTCGTTCAACCATGCCTGGATGCTCCGGATATC
CCAATATGGATCTCGATTGCCTGCTCCCACAGGAATGGGTGCAGTATTTTTATCAAGAGGCCGCACCAGCCCAATCC
GACGTCGCACTTCTGCGGTTCGTGAATCCAGACACAGGCCGCGTGTTGTTTGAGTGCAAATTGCACAAATCAGGATA
CGTTACAGTGGCTCATACTGGACAGCATGACCTGGTGATCCCACCCAACGGATATTTTAGGTTCGACTCCTGGGTGA
ATCAGTTTTATACATTAGCCCCCATGGGGAATGGGACTGGCAGACGCAGGGCTGTCTGA

Figure 32Y

Amino acid sequence of VP1_GII.4_Syd12_P80S+SSTAVATA (SEQ ID NO:77)

MKMASSDANPSDGSAANLVPEVNNEVMALEPVVGSSTAVATAGQQNVIDPWIRNNFVQAPGGEFTVSPRNAPGEIL
WSASLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 32Z

Nucleic acid sequence of human codon optimized VP1_GII.4_Syd12_P80S+SSTAVATA (SEQ ID NO:78)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCAGCTCCACCGCCGTCGCTACAGCCGGTCAGCAGAATGTGATTGACCCGTG
GATACGCAACAATTTTGTCCAAGCCCCTGGTGGGGAGTTCACCGTTAGCCCGAGAAATGCGCCAGGAGAAATCCTG
TGGTCGGCCAGCTTGGGACCCGATCTGAACCCCTATTTGTCACATCTCGCTCGGATGTACAACGGGTATGCCGGCGG
ATTTGAAGTGCAGGTGATTCTGGCTGGGAACGCGTTCACTGCTGGCAAAGTGATCTTTGCAGCGGTGCCTCCCAACT
TCCCCACTGAAGGACTGTCTCCAAGCCAGGTCACAATGTTTCCACACATCGTGGTGGACGTACGGCAGCTAGAGCCT
GTCCTGATTCCCCTCCCTGATGTACGCAATAATTTCTACCACTACAATCAATCCAATGATCCGACCATTAAACTCATCG
CGATGTTGTACACCCCTCTGCGCGCTAACAATGCTGGAGACGACGTATTCACCGTGTCATGCAGAGTGCTCACCAGA
CCTTCACCAGACTTTGACTTTATCTTCTTAGTGCCCCCCACTGTTGAGAGCCGAACCAAGCCCTTTAGTGTCCCCGTAC
TCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

FIGURE 32AA

Amino acid sequence of VP1 GII.4 Syd12 A39V+R53I (SEQ ID NO:188)

MKMASSDANPSDGSAANLVPEVNNEVMALEPVVGAAIAVPVAGQQNVIDPWIINNFVQAPGGEFTVSPR
NAPGEILWSAPLGPDLNPYLSHLARMYNGYAGGFEVQVILAGNAFTAGKVIFAAVPPNFPTEGLSPSQVTMF
PHIVVDVRQLEPVLIPLPDVRNNFYHYNQSNDPTIKLIAMLYTPLRANNAGDDVFTVSCRVLTRPSPDFDFIFLV
PPTVESRTKPFSVPVLTVEEMTNSRFPIPLEKLFTGPSSAFVVQPQNGRCTTDGVLLGTTQLSPVNICTFRGDVT
HITGSRNYTMNLASQNWNDYDPTEEIPAPLGTPDFVGKIQGVLTQTTRTDGSTRGHKATVYTGSADFAPKLG
RVQFETDTDRDFEANQNTKFTPVGVIQDGGTTHRNEPQQWVLPSYSGRNTHNVHLAPAVAPTFPGEQLLFF
RSTMPGCSGYPNMDLDCLLPQEWVQYFYQEAAPAQSDVALLRFVNPDTGRVLFECKLHKSGYVTVAHTGQ
HDLVIPPNGYFRFDSWVNQFYTLAPMGNGTGRRRAV

FIGURE 32BB

Nucleic acid sequence of human codon optimized VP1 GII.4_Syd12_A39V+R53I (SEQ ID NO:189)

ATGAAAATGGCCTCGAGTGACGCTAACCCTAGTGACGGCAGCGCCGCCAATCTTGTGCCTGAGGTTAAT
AATGAGGTGATGGCCCTGGAGCCTGTGGTGGGCGCAGCCATAGCAGTCCCCGTGGCCGGTCAGCAGAA
TGTGATTGACCCGTGGATAATCAACAATTTTGTCCAAGCCCCTGGTGGGGAGTTCACCGTTAGCCCGAGA
AATGCGCCAGGAGAAATCCTGTGGTCGGCCCCATTGGGACCCGATCTGAACCCCTATTTGTCACATCTCG
CTCGGATGTACAACGGGTATGCCGGCGGATTTGAAGTGCAGGTGATTCTGGCTGGGAACGCGTTCACTG
CTGGCAAAGTGATCTTTGCAGCGGTGCCTCCCAACTTCCCCACTGAAGGACTGTCTCCAAGCCAGGTCAC
AATGTTTCCACACATCGTGGTGGACGTACGGCAGCTAGAGCCTGTCCTGATTCCCCTCCCTGATGTACGC
AATAATTTCTACCACTACAATCAATCCAATGATCCGACCATTAAACTCATCGCGATGTTGTACACCCCTCTG
CGCGCTAACAATGCTGGAGACGACGTATTCACCGTGTCATGCAGAGTGCTCACCAGACCTTCACCAGACT
TTGACTTTATCTTCTTAGTGCCCCCCACTGTTGAGAGCCGAACCAAGCCCTTTAGTGTCCCCGTACTCACA
GTCGAGGAGATGACAAATAGCCGCTTTCCAATCCCCCTTGAGAAACTGTTCACAGGACCTTCCTCGGCAT
TCGTGGTTCAGCCACAGAACGGACGCTGCACAACTGACGGCGTGCTGCTCGGAACCACCCAGCTTAGCC
CTGTTAATATCTGTACGTTTAGAGGCGACGTAACTCACATAACTGGCTCACGGAACTATACCATGAATCTG
GCATCACAGAATTGGAATGACTACGACCCAACCGAAGAGATTCCCGCACCTCTTGGAACCCCCGACTTTG
TGGGAAAAATACAGGGCGTCCTGACACAAACCACCAGAACCGATGGCTCCACACGGGGACACAAGGCA
ACCGTCTACACTGGCTCTGCCGATTTTGCCCCGAAACTGGGTAGAGTGCAGTTTGAGACCGACACTGACC
GGGACTTTGAAGCCAATCAGAATACTAAGTTCACACCTGTAGGAGTGATTCAGGACGGGGGCACCACTC
ACCGGAACGAGCCGCAACAATGGGTCCTGCCCTCTTATAGCGGGAGGAATACTCATAATGTGCATTTGG
CTCCTGCAGTGGCTCCCACGTTTCCCGGGGAACAACTGCTCTTTTTTCGTTCAACCATGCCTGGATGCTCC
GGATATCCCAATATGGATCTCGATTGCCTGCTCCCACAGGAATGGGTGCAGTATTTTTATCAAGAGGCCG
CACCAGCCCAATCCGACGTCGCACTTCTGCGGTTCGTGAATCCAGACACAGGCCGCGTGTTGTTTGAGTG
CAAATTGCACAAATCAGGATACGTTACAGTGGCTCATACTGGACAGCATGACCTGGTGATCCCACCCAAC
GGATATTTTAGGTTCGACTCCTGGGTGAATCAGTTTTATACATTAGCCCCCATGGGGAATGGGACTGGCA
GACGCAGGGCTGTCTGA

FIGURE 32CC

Amino acid sequence of VP1 GII.4 Syd12 A39V+R53I+P80S (SEQ ID NO:190)

MKMASSDANPSDGSAANLVPEVNNEVMALEPVVGAAIAVPVAGQQNVIDPWIINNFVQAPGGEFTVSPR
NAPGEILWSASLGPDLNPYLSHLARMYNGYAGGFEVQVILAGNAFTAGKVIFAAVPPNFPTEGLSPSQVTMF
PHIVVDVRQLEPVLIPLPDVRNNFYHYNQSNDPTIKLIAMLYTPLRANNAGDDVFTVSCRVLTRPSPDFDFIFLV
PPTVESRTKPFSVPVLTVEEMTNSRFPIPLEKLFTGPSSAFVVQPQNGRCTTDGVLLGTTQLSPVNICTFRGDVT
HITGSRNYTMNLASQNWNDYDPTEEIPAPLGTPDFVGKIQGVLTQTTRTDGSTRGHKATVYTGSADFAPKLG
RVQFETDTDRDFEANQNTKFTPVGVIQDGGTTHRNEPQQWVLPSYSGRNTHNVHLAPAVAPTFPGEQLLFF
RSTMPGCSGYPNMDLDCLLPQEWVQYFYQEAAPAQSDVALLRFVNPDTGRVLFECKLHKSGYVTVAHTGQ
HDLVIPPNGYFRFDSWVNQFYTLAPMGNGTGRRRAV

FIGURE 32DD

Nucleic acid sequence of human codon optimized VP1 GII.4_Syd12_A39V+R53I+P80S (SEQ ID NO:191)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGTCCCCGTGGCCGGTCAGCAGAATGTGATTGACCCGTG
GATAATCAACAATTTTGTCCAAGCCCCTGGTGGGGAGTTCACCGTTAGCCCGAGAAATGCGCCAGGAGAAATCCTGT
GGTCGGCCAGCTTGGGACCCGATCTGAACCCCTATTTGTCACATCTCGCTCGGATGTACAACGGGTATGCCGGCGGA
TTTGAAGTGCAGGTGATTCTGGCTGGGAACGCGTTCACTGCTGGCAAAGTGATCTTTGCAGCGGTGCCTCCCAACTT
CCCCACTGAAGGACTGTCTCCAAGCCAGGTCACAATGTTTCCACACATCGTGGTGGACGTACGGCAGCTAGAGCCTG
TCCTGATTCCCCTCCCTGATGTACGCAATAATTTCTACCACTACAATCAATCCAATGATCCGACCATTAAACTCATCGC
GATGTTGTACACCCCTCTGCGCGCTAACAATGCTGGAGACGACGTATTCACCGTGTCATGCAGAGTGCTCACCAGAC
CTTCACCAGACTTTGACTTTATCTTCTTAGTGCCCCCCACTGTTGAGAGCCGAACCAAGCCCTTTAGTGTCCCCGTACT
CACAGTCGAGGAGATGACAAATAGCCGCTTTCCAATCCCCCTTGAGAAACTGTTCACAGGACCTTCCTCGGCATTCG
TGGTTCAGCCACAGAACGGACGCTGCACAACTGACGGCGTGCTGCTCGGAACCACCCAGCTTAGCCCTGTTAATATC
TGTACGTTTAGAGGCGACGTAACTCACATAACTGGCTCACGGAACTATACCATGAATCTGGCATCACAGAATTGGAA
TGACTACGACCCAACCGAAGAGATTCCCGCACCTCTTGGAACCCCCGACTTTGTGGGAAAAATACAGGGCGTCCTGA
CACAAACCACCAGAACCGATGGCTCCACACGGGGACACAAGGCAACCGTCTACACTGGCTCTGCCGATTTTGCCCCG
AAACTGGGTAGAGTGCAGTTTGAGACCGACACTGACCGGGACTTTGAAGCCAATCAGAATACTAAGTTCACACCTG
TAGGAGTGATTCAGGACGGGGGCACCACTCACCGGAACGAGCCGCAACAATGGGTCCTGCCCTCTTATAGCGGGA
GGAATACTCATAATGTGCATTTGGCTCCTGCAGTGGCTCCCACGTTTCCCGGGGAACAACTGCTCTTTTTTCGTTCAA
CCATGCCTGGATGCTCCGGATATCCCAATATGGATCTCGATTGCCTGCTCCCACAGGAATGGGTGCAGTATTTTTATC
AAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

FIGURE 32EE

Nucleic acid sequence of human codon optimized VP1 GII.4_Syd12_P80X; where X = A (XXX=GCC), N (XXX=AAC), K(XXX=AAG), or H(XXX=CAC) (SEQ ID NO:287)

ATGAAAATGGCCTCGAGTGACGCTAACCCTAGTGACGGCAGCGCCGCCAATCTTGTGCCTGAGGTTAAT
AATGAGGTGATGGCCCTGGAGCCTGTGGTGGGCGCAGCCATAGCAGCGCCCGTGGCCGGTCAGCAGAA
TGTGATTGACCCGTGGATACGCAACAATTTTGTCCAAGCCCCTGGTGGGGAGTTCACCGTTAGCCCGAGA
AATGCGCCAGGAGAAATCCTGTGGTCGGCCXXXTTGGGACCCGATCTGAACCCCTATTTGTCACATCTCG
CTCGGATGTACAACGGGTATGCCGGCGGATTTGAAGTGCAGGTGATTCTGGCTGGGAACGCGTTCACTG
CTGGCAAAGTGATCTTTGCAGCGGTGCCTCCCAACTTCCCCACTGAAGGACTGTCTCCAAGCCAGGTCAC
AATGTTTCCACACATCGTGGTGGACGTACGGCAGCTAGAGCCTGTCCTGATTCCCCTCCCTGATGTACGC
AATAATTTCTACCACTACAATCAATCCAATGATCCGACCATTAAACTCATCGCGATGTTGTACACCCCTCTG
CGCGCTAACAATGCTGGAGACGACGTATTCACCGTGTCATGCAGAGTGCTCACCAGACCTTCACCAGACT
TTGACTTTATCTTCTTAGTGCCCCCCACTGTTGAGAGCCGAACCAAGCCCTTTAGTGTCCCCGTACTCACA
GTCGAGGAGATGACAAATAGCCGCTTTCCAATCCCCCTTGAGAAACTGTTCACAGGACCTTCCTCGGCAT
TCGTGGTTCAGCCACAGAACGGACGCTGCACAACTGACGGCGTGCTGCTCGGAACCACCCAGCTTAGCC

FIGURE 32EE (cont)

CTGTTAATATCTGTACGTTTAGAGGCGACGTAACTCACATAACTGGCTCACGGAACTATACCATGAATCTG
GCATCACAGAATTGGAATGACTACGACCCAACCGAAGAGATTCCCGCACCTCTTGGAACCCCCGACTTTG
TGGGAAAAATACAGGGCGTCCTGACACAAACCACCAGAACCGATGGCTCCACACGGGGACACAAGGCA
ACCGTCTACACTGGCTCTGCCGATTTTGCCCCGAAACTGGGTAGAGTGCAGTTTGAGACCGACACTGACC
GGGACTTTGAAGCCAATCAGAATACTAAGTTCACACCTGTAGGAGTGATTCAGGACGGGGGCACCACTC
ACCGGAACGAGCCGCAACAATGGGTCCTGCCCTCTTATAGCGGGAGGAATACTCATAATGTGCATTTGG
CTCCTGCAGTGGCTCCCACGTTTCCCGGGGAACAACTGCTCTTTTTTCGTTCAACCATGCCTGGATGCTCC
GGATATCCCAATATGGATCTCGATTGCCTGCTCCCACAGGAATGGGTGCAGTATTTTTATCAAGAGGCCG
CACCAGCCCAATCCGACGTCGCACTTCTGCGGTTCGTGAATCCAGACACAGGCCGCGTGTTGTTTGAGTG
CAAATTGCACAAATCAGGATACGTTACAGTGGCTCATACTGGACAGCATGACCTGGTGATCCCACCCAAC
GGATATTTTAGGTTCGACTCCTGGGTGAATCAGTTTTATACATTAGCCCCCATGGGGAATGGGACTGGCA
GACGCAGGGCTGTCTGA

FIGURE 32FF

Amino acid sequence of VP1_GII.4_Syd12_P80X; where X = A, N, K, or H (SEQ ID NO:286)

MKMASSDANPSDGSAANLVPEVNNEVMALEPVVGAAIAAPVAGQQNVIDPWIRNNFVQAPGGEFTVSPR
NAPGEILWSAXLGPDLNPYLSHLARMYNGYAGGFEVQVILAGNAFTAGKVIFAAVPPNFPTEGLSPSQVTMF
PHIVVDVRQLEPVLIPLPDVRNNFYHYNQSNDPTIKLIAMLYTPLRANNAGDDVFTVSCRVLTRPSPDFDFIFLV
PPTVESRTKPFSVPVLTVEEMTNSRFPIPLEKLFTGPSSAFVVQPQNGRCTTDGVLLGTTQLSPVNICTFRGDVT
HITGSRNYTMNLASQNWNDYDPTEEIPAPLGTPDFVGKIQGVLTQTTRTDGSTRGHKATVYTGSADFAPKLG
RVQFETDTDRDFEANQNTKFTPVGVIQDGGTTHRNEPQQWVLPSYSGRNTHNVHLAPAVAPTFPGEQLLFF
RSTMPGCSGYPNMDLDCLLPQEWVQYFYQEAAPAQSDVALLRFVNPDTGRVLFECKLHKSGYVTVAHTGQ
HDLVIPPNGYFRFDSWVNQFYTLAPMGNGTGRRRAV

FIGURE 32GG (SEQ ID NO:289)

hCod optimize sequence of VP1 GII.4_Syd12_P80S+A39X; X = I(XXX=ATC), M(XXX=ATG), G(XXX=GGC), S(XXX=AGC), E(XXX=GAG), D(XXX=GAC), N(XXX=AAC), Q(XXX=CAG), K(XXX=AAG), or H(XXX=CAC)

ATGAAAATGGCCTCGAGTGACGCTAACCCTAGTGACGGCAGCGCCGCCAATCTTGTGCCTGAGGTTAAT
AATGAGGTGATGGCCCTGGAGCCTGTGGTGGGCGCAGCCATAGCAXXXCCCGTGGCCGGTCAGCAGAA
TGTGATTGACCCGTGGATACGCAACAATTTTGTCCAAGCCCCTGGTGGGGAGTTCACCGTTAGCCCGAGA
AATGCGCCAGGAGAAATCCTGTGGTCGGCCAGCTTGGGACCCGATCTGAACCCCTATTTGTCACATCTCG
CTCGGATGTACAACGGGTATGCCGGCGGATTTGAAGTGCAGGTGATTCTGGCTGGGAACGCGTTCACTG
CTGGCAAAGTGATCTTTGCAGCGGTGCCTCCCAACTTCCCCACTGAAGGACTGTCTCCAAGCCAGGTCAC
AATGTTTCCACACATCGTGGTGGACGTACGGCAGCTAGAGCCTGTCCTGATTCCCCTCCCTGATGTACGC
AATAATTTCTACCACTACAATCAATCCAATGATCCGACCATTAAACTCATCGCGATGTTGTACACCCCTCTG
CGCGCTAACAATGCTGGAGACGACGTATTCACCGTGTCATGCAGAGTGCTCACCAGACCTTCACCAGACT
TTGACTTTATCTTCTTAGTGCCCCCCACTGTTGAGAGCCGAACCAAGCCCTTTAGTGTCCCCGTACTCACA

FIGURE 32GG (cont)

GTCGAGGAGATGACAAATAGCCGCTTTCCAATCCCCCTTGAGAAACTGTTCACAGGACCTTCCTCGGCAT
TCGTGGTTCAGCCACAGAACGGACGCTGCACAACTGACGGCGTGCTGCTCGGAACCACCCAGCTTAGCC
CTGTTAATATCTGTACGTTTAGAGGCGACGTAACTCACATAACTGGCTCACGGAACTATACCATGAATCTG
GCATCACAGAATTGGAATGACTACGACCCAACCGAAGAGATTCCCGCACCTCTTGGAACCCCCGACTTTG
TGGGAAAAATACAGGGCGTCCTGACACAAACCACCAGAACCGATGGCTCCACACGGGGACACAAGGCA
ACCGTCTACACTGGCTCTGCCGATTTTGCCCCGAAACTGGGTAGAGTGCAGTTTGAGACCGACACTGACC
GGGACTTTGAAGCCAATCAGAATACTAAGTTCACACCTGTAGGAGTGATTCAGGACGGGGGCACCACTC
ACCGGAACGAGCCGCAACAATGGGTCCTGCCCTCTTATAGCGGGAGGAATACTCATAATGTGCATTTGG
CTCCTGCAGTGGCTCCCACGTTTCCCGGGGAACAACTGCTCTTTTTTCGTTCAACCATGCCTGGATGCTCC
GGATATCCCAATATGGATCTCGATTGCCTGCTCCCACAGGAATGGGTGCAGTATTTTTATCAAGAGGCCG
CACCAGCCCAATCCGACGTCGCACTTCTGCGGTTCGTGAATCCAGACACAGGCCGCGTGTTGTTTGAGTG
CAAATTGCACAAATCAGGATACGTTACAGTGGCTCATACTGGACAGCATGACCTGGTGATCCCACCCAAC
GGATATTTTAGGTTCGACTCCTGGGTGAATCAGTTTTATACATTAGCCCCCATGGGGAATGGGACTGGCA
GACGCAGGGCTGTCTGA

FIGURE 32HH (SEQ ID NO:288)

Amino acid sequence of VP1_GII.4_Syd12_P80S+A39X; where X = I, M, G, S, E, D, N, Q, K, or H MKMASSDANPSDGSAANLVPEVNNEVMALEPVVGAAIAXPVAGQQNVIDPWIRNNFVQAPGGEFTVSPR
NAPGEILWSASLGPDLNPYLSHLARMYNGYAGGFEVQVILAGNAFTAGKVIFAAVPPNFPTEGLSPSQVTMF
PHIVVDVRQLEPVLIPLPDVRNNFYHYNQSNDPTIKLIAMLYTPLRANNAGDDVFTVSCRVLTRPSPDFDFIFLV
PPTVESRTKPFSVPVLTVEEMTNSRFPIPLEKLFTGPSSAFVVQPQNGRCTTDGVLLGTTQLSPVNICTFRGDVT
HITGSRNYTMNLASQNWNDYDPTEEIPAPLGTPDFVGKIQGVLTQTTRTDGSTRGHKATVYTGSADFAPKLG
RVQFETDTDRDFEANQNTKFTPVGVIQDGGTTHRNEPQQWVLPSYSGRNTHNVHLAPAVAPTFPGEQLLFF
RSTMPGCSGYPNMDLDCLLPQEWVQYFYQEAAPAQSDVALLRFVNPDTGRVLFECKLHKSGYVTVAHTGQ
HDLVIPPNGYFRFDSWVNQFYTLAPMGNGTGRRRAV

Figure 33A

Amino acid sequence of VP1_GII.6_Ohio_E80S (SEQ ID NO:79)

MKMASNDAAPSNDGAANLVPEANNEVMALEPVVGASIAAPVVGQQNIIDPWIRENFVQAPQGEFTVSPRNSPGEMLL
NLSLGPELNPYLSHLSRMYNGYAGGMQVQVVLAGNAFTAGKIIFAAVPPHFPVENINAAQITMCPHVIVDVRQLEPVLLP
LPDIRNRFFHYNQENTSRMRLVAMLYTPLRANSGEDVFTVSCRVLTRPAPDFEFTFLVPPTVESKTKPFSLPILTLGELSNSR
FPAPIDMLYTDPNEGIVVQPQNGRCTLDGTLQGTTQLVPTQICAFRGTLIGQTSRSPDSTDSAPRRRDHPLHVQLKNLDG
TQYDPTDEVPAVLGAIDFKGTVFGVASQRDVSGQQVGATRAHEVHINTTDPRYTPKLGSILMYSESDDFVTGQPVRFTPI
GMGDNDWHQWELPDYPGHLTLNMNLAPAVAPAFPGERILFFRSIVPSAGGYGSGQIDCLIPQEWVQHFYQEAAPSQS
AVALIRYVNPDTGRNIFEAKLHREGFITVANSGNNPIVVPPNGYFRFEAWVNQFYTLTPMGTGQGRRRDQ

Figure 33B

Nucleic acid sequence of human codon optimized VP1_GII.6_Ohio_E80S (SEQ ID NO:80)

ATGAAGATGGCAAGCAACGACGCAGCTCCCTCCAATGATGGTGCCGCCAACCTGGTCCCCGAAGCTAATAATGAGG
TGATGGCGTTAGAGCCGGTGGTTGGCGCATCTATTGCAGCGCCTGTGGTCGGACAGCAGAACATCATTGATCCCTG
GATTCGCGAGAACTTCGTACAAGCTCCACAGGGGGAGTTCACAGTCTCCCCCCGGAACTCCCCGGGCGAGATGCTG
CTCAATCTGAGCCTCGGCCCTGAACTAAACCCTTATCTGTCACACCTTTCACGGATGTACAATGGCTACGCAGGAGG
AATGCAAGTTCAGGTGGTCCTGGCCGGCAATGCTTTCACCGCGGGCAAAATCATCTTTGCGGCCGTTCCTCCACACT
TCCCTGTCGAAAATATCAACGCCGCCCAGATTACTATGTGCCCCCACGTGATTGTGGATGTGCGACAGTTAGAGCCA
GTTCTGCTGCCCCTGCCCGACATCAGAAACCGGTTCTTCCATTACAATCAAGAGAATACTTCACGGATGAGACTTGTT
GCGATGCTGTACACCCCTCTTCGTGCAAATTCCGGCGAAGACGTGTTCACTGTGTCTTGTCGAGTACTTACCCGACCC
GCCCCCGATTTCGAATTCACCTTCCTGGTTCCCCCTACTGTGGAGAGCAAGACAAAACCCTTCAGCCTCCCAATCTTA
ACACTCGGGGAGCTGTCTAATTCACGCTTCCCCGCACCTATTGATATGCTGTATACTGACCCCAACGAGGGGATAGT
GGTGCAGCCCCAAAATGGACGGTGTACTCTCGACGGCACGCTCCAGGGCACAACCCAACTGGTGCCAACCCAGATT
TGTGCATTCAGGGGCACTTTGATTGGGCAGACATCGAGATCTCCAGATTCTACTGATTCCGCGCCAAGGAGGAGGG
ACCACCCACTCCACGTTCAGTTAAAAAACCTGGACGGAACCCAGTACGACCCTACAGACGAGGTCCCCGCTGTCCTC
GGAGCCATCGACTTTAAAGGAACTGTATTTGGAGTGGCATCCCAAAGGGATGTCTCGGGGCAGCAGGTGGGAGCT
ACGAGAGCACATGAAGTCCACATTAACACCACAGACCCAAGATATACCCCAAAACTAGGGTCAATTTTAATGTATTC
GGAATCAGACGATTTTGTTACAGGTCAGCCCGTGCGGTTTACCCCGATCGGAATGGGGGACAACGATTGGCACCAG
TGGGAATTGCCCGATTACCCTGGACACCTCACCTTGAATATGAATCTGGCCCCAGCCGTCGCGCCCGCCTTCCCCGGT
GAGCGGATCCTCTTTTTTAGAAGCATAGTGCCCTCCGCAGGTGGGTATGGATCAGGGCAGATTGATTGCCTGATCCC
CCAAGAATGGGTACAGCATTTCTACCAGGAAGCAGCCCCTAGCCAGTCCGCAGTAGCACTGATCAGATATGTTAATC
CTGATACGGGAAGGAACATCTTCGAAGCAAAACTGCACCGTGAGGGCTTCATTACCGTCGCCAACAGTGGTAATAA
CCCTATTGTGGTGCCTCCTAATGGATACTTCAGGTTTGAGGCATGGGTGAATCAGTTTTATACTCTGACTCCCATGGG
GACAGGCCAGGGGCGACGCCGGGATCAGTGA

Figure 33C

Amino acid sequence of VP1_GII.6_Ohio_S90L (SEQ ID NO:81)

MKMASNDAAPSNDGAANLVPEANNEVMALEPVVGASIAAPVVGQQNIIDPWIRENFVQAPQGEFTVSPRNSPGEMLL
NLELGPELNPYLLHLSRMYNGYAGGMQVQVVLAGNAFTAGKIIFAAVPPHFPVENINAAQITMCPHVIVDVRQLEPVLLP
LPDIRNRFFHYNQENTSRMRLVAMLYTPLRANSGEDVFTVSCRVLTRPAPDFEFTFLVPPTVESKTKPFSLPILTLGELSNSR
FPAPIDMLYTDPNEGIVVQPQNGRCTLDGTLQGTTQLVPTQICAFRGTLIGQTSRSPDSTDSAPRRRDHPLHVQLKNLDG
TQYDPTDEVPAVLGAIDFKGTVFGVASQRDVSGQQVGATRAHEVHINTTDPRYTPKLGSILMYSESDDFVTGQPVRFTPI
GMGDNDWHQWELPDYPGHLTLNMNLAPAVAPAFPGERILFFRSIVPSAGGYGSGQIDCLIPQEWVQHFYQEAAPSQS
AVALIRYVNPDTGRNIFEAKLHREGFITVANSGNNPIVVPPNGYFRFEAWVNQFYTLTPMGTGQGRRRDQ

Figure 33D

Nucleic acid sequence of human codon optimized VP1_GII.6_Ohio_S90L (SEQ ID NO:82)

ATGAAGATGGCAAGCAACGACGCAGCTCCCTCCAATGATGGTGCCGCCAACCTGGTCCCCGAAGCTAATAATGAGG
TGATGGCGTTAGAGCCGGTGGTTGGCGCATCTATTGCAGCGCCTGTGGTCGGACAGCAGAACATCATTGATCCCTG
GATTCGCGAGAACTTCGTACAAGCTCCACAGGGGGAGTTCACAGTCTCCCCCCGGAACTCCCCGGGCGAGATGCTG
CTCAATCTGGAACTCGGCCCTGAACTAAACCCTTATCTGCTCCACCTTTCACGGATGTACAATGGCTACGCAGGAGG

FIGURE 33D (cont)

AATGCAAGTTCAGGTGGTCCTGGCCGGCAATGCTTTCACCGCGGGCAAAATCATCTTTGCGGCCGTTCCTCCACACT
TCCCTGTCGAAAATATCAACGCCGCCCAGATTACTATGTGCCCCCACGTGATTGTGGATGTGCGACAGTTAGAGCCA
GTTCTGCTGCCCCTGCCCGACATCAGAAACCGGTTCTTCCATTACAATCAAGAGAATACTTCACGGATGAGACTTGTT
GCGATGCTGTACACCCCTCTTCGTGCAAATTCCGGCGAAGACGTGTTCACTGTGTCTTGTCGAGTACTTACCCGACCC
GCCCCCGATTTCGAATTCACCTTCCTGGTTCCCCCTACTGTGGAGAGCAAGACAAAACCCTTCAGCCTCCCAATCTTA
ACACTCGGGGAGCTGTCTAATTCACGCTTCCCCGCACCTATTGATATGCTGTATACTGACCCCAACGAGGGGATAGT
GGTGCAGCCCCAAAATGGACGGTGTACTCTCGACGGCACGCTCCAGGGCACAACCCAACTGGTGCCAACCCAGATT
TGTGCATTCAGGGGCACTTTGATTGGGCAGACATCGAGATCTCCAGATTCTACTGATTCCGCGCCAAGGAGGAGGG
ACCACCCACTCCACGTTCAGTTAAAAAACCTGGACGGAACCCAGTACGACCCTACAGACGAGGTCCCCGCTGTCCTC
GGAGCCATCGACTTTAAAGGAACTGTATTTGGAGTGGCATCCCAAAGGGATGTCTCGGGGCAGCAGGTGGGAGCT
ACGAGAGCACATGAAGTCCACATTAACACCACAGACCCAAGATATACCCCAAAACTAGGGTCAATTTTAATGTATTC
GGAATCAGACGATTTTGTTACAGGTCAGCCCGTGCGGTTTACCCCGATCGGAATGGGGGACAACGATTGGCACCAG
TGGGAATTGCCCGATTACCCTGGACACCTCACCTTGAATATGAATCTGGCCCCAGCCGTCGCGCCCGCCTTCCCCGGT
GAGCGGATCCTCTTTTTTAGAAGCATAGTGCCCTCCGCAGGTGGGTATGGATCAGGGCAGATTGATTGCCTGATCCC
CCAAGAATGGGTACAGCATTTCTACCAGGAAGCAGCCCCTAGCCAGTCCGCAGTAGCACTGATCAGATATGTTAATC
CTGATACGGGAAGGAACATCTTCGAAGCAAAACTGCACCGTGAGGGCTTCATTACCGTCGCCAACAGTGGTAATAA
CCCTATTGTGGTGCCTCCTAATGGATACTTCAGGTTTGAGGCATGGGTGAATCAGTTTTATACTCTGACTCCCATGGG
GACAGGCCAGGGGCGACGCCGGGATCAGTGA

Figure 33E

Amino acid sequence of VP1_GII.6_Ohio_E80S+S90L (SEQ ID NO:83)

MKMASNDAAPSNDGAANLVPEANNEVMALEPVVGASIAAPVVGQQNIIDPWIRENFVQAPQGEFTVSPRNSPGEMLL
NLSLGPELNPYLLHLSRMYNGYAGGMQVQVVLAGNAFTAGKIIFAAVPPHFPVENINAAQITMCPHVIVDVRQLEPVLLP
LPDIRNRFFHYNQENTSRMRLVAMLYTPLRANSGEDVFTVSCRVLTRPAPDFEFTFLVPPTVESKTKPFSLPILTLGELSNSR
FPAPIDMLYTDPNEGIVVQPQNGRCTLDGTLQGTTQLVPTQICAFRGTLIGQTSRSPDSTDSAPRRRDHPLHVQLKNLDG
TQYDPTDEVPAVLGAIDFKGTVFGVASQRDVSGQQVGATRAHEVHINTTDPRYTPKLGSILMYSESDDFVTGQPVRFTPI
GMGDNDWHQWELPDYPGHLTLNMNLAPAVAPAFPGERILFFRSIVPSAGGYGSGQIDCLIPQEWVQHFYQEAAPSQS
AVALIRYVNPDTGRNIFEAKLHREGFITVANSGNNPIVVPPNGYFRFEAWVNQFYTLTPMGTGQGRRRDQ

Figure 33F

Nucleic acid sequence of human codon optimized VP1_GII.6_Ohio_E80S+S90L (SEQ IDNO:84)

ATGAAGATGGCAAGCAACGACGCAGCTCCCTCCAATGATGGTGCCGCCAACCTGGTCCCCGAAGCTAATAATGAGG
TGATGGCGTTAGAGCCGGTGGTTGGCGCATCTATTGCAGCGCCTGTGGTCGGACAGCAGAACATCATTGATCCCTG
GATTCGCGAGAACTTCGTACAAGCTCCACAGGGGGAGTTCACAGTCTCCCCCCGGAACTCCCCGGGCGAGATGCTG
CTCAATCTGAGCCTCGGCCCTGAACTAAACCCTTATCTGCTCCACCTTTCACGGATGTACAATGGCTACGCAGGAGGA
ATGCAAGTTCAGGTGGTCCTGGCCGGCAATGCTTTCACCGCGGGCAAAATCATCTTTGCGGCCGTTCCTCCACACTTC
CCTGTCGAAAATATCAACGCCGCCCAGATTACTATGTGCCCCCACGTGATTGTGGATGTGCGACAGTTAGAGCCAGT
TCTGCTGCCCCTGCCCGACATCAGAAACCGGTTCTTCCATTACAATCAAGAGAATACTTCACGGATGAGACTTGTTGC
GATGCTGTACACCCCTCTTCGTGCAAATTCCGGCGAAGACGTGTTCACTGTGTCTTGTCGAGTACTTACCCGACCCGC
CCCCGATTTCGAATTCACCTTCCTGGTTCCCCCTACTGTGGAGAGCAAGACAAAACCCTTCAGCCTCCCAATCTTAAC
ACTCGGGGAGCTGTCTAATTCACGCTTCCCCGCACCTATTGATATGCTGTATACTGACCCCAACGAGGGGATAGTGG

FIGURE 33F (cont)

TGCAGCCCCAAAATGGACGGTGTACTCTCGACGGCACGCTCCAGGGCACAACCCAACTGGTGCCAACCCAGATTTGT
GCATTCAGGGGCACTTTGATTGGGCAGACATCGAGATCTCCAGATTCTACTGATTCCGCGCCAAGGAGGAGGGACC
ACCCACTCCACGTTCAGTTAAAAAACCTGGACGGAACCCAGTACGACCCTACAGACGAGGTCCCCGCTGTCCTCGGA
GCCATCGACTTTAAAGGAACTGTATTTGGAGTGGCATCCCAAAGGGATGTCTCGGGGCAGCAGGTGGGAGCTACGA
GAGCACATGAAGTCCACATTAACACCACAGACCCAAGATATACCCCAAAACTAGGGTCAATTTTAATGTATTCGGAA
TCAGACGATTTTGTTACAGGTCAGCCCGTGCGGTTTACCCCGATCGGAATGGGGGACAACGATTGGCACCAGTGGG
AATTGCCCGATTACCCTGGACACCTCACCTTGAATATGAATCTGGCCCCAGCCGTCGCGCCCGCCTTCCCCGGTGAGC
GGATCCTCTTTTTTAGAAGCATAGTGCCCTCCGCAGGTGGGTATGGATCAGGGCAGATTGATTGCCTGATCCCCCAA
GAATGGGTACAGCATTTCTACCAGGAAGCAGCCCCTAGCCAGTCCGCAGTAGCACTGATCAGATATGTTAATCCTGA
TACGGGAAGGAACATCTTCGAAGCAAAACTGCACCGTGAGGGCTTCATTACCGTCGCCAACAGTGGTAATAACCCT
ATTGTGGTGCCTCCTAATGGATACTTCAGGTTTGAGGCATGGGTGAATCAGTTTTATACTCTGACTCCCATGGGGAC
AGGCCAGGGGCGACGCCGGGATCAGTGA

Figure 34A

Amino acid sequence of VP1_GII.12_HS10_E80S (SEQ ID NO:88)

MKMASNDAAPSNDGAAGLVPEVNNETMALEPVAGASIAAPLTGQNNVIDPWIRLNFVQAPNGEFTVSPRNSPGEVLL
NLSLGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFTLPILTIGELTNS
RFPVPIDELYTSPNESLVVQPQNGRCALDGELQGTTQLLPTAICSFRGRINQKVSGENHVWNMQVTNIDGTPFDPTEDV
PAPLGTPDFSGKLFGVLSQRDHDNACRSHDAVIATNSAKFTPKLGAIQIGTWEQDDVHINQPTKFTPVGLFESEGFNQW
TLPNYSGALTLNMGLAPPVAPTFPGEQILFFRSHIPLKGGVADPVIDCLLPQEWIQHLYQESAPSQTDVALIRFTNPDTGRV
LFEAKLHRSGYITVANTGSRPIVVPANGYFRFDSWVNQFYSLAPMGTGNGRRRVQ

Figure 34B

Nucleic acid sequence of human codon optimized VP1_GII.12_HS10_E80S (SEQ ID NO:89)

ATGAAGATGGCGTCTAATGATGCTGCTCCTTCCAATGATGGCGCAGCCGGCCTGGTCCCTGAAGTGAATAACGAGA
CTATGGCTCTCGAACCCGTGGCCGGAGCCTCAATTGCCGCCCCCCTCACTGGCCAGAACAACGTGATTGATCCCTGG
ATCAGACTGAACTTCGTTCAGGCTCCTAATGGGGAGTTCACCGTGTCCCCGAGAAACTCCCCCGGCGAAGTGTTATT
GAATTTGAGCTTAGGACCAGAACTCAACCCCTATCTGGCACATCTGTCTCGGATGTACAACGGCTATGCGGGCGGAG
TGGAGGTGCAAGTTCTTCTCGCTGGTAATGCATTCACAGCAGGAAAATTAGTATTTGCAGCGGTTCCACCCCATTTTC
CACTTGAAAACATAAGCCCAGGCCAGATCACCATGTTCCCTCACGTGATAATCGACGTGCGGACATTAGAGCCCGTG
CTGCTACCCCTGCCCGACGTGAGGAACAATTTCTTTCACTACAATCAGCAAAATGAACCAAGAATGCGCCTGGTCGC
CATGCTCTATACTCCTTTAAGAAGTAATGGCAGTGGGGATGACGTGTTTACTGTTAGCTGTCGGGTGCTCACCCGAC
CTTCCCCAGATTTCGACTTCAATTATCTGGTCCCCCCCACGGTAGAGTCCAAAACAAAGCCTTTCACTCTTCCAATCCT
TACAATTGGCGAACTGACCAACTCACGCTTTCCAGTGCCTATTGATGAGCTGTACACAAGTCCAAATGAATCCCTTGT
CGTTCAGCCACAGAATGGGCGCTGCGCGCTTGACGGTGAGCTCCAGGGCACAACACAACTGTTGCCAACCGCTATA
TGCTCTTTCAGGGGGCGTATTAATCAGAAGGTCTCCGGGGAGAACCACGTGTGGAACATGCAAGTGACGAATATCG
ACGGGACACCTTTCGATCCAACAGAGGATGTCCCAGCGCCTCTAGGTACCCCTGACTTCTCAGGCAAGTTGTTCGGC
GTCCTTTCCCAGCGCGACCATGATAATGCTTGCCGGAGCCACGATGCCGTCATTGCCACCAACTCAGCCAAATTCACC
CCAAAACTTGGAGCGATACAGATCGGAACTTGGGAACAAGACGACGTCCATATCAACCAACCAACAAAGTTTACCCC
TGTTGGCCTTTTCGAAAGCGAAGGCTTTAACCAGTGGACACTTCCCAATTACAGCGGGGCTCTCACTCTTAATATGG

FIGURE 34B (cont)

GACTCGCACCACCCGTCGCTCCAACGTTTCCTGGTGAGCAGATTTTGTTTTTCCGCAGTCATATTCCACTGAAGGGTG
GAGTTGCTGATCCCGTGATAGACTGCCTCCTCCCTCAGGAATGGATTCAGCACTTGTATCAGGAGTCCGCTCCCTCGC
AGACCGATGTGGCCCTGATACGCTTCACAAACCCCGATACCGGAAGAGTGTTGTTTGAAGCTAAACTTCATCGCTCC
GGTTACATCACAGTAGCCAACACGGGTTCCAGGCCAATCGTAGTTCCGGCAAACGGATACTTTCGATTCGACAGTTG
GGTCAATCAGTTCTACAGCCTGGCTCCAATGGGAACAGGAAATGGGAGGAGGCGTGTGCAGTAA

Figure 34C

Amino acid sequence of VP1_GII.12_HS10_A90L (SEQ ID NO:90)

MKMASNDAAPSNDGAAGLVPEVNNETMALEPVAGASIAAPLTGQNNVIDPWIRLNFVQAPNGEFTVSPRNSPGEVLL
NLELGPELNPYLLHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFTLPILTIGELTNS
RFPVPIDELYTSPNESLVVQPQNGRCALDGELQGTTQLLPTAICSFRGRINQKVSGENHVWNMQVTNIDGTPFDPTEDV
PAPLGTPDFSGKLFGVLSQRDHDNACRSHDAVIATNSAKFTPKLGAIQIGTWEQDDVHINQPTKFTPVGLFESEGFNQW
TLPNYSGALTLNMGLAPPVAPTFPGEQILFFRSHIPLKGGVADPVIDCLLPQEWIQHLYQESAPSQTDVALIRFTNPDTGRV
LFEAKLHRSGYITVANTGSRPIVVPANGYFRFDSWVNQFYSLAPMGTGNGRRRVQ

Figure 34D

Nucleic acid sequence of human codon optimized VP1_GII.12_HS10_A90L (SEQ ID NO:91)

ATGAAGATGGCGTCTAATGATGCTGCTCCTTCCAATGATGGCGCAGCCGGCCTGGTCCCTGAAGTGAATAACGAGA
CTATGGCTCTCGAACCCGTGGCCGGAGCCTCAATTGCCGCCCCCCTCACTGGCCAGAACAACGTGATTGATCCCTGG
ATCAGACTGAACTTCGTTCAGGCTCCTAATGGGGAGTTCACCGTGTCCCCGAGAAACTCCCCCGGCGAAGTGTTATT
GAATTTGGAATTAGGACCAGAACTCAACCCCTATCTGCTCCATCTGTCTCGGATGTACAACGGCTATGCGGGCGGAG
TGGAGGTGCAAGTTCTTCTCGCTGGTAATGCATTCACAGCAGGAAAATTAGTATTTGCAGCGGTTCCACCCCATTTTC
CACTTGAAAACATAAGCCCAGGCCAGATCACCATGTTCCCTCACGTGATAATCGACGTGCGGACATTAGAGCCCGTG
CTGCTACCCCTGCCCGACGTGAGGAACAATTTCTTTCACTACAATCAGCAAAATGAACCAAGAATGCGCCTGGTCGC
CATGCTCTATACTCCTTTAAGAAGTAATGGCAGTGGGGATGACGTGTTTACTGTTAGCTGTCGGGTGCTCACCCGAC
CTTCCCCAGATTTCGACTTCAATTATCTGGTCCCCCCCACGGTAGAGTCCAAAACAAAGCCTTTCACTCTTCCAATCCT
TACAATTGGCGAACTGACCAACTCACGCTTTCCAGTGCCTATTGATGAGCTGTACACAAGTCCAAATGAATCCCTTGT
CGTTCAGCCACAGAATGGGCGCTGCGCGCTTGACGGTGAGCTCCAGGGCACAACACAACTGTTGCCAACCGCTATA
TGCTCTTTCAGGGGGGCGTATTAATCAGAAGGTCTCCGGGGAGAACCACGTGTGGAACATGCAAGTGACGAATATCG
ACGGGACACCTTTCGATCCAACAGAGGATGTCCCAGCGCCTCTAGGTACCCCTGACTTCTCAGGCAAGTTGTTCGGC
GTCCTTTCCCAGCGCGACCATGATAATGCTTGCCGGAGCCACGATGCCGTCATTGCCACCAACTCAGCCAAATTCACC
CCAAAACTTGGAGCGATACAGATCGGAACTTGGGAACAAGACGACGTCCATATCAACCAACCAACAAAGTTTACCCC
TGTTGGCCTTTTCGAAAGCGAAGGCTTTAACCAGTGGACACTTCCCAATTACAGCGGGGCTCTCACTCTTAATATGG
GACTCGCACCACCCGTCGCTCCAACGTTTCCTGGTGAGCAGATTTTGTTTTTCCGCAGTCATATTCCACTGAAGGGTG
GAGTTGCTGATCCCGTGATAGACTGCCTCCTCCCTCAGGAATGGATTCAGCACTTGTATCAGGAGTCCGCTCCCTCGC
AGACCGATGTGGCCCTGATACGCTTCACAAACCCCGATACCGGAAGAGTGTTGTTTGAAGCTAAACTTCATCGCTCC
GGTTACATCACAGTAGCCAACACGGGTTCCAGGCCAATCGTAGTTCCGGCAAACGGATACTTTCGATTCGACAGTTG
GGTCAATCAGTTCTACAGCCTGGCTCCAATGGGAACAGGAAATGGGAGGAGGCGTGTGCAGTAA

Figure 34E

Amino acid sequence of VP1_GII.12_HS10_E80S+A90L (SEQ ID NO:92)

MKMASNDAAPSNDGAAGLVPEVNNETMALEPVAGASIAAPLTGQNNVIDPWIRLNFVQAPNGEFTVSPRNSPGEVLL
NLSLGPELNPYLLHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFTLPILTIGELTNS
RFPVPIDELYTSPNESLVVQPQNGRCALDGELQGTTQLLPTAICSFRGRINQKVSGENHVWNMQVTNIDGTPFDPTEDV
PAPLGTPDFSGKLFGVLSQRDHDNACRSHDAVIATNSAKFTPKLGAIQIGTWEQDDVHINQPTKFTPVGLFESEGFNQW
TLPNYSGALTLNMGLAPPVAPTFPGEQILFFRSHIPLKGGVADPVIDCLLPQEWIQHLYQESAPSQTDVALIRFTNPDTGRV
LFEAKLHRSGYITVANTGSRPIVVPANGYFRFDSWVNQFYSLAPMGTGNGRRRVQ

Figure 34F

Nucleic acid sequence of human codon optimized VP1_GII.12_HS10_E80S+A90L (SEQ ID NO:93)

ATGAAGATGGCGTCTAATGATGCTGCTCCTTCCAATGATGGCGCAGCCGGCCTGGTCCCTGAAGTGAATAACGAGA
CTATGGCTCTCGAACCCGTGGCCGGAGCCTCAATTGCCGCCCCCCTCACTGGCCAGAACAACGTGATTGATCCCTGG
ATCAGACTGAACTTCGTTCAGGCTCCTAATGGGGAGTTCACCGTGTCCCCGAGAAACTCCCCCGGCGAAGTGTTATT
GAATTTGAGCTTAGGACCAGAACTCAACCCCTATCTGCTCCATCTGTCTCGGATGTACAACGGCTATGCGGGCGGAG
TGGAGGTGCAAGTTCTTCTCGCTGGTAATGCATTCACAGCAGGAAAATTAGTATTTGCAGCGGTTCCACCCCATTTTC
CACTTGAAAACATAAGCCCAGGCCAGATCACCATGTTCCCTCACGTGATAATCGACGTGCGGACATTAGAGCCCGTG
CTGCTACCCCTGCCCGACGTGAGGAACAATTTCTTTCACTACAATCAGCAAAATGAACCAAGAATGCGCCTGGTCGC
CATGCTCTATACTCCTTTAAGAAGTAATGGCAGTGGGGATGACGTGTTTACTGTTAGCTGTCGGGTGCTCACCCGAC
CTTCCCCAGATTTCGACTTCAATTATCTGGTCCCCCCCACGGTAGAGTCCAAAACAAAGCCTTTCACTCTTCCAATCCT
TACAATTGGCGAACTGACCAACTCACGCTTTCCAGTGCCTATTGATGAGCTGTACACAAGTCCAAATGAATCCCTTGT
CGTTCAGCCACAGAATGGGCGCTGCGCGCTTGACGGTGAGCTCCAGGGCACAACACAACTGTTGCCAACCGCTATA
TGCTCTTTCAGGGGGCGTATTAATCAGAAGGTCTCCGGGGAGAACCACGTGTGGAACATGCAAGTGACGAATATCG
ACGGGACACCTTTCGATCCAACAGAGGATGTCCCAGCGCCTCTAGGTACCCCTGACTTCTCAGGCAAGTTGTTCGGC
GTCCTTTCCCAGCGCGACCATGATAATGCTTGCCGGAGCCACGATGCCGTCATTGCCACCAACTCAGCCAAATTCACC
CCAAAACTTGGAGCGATACAGATCGGAACTTGGGAACAAGACGACGTCCATATCAACCAACCAACAAAGTTTACCCC
TGTTGGCCTTTTCGAAAGCGAAGGCTTTAACCAGTGGACACTTCCCAATTACAGCGGGGCTCTCACTCTTAATATGG
GACTCGCACCACCCGTCGCTCCAACGTTTCCTGGTGAGCAGATTTTGTTTTTCCGCAGTCATATTCCACTGAAGGGTG
GAGTTGCTGATCCCGTGATAGACTGCCTCCTCCCTCAGGAATGGATTCAGCACTTGTATCAGGAGTCCGCTCCCTCGC
AGACCGATGTGGCCCTGATACGCTTCACAAACCCCGATACCGGAAGAGTGTTGTTTGAAGCTAAACTTCATCGCTCC
GGTTACATCACAGTAGCCAACACGGGTTCCAGGCCAATCGTAGTTCCGGCAAACGGATACTTTCGATTCGACAGTTG
GGTCAATCAGTTCTACAGCCTGGCTCCAATGGGAACAGGAAATGGGAGGAGGCGTGTGCAGTAA

FIGURE 34G

Amino acid sequence of VP1 GII.17 Kawa 2014 A0A077KVU6_A39V (SEQ ID NO:192)

MKMASNDAAPSNDGAAGLVPEGNNETLPLEPVAGAAIAVPVTGQNNIIDPWIRTNFVQAPNGEFTVSPRNS
PGEILLNLELGPDLNPYLAHLSRMYNGYAGGVEVQVLLAGNAFTAGKILFAAVPPNFPVEFLSPAQITMLPHLI
VDVRTLEPIMIPLPDVRNTFFHYNNQPNSRMRLVAMLYTPLRSNGSGDDVFTVSCRVLTRPTPDFEFTYLVPP
SVESKTKPFSLPILTLSELTNSRFPVPIDSLFTAQNNVLQVQCQNGRCTLDGELQGTTQLLPSGICAFRGRVTAE
TDHRDKWHMQLQNLNGTTYDPTDDVPAPLGTPDFKGVVFGVASQRNVGNDAPGSTRAHEAVISTYSPQFV

FIGURE 34G (cont)

PKLGSVNFRSNDNDFQLQPTKFTPVGINDDGDHPFRQWELPDYSGLLTLNMNLAPPVAPNFPGEQLLFFRSF
VPCSGGYNQGIVDCLIPQEWIQHFYQESAPSQSDVALIRYVNPDTGRTLFEAKLHRSGYITVAHSGDYPLVVPA
NGYFRFDSWVNQFYSLAPMGTGNGRRRAQ

FIGURE 34H

Nucleic acid sequence of VP1 hCod GII.17 Kawa 2014 A0A077KVU6_A39V (SEQ ID NO:193)

ATGAAAATGGCATCTAACGACGCAGCCCCCTCAAACGATGGCGCTGCTGGACTCGTGCCGGAGGGGAAT
AATGAGACACTTCCACTAGAGCCGGTTGCAGGCGCCGCTATAGCTGTGCCAGTGACAGGGCAGAATAAT
ATTATAGACCCTTGGATTCGGACAAACTTCGTGCAGGCACCCAACGGCGAGTTTACAGTATCCCCCCGGA
ACTCCCCAGGTGAGATACTCCTGAATCTTGAGCTCGGCCCTGACCTCAATCCATATCTGGCTCATCTGAGC
CGCATGTACAATGGTTACGCTGGGGGGGTCGAAGTGCAGGTCCTCCTGGCCGGAAACGCCTTTACCGCT
GGCAAAATTCTGTTTGCCGCCGTTCCACCAAACTTTCCAGTCGAATTCCTCTCTCCCGCGCAAATAACCAT
GCTGCCACATTTGATCGTTGACGTGCGGACCCTGGAGCCAATAATGATTCCCCTGCCGGATGTGCGTAAC
ACCTTTTTCCATTATAACAATCAGCCAAACTCTCGGATGAGACTTGTTGCTATGCTGTACACCCCCCTGCG
GAGCAACGGCAGTGGCGATGATGTGTTTACCGTGAGTTGCAGAGTCCTGACGCGCCCAACCCCGGACTT
CGAGTTCACCTACCTGGTGCCCCCTTCTGTGGAATCTAAGACCAAACCGTTTTCACTGCCAATCTTAACTCT
CTCCGAACTGACTAACAGCCGGTTTCCAGTACCCATAGATTCTCTTTTTACCGCTCAAAACAACGTACTCC
AAGTCCAGTGCCAGAACGGCCGCTGTACGCTTGATGGTGAGTTGCAGGGGACAACACAGCTACTCCCCA
GTGGCATCTGTGCATTCCGGGGCCGCGTGACCGCTGAGACAGACCATCGTGACAAATGGCACATGCAAC
TCCAAAACTTAAACGGGACCACCTACGACCCAACCGACGACGTCCCTGCTCCGCTAGGGACTCCTGACTT
TAAGGGGGTGGTGTTCGGAGTGGCCTCTCAGCGGAATGTTGGGAATGACGCCCCCGGCTCTACCCGAGC
TCACGAGGCCGTTATCTCAACATATAGCCCCCAATTTGTGCCCAAGCTCGGATCCGTTAATTTTCGTAGTA
ACGACAACGACTTCCAACTGCAACCAACGAAGTTTACGCCAGTGGGGATTAATGATGATGGAGACCATC
CTTTCCGCCAATGGGAACTACCAGATTATTCTGGGCTGCTCACCCTCAATATGAACCTCGCCCCACCCGTG
GCCCCTAATTTCCCCGGTGAGCAGCTGCTGTTTTTTCGGAGCTTTGTGCCATGCAGTGGCGGATATAATCA
AGGCATCGTAGACTGCTTGATTCCCCAAGAGTGGATACAACATTTTTACCAGGAAAGTGCGCCCTCCCAG
TCCGATGTGGCCCTGATACGGTACGTTAACCCCGATACCGGAAGAACATTATTCGAAGCGAAATTGCACA
GATCAGGGTACATTACCGTTGCACATTCCGGCGATTATCCCCTGGTGGTTCCCGCCAACGGTTACTTTAG
GTTCGATAGTTGGGTCAACCAGTTCTATTCACTAGCCCCAATGGGCACCGGTAACGGCAGACGCCGGGCT
CAGTAG

FIGURE 34I

Amino acid sequence of VP1GII.17 Kawa 2014 A0A077KVU6_R53I (SEQ ID NO:194)

MKMASNDAAPSNDGAAGLVPEGNNETLPLEPVAGAAIAAPVTGQNNIIDPWIITNFVQAPNGEFTVSPRNS
PGEILLNLELGPDLNPYLAHLSRMYNGYAGGVEVQVLLAGNAFTAGKILFAAVPPNFPVEFLSPAQITMLPHLI
VDVRTLEPIMIPLPDVRNTFFHYNNQPNSRMRLVAMLYTPLRSNGSGDDVFTVSCRVLTRPTPDFEFTYLVPP
SVESKTKPFSLPILTLSELTNSRFPVPIDSLFTAQNNVLQVQCQNGRCTLDGELQGTTQLLPSGICAFRGRVTAE
TDHRDKWHMQLQNLNGTTYDPTDDVPAPLGTPDFKGVVFGVASQRNVGNDAPGSTRAHEAVISTYSPQFV

FIGURE 34I (cont)

PKLGSVNFRSNDNDFQLQPTKFTPVGINDDGDHPFRQWELPDYSGLLTLNMNLAPPVAPNFPGEQLLFFRSF
VPCSGGYNQGIVDCLIPQEWIQHFYQESAPSQSDVALIRYVNPDTGRTLFEAKLHRSGYITVAHSGDYPLVVPA
NGYFRFDSWVNQFYSLAPMGTGNGRRRAQ

FIGURE 34J

Nucleic acid sequence of VP1 hCod GII.17 Kawa 2014 A0A077KVU6_R53I (SEQ ID NO:195)

ATGAAAATGGCATCTAACGACGCAGCCCCCTCAAACGATGGCGCTGCTGGACTCGTGCCGGAGGGGAAT
AATGAGACACTTCCACTAGAGCCGGTTGCAGGCGCCGCTATAGCTGCCCCAGTGACAGGGCAGAATAAT
ATTATAGACCCTTGGATTATCACAAACTTCGTGCAGGCACCCAACGGCGAGTTTACAGTATCCCCCCGGA
ACTCCCCAGGTGAGATACTCCTGAATCTTGAGCTCGGCCCTGACCTCAATCCATATCTGGCTCATCTGAGC
CGCATGTACAATGGTTACGCTGGGGGGGTCGAAGTGCAGGTCCTCCTGGCCGGAAACGCCTTTACCGCT
GGCAAAATTCTGTTTGCCGCCGTTCCACCAAACTTTCCAGTCGAATTCCTCTCTCCCGCGCAAATAACCAT
GCTGCCACATTTGATCGTTGACGTGCGGACCCTGGAGCCAATAATGATTCCCCTGCCGGATGTGCGTAAC
ACCTTTTTCCATTATAACAATCAGCCAAACTCTCGGATGAGACTTGTTGCTATGCTGTACACCCCCCTGCG
GAGCAACGGCAGTGGCGATGATGTGTTTACCGTGAGTTGCAGAGTCCTGACGCGCCCAACCCCGGACTT
CGAGTTCACCTACCTGGTGCCCCCTTCTGTGGAATCTAAGACCAAACCGTTTTCACTGCCAATCTTAACTCT
CTCCGAACTGACTAACAGCCGGTTTCCAGTACCCATAGATTCTCTTTTTACCGCTCAAAACAACGTACTCC
AAGTCCAGTGCCAGAACGGCCGCTGTACGCTTGATGGTGAGTTGCAGGGGACAACACAGCTACTCCCCA
GTGGCATCTGTGCATTCCGGGGCCGCGTGACCGCTGAGACAGACCATCGTGACAAATGGCACATGCAAC
TCCAAAACTTAAACGGGACCACCTACGACCCAACCGACGACGTCCCTGCTCCGCTAGGGACTCCTGACTT
TAAGGGGGTGGTGTTCGGAGTGGCCTCTCAGCGGAATGTTGGGAATGACGCCCCCGGCTCTACCCGAGC
TCACGAGGCCGTTATCTCAACATATAGCCCCCAATTTGTGCCCAAGCTCGGATCCGTTAATTTTCGTAGTA
ACGACAACGACTTCCAACTGCAACCAACGAAGTTTACGCCAGTGGGGATTAATGATGATGGAGACCATC
CTTTCCGCCAATGGGAACTACCAGATTATTCTGGGCTGCTCACCCTCAATATGAACCTCGCCCCACCCGTG
GCCCCTAATTTCCCCGGTGAGCAGCTGCTGTTTTTTCGGAGCTTTGTGCCATGCAGTGGCGGATATAATCA
AGGCATCGTAGACTGCTTGATTCCCCAAGAGTGGATACAACATTTTTACCAGGAAAGTGCGCCCTCCCAG
TCCGATGTGGCCCTGATACGGTACGTTAACCCCGATACCGGAAGAACATTATTCGAAGCGAAATTGCACA
GATCAGGGTACATTACCGTTGCACATTCCGGCGATTATCCCCTGGTGGTTCCCGCCAACGGTTACTTTAG
GTTCGATAGTTGGGTCAACCAGTTCTATTCACTAGCCCCAATGGGCACCGGTAACGGCAGACGCCGGGCT
CAGTAG

FIGURE 34K

Amino acid sequence of VP1GII.17 Kawa 2014 A0A077KVU6_A90L (SEQ ID NO:196)

MKMASNDAAPSNDGAAGLVPEGNNETLPLEPVAGAAIAAPVTGQNNIIDPWIRTNFVQAPNGEFTVSPRNS
PGEILLNLELGPDLNPYLLHLSRMYNGYAGGVEVQVLLAGNAFTAGKILFAAVPPNFPVEFLSPAQITMLPHLIV
DVRTLEPIMIPLPDVRNTFFHYNNQPNSRMRLVAMLYTPLRSNGSGDDVFTVSCRVLTRPTPDFEFTYLVPPS
VESKTKPFSLPILTLSELTNSRFPVPIDSLFTAQNNVLQVQCQNGRCTLDGELQGTTQLLPSGICAFRGRVTAET
DHRDKWHMQLQNLNGTTYDPTDDVPAPLGTPDFKGVVFGVASQRNVGNDAPGSTRAHEAVISTYSPQFVP

FIGURE 34K (cont)

KLGSVNFRSNDNDFQLQPTKFTPVGINDDGDHPFRQWELPDYSGLLTLNMNLAPPVAPNFPGEQLLFFRSFV
PCSGGYNQGIVDCLIPQEWIQHFYQESAPSQSDVALIRYVNPDTGRTLFEAKLHRSGYITVAHSGDYPLVVPA
NGYFRFDSWVNQFYSLAPMGTGNGRRRAQ

FIGURE 34L

Nucleic acid sequence of VP1 hCod GII.17 Kawa 2014 A0A077KVU6_A90L (SEQ ID NO:197)

ATGAAAATGGCATCTAACGACGCAGCCCCCTCAAACGATGGCGCTGCTGGACTCGTGCCGGAGGGGAAT
AATGAGACACTTCCACTAGAGCCGGTTGCAGGCGCCGCTATAGCTGCCCCAGTGACAGGGCAGAATAAT
ATTATAGACCCTTGGATTCGGACAAACTTCGTGCAGGCACCCAACGGCGAGTTTACAGTATCCCCCCGGA
ACTCCCCAGGTGAGATACTCCTGAATCTTGAGCTCGGCCCTGACCTCAATCCATATCTGCTGCATCTGAGC
CGCATGTACAATGGTTACGCTGGGGGGGTCGAAGTGCAGGTCCTCCTGGCCGGAAACGCCTTTACCGCT
GGCAAAATTCTGTTTGCCGCCGTTCCACCAAACTTTCCAGTCGAATTCCTCTCTCCCGCGCAAATAACCAT
GCTGCCACATTTGATCGTTGACGTGCGGACCCTGGAGCCAATAATGATTCCCCTGCCGGATGTGCGTAAC
ACCTTTTTCCATTATAACAATCAGCCAAACTCTCGGATGAGACTTGTTGCTATGCTGTACACCCCCCTGCG
GAGCAACGGCAGTGGCGATGATGTGTTTACCGTGAGTTGCAGAGTCCTGACGCGCCCAACCCCGGACTT
CGAGTTCACCTACCTGGTGCCCCCTTCTGTGGAATCTAAGACCAAACCGTTTTCACTGCCAATCTTAACTCT
CTCCGAACTGACTAACAGCCGGTTTCCAGTACCCATAGATTCTCTTTTTACCGCTCAAAACAACGTACTCC
AAGTCCAGTGCCAGAACGGCCGCTGTACGCTTGATGGTGAGTTGCAGGGGACAACACAGCTACTCCCCA
GTGGCATCTGTGCATTCCGGGGCCGCGTGACCGCTGAGACAGACCATCGTGACAAATGGCACATGCAAC
TCCAAAACTTAAACGGGACCACCTACGACCCAACCGACGACGTCCCTGCTCCGCTAGGGACTCCTGACTT
TAAGGGGGTGGTGTTCGGAGTGGCCTCTCAGCGGAATGTTGGGAATGACGCCCCCGGCTCTACCCGAGC
TCACGAGGCCGTTATCTCAACATATAGCCCCCAATTTGTGCCCAAGCTCGGATCCGTTAATTTTCGTAGTA
ACGACAACGACTTCCAACTGCAACCAACGAAGTTTACGCCAGTGGGGATTAATGATGATGGAGACCATC
CTTTCCGCCAATGGGAACTACCAGATTATTCTGGGCTGCTCACCCTCAATATGAACCTCGCCCCACCCGTG
GCCCCTAATTTCCCCGGTGAGCAGCTGCTGTTTTTTCGGAGCTTTGTGCCATGCAGTGGCGGATATAATCA
AGGCATCGTAGACTGCTTGATTCCCCAAGAGTGGATACAACATTTTTACCAGGAAAGTGCGCCCTCCCAG
TCCGATGTGGCCCTGATACGGTACGTTAACCCCGATACCGGAAGAACATTATTCGAAGCGAAATTGCACA
GATCAGGGTACATTACCGTTGCACATTCCGGCGATTATCCCCTGGTGGTTCCCGCCAACGGTTACTTTAG
GTTCGATAGTTGGGTCAACCAGTTCTATTCACTAGCCCCAATGGGCACCGGTAACGGCAGACGCCGGGCT
CAGTAG

FIGURE 34M

Amino acid sequence of VP1GII.17 Kawa 2014 A0A077KVU6_A39V+M53I (SEQ ID NO:198)

MKMASNDAAPSNDGAAGLVPEGNNETLPLEPVAGAAIAVPVTGQNNIIDPWIITNFVQAPNGEFTVSPRNS
PGEILLNLELGPDLNPYLAHLSRMYNGYAGGVEVQVLLAGNAFTAGKILFAAVPPNFPVEFLSPAQITMLPHLI
VDVRTLEPIMIPLPDVRNTFFHYNNQPNSRMRLVAMLYTPLRSNGSGDDVFTVSCRVLTRPTPDFEFTYLVPP
SVESKTKPFSLPILTLSELTNSRFPVPIDSLFTAQNNVLQVQCQNGRCTLDGELQGTTQLLPSGICAFRGRVTAE
TDHRDKWHMQLQNLNGTTYDPTDDVPAPLGTPDFKGVVFGVASQRNVGNDAPGSTRAHEAVISTYSPQFV

FIGURE 34M (cont)

PKLGSVNFRSNDNDFQLQPTKFTPVGINDDGDHPFRQWELPDYSGLLTLNMNLAPPVAPNFPGEQLLFFRSF
VPCSGGYNQGIVDCLIPQEWIQHFYQESAPSQSDVALIRYVNPDTGRTLFEAKLHRSGYITVAHSGDYPLVVPA
NGYFRFDSWVNQFYSLAPMGTGNGRRRAQ

FIGURE 34N

Nucleic acid sequence of VP1 hCod GII.17 Kawa 2014 A0A077KVU6_A39V+M53I (SEQ ID NO:199)

ATGAAAATGGCATCTAACGACGCAGCCCCCTCAAACGATGGCGCTGCTGGACTCGTGCCGGAGGGGAAT
AATGAGACACTTCCACTAGAGCCGGTTGCAGGCGCCGCTATAGCTGTGCCAGTGACAGGGCAGAATAAT
ATTATAGACCCTTGGATTATCACAAACTTCGTGCAGGCACCCAACGGCGAGTTTACAGTATCCCCCCGGA
ACTCCCCAGGTGAGATACTCCTGAATCTTGAGCTCGGCCCTGACCTCAATCCATATCTGGCTCATCTGAGC
CGCATGTACAATGGTTACGCTGGGGGGGTCGAAGTGCAGGTCCTCCTGGCCGGAAACGCCTTTACCGCT
GGCAAAATTCTGTTTGCCGCCGTTCCACCAAACTTTCCAGTCGAATTCCTCTCTCCCGCGCAAATAACCAT
GCTGCCACATTTGATCGTTGACGTGCGGACCCTGGAGCCAATAATGATTCCCCTGCCGGATGTGCGTAAC
ACCTTTTTCCATTATAACAATCAGCCAAACTCTCGGATGAGACTTGTTGCTATGCTGTACACCCCCCTGCG
GAGCAACGGCAGTGGCGATGATGTGTTTACCGTGAGTTGCAGAGTCCTGACGCGCCCAACCCCGGACTT
CGAGTTCACCTACCTGGTGCCCCCTTCTGTGGAATCTAAGACCAAACCGTTTTCACTGCCAATCTTAACTCT
CTCCGAACTGACTAACAGCCGGTTTCCAGTACCCATAGATTCTCTTTTTACCGCTCAAAACAACGTACTCC
AAGTCCAGTGCCAGAACGGCCGCTGTACGCTTGATGGTGAGTTGCAGGGGACAACACAGCTACTCCCCA
GTGGCATCTGTGCATTCCGGGGCCGCGTGACCGCTGAGACAGACCATCGTGACAAATGGCACATGCAAC
TCCAAAACTTAAACGGGACCACCTACGACCCAACCGACGACGTCCCTGCTCCGCTAGGGACTCCTGACTT
TAAGGGGGTGGTGTTCGGAGTGGCCTCTCAGCGGAATGTTGGGAATGACGCCCCCGGCTCTACCCGAGC
TCACGAGGCCGTTATCTCAACATATAGCCCCCAATTTGTGCCCAAGCTCGGATCCGTTAATTTTCGTAGTA
ACGACAACGACTTCCAACTGCAACCAACGAAGTTTACGCCAGTGGGGATTAATGATGATGGAGACCATC
CTTTCCGCCAATGGGAACTACCAGATTATTCTGGGCTGCTCACCCTCAATATGAACCTCGCCCCACCCGTG
GCCCCTAATTTCCCCGGTGAGCAGCTGCTGTTTTTTCGGAGCTTTGTGCCATGCAGTGGCGGATATAATCA
AGGCATCGTAGACTGCTTGATTCCCCAAGAGTGGATACAACATTTTTACCAGGAAAGTGCGCCCTCCCAG
TCCGATGTGGCCCTGATACGGTACGTTAACCCCGATACCGGAAGAACATTATTCGAAGCGAAATTGCACA
GATCAGGGTACATTACCGTTGCACATTCCGGCGATTATCCCCTGGTGGTTCCCGCCAACGGTTACTTTAG
GTTCGATAGTTGGGTCAACCAGTTCTATTCACTAGCCCCAATGGGCACCGGTAACGGCAGACGCCGGGCT
CAGTAG

FIGURE 34O

Amino acid sequence of VP1GII.17 Kawa 2014 A0A077KVU6_E80S+A90L (SEQ ID NO:200)

MKMASNDAAPSNDGAAGLVPEGNNETLPLEPVAGAAIAAPVTGQNNIIDPWIRTNFVQAPNGEFTVSPRNS
PGEILLNLSLGPDLNPYLLHLSRMYNGYAGGVEVQVLLAGNAFTAGKILFAAVPPNFPVEFLSPAQITMLPHLIV
DVRTLEPIMIPLPDVRNTFFHYNNQPNSRMRLVAMLYTPLRSNGSGDDVFTVSCRVLTRPTPDFEFTYLVPPS
VESKTKPFSLPILTLSELTNSRFPVPIDSLFTAQNNVLQVQCQNGRCTLDGELQGTTQLLPSGICAFRGRVTAET
DHRDKWHMQLQNLNGTTYDPTDDVPAPLGTPDFKGVVFGVASQRNVGNDAPGSTRAHEAVISTYSPQFVP

FIGURE 34O (cont)

KLGSVNFRSNDNDFQLQPTKFTPVGINDDGDHPFRQWELPDYSGLLTLNMNLAPPVAPNFPGEQLLFFRSFV
PCSGGYNQGIVDCLIPQEWIQHFYQESAPSQSDVALIRYVNPDTGRTLFEAKLHRSGYITVAHSGDYPLVVPA
NGYFRFDSWVNQFYSLAPMGTGNGRRRAQ

FIGURE 34P

Nucleic acid sequence of VP1 hCod GII.17 Kawa 2014 A0A077KVU6_E80S+A90L (SEQ ID NO:201)

ATGAAAATGGCATCTAACGACGCAGCCCCCTCAAACGATGGCGCTGCTGGACTCGTGCCGGAGGGGAAT
AATGAGACACTTCCACTAGAGCCGGTTGCAGGCGCCGCTATAGCTGCCCCAGTGACAGGGCAGAATAAT
ATTATAGACCCTTGGATTCGGACAAACTTCGTGCAGGCACCCAACGGCGAGTTTACAGTATCCCCCCGGA
ACTCCCCAGGTGAGATACTCCTGAATCTTAGCCTCGGCCCTGACCTCAATCCATATCTGCTGCATCTGAGC
CGCATGTACAATGGTTACGCTGGGGGGGTCGAAGTGCAGGTCCTCCTGGCCGGAAACGCCTTTACCGCT
GGCAAAATTCTGTTTGCCGCCGTTCCACCAAACTTTCCAGTCGAATTCCTCTCTCCCGCGCAAATAACCAT
GCTGCCACATTTGATCGTTGACGTGCGGACCCTGGAGCCAATAATGATTCCCCTGCCGGATGTGCGTAAC
ACCTTTTTCCATTATAACAATCAGCCAAACTCTCGGATGAGACTTGTTGCTATGCTGTACACCCCCCTGCG
GAGCAACGGCAGTGGCGATGATGTGTTTACCGTGAGTTGCAGAGTCCTGACGCGCCCAACCCCGGACTT
CGAGTTCACCTACCTGGTGCCCCCTTCTGTGGAATCTAAGACCAAACCGTTTTCACTGCCAATCTTAACTCT
CTCCGAACTGACTAACAGCCGGTTTCCAGTACCCATAGATTCTCTTTTTACCGCTCAAAACAACGTACTCC
AAGTCCAGTGCCAGAACGGCCGCTGTACGCTTGATGGTGAGTTGCAGGGGACAACACAGCTACTCCCCA
GTGGCATCTGTGCATTCCGGGGCCGCGTGACCGCTGAGACAGACCATCGTGACAAATGGCACATGCAAC
TCCAAAACTTAAACGGGACCACCTACGACCCAACCGACGACGTCCCTGCTCCGCTAGGGACTCCTGACTT
TAAGGGGGTGGTGTTCGGAGTGGCCTCTCAGCGGAATGTTGGGAATGACGCCCCCGGCTCTACCCGAGC
TCACGAGGCCGTTATCTCAACATATAGCCCCCAATTTGTGCCCAAGCTCGGATCCGTTAATTTTCGTAGTA
ACGACAACGACTTCCAACTGCAACCAACGAAGTTTACGCCAGTGGGGATTAATGATGATGGAGACCATC
CTTTCCGCCAATGGGAACTACCAGATTATTCTGGGCTGCTCACCCTCAATATGAACCTCGCCCCACCCGTG
GCCCCTAATTTCCCCGGTGAGCAGCTGCTGTTTTTTCGGAGCTTTGTGCCATGCAGTGGCGGATATAATCA
AGGCATCGTAGACTGCTTGATTCCCCAAGAGTGGATACAACATTTTTACCAGGAAAGTGCGCCCTCCCAG
TCCGATGTGGCCCTGATACGGTACGTTAACCCCGATACCGGAAGAACATTATTCGAAGCGAAATTGCACA
GATCAGGGTACATTACCGTTGCACATTCCGGCGATTATCCCCTGGTGGTTCCCGCCAACGGTTACTTTAG
GTTCGATAGTTGGGTCAACCAGTTCTATTCACTAGCCCCAATGGGCACCGGTAACGGCAGACGCCGGGCT
CAGTAG

Figure 35A

Amino acid sequence of VP2_GI.1_Norwalk (SEQ ID NO:99)

MAQAIIGAIAASTAGSALGAGIQVGGEAALQSQRYQQNLQLQENSFKHDREMIGYQVEASNQLLAKNLATRYSLLRAGG
LTSADAARSVAGAPVTRIVDWNGVRVSAPESSATTLRSGGFMSVPIPFASKQKQVQSSGISNPNYSPSSISRTTSWVESQ
NSSRFGNLSPYHAEALNTVWLTPPGSTASSTLSSVPRGYFNTDRLPLFANNRR

Figure 35B

Nucleic acid sequence of human codon optimized VP.2_GI1_Norwalk (SEQ ID NO:100)

ATGGCTCAGGCCATTATTGGCGCCATCGCTGCAAGTACAGCCGGGAGTGCATTGGGGGCCGGAATACAGGTGGGC
GGGGAAGCTGCATTGCAGAGCCAGCGGTACCAGCAAAACCTGCAGTTACAGGAGAATAGCTTTAAACACGACAGG
GAGATGATTGGATATCAGGTGGAGGCCAGCAATCAGCTGCTCGCCAAAAACTTGGCTACTCGATACTCATTACTGCG
CGCCGGGGGGTTGACTAGCGCCGACGCCGCACGATCTGTCGCAGGCGCCCCCGTGACTCGGATCGTAGACTGGAA
CGGGGTACGAGTCTCGGCTCCCGAGTCGTCTGCAACCACCCTGAGGTCGGGAGGGTTTATGTCCGTGCCCATCCCAT
TCGCTAGCAAACAGAAACAGGTCCAGAGCTCCGGAATCTCCAATCCCAATTACTCCCCTAGCTCTATCTCTCGTACCA
CTTCCTGGGTCGAGAGTCAGAACAGCAGTAGATTTGGCAACCTGAGCCCCTACCATGCTGAAGCCCTGAACACTGTG
TGGTTGACTCCACCTGGTAGCACGGCCTCCTCAACCCTGAGTTCCGTGCCTCGCGGGTACTTCAATACCGACAGACTT
CCTCTGTTCGCTAACAACCGCCGCTGA

Figure 36A

Amino acid sequence of VP2_GI.3_Lil08 (SEQ ID NO:94)

MAQAIFGAIAATAAGSAVGAGIQAGTEAALQHQRFQQDLTLQSNTFKHDKEMLGLQVGASTALLQNSLNTRYNMLTD
AGLSSSDAARMVVGAPATRVVDWNGTRISAPRSTATTLRSGGFMTIPTLYKGKQQQKAPTEIGLSNPNYGSSVSSRVAD
WVSSQNSSHSSLGPYHPSALQTTWVTPPGSSSTSTISSVSTVPRYFNTDRLPLFANMRK

Figure 36B

Nucleic acid sequence of human codon optimized VP2_GI.3_Lil08 (SEQ ID NO:95)

ATGGCTCAGGCAATCTTCGGCGCAATCGCTGCCACTGCTGCCGGATCCGCTGTGGGAGCCGGCATACAGGCCGGAA
CTGAGGCGGCCCTTCAGCATCAGCGGTTCCAGCAGGATCTGACATTACAGAGTAACACATTCAAACATGACAAGGA
GATGCTGGGTCTGCAGGTGGGTGCCAGTACTGCCCTGCTCCAAAACTCTCTGAATACCAGATATAACATGTTAACTG
ATGCGGGACTGTCTAGTAGCGACGCAGCTCGCATGGTCGTGGGCGCCCCCAGCTACGAGAGTTGTGGACTGGAATG
GCACCCGAATCAGTGCACCAAGGTCTACAGCCACTACCCTCAGAAGTGGCGGCTTTATGACCATCCCGACTTTATAC
AAGGGCAAACAACAGCAGAAGGCACCTACTGAAATCGGTCTCTCCAATCCCAACTACGGCAGCAGTGTGTCTTCTCG
CGTGGCCGATTGGGTCTCAAGCCAGAACTCCAGTCATAGTTCTCTTGGGCCTTATCATCCATCAGCCTTGCAGACAAC
TTGGGTCACCCCACCCGGGTCCAGTAGCACGTCAACCATCAGTTCCGTCTCCACAGTCCCTCGCTATTTTAATACTGA
TAGGCTTCCCCTGTTCGCAAACATGAGGAAGTGA

Figure 37A

Amino acid sequence of VP2_GII6_HS10 (SEQ ID NO:96)

MASAFLAGLAGDVITNGVGSLINAGANAVNQKVEYDFNKQLQMASFKHDKEMLQSQVLATKQLQQEMMNIRQGVLT
AGGFSPADAARGAVNAPMTKILDWNGTRYWAPNSMKTTSYSGQFSSSPVHKSPAPSQHTALPKSRLQNDFASVYSFPS
SVSSQSTHSTALSAGTGSSRSISPSTATPTLSRTSDWVRGQNERLSPFMDGALQTAFVTPPSSKASSNGTVSTVPKAVLDS
WTPMFNTHRQPLFAHPRRRGESQV

Figure 37B

Nucleic acid sequence of human codon optimized VP2_GII6_HS10 (SEQ ID NO:97)

ATGGCCTCCGCATTTCTAGCTGGATTGGCCGGGGACGTGATCACCAACGGCGTAGGATCGCTGATTAATGCAGGCG
CCAATGCTGTTAATCAGAAGGTTGAATACGACTTCAACAAACAACTGCAGATGGCTTCATTCAAGCACGACAAAGAA
ATGTTGCAGTCACAGGTTCTCGCCACCAAGCAGCTACAACAGGAGATGATGAACATTCGGCAGGGCGTACTGACCG
CTGGAGGATTCAGCCCTGCTGACGCAGCACGGGGGGCCGTGAACGCGCCGATGACCAAGATCCTGGATTGGAACG
GAACTCGGTATTGGGCTCCCAACTCTATGAAAACCACTTCTTACTCTGGTCAGTTCTCCAGCTCGCCAGTCCACAAAA
GTCCGGCCCCTTCACAGCACACAGCACTCCCTAAGTCCAGGCTGCAAAACGACTTTGCCTCCGTGTACTCCTTCCCAT
CCAGCGTGTCATCTCAGAGCACTCATTCAACCGCCCTGTCCGCCGGAACTGGGTCTAGCCGCAGCATTTCCCCAAGC
ACAGCTACTCCAACTCTGAGCAGGACTAGCGATTGGGTCAGAGGACAAAACGAACGACTGTCCCCTTTCATGGACG
GAGCTCTGCAAACCGCCTTCGTCACTCCACCTAGCAGCAAGGCCTCGAGCAACGGTACGGTTAGTACCGTGCCAAAG
GCTGTTCTTGACAGCTGGACCCCCATGTTTAACACACACAGGCAGCCATTGTTTGCACACCCCAGGCGACGGGGAGA
ATCACAAGTTTAG

Figure 38A

Cloning vector 1190 from left to right T-DNA (SEQ ID NO:162)

TGGCAGGATATATTGTGGTGTAAACAAATTGACGCTTAGACAACTTAATAACACATTGCGGACGTTTTTAATGTACT
GAATTAACGCCGAATCCCGGGCTGGTATATTTATATGTTGTCAAATAACTCAAAAACCATAAAAGTTTAAGTTAGCA
AGTGTGTACATTTTTACTTGAACAAAAATATTCACCTACTACTGTTATAAATCATTATTAAACATTAGAGTAAAGAAAT
ATGGATGATAAGAACAAGAGTAGTGATATTTTGACAACAATTTTGTTGCAACATTTGAGAAAATTTTGTTGTTCTCTC
TTTTCATTGGTCAAAAACAATAGAGAGAGAAAAAGGAAGAGGGAGAATAAAAACATAATGTGAGTATGAGAGAGA
AAGTTGTACAAAAGTTGTACCAAAATAGTTGTACAAATATCATTGAGGAATTTGACAAAAGCTACACAAATAAGGGT
TAATTGCTGTAAATAAATAAGGATGACGCATTAGAGAGATGTACCATTAGAGAATTTTTGGCAAGTCATTAAAAAGA
AAGAATAAATTATTTTTAAAATTAAAAGTTGAGTCATTTGATTAAACATGTGATTATTTAATGAATTGATGAAAGAGT
TGGATTAAAGTTGTATTAGTAATTAGAATTTGGTGTCAAATTTAATTTGACATTTGATCTTTTCCTATATATTGCCCCA
TAGAGTCAGTTAACTCATTTTTATATTTCATAGATCAAATAAGAGAAATAACGGTATATTAATCCCTCCAAAAAAAAA
AAACGGTATATTTACTAAAAAATCTAAGCCACGTAGGAGGATAACAGGATCCCCGTAGGAGGATAACATCCAATCC
AACCAATCACAACAATCCTGATGAGATAACCCACTTTAAGCCCACGCATCTGTGGCACATCTACATTATCTAAATCAC
ACATTCTTCCACACATCTGAGCCACACAAAAACCAATCCACATCTTTATCACCCATTCTATAAAAAATCACACTTTGTG
AGTCTACACTTTGATTCCCTTCAAACACATACAAAGAGAAGAGACTAATTAATTAATTAATCATCTTGAGAGAAAATG
GAACGAGCTATACAAGGAAACGACGCTAGGGAACAAGCTAACAGTGAACGTTGGGATGGAGGATCAGGAGGTACC
ACTTCTCCCTTCAAACTTCCTGACGAAAGTCCGAGTTGGACTGAGTGGCGGCTACATAACGATGAGACGAATTCGAA
TCAAGATAATCCCCTTGGTTTCAAGGAAAGCTGGGGTTTCGGGAAAGTTGTATTTAAGAGATATCTCAGATACGACA
GGACGGAAGCTTCACTGCACAGAGTCCTTGGATCTTGGACGGGAGATTCGGTTAACTATGCAGCATCTCGATTTTTC
GGTTTCGACCAGATCGGATGTACCTATAGTATTCGGTTTCGAGGAGTTAGTATCACCGTTTCTGGAGGGTCGCGAAC
TCTTCAGCATCTCTGTGAGATGGCAATTCGGTCTAAGCAAGAACTGCTACAGCTTGCCCCAATCGAAGTGGAAAGTA
ATGTATCAAGAGGATGCCCTGAAGGTACTCAAACCTTCGAAAAAGAAAGCGAGTAAGTTAAAATGCTTCTTCGTCTC
CTATTTATAATATGGTTTGTTATTGTTAATTTTGTTCTTGTAGAAGAGCTTAATTAATCGTTGTTGTTATGAAATACTAT
TTGTATGAGATGAACTGGTGTAATGTAATTCATTTACATAAGTGGAGTCAGAATCAGAATGTTTCCTCCATAACTAAC
TAGACATGAAGACCTGCCGCGTACAATTGTCTTATATTTGAACAACTAAAATTGAACATCTTTTGCCACAACTTTATA
AGTGGTTAATATAGCTCAAATATATGGTCAAGTTCAATAGATTAATAATGGAAATATCAGTTATCGAAATTCATTAAC
AATCAACTTAACGTTATTAACTACTAATTTTATATCATCCCCTTTGATAAATGATAGTACACCAATTAGGAAGGAGCAT
GCTCGCCTAGGAGATTGTCGTTTCCCGCCTTCAGTTTGCAAGCTGCTCTAGCCGTGTAGCCAATACGCAAACCGCCTC

FIGURE 38A (cont)

TCCCCGCGCGTTGGGAATTACTAGCGCGTGTCGACAAGCTTGCATGCCGGTCAACATGGTGGAGCACGACACACTT
GTCTACTCCAAAAATATCAAAGATACAGTCTCAGAAGACCAAAGGGCAATTGAGACTTTTCAACAAAGGGTAATATC
CGGAAACCTCCTCGGATTCCATTGCCCAGCTATCTGTCACTTTATTGTGAAGATAGTGGAAAAGGAAGGTGGCTCCT
ACAAATGCCATCATTGCGATAAAGGAAAGGCCATCGTTGAAGATGCCTCTGCCGACAGTGGTCCCAAAGATGGACC
CCCACCCACGAGGAGCATCGTGGAAAAAGAAGACGTTCCAACCACGTCTTCAAAGCAAGTGGATTGATGTGATAAC
ATGGTGGAGCACGACACACTTGTCTACTCCAAAAATATCAAAGATACAGTCTCAGAAGACCAAAGGGCAATTGAGA
CTTTTCAACAAAGGGTAATATCCGGAAACCTCCTCGGATTCCATTGCCCAGCTATCTGTCACTTTATTGTGAAGATAG
TGGAAAAGGAAGGTGGCTCCTACAAATGCCATCATTGCGATAAAGGAAAGGCCATCGTTGAAGATGCCTCTGCCGA
CAGTGGTCCCAAAGATGGACCCCCACCCACGAGGAGCATCGTGGAAAAAGAAGACGTTCCAACCACGTCTTCAAAG
CAAGTGGATTGATGTGATATCTCCACTGACGTAAGGGATGACGCACAATCCCACTATCCTTCGCAAGACCCTTCCTCT
ATATAAGGAAGTTCATTTCATTTGGAGAGGTATTAAAATCTTAATAGGTTTTGATAAAAGCGAACGTGGGGAAACCC
GAACCAAACCTTCTTCTAAACTCTCTCTCATCTCTCTTAAAGCAAACTTCTCTCTTGTCTTTCTTGCGTGAGCGATCTTC
AACGTTGTCAGATCGTGCTTCGGCACCGCGGATGGCGAAAAACGTTGCGATTTTCGGCTTATTGTTTTCTCTTCTTGT
GTTGGTTCCTTCTCAGATCTTCGCCTGCAGGCTCCTCAGCCAAAACGACACCCCCATCTGTCTATCCACTGGCCCCTG
GATCTGCTGCCCAAACTAACTCCATGGTGACCCTGGGATGCCTGGTCAAGGGCTATTTCCCTGAGCCAGTGACAGTG
ACCTGGAACTCTGGATCCCTGTCCAGCGGTGTGCACACCTTCCCAGCTGTCCTGCAGTCTGACCTCTACACTCTGAGC
AGCTCAGTGACTGTCCCCTCCAGCACCTGGCCCAGCGAGACCGTCACCTGCAACGTTGCCCACCCGGCCAGCAGCAC
CAAGGTGGACAAGAAAATTGTGCCCAGGGATTGTGGTTGTAAGCCTTGCATATGTACAGTCCCAGAAGTATCATCTG
TCTTCATCTTCCCCCCAAAGCCCAAGGATGTGCTCACCATTACTCTGACTCCTAAGGTCACGTGTGTTGTGGTAGACA
TCAGCAAGGATGATCCCGAGGTCCAGTTCAGCTGGTTTGTAGATGATGTGGAGGTGCACACAGCTCAGACGCAACC
CCGGGAGGAGCAGTTCAACAGCACTTTCCGCTCAGTCAGTGAACTTCCCATCATGCACCAGGACTGGCTCAATGGCA
AGGAGCGATCGCTCACCATCACCATCACCATCACCATCACCATTAAAGGCCTATTTTCTTTAGTTTGAATTTACTGTTA
TTCGGTGTGCATTTCTATGTTTGGTGAGCGGTTTTCTGTGCTCAGAGTGTGTTTATTTTATGTAATTTAATTTCTTTGT
GAGCTCCTGTTTAGCAGGTCGTCCCTTCAGCAAGGACACAAAAAGATTTTAATTTTATTAAAAAAAAAAAAAAAAAA
GACCGGGAATTCGATATCAAGCTTATCGACCTGCAGATCGTTCAAACATTTGGCAATAAAGTTTCTTAAGATTGAATC
CTGTTGCCGGTCTTGCGATGATTATCATATAATTTCTGTTGAATTACGTTAAGCATGTAATAATTAACATGTAATGCAT
GACGTTATTTATGAGATGGGTTTTTATGATTAGAGTCCCGCAATTATACATTTAATACGCGATAGAAAACAAAATATA
GCGCGCAAACTAGGATAAATTATCGCGCGCGGTGTCATCTATGTTACTAGATCTCTAGAGTCTCAAGCTTGGCGCGC
CCACGTGACTAGTGGCACTGGCCGTCGTTTTACAACGTCGTGACTGGGAAAACCCTGGCGTTACCCAACTTAATCGC
CTTGCAGCACATCCCCCTTTCGCCAGCTGGCGTAATAGCGAAGAGGCCCGCACCGATCGCCCTTCCCAACAGTTGCG
CAGCCTGAATGGCGAATGCTAGAGCAGCTTGAGCTTGGATCAGATTGTCGTTTCCCGCCTTCAGTTTAAACTATCAG
TGTTTGACAGGATATATTGGCGGGTAAACCTAAGAGAAAAGAGCGTTTA

Figure 38B

Construct 2724 from 2X35S promoter to NOS terminator (SEQ ID NO:163)

GTCAACATGGTGGAGCACGACACACTTGTCTACTCCAAAAATATCAAAGATACAGTCTCAGAAGACCAAAGGGCAA
TTGAGACTTTTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGTCT
TCAAAGCAAGTGGATTGATGTGATAACATGGTGGAGCACGACACACTTGTCTACTCCAAAAATATCAAAGATACAGT
CTCAGAAGACCAAAGGGCAATTGAGACTTTTCAACAAAGGGTAATATCCGGAAACCTCCTCGGATTCCATTGCCCAG
CTATCTGTCACTTTATTGTGAAGATAGTGGAAAAGGAAGGTGGCTCCTACAAATGCCATCATTGCGATAAAGGAAAG
GCCATCGTTGAAGATGCCTCTGCCGACAGTGGTCCCAAAGATGGACCCCCACCCACGAGGAGCATCGTGGAAAAAG
AAGACGTTCCAACCACGTCTTCAAAGCAAGTGGATTGATGTGATATCTCCACTGACGTAAGGGATGACGCACAATCC

FIGURE 38B (cont)

CACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCT
CTTGTCTTTCTTGCGTGAGCGATCTTCAACGTTGTCAGATCGTGCTTCGGCACCAGTACAATGATGATGGCTAGTAAA
GATGCGACCTCCTCTGTGGATGGTGCGTCAGGGGCAGGACAACTCGTACCCGAGGTAAACGCCAGCGACCCACTTG
CCATGGACCCCGTTGCCGGAAGTTCCACAGCAGTGGCCACAGCCGGTCAAGTGAATCCAATTGATCCGTGGATTATC
AACAATTTCGTCCAGGCACCCCAGGGCGAGTTCACAATTTCACCAAACAATACACCGGGCGATGTGCTATTCGATCT
TTCCTTGGGTCCTCACCTTAACCCTTTTCTACTCCATCTCTCACAGATGTACAATGGTTGGGTAGGAAACATGAGAGT
CCGGATCATGCTGGCTGGCAATGCCTTTACCGCTGGCAAGATCATCGTCAGTTGTATTCCTCCCGGATTTGGATCTCA
TAATCTGACCATTGCTCAAGCGACTCTCTTTCCCCATGTCATCGCCGACGTTAGGACCCTGGACCCCATCGAGGTGCC
CCTGGAGGACGTCCGGAATGTTTTGTTCCACAACAACGACAGAAACCAGCAGACGATGAGACTTGTCTGTATGCTCT
ATACCCCACTGCGGACTGGAGGCGGGACTGGAGACTCCTTCGTTGTGGCAGGAAGAGTGATGACATGCCCCTCCCC
CGACTTCAACTTTCTTTTTCTGGTCCCACCAACCGTTGAGCAGAAGACGCGGCCCTTTACACTGCCCAATCTCCCGCTT
TCAAGTCTGAGTAATTCACGGGCCCCATTGCCGATCTCCTCAATGGGAATCTCCCCCGACAACGTCCAGTCTGTCCAA
TTCCAAAATGGGAGATGCACACTGGACGGTCGCCTGGTGGGAACAACTCCGGTGTCCCTCTCACATGTCGCCAAAAT
CCGCGGCACATCAAATGGTACCGTAATCAATCTGACAGAACTTGATGGCACGCCCTTCCATCCCTTTGAAGGACCAG
CCCCTATTGGATTTCCTGATCTGGGAGGTTGCGACTGGCACATAAACATGACACAGTTTGGCCACTCCAGCCAGACA
CAGTATGATGTCGATACAACCCCAGATACCTTCGTGCCACACCTGGGATCTATTCAAGCTAACGGTATTGGATCCGG
CAACTACGTGGGAGTCTTATCTTGGATCTCACCACCATCCCACCCCTCAGGATCCCAGGTTGACTTGTGGAAGATACC
GAATTATGGATCCTCGATCACTGAAGCCACGCACCTCGCACCTTCCGTCTACCCACCAGGTTTTGGAGAAGTCTTGGT
GTTTTTCATGAGCAAAATGCCCGGCCCTGGAGCCTACAATCTCCCTTGCCTACTCCCTCAAGAGTATATTAGTCACCT
CGCATCTGAGCAGGCCCCGACCGTTGGCGAGGCAGCCCTGCTGCATTATGTGGATCCGGACACCGGCAGGAACCTG
GGTGAGTTCAAAGCTTATCCTGACGGTTTTCTAACATGTGTACCAAATGGCGCTTCCAGCGGCCCTCAACAGCTCCCA
ATCAATGGCGTGTTCGTTTTTGTCAGCTGGGTAAGCCGCTTCTACCAGCTGAAGCCCGTGGGGACAGCTTCTTCTGC
CCGCGGACGCCTCGGTCTGCGGAGATAAAGGCCTATTTTCTTTAGTTTGAATTTACTGTTATTCGGTGTGCATTTCTA
TGTTTGGTGAGCGGTTTTCTGTGCTCAGAGTGTGTTTATTTTATGTAATTTAATTTCTTTGTGAGCTCCTGTTTAGCAG
GTCGTCCCTTCAGCAAGGACACAAAAAGATTTTAATTTTATTAAAAAAAAAAAAAAAAAAAGACCGGGAATTCGATAT
CAAGCTTATCGACCTGCAGATCGTTCAAACATTTGGCAATAAAGTTTCTTAAGATTGAATCCTGTTGCCGGTCTTGCG
ATGATTATCATATAATTTCTGTTGAATTACGTTAAGCATGTAATAATTAACATGTAATGCATGACGTTATTTATGAGAT
GGGTTTTTATGATTAGAGTCCCGCAATTATACATTTAATACGCGATAGAAAACAAAATATAGCGCGCAAACTAGGAT
AAATTATCGCGCGCGGTGTCATCTATGTTACTAGAT

Figure 38C

Cloning vector 3677 from left to right T-DNA (SEQ ID NO:164)

TGGCAGGATATATTGTGGTGTAAACAAATTGACGCTTAGACAACTTAATAACACATTGCGGACGTTTTTAATGTACT
GAATTAACGCCGAATCCCGGGCTGGTATATTTATATGTTGTCAAATAACTCAAAAACCATAAAAGTTTAAGTTAGCA
AGTGTGTACATTTTTACTTGAACAAAAATATTCACCTACTACTGTTATAAATCATTATTAAACATTAGAGTAAAGAAAT
ATGGATGATAAGAACAAGAGTAGTGATATTTTGACAACAATTTTGTTGCAACATTTGAGAAAATTTTGTTGTTCTCTC
TTTTCATTGGTCAAAAACAATAGAGAGAGAAAAAGGAAGAGGGAGAATAAAAACATAATGTGAGTATGAGAGAGA
AAGTTGTACAAAAGTTGTACCAAAATAGTTGTACAAATATCATTGAGGAATTTGACAAAAGCTACACAAATAAGGGT
TAATTGCTGTAAATAAATAAGGATGACGCATTAGAGAGATGTACCATTAGAGAATTTTTGGCAAGTCATTAAAAAGA
AAGAATAAATTATTTTTAAAATTAAAAGTTGAGTCATTTGATTAAACATGTGATTATTTAATGAATTGATGAAAGAGT
TGGATTAAAGTTGTATTAGTAATTAGAATTTGGTGTCAAATTTAATTTGACATTTGATCTTTTCCTATATATTGCCCCA
TAGAGTCAGTTAACTCATTTTTATATTTCATAGATCAAATAAGAGAAATAACGGTATATTAATCCCTCCAAAAAAAAA
AAACGGTATATTTACTAAAAAAATCTAAGCCACGTAGGAGGATAACAGGATCCCCGTAGGAGGATAACATCCAATCC
AACCAATCACAACAATCCTGATGAGATAACCCACTTTAAGCCCACGCATCTGTGGCACATCTACATTATCTAAATCAC
ACATTCTTCCACACATCTGAGCCACACAAAAACCAATCCACATCTTTATCACCCATTCTATAAAAAATCACACTTTGTG
AGTCTACACTTTGATTCCCTTCAAACACATACAAAGAGAAGAGACTAATTAATTAATTAATCATCTTGAGAGAAAATG
GAACGAGCTATACAAGGAAACGACGCTAGGGAACAAGCTAACAGTGAACGTTGGGATGGAGGATCAGGAGGTACC

FIGURE 38C (cont)

ACTTCTCCCTTCAAACTTCCTGACGAAAGTCCGAGTTGGACTGAGTGGCGGCTACATAACGATGAGACGAATTCGAA
TCAAGATAATCCCCTTGGTTTCAAGGAAAGCTGGGGTTTCGGGAAAGTTGTATTTAAGAGATATCTCAGATACGACA
GGACGGAAGCTTCACTGCACAGAGTCCTTGGATCTTGGACGGGAGATTCGGTTAACTATGCAGCATCTCGATTTTTC
GGTTTCGACCAGATCGGATGTACCTATAGTATTCGGTTTCGAGGAGTTAGTATCACCGTTTCTGGAGGGTCGCGAAC
TCTTCAGCATCTCTGTGAGATGGCAATTCGGTCTAAGCAAGAACTGCTACAGCTTGCCCCAATCGAAGTGGAAAGTA
ATGTATCAAGAGGATGCCCTGAAGGTACTCAAACCTTCGAAAAAGAAAGCGAGTAAGTTAAAATGCTTCTTCGTCTC
CTATTTATAATATGGTTTGTTATTGTTAATTTTGTTCTTGTAGAAGAGCTTAATTAATCGTTGTTGTTATGAAATACTAT
TTGTATGAGATGAACTGGTGTAATGTAATTCATTTACATAAGTGGAGTCAGAATCAGAATGTTTCCTCCATAACTAAC
TAGACATGAAGACCTGCCGCGTACAATTGTCTTATATTTGAACAACTAAAATTGAACATCTTTTGCCACAACTTTATA
AGTGGTTAATATAGCTCAAATATATGGTCAAGTTCAATAGATTAATAATGGAAATATCAGTTATCGAAATTCATTAAC
AATCAACTTAACGTTATTAACTACTAATTTTATATCATCCCCTTTGATAAATGATAGTACACCAATTAGGAAGGAGCAT
GCTCGCCTAGGAGATTGTCGTTTCCCGCCTTCAGTTTGCAAGCTGCTCTAGCCGTGTAGCCAATACGCAAACCGCCTC
TCCCCGCGCGTTGGGAATTACTAGCGCGTGTCGACAAGCTTGCATGCCGGTCAACATGGTGGAGCACGACACACTT
GTCTACTCCAAAAATATCAAAGATACAGTCTCAGAAGACCAAAGGGCAATTGAGACTTTTCAACAAAGGGTAATATC
CGGAAACCTCCTCGGATTCCATTGCCCAGCTATCTGTCACTTTATTGTGAAGATAGTGGAAAAGGAAGGTGGCTCCT
ACAAATGCCATCATTGCGATAAAGGAAAGGCCATCGTTGAAGATGCCTCTGCCGACAGTGGTCCCAAAGATGGACC
CCCACCCACGAGGAGCATCGTGGAAAAAGAAGACGTTCCAACCACGTCTTCAAAGCAAGTGGATTGATGTGATAAC
ATGGTGGAGCACGACACACTTGTCTACTCCAAAAATATCAAAGATACAGTCTCAGAAGACCAAAGGGCAATTGAGA
CTTTTCAACAAAGGGTAATATCCGGAAACCTCCTCGGATTCCATTGCCCAGCTATCTGTCACTTTATTGTGAAGATAG
TGGAAAAGGAAGGTGGCTCCTACAAATGCCATCATTGCGATAAAGGAAAGGCCATCGTTGAAGATGCCTCTGCCGA
CAGTGGTCCCAAAGATGGACCCCCACCCACGAGGAGCATCGTGGAAAAAGAAGACGTTCCAACCACGTCTTCAAAG
CAAGTGGATTGATGTGATATCTCCACTGACGTAAGGGATGACGCACAATCCCACTATCCTTCGCAAGACCCTTCCTCT
ATATAAGGAAGTTCATTTCATTTGGAGAGGTATTAAAATCTTAATAGGTTTTGATAAAAGCGAACGTGGGGAAACCC
GAACCAAACCTTCTTCTAAACTCTCTCTCATCTCTCTTAAAGCAAACTTCTCTCTTGTCTTTCTTGCGTGAGCGATCTTC
AACGTTGTCAGATCGTGCTTCGGCACCGCGGATGGCGAAAAACGTTGCGATTTTCGGCTTATTGTTTTCTCTTCTTGT
GTTGGTTCCTTCTCAGATCTTCGCCTGCAGGCTCCTCAGCCAAAACGACACCCCCATCTGTCTATCCACTGGCCCCTG
GATCTGCTGCCCAAACTAACTCCATGGTGACCCTGGGATGCCTGGTCAAGGGCTATTTCCCTGAGCCAGTGACAGTG
ACCTGGAACTCTGGATCCCTGTCCAGCGGTGTGCACACCTTCCCAGCTGTCCTGCAGTCTGACCTCTACACTCTGAGC
AGCTCAGTGACTGTCCCCTCCAGCACCTGGCCCAGCGAGACCGTCACCTGCAACGTTGCCCACCCGGCCAGCAGCAC
CAAGGTGGACAAGAAAATTGTGCCCAGGGATTGTGGTTGTAAGCCTTGCATATGTACAGTCCCAGAAGTATCATCTG
TCTTCATCTTCCCCCCAAAGCCCAAGGATGTGCTCACCATTACTCTGACTCCTAAGGTCACGTGTGTTGTGGTAGACA
TCAGCAAGGATGATCCCGAGGTCCAGTTCAGCTGGTTTGTAGATGATGTGGAGGTGCACACAGCTCAGACGCAACC
CCGGGAGGAGCAGTTCAACAGCACTTTCCGCTCAGTCAGTGAACTTCCCATCATGCACCAGGACTGGCTCAATGGCA
AGGAGCGATCGCTCACCATCACCATCACCATCACCATCACCATTAAAGGCCTATTTTCTTTAGTTTGAATTTACTGTTA
TTCGGTGTGCATTTCTATGTTTGGTGAGCGGTTTTCTGTGCTCAGAGTGTGTTTATTTTATGTAATTTAATTTCTTTGT
GAGCTCCTGTTTAGCAGGTCGTCCCTTCAGCAAGGACACAAAAAGATTTTAATTTTATTATCGTTCAAACATTTGGCA
ATAAAGTTTCTTAAGATTGAATCCTGTTGCCGGTCTTGCGATGATTATCATATAATTTCTGTTGAATTACGTTAAGCAT
GTAATAATTAACATGTAATGCATGACGTTATTTATGAGATGGGTTTTTATGATTAGAGTCCCGCAATTATACATTTAA
TACGCGATAGAAAACAAAATATAGCGCGCAAACTAGGATAAATTATCGCGCGCGGTGTCATCTATGTTACTAGATCT
CTAGGTAAAAATCCCAATTATATTTGGTCTAATTTAGTTTGGTATTGAGTAAAACAAATTCGAACCAAACCAAAATAT
AAATATATAGTTTTTATATATATGCCTTTAAGACTTTTTATAGAATTTTCTTTAAAAAATATCTAGAAATATTTGCGACT
CTTCTGGCATGTAATATTTCGTTAAATATGAAGTGCTCCATTTTTATTAACTTTAAATAATTGGTTGTACGATCACTTTC
TTATCAAGTGTTACTAAAATGCGTCAATCTCTTTGTTCTTCCATATTCATATGTCAAAATCTATCAAAATTCTTATATAT
CTTTTTCGAATTTGAAGTGAAATTTCGATAATTTAAAATTAAATAGAACATATCATTATTTAGGTATCATATTGATTTTT
ATACTTAATTACTAAATTTGGTTAACTTTGAAAGTGTACATCAACGAAAAATTAGTCAAACGACTAAAATAAATAAAT
ATCATGTGTTATTAAGAAAATTCTCCTATAAGAATATTTTAATAGATCATATGTTTGTAAAAAAAATTAATTTTTACTA
ACACATATATTTACTTATCAAAAATTTGACAAAGTAAGATTAAAATAATATTCATCTAACAAAAAAAAAACCAGAAAA
TGCTGAAAACCCGGCAAAACCGAACCAATCCAAACCGATATAGTTGGTTTGGTTTGATTTTGATATAAACCGAACCA
ACTCGGTCCATTTGCACCCCTAATCATAATAGCTTTAATATTTCAAGATATTATTAAGTTAACGTTGTCAATATCCTGG
AAATTTTGCAAAATGAATCAAGCCTATATGGCTGTAATATGAATTTAAAAGCAGCTCGATGTGGTGGTAATATGTAA

FIGURE 38C (cont)

TTTACTTGATTCTAAAAAAATATCCCAAGTATTAATAATTTCTGCTAGGAAGAAGGTTAGCTACGATTTACAGCAAAG
CCAGAATACAAAGAACCATAAAGTGATTGAAGCTCGAAATATACGAAGGAACAAATATTTTTAAAAAAATACGCAAT
GACTTGGAACAAAAGAAAGTGATATATTTTTTGTTCTTAAACAAGCATCCCCTCTAAAGAATGGCAGTTTTCCTTTGC
ATGTAACTATTATGCTCCCTTCGTTACAAAAATTTTGGACTACTATTGGGAACTTCTTCTGAAAATTCTAGAGTCTCAA
GCTTGGCGCGCCCACGTGACTAGTGGCACTGGCCGTCGTTTTACAACGTCGTGACTGGGAAAACCCTGGCGTTACCC
AACTTAATCGCCTTGCAGCACATCCCCCTTTCGCCAGCTGGCGTAATAGCGAAGAGGCCCGCACCGATCGCCCTTCCC
AACAGTTGCGCAGCCTGAATGGCGAATGCTAGAGCAGCTTGAGCTTGGATCAGATTGTCGTTTCCCGCCTTCAGTTT
AAACTATCAGTGTTTGACAGGATATATTGGCGGGTAAACCTAAGAGAAAAGAGCGTTTA

Figure 38D

Construct 4133 from 2X35S promoter to NOS terminator (SEQ ID NO:165)

GTCAACATGGTGGAGCACGACACACTTGTCTACTCCAAAAATATCAAAGATACAGTCTCAGAAGACCAAAGGGCAA
TTGAGACTTTTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGTCT
TCAAAGCAAGTGGATTGATGTGATAACATGGTGGAGCACGACACACTTGTCTACTCCAAAAATATCAAAGATACAGT
CTCAGAAGACCAAAGGGCAATTGAGACTTTTCAACAAAGGGTAATATCCGGAAACCTCCTCGGATTCCATTGCCCAG
CTATCTGTCACTTTATTGTGAAGATAGTGGAAAAGGAAGGTGGCTCCTACAAATGCCATCATTGCGATAAAGGAAAG
GCCATCGTTGAAGATGCCTCTGCCGACAGTGGTCCCAAAGATGGACCCCCACCCACGAGGAGCATCGTGGAAAAAG
AAGACGTTCCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCT
CTTGTCTTTCTTGCGTGAGCGATCTTCAACGTTGTCAGATCGTGCTTCGGCACCAGTACAATGAAAATGGCCTCGAGT
GACGCTAACCCTAGTGACGGCAGCGCCGCCAATCTTGTGCCTGAGGTTAATAATGAGGTGATGGCCCTGGAGCCTG
TGGTGGGCGCAGCCATAGCAGCGCCCGTGGCCGGTCAGCAGAATGTGATTGACCCGTGGATACGCAACAATTTTGT
CCAAGCCCCTGGTGGGGAGTTCACCGTTAGCCCGAGAAATGCGCCAGGAGAAATCCTGTGGTCGGCCAGCTTGGGA
CCCGATCTGAACCCCTATTTGTCACATCTCGCTCGGATGTACAACGGGTATGCCGGCGGATTTGAAGTGCAGGTGAT
TCTGGCTGGGAACGCGTTCACTGCTGGCAAAGTGATCTTTGCAGCGGTGCCTCCCAACTTCCCCACTGAAGGACTGT
CTCCAAGCCAGGTCACAATGTTTCCACACATCGTGGTGGACGTACGGCAGCTAGAGCCTGTCCTGATTCCCCTCCCT
GATGTACGCAATAATTTCTACCACTACAATCAATCCAATGATCCGACCATTAAACTCATCGCGATGTTGTACACCCCTC
TGCGCGCTAACAATGCTGGAGACGACGTATTCACCGTGTCATGCAGAGTGCTCACCAGACCTTCACCAGACTTTGAC
TTTATCTTCTTAGTGCCCCCCACTGTTGAGAGCCGAACCAAGCCCTTTAGTGTCCCCGTACTCACAGTCGAGGAGATG
ACAAATAGCCGCTTTCCAATCCCCCTTGAGAAACTGTTCACAGGACCTTCCTCGGCATTCGTGGTTCAGCCACAGAAC
GGACGCTGCACAACTGACGGCGTGCTGCTCGGAACCACCCAGCTTAGCCCTGTTAATATCTGTACGTTTAGAGGCGA
CGTAACTCACATAACTGGCTCACGGAACTATACCATGAATCTGGCATCACAGAATTGGAATGACTACGACCCAACCG
AAGAGATTCCCGCACCTCTTGGAACCCCCGACTTTGTGGGAAAAATACAGGGCGTCCTGACACAAACCACCAGAACC
GATGGCTCCACACGGGGACACAAGGCAACCGTCTACACTGGCTCTGCCGATTTTGCCCCGAAACTGGGTAGAGTGC
AGTTTGAGACCGACACTGACCGGGACTTTGAAGCCAATCAGAATACTAAGTTCACACCTGTAGGAGTGATTCAGGA
CGGGGGCACCACTCACCGGAACGAGCCGCAACAATGGGTCCTGCCCTCTTATAGCGGGAGGAATACTCATAATGTG
CATTTGGCTCCTGCAGTGGCTCCCACGTTTCCCGGGGAACAACTGCTCTTTTTTCGTTCAACCATGCCTGGATGCTCC
GGATATCCCAATATGGATCTCGATTGCCTGCTCCCACAGGAATGGGTGCAGTATTTTTATCAAGAGGCCGCACCAGC
CCAATCCGACGTCGCACTTCTGCGGTTCGTGAATCCAGACACAGGCCGCGTGTTGTTTGAGTGCAAATTGCACAAAT
CAGGATACGTTACAGTGGCTCATACTGGACAGCATGACCTGGTGATCCCACCCAACGGATATTTTAGGTTCGACTCC
TGGGTGAATCAGTTTTATACATTAGCCCCCATGGGGAATGGGACTGGCAGACGCAGGGCTGTCTGAAGGCCTATTT
TCTTTAGTTTGAATTTACTGTTATTCGGTGTGCATTTCTATGTTTGGTGAGCGGTTTTCTGTGCTCAGAGTGTGTTTAT
TTTATGTAATTTAATTTCTTTGTGAGCTCCTGTTTAGCAGGTCGTCCCTTCAGCAAGGACACAAAAAGATTTTAATTTT
ATTATCGTTCAAACATTTGGCAATAAAGTTTCTTAAGATTGAATCCTGTTGCCGGTCTTGCGATGATTATCATATAATT
TCTGTTGAATTACGTTAAGCATGTAATAATTAACATGTAATGCATGACGTTATTTATGAGATGGGTTTTTATGATTAG

FIGURE 38D (cont)

AGTCCCGCAATTATACATTTAATACGCGATAGAAAACAAAATATAGCGCGCAAACTAGGATAAATTATCGCGCGCGG
TGTCATCTATGTTACTAGAT

Figure 38E

Construct 4135 from 2X35S promoter to NOS terminator (SEQ ID NO:166)

GTCAACATGGTGGAGCACGACACACTTGTCTACTCCAAAAATATCAAAGATACAGTCTCAGAAGACCAAAGGGCAA
TTGAGACTTTTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGTCT
TCAAAGCAAGTGGATTGATGTGATAACATGGTGGAGCACGACACACTTGTCTACTCCAAAAATATCAAAGATACAGT
CTCAGAAGACCAAAGGGCAATTGAGACTTTTCAACAAAGGGTAATATCCGGAAACCTCCTCGGATTCCATTGCCCAG
CTATCTGTCACTTTATTGTGAAGATAGTGGAAAAGGAAGGTGGCTCCTACAAATGCCATCATTGCGATAAAGGAAAG
GCCATCGTTGAAGATGCCTCTGCCGACAGTGGTCCCAAAGATGGACCCCCACCCACGAGGAGCATCGTGGAAAAAG
AAGACGTTCCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCT
CTTGTCTTTCTTGCGTGAGCGATCTTCAACGTTGTCAGATCGTGCTTCGGCACCAGTACAATGAAAATGGCCTCGAGT
GACGCTAACCCTAGTGACGGCAGCGCCGCCAATCTTGTGCCTGAGGTTAATAATGAGGTGATGGCCCTGGAGCCTG
TGGTGGGCGCAGCCATAGCAGCGCCCGTGGCCGGTCAGCAGAATGTGATTGACCCGTGGATACGCAACAATTTTGT
CCAAGCCCCTGGTGGGGAGTTCACCGTTAGCCCGAGAAATGCGCCAGGAGAAATCCTGTGGTCGGCCAGCTTGGGA
CCCGATCTGAACCCCTATTTGCTGCATCTCGCTCGGATGTACAACGGGTATGCCGGCGGATTTGAAGTGCAGGTGAT
TCTGGCTGGGAACGCGTTCACTGCTGGCAAAGTGATCTTTGCAGCGGTGCCTCCCAACTTCCCCACTGAAGGACTGT
CTCCAAGCCAGGTCACAATGTTTCCACACATCGTGGTGGACGTACGGCAGCTAGAGCCTGTCCTGATTCCCCTCCCT
GATGTACGCAATAATTTCTACCACTACAATCAATCCAATGATCCGACCATTAAACTCATCGCGATGTTGTACACCCCTC
TGCGCGCTAACAATGCTGGAGACGACGTATTCACCGTGTCATGCAGAGTGCTCACCAGACCTTCACCAGACTTTGAC
TTTATCTTCTTAGTGCCCCCCACTGTTGAGAGCCGAACCAAGCCCTTTAGTGTCCCCGTACTCACAGTCGAGGAGATG
ACAAATAGCCGCTTTCCAATCCCCCTTGAGAAACTGTTCACAGGACCTTCCTCGGCATTCGTGGTTCAGCCACAGAAC
GGACGCTGCACAACTGACGGCGTGCTGCTCGGAACCACCCAGCTTAGCCCTGTTAATATCTGTACGTTTAGAGGCGA
CGTAACTCACATAACTGGCTCACGGAACTATACCATGAATCTGGCATCACAGAATTGGAATGACTACGACCCAACCG
AAGAGATTCCCGCACCTCTTGGAACCCCCGACTTTGTGGGAAAAATACAGGGCGTCCTGACACAAACCACCAGAACC
GATGGCTCCACACGGGGACACAAGGCAACCGTCTACACTGGCTCTGCCGATTTTGCCCCGAAACTGGGTAGAGTGC
AGTTTGAGACCGACACTGACCGGGACTTTGAAGCCAATCAGAATACTAAGTTCACACCTGTAGGAGTGATTCAGGA
CGGGGGCACCACTCACCGGAACGAGCCGCAACAATGGGTCCTGCCCTCTTATAGCGGGAGGAATACTCATAATGTG
CATTTGGCTCCTGCAGTGGCTCCCACGTTTCCCGGGGAACAACTGCTCTTTTTTCGTTCAACCATGCCTGGATGCTCC
GGATATCCCAATATGGATCTCGATTGCCTGCTCCCACAGGAATGGGTGCAGTATTTTTATCAAGAGGCCGCACCAGC
CCAATCCGACGTCGCACTTCTGCGGTTCGTGAATCCAGACACAGGCCGCGTGTTGTTTGAGTGCAAATTGCACAAAT
CAGGATACGTTACAGTGGCTCATACTGGACAGCATGACCTGGTGATCCCACCCAACGGATATTTTAGGTTCGACTCC
TGGGTGAATCAGTTTTATACATTAGCCCCCATGGGGAATGGGACTGGCAGACGCAGGGCTGTCTGAAGGCCTATTT
TCTTTAGTTTGAATTTACTGTTATTCGGTGTGCATTTCTATGTTTGGTGAGCGGTTTTCTGTGCTCAGAGTGTGTTTAT
TTTATGTAATTTAATTTCTTTGTGAGCTCCTGTTTAGCAGGTCGTCCCTTCAGCAAGGACACAAAAAGATTTTAATTTT
ATTATCGTTCAAACATTTGGCAATAAAGTTTCTTAAGATTGAATCCTGTTGCCGGTCTTGCGATGATTATCATATAATT
TCTGTTGAATTACGTTAAGCATGTAATAATTAACATGTAATGCATGACGTTATTTATGAGATGGGTTTTTATGATTAG
AGTCCCGCAATTATACATTTAATACGCGATAGAAAACAAAATATAGCGCGCAAACTAGGATAAATTATCGCGCGCGG
TGTCATCTATGTTACTAGAT

Construct 2724 (VP1 Wt GI.1 hCod)

Construct 3300 (Wt GI.2 hCod)

Construct 3979 (Wt GI.3 hCod)

Construct 4140 (VP1 GI.3_Q84S hCod)

Construct 4141 (VP1 GI.3_S94L hCod)

Construct 4142 (VP1 GI.3_Q84S+S94L hCod)

Construct 4179 (VP1 GI.3_A43V+S94L hCod)

Construct 4180 (VP1 GI.3_M57I+S94L hCod)

Construct 4181 (VP1 GI.3_A43V+M57I+S94L hCod)

Construct 3980 (VP1 Wt GI.5 hCod)

Construct 4130 (VP1 GI.5_Q84S)

Construct 4131 (VP1 GI.5_A94L hCod)

Construct 4132 (VP1 GI.5_Q84S+A94L hCod)

Construct 4210 (VP1 GI.7_R84S hCod)

Construct 4217 (VP1 GI.7_M57I hCod)

Construct 4218 (VP1 GI.7_M57I+R84S hCod)

Construct 3982 (Wt VP1 GII.2 hCod)

Construct 4143 (VP1 GII.2_E80S)

Construct 4144 (VP1 GII.2_A90L hCod)

Construct 4145 (VP1 GII.2_E80S+A90L hCod)

Construct 4182 (VP1 GII.2_A39V+E80S+A90L hCod)

Construct 4183Y (VP1 GII.2_R53I+E80S+A90L hCod)

Construct 4184 (VP1 GII.2_A39V+R53I+E80S+A90L hCod).

Construct 3983 (Wt VP1 GII.3 hCod)

Construct 4146 (VP1 GII.3_E80S hCod)

Construct 4147 (VP1 GII.3_A90L hCod)

Construct 4148 (VP1 GII.3_E80S+A90L)

Construct 3760 (Wt VP1 GII.4 hCod)

Construct 4155 (VP1 GII.4_A39V hCod)

Construct 4156 (VP1 GII.4_V47P hCod)

Construct 4157 (VP1 GII.4_R53I hCod)

Construct 4133 (VP1 GII.4_P80S hCod)

Construct 4134 (VP1 GII.4_S90L hCod)

Construct 4158 (VP1 GII.4_ Δ35-42 hCod)

Construct 4159 (VP1 GII.4_SSTAVATA hCod)

Construct 4165 (VP1 GII.4_A39V+P80S hCod)

Construct 4166 (VP1 GII.4_V47P+P80S hCod)

Construct 4167 (VP1 GII.4_R53I+P80S hCod)

Construct 4135 (VP1 GII.4_P80S+S90L hCod)

Construct 4168 (GII.4_ P80S+Δ35-42 hCod)

Construct 4169 (VP1 GII.4_P80S+SSTAVATA hCod)

Construct 4185 (VP1 GII.4_A39V+R53I hCod);

Construct 4186Y (VP1 GII.4_A39V+R53I+P80S hCod)

Construct 3993 (Wt VP1 GII.6 hCod)

Construct 4149 (VP1 GII.6_E80S hCod)

Construct 4150 (VP1 GII.6_S90L hCod)

Construct 4151 (VP1 GII.6_E80S+S90L)

Construct 3995 (Wt VP1 GII.12 hCod)

Construct 4136 (VP1 GII.12_E80S hCod)

Construct 4137 (VP1 GII.12_A90L hCod)

Construct 4138 (VP1 GII.12_E80S+A90L)

Construct 4234 (VP1 GII.17_A39V hCod)

Construct 4235 (VP1 GII.17_R53I hCod)

Construct 4232 (VP1 GII.17_ A90L hCod)

Construct 4236 (VP1 GII.17_A39V+R53I hCod)

Construct 4233 (VP1 GII.17_E80S+A90L hCod)

Construct 2725 (Wt VP2 GI.1)

Construct 3303 (Wt VP2 GI.3 hCod)

Construct 3307 (Wt VP2 GII.6)

Construct 1190 (Cloning vector 1190)

Construct 3677 (Cloning vector 3677)

GII.4 P80X constructs (cloning vectors), wherein X=A (4281); X=N (4285); X=K (4286); X=H (4287)

GII.4 P80s+A39X constructs (cloning vectors), wherein X=I (4256); X=M (4257); X=G (4258); X=S (4259); X=E (4260); X=D (4261); X=N (4262); X=Q (4263); X=K (4264); X=H (4265)

GI.7 M57X constructs (cloning vectors), wherein X= L 4266); G (4268); S (4269); T (4270; N (4273); Q (4274); K (4275); or H (4276).

GI.3 S94X constructs (cloning vectors), wherein X=V (4288); I (4289); M (4290); T (4292); E (4293); D (4294); N (4295); Q (4296); K (4297); or H (4298).

SEQUENCE LISTING

```
<160> NUMBER OF SEQ ID NOS: 293

<210> SEQ ID NO 1
<211> LENGTH: 530
<212> TYPE: PRT
<213> ORGANISM: Norovirus

<400> SEQUENCE: 1

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255
```

-continued

```
Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530
```

<210> SEQ ID NO 2
<211> LENGTH: 1593
<212> TYPE: DNA
<213> ORGANISM: Norovirus

<400> SEQUENCE: 2

```
atgatgatgg cgtctaagga cgctacatca agcgtggatg gcgctagtgg cgctggtcag      60

ttggtaccgg aggttaatgc ttctgaccct cttgcaatgg atcctgtagc aggttcttcg     120

acagcagtcg cgactgctgg acaagttaat cctattgatc cctggataat taataatttt     180

gtgcaagccc cccaaggtga atttactatt tccccaaata atacccccgg tgatgttttg     240

tttgatttga gtttgggtcc ccatcttaat cctttcttgc tccatctatc acaaatgtat     300

aatggttggg ttggtaacat gagagtcagg attatgctag ctggtaatgc ctttactgcg     360

gggaagataa tagtttcctg cataccccct ggttttggtt cacataatct tactatagca     420

caagcaactc tctttccaca tgtgattgct gatgttagga ctctagaccc cattgaggtg     480

cctttggaag atgttaggaa tgttctcttt cataataatg atagaaatca acaaaccatg     540
```

-continued

```
cgccttgtgt gcatgctgta cacccccctc cgcactggtg gtggtactgg tgattctttt    600

gtagttgcag ggcgagttat gacttgcccc agtcctgatt ttaatttctt gtttttagtc    660

cctcctacgg tggagcagaa aaccaggccc ttcacactcc caaatctgcc attgagttct    720

ctgtctaact cacgtgcccc tctcccaatc agtagtatgg gcatttcccc agacaatgtc    780

cagagtgtgc agttccaaaa tggtcggtgt actctggatg gccgcctggt tggcaccacc    840

ccagtttcat tgtcacatgt tgccaagata agagggacct ccaatggcac tgtaatcaac    900

cttactgaat tggatggcac accctttcac ccttttgagg gccctgcccc cattgggttt    960

ccagacctcg gtggttgtga ttggcatatc aatatgacac agtttggcca ttctagccag   1020

acccagtatg atgtagacac cacccctgac acttttgtcc cccatcttgg ttcaattcag   1080

gcaaatggca ttggcagtgg taattatgtt ggtgttctta gctggatttc ccccccatca   1140

cacccgtctg gctcccaagt tgacctttgg aagatcccca attatgggtc aagtattacg   1200

gaggcaacac atctagcccc ttctgtatac ccccctggtt tcggagaggt attggtcttt   1260

ttcatgtcaa aaatgccagg tcctggtgct tataatttgc cctgtctatt accacaagag   1320

tacatttcac atcttgctag tgaacaagcc cctactgtag gtgaggctgc cctgctccac   1380

tatgttgacc ctgataccgg tcggaatctt ggggaattca aagcataccc tgatggtttc   1440

ctcacttgtg tccccaatgg ggctagctcg ggtccacaac agctgccgat caatggggtc   1500

tttgtctttg tttcatgggt gtccagattt tatcaattaa agcctgtggg aactgccagc   1560

tcggcaagag gtaggcttgg tctgcgccga taa                                1593
```

<210> SEQ ID NO 3
<211> LENGTH: 1593
<212> TYPE: DNA
<213> ORGANISM: Artificial Sequence
<220> FEATURE:
<223> OTHER INFORMATION: Nucleic acid sequence of human codon-optimized VP1 G1.1

<400> SEQUENCE: 3

```
atgatgatgg ctagtaaaga tgcgacctcc tctgtggatg gtgcgtcagg ggcaggacaa     60

ctcgtacccg aggtaaacgc cagcgaccca cttgccatgg accccgttgc cggaagttcc    120

acagcagtgg ccacagccgg tcaagtgaat ccaattgatc cgtggattat caacaatttc    180

gtccaggcac cccagggcga gttcacaatt tcaccaaaca atacaccggg cgatgtgcta    240

ttcgatcttt ccttgggtcc tcaccttaac ccttttctac tccatctctc acagatgtac    300

aatggttggg taggaaacat gagagtccgg atcatgctgg ctggcaatgc ctttaccgct    360

ggcaagatca tcgtcagttg tattcctccc ggatttggat ctcataatct gaccattgct    420

caagcgactc tctttcccca tgtcatcgcc gacgttagga ccctggaccc catcgaggtg    480

cccctggagg acgtccggaa tgttttgttc cacaacaacg acagaaacca gcagacgatg    540

agacttgtct gtatgctcta taccccactg cggactggag gcgggactgg agactccttc    600

gttgtggcag gaagagtgat gacatgcccc tcccccgact tcaactttct ttttctggtc    660

ccaccaaccg ttgagcagaa gacgcggccc tttacactgc ccaatctccc gctttcaagt    720

ctgagtaatt cacgggcccc attgccgatc tcctcaatgg gaatctcccc cgacaacgtc    780

cagtctgtcc aattccaaaa tgggagatgc acactggacg gtcgcctggt gggaacaact    840

ccggtgtccc tctcacatgt cgccaaaatc cgcggcacat caaatggtac cgtaatcaat    900

ctgacagaac ttgatggcac gcccttccat ccctttgaag gaccagcccc tattggattt    960
```

```
cctgatctgg gaggttgcga ctggcacata aacatgacac agtttggcca ctccagccag   1020

acacagtatg atgtcgatac aaccccagat accttcgtgc cacacctggg atctattcaa   1080

gctaacggta ttggatccgg caactacgtg ggagtcttat cttggatctc accaccatcc   1140

cacccctcag gatcccaggt tgacttgtgg aagataccga attatggatc ctcgatcact   1200

gaagccacgc acctcgcacc ttccgtctac ccaccaggtt ttggagaagt cttggtgttt   1260

ttcatgagca aaatgcccgg ccctggagcc tacaatctcc cttgcctact ccctcaagag   1320

tatattagtc acctcgcatc tgagcaggcc ccgaccgttg gcgaggcagc cctgctgcat   1380

tatgtggatc cggacaccgg caggaacctg ggtgagttca aagcttatcc tgacggtttt   1440

ctaacatgtg taccaaatgg cgcttccagc ggccctcaac agctcccaat caatggcgtg   1500

ttcgtttttg tcagctgggt aagccgcttc taccagctga agcccgtggg gacagcttct   1560

tctgcccgcg gacgcctcgg tctgcggaga taa                                1593


<210> SEQ ID NO 4
<211> LENGTH: 546
<212> TYPE: PRT
<213> ORGANISM: Norovirus

<400> SEQUENCE: 4

Met Met Met Ala Ser Lys Asp Ala Pro Gln Ser Ala Asp Gly Ala Ser
1               5                   10                  15

Gly Ala Gly Gln Leu Val Pro Glu Val Asn Thr Ala Asp Pro Leu Pro
            20                  25                  30

Met Glu Pro Val Ala Gly Pro Thr Thr Ala Val Ala Thr Ala Gly Gln
        35                  40                  45

Val Asn Met Ile Asp Pro Trp Ile Val Asn Asn Phe Val Gln Ser Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Ile Leu
            100                 105                 110

Leu Ala Gly Asn Ala Phe Ser Ala Gly Lys Ile Ile Val Cys Cys Val
        115                 120                 125

Pro Pro Gly Phe Thr Ser Ser Ser Leu Thr Ile Ala Gln Ala Thr Leu
    130                 135                 140

Phe Pro His Val Ile Ala Asp Val Arg Thr Leu Glu Pro Ile Glu Met
145                 150                 155                 160

Pro Leu Glu Asp Val Arg Asn Val Leu Tyr His Thr Asn Asp Asn Gln
                165                 170                 175

Pro Thr Met Arg Leu Val Cys Met Leu Tyr Thr Pro Leu Arg Thr Gly
            180                 185                 190

Gly Gly Ser Gly Asn Ser Asp Ser Phe Val Val Ala Gly Arg Val Leu
        195                 200                 205

Thr Ala Pro Ser Ser Asp Phe Ser Phe Leu Phe Leu Val Pro Pro Thr
    210                 215                 220

Ile Glu Gln Lys Thr Arg Ala Phe Thr Val Pro Asn Ile Pro Leu Gln
225                 230                 235                 240

Thr Leu Ser Asn Ser Arg Phe Pro Ser Leu Ile Gln Gly Met Ile Leu
                245                 250                 255
```

-continued

```
Ser Pro Asp Ala Ser Gln Val Val Gln Phe Gln Asn Gly Arg Cys Leu
            260                 265                 270

Ile Asp Gly Gln Leu Leu Gly Thr Thr Pro Ala Thr Ser Gly Gln Leu
        275                 280                 285

Phe Arg Val Arg Gly Lys Ile Asn Gln Gly Ala Arg Thr Leu Asn Leu
    290                 295                 300

Thr Glu Val Asp Gly Lys Pro Phe Met Ala Phe Asp Ser Pro Ala Pro
305                 310                 315                 320

Val Gly Phe Pro Asp Phe Gly Lys Cys Asp Trp His Met Arg Ile Ser
                325                 330                 335

Lys Thr Pro Asn Asn Thr Ser Ser Gly Asp Pro Met Arg Ser Val Asp
            340                 345                 350

Val Gln Thr Asp Val Gln Gly Phe Val Pro His Leu Gly Ser Ile Gln
        355                 360                 365

Phe Asp Glu Val Phe Asn His Pro Thr Gly Asp Tyr Ile Gly Thr Ile
    370                 375                 380

Glu Trp Ile Ser Gln Pro Ser Thr Pro Pro Gly Thr Asp Ile Asn Leu
385                 390                 395                 400

Trp Glu Ile Pro Asp Tyr Gly Ser Ser Leu Ser Gln Ala Ala Asn Leu
                405                 410                 415

Ala Pro Pro Val Phe Pro Pro Gly Phe Gly Glu Ala Leu Val Tyr Phe
            420                 425                 430

Val Ser Ala Phe Pro Gly Pro Asn Asn Arg Ser Ala Pro Asn Asp Val
        435                 440                 445

Pro Cys Leu Leu Pro Gln Glu Tyr Val Thr His Phe Val Ser Glu Gln
    450                 455                 460

Ala Pro Thr Met Gly Asp Ala Ala Leu Leu His Tyr Val Asp Pro Asp
465                 470                 475                 480

Thr Asn Arg Asn Leu Gly Glu Phe Lys Leu Tyr Pro Gly Gly Tyr Leu
                485                 490                 495

Thr Cys Val Pro Asn Gly Val Gly Ala Gly Pro Gln Gln Leu Pro Leu
            500                 505                 510

Asn Gly Val Phe Leu Phe Val Ser Trp Val Ser Arg Phe Tyr Gln Leu
        515                 520                 525

Lys Pro Val Gly Thr Ala Ser Thr Ala Arg Gly Arg Leu Gly Val Arg
    530                 535                 540

Arg Ile
545
```

<210> SEQ ID NO 5
<211> LENGTH: 1641
<212> TYPE: DNA
<213> ORGANISM: Artificial Sequence
<220> FEATURE:
<223> OTHER INFORMATION: Nucleic acid sequence of human codon-optimized
VP1 G1.2 Leuven 2003 D2DEL3

<400> SEQUENCE: 5

```
atgatgatgg cttcaaagga tgctccccaa agcgcggacg gagctagcgg cgccggacag     60

ttggttccgg aagtcaacac tgccgatcca ctgcccatgg aacccgtagc tggtccaaca    120

accgctgttg ccaccgccgg ccaggttaac atgatcgatc catggattgt taataacttt    180

gtacagagcc cccaggggga gttcacaatt tctccgaaca atacccctgg ggacattctg    240

ttcgatctgc aactgggccc acacttgaat cctttcctga gccatctttc acagatgtac    300

aacggatggg ttgggaacat gcgtgttcgg atcctccttg ctggcaacgc cttcagtgct    360
```

```
ggcaagatta tcgtgtgctg cgtaccacca gggtttacct cgagttcatt aaccattgct    420

caggccaccc ttttccctca cgtgatcgca gacgtgcgta ccttagaacc aatcgaaatg    480

cccctggaag atgtacggaa cgtgctgtac catactaatg ataaccagcc aacgatgaga    540

ttagtgtgca tgctgtacac ccccctgaga actggaggag gttctggaaa ttccgacagt    600

tttgtggtgg ctggcagggt cctgaccgct cccagtagcg acttcagctt tttgttcctc    660

gttcctccta caatcgaaca aaaaacaaga gcattcacag tgcccaacat tccactgcag    720

actttaagca attccaggtt tcccagcttg atccagggta tgatcctttc tcccgacgcc    780

tcccaagttg tgcagttcca gaatgggaga tgtcttatcg acggtcagct tctgggaaca    840

acccctgcca cctccgggca actcttccgg gtgagaggca aaatcaatca gggcgccaga    900

acactgaatc tgacagaagt ggacgggaaa ccctttatgg cgttcgatag ccccgcgccc    960

gttggattcc ctgacttcgg caagtgtgat tggcacatgc gcatcagtaa gactcccaac   1020

aacacttcat ctggagaccc catgaggagc gtggatgtcc agaccgacgt gcagggcttc   1080

gtgccgcact tgggatctat ccagttcgat gaggtgttca atcaccctac tggcgactac   1140

ataggcacaa ttgagtggat aagtcaacca tctacacctc cagggaccga cataaacctg   1200

tgggaaattc ctgattacgg gtcatccctg agtcaagctg ccaatcttgc accccctgtc   1260

tttccccccg gctttggtga ggctcttgtt tacttcgtct ctgcatttcc tggtcctaac   1320

aaccgctccg cccctaacga tgttccgtgt ttgttacccc aggaatatgt gactcatttc   1380

gtttccgaac aggcacccac catgggggac gctgccctgc tacactatgt ggaccccgac   1440

accaatagaa acctcggcga gttcaaactc taccccgggg gatacctgac ctgtgttcca   1500

aatggagtgg gagcaggccc acaacagctg cccctgaatg gggtcttcct gttcgtttct   1560

tgggtgtcac gcttttacca gctgaagccc gttggcacag cttctacggc acgcggcagg   1620

ctaggggtcc gccgaatctg a                                             1641
```

```
<210> SEQ ID NO 6
<211> LENGTH: 543
<212> TYPE: PRT
<213> ORGANISM: Artificial Sequence
<220> FEATURE:
<223> OTHER INFORMATION: Amino acid sequence of VP1 GI.3 LillaEdet 2008
      H2DG70

<400> SEQUENCE: 6

Met Met Met Ala Ser Lys Asp Ala Pro Thr Asn Met Asp Gly Thr Ser
1               5                   10                  15

Gly Ala Gly Gln Leu Val Pro Glu Val Ser Thr Ala Glu Pro Ile Ser
            20                  25                  30

Met Glu Pro Val Ala Gly Ala Ala Thr Ala Ala Ala Thr Ala Gly Gln
        35                  40                  45

Val Asn Met Ile Asp Pro Trp Ile Met Ser Asn Tyr Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ala Gln Met Tyr Asn Gly Trp Val Gly Asn Met Lys Val Arg Val Leu
            100                 105                 110

Leu Ala Gly Asn Ala Phe Thr Ala Gly Lys Ile Ile Ile Ser Cys Val
        115                 120                 125
```

```
Pro Pro Gly Phe Ala Ala Gln Asn Val Ser Ile Ala Gln Ala Thr Met
    130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Asn Asn Asp Ser Thr
                165                 170                 175

Pro Thr Met Arg Leu Ile Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205

Thr Cys Pro Ser Pro Asp Phe Asn Phe Leu Phe Leu Val Pro Pro Asn
    210                 215                 220

Val Glu Gln Lys Thr Lys Pro Phe Ser Val Pro Asn Leu Pro Leu Asn
225                 230                 235                 240

Val Leu Ser Asn Ser Arg Val Pro Ser Leu Ile Lys Ser Met Met Val
                245                 250                 255

Ser Gln Asp His Gly Gln Met Val Gln Phe Gln Asn Gly Arg Val Thr
            260                 265                 270

Leu Asp Gly Gln Leu Gln Gly Thr Thr Pro Thr Ser Ala Ser Gln Leu
        275                 280                 285

Cys Lys Ile Arg Gly Thr Val Tyr His Ala Thr Gly Gly Gln Gly Leu
    290                 295                 300

Asn Leu Thr Glu Ile Asp Gly Thr Pro Tyr His Ala Phe Glu Ser Pro
305                 310                 315                 320

Ala Pro Ile Gly Phe Pro Asp Leu Gly Glu Cys Asp Trp His Ile Asn
                325                 330                 335

Ala Ser Pro Ala Asn Ala Phe Thr Asp Gly Ser Ile Ile His Arg Ile
            340                 345                 350

Asp Val Ala Gln Asp Ser Thr Phe Ala Pro His Leu Gly Thr Ile His
        355                 360                 365

Tyr Thr Asn Ala Asp Tyr Asn Ala Asn Val Gly Leu Ile Cys Ser Leu
    370                 375                 380

Glu Trp Leu Ser Pro Pro Ser Gly Gly Ala Pro Lys Val Asn Pro Trp
385                 390                 395                 400

Ala Ile Pro Arg Tyr Gly Ser Thr Leu Thr Glu Ala Ala Gln Leu Ala
                405                 410                 415

Pro Pro Ile Tyr Pro Pro Gly Phe Gly Glu Ala Ile Val Phe Phe Met
            420                 425                 430

Ser Asp Phe Pro Ile Ala Asn Gly Ser Asp Gly Leu Ser Val Pro Cys
        435                 440                 445

Thr Ile Pro Gln Glu Phe Val Thr His Phe Val Asn Glu Gln Ala Pro
    450                 455                 460

Thr Arg Gly Glu Ala Ala Leu Leu His Tyr Val Asp Pro Asp Thr His
465                 470                 475                 480

Arg Asn Leu Gly Glu Phe Lys Leu Tyr Pro Glu Gly Phe Met Thr Cys
                485                 490                 495

Val Pro Asn Ser Ser Gly Ser Gly Pro Gln Thr Leu Pro Ile Asn Gly
            500                 505                 510

Val Phe Thr Phe Ile Ser Trp Val Ser Arg Phe Tyr Gln Leu Lys Pro
        515                 520                 525

Val Gly Thr Thr Gly Pro Val Arg Arg Leu Gly Ile Arg Arg Ser
    530                 535                 540
```

<210> SEQ ID NO 7
<211> LENGTH: 1632
<212> TYPE: DNA
<213> ORGANISM: Artificial Sequence
<220> FEATURE:
<223> OTHER INFORMATION: Nucleic acid sequence of human codon-optimized
      VP1 GI.3 LillaEdet 2008 H2DG70

<400> SEQUENCE: 7

```
atgatgatgg cttccaagga tgctcccaca aacatggatg gaacaagcgg cgcggggcaa     60

cttgtgccgg aggtgtccac ggcggaaccc atttccatgg aacctgtggc cggcgcagcc    120

actgctgccg ccaccgcagg acaggtaaac atgatcgacc cctggatcat gtcaaattac    180

gttcaggctc cacaggggga gtttaccata agcccaaaca acaccccggg tgacatcttg    240

tttgacctgc agctaggacc acacttgaat ccgtttctga gtcacttggc tcagatgtat    300

aatggatggg ttggaaacat gaaggtgcgc gtgctcctgg cgggcaatgc attcacagcc    360

gggaagatta ttatctcttg cgtgccacct ggatttgcag cccagaacgt gtctatcgca    420

caggcaacca tgtttccgca tgtcatcgca gatgtgcgcg tgctagagcc catcgaggtg    480

ccccttgagg acgtgcgcaa cgtcctattc cataacaatg atagcacccc caccatgcgc    540

ttgatatgta tgttatatac tcccctccgc gccagtgggt ccagctccgg gaccgatcct    600

tttgtgattg ctgggcgggt gttgacttgt cctagccctg acttcaactt cctttttctg    660

gtgcctccaa atgtagaaca gaaaacaaag ccattcagcg tgccaaacct gccccttaac    720

gtgctgtcga attcccgagt gccttccctt attaagtcca tgatggtatc tcaggatcac    780

ggtcaaatgg tgcagtttca gaacggccga gtgacgttag acgggcagct gcagggcaca    840

accccaacca gtgccagtca gctgtgtaag atcagaggca ccgtctacca cgcaactggc    900

ggacaggggc tgaatcttac tgagatcgat ggtacccct accatgcatt cgagtcacct     960

gcacctattg gatttcccga tcttggggag tgtgattggc atatcaatgc ttcacctgcc   1020

aacgctttca cagacgggtc tattattcat cgcattgacg tagcacagga tagcacattt   1080

gccccgcacc tgggtaccat ccactatacg aacgcagatt acaacgcaaa cgtgggtctt   1140

atctgtagcc tagagtggct atctccgcca agcggtgggg cccctaaagt taacccatgg   1200

gctattcctc ggtacgggtc tacgctgact gaggccgctc agctggcacc ccccatatat   1260

ccaccaggat tcggggaagc cattgttttc tttatgtccg attttccgat agccaacggt   1320

tcagatggcc ttagtgtccc ttgcacgatt ccacaggaat ttgtgacaca cttcgtaaac   1380

gagcaggctc ctactcgggg cgaggctgcc ttgttgcatt acgtagaccc cgatacccat   1440

agaaacctgg gcgaattcaa actctaccct gaaggtttca tgacctgcgt acctaactcc   1500

tccggcagtg gccctcaaac cttgccgatc aacggcgtgt tcacgtttat cagctgggtt   1560

tcacggtttt accaactcaa gcccgtcgga acaactgggc cagttcggag gctcgggatc   1620

agacggagct ag                                                       1632
```

<210> SEQ ID NO 8
<211> LENGTH: 543
<212> TYPE: PRT
<213> ORGANISM: Norovirus

<400> SEQUENCE: 8

```
Met Met Met Ala Ser Lys Asp Ala Pro Thr Asn Met Asp Gly Thr Ser
1               5                   10                  15

Gly Ala Gly Gln Leu Val Pro Glu Val Ser Thr Ala Glu Pro Ile Ser
```

```
            20                  25                  30

Met Glu Pro Val Ala Gly Ala Ala Thr Ala Ala Ala Thr Ala Gly Gln
        35                  40                  45

Val Asn Met Ile Asp Pro Trp Ile Met Ser Asn Tyr Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Leu His Leu
                85                  90                  95

Ala Gln Met Tyr Asn Gly Trp Val Gly Asn Met Lys Val Arg Val Leu
            100                 105                 110

Leu Ala Gly Asn Ala Phe Thr Ala Gly Lys Ile Ile Ile Ser Cys Val
        115                 120                 125

Pro Pro Gly Phe Ala Ala Gln Asn Val Ser Ile Ala Gln Ala Thr Met
    130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Asn Asn Asp Ser Thr
                165                 170                 175

Pro Thr Met Arg Leu Ile Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205

Thr Cys Pro Ser Pro Asp Phe Asn Phe Leu Phe Leu Val Pro Pro Asn
    210                 215                 220

Val Glu Gln Lys Thr Lys Pro Phe Ser Val Pro Asn Leu Pro Leu Asn
225                 230                 235                 240

Val Leu Ser Asn Ser Arg Val Pro Ser Leu Ile Lys Ser Met Met Val
                245                 250                 255

Ser Gln Asp His Gly Gln Met Val Gln Phe Gln Asn Gly Arg Val Thr
            260                 265                 270

Leu Asp Gly Gln Leu Gln Gly Thr Thr Pro Thr Ser Ala Ser Gln Leu
        275                 280                 285

Cys Lys Ile Arg Gly Thr Val Tyr His Ala Thr Gly Gly Gln Gly Leu
    290                 295                 300

Asn Leu Thr Glu Ile Asp Gly Thr Pro Tyr His Ala Phe Glu Ser Pro
305                 310                 315                 320

Ala Pro Ile Gly Phe Pro Asp Leu Gly Glu Cys Asp Trp His Ile Asn
                325                 330                 335

Ala Ser Pro Ala Asn Ala Phe Thr Asp Gly Ser Ile Ile His Arg Ile
            340                 345                 350

Asp Val Ala Gln Asp Ser Thr Phe Ala Pro His Leu Gly Thr Ile His
        355                 360                 365

Tyr Thr Asn Ala Asp Tyr Asn Ala Asn Val Gly Leu Ile Cys Ser Leu
    370                 375                 380

Glu Trp Leu Ser Pro Pro Ser Gly Gly Ala Pro Lys Val Asn Pro Trp
385                 390                 395                 400

Ala Ile Pro Arg Tyr Gly Ser Thr Leu Thr Glu Ala Ala Gln Leu Ala
                405                 410                 415

Pro Pro Ile Tyr Pro Pro Gly Phe Gly Glu Ala Ile Val Phe Phe Met
            420                 425                 430

Ser Asp Phe Pro Ile Ala Asn Gly Ser Asp Gly Leu Ser Val Pro Cys
        435                 440                 445
```

-continued

```
Thr Ile Pro Gln Glu Phe Val Thr His Phe Val Asn Glu Gln Ala Pro
    450                 455                 460

Thr Arg Gly Glu Ala Ala Leu Leu His Tyr Val Asp Pro Asp Thr His
465                 470                 475                 480

Arg Asn Leu Gly Glu Phe Lys Leu Tyr Pro Glu Gly Phe Met Thr Cys
                485                 490                 495

Val Pro Asn Ser Ser Gly Ser Gly Pro Gln Thr Leu Pro Ile Asn Gly
            500                 505                 510

Val Phe Thr Phe Ile Ser Trp Val Ser Arg Phe Tyr Gln Leu Lys Pro
        515                 520                 525

Val Gly Thr Thr Gly Pro Val Arg Arg Leu Gly Ile Arg Arg Ser
    530                 535                 540
```

<210> SEQ ID NO 9
<211> LENGTH: 1632
<212> TYPE: DNA
<213> ORGANISM: Artificial Sequence
<220> FEATURE:
<223> OTHER INFORMATION: Nucleic acid sequence of human codon optimized VP1 GI.3 Lil08 S94L

<400> SEQUENCE: 9

```
atgatgatgg cttccaagga tgctcccaca aacatggatg gaacaagcgg cgcggggcaa     60
cttgtgccgg aggtgtccac ggcggaaccc atttccatgg aacctgtggc cggcgcagcc    120
actgctgccg ccaccgcagg acaggtaaac atgatcgacc cctggatcat gtcaaattac    180
gttcaggctc cacaggggga gtttaccata agcccaaaca acaccccggg tgacatcttg    240
tttgacctgc agctaggacc acacttgaat ccgtttctgc tccacttggc tcagatgtat    300
aatggatggg ttggaaacat gaaggtgcgc gtgctcctgg cgggcaatgc attcacagcc    360
gggaagatta ttatctcttg cgtgccacct ggatttgcag cccagaacgt gtctatcgca    420
caggcaacca tgtttccgca tgtcatcgca gatgtgcgcg tgctagagcc catcgaggtg    480
ccccttgagg acgtgcgcaa cgtcctattc cataacaatg atagcacccc caccatgcgc    540
ttgatatgta tgttatatac tcccctccgc gccagtgggt ccagctccgg gaccgatcct    600
tttgtgattg ctgggcgggt gttgacttgt cctagccctg acttcaactt cctttttctg    660
gtgcctccaa atgtagaaca gaaaacaaag ccattcagcg tgccaaacct gccccttaac    720
gtgctgtcga attcccgagt gccttccctt attaagtcca tgatggtatc tcaggatcac    780
ggtcaaatgg tgcagtttca gaacggccga gtgacgttag acgggcagct gcagggcaca    840
accccaacca gtgccagtca gctgtgtaag atcagaggca ccgtctacca cgcaactggc    900
ggacaggggc tgaatcttac tgagatcgat ggtacccccct accatgcatt cgagtcacct    960
gcacctattg gatttcccga tcttggggag tgtgattggc atatcaatgc ttcacctgcc   1020
aacgctttca cagacgggtc tattattcat cgcattgacg tagcacagga tagcacattt   1080
gccccgcacc tgggtaccat ccactatacg aacgcagatt acaacgcaaa cgtgggtctt   1140
atctgtagcc tagagtggct atctccgcca agcggtgggg cccctaaagt taacccatgg   1200
gctattcctc ggtacgggtc tacgctgact gaggccgctc agctggcacc ccccatatat   1260
ccaccaggat tcggggaagc cattgttttc tttatgtccg attttccgat agccaacggt   1320
tcagatggcc ttagtgtccc ttgcacgatt ccacaggaat ttgtgacaca cttcgtaaac   1380
gagcaggctc ctactcgggg cgaggctgcc ttgttgcatt acgtagaccc cgatacccat   1440
agaaacctgg gcgaattcaa actctaccct gaaggtttca tgacctgcgt acctaactcc   1500
```

-continued tccggcagtg gccctcaaac cttgccgatc aacggcgtgt tcacgtttat cagctgggtt 1560
tcacggtttt accaactcaa gcccgtcgga acaactgggc cagttcggag gctcgggatc 1620
agacggagct ag 1632

<210> SEQ ID NO 10
<211> LENGTH: 543
<212> TYPE: PRT
<213> ORGANISM: Norovirus

<400> SEQUENCE: 10

Met Met Met Ala Ser Lys Asp Ala Pro Thr Asn Met Asp Gly Thr Ser
1 5 10 15

Gly Ala Gly Gln Leu Val Pro Glu Val Ser Thr Ala Glu Pro Ile Ser
20 25 30

Met Glu Pro Val Ala Gly Ala Ala Thr Ala Ala Ala Thr Ala Gly Gln
35 40 45

Val Asn Met Ile Asp Pro Trp Ile Met Ser Asn Tyr Val Gln Ala Pro
50 55 60

Gln Gly Glu Phe Thr Ile Ser Pro Asn Asn Thr Pro Gly Asp Ile Leu
65 70 75 80

Phe Asp Leu Ser Leu Gly Pro His Leu Asn Pro Phe Leu Leu His Leu
85 90 95

Ala Gln Met Tyr Asn Gly Trp Val Gly Asn Met Lys Val Arg Val Leu
100 105 110

Leu Ala Gly Asn Ala Phe Thr Ala Gly Lys Ile Ile Ile Ser Cys Val
115 120 125

Pro Pro Gly Phe Ala Ala Gln Asn Val Ser Ile Ala Gln Ala Thr Met
130 135 140

Phe Pro His Val Ile Ala Asp Val Arg Val Leu Glu Pro Ile Glu Val
145 150 155 160

Pro Leu Glu Asp Val Arg Asn Val Leu Phe His Asn Asn Asp Ser Thr
165 170 175

Pro Thr Met Arg Leu Ile Cys Met Leu Tyr Thr Pro Leu Arg Ala Ser
180 185 190

Gly Ser Ser Ser Gly Thr Asp Pro Phe Val Ile Ala Gly Arg Val Leu
195 200 205

Thr Cys Pro Ser Pro Asp Phe Asn Phe Leu Phe Leu Val Pro Pro Asn
210 215 220

Val Glu Gln Lys Thr Lys Pro Phe Ser Val Pro Asn Leu Pro Leu Asn
225 230 235 240

Val Leu Ser Asn Ser Arg Val Pro Ser Leu Ile Lys Ser Met Met Val
245 250 255

Ser Gln Asp His Gly Gln Met Val Gln Phe Gln Asn Gly Arg Val Thr
260 265 270

Leu Asp Gly Gln Leu Gln Gly Thr Thr Pro Thr Ser Ala Ser Gln Leu
275 280 285

Cys Lys Ile Arg Gly Thr Val Tyr His Ala Thr Gly Gly Gln Gly Leu
290 295 300

Asn Leu Thr Glu Ile Asp Gly Thr Pro Tyr His Ala Phe Glu Ser Pro
305 310 315 320

Ala Pro Ile Gly Phe Pro Asp Leu Gly Glu Cys Asp Trp His Ile Asn
325 330 335

Ala Ser Pro Ala Asn Ala Phe Thr Asp Gly Ser Ile Ile His Arg Ile

```
            340                 345                 350

Asp Val Ala Gln Asp Ser Thr Phe Ala Pro His Leu Gly Thr Ile His
        355                 360                 365

Tyr Thr Asn Ala Asp Tyr Asn Ala Asn Val Gly Leu Ile Cys Ser Leu
    370                 375                 380

Glu Trp Leu Ser Pro Pro Ser Gly Gly Ala Pro Lys Val Asn Pro Trp
385                 390                 395                 400

Ala Ile Pro Arg Tyr Gly Ser Thr Leu Thr Glu Ala Ala Gln Leu Ala
                405                 410                 415

Pro Pro Ile Tyr Pro Pro Gly Phe Gly Glu Ala Ile Val Phe Phe Met
            420                 425                 430

Ser Asp Phe Pro Ile Ala Asn Gly Ser Asp Gly Leu Ser Val Pro Cys
        435                 440                 445

Thr Ile Pro Gln Glu Phe Val Thr His Phe Val Asn Glu Gln Ala Pro
    450                 455                 460

Thr Arg Gly Glu Ala Ala Leu Leu His Tyr Val Asp Pro Asp Thr His
465                 470                 475                 480

Arg Asn Leu Gly Glu Phe Lys Leu Tyr Pro Glu Gly Phe Met Thr Cys
                485                 490                 495

Val Pro Asn Ser Ser Gly Ser Gly Pro Gln Thr Leu Pro Ile Asn Gly
            500                 505                 510

Val Phe Thr Phe Ile Ser Trp Val Ser Arg Phe Tyr Gln Leu Lys Pro
        515                 520                 525

Val Gly Thr Thr Gly Pro Val Arg Arg Leu Gly Ile Arg Arg Ser
    530                 535                 540
```

<210> SEQ ID NO 11
<211> LENGTH: 1632
<212> TYPE: DNA
<213> ORGANISM: Artificial Sequence
<220> FEATURE:
<223> OTHER INFORMATION: Nucleic acid sequence of human codon optimized
VP1 GI.3 Lil08 Q84S plus sign S94L

<400> SEQUENCE: 11

```
atgatgatgg cttccaagga tgctcccaca aacatggatg gaacaagcgg cgcggggcaa     60

cttgtgccgg aggtgtccac ggcggaaccc atttccatgg aacctgtggc cggcgcagcc    120

actgctgccg ccaccgcagg acaggtaaac atgatcgacc cctggatcat gtcaaattac    180

gttcaggctc cacaggggga gtttaccata agcccaaaca acaccccggg tgacatcttg    240

tttgacctga gcctaggacc acacttgaat ccgtttctgc tccacttggc tcagatgtat    300

aatggatggg ttggaaacat gaaggtgcgc gtgctcctgg cgggcaatgc attcacagcc    360

gggaagatta ttatctcttg cgtgccacct ggatttgcag cccagaacgt gtctatcgca    420

caggcaacca tgtttccgca tgtcatcgca gatgtgcgcg tgctagagcc catcgaggtg    480

ccccttgagg acgtgcgcaa cgtcctattc cataacaatg atagcacccc caccatgcgc    540

ttgatatgta tgttatatac tcccctccgc gccagtgggt ccagctccgg gaccgatcct    600

tttgtgattg ctgggcgggt gttgacttgt cctagccctg acttcaactt cctttttctg    660

gtgcctccaa atgtagaaca gaaaacaaag ccattcagcg tgccaaacct gccccttaac    720

gtgctgtcga attcccgagt gccttccctt attaagtcca tgatggtatc tcaggatcac    780

ggtcaaatgg tgcagtttca gaacggccga gtgacgttag acgggcagct gcagggcaca    840

accccaacca gtgccagtca gctgtgtaag atcagaggca ccgtctacca cgcaactggc    900
```

ggacaggggc tgaatcttac tgagatcgat ggtacccccct accatgcatt cgagtcacct 960
gcacctattg gatttcccga tcttggggag tgtgattggc atatcaatgc ttcacctgcc 1020
aacgctttca cagacgggtc tattattcat cgcattgacg tagcacagga tagcacattt 1080
gccccgcacc tgggtaccat ccactatacg aacgcagatt acaacgcaaa cgtgggtctt 1140
atctgtagcc tagagtggct atctccgcca agcggtgggg cccctaaagt taacccatgg 1200
gctattcctc ggtacgggtc tacgctgact gaggccgctc agctggcacc ccccatatat 1260
ccaccaggat tcggggaagc cattgttttc tttatgtccg attttccgat agccaacggt 1320
tcagatggcc ttagtgtccc ttgcacgatt ccacaggaat ttgtgacaca cttcgtaaac 1380
gagcaggctc ctactcgggg cgaggctgcc ttgttgcatt acgtagaccc cgatacccat 1440
agaaacctgg gcgaattcaa actctaccct gaaggtttca tgacctgcgt acctaactcc 1500
tccggcagtg gccctcaaac cttgccgatc aacggcgtgt tcacgtttat cagctgggtt 1560
tcacggtttt accaactcaa gcccgtcgga acaactgggc cagttcggag gctcgggatc 1620
agacggagct ag 1632

<210> SEQ ID NO 12
<211> LENGTH: 543
<212> TYPE: PRT
<213> ORGANISM: Norovirus

<400> SEQUENCE: 12

Met Met Met Ala Ser Lys Asp Ala Pro Ser Ser Ala Asp Gly Ala Asn
1 5 10 15

Gly Ala Gly Gln Leu Val Pro Glu Val Asn Asn Ala Glu Pro Leu Pro
20 25 30

Leu Asp Pro Val Ala Gly Ala Ser Thr Ala Leu Ala Thr Ala Gly Gln
35 40 45

Val Asn Met Ile Asp Pro Trp Ile Phe Asn Asn Phe Val Gln Ala Pro
50 55 60

Gln Gly Glu Phe Thr Ile Ser Pro Asn Asn Thr Pro Gly Asp Ile Leu
65 70 75 80

Phe Asp Leu Gln Leu Gly Pro His Leu Asn Pro Phe Leu Ala His Leu
85 90 95

Ser Gln Met Tyr Asn Gly Trp Val Gly Asn Met Arg Val Arg Val Ile
100 105 110

Leu Ala Gly Asn Ala Phe Thr Ala Gly Lys Val Ile Ile Cys Cys Val
115 120 125

Pro Pro Gly Phe Gln Ser Arg Thr Leu Ser Ile Ala Gln Ala Thr Leu
130 135 140

Phe Pro His Ile Ile Ala Asp Val Arg Thr Leu Glu Pro Ile Glu Ile
145 150 155 160

Pro Leu Glu Asp Val Arg Asn Thr Leu Tyr His Thr Asn Asp Asn Gln
165 170 175

Pro Thr Met Arg Leu Leu Cys Met Leu Tyr Thr Pro Leu Arg Thr Gly
180 185 190

Gly Gly Ser Gly Gly Thr Asp Ala Phe Val Val Ala Gly Arg Val Leu
195 200 205

Thr Cys Pro Ser Ser Asp Phe Asn Phe Leu Phe Leu Val Pro Pro Thr
210 215 220

Val Glu Gln Lys Thr Arg Pro Phe Ser Val Pro Asn Ile Pro Leu Gln
225 230 235 240

```
Leu Leu Ser Asn Ser Arg Val Pro Asn Leu Ile Gln Ser Met Val Leu
                245                 250                 255

Ser Pro Asp Gln Ala Gln Asn Val Gln Phe Gln Asn Gly Arg Cys Thr
            260                 265                 270

Thr Asp Gly Gln Leu Leu Gly Thr Thr Pro Val Ser Val Ser Gln Ile
        275                 280                 285

Leu Lys Phe Arg Gly Lys Val Ser Ala Gly Ser Lys Val Ile Asn Leu
    290                 295                 300

Thr Glu Leu Asp Gly Ser Pro Phe Leu Ala Phe Glu Ala Pro Ala Pro
305                 310                 315                 320

Thr Gly Phe Pro Asp Leu Gly Thr Ser Asp Trp His Val Glu Met Ser
                325                 330                 335

Leu Asn Ser Asn Ser Gln Ser Ser Gly Asn Pro Ile Leu Leu Arg Asp
            340                 345                 350

Ile His Pro Asn Ser Ser Glu Phe Val Pro His Leu Gly Ser Val Cys
        355                 360                 365

Val Thr Ala Ala Ile Glu Val Ala Gly Asp Tyr Thr Gly Thr Ile Gln
    370                 375                 380

Trp Thr Ser Gln Pro Ser Asn Val Thr Pro Val Pro Asp Val Asn Phe
385                 390                 395                 400

Trp Thr Ile Pro His Tyr Gly Ser Asn Leu Ala Glu Ala Ser Gln Leu
                405                 410                 415

Ala Pro Val Val Tyr Pro Pro Gly Phe Gly Glu Ala Ile Val Tyr Phe
            420                 425                 430

Met Ser Pro Ile Pro Gly Pro Asn Thr Ala His Lys Pro Asn Leu Val
        435                 440                 445

Pro Cys Leu Leu Pro Gln Glu Phe Val Thr His Phe Val Ser Glu Gln
    450                 455                 460

Ala Pro Ser Met Gly Glu Ala Ala Leu Val His Tyr Val Asp Pro Asp
465                 470                 475                 480

Thr Asn Arg Asn Leu Gly Glu Phe Lys Leu Tyr Pro Glu Gly Phe Ile
                485                 490                 495

Thr Cys Val Pro Asn Gly Thr Gly Pro Gln Gln Leu Pro Leu Asn Gly
            500                 505                 510

Val Phe Val Phe Ala Ser Trp Val Ser Arg Phe Tyr Gln Leu Lys Pro
        515                 520                 525

Val Gly Thr Ala Ser Ser Ala Arg Gly Arg Leu Gly Val Arg Arg
    530                 535                 540
```

<210> SEQ ID NO 13
<211> LENGTH: 535
<212> TYPE: PRT
<213> ORGANISM: Norovirus

<400> SEQUENCE: 13

```
Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Met Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80
```

```
Leu Gly Pro Glu Leu Asn Pro Phe Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Ile Pro Pro His Phe
        115                 120                 125

Pro Leu Glu Asn Leu Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Pro Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Thr Leu Pro Ile Leu Thr Ile Gly Glu Leu Ser Asn Ser
225                 230                 235                 240

Arg Phe Pro Val Pro Ile Asp Glu Leu Tyr Thr Ser Pro Asn Glu Gly
                245                 250                 255

Val Val Val Gln Pro Gln Asn Gly Arg Ser Thr Leu Asp Gly Glu Leu
            260                 265                 270

Leu Gly Thr Thr Gln Leu Val Pro Ser Asn Ile Cys Ala Leu Arg Gly
        275                 280                 285

Arg Ile Asn Ala Gln Val Pro Asp Asp His His Gln Trp Asn Leu Gln
    290                 295                 300

Val Thr Asn Ala Asn Gly Thr Ser Phe Asp Pro Thr Glu Asp Val Pro
305                 310                 315                 320

Ala Pro Leu Gly Thr Pro Asp Phe Leu Ala Asn Ile Tyr Gly Val Thr
                325                 330                 335

Ser Gln Arg Asn Pro Asp Asn Thr Cys Arg Ala His Asp Gly Val Leu
            340                 345                 350

Ala Thr Trp Ser Pro Lys Phe Thr Pro Lys Leu Gly Ser Val Val Leu
        355                 360                 365

Gly Thr Trp Glu Glu Ser Asp Leu Asp Leu Asn Gln Pro Thr Arg Phe
    370                 375                 380

Thr Pro Val Gly Leu Tyr Asp Thr Gly His Phe Asp Gln Trp Val Leu
385                 390                 395                 400

Pro Asn Tyr Ser Gly Arg Leu Thr Leu Asn Met Asn Leu Ala Pro Ser
                405                 410                 415

Val Ala Pro Leu Phe Pro Gly Glu Gln Ile Leu Phe Phe Arg Ser His
            420                 425                 430

Ile Pro Leu Lys Gly Gly Thr Ser Asn Gly Ala Ile Asp Cys Leu Leu
        435                 440                 445

Pro Gln Glu Trp Ile Gln His Phe Tyr Gln Glu Ser Ala Pro Ser Pro
    450                 455                 460

Thr Asp Val Ala Leu Ile Arg Tyr Thr Asn Pro Asp Thr Gly Arg Val
465                 470                 475                 480

Leu Phe Glu Ala Lys Leu His Arg Gln Gly Phe Ile Thr Val Ala Asn
                485                 490                 495
```

Ser Gly Ser Arg Pro Ile Val Val Pro Pro Asn Gly Tyr Phe Arg Phe
500 505 510

Asp Ser Trp Val Asn Gln Phe Tyr Ser Leu Ala Pro Met Gly Thr Gly
515 520 525

Asn Gly Arg Arg Arg Val Gln
530 535

<210> SEQ ID NO 14
<211> LENGTH: 542
<212> TYPE: PRT
<213> ORGANISM: Norovirus

<400> SEQUENCE: 14

Met Lys Met Ala Ser Asn Asp Ala Ala Pro Ser Thr Asp Gly Ala Ala
1 5 10 15

Gly Leu Val Pro Glu Ser Asn Asn Glu Val Met Ala Leu Glu Pro Val
20 25 30

Ala Gly Ala Ala Leu Ala Ala Pro Val Thr Gly Gln Thr Asn Ile Ile
35 40 45

Asp Pro Trp Ile Arg Ala Asn Phe Val Gln Ala Pro Asn Gly Glu Phe
50 55 60

Thr Val Ser Pro Arg Asn Ser Pro Gly Glu Val Leu Leu Asn Leu Glu
65 70 75 80

Leu Gly Pro Glu Leu Asn Pro Tyr Leu Ala His Leu Ala Arg Met Tyr
85 90 95

Asn Gly Tyr Ala Gly Gly Met Glu Val Gln Val Met Leu Ala Gly Asn
100 105 110

Ala Phe Thr Ala Gly Lys Leu Val Phe Ala Ala Val Pro Pro His Phe
115 120 125

Pro Val Glu Asn Leu Ser Pro Gln Gln Ile Thr Met Phe Pro His Val
130 135 140

Ile Ile Asp Val Arg Thr Leu Glu Pro Val Leu Leu Pro Leu Pro Asp
145 150 155 160

Val Arg Asn Asn Phe Phe His Tyr Asn Gln Lys Asp Asp Pro Lys Met
165 170 175

Arg Ile Val Ala Met Leu Tyr Thr Pro Leu Arg Ser Asn Gly Ser Gly
180 185 190

Asp Asp Val Phe Thr Val Ser Cys Arg Val Leu Thr Arg Pro Ser Pro
195 200 205

Asp Phe Asp Phe Thr Tyr Leu Val Pro Pro Thr Val Glu Ser Lys Thr
210 215 220

Lys Pro Phe Thr Leu Pro Ile Leu Thr Leu Gly Glu Leu Ser Asn Ser
225 230 235 240

Arg Phe Pro Val Ser Ile Asp Gln Met Tyr Thr Ser Pro Asn Glu Val
245 250 255

Ile Ser Val Gln Cys Gln Asn Gly Arg Cys Thr Leu Asp Gly Glu Leu
260 265 270

Gln Gly Thr Thr Gln Leu Gln Val Ser Gly Ile Cys Ala Phe Lys Gly
275 280 285

Glu Val Thr Ala His Leu His Asp Asn Asp His Leu Tyr Asn Val Thr
290 295 300

Ile Thr Asn Leu Asn Gly Ser Pro Phe Asp Pro Ser Glu Asp Ile Pro
305 310 315 320

Ala Pro Leu Gly Val Pro Asp Phe Gln Gly Arg Val Phe Gly Val Ile
325 330 335

```
Ser Gln Arg Asp Lys His Asn Thr Pro Gly His Asn Glu Pro Ala Asn
            340                 345                 350

Arg Ala His Asp Ala Val Val Pro Thr Tyr Thr Ala Gln Tyr Thr Pro
        355                 360                 365

Lys Leu Gly Gln Ile Gln Ile Gly Thr Trp Gln Thr Asp Asp Leu Thr
    370                 375                 380

Val Asn Gln Pro Val Lys Phe Thr Pro Val Gly Leu Asn Asp Thr Asp
385                 390                 395                 400

His Phe Asn Gln Trp Val Val Pro Arg Tyr Ala Gly Ala Leu Asn Leu
                405                 410                 415

Asn Thr Asn Leu Ala Pro Ser Val Ala Pro Val Phe Pro Gly Glu Arg
            420                 425                 430

Leu Leu Phe Phe Arg Ser Tyr Ile Pro Leu Lys Gly Gly Tyr Gly Thr
        435                 440                 445

Pro Ala Ile Asp Cys Leu Leu Pro Gln Glu Trp Val Gln His Phe Tyr
    450                 455                 460

Gln Glu Ala Ala Pro Ser Met Ser Glu Val Ala Leu Val Arg Tyr Ile
465                 470                 475                 480

Asn Pro Asp Thr Gly Arg Ala Leu Phe Glu Ala Lys Leu His Arg Ala
                485                 490                 495

Gly Phe Met Thr Val Ser Ser Asn Thr Ser Ala Pro Val Val Val Pro
            500                 505                 510

Ala Asn Gly Tyr Phe Arg Phe Asp Ser Trp Val Asn Gln Phe Tyr Ser
        515                 520                 525

Leu Ala Pro Met Gly Thr Gly Asn Gly Arg Arg Arg Ile Gln
    530                 535                 540
```

<210> SEQ ID NO 15
<211> LENGTH: 548
<212> TYPE: PRT
<213> ORGANISM: Norovirus

<400> SEQUENCE: 15

```
Met Lys Met Ala Ser Asn Asp Ala Ala Pro Ser Asn Asp Gly Ala Ala
1               5                   10                  15

Gly Leu Val Pro Glu Ile Ser Ser Glu Ala Met Ala Leu Glu Pro Val
            20                  25                  30

Ala Gly Ala Ala Ile Ala Ala Pro Leu Thr Gly Gln Gln Asn Ile Ile
        35                  40                  45

Asp Pro Trp Ile Met Asn Asn Phe Val Gln Ala Pro Gly Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Ile Asn Pro Tyr Leu Ala His Leu Ala Arg Met Tyr
                85                  90                  95

Asn Gly Tyr Ala Gly Gly Phe Glu Val Gln Val Val Leu Ala Gly Asn
            100                 105                 110

Ala Phe Thr Ala Gly Lys Ile Ile Phe Ala Ala Ile Pro Pro Asn Phe
        115                 120                 125

Pro Ile Asp Asn Leu Ser Ala Ala Gln Ile Thr Met Cys Pro His Val
    130                 135                 140

Ile Val Asp Val Arg Gln Leu Glu Pro Val Asn Leu Pro Met Pro Asp
145                 150                 155                 160

Val Arg Asn Asn Phe Phe His Tyr Asn Gln Gly Ser Asp Ser Arg Leu
```

```
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Ser Phe Asn Phe Leu Val Pro Pro Thr Val Glu Ser Lys Thr
    210                 215                 220

Lys Pro Phe Ser Leu Pro Ile Leu Thr Ile Ser Glu Met Ser Asn Ser
225                 230                 235                 240

Arg Phe Pro Val Pro Ile Asp Ser Leu His Thr Ser Pro Thr Glu Asn
                245                 250                 255

Ile Val Val Gln Cys Gln Asn Gly Arg Val Thr Leu Asp Gly Glu Leu
            260                 265                 270

Met Gly Thr Thr Gln Leu Leu Pro Ser Gln Ile Cys Ala Phe Arg Gly
        275                 280                 285

Thr Leu Thr Arg Ser Thr Ser Arg Ala Ser Asp Gln Ala Asp Thr Ala
    290                 295                 300

Thr Pro Arg Leu Phe Asn Tyr Tyr Trp His Ile Gln Leu Asp Asn Leu
305                 310                 315                 320

Asn Gly Thr Pro Tyr Asp Pro Ala Glu Asp Ile Pro Ala Pro Leu Gly
                325                 330                 335

Thr Pro Asp Phe Arg Gly Lys Val Phe Gly Val Ala Ser Gln Arg Asn
            340                 345                 350

Pro Asp Ala Thr Thr Arg Ala His Glu Ala Lys Ile Asp Thr Thr Ser
        355                 360                 365

Gly Arg Phe Thr Pro Lys Leu Gly Ser Leu Glu Ile Ser Thr Glu Ser
    370                 375                 380

Gly Asp Phe Asp Gln Asn Gln Pro Thr Arg Phe Thr Pro Val Gly Ile
385                 390                 395                 400

Gly Val Asp His Glu Pro Asp Phe Gln Gln Trp Ala Leu Pro Asp Tyr
                405                 410                 415

Ala Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445

Ser Gly Gly Arg Ser Asn Gly Ile Leu Asp Cys Leu Val Pro Gln Glu
    450                 455                 460

Trp Val Gln His Phe Tyr Gln Glu Ser Ala Pro Ser Gln Thr Gln Val
465                 470                 475                 480

Ala Leu Val Arg Tyr Val Asn Pro Asp Thr Gly Arg Val Leu Phe Glu
                485                 490                 495

Ala Lys Leu His Lys Leu Arg Phe Met Thr Ile Ala Lys Ser Gly Asp
            500                 505                 510

Ser Pro Ile Thr Val Pro Pro Asn Gly Tyr Phe Arg Phe Glu Ser Trp
        515                 520                 525

Val Asn Pro Phe Tyr Thr Leu Ala Pro Met Gly Thr Gly Asn Gly Arg
    530                 535                 540

Arg Arg Ile Gln
545
```

<210> SEQ ID NO 16
<211> LENGTH: 540
<212> TYPE: PRT
<213> ORGANISM: Norovirus

<400> SEQUENCE: 16

Met Lys Met Ala Ser Ser Asp Ala Asn Pro Ser Asp Gly Ser Ala Ala
1 5 10 15

Asn Leu Val Pro Glu Val Asn Asn Glu Val Met Ala Leu Glu Pro Val
20 25 30

Val Gly Ala Ala Ile Ala Ala Pro Val Ala Gly Gln Gln Asn Val Ile
35 40 45

Asp Pro Trp Ile Arg Asn Asn Phe Val Gln Ala Pro Gly Gly Glu Phe
50 55 60

Thr Val Ser Pro Arg Asn Ala Pro Gly Glu Ile Leu Trp Ser Ala Pro
65 70 75 80

Leu Gly Pro Asp Leu Asn Pro Tyr Leu Ser His Leu Ala Arg Met Tyr
85 90 95

Asn Gly Tyr Ala Gly Gly Phe Glu Val Gln Val Ile Leu Ala Gly Asn
100 105 110

Ala Phe Thr Ala Gly Lys Val Ile Phe Ala Ala Val Pro Pro Asn Phe
115 120 125

Pro Thr Glu Gly Leu Ser Pro Ser Gln Val Thr Met Phe Pro His Ile
130 135 140

Val Val Asp Val Arg Gln Leu Glu Pro Val Leu Ile Pro Leu Pro Asp
145 150 155 160

Val Arg Asn Asn Phe Tyr His Tyr Asn Gln Ser Asn Asp Pro Thr Ile
165 170 175

Lys Leu Ile Ala Met Leu Tyr Thr Pro Leu Arg Ala Asn Asn Ala Gly
180 185 190

Asp Asp Val Phe Thr Val Ser Cys Arg Val Leu Thr Arg Pro Ser Pro
195 200 205

Asp Phe Asp Phe Ile Phe Leu Val Pro Pro Thr Val Glu Ser Arg Thr
210 215 220

Lys Pro Phe Ser Val Pro Val Leu Thr Val Glu Glu Met Thr Asn Ser
225 230 235 240

Arg Phe Pro Ile Pro Leu Glu Lys Leu Phe Thr Gly Pro Ser Ser Ala
245 250 255

Phe Val Val Gln Pro Gln Asn Gly Arg Cys Thr Thr Asp Gly Val Leu
260 265 270

Leu Gly Thr Thr Gln Leu Ser Pro Val Asn Ile Cys Thr Phe Arg Gly
275 280 285

Asp Val Thr His Ile Thr Gly Ser Arg Asn Tyr Thr Met Asn Leu Ala
290 295 300

Ser Gln Asn Trp Asn Asp Tyr Asp Pro Thr Glu Glu Ile Pro Ala Pro
305 310 315 320

Leu Gly Thr Pro Asp Phe Val Gly Lys Ile Gln Gly Val Leu Thr Gln
325 330 335

Thr Thr Arg Thr Asp Gly Ser Thr Arg Gly His Lys Ala Thr Val Tyr
340 345 350

Thr Gly Ser Ala Asp Phe Ala Pro Lys Leu Gly Arg Val Gln Phe Glu
355 360 365

Thr Asp Thr Asp Arg Asp Phe Glu Ala Asn Gln Asn Thr Lys Phe Thr
370 375 380

Pro Val Gly Val Ile Gln Asp Gly Gly Thr Thr His Arg Asn Glu Pro
385 390 395 400

Gln Gln Trp Val Leu Pro Ser Tyr Ser Gly Arg Asn Thr His Asn Val

```
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540


<210> SEQ ID NO 17
<211> LENGTH: 540
<212> TYPE: PRT
<213> ORGANISM: Norovirus

<400> SEQUENCE: 17

Met Lys Met Ala Ser Asn Asp Ala Thr Pro Ser Asn Asp Gly Ala Ala
1               5                   10                  15

Gly Leu Val Pro Glu Ser Asn Asn Glu Ala Met Ala Leu Glu Pro Val
            20                  25                  30

Val Gly Ala Ser Leu Ala Ala Pro Val Thr Gly Gln Thr Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Val Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Leu Leu Ala Gly Asn
            100                 105                 110

Ala Phe Thr Ala Gly Lys Ile Ile Phe Ala Ala Val Pro Pro Tyr Phe
        115                 120                 125

Pro Val Glu Asn Leu Ser Pro Ser Gln Ile Thr Met Phe Pro His Val
    130                 135                 140

Ile Ile Asp Val Arg Thr Leu Glu Pro Val Leu Leu Pro Met Pro Asp
145                 150                 155                 160

Val Arg Ser Thr Leu Phe His Phe Asn Gln Lys Asp Glu Pro Lys Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Ile Leu Thr Arg Pro Ser Pro
        195                 200                 205

Glu Phe Asp Phe Thr Tyr Leu Val Pro Pro Thr Val Glu Ser Lys Thr
    210                 215                 220

Lys Pro Phe Thr Leu Pro Val Leu Thr Leu Gly Glu Leu Ser Asn Ser
225                 230                 235                 240
```

-continued

```
Arg Phe Pro Leu Ser Ile Asp Glu Met Val Thr Ser Pro Asn Glu Ser
                245                 250                 255

Ile Val Val Gln Pro Gln Asn Gly Arg Val Thr Leu Asp Gly Glu Leu
            260                 265                 270

Leu Gly Thr Thr Gln Leu Gln Ala Cys Asn Ile Cys Ser Ile Arg Gly
        275                 280                 285

Lys Val Thr Gly Gln Val Pro Asn Glu Gln His Met Trp Asn Leu Glu
    290                 295                 300

Ile Thr Asn Leu Asn Gly Thr Gln Phe Asp Pro Thr Asp Asp Val Pro
305                 310                 315                 320

Ala Pro Leu Gly Val Pro Asp Phe Ala Gly Glu Val Phe Gly Val Leu
                325                 330                 335

Ser Gln Arg Asn Arg Gly Glu Ser Asn Pro Ala Asn Arg Ala His Asp
            340                 345                 350

Ala Val Val Ala Thr Tyr Ser Asp Lys Tyr Thr Pro Lys Leu Gly Leu
        355                 360                 365

Val Gln Ile Gly Thr Trp Asn Thr Asn Asp Val Glu Asn Gln Pro Thr
    370                 375                 380

Lys Phe Thr Pro Ile Gly Leu Asn Glu Val Ala Asn Gly His Arg Phe
385                 390                 395                 400

Glu Gln Trp Thr Leu Pro Arg Tyr Ser Gly Ala Leu Thr Leu Asn Met
                405                 410                 415

Asn Leu Ala Pro Ala Val Ala Pro Leu Phe Pro Gly Glu Arg Leu Leu
            420                 425                 430

Phe Phe Arg Ser Tyr Val Pro Leu Lys Gly Gly Phe Gly Asn Pro Ala
        435                 440                 445

Ile Asp Cys Leu Val Pro Gln Glu Trp Val Gln His Phe Tyr Gln Glu
    450                 455                 460

Ser Ala Pro Ser Leu Gly Asp Val Ala Leu Val Arg Tyr Val Asn Pro
465                 470                 475                 480

Asp Thr Gly Arg Val Leu Phe Glu Ala Lys Leu His Lys Gly Gly Phe
                485                 490                 495

Leu Thr Val Ser Ser Thr Ser Thr Gly Pro Val Val Val Pro Ala Asn
            500                 505                 510

Gly Tyr Phe Arg Phe Asp Ser Trp Val Asn Gln Phe Tyr Ser Leu Ala
        515                 520                 525

Pro Met Gly Thr Gly Asn Gly Arg Arg Arg Phe Gln
    530                 535                 540


<210> SEQ ID NO 18
<211> LENGTH: 540
<212> TYPE: PRT
<213> ORGANISM: Norovirus

<400> SEQUENCE: 18

Met Lys Met Ala Ser Asn Asp Ala Ala Pro Ser Asn Asp Gly Ala Ala
1               5                   10                  15

Gly Leu Val Pro Glu Ile Asn Asn Glu Val Met Pro Leu Glu Pro Val
            20                  25                  30

Ala Gly Ala Ser Leu Ala Thr Pro Val Val Gly Gln Gln Asn Ile Ile
        35                  40                  45

Asp Pro Trp Ile Arg Asn Asn Phe Val Gln Ala Pro Ala Gly Glu Phe
    50                  55                  60

Thr Val Ser Pro Arg Asn Ser Pro Gly Glu Ile Leu Leu Asp Leu Glu
65                  70                  75                  80
```

-continued

```
Leu Gly Pro Glu Leu Asn Pro Tyr Leu Ala His Leu Ala Arg Met Tyr
                85                  90                  95

Asn Gly His Ala Gly Gly Met Glu Val Gln Ile Val Leu Ala Gly Asn
            100                 105                 110

Ala Phe Thr Ala Gly Lys Ile Ile Phe Ala Ala Ile Pro Pro Gly Phe
        115                 120                 125

Pro Tyr Glu Asn Leu Ser Pro Ser Gln Ile Thr Met Cys Pro His Val
    130                 135                 140

Ile Ile Asp Val Arg Gln Leu Glu Pro Val Leu Leu Pro Met Pro Asp
145                 150                 155                 160

Ile Arg Asn Asn Phe Phe His Tyr Asn Gln Gly Asn Asp Pro Lys Leu
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Lys Pro Ser Pro
        195                 200                 205

Asp Phe Glu Phe Thr Phe Leu Val Pro Pro Thr Val Glu Ser Lys Thr
    210                 215                 220

Lys Gln Phe Thr Leu Pro Ile Leu Lys Ile Ser Glu Met Thr Asn Ser
225                 230                 235                 240

Arg Phe Pro Val Pro Val Glu Met Met Tyr Thr Ala Arg Asn Glu Asn
                245                 250                 255

Gln Val Val Gln Pro Gln Asn Gly Arg Val Thr Leu Asp Gly Glu Leu
            260                 265                 270

Leu Gly Thr Thr Pro Leu Leu Ala Val Asn Ile Cys Lys Phe Lys Gly
        275                 280                 285

Glu Val Ile Ala Lys Asn Gly Asp Val Arg Ser Tyr Arg Met Asp Met
    290                 295                 300

Glu Ile Thr Asn Thr Asp Gly Thr Pro Ile Asp Pro Thr Glu Asp Thr
305                 310                 315                 320

Pro Gly Pro Ile Gly Ser Pro Asp Phe Gln Gly Ile Leu Phe Gly Val
                325                 330                 335

Ala Ser Gln Arg Asn Lys Asn Glu Gln Asn Pro Ala Thr Arg Ala His
            340                 345                 350

Glu Ala Asn Ile Asn Thr Gly Gly Asp Gln Tyr Ala Pro Lys Leu Ala
        355                 360                 365

Gln Val Lys Phe Phe Ser Glu Ser Gln Asp Phe Glu Val His Gln Pro
    370                 375                 380

Thr Val Phe Thr Pro Val Gly Val Ala Gly Asp Thr Ser His Pro Phe
385                 390                 395                 400

Arg Gln Trp Val Leu Pro Arg Tyr Gly Gly His Leu Thr Asn Asn Thr
                405                 410                 415

His Leu Ala Pro Ala Val Ala Pro Leu Phe Pro Gly Glu Gln Ile Leu
            420                 425                 430

Phe Phe Arg Ser Gln Ile Pro Ser Ser Gly Gly His Glu Leu Gly Tyr
        435                 440                 445

Met Asp Cys Leu Val Pro Gln Glu Trp Val Gln His Phe Tyr Gln Glu
    450                 455                 460

Ala Ala Thr Ala Gln Ser Glu Val Ala Leu Ile Arg Phe Ile Asn Pro
465                 470                 475                 480

Asp Thr Gly Arg Val Leu Phe Glu Ala Lys Leu His Lys Gln Gly Phe
                485                 490                 495
```

-continued

Ile Thr Val Ala His Thr Gly Asp Asn Pro Ile Val Met Pro Pro Asn
500 505 510

Gly Tyr Phe Arg Phe Glu Ala Trp Val Asn Gln Phe Tyr Ser Leu Ala
515 520 525

Pro Val Gly Thr Gly Asn Gly Arg Arg Arg Ile Gln
530 535 540

<210> SEQ ID NO 19
<211> LENGTH: 535
<212> TYPE: PRT
<213> ORGANISM: Norovirus

<400> SEQUENCE: 19

Met Lys Met Ala Ser Asn Asp Ala Ala Pro Ser Asn Asp Gly Ala Ala
1 5 10 15

Gly Leu Val Pro Glu Val Asn Asn Glu Thr Met Ala Leu Glu Pro Val
20 25 30

Ala Gly Ala Ser Ile Ala Ala Pro Leu Thr Gly Gln Asn Asn Val Ile
35 40 45

Asp Pro Trp Ile Arg Leu Asn Phe Val Gln Ala Pro Asn Gly Glu Phe
50 55 60

Thr Val Ser Pro Arg Asn Ser Pro Gly Glu Val Leu Leu Asn Leu Glu
65 70 75 80

Leu Gly Pro Glu Leu Asn Pro Tyr Leu Ala His Leu Ser Arg Met Tyr
85 90 95

Asn Gly Tyr Ala Gly Gly Val Glu Val Gln Val Leu Leu Ala Gly Asn
100 105 110

Ala Phe Thr Ala Gly Lys Leu Val Phe Ala Ala Val Pro Pro His Phe
115 120 125

Pro Leu Glu Asn Ile Ser Pro Gly Gln Ile Thr Met Phe Pro His Val
130 135 140

Ile Ile Asp Val Arg Thr Leu Glu Pro Val Leu Leu Pro Leu Pro Asp
145 150 155 160

Val Arg Asn Asn Phe Phe His Tyr Asn Gln Gln Asn Glu Pro Arg Met
165 170 175

Arg Leu Val Ala Met Leu Tyr Thr Pro Leu Arg Ser Asn Gly Ser Gly
180 185 190

Asp Asp Val Phe Thr Val Ser Cys Arg Val Leu Thr Arg Pro Ser Pro
195 200 205

Asp Phe Asp Phe Asn Tyr Leu Val Pro Pro Thr Val Glu Ser Lys Thr
210 215 220

Lys Pro Phe Thr Leu Pro Ile Leu Thr Ile Gly Glu Leu Thr Asn Ser
225 230 235 240

Arg Phe Pro Val Pro Ile Asp Glu Leu Tyr Thr Ser Pro Asn Glu Ser
245 250 255

Leu Val Val Gln Pro Gln Asn Gly Arg Cys Ala Leu Asp Gly Glu Leu
260 265 270

Gln Gly Thr Thr Gln Leu Leu Pro Thr Ala Ile Cys Ser Phe Arg Gly
275 280 285

Arg Ile Asn Gln Lys Val Ser Gly Glu Asn His Val Trp Asn Met Gln
290 295 300

Val Thr Asn Ile Asp Gly Thr Pro Phe Asp Pro Thr Glu Asp Val Pro
305 310 315 320

Ala Pro Leu Gly Thr Pro Asp Phe Ser Gly Lys Leu Phe Gly Val Leu
325 330 335

```
Ser Gln Arg Asp His Asp Asn Ala Cys Arg Ser His Asp Ala Val Ile
            340                 345                 350

Ala Thr Asn Ser Ala Lys Phe Thr Pro Lys Leu Gly Ala Ile Gln Ile
        355                 360                 365

Gly Thr Trp Glu Gln Asp Asp Val His Ile Asn Gln Pro Thr Lys Phe
    370                 375                 380

Thr Pro Val Gly Leu Phe Glu Ser Glu Gly Phe Asn Gln Trp Thr Leu
385                 390                 395                 400

Pro Asn Tyr Ser Gly Ala Leu Thr Leu Asn Met Gly Leu Ala Pro Pro
                405                 410                 415

Val Ala Pro Thr Phe Pro Gly Glu Gln Ile Leu Phe Phe Arg Ser His
            420                 425                 430

Ile Pro Leu Lys Gly Gly Val Ala Asp Pro Val Ile Asp Cys Leu Leu
        435                 440                 445

Pro Gln Glu Trp Ile Gln His Leu Tyr Gln Glu Ser Ala Pro Ser Gln
    450                 455                 460

Thr Asp Val Ala Leu Ile Arg Phe Thr Asn Pro Asp Thr Gly Arg Val
465                 470                 475                 480

Leu Phe Glu Ala Lys Leu His Arg Ser Gly Tyr Ile Thr Val Ala Asn
                485                 490                 495

Thr Gly Ser Arg Pro Ile Val Val Pro Ala Asn Gly Tyr Phe Arg Phe
            500                 505                 510

Asp Ser Trp Val Asn Gln Phe Tyr Ser Leu Ala Pro Met Gly Thr Gly
        515                 520                 525

Asn Gly Arg Arg Arg Val Gln
    530                 535


<210> SEQ ID NO 20
<211> LENGTH: 547
<212> TYPE: PRT
<213> ORGANISM: Norovirus

<400> SEQUENCE: 20

Met Lys Met Ala Ser Asn Asp Ala Ala Pro Ser Asn Asp Gly Ala Ala
1               5                   10                  15

Asn Leu Val Pro Glu Ala Asn Asn Glu Val Met Ala Leu Glu Pro Val
            20                  25                  30

Val Gly Ala Ser Ile Ala Ala Pro Val Val Gly Gln Gln Asn Ile Ile
        35                  40                  45

Asp Pro Trp Ile Arg Glu Asn Phe Val Gln Ala Pro Gln Gly Glu Phe
    50                  55                  60

Thr Val Ser Pro Arg Asn Ser Pro Gly Glu Met Leu Leu Asn Leu Glu
65                  70                  75                  80

Leu Gly Pro Glu Leu Asn Pro Tyr Leu Ser His Leu Ser Arg Met Tyr
                85                  90                  95

Asn Gly Tyr Ala Gly Gly Met Gln Val Gln Val Val Leu Ala Gly Asn
            100                 105                 110

Ala Phe Thr Ala Gly Lys Ile Ile Phe Ala Ala Val Pro Pro His Phe
        115                 120                 125

Pro Val Glu Asn Ile Asn Ala Ala Gln Ile Thr Met Cys Pro His Val
    130                 135                 140

Ile Val Asp Val Arg Gln Leu Glu Pro Val Leu Leu Pro Leu Pro Asp
145                 150                 155                 160

Ile Arg Asn Arg Phe Phe His Tyr Asn Gln Glu Asn Thr Ser Arg Met
```

```
                165                 170                 175

Arg Leu Val Ala Met Leu Tyr Thr Pro Leu Arg Ala Asn Ser Gly Glu
            180                 185                 190

Asp Val Phe Thr Val Ser Cys Arg Val Leu Thr Arg Pro Ala Pro Asp
        195                 200                 205

Phe Glu Phe Thr Phe Leu Val Pro Pro Thr Val Glu Ser Lys Thr Lys
    210                 215                 220

Pro Phe Ser Leu Pro Ile Leu Thr Leu Gly Glu Leu Ser Asn Ser Arg
225                 230                 235                 240

Phe Pro Ala Pro Ile Asp Met Leu Tyr Thr Asp Pro Asn Glu Gly Ile
                245                 250                 255

Val Val Gln Pro Gln Asn Gly Arg Cys Thr Leu Asp Gly Thr Leu Gln
            260                 265                 270

Gly Thr Thr Gln Leu Val Pro Thr Gln Ile Cys Ala Phe Arg Gly Thr
        275                 280                 285

Leu Ile Gly Gln Thr Ser Arg Ser Pro Asp Ser Thr Asp Ser Ala Pro
    290                 295                 300

Arg Arg Arg Asp His Pro Leu His Val Gln Leu Lys Asn Leu Asp Gly
305                 310                 315                 320

Thr Gln Tyr Asp Pro Thr Asp Glu Val Pro Ala Val Leu Gly Ala Ile
                325                 330                 335

Asp Phe Lys Gly Thr Val Phe Gly Val Ala Ser Gln Arg Asp Val Ser
            340                 345                 350

Gly Gln Gln Val Gly Ala Thr Arg Ala His Glu Val His Ile Asn Thr
        355                 360                 365

Thr Asp Pro Arg Tyr Thr Pro Lys Leu Gly Ser Ile Leu Met Tyr Ser
    370                 375                 380

Glu Ser Asp Asp Phe Val Thr Gly Gln Pro Val Arg Phe Thr Pro Ile
385                 390                 395                 400

Gly Met Gly Asp Asn Asp Trp His Gln Trp Glu Leu Pro Asp Tyr Pro
                405                 410                 415

Gly His Leu Thr Leu Asn Met Asn Leu Ala Pro Ala Val Ala Pro Ala
            420                 425                 430

Phe Pro Gly Glu Arg Ile Leu Phe Phe Arg Ser Ile Val Pro Ser Ala
        435                 440                 445

Gly Gly Tyr Gly Ser Gly Gln Ile Asp Cys Leu Ile Pro Gln Glu Trp
    450                 455                 460

Val Gln His Phe Tyr Gln Glu Ala Ala Pro Ser Gln Ser Ala Val Ala
465                 470                 475                 480

Leu Ile Arg Tyr Val Asn Pro Asp Thr Gly Arg Asn Ile Phe Glu Ala
                485                 490                 495

Lys Leu His Arg Glu Gly Phe Ile Thr Val Ala Asn Ser Gly Asn Asn
            500                 505                 510

Pro Ile Val Val Pro Pro Asn Gly Tyr Phe Arg Phe Glu Ala Trp Val
        515                 520                 525

Asn Gln Phe Tyr Thr Leu Thr Pro Met Gly Thr Gly Gln Gly Arg Arg
    530                 535                 540

Arg Asp Gln
545
```

<210> SEQ ID NO 21
<211> LENGTH: 1644
<212> TYPE: DNA
<213> ORGANISM: Artificial Sequence -continued
<220> FEATURE:
<223> OTHER INFORMATION: Nucleic acid sequence of human codon-optimized VP1 GII.6 Ohio 2012 M9T020

<400> SEQUENCE: 21

```
atgaagatgg caagcaacga cgcagctccc tccaatgatg gtgccgccaa cctggtcccc     60
gaagctaata atgaggtgat ggcgttagag ccggtggttg gcgcatctat tgcagcgcct    120
gtggtcggac agcagaacat cattgatccc tggattcgcg agaacttcgt acaagctcca    180
caggggggagt tcacagtctc cccccggaac tccccgggcg agatgctgct caatctggaa    240
ctcggccctg aactaaaccc ttatctgtca cacctttcac ggatgtacaa tggctacgca    300
ggaggaatgc aagttcaggt ggtcctggcc ggcaatgctt tcaccgcggg caaaatcatc    360
tttgcggccg ttcctccaca cttccctgtc gaaaatatca acgccgccca gattactatg    420
tgcccccacg tgattgtgga tgtgcgacag ttagagccag ttctgctgcc cctgcccgac    480
atcagaaacc ggttcttcca ttacaatcaa gagaatactt cacggatgag acttgttgcg    540
atgctgtaca cccctcttcg tgcaaattcc ggcgaagacg tgttcactgt gtcttgtcga    600
gtacttaccc gacccgcccc cgatttcgaa ttcaccttcc tggttccccc tactgtggag    660
agcaagacaa aacccttcag cctcccaatc ttaacactcg gggagctgtc taattcacgc    720
ttccccgcac ctattgatat gctgtatact gaccccaacg aggggatagt ggtgcagccc    780
caaaatggac ggtgtactct cgacggcacg ctccagggca caacccaact ggtgccaacc    840
cagatttgtg cattcagggg cactttgatt gggcagacat cgagatctcc agattctact    900
gattccgcgc caaggaggag ggaccaccca ctccacgttc agttaaaaaa cctggacgga    960
acccagtacg accctacaga cgaggtcccc gctgtcctcg gagccatcga ctttaaagga   1020
actgtatttg gagtggcatc ccaaagggat gtctcggggc agcaggtggg agctacgaga   1080
gcacatgaag tccacattaa caccacagac ccaagatata ccccaaaact agggtcaatt   1140
ttaatgtatt cggaatcaga cgattttgtt acaggtcagc ccgtgcggtt taccccgatc   1200
ggaatggggg acaacgattg gcaccagtgg gaattgcccg attaccctgg acacctcacc   1260
ttgaatatga atctggcccc agccgtcgcg cccgccttcc ccggtgagcg gatcctcttt   1320
tttagaagca tagtgccctc cgcaggtggg tatggatcag ggcagattga ttgcctgatc   1380
ccccaagaat gggtacagca tttctaccag gaagcagccc ctagccagtc cgcagtagca   1440
ctgatcagat atgttaatcc tgatacggga aggaacatct tcgaagcaaa actgcaccgt   1500
gagggcttca ttaccgtcgc caacagtggt aataacccta ttgtggtgcc tcctaatgga   1560
tacttcaggt ttgaggcatg ggtgaatcag ttttatactc tgactcccat ggggacaggc   1620
caggggcgac gccgggatca gtga                                          1644
```

<210> SEQ ID NO 22
<211> LENGTH: 542
<212> TYPE: PRT
<213> ORGANISM: Norovirus

<400> SEQUENCE: 22

```
Met Lys Met Ala Ser Asn Asp Ala Ala Pro Ser Asn Asp Gly Ala Ala
1               5                   10                  15

Ser Leu Val Pro Glu Ala Ile Asn Glu Thr Met Pro Leu Glu Pro Val
            20                  25                  30

Ala Gly Ala Ser Ile Ala Ala Pro Val Ala Gly Gln Thr Asn Ile Ile
        35                  40                  45
```

```
Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Ile Pro Pro Asn Phe
        115                 120                 125

Pro Val Asp Met Ile Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Val Phe Tyr His Phe Asn Asn Gln Pro Gln Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Ile Tyr Leu Val Pro Pro Ser Val Glu Ser Lys Thr
    210                 215                 220

Lys Pro Phe Thr Leu Pro Ile Leu Thr Ile Ser Glu Leu Thr Asn Ser
225                 230                 235                 240

Arg Phe Pro Ile Ser Ile Glu Gln Leu Tyr Thr Ala Pro Asn Glu Asn
                245                 250                 255

Asn Val Val Gln Cys Gln Asn Gly Arg Cys Thr Leu Asp Gly Glu Leu
            260                 265                 270

Gln Gly Thr Thr Gln Leu Leu Ser Ser Ala Val Cys Ser Tyr Arg Gly
        275                 280                 285

Arg Thr Val Ala Asn Ser Gly Asp Asn Trp Asp Gln Asn Val Leu Gln
    290                 295                 300

Leu Thr Tyr Pro Ser Gly Ala Ser Tyr Asp Pro Thr Asp Glu Val Pro
305                 310                 315                 320

Ala Pro Leu Gly Thr Gln Asp Phe Ser Gly Ile Leu Tyr Gly Val Leu
                325                 330                 335

Thr Gln Asp Asn Val Arg Glu Asn Thr Gly Glu Ala Lys Asn Ala Lys
            340                 345                 350

Gly Val Tyr Ile Ser Thr Thr Ser Gly Lys Phe Thr Pro Lys Ile Gly
        355                 360                 365

Ser Ile Gly Leu His Ser Ile Thr Glu Asp Val Arg Pro Asn Gln Gln
    370                 375                 380

Ser Arg Phe Thr Pro Val Gly Val Ala Gln Asn Glu Asn Thr Pro Phe
385                 390                 395                 400

Gln Gln Trp Val Leu Pro His Tyr Ala Gly Ala Leu Ala Leu Asn Thr
                405                 410                 415

Asn Leu Ala Pro Ala Val Ala Pro Thr Phe Pro Gly Glu Gln Leu Leu
            420                 425                 430

Phe Phe Arg Ser Arg Val Pro Cys Val Gln Gly Leu Gln Gly Gln Asp
        435                 440                 445

Ala Phe Ile Asp Cys Leu Leu Pro Gln Glu Trp Val Asn His Phe Tyr
    450                 455                 460

Gln Glu Ala Ala Pro Ser Gln Ala Asp Val Ala Leu Ile Arg Tyr Val
```

```
465                 470                 475                 480

Asn Pro Asp Thr Gly Arg Thr Leu Phe Glu Ala Lys Leu His Arg Ser
                485                 490                 495

Gly Phe Ile Thr Val Ser His Thr Gly Ala Tyr Pro Leu Val Val Pro
            500                 505                 510

Pro Asn Gly His Phe Arg Phe Asp Ser Trp Val Asn Gln Phe Tyr Ser
        515                 520                 525

Leu Ala Pro Met Gly Thr Gly Asn Gly Arg Arg Arg Val Gln
    530                 535                 540


<210> SEQ ID NO 23
<211> LENGTH: 1629
<212> TYPE: DNA
<213> ORGANISM: Artificial Sequence
<220> FEATURE:
<223> OTHER INFORMATION: Nucleic acid sequence of human codon-optimized
      VP1 GII.17_Kawa_2014_A0A077KVU6

<400> SEQUENCE: 23

atgaaaatgg cttctaatga tgccgcgccc agcaatgatg gtgccgccag ccttgtgccc     60

gaagcaatta acgagacaat gcccttggag ccagtcgccg gggcttctat tgcggcccca    120

gttgctggac agacgaatat catcgatcct tggatacgga ctaattttgt tcaagctcct    180

aacggagagt tcactgtctc cccccgtaat agtcctggcg agatcctgtt gaacctcgag    240

ttggggccag atctcaatcc ttacctggct catctgtcga gaatgtacaa cgggtacgcg    300

gggggggttg aggtgcaggt cttactggca ggtaacgcat tcacagcagg caagattctg    360

tttgcggcca tccctcctaa ttttccagtg gatatgatat ctccagcaca gattacaatg    420

ctgccccatt tgatagtgga tgtgcggaca cttgaaccta tcatgatccc tttgcccgat    480

gtccgaaatg tgttttatca tttcaacaac cagccgcagc caagaatgcg tctcgtcgcg    540

atgctgtaca ccccgttgcg gtccaacggc tctggcgatg atgttttcac agtgtcgtgt    600

cgagtgttaa cccgccctac cccagatttt gagtttatat atctagttcc cccttctgtg    660

gaaagcaaga ctaaaccctt tactcttccc attctgacta tatccgagct taccaactcc    720

cggttcccca tctcaatcga gcaactgtac actgcaccca acgagaacaa cgtagtccag    780

tgccagaacg ggagatgtac cctggacggg gagctccaag ggaccacgca actgttaagt    840

tcagccgttt gcagttacag aggcaggact gtggcgaact ctggtgataa ctgggatcaa    900

aatgtgttgc agctgactta cccatccggc gcaagctacg atccaacaga tgaggtgcca    960

gcgccccttg gcacacagga tttctcagga attctatacg ggtgcttac tcaggataat    1020

gtgcgagaaa atactggcga ggccaagaat gctaaaggag tgtatataag cacgacaagc   1080

ggtaagttta cccccaaaat tggcagtatt gggctccaca gcattactga ggacgtccgc   1140

ccaaaccagc agtctcgttt cactcccgtg ggggtggcac agaacgagaa cacacctttc   1200

cagcagtggg tcttgcccca ttatgcaggt gctttggcgc tcaatacaaa tctggcaccc   1260

gccgtagcgc cgacatttcc tggggagcaa ttgctgttct ttagaagccg cgtcccgtgt   1320

gttcagggct tgcagggcca ggacgcgttc attgattgcc tcttgcccca ggaatgggtc   1380

aaccactttt atcaggaggc agcgccctct caagcagatg tggccctgat aagatatgtg   1440

aatcccgaca caggacggac tttgtttgag gcaaaactcc accggtcagg attcattact   1500

gtgagtcaca caggagccta tccccttgtg gttccaccta atggccactt caggttcgac   1560

tcttgggtca atcagtttta ttcgctggca ccaatgggta ccgggaatgg tcgccgtcgg   1620
```

gtgcaatga 1629

<210> SEQ ID NO 24
<211> LENGTH: 538
<212> TYPE: PRT
<213> ORGANISM: Norovirus

<400> SEQUENCE: 24

```
Met Lys Met Ala Ser Asn Asp Ala Ala Pro Ser Asn Asp Gly Ala Ala
1               5                   10                  15

Gly Leu Val Pro Glu Gly Asn Asn Glu Thr Leu Pro Leu Glu Pro Val
            20                  25                  30

Ala Gly Ala Ala Ile Ala Ala Pro Val Thr Gly Gln Asn Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Val Pro Pro Asn Phe
        115                 120                 125

Pro Val Glu Phe Leu Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Thr Phe Phe His Tyr Asn Asn Gln Pro Asn Ser Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Thr Tyr Leu Val Pro Pro Ser Val Glu Ser Lys Thr
    210                 215                 220

Lys Pro Phe Ser Leu Pro Ile Leu Thr Leu Ser Glu Leu Thr Asn Ser
225                 230                 235                 240

Arg Phe Pro Val Pro Ile Asp Ser Leu Phe Thr Ala Gln Asn Asn Val
                245                 250                 255

Leu Gln Val Gln Cys Gln Asn Gly Arg Cys Thr Leu Asp Gly Glu Leu
            260                 265                 270

Gln Gly Thr Thr Gln Leu Leu Pro Ser Gly Ile Cys Ala Phe Arg Gly
        275                 280                 285

Arg Val Thr Ala Glu Thr Asp His Arg Asp Lys Trp His Met Gln Leu
    290                 295                 300

Gln Asn Leu Asn Gly Thr Thr Tyr Asp Pro Thr Asp Asp Val Pro Ala
305                 310                 315                 320

Pro Leu Gly Thr Pro Asp Phe Lys Gly Val Val Phe Gly Val Ala Ser
                325                 330                 335

Gln Arg Asn Val Gly Asn Asp Ala Pro Gly Ser Thr Arg Ala His Glu
            340                 345                 350

Ala Val Ile Ser Thr Tyr Ser Pro Gln Phe Val Pro Lys Leu Gly Ser
        355                 360                 365
```

```
Val Asn Phe Arg Ser Asn Asp Asn Asp Phe Gln Leu Gln Pro Thr Lys
    370                 375                 380

Phe Thr Pro Val Gly Ile Asn Asp Asp Gly Asp His Pro Phe Arg Gln
385                 390                 395                 400

Trp Glu Leu Pro Asp Tyr Ser Gly Leu Leu Thr Leu Asn Met Asn Leu
                405                 410                 415

Ala Pro Pro Val Ala Pro Asn Phe Pro Gly Glu Gln Leu Leu Phe Phe
            420                 425                 430

Arg Ser Phe Val Pro Cys Ser Gly Gly Tyr Asn Gln Gly Ile Val Asp
        435                 440                 445

Cys Leu Ile Pro Gln Glu Trp Ile Gln His Phe Tyr Gln Glu Ser Ala
    450                 455                 460

Pro Ser Gln Ser Asp Val Ala Leu Ile Arg Tyr Val Asn Pro Asp Thr
465                 470                 475                 480

Gly Arg Thr Leu Phe Glu Ala Lys Leu His Arg Ser Gly Tyr Ile Thr
                485                 490                 495

Val Ala His Ser Gly Asp Tyr Pro Leu Val Val Pro Ala Asn Gly Tyr
            500                 505                 510

Phe Arg Phe Asp Ser Trp Val Asn Gln Phe Tyr Ser Leu Ala Pro Met
        515                 520                 525

Gly Thr Gly Asn Gly Arg Arg Arg Ala Gln
    530                 535


<210> SEQ ID NO 25
<211> LENGTH: 1617
<212> TYPE: DNA
<213> ORGANISM: Artificial Sequence
<220> FEATURE:
<223> OTHER INFORMATION: Nucleic acid sequence of human codon-optimized
      VP1 GII.17_Kawa_2014_A0A077KVU6

<400> SEQUENCE: 25

atgaaaatgg catctaacga cgcagccccc tcaaacgatg gcgctgctgg actcgtgccg     60

gaggggaata atgagacact tccactagag ccggttgcag gcgccgctat agctgcccca    120

gtgacagggc agaataatat tatagaccct tggattcgga caaacttcgt gcaggcaccc    180

aacggcgagt ttacagtatc cccccggaac tccccaggtg agatactcct gaatcttgag    240

ctcggccctg acctcaatcc atatctggct catctgagcc gcatgtacaa tggttacgct    300

ggggggggtcg aagtgcaggt cctcctggcc ggaaacgcct ttaccgctgg caaaattctg    360

tttgccgccg ttccaccaaa ctttccagtc gaattcctct ctcccgcgca aataaccatg    420

ctgccacatt tgatcgttga cgtgcggacc ctggagccaa taatgattcc cctgccggat    480

gtgcgtaaca cctttttcca ttataacaat cagccaaact ctcggatgag acttgttgct    540

atgctgtaca cccccctgcg gagcaacggc agtggcgatg atgtgtttac cgtgagttgc    600

agagtcctga cgcgcccaac cccggacttc gagttcacct acctggtgcc cccttctgtg    660

gaatctaaga ccaaaccgtt ttcactgcca atcttaactc tctccgaact gactaacagc    720

cggtttccag tacccataga ttctcttttt accgctcaaa acaacgtact ccaagtccag    780

tgccagaacg gccgctgtac gcttgatggt gagttgcagg ggacaacaca gctactcccc    840

agtggcatct gtgcattccg ggccgcgtg accgctgaga cagaccatcg tgacaaatgg    900

cacatgcaac tccaaaactt aaacgggacc acctacgacc caaccgacga cgtccctgct    960

ccgctaggga ctcctgactt taagggggtg gtgttcggag tggcctctca gcggaatgtt   1020

gggaatgacg cccccggctc tacccgagct cacgaggccg ttatctcaac atatagcccc   1080
```

-continued caatttgtgc ccaagctcgg atccgttaat tttcgtagta acgacaacga cttccaactg 1140
caaccaacga agtttacgcc agtggggatt aatgatgatg gagaccatcc tttccgccaa 1200
tgggaactac cagattattc tgggctgctc accctcaata tgaacctcgc cccacccgtg 1260
gcccctaatt tccccggtga gcagctgctg ttttttcgga gctttgtgcc atgcagtggc 1320
ggatataatc aaggcatcgt agactgcttg attccccaag agtggataca acatttttac 1380
caggaaagtg cgccctccca gtccgatgtg gccctgatac ggtacgttaa ccccgatacc 1440
ggaagaacat tattcgaagc gaaattgcac agatcagggt acattaccgt tgcacattcc 1500
ggcgattatc ccctggtggt tcccgccaac ggttacttta ggttcgatag ttgggtcaac 1560
cagttctatt cactagcccc aatgggcacc ggtaacggca gacgccgggc tcagtag 1617

<210> SEQ ID NO 26
<211> LENGTH: 539
<212> TYPE: PRT
<213> ORGANISM: Norovirus

<400> SEQUENCE: 26

Met Lys Met Ala Ser Asn Asp Ala Ala Pro Ser Asn Asp Gly Ala Thr
1 5 10 15

Gly Leu Val Pro Glu Ile Asn Thr Glu Thr Leu Pro Leu Glu Pro Val
20 25 30

Ala Gly Ala Ala Ile Ala Ala Pro Val Thr Gly Gln Asn Asn Ile Ile
35 40 45

Asp Pro Trp Ile Arg Asn Asn Phe Val Gln Ala Pro Asn Gly Glu Phe
50 55 60

Thr Val Ser Pro Arg Asn Ser Pro Gly Glu Ile Leu Met Asn Leu Glu
65 70 75 80

Leu Gly Pro Asp Leu Asn Pro Tyr Leu Ala His Leu Ser Arg Met Tyr
85 90 95

Asn Gly Tyr Ala Gly Gly Val Glu Val Gln Val Leu Leu Ala Gly Asn
100 105 110

Ala Phe Thr Ala Gly Lys Ile Leu Phe Ala Ala Val Pro Pro Asn Phe
115 120 125

Pro Val Asp Met Leu Ser Pro Ala Gln Ile Thr Met Leu Pro His Leu
130 135 140

Ile Val Asp Val Arg Thr Leu Glu Pro Ile Met Ile Pro Leu Pro Asp
145 150 155 160

Val Arg Asn Val Phe Tyr His Phe Asn Asn Gln Pro Ala Pro Arg Met
165 170 175

Arg Leu Val Ala Met Leu Tyr Thr Pro Leu Arg Ser Asn Gly Ser Gly
180 185 190

Asp Asp Val Phe Thr Val Ser Cys Arg Val Leu Thr Arg Pro Thr Pro
195 200 205

Asp Phe Glu Phe Thr Tyr Leu Val Pro Pro Ser Val Glu Ser Lys Thr
210 215 220

Lys Pro Phe Thr Leu Pro Ile Leu Thr Ile Gly Glu Leu Thr Asn Ser
225 230 235 240

Arg Phe Pro Ala Pro Ile Asp Gln Leu Tyr Thr Ser Pro Asn Ala Asp
245 250 255

Val Val Val Gln Pro Gln Asn Gly Arg Cys Thr Leu Asp Gly Glu Leu
260 265 270

Gln Gly Thr Thr Gln Leu Leu Thr Thr Ala Ile Cys Ser Tyr Arg Gly

-continued

```
        275                 280                 285

Met Thr Ser Asn Pro Thr Ser Asp Tyr Trp Asp Asp His Leu Leu His
    290                 295                 300

Leu Val His Pro Asn Gly Ala Thr Tyr Asp Pro Thr Glu Asp Val Pro
305                 310                 315                 320

Ala Pro Phe Gly Thr Gln Asp Phe Arg Gly Ile Leu Tyr Gly Met Leu
                325                 330                 335

Thr Gln Asn Pro Arg Thr Ser Gly Asp Glu Ala Ala Asn Ser His Gly
            340                 345                 350

Ile Tyr Ile Ser Ser Thr Ser Glu Lys Phe Thr Pro Lys Leu Gly Thr
        355                 360                 365

Ile Gly Leu His Gln Val Gln Gly Asp Ile Ala Ser Asn Gln Gln Ser
    370                 375                 380

Lys Phe Thr Pro Val Gly Ile Ala Val Asn Gly Asn Thr Pro Phe Arg
385                 390                 395                 400

Gln Trp Glu Leu Pro Asn Tyr Ser Gly Ala Leu Thr Leu Asn Thr Asn
                405                 410                 415

Leu Ala Pro Ala Val Gly Pro Asn Phe Pro Gly Glu Gln Ile Leu Phe
            420                 425                 430

Phe Arg Ser Asn Val Pro Ser Val Gln Gly Gly Gln Pro Ile Glu Ile
        435                 440                 445

Asp Cys Leu Ile Pro Gln Glu Trp Val Ser His Phe Tyr Gln Glu Ser
    450                 455                 460

Ala Pro Ser Gln Ser Asp Val Ala Leu Val Arg Tyr Val Asn Pro Asp
465                 470                 475                 480

Thr Gly Arg Thr Ile Phe Glu Ala Lys Leu His Arg Gln Gly Phe Ile
                485                 490                 495

Thr Ile Ala Ala Thr Gly Ser Asn Pro Val Val Val Pro Pro Asn Gly
            500                 505                 510

Tyr Phe Arg Phe Asp Ser Trp Val Asn Gln Phe Tyr Ala Leu Ala Pro
        515                 520                 525

Met Gly Thr Gly Asn Gly Arg Arg Arg Val Gln
    530                 535


<210> SEQ ID NO 27
<211> LENGTH: 539
<212> TYPE: PRT
<213> ORGANISM: Norovirus

<400> SEQUENCE: 27

Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110
```

```
Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Lys Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Ser Asn Ser
225                 230                 235                 240

Arg Phe Pro Ile Pro Leu Glu Lys Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Thr Phe Arg Gly
        275                 280                 285

Asp Val Thr His Ile Ala Gly Ser His Asp Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Arg Glu Asp Gly Ser Thr Arg Ala His Lys Ala Thr Val Ser
            340                 345                 350

Thr Gly Ser Val His Phe Thr Pro Lys Leu Gly Ser Val Gln Tyr Thr
        355                 360                 365

Thr Asp Thr Asn Asn Asp Phe Gln Thr Gly Gln Asn Thr Lys Phe Thr
    370                 375                 380

Pro Val Gly Val Ile Gln Asp Gly Asn Asn His Gln Asn Glu Pro Gln
385                 390                 395                 400

Gln Trp Val Leu Pro Asn Tyr Ser Gly Arg Thr Gly His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Gln His Phe Tyr Gln Glu Ala
    450                 455                 460

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Lys Ser Gly Tyr Val
                485                 490                 495

Thr Val Ala His Thr Gly Pro His Asp Leu Val Ile Pro Pro Asn Gly
            500                 505                 510

Tyr Phe Arg Phe Asp Ser Trp Val Asn Gln Phe Tyr Thr Leu Ala Pro
        515                 520                 525

Met Gly Asn Gly Ala Gly Arg Arg Arg Ala Leu
```

530 535

<210> SEQ ID NO 28
<211> LENGTH: 540
<212> TYPE: PRT
<213> ORGANISM: Norovirus

<400> SEQUENCE: 28

Met Lys Met Ala Ser Asn Asp Ala Asn Pro Ser Asp Gly Ser Thr Ala
1 5 10 15

Asn Leu Val Pro Glu Val Asn Asn Glu Val Met Ala Leu Glu Pro Val
20 25 30

Val Gly Ala Ala Ile Ala Ala Pro Val Ala Gly Gln Gln Asn Val Ile
35 40 45

Asp Pro Trp Ile Arg Asn Asn Phe Val Gln Ala Pro Gly Gly Glu Phe
50 55 60

Thr Val Ser Pro Arg Asn Ala Pro Gly Glu Ile Leu Trp Ser Ala Pro
65 70 75 80

Leu Gly Pro Asp Leu Asn Pro Tyr Leu Ser His Leu Ala Arg Met Tyr
85 90 95

Asn Gly Tyr Ala Gly Gly Phe Glu Val Gln Val Ile Leu Ala Gly Asn
100 105 110

Ala Phe Thr Ala Gly Lys Ile Ile Phe Ala Ala Val Pro Pro Asn Phe
115 120 125

Pro Thr Glu Gly Leu Ser Pro Ser Gln Val Thr Met Phe Pro His Ile
130 135 140

Ile Val Asp Val Arg Gln Leu Glu Pro Val Leu Ile Pro Leu Pro Asp
145 150 155 160

Val Arg Asn Asn Phe Tyr His Tyr Asn Gln Leu Asn Asp Pro Thr Ile
165 170 175

Lys Leu Ile Ala Met Leu Tyr Thr Pro Leu Arg Ala Asn Asn Ala Gly
180 185 190

Glu Asp Val Phe Thr Val Ser Cys Arg Val Leu Thr Arg Pro Ser Pro
195 200 205

Asp Phe Asp Phe Ile Phe Leu Val Pro Pro Thr Val Glu Ser Arg Thr
210 215 220

Lys Pro Phe Thr Val Pro Ile Leu Thr Val Glu Glu Met Thr Asn Ser
225 230 235 240

Arg Phe Pro Ile Pro Leu Glu Lys Leu Phe Thr Gly Pro Ser Gly Ala
245 250 255

Phe Val Val Gln Pro Gln Asn Gly Arg Cys Thr Thr Asp Gly Val Leu
260 265 270

Leu Gly Thr Thr Gln Leu Ser Pro Val Asn Ile Cys Thr Phe Arg Gly
275 280 285

Asp Val Thr His Ile Ala Gly Thr His Asn Tyr Thr Met Asn Leu Ala
290 295 300

Ser Gln Asn Trp Asn Asn Tyr Asp Pro Thr Glu Glu Ile Pro Ala Pro
305 310 315 320

Leu Gly Thr Pro Asp Phe Val Gly Arg Ile Gln Gly Met Leu Thr Gln
325 330 335

Thr Thr Arg Gly Asp Gly Ser Thr Arg Gly His Lys Ala Thr Val Ser
340 345 350

Thr Gly Asp Val His Phe Thr Pro Lys Leu Gly Ser Ile Gln Phe Asn
355 360 365

```
Thr Asp Thr Asn Asn Asp Phe Glu Thr Gly Gln Asn Thr Lys Phe Thr
    370                 375                 380

Pro Val Gly Val Val Gln Asp Gly Asn Gly Thr His Gln Asn Glu Pro
385                 390                 395                 400

Gln Gln Trp Val Leu Pro Ser Tyr Ser Gly Arg Thr Gly His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540
```

<210> SEQ ID NO 29
<211> LENGTH: 540
<212> TYPE: PRT
<213> ORGANISM: Norovirus

<400> SEQUENCE: 29

```
Met Lys Met Ala Ser Asn Asp Ala Thr Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Val Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Leu Tyr His Tyr Asn Gln Ser Asn Asp Pro Thr Ile
                165                 170                 175

Arg Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205
```

```
Asp Phe Asp Phe Ile Phe Leu Val Pro Pro Thr Val Glu Ser Arg Thr
    210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr Gln Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Arg Ile Gln Gly Val Leu Thr Gln
                325                 330                 335

Thr Thr Arg Arg Asp Gly Ser Thr Arg Gly His Lys Ala Thr Val Ser
            340                 345                 350

Thr Gly Ser Val His Phe Thr Pro Lys Leu Gly Ser Val Gln Phe Ser
        355                 360                 365

Thr Asp Thr Ser Asn Asp Phe Glu Thr Gly Gln Asn Thr Arg Phe Thr
    370                 375                 380

Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ser Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Ala Gly Arg Arg Arg Ala Leu
    530                 535                 540
```

<210> SEQ ID NO 30
<211> LENGTH: 540
<212> TYPE: PRT
<213> ORGANISM: Norovirus

<400> SEQUENCE: 30

```
Met Lys Met Ala Ser Asn Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
```

-continued

```
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Ser Arg Asn Tyr Thr Met Asn Leu Ala
    290                 295                 300

Ser Leu Lys Trp Asn Lys Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Gly Asp Gly Ser Thr Arg Gly His Lys Ala Thr Ile Tyr
            340                 345                 350

Thr Gly Ser Ala Pro Phe Thr Pro Lys Leu Gly Ser Val Gln Phe Ser
        355                 360                 365

Thr Asp Thr Glu Asn Asp Phe Glu Thr His Gln Asn Thr Lys Phe Thr
    370                 375                 380

Pro Val Gly Val Thr Gln Asp Gly Ser Thr Thr His Arg Asn Glu Pro
385                 390                 395                 400

Gln Gln Trp Val Leu Pro Ser Tyr Ser Gly Arg Asn Val His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln His Phe Tyr Gln Glu
    450                 455                 460
```

```
Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 31
<211> LENGTH: 540
<212> TYPE: PRT
<213> ORGANISM: Norovirus

<400> SEQUENCE: 31

Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Met Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Ser Arg Asn Tyr Thr Met Asn Leu Ala
```

```
    290                 295                 300

Ser Gln Asn Trp Asn Ser Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ser Pro Lys Leu Gly Arg Val Gln Phe Ala
        355                 360                 365

Thr Asp Thr Asp Asn Asp Phe Asp Ala Asn Gln Asn Thr Lys Phe Thr
    370                 375                 380

Pro Val Gly Val Ile Gln Asp Gly Asn Thr Ala His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 32
<211> LENGTH: 536
<212> TYPE: PRT
<213> ORGANISM: Norovirus

<400> SEQUENCE: 32

Met Lys Met Ala Ser Asn Asp Ala Thr Pro Ser Asp Asp Gly Ala Ala
1               5                   10                  15

Gly Leu Val Pro Glu Ile Asn Asn Glu Val Met Ala Leu Glu Pro Val
            20                  25                  30

Ala Gly Ala Ser Ile Ala Ala Pro Val Val Gly Gln Gln Asn Ile Ile
        35                  40                  45

Asp Pro Trp Ile Arg Asn Asn Phe Val Gln Ala Pro Ala Gly Glu Phe
    50                  55                  60

Thr Val Ser Pro Arg Asn Ser Pro Gly Glu Leu Leu Leu Asp Leu Glu
65                  70                  75                  80

Leu Gly Pro Glu Leu Asn Pro Tyr Leu Ala His Leu Ala Arg Met Tyr
                85                  90                  95

Asn Gly His Ala Gly Gly Met Glu Val Gln Ile Val Leu Ala Gly Asn
            100                 105                 110

Ala Phe Thr Ala Gly Lys Ile Leu Phe Ala Ala Ile Pro Pro Ser Phe
        115                 120                 125
```

-continued

```
Pro Tyr Glu Asn Leu Ser Pro Ala Gln Leu Thr Met Cys Pro His Val
    130                 135                 140

Ile Val Asp Val Arg Gln Leu Glu Pro Val Leu Leu Pro Met Pro Asp
145                 150                 155                 160

Ile Arg Asn Val Phe Tyr His Tyr Asn Gln Asn Asn Ser Pro Lys Leu
                165                 170                 175

Arg Leu Val Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Gln Phe Thr Phe Leu Val Pro Pro Thr Val Glu Ser Lys Thr
    210                 215                 220

Lys Asn Phe Thr Leu Pro Val Leu Arg Val Ser Glu Met Thr Asn Ser
225                 230                 235                 240

Arg Phe Pro Val Val Leu Asp Gln Met Tyr Thr Ser Arg Asn Glu Asn
                245                 250                 255

Ile Ile Val Gln Pro Gln Asn Gly Arg Cys Thr Thr Asp Gly Glu Leu
            260                 265                 270

Leu Gly Thr Thr Ile Leu Gln Ser Val Ser Ile Cys Asn Phe Lys Gly
        275                 280                 285

Thr Met Gln Ala Lys Leu Asn Glu Glu Pro Arg Tyr Gln Leu Gln Leu
    290                 295                 300

Thr Asn Leu Asp Gly Ser Pro Ile Asp Pro Thr Asp Asp Met Pro Ala
305                 310                 315                 320

Pro Leu Gly Thr Pro Asp Phe Gln Ala Met Leu Tyr Gly Val Ala Ser
                325                 330                 335

Gln Arg Ser Ser Ile Asp Asn Ala Thr Arg Ala His Asp Ala Gln Ile
            340                 345                 350

Asp Thr Ala Gly Asp Thr Phe Ala Pro Lys Ile Gly Gln Val Arg Phe
        355                 360                 365

Lys Ser Ser Ser Asn Asp Phe Asp Leu His Asp Pro Thr Lys Phe Thr
    370                 375                 380

Pro Ile Gly Val Asn Val Asp Asp Gln His Pro Phe Arg Gln Trp Ser
385                 390                 395                 400

Leu Pro Asn Tyr Gly Gly His Leu Ala Leu Asn Asn His Leu Ala Pro
                405                 410                 415

Ala Val Thr Pro Leu Phe Pro Gly Glu Gln Ile Leu Phe Phe Arg Ser
            420                 425                 430

Tyr Ile Pro Ser Ala Gly Gly His Thr Asp Gly Ala Met Asp Cys Leu
        435                 440                 445

Leu Pro Gln Glu Trp Val Glu His Phe Tyr Gln Glu Ala Ala Pro Ser
    450                 455                 460

Gln Ser Asp Ile Ala Leu Val Arg Phe Ile Asn Pro Asp Thr Gly Arg
465                 470                 475                 480

Val Leu Phe Glu Ala Lys Leu His Lys Gln Gly Phe Leu Thr Ile Ala
                485                 490                 495

Ala Ser Gly Asp His Pro Ile Val Met Pro Thr Asn Gly Tyr Phe Arg
            500                 505                 510

Phe Glu Ala Trp Val Asn Pro Phe Tyr Thr Leu Ala Pro Val Gly Thr
        515                 520                 525

Gly Ser Gly Arg Arg Arg Ile Gln
    530                 535
```

<210> SEQ ID NO 33
<211> LENGTH: 1632
<212> TYPE: DNA
<213> ORGANISM: Artificial Sequence
<220> FEATURE:
<223> OTHER INFORMATION: Nucleic acid sequence of human codon-optimized
      VP1 GI.5 Siklos HUN5407 2013 HUN AHW99832

<400> SEQUENCE: 33

```
atgatgatgg cctccaaaga cgctcctagc agtgctgatg gcgctaacgg tgccggccag     60
ctggtccccg aggtgaataa cgccgagcct ctccccttgg acccagtagc cggagcttca    120
acggccctag ctactgccgg acaggttaat atgattgacc cctggatttt caataatttc    180
gtgcaggccc ctcaaggcga gtttactata agccctaaca acacaccagg ggatattctg    240
ttcgacctgc agttaggccc tcatctcaac cccttcttgg cccacctgag ccagatgtac    300
aatggctggg tgggcaacat gcgagtgaga gttatcctcg cagggaacgc ctttaccgct    360
ggtaaggtga tcatttgttg cgtaccacct ggattccagt ctaggacatt aagtattgcg    420
caagctaccc tctttcctca tatcatcgcc gacgtgcgga cactagagcc catcgagatc    480
ccactggagg atgtccggaa taccctgtac cataccaacg ataatcagcc cactatgagg    540
ttactgtgca tgctgtacac gccactccgg actggtgggg gcagtggggg gaccgatgct    600
ttcgtcgttg ccggtagggt gctcacttgc ccgtcatctg actttaactt cctattcctt    660
gtgcccccaa cggtggaaca gaaaacgaga cctttttccg tacctaacat ccctttacag    720
ctcctaagca atagcagagt acctaacctg atccaatcca tggttcttag ccctgatcaa    780
gcgcagaacg tacagtttca gaacgggcgg tgcaccacag atggccagct gcttggtaca    840
actcccgtct ccgtgtctca gatacttaag tttcgcggca aggtctccgc tggatccaaa    900
gtaatcaacc tcactgagct tgatggctct ccctttctgg cgttcgaggc gcccgcccca    960
acaggctttc cagacctggg aacatccgat tggcatgtcg agatgagtct gaatagcaac   1020
tcccagtctt ctggcaatcc aatactgctc cgcgatatcc atcctaattc tagcgagttc   1080
gttccacacc tgggttctgt gtgcgtgacg gctgcaatag aggtggctgg cgactacacg   1140
ggtaccattc agtggacctc tcagccaagt aacgtgaccc ctgtgccaga cgttaacttt   1200
tggacaattc cacactacgg ctctaacttg gccgaagcat cccagcttgc ccccgttgta   1260
tatcccccag gctttggcga agcaatagtt tattttatgt ccccaatccc tggacctaac   1320
acagcacaca agccaaacct cgtcccatgc ctgctgcccc aggagttcgt gactcatttc   1380
gtttcggaac aagccccatc aatgggggag gccgccctgg tccactacgt ggatccagat   1440
accaatcgga atctgggaga attcaaactc taccctgaag gattcattac atgtgtgccc   1500
aatggaacag gaccgcagca gctcccactg aacggtgtct ttgtattcgc atcatgggtt   1560
agccggttct atcaacttaa acccgtgggg acagcttcat ctgcccgggg gcgccttggc   1620
gtgcggcgct ga                                                       1632
```

<210> SEQ ID NO 34
<211> LENGTH: 543
<212> TYPE: PRT
<213> ORGANISM: Norovirus

<400> SEQUENCE: 34

```
Met Met Met Ala Ser Lys Asp Ala Pro Ser Ser Ala Asp Gly Ala Asn
1               5                   10                  15

Gly Ala Gly Gln Leu Val Pro Glu Val Asn Asn Ala Glu Pro Leu Pro
            20                  25                  30
```

-continued

```
Leu Asp Pro Val Ala Gly Ala Ser Thr Ala Leu Ala Thr Ala Gly Gln
        35                  40                  45

Val Asn Met Ile Asp Pro Trp Ile Phe Asn Asn Phe Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Ser Leu Gly Pro His Leu Asn Pro Phe Leu Ala His Leu
                85                  90                  95

Ser Gln Met Tyr Asn Gly Trp Val Gly Asn Met Arg Val Arg Val Ile
            100                 105                 110

Leu Ala Gly Asn Ala Phe Thr Ala Gly Lys Val Ile Ile Cys Cys Val
        115                 120                 125

Pro Pro Gly Phe Gln Ser Arg Thr Leu Ser Ile Ala Gln Ala Thr Leu
    130                 135                 140

Phe Pro His Ile Ile Ala Asp Val Arg Thr Leu Glu Pro Ile Glu Ile
145                 150                 155                 160

Pro Leu Glu Asp Val Arg Asn Thr Leu Tyr His Thr Asn Asp Asn Gln
                165                 170                 175

Pro Thr Met Arg Leu Leu Cys Met Leu Tyr Thr Pro Leu Arg Thr Gly
            180                 185                 190

Gly Gly Ser Gly Gly Thr Asp Ala Phe Val Val Ala Gly Arg Val Leu
        195                 200                 205

Thr Cys Pro Ser Ser Asp Phe Asn Phe Leu Phe Leu Val Pro Pro Thr
    210                 215                 220

Val Glu Gln Lys Thr Arg Pro Phe Ser Val Pro Asn Ile Pro Leu Gln
225                 230                 235                 240

Leu Leu Ser Asn Ser Arg Val Pro Asn Leu Ile Gln Ser Met Val Leu
                245                 250                 255

Ser Pro Asp Gln Ala Gln Asn Val Gln Phe Gln Asn Gly Arg Cys Thr
            260                 265                 270

Thr Asp Gly Gln Leu Leu Gly Thr Thr Pro Val Ser Val Ser Gln Ile
        275                 280                 285

Leu Lys Phe Arg Gly Lys Val Ser Ala Gly Ser Lys Val Ile Asn Leu
    290                 295                 300

Thr Glu Leu Asp Gly Ser Pro Phe Leu Ala Phe Glu Ala Pro Ala Pro
305                 310                 315                 320

Thr Gly Phe Pro Asp Leu Gly Thr Ser Asp Trp His Val Glu Met Ser
                325                 330                 335

Leu Asn Ser Asn Ser Gln Ser Ser Gly Asn Pro Ile Leu Leu Arg Asp
            340                 345                 350

Ile His Pro Asn Ser Ser Glu Phe Val Pro His Leu Gly Ser Val Cys
        355                 360                 365

Val Thr Ala Ala Ile Glu Val Ala Gly Asp Tyr Thr Gly Thr Ile Gln
    370                 375                 380

Trp Thr Ser Gln Pro Ser Asn Val Thr Pro Val Pro Asp Val Asn Phe
385                 390                 395                 400

Trp Thr Ile Pro His Tyr Gly Ser Asn Leu Ala Glu Ala Ser Gln Leu
                405                 410                 415

Ala Pro Val Val Tyr Pro Pro Gly Phe Gly Glu Ala Ile Val Tyr Phe
            420                 425                 430

Met Ser Pro Ile Pro Gly Pro Asn Thr Ala His Lys Pro Asn Leu Val
        435                 440                 445
```

-continued

Pro Cys Leu Leu Pro Gln Glu Phe Val Thr His Phe Val Ser Glu Gln
    450                 455                 460

Ala Pro Ser Met Gly Glu Ala Ala Leu Val His Tyr Val Asp Pro Asp
465                 470                 475                 480

Thr Asn Arg Asn Leu Gly Glu Phe Lys Leu Tyr Pro Glu Gly Phe Ile
                485                 490                 495

Thr Cys Val Pro Asn Gly Thr Gly Pro Gln Gln Leu Pro Leu Asn Gly
            500                 505                 510

Val Phe Val Phe Ala Ser Trp Val Ser Arg Phe Tyr Gln Leu Lys Pro
        515                 520                 525

Val Gly Thr Ala Ser Ser Ala Arg Gly Arg Leu Gly Val Arg Arg
    530                 535                 540

<210> SEQ ID NO 35
<211> LENGTH: 1632
<212> TYPE: DNA
<213> ORGANISM: Artificial Sequence
<220> FEATURE:
<223> OTHER INFORMATION: Nucleic acid sequence of human codon optimized
      VP1 GI.5 Siklos Q84S

<400> SEQUENCE: 35
atgatgatgg cctccaaaga cgctcctagc agtgctgatg gcgctaacgg tgccggccag      60
ctggtccccg aggtgaataa cgccgagcct ctccccttgg acccagtagc cggagcttca     120
acggccctag ctactgccgg acaggttaat atgattgacc cctggatttt caataatttc     180
gtgcaggccc ctcaaggcga gtttactata agccctaaca acacaccagg ggatattctg     240
ttcgacctga gcttaggccc tcatctcaac cccttcttgg cccacctgag ccagatgtac     300
aatggctggg tgggcaacat gcgagtgaga gttatcctcg cagggaacgc ctttaccgct     360
ggtaaggtga tcatttgttg cgtaccacct ggattccagt ctaggacatt aagtattgcg     420
caagctaccc tctttcctca tatcatcgcc gacgtgcgga cactagagcc catcgagatc     480
ccactggagg atgtccggaa taccctgtac cataccaacg ataatcagcc cactatgagg     540
ttactgtgca tgctgtacac gccactccgg actggtgggg gcagtggggg gaccgatgct     600
ttcgtcgttg ccggtagggt gctcacttgc ccgtcatctg actttaactt cctattcctt     660
gtgcccccaa cggtggaaca gaaaacgaga cctttttccg tacctaacat ccctttacag     720
ctcctaagca atagcagagt acctaacctg atccaatcca tggttcttag ccctgatcaa     780
gcgcagaacg tacagtttca gaacgggcgg tgcaccacag atggccagct gcttggtaca     840
actcccgtct ccgtgtctca gatacttaag tttcgcggca aggtctccgc tggatccaaa     900
gtaatcaacc tcactgagct tgatggctct cccttctgg cgttcgaggc gcccgcccca     960
acaggctttc cagacctggg aacatccgat tggcatgtcg agatgagtct gaatagcaac    1020
tcccagtctt ctggcaatcc aatactgctc cgcgatatcc atcctaattc tagcgagttc    1080
gttccacacc tgggttctgt gtgcgtgacg gctgcaatag aggtggctgg cgactacacg    1140
ggtaccattc agtggacctc tcagccaagt aacgtgaccc ctgtgccaga cgttaacttt    1200
tggacaattc cacactacgg ctctaacttg gccgaagcat cccagcttgc ccccgttgta    1260
tatcccccag gctttggcga agcaatagtt tattttatgt ccccaatccc tggacctaac    1320
acagcacaca agccaaacct cgtcccatgc ctgctgcccc aggagttcgt gactcatttc    1380
gtttcggaac aagccccatc aatgggggag gccgccctgg tccactacgt ggatccagat    1440
accaatcgga atctgggaga attcaaactc taccctgaag gattcattac atgtgtgccc    1500
aatggaacag gaccgcagca gctcccactg aacggtgtct ttgtattcgc atcatgggtt 1560
agccggttct atcaacttaa acccgtgggg acagcttcat ctgcccgggg gcgccttggc 1620
gtgcggcgct ga 1632

<210> SEQ ID NO 36
<211> LENGTH: 543
<212> TYPE: PRT
<213> ORGANISM: Norovirus

<400> SEQUENCE: 36

Met Met Met Ala Ser Lys Asp Ala Pro Ser Ser Ala Asp Gly Ala Asn
1 5 10 15

Gly Ala Gly Gln Leu Val Pro Glu Val Asn Asn Ala Glu Pro Leu Pro
20 25 30

Leu Asp Pro Val Ala Gly Ala Ser Thr Ala Leu Ala Thr Ala Gly Gln
35 40 45

Val Asn Met Ile Asp Pro Trp Ile Phe Asn Asn Phe Val Gln Ala Pro
50 55 60

Gln Gly Glu Phe Thr Ile Ser Pro Asn Asn Thr Pro Gly Asp Ile Leu
65 70 75 80

Phe Asp Leu Gln Leu Gly Pro His Leu Asn Pro Phe Leu Leu His Leu
85 90 95

Ser Gln Met Tyr Asn Gly Trp Val Gly Asn Met Arg Val Arg Val Ile
100 105 110

Leu Ala Gly Asn Ala Phe Thr Ala Gly Lys Val Ile Ile Cys Cys Val
115 120 125

Pro Pro Gly Phe Gln Ser Arg Thr Leu Ser Ile Ala Gln Ala Thr Leu
130 135 140

Phe Pro His Ile Ile Ala Asp Val Arg Thr Leu Glu Pro Ile Glu Ile
145 150 155 160

Pro Leu Glu Asp Val Arg Asn Thr Leu Tyr His Thr Asn Asp Asn Gln
165 170 175

Pro Thr Met Arg Leu Leu Cys Met Leu Tyr Thr Pro Leu Arg Thr Gly
180 185 190

Gly Gly Ser Gly Gly Thr Asp Ala Phe Val Val Ala Gly Arg Val Leu
195 200 205

Thr Cys Pro Ser Ser Asp Phe Asn Phe Leu Phe Leu Val Pro Pro Thr
210 215 220

Val Glu Gln Lys Thr Arg Pro Phe Ser Val Pro Asn Ile Pro Leu Gln
225 230 235 240

Leu Leu Ser Asn Ser Arg Val Pro Asn Leu Ile Gln Ser Met Val Leu
245 250 255

Ser Pro Asp Gln Ala Gln Asn Val Gln Phe Gln Asn Gly Arg Cys Thr
260 265 270

Thr Asp Gly Gln Leu Leu Gly Thr Thr Pro Val Ser Val Ser Gln Ile
275 280 285

Leu Lys Phe Arg Gly Lys Val Ser Ala Gly Ser Lys Val Ile Asn Leu
290 295 300

Thr Glu Leu Asp Gly Ser Pro Phe Leu Ala Phe Glu Ala Pro Ala Pro
305 310 315 320

Thr Gly Phe Pro Asp Leu Gly Thr Ser Asp Trp His Val Glu Met Ser
325 330 335

Leu Asn Ser Asn Ser Gln Ser Ser Gly Asn Pro Ile Leu Leu Arg Asp
340 345 350

```
Ile His Pro Asn Ser Ser Glu Phe Val Pro His Leu Gly Ser Val Cys
        355                 360                 365

Val Thr Ala Ala Ile Glu Val Ala Gly Asp Tyr Thr Gly Thr Ile Gln
    370                 375                 380

Trp Thr Ser Gln Pro Ser Asn Val Thr Pro Val Pro Asp Val Asn Phe
385                 390                 395                 400

Trp Thr Ile Pro His Tyr Gly Ser Asn Leu Ala Glu Ala Ser Gln Leu
                405                 410                 415

Ala Pro Val Val Tyr Pro Pro Gly Phe Gly Glu Ala Ile Val Tyr Phe
            420                 425                 430

Met Ser Pro Ile Pro Gly Pro Asn Thr Ala His Lys Pro Asn Leu Val
        435                 440                 445

Pro Cys Leu Leu Pro Gln Glu Phe Val Thr His Phe Val Ser Glu Gln
    450                 455                 460

Ala Pro Ser Met Gly Glu Ala Ala Leu Val His Tyr Val Asp Pro Asp
465                 470                 475                 480

Thr Asn Arg Asn Leu Gly Glu Phe Lys Leu Tyr Pro Glu Gly Phe Ile
                485                 490                 495

Thr Cys Val Pro Asn Gly Thr Gly Pro Gln Gln Leu Pro Leu Asn Gly
            500                 505                 510

Val Phe Val Phe Ala Ser Trp Val Ser Arg Phe Tyr Gln Leu Lys Pro
        515                 520                 525

Val Gly Thr Ala Ser Ser Ala Arg Gly Arg Leu Gly Val Arg Arg
    530                 535                 540
```

<210> SEQ ID NO 37
<211> LENGTH: 1632
<212> TYPE: DNA
<213> ORGANISM: Artificial Sequence
<220> FEATURE:
<223> OTHER INFORMATION: Nucleic acid sequence of human codon optimized VP1 GI.5 siklos A94L

<400> SEQUENCE: 37

```
atgatgatgg cctccaaaga cgctcctagc agtgctgatg gcgctaacgg tgccggccag     60

ctggtccccg aggtgaataa cgccgagcct ctccccttgg acccagtagc cggagcttca    120

acggccctag ctactgccgg acaggttaat atgattgacc cctggatttt caataatttc    180

gtgcaggccc ctcaaggcga gtttactata agccctaaca acacaccagg ggatattctg    240

ttcgacctgc agttaggccc tcatctcaac cccttcttgc tccacctgag ccagatgtac    300

aatggctggg tgggcaacat gcgagtgaga gttatcctcg cagggaacgc ctttaccgct    360

ggtaaggtga tcatttgttg cgtaccacct ggattccagt ctaggacatt aagtattgcg    420

caagctaccc tctttcctca tatcatcgcc gacgtgcgga cactagagcc catcgagatc    480

ccactggagg atgtccggaa taccctgtac cataccaacg ataatcagcc cactatgagg    540

ttactgtgca tgctgtacac gccactccgg actggtgggg gcagtggggg gaccgatgct    600

ttcgtcgttg ccggtagggt gctcacttgc ccgtcatctg actttaactt cctattcctt    660

gtgcccccaa cggtggaaca gaaaacgaga cctttttccg tacctaacat ccctttacag    720

ctcctaagca atagcagagt acctaacctg atccaatcca tggttcttag ccctgatcaa    780

gcgcagaacg tacagtttca gaacgggcgg tgcaccacag atggccagct gcttggtaca    840

actcccgtct ccgtgtctca gatacttaag tttcgcggca aggtctccgc tggatccaaa    900

gtaatcaacc tcactgagct tgatggctct ccctttctgg cgttcgaggc gcccgcccca    960
```

acaggctttc cagacctggg aacatccgat tggcatgtcg agatgagtct gaatagcaac 1020
tcccagtctt ctggcaatcc aatactgctc cgcgatatcc atcctaattc tagcgagttc 1080
gttccacacc tgggttctgt gtgcgtgacg gctgcaatag aggtggctgg cgactacacg 1140
ggtaccattc agtggacctc tcagccaagt aacgtgaccc ctgtgccaga cgttaacttt 1200
tggacaattc cacactacgg ctctaacttg gccgaagcat cccagcttgc ccccgttgta 1260
tatcccccag gctttggcga agcaatagtt tattttatgt ccccaatccc tggacctaac 1320
acagcacaca agccaaacct cgtcccatgc ctgctgcccc aggagttcgt gactcatttc 1380
gtttcggaac aagccccatc aatgggggag gccgccctgg tccactacgt ggatccagat 1440
accaatcgga atctgggaga attcaaactc taccctgaag gattcattac atgtgtgccc 1500
aatggaacag gaccgcagca gctcccactg aacggtgtct ttgtattcgc atcatgggtt 1560
agccggttct atcaacttaa acccgtgggg acagcttcat ctgcccgggg gcgccttggc 1620
gtgcggcgct ga 1632

<210> SEQ ID NO 38
<211> LENGTH: 543
<212> TYPE: PRT
<213> ORGANISM: Norovirus

<400> SEQUENCE: 38

Met Met Met Ala Ser Lys Asp Ala Pro Ser Ser Ala Asp Gly Ala Asn
1 5 10 15

Gly Ala Gly Gln Leu Val Pro Glu Val Asn Asn Ala Glu Pro Leu Pro
20 25 30

Leu Asp Pro Val Ala Gly Ala Ser Thr Ala Leu Ala Thr Ala Gly Gln
35 40 45

Val Asn Met Ile Asp Pro Trp Ile Phe Asn Asn Phe Val Gln Ala Pro
50 55 60

Gln Gly Glu Phe Thr Ile Ser Pro Asn Asn Thr Pro Gly Asp Ile Leu
65 70 75 80

Phe Asp Leu Ser Leu Gly Pro His Leu Asn Pro Phe Leu Leu His Leu
85 90 95

Ser Gln Met Tyr Asn Gly Trp Val Gly Asn Met Arg Val Arg Val Ile
100 105 110

Leu Ala Gly Asn Ala Phe Thr Ala Gly Lys Val Ile Ile Cys Cys Val
115 120 125

Pro Pro Gly Phe Gln Ser Arg Thr Leu Ser Ile Ala Gln Ala Thr Leu
130 135 140

Phe Pro His Ile Ile Ala Asp Val Arg Thr Leu Glu Pro Ile Glu Ile
145 150 155 160

Pro Leu Glu Asp Val Arg Asn Thr Leu Tyr His Thr Asn Asp Asn Gln
165 170 175

Pro Thr Met Arg Leu Leu Cys Met Leu Tyr Thr Pro Leu Arg Thr Gly
180 185 190

Gly Gly Ser Gly Gly Thr Asp Ala Phe Val Val Ala Gly Arg Val Leu
195 200 205

Thr Cys Pro Ser Ser Asp Phe Asn Phe Leu Phe Leu Val Pro Pro Thr
210 215 220

Val Glu Gln Lys Thr Arg Pro Phe Ser Val Pro Asn Ile Pro Leu Gln
225 230 235 240

Leu Leu Ser Asn Ser Arg Val Pro Asn Leu Ile Gln Ser Met Val Leu 245 250 255

Ser Pro Asp Gln Ala Gln Asn Val Gln Phe Gln Asn Gly Arg Cys Thr
260 265 270

Thr Asp Gly Gln Leu Leu Gly Thr Thr Pro Val Ser Val Ser Gln Ile
275 280 285

Leu Lys Phe Arg Gly Lys Val Ser Ala Gly Ser Lys Val Ile Asn Leu
290 295 300

Thr Glu Leu Asp Gly Ser Pro Phe Leu Ala Phe Glu Ala Pro Ala Pro
305 310 315 320

Thr Gly Phe Pro Asp Leu Gly Thr Ser Asp Trp His Val Glu Met Ser
325 330 335

Leu Asn Ser Asn Ser Gln Ser Ser Gly Asn Pro Ile Leu Leu Arg Asp
340 345 350

Ile His Pro Asn Ser Ser Glu Phe Val Pro His Leu Gly Ser Val Cys
355 360 365

Val Thr Ala Ala Ile Glu Val Ala Gly Asp Tyr Thr Gly Thr Ile Gln
370 375 380

Trp Thr Ser Gln Pro Ser Asn Val Thr Pro Val Pro Asp Val Asn Phe
385 390 395 400

Trp Thr Ile Pro His Tyr Gly Ser Asn Leu Ala Glu Ala Ser Gln Leu
405 410 415

Ala Pro Val Val Tyr Pro Pro Gly Phe Gly Glu Ala Ile Val Tyr Phe
420 425 430

Met Ser Pro Ile Pro Gly Pro Asn Thr Ala His Lys Pro Asn Leu Val
435 440 445

Pro Cys Leu Leu Pro Gln Glu Phe Val Thr His Phe Val Ser Glu Gln
450 455 460

Ala Pro Ser Met Gly Glu Ala Ala Leu Val His Tyr Val Asp Pro Asp
465 470 475 480

Thr Asn Arg Asn Leu Gly Glu Phe Lys Leu Tyr Pro Glu Gly Phe Ile
485 490 495

Thr Cys Val Pro Asn Gly Thr Gly Pro Gln Gln Leu Pro Leu Asn Gly
500 505 510

Val Phe Val Phe Ala Ser Trp Val Ser Arg Phe Tyr Gln Leu Lys Pro
515 520 525

Val Gly Thr Ala Ser Ser Ala Arg Gly Arg Leu Gly Val Arg Arg
530 535 540

<210> SEQ ID NO 39
<211> LENGTH: 1632
<212> TYPE: DNA
<213> ORGANISM: Artificial Sequence
<220> FEATURE:
<223> OTHER INFORMATION: Nucleic acid sequence of human codon optimized VP1 GI.5 siklos Q84S plus sign A94L

<400> SEQUENCE: 39
atgatgatgg cctccaaaga cgctcctagc agtgctgatg gcgctaacgg tgccggccag 60
ctggtccccg aggtgaataa cgccgagcct ctccccttgg acccagtagc cggagcttca 120
acggccctag ctactgccgg acaggttaat atgattgacc cctggatttt caataatttc 180
gtgcaggccc ctcaaggcga gtttactata agccctaaca acacaccagg ggatattctg 240
ttcgacctga gcttaggccc tcatctcaac cccttcttgc tccacctgag ccagatgtac 300
aatggctggg tgggcaacat gcgagtgaga gttatcctcg cagggaacgc ctttaccgct 360
ggtaaggtga tcatttgttg cgtaccacct ggattccagt ctaggacatt aagtattgcg 420
caagctaccc tctttcctca tatcatcgcc gacgtgcgga cactagagcc catcgagatc 480
ccactggagg atgtccggaa taccctgtac cataccaacg ataatcagcc cactatgagg 540
ttactgtgca tgctgtacac gccactccgg actggtgggg gcagtggggg gaccgatgct 600
ttcgtcgttg ccggtagggt gctcacttgc ccgtcatctg actttaactt cctattcctt 660
gtgcccccaa cggtggaaca gaaaacgaga cctttttccg tacctaacat ccctttacag 720
ctcctaagca atagcagagt acctaacctg atccaatcca tggttcttag ccctgatcaa 780
gcgcagaacg tacagtttca gaacgggcgg tgcaccacag atggccagct gcttggtaca 840
actcccgtct ccgtgtctca gatacttaag tttcgcggca aggtctccgc tggatccaaa 900
gtaatcaacc tcactgagct tgatggctct ccctttctgg cgttcgaggc gcccgcccca 960
acaggctttc cagacctggg aacatccgat tggcatgtcg agatgagtct gaatagcaac 1020
tcccagtctt ctggcaatcc aatactgctc cgcgatatcc atcctaattc tagcgagttc 1080
gttccacacc tgggttctgt gtgcgtgacg gctgcaatag aggtggctgg cgactacacg 1140
ggtaccattc agtggacctc tcagccaagt aacgtgaccc ctgtgccaga cgttaacttt 1200
tggacaattc cacactacgg ctctaacttg gccgaagcat cccagcttgc ccccgttgta 1260
tatcccccag gctttggcga agcaatagtt tattttatgt ccccaatccc tggacctaac 1320
acagcacaca agccaaacct cgtcccatgc ctgctgcccc aggagttcgt gactcatttc 1380
gtttcggaac aagccccatc aatgggggag gccgccctgg tccactacgt ggatccagat 1440
accaatcgga atctgggaga attcaaactc taccctgaag gattcattac atgtgtgccc 1500
aatggaacag gaccgcagca gctcccactg aacggtgtct ttgtattcgc atcatgggtt 1560
agccggttct atcaacttaa acccgtgggg acagcttcat ctgcccgggg gcgccttggc 1620
gtgcggcgct ga 1632

<210> SEQ ID NO 40
<211> LENGTH: 1629
<212> TYPE: DNA
<213> ORGANISM: Artificial Sequence
<220> FEATURE:
<223> OTHER INFORMATION: Nucleic acid sequence of human codon-optimized VP1 GII.2 CGMH47 2011 TW AGT39206

<400> SEQUENCE: 40
atgaagatgg catccaacga cgccgcaccc agcacagacg gagctgccgg attggtaccc 60
gagtctaata acgaggtgat ggccttggag cctgttgcag gggctgccct cgcagctcct 120
gtgaccgggc agacaaatat catcgatcct tggattagag ctaatttcgt gcaagcccca 180
aatggggagt ttacggtcag ccctagaaat agccctgggg aagtgctcct caatctcgag 240
ctgggaccag aacttaatcc gtacctggct cacctggccc ggatgtacaa tggatatgca 300
ggagggatgg aggtgcaggt tatgctggct ggcaatgcct ttacagcagg caaactcgtt 360
ttcgcagccg tccctcccca cttcccagtt gaaaatcttt cccctcagca gattaccatg 420
tttccccatg tcatcatcga tgtgcgtacc ctggaacctg tgctgttgcc tttaccagac 480
gtgcggaata atttctttca ctataatcag aaggatgacc caaaaatgcg gatcgttgcg 540
atgctttata ctcccctgcg tagcaatggt agtggggatg acgtttttac agtgagttgt 600
cgggtactaa ctcgcccttc accagacttc gactttacgt acttggtgcc tcccactgtc 660
gaaagcaaaa ctaagccatt cacacttccc atcctcaccc tcggagaact ctcgaactcc 720

```
cgcttccctg tttcaattga tcagatgtac acgtctccaa atgaagtcat ttctgtgcag    780

tgtcagaacg gcaggtgcac cttagacggt gaactgcagg ggacaacgca gttgcaggtc    840

agtggaattt gcgcctttaa gggcgaagtg acagctcacc tccacgacaa cgatcatctc    900

tacaatgtta ctattactaa tctcaatgga agtcctttcg acccctcgga agatattccc    960

gctccactcg gagtacctga ctttcaggga cgcgtcttcg gcgtgatatc acaacgagat   1020

aagcataaca caccoggaca taatgagcca gccaatagag cccacgacgc agtcgttccg   1080

acctatacgg ctcagtacac cccaaagctc ggccagatac aaatcgggac ttggcagacc   1140

gatgacctca ctgtgaatca acctgtgaaa ttcactccag taggtctgaa tgatacagac   1200

cactttaacc agtgggtggt ccctagatac gccggagcct tgaacctaaa cactaacctt   1260

gccccttccg ttgcacctgt gtttccgggg gagcggttgc tcttctttag aagctatatt   1320

cctctgaagg gcgggtatgg tactccagca atcgactgcc tgctacctca ggagtgggtt   1380

caacatttct atcaagaggc cgcacctagt atgagcgagg tggctttggt cagatacatc   1440

aatccagaca caggaagagc actgttcgag gccaagctgc acagagccgg cttcatgacc   1500

gtctcatcca atacatccgc acccgtagta gtccccgcca acgggtactt cagattcgac   1560

agttgggtga atcagtttta ctcgttggcc cccatgggca cagggaacgg tcgccgacgg   1620

atccagtaa                                                           1629
```

<210> SEQ ID NO 41
<211> LENGTH: 542
<212> TYPE: PRT
<213> ORGANISM: Norovirus

<400> SEQUENCE: 41

```
Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
            20                  25                  30

Ala Gly Ala Ala Leu Ala Ala Pro Val Thr Gly Gln Thr Asn Ile Ile
        35                  40                  45

Asp Pro Trp Ile Arg Ala Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Leu His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205
```

```
Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
        275                 280                 285

Glu Val Thr Ala His Leu His Asp Asn Asp His Leu Tyr Asn Val Thr
    290                 295                 300

Ile Thr Asn Leu Asn Gly Ser Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Ser Gln Arg Asp Lys His Asn Thr Pro Gly His Asn Glu Pro Ala Asn
            340                 345                 350

Arg Ala His Asp Ala Val Val Pro Thr Tyr Thr Ala Gln Tyr Thr Pro
        355                 360                 365

Lys Leu Gly Gln Ile Gln Ile Gly Thr Trp Gln Thr Asp Asp Leu Thr
    370                 375                 380

Val Asn Gln Pro Val Lys Phe Thr Pro Val Gly Leu Asn Asp Thr Asp
385                 390                 395                 400

His Phe Asn Gln Trp Val Val Pro Arg Tyr Ala Gly Ala Leu Asn Leu
                405                 410                 415

Asn Thr Asn Leu Ala Pro Ser Val Ala Pro Val Phe Pro Gly Glu Arg
            420                 425                 430

Leu Leu Phe Phe Arg Ser Tyr Ile Pro Leu Lys Gly Gly Tyr Gly Thr
        435                 440                 445

Pro Ala Ile Asp Cys Leu Leu Pro Gln Glu Trp Val Gln His Phe Tyr
    450                 455                 460

Gln Glu Ala Ala Pro Ser Met Ser Glu Val Ala Leu Val Arg Tyr Ile
465                 470                 475                 480

Asn Pro Asp Thr Gly Arg Ala Leu Phe Glu Ala Lys Leu His Arg Ala
                485                 490                 495

Gly Phe Met Thr Val Ser Ser Asn Thr Ser Ala Pro Val Val Val Pro
            500                 505                 510

Ala Asn Gly Tyr Phe Arg Phe Asp Ser Trp Val Asn Gln Phe Tyr Ser
        515                 520                 525

Leu Ala Pro Met Gly Thr Gly Asn Gly Arg Arg Arg Ile Gln
    530                 535                 540
```

<210> SEQ ID NO 42
<211> LENGTH: 1629
<212> TYPE: DNA
<213> ORGANISM: Artificial Sequence
<220> FEATURE:
<223> OTHER INFORMATION: Nucleic acid sequence of human codon optimized VP1 GII.2 CGMH47 A90L

<400> SEQUENCE: 42

```
atgaagatgg catccaacga cgccgcaccc agcacagacg gagctgccgg attggtaccc     60

gagtctaata acgaggtgat ggccttggag cctgttgcag gggctgccct cgcagctcct    120

gtgaccgggc agacaaatat catcgatcct tggattagag ctaatttcgt gcaagcccca    180
```

-continued

```
aatggggagt ttacggtcag ccctagaaat agccctgggg aagtgctcct caatctcgag    240

ctgggaccag aacttaatcc gtacctgctc cacctggccc ggatgtacaa tggatatgca    300

ggagggatgg aggtgcaggt tatgctggct ggcaatgcct ttacagcagg caaactcgtt    360

ttcgcagccg tccctcccca cttcccagtt gaaaatcttt cccctcagca gattaccatg    420

tttccccatg tcatcatcga tgtgcgtacc ctggaacctg tgctgttgcc tttaccagac    480

gtgcggaata atttctttca ctataatcag aaggatgacc caaaaatgcg gatcgttgcg    540

atgctttata ctcccctgcg tagcaatggt agtggggatg acgtttttac agtgagttgt    600

cgggtactaa ctcgcccttc accagacttc gactttacgt acttggtgcc tcccactgtc    660

gaaagcaaaa ctaagccatt cacacttccc atcctcaccc tcggagaact ctcgaactcc    720

cgcttccctg tttcaattga tcagatgtac acgtctccaa atgaagtcat ttctgtgcag    780

tgtcagaacg gcaggtgcac cttagacggt gaactgcagg ggacaacgca gttgcaggtc    840

agtggaattt gcgcctttaa gggcgaagtg acagctcacc tccacgacaa cgatcatctc    900

tacaatgtta ctattactaa tctcaatgga agtcctttcg acccctcgga agatattccc    960

gctccactcg gagtacctga ctttcaggga cgcgtcttcg gcgtgatatc acaacgagat   1020

aagcataaca cacccggaca taatgagcca gccaatagag cccacgacgc agtcgttccg   1080

acctatacgg ctcagtacac cccaaagctc ggccagatac aaatcgggac ttggcagacc   1140

gatgacctca ctgtgaatca acctgtgaaa ttcactccag taggtctgaa tgatacagac   1200

cactttaacc agtgggtggt ccctagatac gccggagcct tgaacctaaa cactaacctt   1260

gccccttccg ttgcacctgt gtttccgggg gagcggttgc tcttctttag aagctatatt   1320

cctctgaagg gcgggtatgg tactccagca atcgactgcc tgctacctca ggagtgggtt   1380

caacatttct atcaagaggc cgcacctagt atgagcgagg tggctttggt cagatacatc   1440

aatccagaca caggaagagc actgttcgag gccaagctgc acagagccgg cttcatgacc   1500

gtctcatcca atacatccgc acccgtagta gtccccgcca acgggtactt cagattcgac   1560

agttgggtga atcagtttta ctcgttggcc cccatgggca cagggaacgg tcgccgacgg   1620

atccagtaa                                                           1629
```

<210> SEQ ID NO 43
<211> LENGTH: 542
<212> TYPE: PRT
<213> ORGANISM: Norovirus

<400> SEQUENCE: 43

```
Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
            20                  25                  30

Ala Gly Ala Ala Leu Ala Ala Pro Val Thr Gly Gln Thr Asn Ile Ile
        35                  40                  45

Asp Pro Trp Ile Arg Ala Asn Phe Val Gln Ala Pro Asn Gly Glu Phe
    50                  55                  60

Thr Val Ser Pro Arg Asn Ser Pro Gly Glu Val Leu Leu Asn Leu Ser
65                  70                  75                  80

Leu Gly Pro Glu Leu Asn Pro Tyr Leu Leu His Leu Ala Arg Met Tyr
                85                  90                  95

Asn Gly Tyr Ala Gly Gly Met Glu Val Gln Val Met Leu Ala Gly Asn
            100                 105                 110
```

```
Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
        275                 280                 285

Glu Val Thr Ala His Leu His Asp Asn Asp His Leu Tyr Asn Val Thr
    290                 295                 300

Ile Thr Asn Leu Asn Gly Ser Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Ser Gln Arg Asp Lys His Asn Thr Pro Gly His Asn Glu Pro Ala Asn
            340                 345                 350

Arg Ala His Asp Ala Val Val Pro Thr Tyr Thr Ala Gln Tyr Thr Pro
        355                 360                 365

Lys Leu Gly Gln Ile Gln Ile Gly Thr Trp Gln Thr Asp Asp Leu Thr
    370                 375                 380

Val Asn Gln Pro Val Lys Phe Thr Pro Val Gly Leu Asn Asp Thr Asp
385                 390                 395                 400

His Phe Asn Gln Trp Val Val Pro Arg Tyr Ala Gly Ala Leu Asn Leu
                405                 410                 415

Asn Thr Asn Leu Ala Pro Ser Val Ala Pro Val Phe Pro Gly Glu Arg
            420                 425                 430

Leu Leu Phe Phe Arg Ser Tyr Ile Pro Leu Lys Gly Gly Tyr Gly Thr
        435                 440                 445

Pro Ala Ile Asp Cys Leu Leu Pro Gln Glu Trp Val Gln His Phe Tyr
    450                 455                 460

Gln Glu Ala Ala Pro Ser Met Ser Glu Val Ala Leu Val Arg Tyr Ile
465                 470                 475                 480

Asn Pro Asp Thr Gly Arg Ala Leu Phe Glu Ala Lys Leu His Arg Ala
                485                 490                 495

Gly Phe Met Thr Val Ser Ser Asn Thr Ser Ala Pro Val Val Val Pro
            500                 505                 510

Ala Asn Gly Tyr Phe Arg Phe Asp Ser Trp Val Asn Gln Phe Tyr Ser
        515                 520                 525
```

```
Leu Ala Pro Met Gly Thr Gly Asn Gly Arg Arg Arg Ile Gln
    530                 535                 540


<210> SEQ ID NO 44
<211> LENGTH: 1629
<212> TYPE: DNA
<213> ORGANISM: Artificial Sequence
<220> FEATURE:
<223> OTHER INFORMATION: Nucleic acid sequence of human codon optimized
      VP1 GII.2 CGMH47 E80S plus sign A90L

<400> SEQUENCE: 44

atgaagatgg catccaacga cgccgcaccc agcacagacg gagctgccgg attggtaccc     60

gagtctaata acgaggtgat ggccttggag cctgttgcag gggctgccct cgcagctcct    120

gtgaccgggc agacaaatat catcgatcct tggattagag ctaatttcgt gcaagcccca    180

aatggggagt ttacggtcag ccctagaaat agccctgggg aagtgctcct caatctcagc    240

ctgggaccag aacttaatcc gtacctgctc cacctggccc ggatgtacaa tggatatgca    300

ggagggatgg aggtgcaggt tatgctggct ggcaatgcct ttacagcagg caaactcgtt    360

ttcgcagccg tccctcccca cttcccagtt gaaaatcttt cccctcagca gattaccatg    420

tttccccatg tcatcatcga tgtgcgtacc ctggaacctg tgctgttgcc tttaccagac    480

gtgcggaata atttctttca ctataatcag aaggatgacc caaaaatgcg gatcgttgcg    540

atgctttata ctcccctgcg tagcaatggt agtggggatg acgtttttac agtgagttgt    600

cgggtactaa ctcgcccttc accagacttc gactttacgt acttggtgcc tcccactgtc    660

gaaagcaaaa ctaagccatt cacacttccc atcctcaccc tcggagaact ctcgaactcc    720

cgcttccctg tttcaattga tcagatgtac acgtctccaa atgaagtcat ttctgtgcag    780

tgtcagaacg gcaggtgcac cttagacggt gaactgcagg ggacaacgca gttgcaggtc    840

agtggaattt gcgcctttaa gggcgaagtg acagctcacc tccacgacaa cgatcatctc    900

tacaatgtta ctattactaa tctcaatgga agtcctttcg acccctcgga agatattccc    960

gctccactcg gagtacctga ctttcaggga cgcgtcttcg gcgtgatatc acaacgagat   1020

aagcataaca cacccggaca taatgagcca gccaatagag cccacgacgc agtcgttccg   1080

acctatacgg ctcagtacac cccaaagctc ggccagatac aaatcgggac ttggcagacc   1140

gatgacctca ctgtgaatca acctgtgaaa ttcactccag taggtctgaa tgatacagac   1200

cactttaacc agtgggtggt ccctagatac gccggagcct tgaacctaaa cactaacctt   1260

gccccttccg ttgcacctgt gtttccgggg gagcggttgc tcttctttag aagctatatt   1320

cctctgaagg gcgggtatgg tactccagca atcgactgcc tgctacctca ggagtgggtt   1380

caacatttct atcaagaggc cgcacctagt atgagcgagg tggctttggt cagatacatc   1440

aatccagaca caggaagagc actgttcgag gccaagctgc acagagccgg cttcatgacc   1500

gtctcatcca atacatccgc acccgtagta gtccccgcca acgggtactt cagattcgac   1560

agttgggtga atcagtttta ctcgttggcc cccatgggca cagggaacgg tcgccgacgg   1620

atccagtaa                                                           1629


<210> SEQ ID NO 45
<211> LENGTH: 1647
<212> TYPE: DNA
<213> ORGANISM: Artificial Sequence
<220> FEATURE:
<223> OTHER INFORMATION: Nucleic acid sequence of human codon-optimized
      VP1 GII.3_Jingzhou_2013402_CHN AGX01095
```

-continued

<400> SEQUENCE: 45

```
atgaaaatgg cttccaacga tgcagcaccc tctaatgatg gcgctgccgg acttgtgccg     60
gagattagct ctgaggctat ggccctagaa ccagtagccg gggcagccat agctgcccca    120
ctgactggcc agcagaatat cattgacccc tggataatga acaatttcgt gcaggcaccg    180
gggggagaat tcacggtctc tcctcgaaac tcccccgggg aggttctctt gaatttggaa    240
ctgggccctg aaattaatcc ttatctggcc catctagccc gaatgtacaa cggctacgcc    300
ggaggtttcg aggtccaggt ggtgctcgct ggtaacgcct tcacagctgg caagatcatt    360
tttgcagcaa tccctccaaa cttccctatc gataatctta gtgccgccca gatcacaatg    420
tgccctcacg ttatcgtaga tgtgaggcag ctggaacctg tcaatctccc aatgcccgac    480
gtgcgcaaca acttctttca ctataaccag ggatctgact cccgccttcg ccttatcgct    540
atgctgtaca cccctctgag ggctaacaat tccggagatg acgttttcac tgtgagttgt    600
cgagtcctga cacgtccatc tcctgacttt agctttaatt tcctcgtgcc ccccacagtg    660
gaatccaaaa ctaagccatt ctctctgcca attcttacca ttagcgaaat gtcgaatagt    720
aggttcccgg tgcccataga ttcactgcat accagtccaa cagaaaacat cgtcgtacag    780
tgtcagaacg gacgcgtgac tctcgacggg gagcttatgg gcactaccca gctgctgccc    840
agccagatat gcgccttccg cggcacactg actagaagca cttcgcgtgc ttctgaccag    900
gcagatacag ctacaccaag gctgttcaat tattattggc atatacaact cgataatctg    960
aatggcactc cttatgaccc agccgaggac atccccgccc cacttggcac cccggacttt   1020
agagggaagg tctttggagt ggcttctcaa agaaatcccg acgcaaccac ccgggcccac   1080
gaggccaaaa tcgatactac atcagggcgt ttcaccccta agttaggcag tctggagata   1140
tctaccgaaa gtggagattt cgatcagaac cagccaaccc ggtttacccc cgtgggaatc   1200
ggggttgacc acgaaccgga tttccagcag tgggctctgc ctgattacgc aggccagttc   1260
acacataaca tgaatcttgc ccccgctgtg gcccccaact tcccgggaga acaacttctg   1320
tttttcagga gccaactgcc ttccagcggc ggccgatcta acgggatttt ggactgtctc   1380
gtgccccagg aatgggtgca gcatttttac caggagtccg cgccctccca gacgcaggtg   1440
gctctggtta gatatgtcaa tcccgacacc ggcagggtgc tatttgaggc aaagctgcac   1500
aagcttcgct ttatgactat cgctaagagc ggtgattcgc ctattacagt gccccccaac   1560
ggatacttca gatttgagag ttgggtgaac ccattctata ccctggcccc catgggtaca   1620
ggcaatggca gacggcggat ccagtaa                                       1647
```

<210> SEQ ID NO 46
<211> LENGTH: 548
<212> TYPE: PRT
<213> ORGANISM: Norovirus

<400> SEQUENCE: 46

```
Met Lys Met Ala Ser Asn Asp Ala Ala Pro Ser Asn Asp Gly Ala Ala
1               5                   10                  15

Gly Leu Val Pro Glu Ile Ser Ser Glu Ala Met Ala Leu Glu Pro Val
            20                  25                  30

Ala Gly Ala Ala Ile Ala Ala Pro Leu Thr Gly Gln Gln Asn Ile Ile
        35                  40                  45

Asp Pro Trp Ile Met Asn Asn Phe Val Gln Ala Pro Gly Gly Glu Phe
    50                  55                  60

Thr Val Ser Pro Arg Asn Ser Pro Gly Glu Val Leu Leu Asn Leu Ser
```

-continued

```
65                  70                  75                  80

Leu Gly Pro Glu Ile Asn Pro Tyr Leu Ala His Leu Ala Arg Met Tyr
                85                  90                  95

Asn Gly Tyr Ala Gly Gly Phe Glu Val Gln Val Val Leu Ala Gly Asn
            100                 105                 110

Ala Phe Thr Ala Gly Lys Ile Ile Phe Ala Ala Ile Pro Pro Asn Phe
        115                 120                 125

Pro Ile Asp Asn Leu Ser Ala Ala Gln Ile Thr Met Cys Pro His Val
    130                 135                 140

Ile Val Asp Val Arg Gln Leu Glu Pro Val Asn Leu Pro Met Pro Asp
145                 150                 155                 160

Val Arg Asn Asn Phe Phe His Tyr Asn Gln Gly Ser Asp Ser Arg Leu
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Ser Phe Asn Phe Leu Val Pro Pro Thr Val Glu Ser Lys Thr
    210                 215                 220

Lys Pro Phe Ser Leu Pro Ile Leu Thr Ile Ser Glu Met Ser Asn Ser
225                 230                 235                 240

Arg Phe Pro Val Pro Ile Asp Ser Leu His Thr Ser Pro Thr Glu Asn
                245                 250                 255

Ile Val Val Gln Cys Gln Asn Gly Arg Val Thr Leu Asp Gly Glu Leu
            260                 265                 270

Met Gly Thr Thr Gln Leu Leu Pro Ser Gln Ile Cys Ala Phe Arg Gly
        275                 280                 285

Thr Leu Thr Arg Ser Thr Ser Arg Ala Ser Asp Gln Ala Asp Thr Ala
    290                 295                 300

Thr Pro Arg Leu Phe Asn Tyr Tyr Trp His Ile Gln Leu Asp Asn Leu
305                 310                 315                 320

Asn Gly Thr Pro Tyr Asp Pro Ala Glu Asp Ile Pro Ala Pro Leu Gly
                325                 330                 335

Thr Pro Asp Phe Arg Gly Lys Val Phe Gly Val Ala Ser Gln Arg Asn
            340                 345                 350

Pro Asp Ala Thr Thr Arg Ala His Glu Ala Lys Ile Asp Thr Thr Ser
        355                 360                 365

Gly Arg Phe Thr Pro Lys Leu Gly Ser Leu Glu Ile Ser Thr Glu Ser
    370                 375                 380

Gly Asp Phe Asp Gln Asn Gln Pro Thr Arg Phe Thr Pro Val Gly Ile
385                 390                 395                 400

Gly Val Asp His Glu Pro Asp Phe Gln Gln Trp Ala Leu Pro Asp Tyr
                405                 410                 415

Ala Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445

Ser Gly Gly Arg Ser Asn Gly Ile Leu Asp Cys Leu Val Pro Gln Glu
    450                 455                 460

Trp Val Gln His Phe Tyr Gln Glu Ser Ala Pro Ser Gln Thr Gln Val
465                 470                 475                 480

Ala Leu Val Arg Tyr Val Asn Pro Asp Thr Gly Arg Val Leu Phe Glu
                485                 490                 495
```

Ala Lys Leu His Lys Leu Arg Phe Met Thr Ile Ala Lys Ser Gly Asp
500 505 510

Ser Pro Ile Thr Val Pro Pro Asn Gly Tyr Phe Arg Phe Glu Ser Trp
515 520 525

Val Asn Pro Phe Tyr Thr Leu Ala Pro Met Gly Thr Gly Asn Gly Arg
530 535 540

Arg Arg Ile Gln
545

<210> SEQ ID NO 47
<211> LENGTH: 1647
<212> TYPE: DNA
<213> ORGANISM: Artificial Sequence
<220> FEATURE:
<223> OTHER INFORMATION: Nucleic acid sequence of human codon optimized VP1_GII.3_Jing_E80S

<400> SEQUENCE: 47
atgaaaatgg cttccaacga tgcagcaccc tctaatgatg gcgctgccgg acttgtgccg 60
gagattagct ctgaggctat ggccctagaa ccagtagccg gggcagccat agctgcccca 120
ctgactggcc agcagaatat cattgacccc tggataatga acaatttcgt gcaggcaccg 180
gggggagaat tcacggtctc tcctcgaaac tcccccgggg aggttctctt gaatttgagc 240
ctgggccctg aaattaatcc ttatctggcc catctagccc gaatgtacaa cggctacgcc 300
ggaggtttcg aggtccaggt ggtgctcgct ggtaacgcct tcacagctgg caagatcatt 360
tttgcagcaa tccctccaaa cttccctatc gataatctta gtgccgccca gatcacaatg 420
tgccctcacg ttatcgtaga tgtgaggcag ctggaacctg tcaatctccc aatgcccgac 480
gtgcgcaaca acttctttca ctataaccag ggatctgact cccgccttcg ccttatcgct 540
atgctgtaca cccctctgag ggctaacaat tccggagatg acgttttcac tgtgagttgt 600
cgagtcctga cacgtccatc tcctgacttt agctttaatt tcctcgtgcc ccccacagtg 660
gaatccaaaa ctaagccatt ctctctgcca attcttacca ttagcgaaat gtcgaatagt 720
aggttcccgg tgcccataga ttcactgcat accagtccaa cagaaaacat cgtcgtacag 780
tgtcagaacg gacgcgtgac tctcgacggg gagcttatgg gcactaccca gctgctgccc 840
agccagatat gcgccttccg cggcacactg actagaagca cttcgcgtgc ttctgaccag 900
gcagatacag ctacaccaag gctgttcaat tattattggc atatacaact cgataatctg 960
aatggcactc cttatgaccc agccgaggac atccccgccc cacttggcac cccggacttt 1020
agagggaagg tctttggagt ggcttctcaa agaaatcccg acgcaaccac ccgggcccac 1080
gaggccaaaa tcgatactac atcagggcgt ttcaccccta agttaggcag tctggagata 1140
tctaccgaaa gtggagattt cgatcagaac cagccaaccc ggtttacccc cgtgggaatc 1200
ggggttgacc acgaaccgga tttccagcag tgggctctgc ctgattacgc aggccagttc 1260
acacataaca tgaatcttgc ccccgctgtg gcccccaact tcccgggaga acaacttctg 1320
tttttcagga gccaactgcc ttccagcggc ggccgatcta acgggatttt ggactgtctc 1380
gtgccccagg aatgggtgca gcatttttac caggagtccg cgccctccca gacgcaggtg 1440
gctctggtta gatatgtcaa tcccgacacc ggcagggtgc tatttgaggc aaagctgcac 1500
aagcttcgct ttatgactat cgctaagagc ggtgattcgc ctattacagt gccccccaac 1560
ggatacttca gatttgagag ttgggtgaac ccattctata ccctggcccc catgggtaca 1620
ggcaatggca gacggcggat ccagtaa 1647

<210> SEQ ID NO 48
<211> LENGTH: 548
<212> TYPE: PRT
<213> ORGANISM: Norovirus

<400> SEQUENCE: 48

Met Lys Met Ala Ser Asn Asp Ala Ala Pro Ser Asn Asp Gly Ala Ala
1 5 10 15

Gly Leu Val Pro Glu Ile Ser Ser Glu Ala Met Ala Leu Glu Pro Val
20 25 30

Ala Gly Ala Ala Ile Ala Ala Pro Leu Thr Gly Gln Gln Asn Ile Ile
35 40 45

Asp Pro Trp Ile Met Asn Asn Phe Val Gln Ala Pro Gly Gly Glu Phe
50 55 60

Thr Val Ser Pro Arg Asn Ser Pro Gly Glu Val Leu Leu Asn Leu Glu
65 70 75 80

Leu Gly Pro Glu Ile Asn Pro Tyr Leu Leu His Leu Ala Arg Met Tyr
85 90 95

Asn Gly Tyr Ala Gly Gly Phe Glu Val Gln Val Val Leu Ala Gly Asn
100 105 110

Ala Phe Thr Ala Gly Lys Ile Ile Phe Ala Ala Ile Pro Pro Asn Phe
115 120 125

Pro Ile Asp Asn Leu Ser Ala Ala Gln Ile Thr Met Cys Pro His Val
130 135 140

Ile Val Asp Val Arg Gln Leu Glu Pro Val Asn Leu Pro Met Pro Asp
145 150 155 160

Val Arg Asn Asn Phe Phe His Tyr Asn Gln Gly Ser Asp Ser Arg Leu
165 170 175

Arg Leu Ile Ala Met Leu Tyr Thr Pro Leu Arg Ala Asn Asn Ser Gly
180 185 190

Asp Asp Val Phe Thr Val Ser Cys Arg Val Leu Thr Arg Pro Ser Pro
195 200 205

Asp Phe Ser Phe Asn Phe Leu Val Pro Pro Thr Val Glu Ser Lys Thr
210 215 220

Lys Pro Phe Ser Leu Pro Ile Leu Thr Ile Ser Glu Met Ser Asn Ser
225 230 235 240

Arg Phe Pro Val Pro Ile Asp Ser Leu His Thr Ser Pro Thr Glu Asn
245 250 255

Ile Val Val Gln Cys Gln Asn Gly Arg Val Thr Leu Asp Gly Glu Leu
260 265 270

Met Gly Thr Thr Gln Leu Leu Pro Ser Gln Ile Cys Ala Phe Arg Gly
275 280 285

Thr Leu Thr Arg Ser Thr Ser Arg Ala Ser Asp Gln Ala Asp Thr Ala
290 295 300

Thr Pro Arg Leu Phe Asn Tyr Tyr Trp His Ile Gln Leu Asp Asn Leu
305 310 315 320

Asn Gly Thr Pro Tyr Asp Pro Ala Glu Asp Ile Pro Ala Pro Leu Gly
325 330 335

Thr Pro Asp Phe Arg Gly Lys Val Phe Gly Val Ala Ser Gln Arg Asn
340 345 350

Pro Asp Ala Thr Thr Arg Ala His Glu Ala Lys Ile Asp Thr Thr Ser
355 360 365

Gly Arg Phe Thr Pro Lys Leu Gly Ser Leu Glu Ile Ser Thr Glu Ser 370 375 380

Gly Asp Phe Asp Gln Asn Gln Pro Thr Arg Phe Thr Pro Val Gly Ile
385 390 395 400

Gly Val Asp His Glu Pro Asp Phe Gln Gln Trp Ala Leu Pro Asp Tyr
405 410 415

Ala Gly Gln Phe Thr His Asn Met Asn Leu Ala Pro Ala Val Ala Pro
420 425 430

Asn Phe Pro Gly Glu Gln Leu Leu Phe Phe Arg Ser Gln Leu Pro Ser
435 440 445

Ser Gly Gly Arg Ser Asn Gly Ile Leu Asp Cys Leu Val Pro Gln Glu
450 455 460

Trp Val Gln His Phe Tyr Gln Glu Ser Ala Pro Ser Gln Thr Gln Val
465 470 475 480

Ala Leu Val Arg Tyr Val Asn Pro Asp Thr Gly Arg Val Leu Phe Glu
485 490 495

Ala Lys Leu His Lys Leu Arg Phe Met Thr Ile Ala Lys Ser Gly Asp
500 505 510

Ser Pro Ile Thr Val Pro Pro Asn Gly Tyr Phe Arg Phe Glu Ser Trp
515 520 525

Val Asn Pro Phe Tyr Thr Leu Ala Pro Met Gly Thr Gly Asn Gly Arg
530 535 540

Arg Arg Ile Gln
545

<210> SEQ ID NO 49
<211> LENGTH: 1647
<212> TYPE: DNA
<213> ORGANISM: Artificial Sequence
<220> FEATURE:
<223> OTHER INFORMATION: Nucleic acid sequence of human codon optimized
VP1_GII.3_Jing_A90L

<400> SEQUENCE: 49
atgaaaatgg cttccaacga tgcagcaccc tctaatgatg gcgctgccgg acttgtgccg 60
gagattagct ctgaggctat ggccctagaa ccagtagccg gggcagccat agctgcccca 120
ctgactggcc agcagaatat cattgacccc tggataatga acaatttcgt gcaggcaccg 180
gggggagaat tcacggtctc tcctcgaaac tcccccgggg aggttctctt gaatttggaa 240
ctgggccctg aaattaatcc ttatctgctc catctagccc gaatgtacaa cggctacgcc 300
ggaggtttcg aggtccaggt ggtgctcgct ggtaacgcct tcacagctgg caagatcatt 360
tttgcagcaa tccctccaaa cttccctatc gataatctta gtgccgccca gatcacaatg 420
tgccctcacg ttatcgtaga tgtgaggcag ctggaacctg tcaatctccc aatgcccgac 480
gtgcgcaaca acttctttca ctataaccag ggatctgact cccgccttcg ccttatcgct 540
atgctgtaca cccctctgag ggctaacaat tccggagatg acgttttcac tgtgagttgt 600
cgagtcctga cacgtccatc tcctgacttt agctttaatt tcctcgtgcc ccccacagtg 660
gaatccaaaa ctaagccatt ctctctgcca attcttacca ttagcgaaat gtcgaatagt 720
aggttcccgg tgcccataga ttcactgcat accagtccaa cagaaaacat cgtcgtacag 780
tgtcagaacg gacgcgtgac tctcgacggg gagcttatgg gcactaccca gctgctgccc 840
agccagatat gcgccttccg cggcacactg actagaagca cttcgcgtgc ttctgaccag 900
gcagatacag ctacaccaag gctgttcaat tattattggc atatacaact cgataatctg 960
aatggcactc cttatgaccc agccgaggac atccccgccc cacttggcac cccggacttt 1020

```
agagggaagg tctttggagt ggcttctcaa agaaatcccg acgcaaccac ccgggcccac   1080

gaggccaaaa tcgatactac atcagggcgt ttcaccccta agttaggcag tctggagata   1140

tctaccgaaa gtggagattt cgatcagaac cagccaaccc ggtttacccc cgtgggaatc   1200

ggggttgacc acgaaccgga tttccagcag tgggctctgc ctgattacgc aggccagttc   1260

acacataaca tgaatcttgc cccgctgtg gcccccaact tcccgggaga acaacttctg   1320

tttttcagga gccaactgcc ttccagcggc ggccgatcta acgggatttt ggactgtctc   1380

gtgccccagg aatgggtgca gcatttttac caggagtccg cgccctccca gacgcaggtg   1440

gctctggtta gatatgtcaa tcccgacacc ggcagggtgc tatttgaggc aaagctgcac   1500

aagcttcgct ttatgactat cgctaagagc ggtgattcgc ctattacagt gccccccaac   1560

ggatacttca gatttgagag ttgggtgaac ccattctata ccctggcccc catgggtaca   1620

ggcaatggca gacggcggat ccagtaa                                        1647
```

<210> SEQ ID NO 50
<211> LENGTH: 548
<212> TYPE: PRT
<213> ORGANISM: Norovirus

<400> SEQUENCE: 50

```
Met Lys Met Ala Ser Asn Asp Ala Ala Pro Ser Asn Asp Gly Ala Ala
1               5                   10                  15

Gly Leu Val Pro Glu Ile Ser Ser Glu Ala Met Ala Leu Glu Pro Val
            20                  25                  30

Ala Gly Ala Ala Ile Ala Ala Pro Leu Thr Gly Gln Gln Asn Ile Ile
        35                  40                  45

Asp Pro Trp Ile Met Asn Asn Phe Val Gln Ala Pro Gly Gly Glu Phe
    50                  55                  60

Thr Val Ser Pro Arg Asn Ser Pro Gly Glu Val Leu Leu Asn Leu Ser
65                  70                  75                  80

Leu Gly Pro Glu Ile Asn Pro Tyr Leu Leu His Leu Ala Arg Met Tyr
                85                  90                  95

Asn Gly Tyr Ala Gly Gly Phe Glu Val Gln Val Val Leu Ala Gly Asn
            100                 105                 110

Ala Phe Thr Ala Gly Lys Ile Ile Phe Ala Ala Ile Pro Pro Asn Phe
        115                 120                 125

Pro Ile Asp Asn Leu Ser Ala Ala Gln Ile Thr Met Cys Pro His Val
    130                 135                 140

Ile Val Asp Val Arg Gln Leu Glu Pro Val Asn Leu Pro Met Pro Asp
145                 150                 155                 160

Val Arg Asn Asn Phe Phe His Tyr Asn Gln Gly Ser Asp Ser Arg Leu
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Ser Phe Asn Phe Leu Val Pro Pro Thr Val Glu Ser Lys Thr
    210                 215                 220

Lys Pro Phe Ser Leu Pro Ile Leu Thr Ile Ser Glu Met Ser Asn Ser
225                 230                 235                 240

Arg Phe Pro Val Pro Ile Asp Ser Leu His Thr Ser Pro Thr Glu Asn
                245                 250                 255
```

```
Ile Val Val Gln Cys Gln Asn Gly Arg Val Thr Leu Asp Gly Glu Leu
            260                 265                 270

Met Gly Thr Thr Gln Leu Leu Pro Ser Gln Ile Cys Ala Phe Arg Gly
        275                 280                 285

Thr Leu Thr Arg Ser Thr Ser Arg Ala Ser Asp Gln Ala Asp Thr Ala
    290                 295                 300

Thr Pro Arg Leu Phe Asn Tyr Tyr Trp His Ile Gln Leu Asp Asn Leu
305                 310                 315                 320

Asn Gly Thr Pro Tyr Asp Pro Ala Glu Asp Ile Pro Ala Pro Leu Gly
                325                 330                 335

Thr Pro Asp Phe Arg Gly Lys Val Phe Gly Val Ala Ser Gln Arg Asn
            340                 345                 350

Pro Asp Ala Thr Thr Arg Ala His Glu Ala Lys Ile Asp Thr Thr Ser
        355                 360                 365

Gly Arg Phe Thr Pro Lys Leu Gly Ser Leu Glu Ile Ser Thr Glu Ser
    370                 375                 380

Gly Asp Phe Asp Gln Asn Gln Pro Thr Arg Phe Thr Pro Val Gly Ile
385                 390                 395                 400

Gly Val Asp His Glu Pro Asp Phe Gln Gln Trp Ala Leu Pro Asp Tyr
                405                 410                 415

Ala Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445

Ser Gly Gly Arg Ser Asn Gly Ile Leu Asp Cys Leu Val Pro Gln Glu
    450                 455                 460

Trp Val Gln His Phe Tyr Gln Glu Ser Ala Pro Ser Gln Thr Gln Val
465                 470                 475                 480

Ala Leu Val Arg Tyr Val Asn Pro Asp Thr Gly Arg Val Leu Phe Glu
                485                 490                 495

Ala Lys Leu His Lys Leu Arg Phe Met Thr Ile Ala Lys Ser Gly Asp
            500                 505                 510

Ser Pro Ile Thr Val Pro Pro Asn Gly Tyr Phe Arg Phe Glu Ser Trp
        515                 520                 525

Val Asn Pro Phe Tyr Thr Leu Ala Pro Met Gly Thr Gly Asn Gly Arg
    530                 535                 540

Arg Arg Ile Gln
545
```

<210> SEQ ID NO 51
<211> LENGTH: 1647
<212> TYPE: DNA
<213> ORGANISM: Artificial Sequence
<220> FEATURE:
<223> OTHER INFORMATION: Nucleic acid sequence of human codon optimized VP1_GII.3_Jing_E80S+A90L

<400> SEQUENCE: 51

```
atgaaaatgg cttccaacga tgcagcaccc tctaatgatg gcgctgccgg acttgtgccg     60

gagattagct ctgaggctat ggccctagaa ccagtagccg gggcagccat agctgcccca    120

ctgactggcc agcagaatat cattgacccc tggataatga acaatttcgt gcaggcaccg    180

gggggagaat tcacggtctc tcctcgaaac tcccccgggg aggttctctt gaatttgagc    240

ctgggccctg aaattaatcc ttatctgctc catctagccc gaatgtacaa cggctacgcc    300

ggaggtttcg aggtccaggt ggtgctcgct ggtaacgcct tcacagctgg caagatcatt    360
```

```
tttgcagcaa tccctccaaa cttccctatc gataatctta gtgccgccca gatcacaatg    420
tgccctcacg ttatcgtaga tgtgaggcag ctggaacctg tcaatctccc aatgcccgac    480
gtgcgcaaca acttctttca ctataaccag ggatctgact cccgccttcg ccttatcgct    540
atgctgtaca cccctctgag ggctaacaat tccggagatg acgttttcac tgtgagttgt    600
cgagtcctga cacgtccatc tcctgacttt agctttaatt tcctcgtgcc ccccacagtg    660
gaatccaaaa ctaagccatt ctctctgcca attcttacca ttagcgaaat gtcgaatagt    720
aggttcccgg tgcccataga ttcactgcat accagtccaa cagaaaacat cgtcgtacag    780
tgtcagaacg gacgcgtgac tctcgacggg gagcttatgg gcactaccca gctgctgccc    840
agccagatat gcgccttccg cggcacactg actagaagca cttcgcgtgc ttctgaccag    900
gcagatacag ctacaccaag gctgttcaat tattattggc atatacaact cgataatctg    960
aatggcactc cttatgaccc agccgaggac atccccgccc cacttggcac cccggacttt   1020
agagggaagg tctttggagt ggcttctcaa agaaatcccg acgcaaccac ccgggcccac   1080
gaggccaaaa tcgatactac atcagggcgt ttcaccccta agttaggcag tctggagata   1140
tctaccgaaa gtggagattt cgatcagaac cagccaaccc ggtttacccc cgtgggaatc   1200
ggggttgacc acgaaccgga tttccagcag tgggctctgc ctgattacgc aggccagttc   1260
acacataaca tgaatcttgc ccccgctgtg gcccccaact tcccgggaga acaacttctg   1320
tttttcagga gccaactgcc ttccagcggc ggccgatcta acgggatttt ggactgtctc   1380
gtgccccagg aatgggtgca gcatttttac caggagtccg cgccctccca gacgcaggtg   1440
gctctggtta gatatgtcaa tcccgacacc ggcagggtgc tatttgaggc aaagctgcac   1500
aagcttcgct ttatgactat cgctaagagc ggtgattcgc ctattacagt gccccccaac   1560
ggatacttca gatttgagag ttgggtgaac ccattctata ccctggcccc catgggtaca   1620
ggcaatggca gacggcggat ccagtaa                                       1647
```

<210> SEQ ID NO 52
<211> LENGTH: 1623
<212> TYPE: DNA
<213> ORGANISM: Artificial Sequence
<220> FEATURE:
<223> OTHER INFORMATION: Nucleic acid sequence of human codon-optimized VP1 GII.4_Sydney_2012_K4LM89

<400> SEQUENCE: 52

```
atgaaaatgg cctcgagtga cgctaaccct agtgacggca gcgccgccaa tcttgtgcct     60
gaggttaata atgaggtgat ggccctggag cctgtggtgg gcgcagccat agcagcgccc    120
gtggccggtc agcagaatgt gattgacccg tggatacgca acaattttgt ccaagcccct    180
ggtggggagt tcaccgttag cccgagaaat gcgccaggag aaatcctgtg gtcggcccca    240
ttgggacccg atctgaaccc ctatttgtca catctcgctc ggatgtacaa cgggtatgcc    300
ggcggatttg aagtgcaggt gattctggct gggaacgcgt tcactgctgg caaagtgatc    360
tttgcagcgg tgcctcccaa cttccccact gaaggactgt ctccaagcca ggtcacaatg    420
tttccacaca tcgtggtgga cgtacggcag ctagagcctg tcctgattcc cctccctgat    480
gtacgcaata atttctacca ctacaatcaa tccaatgatc cgaccattaa actcatcgcg    540
atgttgtaca cccctctgcg cgctaacaat gctggagacg acgtattcac cgtgtcatgc    600
agagtgctca ccagaccttc accagacttt gactttatct tcttagtgcc ccccactgtt    660
gagagccgaa ccaagccctt tagtgtcccc gtactcacag tcgaggagat gacaaatagc    720
```

```
cgctttccaa tccccttga gaaactgttc acaggacctt cctcggcatt cgtggttcag      780

ccacagaacg gacgctgcac aactgacggc gtgctgctcg gaaccaccca gcttagccct      840

gttaatatct gtacgtttag aggcgacgta actcacataa ctggctcacg gaactatacc      900

atgaatctgg catcacagaa ttggaatgac tacgacccaa ccgaagagat tcccgcacct      960

cttggaaccc ccgactttgt gggaaaaata cagggcgtcc tgacacaaac caccagaacc     1020

gatggctcca cacggggaca caaggcaacc gtctacactg gctctgccga ttttgccccg     1080

aaactgggta gagtgcagtt tgagaccgac actgaccggg actttgaagc caatcagaat     1140

actaagttca cacctgtagg agtgattcag gacgggggca ccactcaccg gaacgagccg     1200

caacaatggg tcctgccctc ttatagcggg aggaatactc ataatgtgca tttggctcct     1260

gcagtggctc ccacgtttcc cggggaacaa ctgctctttt ttcgttcaac catgcctgga     1320

tgctccggat atcccaatat ggatctcgat tgcctgctcc cacaggaatg ggtgcagtat     1380

ttttatcaag aggccgcacc agcccaatcc gacgtcgcac ttctgcggtt cgtgaatcca     1440

gacacaggcc gcgtgttgtt tgagtgcaaa ttgcacaaat caggatacgt tacagtggct     1500

catactggac agcatgacct ggtgatccca cccaacggat attttaggtt cgactcctgg     1560

gtgaatcagt tttatacatt agcccccatg gggaatggga ctggcagacg cagggctgtc     1620

tga                                                                   1623
```

<210> SEQ ID NO 53
<211> LENGTH: 540
<212> TYPE: PRT
<213> ORGANISM: Norovirus

<400> SEQUENCE: 53

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Val Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205
```

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540

<210> SEQ ID NO 54
<211> LENGTH: 1623
<212> TYPE: DNA
<213> ORGANISM: Artificial Sequence
<220> FEATURE:
<223> OTHER INFORMATION: Nucleic acid sequence of human codon optimized
      VP1_GII.4_Syd12_A39V

<400> SEQUENCE: 54
atgaaaatgg cctcgagtga cgctaaccct agtgacggca gcgccgccaa tcttgtgcct      60
gaggttaata atgaggtgat ggccctggag cctgtggtgg gcgcagccat agcagtcccc     120

```
gtggccggtc agcagaatgt gattgacccg tggatacgca acaattttgt ccaagcccct    180

ggtggggagt tcaccgttag cccgagaaat gcgccaggag aaatcctgtg gtcggcccca    240

ttgggacccg atctgaaccc ctatttgtca catctcgctc ggatgtacaa cgggtatgcc    300

ggcggatttg aagtgcaggt gattctggct gggaacgcgt tcactgctgg caaagtgatc    360

tttgcagcgg tgcctcccaa cttccccact gaaggactgt ctccaagcca ggtcacaatg    420

tttccacaca tcgtggtgga cgtacggcag ctagagcctg tcctgattcc cctccctgat    480

gtacgcaata atttctacca ctacaatcaa tccaatgatc cgaccattaa actcatcgcg    540

atgttgtaca cccctctgcg cgctaacaat gctggagacg acgtattcac cgtgtcatgc    600

agagtgctca ccagaccttc accagacttt gactttatct tcttagtgcc ccccactgtt    660

gagagccgaa ccaagccctt tagtgtcccc gtactcacag tcgaggagat gacaaatagc    720

cgctttccaa tccccttga gaaactgttc acaggacctt cctcggcatt cgtggttcag     780

ccacagaacg gacgctgcac aactgacggc gtgctgctcg gaaccaccca gcttagccct    840

gttaatatct gtacgtttag aggcgacgta actcacataa ctggctcacg gaactatacc    900

atgaatctgg catcacagaa ttggaatgac tacgacccaa ccgaagagat tcccgcacct    960

cttggaaccc ccgactttgt gggaaaaata cagggcgtcc tgacacaaac caccagaacc   1020

gatggctcca cacggggaca caaggcaacc gtctacactg gctctgccga ttttgccccg   1080

aaactgggta gagtgcagtt tgagaccgac actgaccggg actttgaagc caatcagaat   1140

actaagttca cacctgtagg agtgattcag gacgggggca ccactcaccg gaacgagccg   1200

caacaatggg tcctgccctc ttatagcggg aggaatactc ataatgtgca tttggctcct   1260

gcagtggctc ccacgtttcc cggggaacaa ctgctctttt ttcgttcaac catgcctgga   1320

tgctccggat atcccaatat ggatctcgat tgcctgctcc cacaggaatg ggtgcagtat   1380

ttttatcaag aggccgcacc agcccaatcc gacgtcgcac ttctgcggtt cgtgaatcca   1440

gacacaggcc gcgtgttgtt tgagtgcaaa ttgcacaaat caggatacgt tacagtggct   1500

catactggac agcatgacct ggtgatccca cccaacggat attttaggtt cgactcctgg   1560

gtgaatcagt tttatacatt agcccccatg ggaatggga ctggcagacg cagggctgtc    1620

tga                                                                 1623
```

<210> SEQ ID NO 55
<211> LENGTH: 540
<212> TYPE: PRT
<213> ORGANISM: Norovirus

<400> SEQUENCE: 55

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Pro Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
```

-continued

```
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525
```

-continued

Pro Met Gly Asn Gly Thr Gly Arg Arg Arg Ala Val
    530                 535                 540

<210> SEQ ID NO 56
<211> LENGTH: 1623
<212> TYPE: DNA
<213> ORGANISM: Artificial Sequence
<220> FEATURE:
<223> OTHER INFORMATION: Nucleic acid sequence of human codon optimized VP1_GII.4_Syd12_V47P

<400> SEQUENCE: 56
atgaaaatgg cctcgagtga cgctaaccct agtgacggca gcgccgccaa tcttgtgcct 60
gaggttaata atgaggtgat ggccctggag cctgtggtgg gcgcagccat agcagcgccc 120
gtggccggtc agcagaatcc cattgacccg tggatacgca acaattttgt ccaagcccct 180
ggtggggagt tcaccgttag cccgagaaat gcgccaggag aaatcctgtg gtcggcccca 240
ttgggacccg atctgaaccc ctatttgtca catctcgctc ggatgtacaa cgggtatgcc 300
ggcggatttg aagtgcaggt gattctggct gggaacgcgt tcactgctgg caaagtgatc 360
tttgcagcgg tgcctcccaa cttccccact gaaggactgt ctccaagcca ggtcacaatg 420
tttccacaca tcgtggtgga cgtacggcag ctagagcctg tcctgattcc cctccctgat 480
gtacgcaata atttctacca ctacaatcaa tccaatgatc cgaccattaa actcatcgcg 540
atgttgtaca cccctctgcg cgctaacaat gctggagacg acgtattcac cgtgtcatgc 600
agagtgctca ccagaccttc accagacttt gactttatct tcttagtgcc ccccactgtt 660
gagagccgaa ccaagccctt tagtgtcccc gtactcacag tcgaggagat gacaaatagc 720
cgctttccaa tccccttga gaaactgttc acaggacctt cctcggcatt cgtggttcag 780
ccacagaacg gacgctgcac aactgacggc gtgctgctcg gaaccaccca gcttagccct 840
gttaatatct gtacgtttag aggcgacgta actcacataa ctggctcacg gaactatacc 900
atgaatctgg catcacagaa ttggaatgac tacgacccaa ccgaagagat tcccgcacct 960
cttggaaccc ccgactttgt gggaaaaata cagggcgtcc tgacacaaac caccagaacc 1020
gatggctcca cacggggaca caaggcaacc gtctacactg gctctgccga ttttgccccg 1080
aaactgggta gagtgcagtt tgagaccgac actgaccggg actttgaagc caatcagaat 1140
actaagttca cacctgtagg agtgattcag gacgggggca ccactcaccg gaacgagccg 1200
caacaatggg tcctgccctc ttatagcggg aggaatactc ataatgtgca tttggctcct 1260
gcagtggctc ccacgtttcc cggggaacaa ctgctctttt ttcgttcaac catgcctgga 1320
tgctccggat atcccaatat ggatctcgat tgcctgctcc cacaggaatg ggtgcagtat 1380
ttttatcaag aggccgcacc agcccaatcc gacgtcgcac ttctgcggtt cgtgaatcca 1440
gacacaggcc gcgtgttgtt tgagtgcaaa ttgcacaaat caggatacgt tacagtggct 1500
catactggac agcatgacct ggtgatccca cccaacggat attttaggtt cgactcctgg 1560
gtgaatcagt tttatacatt agcccccatg ggaatggga ctggcagacg cagggctgtc 1620
tga 1623

<210> SEQ ID NO 57
<211> LENGTH: 540
<212> TYPE: PRT
<213> ORGANISM: Norovirus

<400> SEQUENCE: 57

-continued

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Ile Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
```

```
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540


<210> SEQ ID NO 58
<211> LENGTH: 1623
<212> TYPE: DNA
<213> ORGANISM: Artificial Sequqence
<220> FEATURE:
<223> OTHER INFORMATION: Nucleic acid sequence of human codon optimized
      VP1_GII.4_Syd12_R53I

<400> SEQUENCE: 58

atgaaaatgg cctcgagtga cgctaaccct agtgacggca gcgccgccaa tcttgtgcct     60

gaggttaata atgaggtgat ggccctggag cctgtggtgg gcgcagccat agcagcgccc    120

gtggccggtc agcagaatgt gattgacccg tggataatca acaattttgt ccaagcccct    180

ggtggggagt tcaccgttag cccgagaaat gcgccaggag aaatcctgtg gtcggcccca    240

ttgggacccg atctgaaccc ctatttgtca catctcgctc ggatgtacaa cgggtatgcc    300

ggcggatttg aagtgcaggt gattctggct gggaacgcgt tcactgctgg caaagtgatc    360

tttgcagcgg tgcctcccaa cttccccact gaaggactgt ctccaagcca ggtcacaatg    420

tttccacaca tcgtggtgga cgtacggcag ctagagcctg tcctgattcc cctccctgat    480

gtacgcaata atttctacca ctacaatcaa tccaatgatc cgaccattaa actcatcgcg    540

atgttgtaca cccctctgcg cgctaacaat gctggagacg acgtattcac cgtgtcatgc    600

agagtgctca ccagaccttc accagacttt gactttatct tcttagtgcc ccccactgtt    660

gagagccgaa ccaagccctt tagtgtcccc gtactcacag tcgaggagat gacaaatagc    720

cgctttccaa tccccttga gaaactgttc acaggacctt cctcggcatt cgtggttcag    780

ccacagaacg gacgctgcac aactgacggc gtgctgctcg gaaccaccca gcttagccct    840

gttaatatct gtacgtttag aggcgacgta actcacataa ctggctcacg gaactatacc    900

atgaatctgg catcacagaa ttggaatgac tacgacccaa ccgaagagat tcccgcacct    960

cttggaaccc ccgactttgt gggaaaaata cagggcgtcc tgacacaaac caccagaacc   1020

gatggctcca cacggggaca caaggcaacc gtctacactg gctctgccga ttttgccccg   1080

aaactgggta gagtgcagtt tgagaccgac actgaccggg actttgaagc caatcagaat   1140

actaagttca cacctgtagg agtgattcag gacgggggca ccactcaccg gaacgagccg   1200

caacaatggg tcctgccctc ttatagcggg aggaatactc ataatgtgca tttggctcct   1260

gcagtggctc ccacgtttcc cggggaacaa ctgctctttt ttcgttcaac catgcctgga   1320

tgctccggat atcccaatat ggatctcgat tgcctgctcc cacaggaatg ggtgcagtat   1380
```

```
ttttatcaag aggccgcacc agcccaatcc gacgtcgcac ttctgcggtt cgtgaatcca   1440

gacacaggcc gcgtgttgtt tgagtgcaaa ttgcacaaat caggatacgt tacagtggct   1500

catactggac agcatgacct ggtgatccca cccaacggat attttaggtt cgactcctgg   1560

gtgaatcagt tttatacatt agcccccatg ggaatggga ctggcagacg cagggctgtc   1620

tga                                                                  1623


<210> SEQ ID NO 59
<211> LENGTH: 540
<212> TYPE: PRT
<213> ORGANISM: Norovirus

<400> SEQUENCE: 59

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320
```

-continued

```
Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 60
<211> LENGTH: 1623
<212> TYPE: DNA
<213> ORGANISM: Artificial Sequence
<220> FEATURE:
<223> OTHER INFORMATION: Nucleic acid sequence of human codon optimized VP1_GII.4_Syd12_P80S

<400> SEQUENCE: 60

```
atgaaaatgg cctcgagtga cgctaaccct agtgacggca gcgccgccaa tcttgtgcct      60

gaggttaata atgaggtgat ggccctggag cctgtggtgg gcgcagccat agcagcgccc     120

gtggccggtc agcagaatgt gattgacccg tggatacgca acaattttgt ccaagcccct     180

ggtggggagt tcaccgttag cccgagaaat gcgccaggag aaatcctgtg gtcggccagc     240

ttgggacccg atctgaaccc ctatttgtca catctcgctc ggatgtacaa cgggtatgcc     300

ggcggatttg aagtgcaggt gattctggct gggaacgcgt tcactgctgg caaagtgatc     360

tttgcagcgg tgcctcccaa cttccccact gaaggactgt ctccaagcca ggtcacaatg     420

tttccacaca tcgtggtgga cgtacggcag ctagagcctg tcctgattcc cctccctgat     480

gtacgcaata atttctacca ctacaatcaa tccaatgatc cgaccattaa actcatcgcg     540

atgttgtaca cccctctgcg cgctaacaat gctggagacg acgtattcac cgtgtcatgc     600

agagtgctca ccagaccttc accagacttt gactttatct tcttagtgcc ccccactgtt     660

gagagccgaa ccaagccctt tagtgtcccc gtactcacag tcgaggagat gacaaatagc     720

cgctttccaa tcccccttga gaaactgttc acaggacctt cctcggcatt cgtggttcag     780
```

```
ccacagaacg gacgctgcac aactgacggc gtgctgctcg gaaccaccca gcttagccct    840

gttaatatct gtacgtttag aggcgacgta actcacataa ctggctcacg gaactatacc    900

atgaatctgg catcacagaa ttggaatgac tacgacccaa ccgaagagat tcccgcacct    960

cttggaaccc ccgactttgt gggaaaaata cagggcgtcc tgacacaaac caccagaacc   1020

gatggctcca cacggggaca caaggcaacc gtctacactg gctctgccga ttttgccccg   1080

aaactgggta gagtgcagtt tgagaccgac actgaccggg actttgaagc caatcagaat   1140

actaagttca cacctgtagg agtgattcag gacgggggca ccactcaccg gaacgagccg   1200

caacaatggg tcctgccctc ttatagcggg aggaatactc ataatgtgca tttggctcct   1260

gcagtggctc ccacgtttcc cggggaacaa ctgctctttt ttcgttcaac catgcctgga   1320

tgctccggat atcccaatat ggatctcgat tgcctgctcc cacaggaatg ggtgcagtat   1380

ttttatcaag aggccgcacc agcccaatcc gacgtcgcac ttctgcggtt cgtgaatcca   1440

gacacaggcc gcgtgttgtt tgagtgcaaa ttgcacaaat caggatacgt tacagtggct   1500

catactggac agcatgacct ggtgatccca cccaacggat attttaggtt cgactcctgg   1560

gtgaatcagt tttatacatt agcccccatg gggaatggga ctggcagacg cagggctgtc   1620

tga                                                                1623
```

<210> SEQ ID NO 61
<211> LENGTH: 540
<212> TYPE: PRT
<213> ORGANISM: Norovirus

<400> SEQUENCE: 61

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Leu His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220
```

-continued

Lys Pro Phe Ser Val Pro Val Leu Thr Val Glu Glu Met Thr Asn Ser
225 230 235 240

Arg Phe Pro Ile Pro Leu Glu Lys Leu Phe Thr Gly Pro Ser Ser Ala
245 250 255

Phe Val Val Gln Pro Gln Asn Gly Arg Cys Thr Thr Asp Gly Val Leu
260 265 270

Leu Gly Thr Thr Gln Leu Ser Pro Val Asn Ile Cys Thr Phe Arg Gly
275 280 285

Asp Val Thr His Ile Thr Gly Ser Arg Asn Tyr Thr Met Asn Leu Ala
290 295 300

Ser Gln Asn Trp Asn Asp Tyr Asp Pro Thr Glu Glu Ile Pro Ala Pro
305 310 315 320

Leu Gly Thr Pro Asp Phe Val Gly Lys Ile Gln Gly Val Leu Thr Gln
325 330 335

Thr Thr Arg Thr Asp Gly Ser Thr Arg Gly His Lys Ala Thr Val Tyr
340 345 350

Thr Gly Ser Ala Asp Phe Ala Pro Lys Leu Gly Arg Val Gln Phe Glu
355 360 365

Thr Asp Thr Asp Arg Asp Phe Glu Ala Asn Gln Asn Thr Lys Phe Thr
370 375 380

Pro Val Gly Val Ile Gln Asp Gly Gly Thr Thr His Arg Asn Glu Pro
385 390 395 400

Gln Gln Trp Val Leu Pro Ser Tyr Ser Gly Arg Asn Thr His Asn Val
405 410 415

His Leu Ala Pro Ala Val Ala Pro Thr Phe Pro Gly Glu Gln Leu Leu
420 425 430

Phe Phe Arg Ser Thr Met Pro Gly Cys Ser Gly Tyr Pro Asn Met Asp
435 440 445

Leu Asp Cys Leu Leu Pro Gln Glu Trp Val Gln Tyr Phe Tyr Gln Glu
450 455 460

Ala Ala Pro Ala Gln Ser Asp Val Ala Leu Leu Arg Phe Val Asn Pro
465 470 475 480

Asp Thr Gly Arg Val Leu Phe Glu Cys Lys Leu His Lys Ser Gly Tyr
485 490 495

Val Thr Val Ala His Thr Gly Gln His Asp Leu Val Ile Pro Pro Asn
500 505 510

Gly Tyr Phe Arg Phe Asp Ser Trp Val Asn Gln Phe Tyr Thr Leu Ala
515 520 525

Pro Met Gly Asn Gly Thr Gly Arg Arg Arg Ala Val
530 535 540

<210> SEQ ID NO 62
<211> LENGTH: 1623
<212> TYPE: DNA
<213> ORGANISM: Artificial Sequence
<220> FEATURE:
<223> OTHER INFORMATION: Nucleic acid sequence of human codon optimized
VP1_GII.4_Syd12_S90L

<400> SEQUENCE: 62
atgaaaatgg cctcgagtga cgctaaccct agtgacggca gcgccgccaa tcttgtgcct 60
gaggttaata atgaggtgat ggccctggag cctgtggtgg gcgcagccat agcagcgccc 120
gtggccggtc agcagaatgt gattgacccg tggatacgca acaattttgt ccaagcccct 180
ggtggggagt tcaccgttag cccgagaaat gcgccaggag aaatcctgtg gtcggcccca 240

```
ttgggacccg atctgaaccc ctatttgctg catctcgctc ggatgtacaa cgggtatgcc    300

ggcggatttg aagtgcaggt gattctggct gggaacgcgt tcactgctgg caaagtgatc    360

tttgcagcgg tgcctcccaa cttccccact gaaggactgt ctccaagcca ggtcacaatg    420

tttccacaca tcgtggtgga cgtacggcag ctagagcctg tcctgattcc cctccctgat    480

gtacgcaata atttctacca ctacaatcaa tccaatgatc cgaccattaa actcatcgcg    540

atgttgtaca cccctctgcg cgctaacaat gctggagacg acgtattcac cgtgtcatgc    600

agagtgctca ccagaccttc accagacttt gactttatct tcttagtgcc ccccactgtt    660

gagagccgaa ccaagccctt tagtgtcccc gtactcacag tcgaggagat gacaaatagc    720

cgctttccaa tcccccttga gaaactgttc acaggacctt cctcggcatt cgtggttcag    780

ccacagaacg gacgctgcac aactgacggc gtgctgctcg gaaccaccca gcttagccct    840

gttaatatct gtacgtttag aggcgacgta actcacataa ctggctcacg gaactatacc    900

atgaatctgg catcacagaa ttggaatgac tacgacccaa ccgaagagat tcccgcacct    960

cttggaaccc ccgactttgt gggaaaaata cagggcgtcc tgacacaaac caccagaacc   1020

gatggctcca cacggggaca caaggcaacc gtctacactg gctctgccga ttttgccccg   1080

aaactgggta gagtgcagtt tgagaccgac actgaccggg actttgaagc caatcagaat   1140

actaagttca cacctgtagg agtgattcag gacgggggca ccactcaccg gaacgagccg   1200

caacaatggg tcctgccctc ttatagcggg aggaatactc ataatgtgca tttggctcct   1260

gcagtggctc ccacgtttcc cggggaacaa ctgctctttt ttcgttcaac catgcctgga   1320

tgctccggat atcccaatat ggatctcgat tgcctgctcc cacaggaatg ggtgcagtat   1380

ttttatcaag aggccgcacc agcccaatcc gacgtcgcac ttctgcggtt cgtgaatcca   1440

gacacaggcc gcgtgttgtt tgagtgcaaa ttgcacaaat caggatacgt tacagtggct   1500

catactggac agcatgacct ggtgatccca cccaacggat attttaggtt cgactcctgg   1560

gtgaatcagt tttatacatt agcccccatg ggaatggga ctggcagacg cagggctgtc   1620

tga                                                                 1623
```

<210> SEQ ID NO 63
<211> LENGTH: 532
<212> TYPE: PRT
<213> ORGANISM: Norovirus

<400> SEQUENCE: 63

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Gly Gln Gln Asn Val Ile Asp Pro Trp Ile Arg Asn Asn Phe
        35                  40                  45

Val Gln Ala Pro Gly Gly Glu Phe Thr Val Ser Pro Arg Asn Ala Pro
    50                  55                  60

Gly Glu Ile Leu Trp Ser Ala Pro Leu Gly Pro Asp Leu Asn Pro Tyr
65                  70                  75                  80

Leu Ser His Leu Ala Arg Met Tyr Asn Gly Tyr Ala Gly Gly Phe Glu
                85                  90                  95

Val Gln Val Ile Leu Ala Gly Asn Ala Phe Thr Ala Gly Lys Val Ile
            100                 105                 110

Phe Ala Ala Val Pro Pro Asn Phe Pro Thr Glu Gly Leu Ser Pro Ser
```

```
        115                 120                 125

Gln Val Thr Met Phe Pro His Ile Val Val Asp Val Arg Gln Leu Glu
    130                 135                 140

Pro Val Leu Ile Pro Leu Pro Asp Val Arg Asn Asn Phe Tyr His Tyr
145                 150                 155                 160

Asn Gln Ser Asn Asp Pro Thr Ile Lys Leu Ile Ala Met Leu Tyr Thr
                165                 170                 175

Pro Leu Arg Ala Asn Asn Ala Gly Asp Asp Val Phe Thr Val Ser Cys
            180                 185                 190

Arg Val Leu Thr Arg Pro Ser Pro Asp Phe Asp Phe Ile Phe Leu Val
        195                 200                 205

Pro Pro Thr Val Glu Ser Arg Thr Lys Pro Phe Ser Val Pro Val Leu
    210                 215                 220

Thr Val Glu Glu Met Thr Asn Ser Arg Phe Pro Ile Pro Leu Glu Lys
225                 230                 235                 240

Leu Phe Thr Gly Pro Ser Ser Ala Phe Val Val Gln Pro Gln Asn Gly
                245                 250                 255

Arg Cys Thr Thr Asp Gly Val Leu Leu Gly Thr Thr Gln Leu Ser Pro
            260                 265                 270

Val Asn Ile Cys Thr Phe Arg Gly Asp Val Thr His Ile Thr Gly Ser
        275                 280                 285

Arg Asn Tyr Thr Met Asn Leu Ala Ser Gln Asn Trp Asn Asp Tyr Asp
    290                 295                 300

Pro Thr Glu Glu Ile Pro Ala Pro Leu Gly Thr Pro Asp Phe Val Gly
305                 310                 315                 320

Lys Ile Gln Gly Val Leu Thr Gln Thr Thr Arg Thr Asp Gly Ser Thr
                325                 330                 335

Arg Gly His Lys Ala Thr Val Tyr Thr Gly Ser Ala Asp Phe Ala Pro
            340                 345                 350

Lys Leu Gly Arg Val Gln Phe Glu Thr Asp Thr Asp Arg Asp Phe Glu
        355                 360                 365

Ala Asn Gln Asn Thr Lys Phe Thr Pro Val Gly Val Ile Gln Asp Gly
    370                 375                 380

Gly Thr Thr His Arg Asn Glu Pro Gln Gln Trp Val Leu Pro Ser Tyr
385                 390                 395                 400

Ser Gly Arg Asn Thr His Asn Val His Leu Ala Pro Ala Val Ala Pro
                405                 410                 415

Thr Phe Pro Gly Glu Gln Leu Leu Phe Phe Arg Ser Thr Met Pro Gly
            420                 425                 430

Cys Ser Gly Tyr Pro Asn Met Asp Leu Asp Cys Leu Leu Pro Gln Glu
        435                 440                 445

Trp Val Gln Tyr Phe Tyr Gln Glu Ala Ala Pro Ala Gln Ser Asp Val
    450                 455                 460

Ala Leu Leu Arg Phe Val Asn Pro Asp Thr Gly Arg Val Leu Phe Glu
465                 470                 475                 480

Cys Lys Leu His Lys Ser Gly Tyr Val Thr Val Ala His Thr Gly Gln
                485                 490                 495

His Asp Leu Val Ile Pro Pro Asn Gly Tyr Phe Arg Phe Asp Ser Trp
            500                 505                 510

Val Asn Gln Phe Tyr Thr Leu Ala Pro Met Gly Asn Gly Thr Gly Arg
        515                 520                 525

Arg Arg Ala Val
    530
```

<210> SEQ ID NO 64
<211> LENGTH: 1599
<212> TYPE: DNA
<213> ORGANISM: Artificial Sequence
<220> FEATURE:
<223> OTHER INFORMATION: Nucleic acid sequence of human codon optimized
VP1_GII.4_Syd12_delta 35-42

<400> SEQUENCE: 64

```
atgaaaatgg cctcgagtga cgctaaccct agtgacggca gcgccgccaa tcttgtgcct     60

gaggttaata atgaggtgat ggccctggag cctgtggtgg gcggtcagca gaatgtgatt    120

gacccgtgga tacgcaacaa ttttgtccaa gcccctggtg gggagttcac cgttagcccg    180

agaaatgcgc caggagaaat cctgtggtcg gccccattgg gacccgatct gaacccctat    240

ttgtcacatc tcgctcggat gtacaacggg tatgccggcg gatttgaagt gcaggtgatt    300

ctggctggga acgcgttcac tgctggcaaa gtgatctttg cagcggtgcc tcccaacttc    360

cccactgaag gactgtctcc aagccaggtc acaatgtttc cacacatcgt ggtggacgta    420

cggcagctag agcctgtcct gattcccctc cctgatgtac gcaataattt ctaccactac    480

aatcaatcca atgatccgac cattaaactc atcgcgatgt tgtacacccc tctgcgcgct    540

aacaatgctg gagacgacgt attcaccgtg tcatgcagag tgctcaccag accttcacca    600

gactttgact ttatcttctt agtgccccc actgttgaga gccgaaccaa gccctttagt    660

gtccccgtac tcacagtcga ggagatgaca aatagccgct ttccaatccc ccttgagaaa    720

ctgttcacag gaccttcctc ggcattcgtg gttcagccac agaacggacg ctgcacaact    780

gacggcgtgc tgctcggaac cacccagctt agccctgtta atatctgtac gtttagaggc    840

gacgtaactc acataactgg ctcacggaac tataccatga atctggcatc acagaattgg    900

aatgactacg acccaaccga agagattccc gcacctcttg gaacccccga ctttgtggga    960

aaaatacagg gcgtcctgac acaaaccacc agaaccgatg gctccacacg gggacacaag   1020

gcaaccgtct acactggctc tgccgatttt gccccgaaac tgggtagagt gcagtttgag   1080

accgacactg accgggactt tgaagccaat cagaatacta agttcacacc tgtaggagtg   1140

attcaggacg ggggcaccac tcaccggaac gagccgcaac aatgggtcct gccctcttat   1200

agcgggagga atactcataa tgtgcatttg gctcctgcag tggctcccac gtttcccggg   1260

gaacaactgc tctttttcg ttcaaccatg cctggatgct ccggatatcc caatatggat   1320

ctcgattgcc tgctcccaca ggaatgggtg cagtattttt atcaagaggc cgcaccagcc   1380

caatccgacg tcgcacttct gcggttcgtg aatccagaca caggccgcgt gttgtttgag   1440

tgcaaattgc acaaatcagg atacgttaca gtggctcata ctggacagca tgacctggtg   1500

atcccaccca acggatattt taggttcgac tcctgggtga atcagtttta tacattagcc   1560

cccatgggga atgggactgg cagacgcagg gctgtctga                          1599
```

<210> SEQ ID NO 65
<211> LENGTH: 540
<212> TYPE: PRT
<213> ORGANISM: Norovirus

<400> SEQUENCE: 65

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30
```

Val Gly Ser Ser Thr Ala Val Ala Thr Ala Gly Gln Gln Asn Val Ile
35 40 45

Asp Pro Trp Ile Arg Asn Asn Phe Val Gln Ala Pro Gly Gly Glu Phe
50 55 60

Thr Val Ser Pro Arg Asn Ala Pro Gly Glu Ile Leu Trp Ser Ala Pro
65 70 75 80

Leu Gly Pro Asp Leu Asn Pro Tyr Leu Ser His Leu Ala Arg Met Tyr
85 90 95

Asn Gly Tyr Ala Gly Gly Phe Glu Val Gln Val Ile Leu Ala Gly Asn
100 105 110

Ala Phe Thr Ala Gly Lys Val Ile Phe Ala Ala Val Pro Pro Asn Phe
115 120 125

Pro Thr Glu Gly Leu Ser Pro Ser Gln Val Thr Met Phe Pro His Ile
130 135 140

Val Val Asp Val Arg Gln Leu Glu Pro Val Leu Ile Pro Leu Pro Asp
145 150 155 160

Val Arg Asn Asn Phe Tyr His Tyr Asn Gln Ser Asn Asp Pro Thr Ile
165 170 175

Lys Leu Ile Ala Met Leu Tyr Thr Pro Leu Arg Ala Asn Asn Ala Gly
180 185 190

Asp Asp Val Phe Thr Val Ser Cys Arg Val Leu Thr Arg Pro Ser Pro
195 200 205

Asp Phe Asp Phe Ile Phe Leu Val Pro Pro Thr Val Glu Ser Arg Thr
210 215 220

Lys Pro Phe Ser Val Pro Val Leu Thr Val Glu Glu Met Thr Asn Ser
225 230 235 240

Arg Phe Pro Ile Pro Leu Glu Lys Leu Phe Thr Gly Pro Ser Ser Ala
245 250 255

Phe Val Val Gln Pro Gln Asn Gly Arg Cys Thr Thr Asp Gly Val Leu
260 265 270

Leu Gly Thr Thr Gln Leu Ser Pro Val Asn Ile Cys Thr Phe Arg Gly
275 280 285

Asp Val Thr His Ile Thr Gly Ser Arg Asn Tyr Thr Met Asn Leu Ala
290 295 300

Ser Gln Asn Trp Asn Asp Tyr Asp Pro Thr Glu Glu Ile Pro Ala Pro
305 310 315 320

Leu Gly Thr Pro Asp Phe Val Gly Lys Ile Gln Gly Val Leu Thr Gln
325 330 335

Thr Thr Arg Thr Asp Gly Ser Thr Arg Gly His Lys Ala Thr Val Tyr
340 345 350

Thr Gly Ser Ala Asp Phe Ala Pro Lys Leu Gly Arg Val Gln Phe Glu
355 360 365

Thr Asp Thr Asp Arg Asp Phe Glu Ala Asn Gln Asn Thr Lys Phe Thr
370 375 380

Pro Val Gly Val Ile Gln Asp Gly Gly Thr Thr His Arg Asn Glu Pro
385 390 395 400

Gln Gln Trp Val Leu Pro Ser Tyr Ser Gly Arg Asn Thr His Asn Val
405 410 415

His Leu Ala Pro Ala Val Ala Pro Thr Phe Pro Gly Glu Gln Leu Leu
420 425 430

Phe Phe Arg Ser Thr Met Pro Gly Cys Ser Gly Tyr Pro Asn Met Asp
435 440 445

```
Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540


<210> SEQ ID NO 66
<211> LENGTH: 1623
<212> TYPE: DNA
<213> ORGANISM: Artificial Sequence
<220> FEATURE:
<223> OTHER INFORMATION: Nucleic acid sequence of human codon optimized
      VP1_GII.4_Syd12_SSTAVATA

<400> SEQUENCE: 66

atgaaaatgg cctcgagtga cgctaaccct agtgacggca gcgccgccaa tcttgtgcct      60

gaggttaata atgaggtgat ggccctggag cctgtggtgg gcagctccac cgccgtcgct     120

acagccggtc agcagaatgt gattgacccg tggatacgca acaattttgt ccaagcccct     180

ggtggggagt tcaccgttag cccgagaaat gcgccaggag aaatcctgtg gtcggcccca     240

ttgggacccg atctgaaccc ctatttgtca catctcgctc ggatgtacaa cgggtatgcc     300

ggcggatttg aagtgcaggt gattctggct gggaacgcgt tcactgctgg caaagtgatc     360

tttgcagcgg tgcctcccaa cttccccact gaaggactgt ctccaagcca ggtcacaatg     420

tttccacaca tcgtggtgga cgtacggcag ctagagcctg tcctgattcc cctccctgat     480

gtacgcaata atttctacca ctacaatcaa tccaatgatc cgaccattaa actcatcgcg     540

atgttgtaca cccctctgcg cgctaacaat gctggagacg acgtattcac cgtgtcatgc     600

agagtgctca ccagaccttc accagacttt gactttatct tcttagtgcc ccccactgtt     660

gagagccgaa ccaagccctt tagtgtcccc gtactcacag tcgaggagat gacaaatagc     720

cgctttccaa tccccttga gaaactgttc acaggacctt cctcggcatt cgtggttcag     780

ccacagaacg gacgctgcac aactgacggc gtgctgctcg gaaccaccca gcttagccct     840

gttaatatct gtacgtttag aggcgacgta actcacataa ctggctcacg gaactatacc     900

atgaatctgg catcacagaa ttggaatgac tacgacccaa ccgaagagat tcccgcacct     960

cttggaaccc ccgactttgt gggaaaaata cagggcgtcc tgacacaaac caccagaacc    1020

gatggctcca cacggggaca caaggcaacc gtctacactg gctctgccga ttttgccccg    1080

aaactgggta gagtgcagtt tgagaccgac actgaccggg actttgaagc caatcagaat    1140

actaagttca cacctgtagg agtgattcag gacgggggca ccactcaccg gaacgagccg    1200

caacaatggg tcctgccctc ttatagcggg aggaatactc ataatgtgca tttggctcct    1260

gcagtggctc ccacgtttcc cggggaacaa ctgctctttt ttcgttcaac catgcctgga    1320

tgctccggat atcccaatat ggatctcgat tgcctgctcc cacaggaatg ggtgcagtat    1380

ttttatcaag aggccgcacc agcccaatcc gacgtcgcac ttctgcggtt cgtgaatcca    1440

gacacaggcc gcgtgttgtt tgagtgcaaa ttgcacaaat caggatacgt tacagtggct    1500
```

catactggac agcatgacct ggtgatccca cccaacggat attttaggtt cgactcctgg 1560
gtgaatcagt tttatacatt agcccccatg gggaatggga ctggcagacg cagggctgtc 1620
tga 1623

<210> SEQ ID NO 67
<211> LENGTH: 540
<212> TYPE: PRT
<213> ORGANISM: Norovirus

<400> SEQUENCE: 67

Met Lys Met Ala Ser Ser Asp Ala Asn Pro Ser Asp Gly Ser Ala Ala
1 5 10 15

Asn Leu Val Pro Glu Val Asn Asn Glu Val Met Ala Leu Glu Pro Val
20 25 30

Val Gly Ala Ala Ile Ala Val Pro Val Ala Gly Gln Gln Asn Val Ile
35 40 45

Asp Pro Trp Ile Arg Asn Asn Phe Val Gln Ala Pro Gly Gly Glu Phe
50 55 60

Thr Val Ser Pro Arg Asn Ala Pro Gly Glu Ile Leu Trp Ser Ala Ser
65 70 75 80

Leu Gly Pro Asp Leu Asn Pro Tyr Leu Ser His Leu Ala Arg Met Tyr
85 90 95

Asn Gly Tyr Ala Gly Gly Phe Glu Val Gln Val Ile Leu Ala Gly Asn
100 105 110

Ala Phe Thr Ala Gly Lys Val Ile Phe Ala Ala Val Pro Pro Asn Phe
115 120 125

Pro Thr Glu Gly Leu Ser Pro Ser Gln Val Thr Met Phe Pro His Ile
130 135 140

Val Val Asp Val Arg Gln Leu Glu Pro Val Leu Ile Pro Leu Pro Asp
145 150 155 160

Val Arg Asn Asn Phe Tyr His Tyr Asn Gln Ser Asn Asp Pro Thr Ile
165 170 175

Lys Leu Ile Ala Met Leu Tyr Thr Pro Leu Arg Ala Asn Asn Ala Gly
180 185 190

Asp Asp Val Phe Thr Val Ser Cys Arg Val Leu Thr Arg Pro Ser Pro
195 200 205

Asp Phe Asp Phe Ile Phe Leu Val Pro Pro Thr Val Glu Ser Arg Thr
210 215 220

Lys Pro Phe Ser Val Pro Val Leu Thr Val Glu Glu Met Thr Asn Ser
225 230 235 240

Arg Phe Pro Ile Pro Leu Glu Lys Leu Phe Thr Gly Pro Ser Ser Ala
245 250 255

Phe Val Val Gln Pro Gln Asn Gly Arg Cys Thr Thr Asp Gly Val Leu
260 265 270

Leu Gly Thr Thr Gln Leu Ser Pro Val Asn Ile Cys Thr Phe Arg Gly
275 280 285

Asp Val Thr His Ile Thr Gly Ser Arg Asn Tyr Thr Met Asn Leu Ala
290 295 300

Ser Gln Asn Trp Asn Asp Tyr Asp Pro Thr Glu Glu Ile Pro Ala Pro
305 310 315 320

Leu Gly Thr Pro Asp Phe Val Gly Lys Ile Gln Gly Val Leu Thr Gln
325 330 335

Thr Thr Arg Thr Asp Gly Ser Thr Arg Gly His Lys Ala Thr Val Tyr
340 345 350

```
Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 68
<211> LENGTH: 1623
<212> TYPE: DNA
<213> ORGANISM: Artificial Sequence
<220> FEATURE:
<223> OTHER INFORMATION: Nucleic acid sequence of human codon optimized VP1_GII.4_Syd12_P80S plus sign A39V

<400> SEQUENCE: 68

```
atgaaaatgg cctcgagtga cgctaaccct agtgacggca gcgccgccaa tcttgtgcct      60

gaggttaata atgaggtgat ggccctggag cctgtggtgg gcgcagccat agcagtcccc     120

gtggccggtc agcagaatgt gattgacccg tggatacgca acaattttgt ccaagcccct     180

ggtggggagt tcaccgttag cccgagaaat gcgccaggag aaatcctgtg gtcggccagc     240

ttgggacccg atctgaaccc ctatttgtca catctcgctc ggatgtacaa cgggtatgcc     300

ggcggatttg aagtgcaggt gattctggct gggaacgcgt tcactgctgg caaagtgatc     360

tttgcagcgg tgcctcccaa cttccccact gaaggactgt ctccaagcca ggtcacaatg     420

tttccacaca tcgtggtgga cgtacggcag ctagagcctg tcctgattcc cctccctgat     480

gtacgcaata atttctacca ctacaatcaa tccaatgatc cgaccattaa actcatcgcg     540

atgttgtaca cccctctgcg cgctaacaat gctggagacg acgtattcac cgtgtcatgc     600

agagtgctca ccagaccttc accagacttt gactttatct tcttagtgcc ccccactgtt     660

gagagccgaa ccaagccctt tagtgtcccc gtactcacag tcgaggagat gacaaatagc     720

cgctttccaa tccccttga gaaactgttc acaggacctt cctcggcatt cgtggttcag     780

ccacagaacg gacgctgcac aactgacggc gtgctgctcg gaaccaccca gcttagccct     840

gttaatatct gtacgtttag aggcgacgta actcacataa ctggctcacg gaactatacc     900

atgaatctgg catcacagaa ttggaatgac tacgacccaa ccgaagagat tcccgcacct     960
```

```
cttggaaccc ccgactttgt gggaaaaata cagggcgtcc tgacacaaac caccagaacc   1020

gatggctcca cacggggaca caaggcaacc gtctacactg gctctgccga ttttgccccg   1080

aaactgggta gagtgcagtt tgagaccgac actgaccggg actttgaagc caatcagaat   1140

actaagttca cacctgtagg agtgattcag gacgggggca ccactcaccg gaacgagccg   1200

caacaatggg tcctgccctc ttatagcggg aggaatactc ataatgtgca tttggctcct   1260

gcagtggctc ccacgtttcc cggggaacaa ctgctctttt ttcgttcaac catgcctgga   1320

tgctccggat atcccaatat ggatctcgat tgcctgctcc cacaggaatg ggtgcagtat   1380

ttttatcaag aggccgcacc agcccaatcc gacgtcgcac ttctgcggtt cgtgaatcca   1440

gacacaggcc gcgtgttgtt tgagtgcaaa ttgcacaaat caggatacgt tacagtggct   1500

catactggac agcatgacct ggtgatccca cccaacggat attttaggtt cgactcctgg   1560

gtgaatcagt tttatacatt agcccccatg ggaatggga ctggcagacg cagggctgtc   1620

tga                                                                 1623
```

<210> SEQ ID NO 69
<211> LENGTH: 540
<212> TYPE: PRT
<213> ORGANISM: Norovirus

<400> SEQUENCE: 69

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Pro Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
```

```
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 70
<211> LENGTH: 1623
<212> TYPE: DNA
<213> ORGANISM: Artificial Sequence
<220> FEATURE:
<223> OTHER INFORMATION: Nucleic acid sequence of human codon optimized
      VP1_GII.4_Syd12_P80S plus sign V47P

<400> SEQUENCE: 70

```
atgaaaatgg cctcgagtga cgctaaccct agtgacggca gcgccgccaa tcttgtgcct     60

gaggttaata atgaggtgat ggccctggag cctgtggtgg gcgcagccat agcagcgccc    120

gtggccggtc agcagaatcc cattgacccg tggatacgca acaattttgt ccaagcccct    180

ggtggggagt tcaccgttag cccgagaaat gcgccaggag aaatcctgtg gtcggccagc    240

ttgggacccg atctgaaccc ctatttgtca catctcgctc ggatgtacaa cgggtatgcc    300

ggcggatttg aagtgcaggt gattctggct gggaacgcgt tcactgctgg caaagtgatc    360
```

-continued

```
tttgcagcgg tgcctcccaa cttccccact gaaggactgt ctccaagcca ggtcacaatg    420

tttccacaca tcgtggtgga cgtacggcag ctagagcctg tcctgattcc cctccctgat    480

gtacgcaata atttctacca ctacaatcaa tccaatgatc cgaccattaa actcatcgcg    540

atgttgtaca cccctctgcg cgctaacaat gctggagacg acgtattcac cgtgtcatgc    600

agagtgctca ccagaccttc accagacttt gactttatct tcttagtgcc ccccactgtt    660

gagagccgaa ccaagccctt tagtgtcccc gtactcacag tcgaggagat gacaaatagc    720

cgctttccaa tccccttga gaaactgttc acaggacctt cctcggcatt cgtggttcag     780

ccacagaacg gacgctgcac aactgacggc gtgctgctcg gaaccaccca gcttagccct    840

gttaatatct gtacgtttag aggcgacgta actcacataa ctggctcacg gaactatacc    900

atgaatctgg catcacagaa ttggaatgac tacgacccaa ccgaagagat tcccgcacct    960

cttggaaccc ccgactttgt gggaaaaata cagggcgtcc tgacacaaac caccagaacc   1020

gatggctcca cacggggaca caaggcaacc gtctacactg gctctgccga ttttgccccg   1080

aaactgggta gagtgcagtt tgagaccgac actgaccggg actttgaagc caatcagaat   1140

actaagttca cacctgtagg agtgattcag gacgggggca ccactcaccg gaacgagccg   1200

caacaatggg tcctgccctc ttatagcggg aggaatactc ataatgtgca tttggctcct   1260

gcagtggctc ccacgtttcc cggggaacaa ctgctctttt ttcgttcaac catgcctgga   1320

tgctccggat atcccaatat ggatctcgat tgcctgctcc cacaggaatg ggtgcagtat   1380

ttttatcaag aggccgcacc agcccaatcc gacgtcgcac ttctgcggtt cgtgaatcca   1440

gacacaggcc gcgtgttgtt tgagtgcaaa ttgcacaaat caggatacgt tacagtggct   1500

catactggac agcatgacct ggtgatccca cccaacggat attttaggtt cgactcctgg   1560

gtgaatcagt tttatacatt agccccatg gggaatggga ctggcagacg cagggctgtc    1620

tga                                                                 1623
```

<210> SEQ ID NO 71
<211> LENGTH: 540
<212> TYPE: PRT
<213> ORGANISM: Norovirus

<400> SEQUENCE: 71

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Ile Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140
```

```
Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 72
<211> LENGTH: 1623
<212> TYPE: DNA

<213> ORGANISM: Artificial Sequence
<220> FEATURE:
<223> OTHER INFORMATION: Nucleic acid sequence of human codon optimized VP1_GII.4_Syd12_P80S plus sign R53I

<400> SEQUENCE: 72

```
atgaaaatgg cctcgagtga cgctaaccct agtgacggca gcgccgccaa tcttgtgcct     60

gaggttaata atgaggtgat ggccctggag cctgtggtgg gcgcagccat agcagcgccc    120

gtggccggtc agcagaatgt gattgacccg tggataatca acaattttgt ccaagcccct    180

ggtggggagt tcaccgttag cccgagaaat gcgccaggag aaatcctgtg gtcggccagc    240

ttgggacccg atctgaaccc ctatttgtca catctcgctc ggatgtacaa cgggtatgcc    300

ggcggatttg aagtgcaggt gattctggct gggaacgcgt tcactgctgg caaagtgatc    360

tttgcagcgg tgcctcccaa cttccccact gaaggactgt ctccaagcca ggtcacaatg    420

tttccacaca tcgtggtgga cgtacggcag ctagagcctg tcctgattcc cctccctgat    480

gtacgcaata atttctacca ctacaatcaa tccaatgatc cgaccattaa actcatcgcg    540

atgttgtaca cccctctgcg cgctaacaat gctggagacg acgtattcac cgtgtcatgc    600

agagtgctca ccagaccttc accagacttt gactttatct tcttagtgcc ccccactgtt    660

gagagccgaa ccaagccctt tagtgtcccc gtactcacag tcgaggagat gacaaatagc    720

cgctttccaa tcccccttga gaaactgttc acaggacctt cctcggcatt cgtggttcag    780

ccacagaacg gacgctgcac aactgacggc gtgctgctcg gaaccaccca gcttagccct    840

gttaatatct gtacgtttag aggcgacgta actcacataa ctggctcacg gaactatacc    900

atgaatctgg catcacagaa ttggaatgac tacgacccaa ccgaagagat tcccgcacct    960

cttggaaccc ccgactttgt gggaaaaata cagggcgtcc tgacacaaac caccagaacc   1020

gatggctcca cacggggaca caaggcaacc gtctacactg gctctgccga ttttgccccg   1080

aaactgggta gagtgcagtt tgagaccgac actgaccggg actttgaagc caatcagaat   1140

actaagttca cacctgtagg agtgattcag gacgggggca ccactcaccg gaacgagccg   1200

caacaatggg tcctgccctc ttatagcggg aggaatactc ataatgtgca tttggctcct   1260

gcagtggctc ccacgtttcc cggggaacaa ctgctctttt ttcgttcaac catgcctgga   1320

tgctccggat atcccaatat ggatctcgat tgcctgctcc cacaggaatg ggtgcagtat   1380

ttttatcaag aggccgcacc agcccaatcc gacgtcgcac ttctgcggtt cgtgaatcca   1440

gacacaggcc gcgtgttgtt tgagtgcaaa ttgcacaaat caggatacgt tacagtggct   1500

catactggac agcatgacct ggtgatccca cccaacggat attttaggtt cgactcctgg   1560

gtgaatcagt tttatacatt agcccccatg ggaatggga ctggcagacg cagggctgtc    1620

tga                                                                 1623
```

<210> SEQ ID NO 73
<211> LENGTH: 540
<212> TYPE: PRT
<213> ORGANISM: Norovirus

<400> SEQUENCE: 73

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45
```

-continued

```
Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Leu His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460
```

```
Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 74
<211> LENGTH: 1623
<212> TYPE: DNA
<213> ORGANISM: Artificial Sequence
<220> FEATURE:
<223> OTHER INFORMATION: Nucleic acid sequence of human codon optimized VP1_GII.4_Syd12_P80S plus sign S90L

<400> SEQUENCE: 74

```
atgaaaatgg cctcgagtga cgctaaccct agtgacggca gcgccgccaa tcttgtgcct     60

gaggttaata atgaggtgat ggccctggag cctgtggtgg gcgcagccat agcagcgccc    120

gtggccggtc agcagaatgt gattgacccg tggatacgca acaattttgt ccaagcccct    180

ggtggggagt tcaccgttag cccgagaaat gcgccaggag aaatcctgtg gtcggccagc    240

ttgggacccg atctgaaccc ctatttgctg catctcgctc ggatgtacaa cgggtatgcc    300

ggcggatttg aagtgcaggt gattctggct gggaacgcgt tcactgctgg caaagtgatc    360

tttgcagcgg tgcctcccaa cttccccact gaaggactgt ctccaagcca ggtcacaatg    420

tttccacaca tcgtggtgga cgtacggcag ctagagcctg tcctgattcc cctccctgat    480

gtacgcaata atttctacca ctacaatcaa tccaatgatc cgaccattaa actcatcgcg    540

atgttgtaca cccctctgcg cgctaacaat gctggagacg acgtattcac cgtgtcatgc    600

agagtgctca ccagaccttc accagacttt gactttatct tcttagtgcc ccccactgtt    660

gagagccgaa ccaagccctt tagtgtcccc gtactcacag tcgaggagat gacaaatagc    720

cgctttccaa tccccttga gaaactgttc acaggacctt cctcggcatt cgtggttcag    780

ccacagaacg gacgctgcac aactgacggc gtgctgctcg gaaccaccca gcttagccct    840

gttaatatct gtacgtttag aggcgacgta actcacataa ctggctcacg gaactatacc    900

atgaatctgg catcacagaa ttggaatgac tacgacccaa ccgaagagat tcccgcacct    960

cttggaaccc ccgactttgt gggaaaaata cagggcgtcc tgacacaaac caccagaacc   1020

gatggctcca cacggggaca caaggcaacc gtctacactg gctctgccga ttttgccccg   1080

aaactgggta gagtgcagtt tgagaccgac actgaccggg actttgaagc caatcagaat   1140

actaagttca cacctgtagg agtgattcag gacgggggca ccactcaccg gaacgagccg   1200

caacaatggg tcctgccctc ttatagcggg aggaatactc ataatgtgca tttggctcct   1260

gcagtggctc ccacgtttcc cggggaacaa ctgctctttt ttcgttcaac catgcctgga   1320

tgctccggat atcccaatat ggatctcgat tgcctgctcc cacaggaatg ggtgcagtat   1380

ttttatcaag aggccgcacc agcccaatcc gacgtcgcac ttctgcggtt cgtgaatcca   1440

gacacaggcc gcgtgttgtt tgagtgcaaa ttgcacaaat caggatacgt tacagtggct   1500

catactggac agcatgacct ggtgatccca cccaacggat attttaggtt cgactcctgg   1560

gtgaatcagt tttatacatt agccccccatg gggaatggga ctggcagacg cagggctgtc   1620
```

tga 1623

<210> SEQ ID NO 75
<211> LENGTH: 532
<212> TYPE: PRT
<213> ORGANISM: Norovirus

<400> SEQUENCE: 75

Met Lys Met Ala Ser Ser Asp Ala Asn Pro Ser Asp Gly Ser Ala Ala
1 5 10 15

Asn Leu Val Pro Glu Val Asn Asn Glu Val Met Ala Leu Glu Pro Val
20 25 30

Val Gly Gly Gln Gln Asn Val Ile Asp Pro Trp Ile Arg Asn Asn Phe
35 40 45

Val Gln Ala Pro Gly Gly Glu Phe Thr Val Ser Pro Arg Asn Ala Pro
50 55 60

Gly Glu Ile Leu Trp Ser Ala Ser Leu Gly Pro Asp Leu Asn Pro Tyr
65 70 75 80

Leu Ser His Leu Ala Arg Met Tyr Asn Gly Tyr Ala Gly Gly Phe Glu
85 90 95

Val Gln Val Ile Leu Ala Gly Asn Ala Phe Thr Ala Gly Lys Val Ile
100 105 110

Phe Ala Ala Val Pro Pro Asn Phe Pro Thr Glu Gly Leu Ser Pro Ser
115 120 125

Gln Val Thr Met Phe Pro His Ile Val Val Asp Val Arg Gln Leu Glu
130 135 140

Pro Val Leu Ile Pro Leu Pro Asp Val Arg Asn Asn Phe Tyr His Tyr
145 150 155 160

Asn Gln Ser Asn Asp Pro Thr Ile Lys Leu Ile Ala Met Leu Tyr Thr
165 170 175

Pro Leu Arg Ala Asn Asn Ala Gly Asp Asp Val Phe Thr Val Ser Cys
180 185 190

Arg Val Leu Thr Arg Pro Ser Pro Asp Phe Asp Phe Ile Phe Leu Val
195 200 205

Pro Pro Thr Val Glu Ser Arg Thr Lys Pro Phe Ser Val Pro Val Leu
210 215 220

Thr Val Glu Glu Met Thr Asn Ser Arg Phe Pro Ile Pro Leu Glu Lys
225 230 235 240

Leu Phe Thr Gly Pro Ser Ser Ala Phe Val Val Gln Pro Gln Asn Gly
245 250 255

Arg Cys Thr Thr Asp Gly Val Leu Leu Gly Thr Thr Gln Leu Ser Pro
260 265 270

Val Asn Ile Cys Thr Phe Arg Gly Asp Val Thr His Ile Thr Gly Ser
275 280 285

Arg Asn Tyr Thr Met Asn Leu Ala Ser Gln Asn Trp Asn Asp Tyr Asp
290 295 300

Pro Thr Glu Glu Ile Pro Ala Pro Leu Gly Thr Pro Asp Phe Val Gly
305 310 315 320

Lys Ile Gln Gly Val Leu Thr Gln Thr Thr Arg Thr Asp Gly Ser Thr
325 330 335

Arg Gly His Lys Ala Thr Val Tyr Thr Gly Ser Ala Asp Phe Ala Pro
340 345 350

Lys Leu Gly Arg Val Gln Phe Glu Thr Asp Thr Asp Arg Asp Phe Glu
355 360 365

```
Ala Asn Gln Asn Thr Lys Phe Thr Pro Val Gly Val Ile Gln Asp Gly
    370                 375                 380

Gly Thr Thr His Arg Asn Glu Pro Gln Gln Trp Val Leu Pro Ser Tyr
385                 390                 395                 400

Ser Gly Arg Asn Thr His Asn Val His Leu Ala Pro Ala Val Ala Pro
                405                 410                 415

Thr Phe Pro Gly Glu Gln Leu Leu Phe Phe Arg Ser Thr Met Pro Gly
            420                 425                 430

Cys Ser Gly Tyr Pro Asn Met Asp Leu Asp Cys Leu Leu Pro Gln Glu
        435                 440                 445

Trp Val Gln Tyr Phe Tyr Gln Glu Ala Ala Pro Ala Gln Ser Asp Val
    450                 455                 460

Ala Leu Leu Arg Phe Val Asn Pro Asp Thr Gly Arg Val Leu Phe Glu
465                 470                 475                 480

Cys Lys Leu His Lys Ser Gly Tyr Val Thr Val Ala His Thr Gly Gln
                485                 490                 495

His Asp Leu Val Ile Pro Pro Asn Gly Tyr Phe Arg Phe Asp Ser Trp
            500                 505                 510

Val Asn Gln Phe Tyr Thr Leu Ala Pro Met Gly Asn Gly Thr Gly Arg
        515                 520                 525

Arg Arg Ala Val
    530


<210> SEQ ID NO 76
<211> LENGTH: 1599
<212> TYPE: DNA
<213> ORGANISM: Artificial Sequence
<220> FEATURE:
<223> OTHER INFORMATION: Nucleic acid sequence of human codon optimized
      VP1_GII.4_Syd12_P80Splus sign delta 35-42

<400> SEQUENCE: 76

atgaaaatgg cctcgagtga cgctaaccct agtgacggca gcgccgccaa tcttgtgcct      60

gaggttaata atgaggtgat ggccctggag cctgtggtgg gcggtcagca gaatgtgatt     120

gacccgtgga tacgcaacaa ttttgtccaa gcccctggtg gggagttcac cgttagcccg     180

agaaatgcgc caggagaaat cctgtggtcg gccagcttgg gacccgatct gaacccctat     240

ttgtcacatc tcgctcggat gtacaacggg tatgccggcg gatttgaagt gcaggtgatt     300

ctggctggga acgcgttcac tgctggcaaa gtgatctttg cagcggtgcc tcccaacttc     360

cccactgaag gactgtctcc aagccaggtc acaatgtttc cacacatcgt ggtggacgta     420

cggcagctag agcctgtcct gattcccctc cctgatgtac gcaataattt ctaccactac     480

aatcaatcca atgatccgac cattaaactc atcgcgatgt tgtacacccc tctgcgcgct     540

aacaatgctg gagacgacgt attcaccgtg tcatgcagag tgctcaccag accttcacca     600

gactttgact ttatcttctt agtgcccccc actgttgaga gccgaaccaa gccctttagt     660

gtccccgtac tcacagtcga ggagatgaca aatagccgct ttccaatccc ccttgagaaa     720

ctgttcacag gaccttcctc ggcattcgtg gttcagccac agaacggacg ctgcacaact     780

gacggcgtgc tgctcggaac cacccagctt agccctgtta atatctgtac gtttagaggc     840

gacgtaactc acataactgg ctcacggaac tataccatga atctggcatc acagaattgg     900

aatgactacg acccaaccga agagattccc gcacctcttg gaacccccga ctttgtggga     960

aaaatacagg gcgtcctgac acaaaccacc agaaccgatg gctccacacg gggacacaag    1020
```

```
gcaaccgtct acactggctc tgccgatttt gccccgaaac tgggtagagt gcagtttgag    1080

accgacactg accgggactt tgaagccaat cagaatacta agttcacacc tgtaggagtg    1140

attcaggacg ggggcaccac tcaccggaac gagccgcaac aatgggtcct gccctcttat    1200

agcgggagga atactcataa tgtgcatttg gctcctgcag tggctcccac gtttcccggg    1260

gaacaactgc tcttttttcg ttcaaccatg cctggatgct ccggatatcc caatatggat    1320

ctcgattgcc tgctcccaca ggaatgggtg cagtattttt atcaagaggc cgcaccagcc    1380

caatccgacg tcgcacttct gcggttcgtg aatccagaca caggccgcgt gttgtttgag    1440

tgcaaattgc acaaatcagg atacgttaca gtggctcata ctggacagca tgacctggtg    1500

atcccaccca acggatattt taggttcgac tcctgggtga atcagtttta tacattagcc    1560

cccatgggga atgggactgg cagacgcagg gctgtctga                           1599
```

<210> SEQ ID NO 77
<211> LENGTH: 540
<212> TYPE: PRT
<213> ORGANISM: Norovirus

<400> SEQUENCE: 77

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
                20                  25                  30

Val Gly Ser Ser Thr Ala Val Ala Thr Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
                100                 105                 110

Ala Phe Thr Ala Gly Lys Val Ile Phe Ala Ala Val Pro Pro Asn Phe
            115                 120                 125

Pro Thr Glu Gly Leu Ser Pro Ser Gln Val Thr Met Phe Pro His Ile
        130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
                180                 185                 190

Asp Asp Val Phe Thr Val Ser Cys Arg Val Leu Thr Arg Pro Ser Pro
            195                 200                 205

Asp Phe Asp Phe Ile Phe Leu Val Pro Pro Thr Val Glu Ser Arg Thr
        210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270
```

```
Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 78
<211> LENGTH: 1623
<212> TYPE: DNA
<213> ORGANISM: Artificial Sequence
<220> FEATURE:
<223> OTHER INFORMATION: Nucleic acid sequence of human codon optimized VP1_GII.4_Syd12_P80S plus sign SSTAVATA

<400> SEQUENCE: 78

```
atgaaaatgg cctcgagtga cgctaaccct agtgacggca gcgccgccaa tcttgtgcct      60

gaggttaata atgaggtgat ggccctggag cctgtggtgg gcagctccac cgccgtcgct     120

acagccggtc agcagaatgt gattgacccg tggatacgca acaattttgt ccaagcccct     180

ggtggggagt tcaccgttag cccgagaaat gcgccaggag aaatcctgtg gtcggccagc     240

ttgggacccg atctgaaccc ctatttgtca catctcgctc ggatgtacaa cgggtatgcc     300

ggcggatttg aagtgcaggt gattctggct gggaacgcgt tcactgctgg caaagtgatc     360

tttgcagcgg tgcctcccaa cttccccact gaaggactgt ctccaagcca ggtcacaatg     420

tttccacaca tcgtggtgga cgtacggcag ctagagcctg tcctgattcc cctccctgat     480

gtacgcaata atttctacca ctacaatcaa tccaatgatc cgaccattaa actcatcgcg     540
```

-continued

```
atgttgtaca cccctctgcg cgctaacaat gctggagacg acgtattcac cgtgtcatgc    600

agagtgctca ccagaccttc accagacttt gactttatct tcttagtgcc ccccactgtt    660

gagagccgaa ccaagccctt tagtgtcccc gtactcacag tcgaggagat gacaaatagc    720

cgctttccaa tccccttga gaaactgttc acaggacctt cctcggcatt cgtggttcag    780

ccacagaacg gacgctgcac aactgacggc gtgctgctcg gaaccaccca gcttagccct    840

gttaatatct gtacgtttag aggcgacgta actcacataa ctggctcacg gaactatacc    900

atgaatctgg catcacagaa ttggaatgac tacgacccaa ccgaagagat tcccgcacct    960

cttggaaccc ccgactttgt gggaaaaata cagggcgtcc tgacacaaac caccagaacc   1020

gatggctcca cacggggaca caaggcaacc gtctacactg gctctgccga ttttgccccg   1080

aaactgggta gagtgcagtt tgagaccgac actgaccggg actttgaagc caatcagaat   1140

actaagttca cacctgtagg agtgattcag gacgggggca ccactcaccg gaacgagccg   1200

caacaatggg tcctgccctc ttatagcggg aggaatactc ataatgtgca tttggctcct   1260

gcagtggctc ccacgtttcc cggggaacaa ctgctctttt ttcgttcaac catgcctgga   1320

tgctccggat atcccaatat ggatctcgat tgcctgctcc cacaggaatg ggtgcagtat   1380

ttttatcaag aggccgcacc agcccaatcc gacgtcgcac ttctgcggtt cgtgaatcca   1440

gacacaggcc gcgtgttgtt tgagtgcaaa ttgcacaaat caggatacgt tacagtggct   1500

catactggac agcatgacct ggtgatccca cccaacggat attttaggtt cgactcctgg   1560

gtgaatcagt tttatacatt agcccccatg ggaatggga ctggcagacg cagggctgtc   1620

tga                                                                 1623
```

<210> SEQ ID NO 79
<211> LENGTH: 547
<212> TYPE: PRT
<213> ORGANISM: Norovirus

<400> SEQUENCE: 79

```
Met Lys Met Ala Ser Asn Asp Ala Ala Pro Ser Asn Asp Gly Ala Ala
1               5                   10                  15

Asn Leu Val Pro Glu Ala Asn Asn Glu Val Met Ala Leu Glu Pro Val
            20                  25                  30

Val Gly Ala Ser Ile Ala Ala Pro Val Val Gly Gln Gln Asn Ile Ile
        35                  40                  45

Asp Pro Trp Ile Arg Glu Asn Phe Val Gln Ala Pro Gln Gly Glu Phe
    50                  55                  60

Thr Val Ser Pro Arg Asn Ser Pro Gly Glu Met Leu Leu Asn Leu Ser
65                  70                  75                  80

Leu Gly Pro Glu Leu Asn Pro Tyr Leu Ser His Leu Ser Arg Met Tyr
                85                  90                  95

Asn Gly Tyr Ala Gly Gly Met Gln Val Gln Val Val Leu Ala Gly Asn
            100                 105                 110

Ala Phe Thr Ala Gly Lys Ile Ile Phe Ala Ala Val Pro Pro His Phe
        115                 120                 125

Pro Val Glu Asn Ile Asn Ala Ala Gln Ile Thr Met Cys Pro His Val
    130                 135                 140

Ile Val Asp Val Arg Gln Leu Glu Pro Val Leu Leu Pro Leu Pro Asp
145                 150                 155                 160

Ile Arg Asn Arg Phe Phe His Tyr Asn Gln Glu Asn Thr Ser Arg Met
                165                 170                 175
```

```
Arg Leu Val Ala Met Leu Tyr Thr Pro Leu Arg Ala Asn Ser Gly Glu
            180                 185                 190

Asp Val Phe Thr Val Ser Cys Arg Val Leu Thr Arg Pro Ala Pro Asp
        195                 200                 205

Phe Glu Phe Thr Phe Leu Val Pro Pro Thr Val Glu Ser Lys Thr Lys
    210                 215                 220

Pro Phe Ser Leu Pro Ile Leu Thr Leu Gly Glu Leu Ser Asn Ser Arg
225                 230                 235                 240

Phe Pro Ala Pro Ile Asp Met Leu Tyr Thr Asp Pro Asn Glu Gly Ile
                245                 250                 255

Val Val Gln Pro Gln Asn Gly Arg Cys Thr Leu Asp Gly Thr Leu Gln
            260                 265                 270

Gly Thr Thr Gln Leu Val Pro Thr Gln Ile Cys Ala Phe Arg Gly Thr
        275                 280                 285

Leu Ile Gly Gln Thr Ser Arg Ser Pro Asp Ser Thr Asp Ser Ala Pro
    290                 295                 300

Arg Arg Arg Asp His Pro Leu His Val Gln Leu Lys Asn Leu Asp Gly
305                 310                 315                 320

Thr Gln Tyr Asp Pro Thr Asp Glu Val Pro Ala Val Leu Gly Ala Ile
                325                 330                 335

Asp Phe Lys Gly Thr Val Phe Gly Val Ala Ser Gln Arg Asp Val Ser
            340                 345                 350

Gly Gln Gln Val Gly Ala Thr Arg Ala His Glu Val His Ile Asn Thr
        355                 360                 365

Thr Asp Pro Arg Tyr Thr Pro Lys Leu Gly Ser Ile Leu Met Tyr Ser
    370                 375                 380

Glu Ser Asp Asp Phe Val Thr Gly Gln Pro Val Arg Phe Thr Pro Ile
385                 390                 395                 400

Gly Met Gly Asp Asn Asp Trp His Gln Trp Glu Leu Pro Asp Tyr Pro
                405                 410                 415

Gly His Leu Thr Leu Asn Met Asn Leu Ala Pro Ala Val Ala Pro Ala
            420                 425                 430

Phe Pro Gly Glu Arg Ile Leu Phe Phe Arg Ser Ile Val Pro Ser Ala
        435                 440                 445

Gly Gly Tyr Gly Ser Gly Gln Ile Asp Cys Leu Ile Pro Gln Glu Trp
    450                 455                 460

Val Gln His Phe Tyr Gln Glu Ala Ala Pro Ser Gln Ser Ala Val Ala
465                 470                 475                 480

Leu Ile Arg Tyr Val Asn Pro Asp Thr Gly Arg Asn Ile Phe Glu Ala
                485                 490                 495

Lys Leu His Arg Glu Gly Phe Ile Thr Val Ala Asn Ser Gly Asn Asn
            500                 505                 510

Pro Ile Val Val Pro Pro Asn Gly Tyr Phe Arg Phe Glu Ala Trp Val
        515                 520                 525

Asn Gln Phe Tyr Thr Leu Thr Pro Met Gly Thr Gly Gln Gly Arg Arg
    530                 535                 540

Arg Asp Gln
545
```

<210> SEQ ID NO 80
<211> LENGTH: 1644
<212> TYPE: DNA
<213> ORGANISM: Artificial Sequence
<220> FEATURE:

-continued

<223> OTHER INFORMATION: Nucleic acid sequence of human codon optimized VP1_GII.6_Ohio_E80S

<400> SEQUENCE: 80
atgaagatgg caagcaacga cgcagctccc tccaatgatg gtgccgccaa cctggtcccc 60
gaagctaata atgaggtgat ggcgttagag ccggtggttg gcgcatctat tgcagcgcct 120
gtggtcggac agcagaacat cattgatccc tggattcgcg agaacttcgt acaagctcca 180
cagggggagt tcacagtctc cccccggaac tccccgggcg agatgctgct caatctgagc 240
ctcggccctg aactaaaccc ttatctgtca cacctttcac ggatgtacaa tggctacgca 300
ggaggaatgc aagttcaggt ggtcctggcc ggcaatgctt tcaccgcggg caaaatcatc 360
tttgcggccg ttcctccaca cttccctgtc gaaaatatca acgccgccca gattactatg 420
tgcccccacg tgattgtgga tgtgcgacag ttagagccag ttctgctgcc cctgcccgac 480
atcagaaacc ggttcttcca ttacaatcaa gagaatactt cacggatgag acttgttgcg 540
atgctgtaca cccctcttcg tgcaaattcc ggcgaagacg tgttcactgt gtcttgtcga 600
gtacttaccc gacccgcccc cgatttcgaa ttcaccttcc tggttccccc tactgtggag 660
agcaagacaa aacccttcag cctcccaatc ttaacactcg gggagctgtc taattcacgc 720
ttccccgcac ctattgatat gctgtatact gaccccaacg aggggatagt ggtgcagccc 780
caaaatggac ggtgtactct cgacggcacg ctccagggca caacccaact ggtgccaacc 840
cagatttgtg cattcagggg cactttgatt gggcagacat cgagatctcc agattctact 900
gattccgcgc caaggaggag ggaccaccca ctccacgttc agttaaaaaa cctggacgga 960
acccagtacg accctacaga cgaggtcccc gctgtcctcg gagccatcga ctttaaagga 1020
actgtatttg gagtggcatc ccaaagggat gtctcggggc agcaggtggg agctacgaga 1080
gcacatgaag tccacattaa caccacagac ccaagatata ccccaaaact agggtcaatt 1140
ttaatgtatt cggaatcaga cgattttgtt acaggtcagc ccgtgcggtt taccccgatc 1200
ggaatggggg acaacgattg gcaccagtgg gaattgcccg attaccctgg acacctcacc 1260
ttgaatatga atctggcccc agccgtcgcg cccgccttcc ccggtgagcg gatcctcttt 1320
tttagaagca tagtgccctc cgcaggtggg tatggatcag ggcagattga ttgcctgatc 1380
ccccaagaat gggtacagca tttctaccag gaagcagccc ctagccagtc cgcagtagca 1440
ctgatcagat atgttaatcc tgatacggga aggaacatct tcgaagcaaa actgcaccgt 1500
gagggcttca ttaccgtcgc caacagtggt aataacccta ttgtggtgcc tcctaatgga 1560
tacttcaggt ttgaggcatg ggtgaatcag ttttatactc tgactcccat ggggacaggc 1620
caggggcgac gccgggatca gtga 1644

<210> SEQ ID NO 81
<211> LENGTH: 547
<212> TYPE: PRT
<213> ORGANISM: Norovirus

<400> SEQUENCE: 81

Met Lys Met Ala Ser Asn Asp Ala Ala Pro Ser Asn Asp Gly Ala Ala
1 5 10 15

Asn Leu Val Pro Glu Ala Asn Asn Glu Val Met Ala Leu Glu Pro Val
20 25 30

Val Gly Ala Ser Ile Ala Ala Pro Val Val Gly Gln Gln Asn Ile Ile
35 40 45

Asp Pro Trp Ile Arg Glu Asn Phe Val Gln Ala Pro Gln Gly Glu Phe

```
    50                  55                  60

Thr Val Ser Pro Arg Asn Ser Pro Gly Glu Met Leu Leu Asn Leu Glu
65                  70                  75                  80

Leu Gly Pro Glu Leu Asn Pro Tyr Leu Leu His Leu Ser Arg Met Tyr
                85                  90                  95

Asn Gly Tyr Ala Gly Gly Met Gln Val Gln Val Val Leu Ala Gly Asn
            100                 105                 110

Ala Phe Thr Ala Gly Lys Ile Ile Phe Ala Ala Val Pro Pro His Phe
        115                 120                 125

Pro Val Glu Asn Ile Asn Ala Ala Gln Ile Thr Met Cys Pro His Val
    130                 135                 140

Ile Val Asp Val Arg Gln Leu Glu Pro Val Leu Leu Pro Leu Pro Asp
145                 150                 155                 160

Ile Arg Asn Arg Phe Phe His Tyr Asn Gln Glu Asn Thr Ser Arg Met
                165                 170                 175

Arg Leu Val Ala Met Leu Tyr Thr Pro Leu Arg Ala Asn Ser Gly Glu
            180                 185                 190

Asp Val Phe Thr Val Ser Cys Arg Val Leu Thr Arg Pro Ala Pro Asp
        195                 200                 205

Phe Glu Phe Thr Phe Leu Val Pro Pro Thr Val Glu Ser Lys Thr Lys
    210                 215                 220

Pro Phe Ser Leu Pro Ile Leu Thr Leu Gly Glu Leu Ser Asn Ser Arg
225                 230                 235                 240

Phe Pro Ala Pro Ile Asp Met Leu Tyr Thr Asp Pro Asn Glu Gly Ile
                245                 250                 255

Val Val Gln Pro Gln Asn Gly Arg Cys Thr Leu Asp Gly Thr Leu Gln
            260                 265                 270

Gly Thr Thr Gln Leu Val Pro Thr Gln Ile Cys Ala Phe Arg Gly Thr
        275                 280                 285

Leu Ile Gly Gln Thr Ser Arg Ser Pro Asp Ser Thr Asp Ser Ala Pro
    290                 295                 300

Arg Arg Arg Asp His Pro Leu His Val Gln Leu Lys Asn Leu Asp Gly
305                 310                 315                 320

Thr Gln Tyr Asp Pro Thr Asp Glu Val Pro Ala Val Leu Gly Ala Ile
                325                 330                 335

Asp Phe Lys Gly Thr Val Phe Gly Val Ala Ser Gln Arg Asp Val Ser
            340                 345                 350

Gly Gln Gln Val Gly Ala Thr Arg Ala His Glu Val His Ile Asn Thr
        355                 360                 365

Thr Asp Pro Arg Tyr Thr Pro Lys Leu Gly Ser Ile Leu Met Tyr Ser
    370                 375                 380

Glu Ser Asp Asp Phe Val Thr Gly Gln Pro Val Arg Phe Thr Pro Ile
385                 390                 395                 400

Gly Met Gly Asp Asn Asp Trp His Gln Trp Glu Leu Pro Asp Tyr Pro
                405                 410                 415

Gly His Leu Thr Leu Asn Met Asn Leu Ala Pro Ala Val Ala Pro Ala
            420                 425                 430

Phe Pro Gly Glu Arg Ile Leu Phe Phe Arg Ser Ile Val Pro Ser Ala
        435                 440                 445

Gly Gly Tyr Gly Ser Gly Gln Ile Asp Cys Leu Ile Pro Gln Glu Trp
    450                 455                 460

Val Gln His Phe Tyr Gln Glu Ala Ala Pro Ser Gln Ser Ala Val Ala
465                 470                 475                 480
```

```
Leu Ile Arg Tyr Val Asn Pro Asp Thr Gly Arg Asn Ile Phe Glu Ala
                485                 490                 495

Lys Leu His Arg Glu Gly Phe Ile Thr Val Ala Asn Ser Gly Asn Asn
            500                 505                 510

Pro Ile Val Val Pro Pro Asn Gly Tyr Phe Arg Phe Glu Ala Trp Val
        515                 520                 525

Asn Gln Phe Tyr Thr Leu Thr Pro Met Gly Thr Gly Gln Gly Arg Arg
    530                 535                 540

Arg Asp Gln
545


<210> SEQ ID NO 82
<211> LENGTH: 1644
<212> TYPE: DNA
<213> ORGANISM: Artificial Sequence
<220> FEATURE:
<223> OTHER INFORMATION: Nucleic acid sequence of human codon optimized
      VP1_GII.6_Ohio_S90L

<400> SEQUENCE: 82

atgaagatgg caagcaacga cgcagctccc tccaatgatg gtgccgccaa cctggtcccc     60

gaagctaata atgaggtgat ggcgttagag ccggtggttg gcgcatctat tgcagcgcct    120

gtggtcggac agcagaacat cattgatccc tggattcgcg agaacttcgt acaagctcca    180

caggggggagt tcacagtctc cccccggaac tccccgggcg agatgctgct caatctggaa    240

ctcggccctg aactaaaccc ttatctgctc cacctttcac ggatgtacaa tggctacgca    300

ggaggaatgc aagttcaggt ggtcctggcc ggcaatgctt tcaccgcggg caaaatcatc    360

tttgcggccg ttcctccaca cttccctgtc gaaaatatca acgccgccca gattactatg    420

tgcccccacg tgattgtgga tgtgcgacag ttagagccag ttctgctgcc cctgcccgac    480

atcagaaacc ggttcttcca ttacaatcaa gagaatactt cacggatgag acttgttgcg    540

atgctgtaca cccctcttcg tgcaaattcc ggcgaagacg tgttcactgt gtcttgtcga    600

gtacttaccc gacccgcccc cgatttcgaa ttcaccttcc tggttccccc tactgtggag    660

agcaagacaa aacccttcag cctcccaatc ttaacactcg gggagctgtc taattcacgc    720

ttccccgcac ctattgatat gctgtatact gaccccaacg aggggatagt ggtgcagccc    780

caaaatggac ggtgtactct cgacggcacg ctccagggca caacccaact ggtgccaacc    840

cagatttgtg cattcagggg cactttgatt gggcagacat cgagatctcc agattctact    900

gattccgcgc caaggaggag ggaccaccca ctccacgttc agttaaaaaa cctggacgga    960

acccagtacg accctacaga cgaggtcccc gctgtcctcg gagccatcga ctttaaagga   1020

actgtatttg gagtggcatc ccaaagggat gtctcggggc agcaggtggg agctacgaga   1080

gcacatgaag tccacattaa caccacagac ccaagatata ccccaaaact agggtcaatt   1140

ttaatgtatt cggaatcaga cgattttgtt acaggtcagc ccgtgcggtt taccccgatc   1200

ggaatggggg acaacgattg gcaccagtgg gaattgcccg attaccctgg acacctcacc   1260

ttgaatatga atctggcccc agccgtcgcg cccgccttcc ccggtgagcg gatcctcttt   1320

tttagaagca tagtgccctc cgcaggtggg tatggatcag ggcagattga ttgcctgatc   1380

ccccaagaat gggtacagca tttctaccag gaagcagccc ctagccagtc cgcagtagca   1440

ctgatcagat atgttaatcc tgatacggga aggaacatct tcgaagcaaa actgcaccgt   1500

gagggcttca ttaccgtcgc caacagtggt aataacccta ttgtggtgcc tcctaatgga   1560
```

tacttcaggt ttgaggcatg ggtgaatcag ttttatactc tgactcccat ggggacaggc 1620
caggggcgac gccgggatca gtga 1644

<210> SEQ ID NO 83
<211> LENGTH: 547
<212> TYPE: PRT
<213> ORGANISM: Norovirus

<400> SEQUENCE: 83

```
Met Lys Met Ala Ser Asn Asp Ala Ala Pro Ser Asn Asp Gly Ala Ala
1               5                   10                  15

Asn Leu Val Pro Glu Ala Asn Asn Glu Val Met Ala Leu Glu Pro Val
            20                  25                  30

Val Gly Ala Ser Ile Ala Ala Pro Val Val Gly Gln Gln Asn Ile Ile
        35                  40                  45

Asp Pro Trp Ile Arg Glu Asn Phe Val Gln Ala Pro Gln Gly Glu Phe
    50                  55                  60

Thr Val Ser Pro Arg Asn Ser Pro Gly Glu Met Leu Leu Asn Leu Ser
65                  70                  75                  80

Leu Gly Pro Glu Leu Asn Pro Tyr Leu Leu His Leu Ser Arg Met Tyr
                85                  90                  95

Asn Gly Tyr Ala Gly Gly Met Gln Val Gln Val Val Leu Ala Gly Asn
            100                 105                 110

Ala Phe Thr Ala Gly Lys Ile Ile Phe Ala Ala Val Pro Pro His Phe
        115                 120                 125

Pro Val Glu Asn Ile Asn Ala Ala Gln Ile Thr Met Cys Pro His Val
    130                 135                 140

Ile Val Asp Val Arg Gln Leu Glu Pro Val Leu Leu Pro Leu Pro Asp
145                 150                 155                 160

Ile Arg Asn Arg Phe Phe His Tyr Asn Gln Glu Asn Thr Ser Arg Met
                165                 170                 175

Arg Leu Val Ala Met Leu Tyr Thr Pro Leu Arg Ala Asn Ser Gly Glu
            180                 185                 190

Asp Val Phe Thr Val Ser Cys Arg Val Leu Thr Arg Pro Ala Pro Asp
        195                 200                 205

Phe Glu Phe Thr Phe Leu Val Pro Pro Thr Val Glu Ser Lys Thr Lys
    210                 215                 220

Pro Phe Ser Leu Pro Ile Leu Thr Leu Gly Glu Leu Ser Asn Ser Arg
225                 230                 235                 240

Phe Pro Ala Pro Ile Asp Met Leu Tyr Thr Asp Pro Asn Glu Gly Ile
                245                 250                 255

Val Val Gln Pro Gln Asn Gly Arg Cys Thr Leu Asp Gly Thr Leu Gln
            260                 265                 270

Gly Thr Thr Gln Leu Val Pro Thr Gln Ile Cys Ala Phe Arg Gly Thr
        275                 280                 285

Leu Ile Gly Gln Thr Ser Arg Ser Pro Asp Ser Thr Asp Ser Ala Pro
    290                 295                 300

Arg Arg Arg Asp His Pro Leu His Val Gln Leu Lys Asn Leu Asp Gly
305                 310                 315                 320

Thr Gln Tyr Asp Pro Thr Asp Glu Val Pro Ala Val Leu Gly Ala Ile
                325                 330                 335

Asp Phe Lys Gly Thr Val Phe Gly Val Ala Ser Gln Arg Asp Val Ser
            340                 345                 350

Gly Gln Gln Val Gly Ala Thr Arg Ala His Glu Val His Ile Asn Thr
```

```
        355                 360                 365

Thr Asp Pro Arg Tyr Thr Pro Lys Leu Gly Ser Ile Leu Met Tyr Ser
    370                 375                 380

Glu Ser Asp Asp Phe Val Thr Gly Gln Pro Val Arg Phe Thr Pro Ile
385                 390                 395                 400

Gly Met Gly Asp Asn Asp Trp His Gln Trp Glu Leu Pro Asp Tyr Pro
                405                 410                 415

Gly His Leu Thr Leu Asn Met Asn Leu Ala Pro Ala Val Ala Pro Ala
            420                 425                 430

Phe Pro Gly Glu Arg Ile Leu Phe Phe Arg Ser Ile Val Pro Ser Ala
        435                 440                 445

Gly Gly Tyr Gly Ser Gly Gln Ile Asp Cys Leu Ile Pro Gln Glu Trp
    450                 455                 460

Val Gln His Phe Tyr Gln Glu Ala Ala Pro Ser Gln Ser Ala Val Ala
465                 470                 475                 480

Leu Ile Arg Tyr Val Asn Pro Asp Thr Gly Arg Asn Ile Phe Glu Ala
                485                 490                 495

Lys Leu His Arg Glu Gly Phe Ile Thr Val Ala Asn Ser Gly Asn Asn
            500                 505                 510

Pro Ile Val Val Pro Pro Asn Gly Tyr Phe Arg Phe Glu Ala Trp Val
        515                 520                 525

Asn Gln Phe Tyr Thr Leu Thr Pro Met Gly Thr Gly Gln Gly Arg Arg
    530                 535                 540

Arg Asp Gln
545


<210> SEQ ID NO 84
<211> LENGTH: 1644
<212> TYPE: DNA
<213> ORGANISM: Artificial Sequence
<220> FEATURE:
<223> OTHER INFORMATION: Nucleic acid sequence of human codon optimized
      VP1_GII.6_Ohio_E80S plus sign S90L

<400> SEQUENCE: 84

atgaagatgg caagcaacga cgcagctccc tccaatgatg gtgccgccaa cctggtcccc     60

gaagctaata atgaggtgat ggcgttagag ccggtggttg gcgcatctat tgcagcgcct    120

gtggtcggac agcagaacat cattgatccc tggattcgcg agaacttcgt acaagctcca    180

caggggggagt tcacagtctc cccccggaac tccccgggcg agatgctgct caatctgagc    240

ctcggccctg aactaaaccc ttatctgctc cacctttcac ggatgtacaa tggctacgca    300

ggaggaatgc aagttcaggt ggtcctggcc ggcaatgctt tcaccgcggg caaaatcatc    360

tttgcggccg ttcctccaca cttccctgtc gaaaatatca acgccgccca gattactatg    420

tgccccccacg tgattgtgga tgtgcgacag ttagagccag ttctgctgcc cctgcccgac    480

atcagaaacc ggttcttcca ttacaatcaa gagaatactt cacggatgag acttgttgcg    540

atgctgtaca cccctcttcg tgcaaattcc ggcgaagacg tgttcactgt gtcttgtcga    600

gtacttaccc gacccgcccc cgatttcgaa ttcaccttcc tggttccccc tactgtggag    660

agcaagacaa aacccttcag cctcccaatc ttaacactcg gggagctgtc taattcacgc    720

ttccccgcac ctattgatat gctgtatact gaccccaacg aggggatagt ggtgcagccc    780

caaaatggac ggtgtactct cgacggcacg ctccagggca caacccaact ggtgccaacc    840

cagatttgtg cattcagggg cactttgatt gggcagacat cgagatctcc agattctact    900
```

-continued

```
gattccgcgc caaggaggag ggaccaccca ctccacgttc agttaaaaaa cctggacgga    960

acccagtacg accctacaga cgaggtcccc gctgtcctcg gagccatcga ctttaaagga   1020

actgtatttg gagtggcatc ccaaagggat gtctcggggc agcaggtggg agctacgaga   1080

gcacatgaag tccacattaa caccacagac ccaagatata ccccaaaact agggtcaatt   1140

ttaatgtatt cggaatcaga cgattttgtt acaggtcagc ccgtgcggtt taccccgatc   1200

ggaatggggg acaacgattg gcaccagtgg gaattgcccg attaccctgg acacctcacc   1260

ttgaatatga atctggcccc agccgtcgcg cccgccttcc ccggtgagcg gatcctcttt   1320

tttagaagca tagtgccctc cgcaggtggg tatggatcag ggcagattga ttgcctgatc   1380

ccccaagaat gggtacagca tttctaccag gaagcagccc ctagccagtc cgcagtagca   1440

ctgatcagat atgttaatcc tgatacggga aggaacatct tcgaagcaaa actgcaccgt   1500

gagggcttca ttaccgtcgc caacagtggt aataacccta ttgtggtgcc tcctaatgga   1560

tacttcaggt ttgaggcatg ggtgaatcag ttttatactc tgactcccat ggggacaggc   1620

caggggcgac gccgggatca gtga                                          1644
```

<210> SEQ ID NO 85
<211> LENGTH: 542
<212> TYPE: PRT
<213> ORGANISM: Norovirus

<400> SEQUENCE: 85

```
Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
            20                  25                  30

Ala Gly Ala Ala Leu Ala Ala Pro Val Thr Gly Gln Thr Asn Ile Ile
        35                  40                  45

Asp Pro Trp Ile Arg Ala Asn Phe Val Gln Ala Pro Asn Gly Glu Phe
    50                  55                  60

Thr Val Ser Pro Arg Asn Ser Pro Gly Glu Val Leu Leu Asn Leu Ser
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240
```

```
Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
        275                 280                 285

Glu Val Thr Ala His Leu His Asp Asn Asp His Leu Tyr Asn Val Thr
    290                 295                 300

Ile Thr Asn Leu Asn Gly Ser Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Ser Gln Arg Asp Lys His Asn Thr Pro Gly His Asn Glu Pro Ala Asn
            340                 345                 350

Arg Ala His Asp Ala Val Val Pro Thr Tyr Thr Ala Gln Tyr Thr Pro
        355                 360                 365

Lys Leu Gly Gln Ile Gln Ile Gly Thr Trp Gln Thr Asp Asp Leu Thr
    370                 375                 380

Val Asn Gln Pro Val Lys Phe Thr Pro Val Gly Leu Asn Asp Thr Asp
385                 390                 395                 400

His Phe Asn Gln Trp Val Val Pro Arg Tyr Ala Gly Ala Leu Asn Leu
                405                 410                 415

Asn Thr Asn Leu Ala Pro Ser Val Ala Pro Val Phe Pro Gly Glu Arg
            420                 425                 430

Leu Leu Phe Phe Arg Ser Tyr Ile Pro Leu Lys Gly Gly Tyr Gly Thr
        435                 440                 445

Pro Ala Ile Asp Cys Leu Leu Pro Gln Glu Trp Val Gln His Phe Tyr
    450                 455                 460

Gln Glu Ala Ala Pro Ser Met Ser Glu Val Ala Leu Val Arg Tyr Ile
465                 470                 475                 480

Asn Pro Asp Thr Gly Arg Ala Leu Phe Glu Ala Lys Leu His Arg Ala
                485                 490                 495

Gly Phe Met Thr Val Ser Ser Asn Thr Ser Ala Pro Val Val Val Pro
            500                 505                 510

Ala Asn Gly Tyr Phe Arg Phe Asp Ser Trp Val Asn Gln Phe Tyr Ser
        515                 520                 525

Leu Ala Pro Met Gly Thr Gly Asn Gly Arg Arg Arg Ile Gln
    530                 535                 540
```

<210> SEQ ID NO 86
<211> LENGTH: 1629
<212> TYPE: DNA
<213> ORGANISM: Artificial Sequence
<220> FEATURE:
<223> OTHER INFORMATION: Nucleic acid sequence of human codon optimized
VP1_GII.2_CGMH47_E80S_

<400> SEQUENCE: 86

```
atgaagatgg catccaacga cgccgcaccc agcacagacg gagctgccgg attggtaccc      60

gagtctaata acgaggtgat ggccttggag cctgttgcag gggctgccct cgcagctcct     120

gtgaccgggc agacaaatat catcgatcct tggattagag ctaatttcgt gcaagcccca     180

aatggggagt ttacggtcag ccctagaaat agccctgggg aagtgctcct caatctcagc     240

ctgggaccag aacttaatcc gtacctggct cacctggccc ggatgtacaa tggatatgca     300

ggagggatgg aggtgcaggt tatgctggct ggcaatgcct ttacagcagg caaactcgtt     360
```

ttcgcagccg tccctcccca cttcccagtt gaaaatcttt cccctcagca gattaccatg 420
tttccccatg tcatcatcga tgtgcgtacc ctggaacctg tgctgttgcc tttaccagac 480
gtgcggaata atttctttca ctataatcag aaggatgacc caaaaatgcg gatcgttgcg 540
atgctttata ctcccctgcg tagcaatggt agtggggatg acgtttttac agtgagttgt 600
cgggtactaa ctcgcccttc accagacttc gactttacgt acttggtgcc tcccactgtc 660
gaaagcaaaa ctaagccatt cacacttccc atcctcaccc tcggagaact ctcgaactcc 720
cgcttccctg tttcaattga tcagatgtac acgtctccaa atgaagtcat ttctgtgcag 780
tgtcagaacg gcaggtgcac cttagacggt gaactgcagg ggacaacgca gttgcaggtc 840
agtggaattt gcgcctttaa gggcgaagtg acagctcacc tccacgacaa cgatcatctc 900
tacaatgtta ctattactaa tctcaatgga agtcctttcg acccctcgga agatattccc 960
gctccactcg gagtacctga ctttcaggga cgcgtcttcg gcgtgatatc acaacgagat 1020
aagcataaca cacccggaca taatgagcca gccaatagag cccacgacgc agtcgttccg 1080
acctatacgg ctcagtacac cccaaagctc ggccagatac aaatcgggac ttggcagacc 1140
gatgacctca ctgtgaatca acctgtgaaa ttcactccag taggtctgaa tgatacagac 1200
cactttaacc agtgggtggt ccctagatac gccggagcct tgaacctaaa cactaacctt 1260
gccccttccg ttgcacctgt gtttccgggg gagcggttgc tcttctttag aagctatatt 1320
cctctgaagg gcgggtatgg tactccagca atcgactgcc tgctacctca ggagtgggtt 1380
caacatttct atcaagaggc cgcacctagt atgagcgagg tggctttggt cagatacatc 1440
aatccagaca caggaagagc actgttcgag gccaagctgc acagagccgg cttcatgacc 1500
gtctcatcca atacatccgc acccgtagta gtccccgcca acgggtactt cagattcgac 1560
agttgggtga atcagtttta ctcgttggcc cccatgggca cagggaacgg tcgccgacgg 1620
atccagtaa 1629

<210> SEQ ID NO 87
<211> LENGTH: 1608
<212> TYPE: DNA
<213> ORGANISM: Artificial Sequence
<220> FEATURE:
<223> OTHER INFORMATION: Nucleic acid sequence of human codon-optimized VP1 GII.12_HS206_2010_USA_

<400> SEQUENCE: 87
atgaagatgg cgtctaatga tgctgctcct tccaatgatg gcgcagccgg cctggtccct 60
gaagtgaata acgagactat ggctctcgaa cccgtggccg gagcctcaat tgccgccccc 120
ctcactggcc agaacaacgt gattgatccc tggatcagac tgaacttcgt tcaggctcct 180
aatggggagt tcaccgtgtc cccgagaaac tcccccggcg aagtgttatt gaatttggaa 240
ttaggaccag aactcaaccc ctatctggca catctgtctc ggatgtacaa cggctatgcg 300
ggcggagtgg aggtgcaagt tcttctcgct ggtaatgcat tcacagcagg aaaattagta 360
tttgcagcgg ttccacccca ttttccactt gaaaacataa gcccaggcca gatcaccatg 420
ttccctcacg tgataatcga cgtgcggaca ttagagcccg tgctgctacc cctgcccgac 480
gtgaggaaca atttctttca ctacaatcag caaaatgaac caagaatgcg cctggtcgcc 540
atgctctata ctcctttaag aagtaatggc agtggggatg acgtgtttac tgttagctgt 600
cgggtgctca cccgaccttc cccagatttc gacttcaatt atctggtccc ccccacggta 660
gagtccaaaa caaagccttt cactcttcca atccttacaa ttggcgaact gaccaactca 720

```
cgctttccag tgcctattga tgagctgtac acaagtccaa atgaatccct tgtcgttcag    780

ccacagaatg ggcgctgcgc gcttgacggt gagctccagg gcacaacaca actgttgcca    840

accgctatat gctctttcag ggggcgtatt aatcagaagg tctccgggga gaaccacgtg    900

tggaacatgc aagtgacgaa tatcgacggg acacctttcg atccaacaga ggatgtccca    960

gcgcctctag gtacccctga cttctcaggc aagttgttcg gcgtcctttc ccagcgcgac   1020

catgataatg cttgccggag ccacgatgcc gtcattgcca ccaactcagc caaattcacc   1080

ccaaaacttg gagcgataca gatcggaact tgggaacaag acgacgtcca tatcaaccaa   1140

ccaacaaagt ttacccctgt tggccttttc gaaagcgaag gctttaacca gtggacactt   1200

cccaattaca gcggggctct cactcttaat atggactcg caccacccgt cgctccaacg    1260

tttcctggtg agcagatttt gtttttccgc agtcatattc cactgaaggg tggagttgct   1320

gatcccgtga tagactgcct cctccctcag gaatggattc agcacttgta tcaggagtcc   1380

gctccctcgc agaccgatgt ggccctgata cgcttcacaa accccgatac cggaagagtg   1440

ttgtttgaag ctaaacttca tcgctccggt tacatcacag tagccaacac gggttccagg   1500

ccaatcgtag ttccggcaaa cggatacttt cgattcgaca gttgggtcaa tcagttctac   1560

agcctggctc caatgggaac aggaaatggg aggaggcgtg tgcagtaa                1608
```

<210> SEQ ID NO 88
<211> LENGTH: 535
<212> TYPE: PRT
<213> ORGANISM: Norovirus

<400> SEQUENCE: 88

```
Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Ser
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
```

```
    210                 215                 220

Lys Pro Phe Thr Leu Pro Ile Leu Thr Ile Gly Glu Leu Thr Asn Ser
225                 230                 235                 240

Arg Phe Pro Val Pro Ile Asp Glu Leu Tyr Thr Ser Pro Asn Glu Ser
                245                 250                 255

Leu Val Val Gln Pro Gln Asn Gly Arg Cys Ala Leu Asp Gly Glu Leu
            260                 265                 270

Gln Gly Thr Thr Gln Leu Leu Pro Thr Ala Ile Cys Ser Phe Arg Gly
        275                 280                 285

Arg Ile Asn Gln Lys Val Ser Gly Glu Asn His Val Trp Asn Met Gln
    290                 295                 300

Val Thr Asn Ile Asp Gly Thr Pro Phe Asp Pro Thr Glu Asp Val Pro
305                 310                 315                 320

Ala Pro Leu Gly Thr Pro Asp Phe Ser Gly Lys Leu Phe Gly Val Leu
                325                 330                 335

Ser Gln Arg Asp His Asp Asn Ala Cys Arg Ser His Asp Ala Val Ile
            340                 345                 350

Ala Thr Asn Ser Ala Lys Phe Thr Pro Lys Leu Gly Ala Ile Gln Ile
        355                 360                 365

Gly Thr Trp Glu Gln Asp Asp Val His Ile Asn Gln Pro Thr Lys Phe
    370                 375                 380

Thr Pro Val Gly Leu Phe Glu Ser Glu Gly Phe Asn Gln Trp Thr Leu
385                 390                 395                 400

Pro Asn Tyr Ser Gly Ala Leu Thr Leu Asn Met Gly Leu Ala Pro Pro
                405                 410                 415

Val Ala Pro Thr Phe Pro Gly Glu Gln Ile Leu Phe Phe Arg Ser His
            420                 425                 430

Ile Pro Leu Lys Gly Gly Val Ala Asp Pro Val Ile Asp Cys Leu Leu
        435                 440                 445

Pro Gln Glu Trp Ile Gln His Leu Tyr Gln Glu Ser Ala Pro Ser Gln
    450                 455                 460

Thr Asp Val Ala Leu Ile Arg Phe Thr Asn Pro Asp Thr Gly Arg Val
465                 470                 475                 480

Leu Phe Glu Ala Lys Leu His Arg Ser Gly Tyr Ile Thr Val Ala Asn
                485                 490                 495

Thr Gly Ser Arg Pro Ile Val Val Pro Ala Asn Gly Tyr Phe Arg Phe
            500                 505                 510

Asp Ser Trp Val Asn Gln Phe Tyr Ser Leu Ala Pro Met Gly Thr Gly
        515                 520                 525

Asn Gly Arg Arg Arg Val Gln
    530                 535
```

<210> SEQ ID NO 89
<211> LENGTH: 1608
<212> TYPE: DNA
<213> ORGANISM: Artificial Sequence
<220> FEATURE:
<223> OTHER INFORMATION: Nucleic acid sequence of human codon optimized VP1_GII.12_HS10_E80S

<400> SEQUENCE: 89

```
atgaagatgg cgtctaatga tgctgctcct tccaatgatg gcgcagccgg cctggtccct      60

gaagtgaata acgagactat ggctctcgaa cccgtggccg gagcctcaat tgccgccccc     120

ctcactggcc agaacaacgt gattgatccc tggatcagac tgaacttcgt tcaggctcct     180
```

```
aatggggagt tcaccgtgtc cccgagaaac tccccccggcg aagtgttatt gaatttgagc    240

ttaggaccag aactcaaccc ctatctggca catctgtctc ggatgtacaa cggctatgcg    300

ggcggagtgg aggtgcaagt tcttctcgct ggtaatgcat tcacagcagg aaaattagta    360

tttgcagcgg ttccacccca ttttccactt gaaaacataa gcccaggcca gatcaccatg    420

ttccctcacg tgataatcga cgtgcggaca ttagagcccg tgctgctacc cctgcccgac    480

gtgaggaaca atttctttca ctacaatcag caaaatgaac caagaatgcg cctggtcgcc    540

atgctctata ctcctttaag aagtaatggc agtggggatg acgtgtttac tgttagctgt    600

cgggtgctca cccgaccttc cccagatttc gacttcaatt atctggtccc ccccacggta    660

gagtccaaaa caaagccttt cactcttcca atccttacaa ttggcgaact gaccaactca    720

cgctttccag tgcctattga tgagctgtac acaagtccaa atgaatccct tgtcgttcag    780

ccacagaatg ggcgctgcgc gcttgacggt gagctccagg gcacaacaca actgttgcca    840

accgctatat gctctttcag gggcgtattt aatcagaagg tctccgggga gaaccacgtg    900

tggaacatgc aagtgacgaa tatcgacggg acacctttcg atccaacaga ggatgtccca    960

gcgcctctag gtacccctga cttctcaggc aagttgttcg gcgtcctttc ccagcgcgac   1020

catgataatg cttgccggag ccacgatgcc gtcattgcca ccaactcagc caaattcacc   1080

ccaaaacttg gagcgataca gatcggaact tgggaacaag acgacgtcca tatcaaccaa   1140

ccaacaaagt ttacccctgt tggccttttc gaaagcgaag gctttaacca gtggacactt   1200

cccaattaca gcggggctct cactcttaat atgggactcg caccacccgt cgctccaacg   1260

tttcctggtg agcagatttt gtttttccgc agtcatattc cactgaaggg tggagttgct   1320

gatcccgtga tagactgcct cctccctcag gaatggattc agcacttgta tcaggagtcc   1380

gctccctcgc agaccgatgt ggccctgata cgcttcacaa accccgatac cggaagagtg   1440

ttgtttgaag ctaaacttca tcgctccggt tacatcacag tagccaacac gggttccagg   1500

ccaatcgtag ttccggcaaa cggatacttt cgattcgaca gttgggtcaa tcagttctac   1560

agcctggctc caatgggaac aggaaatggg aggaggcgtg tgcagtaa                 1608
```

<210> SEQ ID NO 90
<211> LENGTH: 535
<212> TYPE: PRT
<213> ORGANISM: Norovirus

<400> SEQUENCE: 90

```
Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Leu His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125
```

-continued

```
Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Thr Leu Pro Ile Leu Thr Ile Gly Glu Leu Thr Asn Ser
225                 230                 235                 240

Arg Phe Pro Val Pro Ile Asp Glu Leu Tyr Thr Ser Pro Asn Glu Ser
                245                 250                 255

Leu Val Val Gln Pro Gln Asn Gly Arg Cys Ala Leu Asp Gly Glu Leu
            260                 265                 270

Gln Gly Thr Thr Gln Leu Leu Pro Thr Ala Ile Cys Ser Phe Arg Gly
        275                 280                 285

Arg Ile Asn Gln Lys Val Ser Gly Glu Asn His Val Trp Asn Met Gln
    290                 295                 300

Val Thr Asn Ile Asp Gly Thr Pro Phe Asp Pro Thr Glu Asp Val Pro
305                 310                 315                 320

Ala Pro Leu Gly Thr Pro Asp Phe Ser Gly Lys Leu Phe Gly Val Leu
                325                 330                 335

Ser Gln Arg Asp His Asp Asn Ala Cys Arg Ser His Asp Ala Val Ile
            340                 345                 350

Ala Thr Asn Ser Ala Lys Phe Thr Pro Lys Leu Gly Ala Ile Gln Ile
        355                 360                 365

Gly Thr Trp Glu Gln Asp Asp Val His Ile Asn Gln Pro Thr Lys Phe
    370                 375                 380

Thr Pro Val Gly Leu Phe Glu Ser Glu Gly Phe Asn Gln Trp Thr Leu
385                 390                 395                 400

Pro Asn Tyr Ser Gly Ala Leu Thr Leu Asn Met Gly Leu Ala Pro Pro
                405                 410                 415

Val Ala Pro Thr Phe Pro Gly Glu Gln Ile Leu Phe Phe Arg Ser His
            420                 425                 430

Ile Pro Leu Lys Gly Gly Val Ala Asp Pro Val Ile Asp Cys Leu Leu
        435                 440                 445

Pro Gln Glu Trp Ile Gln His Leu Tyr Gln Glu Ser Ala Pro Ser Gln
    450                 455                 460

Thr Asp Val Ala Leu Ile Arg Phe Thr Asn Pro Asp Thr Gly Arg Val
465                 470                 475                 480

Leu Phe Glu Ala Lys Leu His Arg Ser Gly Tyr Ile Thr Val Ala Asn
                485                 490                 495

Thr Gly Ser Arg Pro Ile Val Val Pro Ala Asn Gly Tyr Phe Arg Phe
            500                 505                 510

Asp Ser Trp Val Asn Gln Phe Tyr Ser Leu Ala Pro Met Gly Thr Gly
        515                 520                 525

Asn Gly Arg Arg Arg Val Gln
    530                 535
```

<210> SEQ ID NO 91
<211> LENGTH: 1608
<212> TYPE: DNA
<213> ORGANISM: Artificial Sequence
<220> FEATURE:
<223> OTHER INFORMATION: Nucleic acid sequence of human codon optimized VP1_GII.12_HS10_A90L

<400> SEQUENCE: 91

```
atgaagatgg cgtctaatga tgctgctcct tccaatgatg gcgcagccgg cctggtccct     60

gaagtgaata acgagactat ggctctcgaa cccgtggccg gagcctcaat tgccgccccc    120

ctcactggcc agaacaacgt gattgatccc tggatcagac tgaacttcgt tcaggctcct    180

aatggggagt tcaccgtgtc cccgagaaac tcccccggcg aagtgttatt gaatttggaa    240

ttaggaccag aactcaaccc ctatctgctc catctgtctc ggatgtacaa cggctatgcg    300

ggcggagtgg aggtgcaagt tcttctcgct ggtaatgcat tcacagcagg aaaattagta    360

tttgcagcgg ttccacccca ttttccactt gaaaacataa gcccaggcca gatcaccatg    420

ttccctcacg tgataatcga cgtgcggaca ttagagcccg tgctgctacc cctgcccgac    480

gtgaggaaca atttctttca ctacaatcag caaaatgaac caagaatgcg cctggtcgcc    540

atgctctata ctcctttaag aagtaatggc agtggggatg acgtgtttac tgttagctgt    600

cgggtgctca cccgaccttc cccagatttc gacttcaatt atctggtccc ccccacggta    660

gagtccaaaa caaagccttt cactcttcca atccttacaa ttggcgaact gaccaactca    720

cgctttccag tgcctattga tgagctgtac acaagtccaa atgaatccct tgtcgttcag    780

ccacagaatg ggcgctgcgc gcttgacggt gagctccagg gcacaacaca actgttgcca    840

accgctatat gctctttcag gggcgtattt aatcagaagg tctccgggga gaaccacgtg    900

tggaacatgc aagtgacgaa tatcgacggg acacctttcg atccaacaga ggatgtccca    960

gcgcctctag gtacccctga cttctcaggc aagttgttcg gcgtcctttc ccagcgcgac   1020

catgataatg cttgccggag ccacgatgcc gtcattgcca ccaactcagc caaattcacc   1080

ccaaaacttg gagcgataca gatcggaact tgggaacaag acgacgtcca tatcaaccaa   1140

ccaacaaagt ttacccctgt tggccttttc gaaagcgaag gctttaacca gtggacactt   1200

cccaattaca gcggggctct cactcttaat atgggactcg caccacccgt cgctccaacg   1260

tttcctggtg agcagatttt gtttttccgc agtcatattc cactgaaggg tggagttgct   1320

gatcccgtga tagactgcct cctccctcag gaatggattc agcacttgta tcaggagtcc   1380

gctccctcgc agaccgatgt ggccctgata cgcttcacaa accccgatac cggaagagtg   1440

ttgtttgaag ctaaacttca tcgctccggt tacatcacag tagccaacac gggttccagg   1500

ccaatcgtag ttccggcaaa cggatacttt cgattcgaca gttgggtcaa tcagttctac   1560

agcctggctc caatgggaac aggaaatggg aggaggcgtg tgcagtaa               1608
```

<210> SEQ ID NO 92
<211> LENGTH: 535
<212> TYPE: PRT
<213> ORGANISM: Norovirus

<400> SEQUENCE: 92

```
Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30
```

-continued

```
Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Ser
65                  70                  75                  80

Leu Gly Pro Glu Leu Asn Pro Tyr Leu Leu His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Thr Leu Pro Ile Leu Thr Ile Gly Glu Leu Thr Asn Ser
225                 230                 235                 240

Arg Phe Pro Val Pro Ile Asp Glu Leu Tyr Thr Ser Pro Asn Glu Ser
                245                 250                 255

Leu Val Val Gln Pro Gln Asn Gly Arg Cys Ala Leu Asp Gly Glu Leu
            260                 265                 270

Gln Gly Thr Thr Gln Leu Leu Pro Thr Ala Ile Cys Ser Phe Arg Gly
        275                 280                 285

Arg Ile Asn Gln Lys Val Ser Gly Glu Asn His Val Trp Asn Met Gln
    290                 295                 300

Val Thr Asn Ile Asp Gly Thr Pro Phe Asp Pro Thr Glu Asp Val Pro
305                 310                 315                 320

Ala Pro Leu Gly Thr Pro Asp Phe Ser Gly Lys Leu Phe Gly Val Leu
                325                 330                 335

Ser Gln Arg Asp His Asp Asn Ala Cys Arg Ser His Asp Ala Val Ile
            340                 345                 350

Ala Thr Asn Ser Ala Lys Phe Thr Pro Lys Leu Gly Ala Ile Gln Ile
        355                 360                 365

Gly Thr Trp Glu Gln Asp Asp Val His Ile Asn Gln Pro Thr Lys Phe
    370                 375                 380

Thr Pro Val Gly Leu Phe Glu Ser Glu Gly Phe Asn Gln Trp Thr Leu
385                 390                 395                 400

Pro Asn Tyr Ser Gly Ala Leu Thr Leu Asn Met Gly Leu Ala Pro Pro
                405                 410                 415

Val Ala Pro Thr Phe Pro Gly Glu Gln Ile Leu Phe Phe Arg Ser His
            420                 425                 430

Ile Pro Leu Lys Gly Gly Val Ala Asp Pro Val Ile Asp Cys Leu Leu
        435                 440                 445

Pro Gln Glu Trp Ile Gln His Leu Tyr Gln Glu Ser Ala Pro Ser Gln
```

450 455 460

Thr Asp Val Ala Leu Ile Arg Phe Thr Asn Pro Asp Thr Gly Arg Val
465 470 475 480

Leu Phe Glu Ala Lys Leu His Arg Ser Gly Tyr Ile Thr Val Ala Asn
485 490 495

Thr Gly Ser Arg Pro Ile Val Val Pro Ala Asn Gly Tyr Phe Arg Phe
500 505 510

Asp Ser Trp Val Asn Gln Phe Tyr Ser Leu Ala Pro Met Gly Thr Gly
515 520 525

Asn Gly Arg Arg Arg Val Gln
530 535

<210> SEQ ID NO 93
<211> LENGTH: 1608
<212> TYPE: DNA
<213> ORGANISM: Artificial Sequence
<220> FEATURE:
<223> OTHER INFORMATION: Nucleic acid sequence of human codon optimized VP1_GII.12_HS10_E80S plus sign A90L

<400> SEQUENCE: 93
atgaagatgg cgtctaatga tgctgctcct tccaatgatg gcgcagccgg cctggtccct 60
gaagtgaata acgagactat ggctctcgaa cccgtggccg gagcctcaat tgccgccccc 120
ctcactggcc agaacaacgt gattgatccc tggatcagac tgaacttcgt tcaggctcct 180
aatggggagt tcaccgtgtc cccgagaaac tcccccggcg aagtgttatt gaatttgagc 240
ttaggaccag aactcaaccc ctatctgctc catctgtctc ggatgtacaa cggctatgcg 300
ggcggagtgg aggtgcaagt tcttctcgct ggtaatgcat tcacagcagg aaaattagta 360
tttgcagcgg ttccacccca ttttccactt gaaaacataa gcccaggcca gatcaccatg 420
ttccctcacg tgataatcga cgtgcggaca ttagagcccg tgctgctacc cctgcccgac 480
gtgaggaaca atttctttca ctacaatcag caaaatgaac caagaatgcg cctggtcgcc 540
atgctctata ctcctttaag aagtaatggc agtggggatg acgtgtttac tgttagctgt 600
cgggtgctca cccgaccttc cccagatttc gacttcaatt atctggtccc ccccacggta 660
gagtccaaaa caaagccttt cactcttcca atccttacaa ttggcgaact gaccaactca 720
cgctttccag tgcctattga tgagctgtac acaagtccaa atgaatccct tgtcgttcag 780
ccacagaatg ggcgctgcgc gcttgacggt gagctccagg gcacaacaca actgttgcca 840
accgctatat gctctttcag gggcgtatt aatcagaagg tctccgggga gaaccacgtg 900
tggaacatgc aagtgacgaa tatcgacggg acacctttcg atccaacaga ggatgtccca 960
gcgcctctag gtaccccctga cttctcaggc aagttgttcg gcgtcctttc ccagcgcgac 1020
catgataatg cttgccggag ccacgatgcc gtcattgcca ccaactcagc caaattcacc 1080
ccaaaacttg gagcgataca gatcggaact tgggaacaag acgacgtcca tatcaaccaa 1140
ccaacaaagt ttacccctgt tggccttttc gaaagcgaag gctttaacca gtggacactt 1200
cccaattaca gcggggctct cactcttaat atgggactcg caccacccgt cgctccaacg 1260
tttcctggtg agcagatttt gtttttccgc agtcatattc cactgaaggg tggagttgct 1320
gatcccgtga tagactgcct cctccctcag gaatggattc agcacttgta tcaggagtcc 1380
gctccctcgc agaccgatgt ggccctgata cgcttcacaa accccgatac cggaagagtg 1440
ttgtttgaag ctaaacttca tcgctccggt tacatcacag tagccaacac gggttccagg 1500
ccaatcgtag ttccggcaaa cggatacttt cgattcgaca gttgggtcaa tcagttctac 1560
agcctggctc caatgggaac aggaaatggg aggaggcgtg tgcagtaa 1608

<210> SEQ ID NO 94
<211> LENGTH: 215
<212> TYPE: PRT
<213> ORGANISM: Norovirus

<400> SEQUENCE: 94

Met Ala Gln Ala Ile Phe Gly Ala Ile Ala Ala Thr Ala Ala Gly Ser
1 5 10 15

Ala Val Gly Ala Gly Ile Gln Ala Gly Thr Glu Ala Ala Leu Gln His
20 25 30

Gln Arg Phe Gln Gln Asp Leu Thr Leu Gln Ser Asn Thr Phe Lys His
35 40 45

Asp Lys Glu Met Leu Gly Leu Gln Val Gly Ala Ser Thr Ala Leu Leu
50 55 60

Gln Asn Ser Leu Asn Thr Arg Tyr Asn Met Leu Thr Asp Ala Gly Leu
65 70 75 80

Ser Ser Ser Asp Ala Ala Arg Met Val Val Gly Ala Pro Ala Thr Arg
85 90 95

Val Val Asp Trp Asn Gly Thr Arg Ile Ser Ala Pro Arg Ser Thr Ala
100 105 110

Thr Thr Leu Arg Ser Gly Gly Phe Met Thr Ile Pro Thr Leu Tyr Lys
115 120 125

Gly Lys Gln Gln Gln Lys Ala Pro Thr Glu Ile Gly Leu Ser Asn Pro
130 135 140

Asn Tyr Gly Ser Ser Val Ser Ser Arg Val Ala Asp Trp Val Ser Ser
145 150 155 160

Gln Asn Ser Ser His Ser Ser Leu Gly Pro Tyr His Pro Ser Ala Leu
165 170 175

Gln Thr Thr Trp Val Thr Pro Pro Gly Ser Ser Ser Thr Ser Thr Ile
180 185 190

Ser Ser Val Ser Thr Val Pro Arg Tyr Phe Asn Thr Asp Arg Leu Pro
195 200 205

Leu Phe Ala Asn Met Arg Lys
210 215

<210> SEQ ID NO 95
<211> LENGTH: 648
<212> TYPE: DNA
<213> ORGANISM: Artificial Sequence
<220> FEATURE:
<223> OTHER INFORMATION: Nucleic acid sequence of human codon optimized VP2_GI.3_Lil08

<400> SEQUENCE: 95
atggctcagg caatcttcgg cgcaatcgct gccactgctg ccggatccgc tgtgggagcc 60
ggcatacagg ccggaactga ggcggccctt cagcatcagc ggttccagca ggatctgaca 120
ttacagagta acacattcaa acatgacaag gagatgctgg gtctgcaggt gggtgccagt 180
actgccctgc tccaaaactc tctgaatacc agatataaca tgttaactga tgcgggactg 240
tctagtagcg acgcagctcg catggtcgtg ggcgccccag ctacgagagt tgtggactgg 300
aatggcaccc gaatcagtgc accaaggtct acagccacta ccctcagaag tggcggcttt 360
atgaccatcc cgactttata caagggcaaa caacagcaga aggcacctac tgaaatcggt 420
ctctccaatc ccaactacgg cagcagtgtg tcttctcgcg tggccgattg ggtctcaagc 480
cagaactcca gtcatagttc tcttgggcct tatcatccat cagccttgca gacaacttgg 540
gtcaccccac ccgggtccag tagcacgtca accatcagtt ccgtctccac agtccctcgc 600
tattttaata ctgataggct tcccctgttc gcaaacatga ggaagtga 648

<210> SEQ ID NO 96
<211> LENGTH: 259
<212> TYPE: PRT
<213> ORGANISM: Norovirus

<400> SEQUENCE: 96

Met Ala Ser Ala Phe Leu Ala Gly Leu Ala Gly Asp Val Ile Thr Asn
1 5 10 15

Gly Val Gly Ser Leu Ile Asn Ala Gly Ala Asn Ala Val Asn Gln Lys
20 25 30

Val Glu Tyr Asp Phe Asn Lys Gln Leu Gln Met Ala Ser Phe Lys His
35 40 45

Asp Lys Glu Met Leu Gln Ser Gln Val Leu Ala Thr Lys Gln Leu Gln
50 55 60

Gln Glu Met Met Asn Ile Arg Gln Gly Val Leu Thr Ala Gly Gly Phe
65 70 75 80

Ser Pro Ala Asp Ala Ala Arg Gly Ala Val Asn Ala Pro Met Thr Lys
85 90 95

Ile Leu Asp Trp Asn Gly Thr Arg Tyr Trp Ala Pro Asn Ser Met Lys
100 105 110

Thr Thr Ser Tyr Ser Gly Gln Phe Ser Ser Ser Pro Val His Lys Ser
115 120 125

Pro Ala Pro Ser Gln His Thr Ala Leu Pro Lys Ser Arg Leu Gln Asn
130 135 140

Asp Phe Ala Ser Val Tyr Ser Phe Pro Ser Ser Val Ser Ser Gln Ser
145 150 155 160

Thr His Ser Thr Ala Leu Ser Ala Gly Thr Gly Ser Ser Arg Ser Ile
165 170 175

Ser Pro Ser Thr Ala Thr Pro Thr Leu Ser Arg Thr Ser Asp Trp Val
180 185 190

Arg Gly Gln Asn Glu Arg Leu Ser Pro Phe Met Asp Gly Ala Leu Gln
195 200 205

Thr Ala Phe Val Thr Pro Pro Ser Ser Lys Ala Ser Ser Asn Gly Thr
210 215 220

Val Ser Thr Val Pro Lys Ala Val Leu Asp Ser Trp Thr Pro Met Phe
225 230 235 240

Asn Thr His Arg Gln Pro Leu Phe Ala His Pro Arg Arg Arg Gly Glu
245 250 255

Ser Gln Val

<210> SEQ ID NO 97
<211> LENGTH: 780
<212> TYPE: DNA
<213> ORGANISM: Artificial Sequence
<220> FEATURE:
<223> OTHER INFORMATION: Nucleic acid sequence of human codon optimized VP2_GII6_HS10

<400> SEQUENCE: 97
atggcctccg catttctagc tggattggcc ggggacgtga tcaccaacgg cgtaggatcg 60
ctgattaatg caggcgccaa tgctgttaat cagaaggttg aatacgactt caacaaacaa 120

```
ctgcagatgg cttcattcaa gcacgacaaa gaaatgttgc agtcacaggt tctcgccacc    180

aagcagctac aacaggagat gatgaacatt cggcagggcg tactgaccgc tggaggattc    240

agccctgctg acgcagcacg gggggccgtg aacgcgccga tgaccaagat cctggattgg    300

aacggaactc ggtattgggc tcccaactct atgaaaacca cttcttactc tggtcagttc    360

tccagctcgc cagtccacaa aagtccggcc ccttcacagc acacagcact ccctaagtcc    420

aggctgcaaa acgactttgc ctccgtgtac tccttcccat ccagcgtgtc atctcagagc    480

actcattcaa ccgccctgtc cgccggaact gggtctagcc gcagcatttc cccaagcaca    540

gctactccaa ctctgagcag gactagcgat tgggtcagag gacaaaacga acgactgtcc    600

cctttcatgg acggagctct gcaaaccgcc ttcgtcactc cacctagcag caaggcctcg    660

agcaacggta cggttagtac cgtgccaaag gctgttcttg acagctggac ccccatgttt    720

aacacacaca ggcagccatt gtttgcacac cccaggcgac ggggagaatc acaagtttag    780
```

<210> SEQ ID NO 98
<211> LENGTH: 543
<212> TYPE: PRT
<213> ORGANISM: Norovirus

<400> SEQUENCE: 98

```
Met Met Met Ala Ser Lys Asp Ala Pro Thr Asn Met Asp Gly Thr Ser
1               5                   10                  15

Gly Ala Gly Gln Leu Val Pro Glu Val Ser Thr Ala Glu Pro Ile Ser
            20                  25                  30

Met Glu Pro Val Ala Gly Ala Ala Thr Ala Ala Ala Thr Ala Gly Gln
        35                  40                  45

Val Asn Met Ile Asp Pro Trp Ile Met Ser Asn Tyr Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Ser Leu Gly Pro His Leu Asn Pro Phe Leu Ser His Leu
                85                  90                  95

Ala Gln Met Tyr Asn Gly Trp Val Gly Asn Met Lys Val Arg Val Leu
            100                 105                 110

Leu Ala Gly Asn Ala Phe Thr Ala Gly Lys Ile Ile Ile Ser Cys Val
        115                 120                 125

Pro Pro Gly Phe Ala Ala Gln Asn Val Ser Ile Ala Gln Ala Thr Met
    130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Asn Asn Asp Ser Thr
                165                 170                 175

Pro Thr Met Arg Leu Ile Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205

Thr Cys Pro Ser Pro Asp Phe Asn Phe Leu Phe Leu Val Pro Pro Asn
    210                 215                 220

Val Glu Gln Lys Thr Lys Pro Phe Ser Val Pro Asn Leu Pro Leu Asn
225                 230                 235                 240

Val Leu Ser Asn Ser Arg Val Pro Ser Leu Ile Lys Ser Met Met Val
                245                 250                 255
```

-continued

```
Ser Gln Asp His Gly Gln Met Val Gln Phe Gln Asn Gly Arg Val Thr
            260                 265                 270

Leu Asp Gly Gln Leu Gln Gly Thr Thr Pro Thr Ser Ala Ser Gln Leu
        275                 280                 285

Cys Lys Ile Arg Gly Thr Val Tyr His Ala Thr Gly Gly Gln Gly Leu
    290                 295                 300

Asn Leu Thr Glu Ile Asp Gly Thr Pro Tyr His Ala Phe Glu Ser Pro
305                 310                 315                 320

Ala Pro Ile Gly Phe Pro Asp Leu Gly Glu Cys Asp Trp His Ile Asn
                325                 330                 335

Ala Ser Pro Ala Asn Ala Phe Thr Asp Gly Ser Ile Ile His Arg Ile
            340                 345                 350

Asp Val Ala Gln Asp Ser Thr Phe Ala Pro His Leu Gly Thr Ile His
        355                 360                 365

Tyr Thr Asn Ala Asp Tyr Asn Ala Asn Val Gly Leu Ile Cys Ser Leu
    370                 375                 380

Glu Trp Leu Ser Pro Pro Ser Gly Gly Ala Pro Lys Val Asn Pro Trp
385                 390                 395                 400

Ala Ile Pro Arg Tyr Gly Ser Thr Leu Thr Glu Ala Ala Gln Leu Ala
                405                 410                 415

Pro Pro Ile Tyr Pro Pro Gly Phe Gly Glu Ala Ile Val Phe Phe Met
            420                 425                 430

Ser Asp Phe Pro Ile Ala Asn Gly Ser Asp Gly Leu Ser Val Pro Cys
        435                 440                 445

Thr Ile Pro Gln Glu Phe Val Thr His Phe Val Asn Glu Gln Ala Pro
    450                 455                 460

Thr Arg Gly Glu Ala Ala Leu Leu His Tyr Val Asp Pro Asp Thr His
465                 470                 475                 480

Arg Asn Leu Gly Glu Phe Lys Leu Tyr Pro Glu Gly Phe Met Thr Cys
                485                 490                 495

Val Pro Asn Ser Ser Gly Ser Gly Pro Gln Thr Leu Pro Ile Asn Gly
            500                 505                 510

Val Phe Thr Phe Ile Ser Trp Val Ser Arg Phe Tyr Gln Leu Lys Pro
        515                 520                 525

Val Gly Thr Thr Gly Pro Val Arg Arg Leu Gly Ile Arg Arg Ser
    530                 535                 540


<210> SEQ ID NO 99
<211> LENGTH: 212
<212> TYPE: PRT
<213> ORGANISM: Norovirus

<400> SEQUENCE: 99

Met Ala Gln Ala Ile Ile Gly Ala Ile Ala Ala Ser Thr Ala Gly Ser
1               5                   10                  15

Ala Leu Gly Ala Gly Ile Gln Val Gly Gly Glu Ala Ala Leu Gln Ser
            20                  25                  30

Gln Arg Tyr Gln Gln Asn Leu Gln Leu Gln Glu Asn Ser Phe Lys His
        35                  40                  45

Asp Arg Glu Met Ile Gly Tyr Gln Val Glu Ala Ser Asn Gln Leu Leu
    50                  55                  60

Ala Lys Asn Leu Ala Thr Arg Tyr Ser Leu Leu Arg Ala Gly Gly Leu
65                  70                  75                  80

Thr Ser Ala Asp Ala Ala Arg Ser Val Ala Gly Ala Pro Val Thr Arg
                85                  90                  95
```

Ile Val Asp Trp Asn Gly Val Arg Val Ser Ala Pro Glu Ser Ser Ala
100 105 110

Thr Thr Leu Arg Ser Gly Gly Phe Met Ser Val Pro Ile Pro Phe Ala
115 120 125

Ser Lys Gln Lys Gln Val Gln Ser Ser Gly Ile Ser Asn Pro Asn Tyr
130 135 140

Ser Pro Ser Ser Ile Ser Arg Thr Thr Ser Trp Val Glu Ser Gln Asn
145 150 155 160

Ser Ser Arg Phe Gly Asn Leu Ser Pro Tyr His Ala Glu Ala Leu Asn
165 170 175

Thr Val Trp Leu Thr Pro Pro Gly Ser Thr Ala Ser Ser Thr Leu Ser
180 185 190

Ser Val Pro Arg Gly Tyr Phe Asn Thr Asp Arg Leu Pro Leu Phe Ala
195 200 205

Asn Asn Arg Arg
210

<210> SEQ ID NO 100
<211> LENGTH: 639
<212> TYPE: DNA
<213> ORGANISM: Artificial Sequence
<220> FEATURE:
<223> OTHER INFORMATION: Nucleic acid sequence of human codon optimized VP.2_GI1_Norwalk

<400> SEQUENCE: 100
atggctcagg ccattattgg cgccatcgct gcaagtacag ccgggagtgc attgggggcc 60
ggaatacagg tgggcgggga agctgcattg cagagccagc ggtaccagca aaacctgcag 120
ttacaggaga atagctttaa acacgacagg gagatgattg gatatcaggt ggaggccagc 180
aatcagctgc tcgccaaaaa cttggctact cgatactcat tactgcgcgc cggggggttg 240
actagcgccg acgccgcacg atctgtcgca ggcgcccccg tgactcggat cgtagactgg 300
aacggggtac gagtctcggc tcccgagtcg tctgcaacca ccctgaggtc gggagggttt 360
atgtccgtgc ccatcccatt cgctagcaaa cagaaacagg tccagagctc cggaatctcc 420
aatcccaatt actcccctag ctctatctct cgtaccactt cctgggtcga gagtcagaac 480
agcagtagat ttggcaacct gagcccctac catgctgaag ccctgaacac tgtgtggttg 540
actccacctg gtagcacggc ctcctcaacc ctgagttccg tgcctcgcgg gtacttcaat 600
accgacagac ttcctctgtt cgctaacaac cgccgctga 639

<210> SEQ ID NO 101
<211> LENGTH: 538
<212> TYPE: PRT
<213> ORGANISM: Norovirus

<400> SEQUENCE: 101

Met Met Met Ala Ser Lys Asp Ala Pro Ser Asn Met Asp Gly Thr Ser
1 5 10 15

Gly Ala Gly Gln Leu Val Pro Glu Val Asn Ala Ala Glu Pro Leu Pro
20 25 30

Leu Glu Pro Val Val Gly Ala Ala Thr Ala Val Ala Thr Ala Gly Gln
35 40 45

Val Asn Met Ile Asp Pro Trp Ile Met Asn Asn Phe Val Gln Ala Pro
50 55 60

Glu Gly Glu Phe Thr Ile Ser Pro Asn Asn Thr Pro Gly Asp Ile Leu

-continued

```
65                  70                  75                  80

Phe Asp Leu Arg Leu Gly Pro His Leu Asn Pro Phe Leu Leu His Leu
                85                  90                  95

Ser Gln Met Tyr Asn Gly Trp Val Gly Asn Met Arg Val Arg Val Met
            100                 105                 110

Leu Ala Gly Asn Ala Phe Ser Ala Gly Lys Ile Ile Ile Cys Cys Val
        115                 120                 125

Pro Pro Gly Phe Glu Ser Gln Asn Ile Ser Ile Gly Gln Ala Thr Met
    130                 135                 140

Phe Pro His Val Ile Ala Asp Val Arg Val Leu Glu Pro Ile Glu Val
145                 150                 155                 160

Pro Leu Asp Asp Val Arg Asn Val Leu Phe His Thr Asn Glu Asn Arg
                165                 170                 175

Pro Thr Met Arg Leu Leu Cys Met Leu Tyr Thr Pro Leu Arg Ala Gly
            180                 185                 190

Gly Ala Ser Ser Gly Thr Asp Pro Phe Val Ile Ala Gly Arg Val Leu
        195                 200                 205

Thr Cys Pro Ala Pro Asp Phe Asn Phe Leu Phe Leu Val Pro Pro Ser
    210                 215                 220

Val Glu Gln Lys Thr Arg Gln Leu Thr Ile Pro Asn Ile Pro Leu Asn
225                 230                 235                 240

Asn Leu Ala Asn Ser Arg Val Pro Ala Met Ile Asn Lys Met Thr Val
                245                 250                 255

Ser Ala Asp Gln Asn Gln Val Val Gln Phe Gln Asn Gly Arg Cys Thr
            260                 265                 270

Leu Glu Gly Gln Leu Leu Gly Thr Thr Pro Val Ser Ala Asn Gln Val
        275                 280                 285

Ala Arg Ile Arg Gly Lys Val Phe Ser Thr Asn Ser Gly Thr Gly Leu
    290                 295                 300

Asn Leu Thr Glu Val Asp Gly Thr Pro Tyr His Ala Phe Glu Ser Pro
305                 310                 315                 320

Ala Pro Leu Gly Phe Pro Asp Ile Gly Asn Cys Asp Trp His Val Tyr
                325                 330                 335

Ala Phe Lys Val Asn Gln Asn Thr Gly Asp Pro Met Tyr Arg Leu Asp
            340                 345                 350

Ile Thr Gln Gly Asn Ser Phe Ala Pro His Leu Gly Ser Ile Glu Phe
        355                 360                 365

Ser Ser Glu Asn His Pro Ser Gly Asp Gln Leu Gly Thr Leu Thr Trp
    370                 375                 380

Ile Ser Pro Leu Asn Asn Ala Ser Arg Val Asp Pro Trp Lys Ile Pro
385                 390                 395                 400

Thr Tyr Gly Ser Thr Leu Thr Glu Ser Thr Asn Leu Ala Pro Pro Ile
                405                 410                 415

Phe Pro Pro Gly Phe Gly Glu Ala Ile Val Tyr Phe Met Ser Asp Phe
            420                 425                 430

Pro Ile Val Ser Gly Asn Thr Ala Gln Ile Pro Cys Thr Leu Pro Gln
        435                 440                 445

Glu Phe Val Ser Ser Phe Val Glu Gln Gln Ala Pro Ile Arg Gly Glu
    450                 455                 460

Ala Ala Leu Leu His Tyr Val Asp Pro Asp Thr His Arg Asn Leu Gly
465                 470                 475                 480

Glu Phe Lys Leu Tyr Pro Asp Gly Phe Ile Thr Cys Val Pro Asn Thr
                485                 490                 495
```

Gly Gly Gly Pro Gln Asn Leu Pro Ser Asn Gly Val Phe Val Phe Ser
500 505 510

Ser Trp Val Ser Arg Tyr Tyr Gln Leu Lys Pro Val Gly Thr Thr Gly
515 520 525

Pro Val Arg Arg Leu Gly Val Arg Arg Val
530 535

<210> SEQ ID NO 102
<211> LENGTH: 49
<212> TYPE: DNA
<213> ORGANISM: Artificial Sequence
<220> FEATURE:
<223> OTHER INFORMATION: Primer IF-NoV(US68)VP1(ORF1)(hCod).c

<400> SEQUENCE: 102
tcgtgcttcg gcaccagtac aatgatgatg gctagtaaag atgcgacct 49

<210> SEQ ID NO 103
<211> LENGTH: 52
<212> TYPE: DNA
<213> ORGANISM: Artificial Sequence
<220> FEATURE:
<223> OTHER INFORMATION: Primer IF-NoV(US68)VP1(ORF1)(hCod).r

<400> SEQUENCE: 103
actaaagaaa ataggccttt atctccgcag accgaggcgt ccgcgggcag aa 52

<210> SEQ ID NO 104
<211> LENGTH: 49
<212> TYPE: DNA
<213> ORGANISM: Artificial Sequence
<220> FEATURE:
<223> OTHER INFORMATION: Primer IF-GI3Lil08VP1.c

<400> SEQUENCE: 104
tcgtgcttcg gcaccagtac aatgatgatg gcttccaagg atgctccca 49

<210> SEQ ID NO 105
<211> LENGTH: 49
<212> TYPE: DNA
<213> ORGANISM: Artificial Sequence
<220> FEATURE:
<223> OTHER INFORMATION: Primer IF-GI3Lil08VP1.r

<400> SEQUENCE: 105
actaaagaaa ataggcctct agctccgtct gatcccgagc ctccgaact 49

<210> SEQ ID NO 106
<211> LENGTH: 59
<212> TYPE: DNA
<213> ORGANISM: Artificial Sequence
<220> FEATURE:
<223> OTHER INFORMATION: Primer VP1_GI.3Lil08(S94L).r

<400> SEQUENCE: 106
ctgagccaag tggagcagaa acggattcaa gtgtggtcct agctgcaggt caaacaaga 59

<210> SEQ ID NO 107
<211> LENGTH: 56
<212> TYPE: DNA
<213> ORGANISM: Artificial Sequence
<220> FEATURE:
<223> OTHER INFORMATION: Primer VP1_GI.3Lil08(S94L).c

<400> SEQUENCE: 107
aggaccacac ttgaatccgt ttctgctcca cttggctcag atgtataatg gatggg 56

<210> SEQ ID NO 108
<211> LENGTH: 57
<212> TYPE: DNA
<213> ORGANISM: Artificial Sequence
<220> FEATURE:
<223> OTHER INFORMATION: Primer VP1_GI.3Lil08(Q84S).r

<400> SEQUENCE: 108
gtgtggtcct aggctcaggt caaacaagat gtcacccggg gtgttgtttg ggcttat 57

<210> SEQ ID NO 109
<211> LENGTH: 48
<212> TYPE: DNA
<213> ORGANISM: Artificial Sequence
<220> FEATURE:
<223> OTHER INFORMATION: Primer VP1_GI.3Lil08(Q84S).c

<400> SEQUENCE: 109
ggtgacatct tgtttgacct gagcctagga ccacacttga atccgttt 48

<210> SEQ ID NO 110
<211> LENGTH: 48
<212> TYPE: DNA
<213> ORGANISM: Artificial Sequence
<220> FEATURE:
<223> OTHER INFORMATION: Primer IF-GI3Lil08VP2.c

<400> SEQUENCE: 110
tcgtgcttcg gcaccagtac aatggctcag gcaatcttcg gcgcaatc 48

<210> SEQ ID NO 111
<211> LENGTH: 49
<212> TYPE: DNA
<213> ORGANISM: Artificial Sequence
<220> FEATURE:
<223> OTHER INFORMATION: Primer IF-GI3Lil08VP2.r

<400> SEQUENCE: 111
actaaagaaa ataggccttc acttcctcat gtttgcgaac aggggaagc 49

<210> SEQ ID NO 112
<211> LENGTH: 48
<212> TYPE: DNA
<213> ORGANISM: Artificial Sequence
<220> FEATURE:
<223> OTHER INFORMATION: Primer IF-(160)GI.5_Sikl13_VP1.c

<400> SEQUENCE: 112
tcgtgcttcg gcaccagtac aatgatgatg gcctccaaag acgctcct 48

<210> SEQ ID NO 113
<211> LENGTH: 53
<212> TYPE: DNA
<213> ORGANISM: Artificial Sequence
<220> FEATURE:
<223> OTHER INFORMATION: Primer IF-GI.5_Sikl13_VP1.r

<400> SEQUENCE: 113
actaaagaaa ataggccttc agcgccgcac gccaaggcgc ccccgggcag atg 53

<210> SEQ ID NO 114
<211> LENGTH: 51
<212> TYPE: DNA

<213> ORGANISM: Artificial Sequence
<220> FEATURE:
<223> OTHER INFORMATION: Primer GI.5(hCod)(Q84S).r

<400> SEQUENCE: 114
gatgagggcc taagctcagg tcgaacagaa tatcccctgg tgtgttgtta g 51

<210> SEQ ID NO 115
<211> LENGTH: 51
<212> TYPE: DNA
<213> ORGANISM: Artificial Sequence
<220> FEATURE:
<223> OTHER INFORMATION: Primer GI.5(hCod)(Q84S).c

<400> SEQUENCE: 115
tattctgttc gacctgagct taggccctca tctcaacccc ttcttggccc a 51

<210> SEQ ID NO 116
<211> LENGTH: 50
<212> TYPE: DNA
<213> ORGANISM: Artificial Sequence
<220> FEATURE:
<223> OTHER INFORMATION: Primer GI.5(hCod)(A94L).r

<400> SEQUENCE: 116
atctggctca ggtggagcaa gaaggggttg agatgagggc ctaactgcag 50

<210> SEQ ID NO 117
<211> LENGTH: 51
<212> TYPE: DNA
<213> ORGANISM: Artificial Sequence
<220> FEATURE:
<223> OTHER INFORMATION: Primer GI.5(hCod)(A94L).c

<400> SEQUENCE: 117
tctcaacccc ttcttgctcc acctgagcca gatgtacaat ggctgggtgg g 51

<210> SEQ ID NO 118
<211> LENGTH: 54
<212> TYPE: DNA
<213> ORGANISM: Artificial Sequence
<220> FEATURE:
<223> OTHER INFORMATION: Primer IF-(160)GII.2_CGMH11_VP1.c

<400> SEQUENCE: 118
tcgtgcttcg gcaccagtac aatgaagatg gcatccaacg acgccgcacc cagc 54

<210> SEQ ID NO 119
<211> LENGTH: 53
<212> TYPE: DNA
<213> ORGANISM: Artificial Sequence
<220> FEATURE:
<223> OTHER INFORMATION: Primer IF-GII.2_CGMH11_VP1.r

<400> SEQUENCE: 119
actaaagaaa ataggccttt actggatccg tcggcgaccg ttccctgtgc cca 53

<210> SEQ ID NO 120
<211> LENGTH: 59
<212> TYPE: DNA
<213> ORGANISM: Artificial Sequence
<220> FEATURE:
<223> OTHER INFORMATION: Primer VP1_GII.2CGMH11(E80S).r

<400> SEQUENCE: 120
ttctggtccc aggctgagat tgaggagcac ttccccaggg ctatttctag ggctgaccg 59

<210> SEQ ID NO 121
<211> LENGTH: 48
<212> TYPE: DNA
<213> ORGANISM: Artificial Sequence
<220> FEATURE:
<223> OTHER INFORMATION: Primer VP1_GII.2CGMH11(E80S).c

<400> SEQUENCE: 121
ggaagtgctc ctcaatctca gcctgggacc agaacttaat ccgtacct 48

<210> SEQ ID NO 122
<211> LENGTH: 59
<212> TYPE: DNA
<213> ORGANISM: Artificial Sequence
<220> FEATURE:
<223> OTHER INFORMATION: Primer VP1_GII.2CGMH11(A90L).r

<400> SEQUENCE: 122
tccgggccag gtggagcagg tacggattaa gttctggtcc cagctcgaga ttgaggagc 59

<210> SEQ ID NO 123
<211> LENGTH: 59
<212> TYPE: DNA
<213> ORGANISM: Artificial Sequence
<220> FEATURE:
<223> OTHER INFORMATION: Primer VP1_GII.2CGMH11(A90L).c

<400> SEQUENCE: 123
gggaccagaa cttaatccgt acctgctcca cctggcccgg atgtacaatg gatatgcag 59

<210> SEQ ID NO 124
<211> LENGTH: 52
<212> TYPE: DNA
<213> ORGANISM: Artificial Sequence
<220> FEATURE:
<223> OTHER INFORMATION: Primer IF-(160)GII.3_Jing13_VP1.c

<400> SEQUENCE: 124
tcgtgcttcg gcaccagtac aatgaaaatg gcttccaacg atgcagcacc ct 52

<210> SEQ ID NO 125
<211> LENGTH: 50
<212> TYPE: DNA
<213> ORGANISM: Artificial Sequence
<220> FEATURE:
<223> OTHER INFORMATION: Primer IF-GII.3_Jing13_VP1.r

<400> SEQUENCE: 125
actaaagaaa ataggccttt actggatccg ccgtctgcca ttgcctgtac 50

<210> SEQ ID NO 126
<211> LENGTH: 59
<212> TYPE: DNA
<213> ORGANISM: Artificial Sequence
<220> FEATURE:
<223> OTHER INFORMATION: Primer VP1_GII.3Jing13(E80S).r

<400> SEQUENCE: 126
atttcagggc ccaggctcaa attcaagaga acctccccgg gggagtttcg aggagagac 59

<210> SEQ ID NO 127
<211> LENGTH: 48
<212> TYPE: DNA
<213> ORGANISM: Artificial Sequence
<220> FEATURE:

<223> OTHER INFORMATION: Primer VP1_GII.3Jing13(E80S).c

<400> SEQUENCE: 127
ggaggttctc ttgaatttga gcctgggccc tgaaattaat ccttatct 48

<210> SEQ ID NO 128
<211> LENGTH: 59
<212> TYPE: DNA
<213> ORGANISM: Artificial Sequence
<220> FEATURE:
<223> OTHER INFORMATION: Primer VP1_GII.3Jing13(A90L).r

<400> SEQUENCE: 128
attcgggcta gatggagcag ataaggatta atttcagggc ccagttccaa attcaagag 59

<210> SEQ ID NO 129
<211> LENGTH: 56
<212> TYPE: DNA
<213> ORGANISM: Artificial Sequence
<220> FEATURE:
<223> OTHER INFORMATION: Primer VP1_GII.3Jing13(A90L).c

<400> SEQUENCE: 129
gggccctgaa attaatcctt atctgctcca tctagcccga atgtacaacg gctacg 56

<210> SEQ ID NO 130
<211> LENGTH: 49
<212> TYPE: DNA
<213> ORGANISM: Artificial Sequence
<220> FEATURE:
<223> OTHER INFORMATION: Primer IF-GII.4Syd12VP1.c

<400> SEQUENCE: 130
tcgtgcttcg gcaccagtac aatgaaaatg gcctcgagtg acgctaacc 49

<210> SEQ ID NO 131
<211> LENGTH: 48
<212> TYPE: DNA
<213> ORGANISM: Artificial Sequence
<220> FEATURE:
<223> OTHER INFORMATION: Primer IF-GII.4Syd12VP1.r

<400> SEQUENCE: 131
actaaagaaa ataggccttc agacagccct gcgtctgcca gtcccatt 48

<210> SEQ ID NO 132
<211> LENGTH: 54
<212> TYPE: DNA
<213> ORGANISM: Artificial Sequence
<220> FEATURE:
<223> OTHER INFORMATION: Primer VP1_GII.4Syd12(A39V).r

<400> SEQUENCE: 132
gaccggccac ggggactgct atggctgcgc ccaccacagg ctccagggcc atca 54

<210> SEQ ID NO 133
<211> LENGTH: 54
<212> TYPE: DNA
<213> ORGANISM: Artificial Sequence
<220> FEATURE:
<223> OTHER INFORMATION: Primer VP1_GII.4Syd12(A39V).c

<400> SEQUENCE: 133
gggcgcagcc atagcagtcc ccgtggccgg tcagcagaat gtgattgacc cgtg 54

<210> SEQ ID NO 134
<211> LENGTH: 51
<212> TYPE: DNA
<213> ORGANISM: Artificial Sequence
<220> FEATURE:
<223> OTHER INFORMATION: Primer VP1_GII.4Syd12(V47P).r

<400> SEQUENCE: 134
cgtatccacg ggtcaatggg attctgctga ccggccacgg gcgctgctat g 51

<210> SEQ ID NO 135
<211> LENGTH: 53
<212> TYPE: DNA
<213> ORGANISM: Artificial Sequence
<220> FEATURE:
<223> OTHER INFORMATION: Primer VP1_GII.4Syd12(V47P).c

<400> SEQUENCE: 135
ggccggtcag cagaatccca ttgacccgtg gatacgcaac aattttgtcc aag 53

<210> SEQ ID NO 136
<211> LENGTH: 48
<212> TYPE: DNA
<213> ORGANISM: Artificial Sequence
<220> FEATURE:
<223> OTHER INFORMATION: Primer VP1_GII.4Syd12(R53I).r

<400> SEQUENCE: 136
tggacaaaat tgttgattat ccacgggtca atcacattct gctgaccg 48

<210> SEQ ID NO 137
<211> LENGTH: 50
<212> TYPE: DNA
<213> ORGANISM: Artificial Sequence
<220> FEATURE:
<223> OTHER INFORMATION: Primer VP1_GII.4Syd12(R53I).c

<400> SEQUENCE: 137
gattgacccg tggataatca acaattttgt ccaagcccct ggtggggagt 50

<210> SEQ ID NO 138
<211> LENGTH: 50
<212> TYPE: DNA
<213> ORGANISM: Artificial Sequence
<220> FEATURE:
<223> OTHER INFORMATION: Primer GII.4(P80S).r

<400> SEQUENCE: 138
gatcgggtcc caagctggcc gaccacagga tttctcctgg cgcatttctc 50

<210> SEQ ID NO 139
<211> LENGTH: 50
<212> TYPE: DNA
<213> ORGANISM: Artificial Sequence
<220> FEATURE:
<223> OTHER INFORMATION: Primer GII.4(P80S).c

<400> SEQUENCE: 139
aatcctgtgg tcggccagct tgggacccga tctgaacccc tatttgtcac 50

<210> SEQ ID NO 140
<211> LENGTH: 56
<212> TYPE: DNA
<213> ORGANISM: Artificial Sequence
<220> FEATURE:
<223> OTHER INFORMATION: Primer GII.4(S90L).r

<400> SEQUENCE: 140
atccgagcga gatgcagcaa ataggggttc agatcgggtc ccaatggggc cgacca 56

<210> SEQ ID NO 141
<211> LENGTH: 48
<212> TYPE: DNA
<213> ORGANISM: Artificial Sequence
<220> FEATURE:
<223> OTHER INFORMATION: Primer GII.4(S90L).c

<400> SEQUENCE: 141
tctgaacccc tatttgctgc atctcgctcg gatgtacaac gggtatgc 48

<210> SEQ ID NO 142
<211> LENGTH: 50
<212> TYPE: DNA
<213> ORGANISM: Artificial Sequence
<220> FEATURE:
<223> OTHER INFORMATION: Primer VP1_GII.4Syd12(Del(35-42)).r

<400> SEQUENCE: 142
cacattctgc tgaccgccca ccacaggctc cagggccatc acctcattat 50

<210> SEQ ID NO 143
<211> LENGTH: 48
<212> TYPE: DNA
<213> ORGANISM: Artificial Sequence
<220> FEATURE:
<223> OTHER INFORMATION: Primer VP1_GII.4Syd12(Del(35-42)).c

<400> SEQUENCE: 143
ggagcctgtg gtgggcggtc agcagaatgt gattgacccg tggatacg 48

<210> SEQ ID NO 144
<211> LENGTH: 60
<212> TYPE: DNA
<213> ORGANISM: Artificial Sequence
<220> FEATURE:
<223> OTHER INFORMATION: Primer VP1_GII.4Syd12(SSTAVATA).r

<400> SEQUENCE: 144
ctgaccggct gtagcgacgg cggtggagct gcccaccaca ggctccaggg ccatcacctc 60

<210> SEQ ID NO 145
<211> LENGTH: 60
<212> TYPE: DNA
<213> ORGANISM: Artificial Sequence
<220> FEATURE:
<223> OTHER INFORMATION: Primer VP1_GII.4Syd12(SSTAVATA).c

<400> SEQUENCE: 145
tgtggtgggc agctccaccg ccgtcgctac agccggtcag cagaatgtga ttgacccgtg 60

<210> SEQ ID NO 146
<211> LENGTH: 49
<212> TYPE: DNA
<213> ORGANISM: Artificial Sequence
<220> FEATURE:
<223> OTHER INFORMATION: Primer IF-GII.6Ohi12VP1.c

<400> SEQUENCE: 146
tcgtgcttcg gcaccagtac aatgaagatg gcaagcaacg acgcagctc 49

<210> SEQ ID NO 147
<211> LENGTH: 54

<212> TYPE: DNA
<213> ORGANISM: Artificial Sequence
<220> FEATURE:
<223> OTHER INFORMATION: Primer IF-GII.6Ohi12VP1.r

<400> SEQUENCE: 147
actaaagaaa ataggccttc actgatcccg gcgtcgcccc tggcctgtcc ccat 54

<210> SEQ ID NO 148
<211> LENGTH: 51
<212> TYPE: DNA
<213> ORGANISM: Artificial Sequence
<220> FEATURE:
<223> OTHER INFORMATION: Primer IF-GII.6HS10VP2.c

<400> SEQUENCE: 148
tcgtgcttcg gcaccagtac aatggcctcc gcatttctag ctggattggc c 51

<210> SEQ ID NO 149
<211> LENGTH: 53
<212> TYPE: DNA
<213> ORGANISM: Artificial Sequence
<220> FEATURE:
<223> OTHER INFORMATION: Primer IF-GII.6HS10VP2.r

<400> SEQUENCE: 149
actaaagaaa ataggcctct aaacttgtga ttctccccgt cgcctggggt gtg 53

<210> SEQ ID NO 150
<211> LENGTH: 59
<212> TYPE: DNA
<213> ORGANISM: Artificial Sequence
<220> FEATURE:
<223> OTHER INFORMATION: Primer VP1_GII.6Ohi12(E80S).r

<400> SEQUENCE: 150
agttcagggc cgaggctcag attgagcagc atctcgcccg gggagttccg gggggagac 59

<210> SEQ ID NO 151
<211> LENGTH: 48
<212> TYPE: DNA
<213> ORGANISM: Artificial Sequence
<220> FEATURE:
<223> OTHER INFORMATION: Primer VP1_GII.6Ohi12(E80S).c

<400> SEQUENCE: 151
cgagatgctg ctcaatctga gcctcggccc tgaactaaac ccttatct 48

<210> SEQ ID NO 152
<211> LENGTH: 59
<212> TYPE: DNA
<213> ORGANISM: Artificial Sequence
<220> FEATURE:
<223> OTHER INFORMATION: Primer VP1_GII.6Ohi12(S90L).c

<400> SEQUENCE: 152
ccctgaacta aacccttatc tgctccacct ttcacggatg tacaatggct acgcaggag 59

<210> SEQ ID NO 153
<211> LENGTH: 52
<212> TYPE: DNA
<213> ORGANISM: Artificial Sequence
<220> FEATURE:
<223> OTHER INFORMATION: Primer IF-(160)GII.12_HS10_VP1.c

<400> SEQUENCE: 153
tcgtgcttcg gcaccagtac aatgaagatg gcgtctaatg atgctgctcc tt 52

<210> SEQ ID NO 154
<211> LENGTH: 54
<212> TYPE: DNA
<213> ORGANISM: Artificial Sequence
<220> FEATURE:
<223> OTHER INFORMATION: Primer IF-GII.12_HS10_VP1.r

<400> SEQUENCE: 154
actaaagaaa ataggccttt actgcacacg cctcctccca tttcctgttc ccat 54

<210> SEQ ID NO 155
<211> LENGTH: 48
<212> TYPE: DNA
<213> ORGANISM: Artificial Sequence
<220> FEATURE:
<223> OTHER INFORMATION: Primer GII.12(E80S).r

<400> SEQUENCE: 155
agttctggtc ctaagctcaa attcaataac acttcgccgg gggagttt 48

<210> SEQ ID NO 156
<211> LENGTH: 49
<212> TYPE: DNA
<213> ORGANISM: Artificial Sequence
<220> FEATURE:
<223> OTHER INFORMATION: Primer GII.12(E80S).c

<400> SEQUENCE: 156
agtgttattg aatttgagct taggaccaga actcaacccc tatctggca 49

<210> SEQ ID NO 157
<211> LENGTH: 50
<212> TYPE: DNA
<213> ORGANISM: Artificial Sequence
<220> FEATURE:
<223> OTHER INFORMATION: Primer GII.12(A90L).r

<400> SEQUENCE: 157
atccgagaca gatggagcag ataggggttg agttctggtc ctaattccaa 50

<210> SEQ ID NO 158
<211> LENGTH: 57
<212> TYPE: DNA
<213> ORGANISM: Artificial Sequence
<220> FEATURE:
<223> OTHER INFORMATION: Primer GII.12(A90L).c

<400> SEQUENCE: 158
actcaacccc tatctgctcc atctgtctcg gatgtacaac ggctatgcgg gcggagt 57

<210> SEQ ID NO 159
<211> LENGTH: 47
<212> TYPE: DNA
<213> ORGANISM: Artificial Sequence
<220> FEATURE:
<223> OTHER INFORMATION: Primer IF-NoV(US68)VP2(ORF3)(hCod).c

<400> SEQUENCE: 159
tcgtgcttcg gcaccagtac aatggctcag gccattattg gcgccat 47

<210> SEQ ID NO 160
<211> LENGTH: 47
<212> TYPE: DNA
<213> ORGANISM: Artificial Sequqence
<220> FEATURE:
<223> OTHER INFORMATION: Primer IF-NoV(US68)VP2(ORF3)(hCod).c

<400> SEQUENCE: 160
tcgtgcttcg gcaccagtac aatggctcag gccattattg gcgccat 47

<210> SEQ ID NO 161
<211> LENGTH: 50
<212> TYPE: DNA
<213> ORGANISM: Artificial Sequence
<220> FEATURE:
<223> OTHER INFORMATION: Primer IF-NoV(US68)VP2(ORF3)(hCod).r

<400> SEQUENCE: 161
actaaagaaa ataggccttc agcggcggtt gttagcgaac agaggaagtc 50

<210> SEQ ID NO 162
<211> LENGTH: 4540
<212> TYPE: DNA
<213> ORGANISM: Artificial Sequence
<220> FEATURE:
<223> OTHER INFORMATION: Cloning vector 1190 from left to right T-DNA

<400> SEQUENCE: 162
tggcaggata tattgtggtg taaacaaatt gacgcttaga caacttaata acacattgcg 60
gacgttttta atgtactgaa ttaacgccga atcccgggct ggtatattta tatgttgtca 120
aataactcaa aaaccataaa agtttaagtt agcaagtgtg tacattttta cttgaacaaa 180
aatattcacc tactactgtt ataaatcatt attaaacatt agagtaaaga aatatggatg 240
ataagaacaa gagtagtgat attttgacaa caattttgtt gcaacatttg agaaaatttt 300
gttgttctct cttttcattg gtcaaaaaca atagagagag aaaaaggaag agggagaata 360
aaaacataat gtgagtatga gagagaaagt tgtacaaaag ttgtaccaaa atagttgtac 420
aaatatcatt gaggaatttg acaaaagcta cacaaataag ggttaattgc tgtaaataaa 480
taaggatgac gcattagaga gatgtaccat tagagaattt ttggcaagtc attaaaaaga 540
aagaataaat tatttttaaa attaaaagtt gagtcatttg attaaacatg tgattattta 600
atgaattgat gaaagagttg gattaaagtt gtattagtaa ttagaatttg gtgtcaaatt 660
taatttgaca tttgatcttt tcctatatat tgccccatag agtcagttaa ctcattttta 720
tatttcatag atcaaataag agaaataacg gtatattaat ccctccaaaa aaaaaaaacg 780
gtatatttac taaaaaatct aagccacgta ggaggataac aggatccccg taggaggata 840
acatccaatc caaccaatca caacaatcct gatgagataa cccactttaa gcccacgcat 900
ctgtggcaca tctacattat ctaaatcaca cattcttcca cacatctgag ccacacaaaa 960
accaatccac atctttatca cccattctat aaaaaatcac actttgtgag tctacacttt 1020
gattcccttc aaacacatac aaagagaaga gactaattaa ttaattaatc atcttgagag 1080
aaaatggaac gagctataca aggaaacgac gctagggaac aagctaacag tgaacgttgg 1140
gatggaggat caggaggtac cacttctccc ttcaaacttc ctgacgaaag tccgagttgg 1200
actgagtggc ggctacataa cgatgagacg aattcgaatc aagataatcc ccttggtttc 1260
aaggaaagct ggggtttcgg gaaagttgta tttaagagat atctcagata cgacaggacg 1320
gaagcttcac tgcacagagt ccttggatct tggacgggag attcggttaa ctatgcagca 1380
tctcgatttt tcggtttcga ccagatcgga tgtacctata gtattcggtt tcgaggagtt 1440
agtatcaccg tttctggagg gtcgcgaact cttcagcatc tctgtgagat ggcaattcgg 1500

-continued

```
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaca agcttgcatg ccggtcaaca tggtggagca   2160
cgacacactt gtctactcca aaaatatcaa agatacagtc tcagaagacc aaagggcaat   2220
tgagactttt caacaaaggg taatatccgg aaacctcctc ggattccatt gcccagctat   2280
ctgtcacttt attgtgaaga tagtggaaaa ggaaggtggc tcctacaaat gccatcattg   2340
cgataaagga aaggccatcg ttgaagatgc ctctgccgac agtggtccca aagatggacc   2400
cccacccacg aggagcatcg tggaaaaaga agacgttcca accacgtctt caaagcaagt   2460
ggattgatgt gataacatgg tggagcacga cacacttgtc tactccaaaa atatcaaaga   2520
tacagtctca gaagaccaaa gggcaattga gacttttcaa caaagggtaa tatccggaaa   2580
cctcctcgga ttccattgcc cagctatctg tcactttatt gtgaagatag tggaaaagga   2640
aggtggctcc tacaaatgcc atcattgcga taaaggaaag gccatcgttg aagatgcctc   2700
tgccgacagt ggtcccaaag atggaccccc acccacgagg agcatcgtgg aaaaagaaga   2760
cgttccaacc acgtcttcaa agcaagtgga ttgatgtgat atctccactg acgtaaggga   2820
tgacgcacaa tcccactatc cttcgcaaga cccttcctct atataaggaa gttcatttca   2880
tttggagagg tattaaaatc ttaataggtt ttgataaaag cgaacgtggg gaaacccgaa   2940
ccaaaccttc ttctaaactc tctctcatct ctcttaaagc aaacttctct cttgtctttc   3000
ttgcgtgagc gatcttcaac gttgtcagat cgtgcttcgg caccgcggat ggcgaaaaac   3060
gttgcgattt tcggcttatt gttttctctt cttgtgttgg ttccttctca gatcttcgcc   3120
tgcaggctcc tcagccaaaa cgacaccccc atctgtctat ccactggccc ctggatctgc   3180
tgcccaaact aactccatgg tgaccctggg atgcctggtc aagggctatt tccctgagcc   3240
agtgacagtg acctggaact ctggatccct gtccagcggt gtgcacacct tcccagctgt   3300
cctgcagtct gacctctaca ctctgagcag ctcagtgact gtcccctcca gcacctggcc   3360
cagcgagacc gtcacctgca acgttgccca cccggccagc agcaccaagg tggacaagaa   3420
aattgtgccc agggattgtg gttgtaagcc ttgcatatgt acagtcccag aagtatcatc   3480
tgtcttcatc ttccccccaa agcccaagga tgtgctcacc attactctga ctcctaaggt   3540
cacgtgtgtt gtggtagaca tcagcaagga tgatcccgag gtccagttca gctggtttgt   3600
agatgatgtg gaggtgcaca cagctcagac gcaaccccgg gaggagcagt tcaacagcac   3660
tttccgctca gtcagtgaac ttcccatcat gcaccaggac tggctcaatg gcaaggagcg   3720
atcgctcacc atcaccatca ccatcaccat caccattaaa ggcctatttt ctttagtttg   3780
aatttactgt tattcggtgt gcatttctat gtttggtgag cggttttctg tgctcagagt   3840
gtgtttattt tatgtaattt aatttctttg tgagctcctg tttagcaggt cgtcccttca   3900
```

gcaaggacac aaaaagattt taattttatt aaaaaaaaaa aaaaaaaaga ccgggaattc 3960
gatatcaagc ttatcgacct gcagatcgtt caaacatttg gcaataaagt ttcttaagat 4020
tgaatcctgt tgccggtctt gcgatgatta tcatataatt tctgttgaat tacgttaagc 4080
atgtaataat taacatgtaa tgcatgacgt tatttatgag atgggttttt atgattagag 4140
tcccgcaatt atacatttaa tacgcgatag aaaacaaaat atagcgcgca aactaggata 4200
aattatcgcg cgcggtgtca tctatgttac tagatctcta gagtctcaag cttggcgcgc 4260
ccacgtgact agtggcactg gccgtcgttt tacaacgtcg tgactgggaa aaccctggcg 4320
ttacccaact taatcgcctt gcagcacatc ccccttttcgc cagctggcgt aatagcgaag 4380
aggcccgcac cgatcgccct tcccaacagt tgcgcagcct gaatggcgaa tgctagagca 4440
gcttgagctt ggatcagatt gtcgtttccc gccttcagtt taaactatca gtgtttgaca 4500
ggatatattg gcgggtaaac ctaagagaaa agagcgttta 4540

<210> SEQ ID NO 163
<211> LENGTH: 2976
<212> TYPE: DNA
<213> ORGANISM: Artificial Sequence
<220> FEATURE:
<223> OTHER INFORMATION: Construct 2724 from 2X35S promoter to NOS terminator

<400> SEQUENCE: 163
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaatg atgatggcta gtaaagatgc gacctcctct gtggatggtg cgtcaggggc 960
aggacaactc gtacccgagg taaacgccag cgacccactt gccatggacc ccgttgccgg 1020
aagttccaca gcagtggcca cagccggtca agtgaatcca attgatccgt ggattatcaa 1080
caatttcgtc caggcacccc agggcgagtt cacaatttca ccaaacaata caccgggcga 1140
tgtgctattc gatctttcct tgggtcctca ccttaaccct tttctactcc atctctcaca 1200
gatgtacaat ggttgggtag gaaacatgag agtccggatc atgctggctg gcaatgcctt 1260
taccgctggc aagatcatcg tcagttgtat tcctcccgga tttggatctc ataatctgac 1320
cattgctcaa gcgactctct ttccccatgt catcgccgac gttaggaccc tggaccccat 1380
cgaggtgccc ctggaggacg tccggaatgt tttgttccac aacaacgaca gaaaccagca 1440
gacgatgaga cttgtctgta tgctctatac cccactgcgg actggaggcg ggactggaga 1500
ctccttcgtt gtggcaggaa gagtgatgac atgcccctcc cccgacttca actttctttt 1560
tctggtccca ccaaccgttg agcagaagac gcggcccttt acactgccca atctcccgct 1620
ttcaagtctg agtaattcac gggccccatt gccgatctcc tcaatgggaa tctcccccga 1680
caacgtccag tctgtccaat tccaaaatgg gagatgcaca ctggacggtc gcctggtggg 1740
aacaactccg gtgtccctct cacatgtcgc caaaatccgc ggcacatcaa atggtaccgt 1800
aatcaatctg acagaacttg atggcacgcc cttccatccc tttgaaggac cagcccctat 1860
tggatttcct gatctgggag gttgcgactg gcacataaac atgacacagt ttggccactc 1920
cagccagaca cagtatgatg tcgatacaac cccagatacc ttcgtgccac acctgggatc 1980
tattcaagct aacggtattg gatccggcaa ctacgtggga gtcttatctt ggatctcacc 2040
accatcccac ccctcaggat cccaggttga cttgtggaag ataccgaatt atggatcctc 2100
gatcactgaa gccacgcacc tcgcaccttc cgtctaccca ccaggttttg gagaagtctt 2160
ggtgtttttc atgagcaaaa tgcccggccc tggagcctac aatctccctt gcctactccc 2220
tcaagagtat attagtcacc tcgcatctga gcaggccccg accgttggcg aggcagccct 2280
gctgcattat gtggatccgg acaccggcag gaacctgggt gagttcaaag cttatcctga 2340
cggttttcta acatgtgtac caaatggcgc ttccagcggc cctcaacagc tcccaatcaa 2400
tggcgtgttc gtttttgtca gctgggtaag ccgcttctac cagctgaagc ccgtggggac 2460
agcttcttct gcccgcggac gcctcggtct gcggagataa aggcctattt tctttagttt 2520
gaatttactg ttattcggtg tgcatttcta tgtttggtga gcggttttct gtgctcagag 2580
tgtgtttatt ttatgtaatt taatttcttt gtgagctcct gtttagcagg tcgtcccttc 2640
agcaaggaca caaaaagatt ttaattttat taaaaaaaaa aaaaaaaaag accgggaatt 2700
cgatatcaag cttatcgacc tgcagatcgt tcaaacattt ggcaataaag tttcttaaga 2760
ttgaatcctg ttgccggtct tgcgatgatt atcatataat ttctgttgaa ttacgttaag 2820
catgtaataa ttaacatgta atgcatgacg ttatttatga gatgggtttt tatgattaga 2880
gtcccgcaat tatacattta atacgcgata gaaaacaaaa tatagcgcgc aaactaggat 2940
aaattatcgc gcgcggtgtc atctatgtta ctagat 2976

<210> SEQ ID NO 164
<211> LENGTH: 5652
<212> TYPE: DNA
<213> ORGANISM: Artificial Sequence
<220> FEATURE:
<223> OTHER INFORMATION: Cloning vector 3677 from left to right T-DNA

<400> SEQUENCE: 164
tggcaggata tattgtggtg taaacaaatt gacgcttaga caacttaata acacattgcg 60
gacgttttta atgtactgaa ttaacgccga atcccgggct ggtatattta tatgttgtca 120
aataactcaa aaaccataaa agtttaagtt agcaagtgtg tacattttta cttgaacaaa 180
aatattcacc tactactgtt ataaatcatt attaaacatt agagtaaaga aatatggatg 240
ataagaacaa gagtagtgat attttgacaa caattttgtt gcaacatttg agaaaatttt 300
gttgttctct cttttcattg gtcaaaaaca atagagagag aaaaaggaag agggagaata 360
aaaacataat gtgagtatga gagagaaagt tgtacaaaag ttgtaccaaa atagttgtac 420
aaatatcatt gaggaatttg acaaaagcta cacaaataag ggttaattgc tgtaaataaa 480
taaggatgac gcattagaga gatgtaccat tagagaattt ttggcaagtc attaaaaaga 540
aagaataaat tatttttaaa attaaaagtt gagtcatttg attaaacatg tgattattta 600
atgaattgat gaaagagttg gattaaagtt gtattagtaa ttagaatttg gtgtcaaatt 660
taatttgaca tttgatcttt tcctatatat tgccccatag agtcagttaa ctcattttta 720
tatttcatag atcaaataag agaaataacg gtatattaat ccctccaaaa aaaaaaaacg 780
gtatatttac taaaaaatct aagccacgta ggaggataac aggatccccg taggaggata 840
acatccaatc caaccaatca caacaatcct gatgagataa cccactttaa gcccacgcat 900
ctgtggcaca tctacattat ctaaatcaca cattcttcca cacatctgag ccacacaaaa 960
accaatccac atctttatca cccattctat aaaaaatcac actttgtgag tctacacttt 1020
gattcccttc aaacacatac aaagagaaga gactaattaa ttaattaatc atcttgagag 1080
aaaatggaac gagctataca aggaaacgac gctagggaac aagctaacag tgaacgttgg 1140
gatggaggat caggaggtac cacttctccc ttcaaacttc ctgacgaaag tccgagttgg 1200
actgagtggc ggctacataa cgatgagacg aattcgaatc aagataatcc ccttggtttc 1260
aaggaaagct ggggtttcgg gaaagttgta tttaagagat atctcagata cgacaggacg 1320
gaagcttcac tgcacagagt ccttggatct tggacgggag attcggttaa ctatgcagca 1380
tctcgatttt tcggtttcga ccagatcgga tgtacctata gtattcggtt tcgaggagtt 1440
agtatcaccg tttctggagg gtcgcgaact cttcagcatc tctgtgagat ggcaattcgg 1500
tctaagcaag aactgctaca gcttgcccca atcgaagtgg aaagtaatgt atcaagagga 1560
tgccctgaag gtactcaaac cttcgaaaaa gaaagcgagt aagttaaaat gcttcttcgt 1620
ctcctattta taatatggtt tgttattgtt aattttgttc ttgtagaaga gcttaattaa 1680
tcgttgttgt tatgaaatac tatttgtatg agatgaactg gtgtaatgta attcatttac 1740
ataagtggag tcagaatcag aatgtttcct ccataactaa ctagacatga agacctgccg 1800
cgtacaattg tcttatattt gaacaactaa aattgaacat cttttgccac aactttataa 1860
gtggttaata tagctcaaat atatggtcaa gttcaataga ttaataatgg aaatatcagt 1920
tatcgaaatt cattaacaat caacttaacg ttattaacta ctaattttat atcatcccct 1980
ttgataaatg atagtacacc aattaggaag gagcatgctc gcctaggaga ttgtcgtttc 2040
ccgccttcag tttgcaagct gctctagccg tgtagccaat acgcaaaccg cctctccccg 2100
cgcgttggga attactagcg cgtgtcgaca agcttgcatg ccggtcaaca tggtggagca 2160
cgacacactt gtctactcca aaaatatcaa agatacagtc tcagaagacc aaagggcaat 2220
tgagactttt caacaaaggg taatatccgg aaacctcctc ggattccatt gcccagctat 2280
ctgtcacttt attgtgaaga tagtggaaaa ggaaggtggc tcctacaaat gccatcattg 2340
cgataaagga aaggccatcg ttgaagatgc ctctgccgac agtggtccca aagatggacc 2400
cccacccacg aggagcatcg tggaaaaaga agacgttcca accacgtctt caaagcaagt 2460
ggattgatgt gataacatgg tggagcacga cacacttgtc tactccaaaa atatcaaaga 2520
tacagtctca gaagaccaaa gggcaattga gacttttcaa caaagggtaa tatccggaaa 2580
cctcctcgga ttccattgcc cagctatctg tcactttatt gtgaagatag tggaaaagga 2640
aggtggctcc tacaaatgcc atcattgcga taaaggaaag gccatcgttg aagatgcctc 2700
tgccgacagt ggtcccaaag atggaccccc acccacgagg agcatcgtgg aaaaagaaga 2760
cgttccaacc acgtcttcaa agcaagtgga ttgatgtgat atctccactg acgtaaggga 2820

-continued

```
tgacgcacaa tcccactatc cttcgcaaga cccttcctct atataaggaa gttcatttca   2880
tttggagagg tattaaaatc ttaataggtt ttgataaaag cgaacgtggg gaaacccgaa   2940
ccaaaccttc ttctaaactc tctctcatct ctcttaaagc aaacttctct cttgtctttc   3000
ttgcgtgagc gatcttcaac gttgtcagat cgtgcttcgg caccgcggat ggcgaaaaac   3060
gttgcgattt tcggcttatt gttttctctt cttgtgttgg ttccttctca gatcttcgcc   3120
tgcaggctcc tcagccaaaa cgacaccccc atctgtctat ccactggccc ctggatctgc   3180
tgcccaaact aactccatgg tgaccctggg atgcctggtc aagggctatt tccctgagcc   3240
agtgacagtg acctggaact ctggatccct gtccagcggt gtgcacacct tcccagctgt   3300
cctgcagtct gacctctaca ctctgagcag ctcagtgact gtcccctcca gcacctggcc   3360
cagcgagacc gtcacctgca acgttgccca cccggccagc agcaccaagg tggacaagaa   3420
aattgtgccc agggattgtg gttgtaagcc ttgcatatgt acagtcccag aagtatcatc   3480
tgtcttcatc ttccccccaa agcccaagga tgtgctcacc attactctga ctcctaaggt   3540
cacgtgtgtt gtggtagaca tcagcaagga tgatcccgag gtccagttca gctggtttgt   3600
agatgatgtg gaggtgcaca cagctcagac gcaaccccgg gaggagcagt tcaacagcac   3660
tttccgctca gtcagtgaac ttcccatcat gcaccaggac tggctcaatg gcaaggagcg   3720
atcgctcacc atcaccatca ccatcaccat caccattaaa ggcctatttt ctttagtttg   3780
aatttactgt tattcggtgt gcatttctat gtttggtgag cggttttctg tgctcagagt   3840
gtgtttattt tatgtaattt aatttctttg tgagctcctg tttagcaggt cgtcccttca   3900
gcaaggacac aaaaagattt taattttatt atcgttcaaa catttggcaa taaagtttct   3960
taagattgaa tcctgttgcc ggtcttgcga tgattatcat ataatttctg ttgaattacg   4020
ttaagcatgt aataattaac atgtaatgca tgacgttatt tatgagatgg gtttttatga   4080
ttagagtccc gcaattatac atttaatacg cgatagaaaa caaaatatag cgcgcaaact   4140
aggataaatt atcgcgcgcg gtgtcatcta tgttactaga tctctaggta aaaatcccaa   4200
ttatatttgg tctaatttag tttggtattg agtaaaacaa attcgaacca aaccaaaata   4260
taaatatata gtttttatat atatgccttt aagacttttt atagaatttt ctttaaaaaa   4320
tatctagaaa tatttgcgac tcttctggca tgtaatattt cgttaaatat gaagtgctcc   4380
atttttatta actttaaata attggttgta cgatcacttt cttatcaagt gttactaaaa   4440
tgcgtcaatc tctttgttct tccatattca tatgtcaaaa tctatcaaaa ttcttatata   4500
tctttttcga atttgaagtg aaatttcgat aatttaaaat taaatagaac atatcattat   4560
ttaggtatca tattgatttt tatacttaat tactaaattt ggttaacttt gaaagtgtac   4620
atcaacgaaa aattagtcaa acgactaaaa taaataaata tcatgtgtta ttaagaaaat   4680
tctcctataa gaatatttta atagatcata tgtttgtaaa aaaaattaat ttttactaac   4740
acatatattt acttatcaaa aatttgacaa agtaagatta aaataatatt catctaacaa   4800
aaaaaaaacc agaaaatgct gaaaacccgg caaaaccgaa ccaatccaaa ccgatatagt   4860
tggtttggtt tgattttgat ataaaccgaa ccaactcggt ccatttgcac ccctaatcat   4920
aatagcttta atatttcaag atattattaa gttaacgttg tcaatatcct ggaaattttg   4980
caaaatgaat caagcctata tggctgtaat atgaatttaa aagcagctcg atgtggtggt   5040
aatatgtaat ttacttgatt ctaaaaaaat atcccaagta ttaataattt ctgctaggaa   5100
gaaggttagc tacgatttac agcaaagcca gaatacaaag aaccataaag tgattgaagc   5160
```

-continued

```
tcgaaatata cgaaggaaca aatattttta aaaaaatacg caatgacttg gaacaaaaga   5220

aagtgatata tttttgttc ttaaacaagc atcccctcta aagaatggca gttttccttt   5280

gcatgtaact attatgctcc cttcgttaca aaaattttgg actactattg ggaacttctt   5340

ctgaaaattc tagagtctca agcttggcgc gcccacgtga ctagtggcac tggccgtcgt   5400

tttacaacgt cgtgactggg aaaaccctgg cgttacccaa cttaatcgcc ttgcagcaca   5460

tccccctttc gccagctggc gtaatagcga agaggcccgc accgatcgcc cttcccaaca   5520

gttgcgcagc ctgaatggcg aatgctagag cagcttgagc ttggatcaga ttgtcgtttc   5580

ccgccttcag tttaaactat cagtgtttga caggatatat tggcgggtaa acctaagaga   5640

aaagagcgtt ta                                                        5652
```

<210> SEQ ID NO 165
<211> LENGTH: 2952
<212> TYPE: DNA
<213> ORGANISM: Artificial Sequence
<220> FEATURE:
<223> OTHER INFORMATION: Construct 4133 from 2X35S promoter to NOS terminator

<400> SEQUENCE: 165

```
gtcaacatgg tggagcacga cacacttgtc tactccaaaa atatcaaaga tacagtctca     60

gaagaccaaa gggcaattga gacttttcaa caaagggtaa tatccggaaa cctcctcgga    120

ttccattgcc cagctatctg tcactttatt gtgaagatag tggaaaagga aggtggctcc    180

tacaaatgcc atcattgcga taaaggaaag gccatcgttg aagatgcctc tgccgacagt    240

ggtcccaaag atggaccccc acccacgagg agcatcgtgg aaaaagaaga cgttccaacc    300

acgtcttcaa agcaagtgga ttgatgtgat aacatggtgg agcacgacac acttgtctac    360

tccaaaaata tcaaagatac agtctcagaa gaccaaaggg caattgagac ttttcaacaa    420

agggtaatat ccggaaacct cctcggattc cattgcccag ctatctgtca ctttattgtg    480

aagatagtgg aaaaggaagg tggctcctac aaatgccatc attgcgataa aggaaaggcc    540

atcgttgaag atgcctctgc cgacagtggt cccaaagatg gacccccacc cacgaggagc    600

atcgtggaaa aagaagacgt tccaaccacg tcttcaaagc aagtggattg atgtgatatc    660

tccactgacg taagggatga cgcacaatcc cactatcctt cgcaagaccc ttcctctata    720

taaggaagtt catttcattt ggagaggtat taaaatctta ataggttttg ataaaagcga    780

acgtggggaa acccgaacca aaccttcttc taaactctct ctcatctctc ttaaagcaaa    840

cttctctctt gtctttcttg cgtgagcgat cttcaacgtt gtcagatcgt gcttcggcac    900

cagtacaatg aaaatggcct cgagtgacgc taaccctagt gacggcagcg ccgccaatct    960

tgtgcctgag gttaataatg aggtgatggc cctggagcct gtggtgggcg cagccatagc   1020

agcgcccgtg gccggtcagc agaatgtgat tgacccgtgg atacgcaaca attttgtcca   1080

agcccctggt ggggagttca ccgttagccc gagaaatgcg ccaggagaaa tcctgtggtc   1140

ggccagcttg ggacccgatc tgaaccccta tttgtcacat ctcgctcgga tgtacaacgg   1200

gtatgccggc ggatttgaag tgcaggtgat tctggctggg aacgcgttca ctgctggcaa   1260

agtgatcttt gcagcggtgc ctcccaactt ccccactgaa ggactgtctc caagccaggt   1320

cacaatgttt ccacacatcg tggtggacgt acggcagcta gagcctgtcc tgattcccct   1380

ccctgatgta cgcaataatt tctaccacta caatcaatcc aatgatccga ccattaaact   1440

catcgcgatg ttgtacaccc ctctgcgcgc taacaatgct ggagacgacg tattcaccgt   1500
```

gtcatgcaga gtgctcacca gaccttcacc agactttgac tttatcttct tagtgccccc 1560
cactgttgag agccgaacca agccctttag tgtccccgta ctcacagtcg aggagatgac 1620
aaatagccgc tttccaatcc cccttgagaa actgttcaca ggaccttcct cggcattcgt 1680
ggttcagcca cagaacggac gctgcacaac tgacggcgtg ctgctcggaa ccacccagct 1740
tagccctgtt aatatctgta cgtttagagg cgacgtaact cacataactg gctcacggaa 1800
ctataccatg aatctggcat cacagaattg gaatgactac gacccaaccg aagagattcc 1860
cgcacctctt ggaacccccg actttgtggg aaaaatacag ggcgtcctga cacaaaccac 1920
cagaaccgat ggctccacac ggggacacaa ggcaaccgtc tacactggct ctgccgattt 1980
tgccccgaaa ctgggtagag tgcagtttga gaccgacact gaccgggact ttgaagccaa 2040
tcagaatact aagttcacac ctgtaggagt gattcaggac gggggcacca ctcaccggaa 2100
cgagccgcaa caatgggtcc tgccctctta tagcgggagg aatactcata atgtgcattt 2160
ggctcctgca gtggctccca cgtttcccgg ggaacaactg ctcttttttc gttcaaccat 2220
gcctggatgc tccggatatc ccaatatgga tctcgattgc ctgctcccac aggaatgggt 2280
gcagtatttt tatcaagagg ccgcaccagc ccaatccgac gtcgcacttc tgcggttcgt 2340
gaatccagac acaggccgcg tgttgtttga gtgcaaattg cacaaatcag gatacgttac 2400
agtggctcat actggacagc atgacctggt gatcccaccc aacggatatt ttaggttcga 2460
ctcctgggtg aatcagtttt atacattagc ccccatgggg aatgggactg gcagacgcag 2520
ggctgtctga aggcctattt tctttagttt gaatttactg ttattcggtg tgcatttcta 2580
tgtttggtga gcggttttct gtgctcagag tgtgtttatt ttatgtaatt taatttcttt 2640
gtgagctcct gtttagcagg tcgtcccttc agcaaggaca caaaaagatt ttaattttat 2700
tatcgttcaa acatttggca ataaagtttc ttaagattga atcctgttgc cggtcttgcg 2760
atgattatca tataatttct gttgaattac gttaagcatg taataattaa catgtaatgc 2820
atgacgttat ttatgagatg ggtttttatg attagagtcc cgcaattata catttaatac 2880
gcgatagaaa acaaaatata gcgcgcaaac taggataaat tatcgcgcgc ggtgtcatct 2940
atgttactag at 2952

<210> SEQ ID NO 166
<211> LENGTH: 2952
<212> TYPE: DNA
<213> ORGANISM: Artificial Sequence
<220> FEATURE:
<223> OTHER INFORMATION: Construct 4135 from 2X35S promoter to NOS terminator

<400> SEQUENCE: 166
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540

```
atcgttgaag atgcctctgc cgacagtggt cccaaagatg gacccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaatg aaaatggcct cgagtgacgc taaccctagt gacggcagcg ccgccaatct    960
tgtgcctgag gttaataatg aggtgatggc cctggagcct gtggtgggcg cagccatagc   1020
agcgcccgtg gccggtcagc agaatgtgat tgacccgtgg atacgcaaca attttgtcca   1080
agcccctggt ggggagttca ccgttagccc gagaaatgcg ccaggagaaa tcctgtggtc   1140
ggccagcttg ggacccgatc tgaaccccta tttgctgcat ctcgctcgga tgtacaacgg   1200
gtatgccggc ggatttgaag tgcaggtgat tctggctggg aacgcgttca ctgctggcaa   1260
agtgatcttt gcagcggtgc ctcccaactt ccccactgaa ggactgtctc caagccaggt   1320
cacaatgttt ccacacatcg tggtggacgt acggcagcta gagcctgtcc tgattcccct   1380
ccctgatgta cgcaataatt tctaccacta caatcaatcc aatgatccga ccattaaact   1440
catcgcgatg ttgtacaccc ctctgcgcgc taacaatgct ggagacgacg tattcaccgt   1500
gtcatgcaga gtgctcacca gaccttcacc agactttgac tttatcttct tagtgccccc   1560
cactgttgag agccgaacca agccctttag tgtccccgta ctcacagtcg aggagatgac   1620
aaatagccgc tttccaatcc cccttgagaa actgttcaca ggaccttcct cggcattcgt   1680
ggttcagcca cagaacggac gctgcacaac tgacggcgtg ctgctcggaa ccacccagct   1740
tagccctgtt aatatctgta cgtttagagg cgacgtaact cacataactg gctcacggaa   1800
ctataccatg aatctggcat cacagaattg gaatgactac gacccaaccg aagagattcc   1860
cgcacctctt ggaacccccg actttgtggg aaaaatacag ggcgtcctga cacaaaccac   1920
cagaaccgat ggctccacac ggggacacaa ggcaaccgtc tacactggct ctgccgattt   1980
tgccccgaaa ctgggtagag tgcagtttga gaccgacact gaccgggact ttgaagccaa   2040
tcagaatact aagttcacac ctgtaggagt gattcaggac gggggcacca ctcaccggaa   2100
cgagccgcaa caatgggtcc tgccctctta tagcgggagg aatactcata atgtgcattt   2160
ggctcctgca gtggctccca cgtttcccgg ggaacaactg ctcttttttc gttcaaccat   2220
gcctggatgc tccggatatc ccaatatgga tctcgattgc ctgctcccac aggaatgggt   2280
gcagtatttt tatcaagagg ccgcaccagc ccaatccgac gtcgcacttc tgcggttcgt   2340
gaatccagac acaggccgcg tgttgtttga gtgcaaattg cacaaatcag gatacgttac   2400
agtggctcat actggacagc atgacctggt gatcccaccc aacggatatt ttaggttcga   2460
ctcctgggtg aatcagtttt atacattagc cccccatgggg aatgggactg gcagacgcag   2520
ggctgtctga aggcctattt tctttagttt gaatttactg ttattcggtg tgcatttcta   2580
tgtttggtga gcggttttct gtgctcagag tgtgtttatt ttatgtaatt taatttcttt   2640
gtgagctcct gtttagcagg tcgtcccttc agcaaggaca caaaaagatt ttaattttat   2700
tatcgttcaa acatttggca ataaagtttc ttaagattga atcctgttgc cggtcttgcg   2760
atgattatca tataatttct gttgaattac gttaagcatg taataattaa catgtaatgc   2820
atgacgttat ttatgagatg ggtttttatg attagagtcc cgcaattata catttaatac   2880
gcgatagaaa acaaaatata gcgcgcaaac taggataaat tatcgcgcgc ggtgtcatct   2940
```

atgttactag at 2952

<210> SEQ ID NO 167
<211> LENGTH: 1632
<212> TYPE: DNA
<213> ORGANISM: Artificial Sequence
<220> FEATURE:
<223> OTHER INFORMATION: Nucleic acid sequence of human codon optimized
VP1_GI.3_Lil08_Q84S

<400> SEQUENCE: 167
atgatgatgg cttccaagga tgctcccaca aacatggatg gaacaagcgg cgcggggcaa 60
cttgtgccgg aggtgtccac ggcggaaccc atttccatgg aacctgtggc cggcgcagcc 120
actgctgccg ccaccgcagg acaggtaaac atgatcgacc cctggatcat gtcaaattac 180
gttcaggctc cacaggggga gtttaccata agcccaaaca acaccccggg tgacatcttg 240
tttgacctga gcctaggacc acacttgaat ccgtttctga gtcacttggc tcagatgtat 300
aatggatggg ttggaaacat gaaggtgcgc gtgctcctgg cgggcaatgc attcacagcc 360
gggaagatta ttatctcttg cgtgccacct ggatttgcag cccagaacgt gtctatcgca 420
caggcaacca tgtttccgca tgtcatcgca gatgtgcgcg tgctagagcc catcgaggtg 480
ccccttgagg acgtgcgcaa cgtcctattc cataacaatg atagcacccc caccatgcgc 540
ttgatatgta tgttatatac tcccctccgc gccagtgggt ccagctccgg gaccgatcct 600
tttgtgattg ctgggcgggt gttgacttgt cctagccctg acttcaactt cctttttctg 660
gtgcctccaa atgtagaaca gaaaacaaag ccattcagcg tgccaaacct gccccttaac 720
gtgctgtcga attcccgagt gccttccctt attaagtcca tgatggtatc tcaggatcac 780
ggtcaaatgg tgcagtttca gaacggccga gtgacgttag acgggcagct gcagggcaca 840
accccaacca gtgccagtca gctgtgtaag atcagaggca ccgtctacca cgcaactggc 900
ggacaggggc tgaatcttac tgagatcgat ggtaccccct accatgcatt cgagtcacct 960
gcacctattg gatttcccga tcttggggag tgtgattggc atatcaatgc ttcacctgcc 1020
aacgctttca cagacgggtc tattattcat cgcattgacg tagcacagga tagcacattt 1080
gccccgcacc tgggtaccat ccactatacg aacgcagatt acaacgcaaa cgtgggtctt 1140
atctgtagcc tagagtggct atctccgcca agcggtgggg cccctaaagt taacccatgg 1200
gctattcctc ggtacgggtc tacgctgact gaggccgctc agctggcacc ccccatatat 1260
ccaccaggat tcggggaagc cattgttttc tttatgtccg attttccgat agccaacggt 1320
tcagatggcc ttagtgtccc ttgcacgatt ccacaggaat ttgtgacaca cttcgtaaac 1380
gagcaggctc ctactcgggg cgaggctgcc ttgttgcatt acgtagaccc cgatacccat 1440
agaaacctgg gcgaattcaa actctaccct gaaggtttca tgacctgcgt acctaactcc 1500
tccggcagtg gccctcaaac cttgccgatc aacggcgtgt tcacgtttat cagctgggtt 1560
tcacggtttt accaactcaa gcccgtcgga acaactgggc cagttcggag gctcgggatc 1620
agacggagct ag 1632

<210> SEQ ID NO 168
<211> LENGTH: 8
<212> TYPE: PRT
<213> ORGANISM: Artificial Sequence
<220> FEATURE:
<223> OTHER INFORMATION: Mutation of SEQ ID NO;1 at positions 39-46

<400> SEQUENCE: 168

```
Ser Ser Thr Ala Val Ala Thr Ala
1               5
```

<210> SEQ ID NO 169
<211> LENGTH: 1632
<212> TYPE: DNA
<213> ORGANISM: Artificial Sequence
<220> FEATURE:
<223> OTHER INFORMATION: Nucleic acid sequence of human codon optimized VP1_GI.3_Lil08_A43V plus sign

<400> SEQUENCE: 169

```
atgatgatgg cttccaagga tgctcccaca aacatggatg gaacaagcgg cgcggggcaa     60

cttgtgccgg aggtgtccac ggcggaaccc atttccatgg aacctgtggc cggcgcagcc    120

actgctgtgg ccaccgcagg acaggtaaac atgatcgacc cctggatcat gtcaaattac    180

gttcaggctc cacaggggga gtttaccata agcccaaaca acaccccggg tgacatcttg    240

tttgacctgc agctaggacc acacttgaat ccgtttctgc tccacttggc tcagatgtat    300

aatggatggg ttggaaacat gaaggtgcgc gtgctcctgg cgggcaatgc attcacagcc    360

gggaagatta ttatctcttg cgtgccacct ggatttgcag cccagaacgt gtctatcgca    420

caggcaacca tgtttccgca tgtcatcgca gatgtgcgcg tgctagagcc catcgaggtg    480

ccccttgagg acgtgcgcaa cgtcctattc cataacaatg atagcacccc caccatgcgc    540

ttgatatgta tgttatatac tcccctccgc gccagtgggt ccagctccgg gaccgatcct    600

tttgtgattg ctgggcgggt gttgacttgt cctagccctg acttcaactt cctttttctg    660

gtgcctccaa atgtagaaca gaaaacaaag ccattcagcg tgccaaacct gccccttaac    720

gtgctgtcga attcccgagt gccttccctt attaagtcca tgatggtatc tcaggatcac    780

ggtcaaatgg tgcagtttca gaacggccga gtgacgttag acgggcagct gcagggcaca    840

accccaacca gtgccagtca gctgtgtaag atcagaggca ccgtctacca cgcaactggc    900

ggacaggggc tgaatcttac tgagatcgat ggtacccccct accatgcatt cgagtcacct    960

gcacctattg gatttcccga tcttggggag tgtgattggc atatcaatgc ttcacctgcc   1020

aacgctttca cagacgggtc tattattcat cgcattgacg tagcacagga tagcacattt   1080

gccccgcacc tgggtaccat ccactatacg aacgcagatt acaacgcaaa cgtgggtctt   1140

atctgtagcc tagagtggct atctccgcca agcggtgggg cccctaaagt taacccatgg   1200

gctattcctc ggtacgggtc tacgctgact gaggccgctc agctggcacc ccccatatat   1260

ccaccaggat tcggggaagc cattgttttc tttatgtccg attttccgat agccaacggt   1320

tcagatggcc ttagtgtccc ttgcacgatt ccacaggaat ttgtgacaca cttcgtaaac   1380

gagcaggctc ctactcgggg cgaggctgcc ttgttgcatt acgtagaccc cgatacccat   1440

agaaacctgg gcgaattcaa actctaccct gaaggtttca tgacctgcgt acctaactcc   1500

tccggcagtg gccctcaaac cttgccgatc aacggcgtgt tcacgtttat cagctgggtt   1560

tcacggtttt accaactcaa gcccgtcgga acaactgggc cagttcggag gctcgggatc   1620

agacggagct ag                                                       1632
```

<210> SEQ ID NO 170
<211> LENGTH: 543
<212> TYPE: PRT
<213> ORGANISM: Norovirus

<400> SEQUENCE: 170

-continued

```
Met Met Met Ala Ser Lys Asp Ala Pro Thr Asn Met Asp Gly Thr Ser
1               5                   10                  15

Gly Ala Gly Gln Leu Val Pro Glu Val Ser Thr Ala Glu Pro Ile Ser
            20                  25                  30

Met Glu Pro Val Ala Gly Ala Ala Thr Ala Val Ala Thr Ala Gly Gln
        35                  40                  45

Val Asn Met Ile Asp Pro Trp Ile Met Ser Asn Tyr Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Leu His Leu
                85                  90                  95

Ala Gln Met Tyr Asn Gly Trp Val Gly Asn Met Lys Val Arg Val Leu
            100                 105                 110

Leu Ala Gly Asn Ala Phe Thr Ala Gly Lys Ile Ile Ile Ser Cys Val
        115                 120                 125

Pro Pro Gly Phe Ala Ala Gln Asn Val Ser Ile Ala Gln Ala Thr Met
    130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Asn Asn Asp Ser Thr
                165                 170                 175

Pro Thr Met Arg Leu Ile Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205

Thr Cys Pro Ser Pro Asp Phe Asn Phe Leu Phe Leu Val Pro Pro Asn
    210                 215                 220

Val Glu Gln Lys Thr Lys Pro Phe Ser Val Pro Asn Leu Pro Leu Asn
225                 230                 235                 240

Val Leu Ser Asn Ser Arg Val Pro Ser Leu Ile Lys Ser Met Met Val
                245                 250                 255

Ser Gln Asp His Gly Gln Met Val Gln Phe Gln Asn Gly Arg Val Thr
            260                 265                 270

Leu Asp Gly Gln Leu Gln Gly Thr Thr Pro Thr Ser Ala Ser Gln Leu
        275                 280                 285

Cys Lys Ile Arg Gly Thr Val Tyr His Ala Thr Gly Gly Gln Gly Leu
    290                 295                 300

Asn Leu Thr Glu Ile Asp Gly Thr Pro Tyr His Ala Phe Glu Ser Pro
305                 310                 315                 320

Ala Pro Ile Gly Phe Pro Asp Leu Gly Glu Cys Asp Trp His Ile Asn
                325                 330                 335

Ala Ser Pro Ala Asn Ala Phe Thr Asp Gly Ser Ile Ile His Arg Ile
            340                 345                 350

Asp Val Ala Gln Asp Ser Thr Phe Ala Pro His Leu Gly Thr Ile His
        355                 360                 365

Tyr Thr Asn Ala Asp Tyr Asn Ala Asn Val Gly Leu Ile Cys Ser Leu
    370                 375                 380

Glu Trp Leu Ser Pro Pro Ser Gly Gly Ala Pro Lys Val Asn Pro Trp
385                 390                 395                 400

Ala Ile Pro Arg Tyr Gly Ser Thr Leu Thr Glu Ala Ala Gln Leu Ala
                405                 410                 415

Pro Pro Ile Tyr Pro Pro Gly Phe Gly Glu Ala Ile Val Phe Phe Met
```

```
            420                 425                 430

Ser Asp Phe Pro Ile Ala Asn Gly Ser Asp Gly Leu Ser Val Pro Cys
        435                 440                 445

Thr Ile Pro Gln Glu Phe Val Thr His Phe Val Asn Glu Gln Ala Pro
    450                 455                 460

Thr Arg Gly Glu Ala Ala Leu Leu His Tyr Val Asp Pro Asp Thr His
465                 470                 475                 480

Arg Asn Leu Gly Glu Phe Lys Leu Tyr Pro Glu Gly Phe Met Thr Cys
                485                 490                 495

Val Pro Asn Ser Ser Gly Ser Gly Pro Gln Thr Leu Pro Ile Asn Gly
            500                 505                 510

Val Phe Thr Phe Ile Ser Trp Val Ser Arg Phe Tyr Gln Leu Lys Pro
        515                 520                 525

Val Gly Thr Thr Gly Pro Val Arg Arg Leu Gly Ile Arg Arg Ser
    530                 535                 540
```

<210> SEQ ID NO 171
<211> LENGTH: 1632
<212> TYPE: DNA
<213> ORGANISM: Artificial Sequence
<220> FEATURE:
<223> OTHER INFORMATION: Nucleic acid sequence of human codon optimized VP1_GI.3_Lil08_M57I plus sign S94L

<400> SEQUENCE: 171

```
atgatgatgg cttccaagga tgctcccaca aacatggatg gaacaagcgg cgcggggcaa     60
cttgtgccgg aggtgtccac ggcggaaccc atttccatgg aacctgtggc cggcgcagcc    120
actgctgccg ccaccgcagg acaggtaaac atgatcgacc cctggatcat ctcaaattac    180
gttcaggctc cacaggggga gtttaccata agcccaaaca acaccccggg tgacatcttg    240
tttgacctgc agctaggacc acacttgaat ccgtttctgc tccacttggc tcagatgtat    300
aatggatggg ttggaaacat gaaggtgcgc gtgctcctgg cgggcaatgc attcacagcc    360
gggaagatta ttatctcttg cgtgccacct ggatttgcag cccagaacgt gtctatcgca    420
caggcaacca tgtttccgca tgtcatcgca gatgtgcgcg tgctagagcc catcgaggtg    480
ccccttgagg acgtgcgcaa cgtcctattc cataacaatg atagcacccc caccatgcgc    540
ttgatatgta tgttatatac tcccctccgc gccagtgggt ccagctccgg gaccgatcct    600
tttgtgattg ctgggcgggt gttgacttgt cctagccctg acttcaactt cctttttctg    660
gtgcctccaa atgtagaaca gaaaacaaag ccattcagcg tgccaaacct gccccttaac    720
gtgctgtcga attcccgagt gccttccctt attaagtcca tgatggtatc tcaggatcac    780
ggtcaaatgg tgcagtttca gaacggccga gtgacgttag acgggcagct gcagggcaca    840
accccaacca gtgccagtca gctgtgtaag atcagaggca ccgtctacca cgcaactggc    900
ggacaggggc tgaatcttac tgagatcgat ggtaccccct accatgcatt cgagtcacct    960
gcacctattg gatttcccga tcttggggag tgtgattggc atatcaatgc ttcacctgcc   1020
aacgctttca cagacgggtc tattattcat cgcattgacg tagcacagga tagcacattt   1080
gccccgcacc tgggtaccat ccactatacg aacgcagatt acaacgcaaa cgtgggtctt   1140
atctgtagcc tagagtggct atctccgcca agcggtgggg cccctaaagt taacccatgg   1200
gctattcctc ggtacgggtc tacgctgact gaggccgctc agctggcacc ccccatatat   1260
ccaccaggat tcggggaagc cattgttttc tttatgtccg attttccgat agccaacggt   1320
tcagatggcc ttagtgtccc ttgcacgatt ccacaggaat ttgtgacaca cttcgtaaac   1380
```

gagcaggctc ctactcgggg cgaggctgcc ttgttgcatt acgtagaccc cgatacccat 1440
agaaacctgg gcgaattcaa actctaccct gaaggtttca tgacctgcgt acctaactcc 1500
tccggcagtg gccctcaaac cttgccgatc aacggcgtgt tcacgtttat cagctgggtt 1560
tcacggtttt accaactcaa gcccgtcgga acaactgggc cagttcggag gctcgggatc 1620
agacggagct ag 1632

<210> SEQ ID NO 172
<211> LENGTH: 543
<212> TYPE: PRT
<213> ORGANISM: Norovirus

<400> SEQUENCE: 172

Met Met Met Ala Ser Lys Asp Ala Pro Thr Asn Met Asp Gly Thr Ser
1 5 10 15

Gly Ala Gly Gln Leu Val Pro Glu Val Ser Thr Ala Glu Pro Ile Ser
20 25 30

Met Glu Pro Val Ala Gly Ala Ala Thr Ala Ala Ala Thr Ala Gly Gln
35 40 45

Val Asn Met Ile Asp Pro Trp Ile Ile Ser Asn Tyr Val Gln Ala Pro
50 55 60

Gln Gly Glu Phe Thr Ile Ser Pro Asn Asn Thr Pro Gly Asp Ile Leu
65 70 75 80

Phe Asp Leu Gln Leu Gly Pro His Leu Asn Pro Phe Leu Leu His Leu
85 90 95

Ala Gln Met Tyr Asn Gly Trp Val Gly Asn Met Lys Val Arg Val Leu
100 105 110

Leu Ala Gly Asn Ala Phe Thr Ala Gly Lys Ile Ile Ile Ser Cys Val
115 120 125

Pro Pro Gly Phe Ala Ala Gln Asn Val Ser Ile Ala Gln Ala Thr Met
130 135 140

Phe Pro His Val Ile Ala Asp Val Arg Val Leu Glu Pro Ile Glu Val
145 150 155 160

Pro Leu Glu Asp Val Arg Asn Val Leu Phe His Asn Asn Asp Ser Thr
165 170 175

Pro Thr Met Arg Leu Ile Cys Met Leu Tyr Thr Pro Leu Arg Ala Ser
180 185 190

Gly Ser Ser Ser Gly Thr Asp Pro Phe Val Ile Ala Gly Arg Val Leu
195 200 205

Thr Cys Pro Ser Pro Asp Phe Asn Phe Leu Phe Leu Val Pro Pro Asn
210 215 220

Val Glu Gln Lys Thr Lys Pro Phe Ser Val Pro Asn Leu Pro Leu Asn
225 230 235 240

Val Leu Ser Asn Ser Arg Val Pro Ser Leu Ile Lys Ser Met Met Val
245 250 255

Ser Gln Asp His Gly Gln Met Val Gln Phe Gln Asn Gly Arg Val Thr
260 265 270

Leu Asp Gly Gln Leu Gln Gly Thr Thr Pro Thr Ser Ala Ser Gln Leu
275 280 285

Cys Lys Ile Arg Gly Thr Val Tyr His Ala Thr Gly Gly Gln Gly Leu
290 295 300

Asn Leu Thr Glu Ile Asp Gly Thr Pro Tyr His Ala Phe Glu Ser Pro
305 310 315 320

```
Ala Pro Ile Gly Phe Pro Asp Leu Gly Glu Cys Asp Trp His Ile Asn
                325                 330                 335

Ala Ser Pro Ala Asn Ala Phe Thr Asp Gly Ser Ile Ile His Arg Ile
            340                 345                 350

Asp Val Ala Gln Asp Ser Thr Phe Ala Pro His Leu Gly Thr Ile His
        355                 360                 365

Tyr Thr Asn Ala Asp Tyr Asn Ala Asn Val Gly Leu Ile Cys Ser Leu
    370                 375                 380

Glu Trp Leu Ser Pro Pro Ser Gly Gly Ala Pro Lys Val Asn Pro Trp
385                 390                 395                 400

Ala Ile Pro Arg Tyr Gly Ser Thr Leu Thr Glu Ala Ala Gln Leu Ala
                405                 410                 415

Pro Pro Ile Tyr Pro Pro Gly Phe Gly Glu Ala Ile Val Phe Phe Met
            420                 425                 430

Ser Asp Phe Pro Ile Ala Asn Gly Ser Asp Gly Leu Ser Val Pro Cys
        435                 440                 445

Thr Ile Pro Gln Glu Phe Val Thr His Phe Val Asn Glu Gln Ala Pro
    450                 455                 460

Thr Arg Gly Glu Ala Ala Leu Leu His Tyr Val Asp Pro Asp Thr His
465                 470                 475                 480

Arg Asn Leu Gly Glu Phe Lys Leu Tyr Pro Glu Gly Phe Met Thr Cys
                485                 490                 495

Val Pro Asn Ser Ser Gly Ser Gly Pro Gln Thr Leu Pro Ile Asn Gly
            500                 505                 510

Val Phe Thr Phe Ile Ser Trp Val Ser Arg Phe Tyr Gln Leu Lys Pro
        515                 520                 525

Val Gly Thr Thr Gly Pro Val Arg Arg Leu Gly Ile Arg Arg Ser
    530                 535                 540
```

<210> SEQ ID NO 173
<211> LENGTH: 1632
<212> TYPE: DNA
<213> ORGANISM: Artificial Sequence
<220> FEATURE:
<223> OTHER INFORMATION: Nucleic acid sequence of human codon optimized VP1_GI.3_Lil08_A43Vplus sign M57Iplus sign S94L

<400> SEQUENCE: 173

```
atgatgatgg cttccaagga tgctcccaca aacatggatg gaacaagcgg cgcggggcaa     60

cttgtgccgg aggtgtccac ggcggaaccc atttccatgg aacctgtggc cggcgcagcc    120

actgctgtgg ccaccgcagg acaggtaaac atgatcgacc cctggatcat ctcaaattac    180

gttcaggctc cacaggggga gtttaccata agcccaaaca acaccccggg tgacatcttg    240

tttgacctgc agctaggacc acacttgaat ccgtttctgc tccacttggc tcagatgtat    300

aatggatggg ttggaaacat gaaggtgcgc gtgctcctgg cgggcaatgc attcacagcc    360

gggaagatta ttatctcttg cgtgccacct ggatttgcag cccagaacgt gtctatcgca    420

caggcaacca tgtttccgca tgtcatcgca gatgtgcgcg tgctagagcc catcgaggtg    480

ccccttgagg acgtgcgcaa cgtcctattc cataacaatg atagcacccc caccatgcgc    540

ttgatatgta tgttatatac tcccctccgc gccagtgggt ccagctccgg gaccgatcct    600

tttgtgattg ctgggcgggt gttgacttgt cctagccctg acttcaactt cctttttctg    660

gtgcctccaa atgtagaaca gaaaacaaag ccattcagcg tgccaaacct gccccttaac    720

gtgctgtcga attcccgagt gccttccctt attaagtcca tgatggtatc tcaggatcac    780
```

ggtcaaatgg tgcagtttca gaacggccga gtgacgttag acgggcagct gcagggcaca 840
accccaacca gtgccagtca gctgtgtaag atcagaggca ccgtctacca cgcaactggc 900
ggacaggggc tgaatcttac tgagatcgat ggtacccct accatgcatt cgagtcacct 960
gcacctattg gatttcccga tcttggggag tgtgattggc atatcaatgc ttcacctgcc 1020
aacgctttca cagacgggtc tattattcat cgcattgacg tagcacagga tagcacattt 1080
gccccgcacc tgggtaccat ccactatacg aacgcagatt acaacgcaaa cgtgggtctt 1140
atctgtagcc tagagtggct atctccgcca agcggtgggg cccctaaagt taacccatgg 1200
gctattcctc ggtacgggtc tacgctgact gaggccgctc agctggcacc ccccatatat 1260
ccaccaggat tcggggaagc cattgttttc tttatgtccg attttccgat agccaacggt 1320
tcagatggcc ttagtgtccc ttgcacgatt ccacaggaat ttgtgacaca cttcgtaaac 1380
gagcaggctc ctactcgggg cgaggctgcc ttgttgcatt acgtagaccc cgatacccat 1440
agaaacctgg gcgaattcaa actctaccct gaaggtttca tgacctgcgt acctaactcc 1500
tccggcagtg gccctcaaac cttgccgatc aacggcgtgt tcacgtttat cagctgggtt 1560
tcacggtttt accaactcaa gcccgtcgga acaactgggc cagttcggag gctcgggatc 1620
agacggagct ag 1632

<210> SEQ ID NO 174
<211> LENGTH: 543
<212> TYPE: PRT
<213> ORGANISM: Norovirus

<400> SEQUENCE: 174

Met Met Met Ala Ser Lys Asp Ala Pro Thr Asn Met Asp Gly Thr Ser
1 5 10 15

Gly Ala Gly Gln Leu Val Pro Glu Val Ser Thr Ala Glu Pro Ile Ser
20 25 30

Met Glu Pro Val Ala Gly Ala Ala Thr Ala Val Ala Thr Ala Gly Gln
35 40 45

Val Asn Met Ile Asp Pro Trp Ile Ile Ser Asn Tyr Val Gln Ala Pro
50 55 60

Gln Gly Glu Phe Thr Ile Ser Pro Asn Asn Thr Pro Gly Asp Ile Leu
65 70 75 80

Phe Asp Leu Gln Leu Gly Pro His Leu Asn Pro Phe Leu Leu His Leu
85 90 95

Ala Gln Met Tyr Asn Gly Trp Val Gly Asn Met Lys Val Arg Val Leu
100 105 110

Leu Ala Gly Asn Ala Phe Thr Ala Gly Lys Ile Ile Ile Ser Cys Val
115 120 125

Pro Pro Gly Phe Ala Ala Gln Asn Val Ser Ile Ala Gln Ala Thr Met
130 135 140

Phe Pro His Val Ile Ala Asp Val Arg Val Leu Glu Pro Ile Glu Val
145 150 155 160

Pro Leu Glu Asp Val Arg Asn Val Leu Phe His Asn Asn Asp Ser Thr
165 170 175

Pro Thr Met Arg Leu Ile Cys Met Leu Tyr Thr Pro Leu Arg Ala Ser
180 185 190

Gly Ser Ser Ser Gly Thr Asp Pro Phe Val Ile Ala Gly Arg Val Leu
195 200 205

Thr Cys Pro Ser Pro Asp Phe Asn Phe Leu Phe Leu Val Pro Pro Asn
210 215 220

Val Glu Gln Lys Thr Lys Pro Phe Ser Val Pro Asn Leu Pro Leu Asn
225 230 235 240

Val Leu Ser Asn Ser Arg Val Pro Ser Leu Ile Lys Ser Met Met Val
245 250 255

Ser Gln Asp His Gly Gln Met Val Gln Phe Gln Asn Gly Arg Val Thr
260 265 270

Leu Asp Gly Gln Leu Gln Gly Thr Thr Pro Thr Ser Ala Ser Gln Leu
275 280 285

Cys Lys Ile Arg Gly Thr Val Tyr His Ala Thr Gly Gly Gln Gly Leu
290 295 300

Asn Leu Thr Glu Ile Asp Gly Thr Pro Tyr His Ala Phe Glu Ser Pro
305 310 315 320

Ala Pro Ile Gly Phe Pro Asp Leu Gly Glu Cys Asp Trp His Ile Asn
325 330 335

Ala Ser Pro Ala Asn Ala Phe Thr Asp Gly Ser Ile Ile His Arg Ile
340 345 350

Asp Val Ala Gln Asp Ser Thr Phe Ala Pro His Leu Gly Thr Ile His
355 360 365

Tyr Thr Asn Ala Asp Tyr Asn Ala Asn Val Gly Leu Ile Cys Ser Leu
370 375 380

Glu Trp Leu Ser Pro Pro Ser Gly Gly Ala Pro Lys Val Asn Pro Trp
385 390 395 400

Ala Ile Pro Arg Tyr Gly Ser Thr Leu Thr Glu Ala Ala Gln Leu Ala
405 410 415

Pro Pro Ile Tyr Pro Pro Gly Phe Gly Glu Ala Ile Val Phe Phe Met
420 425 430

Ser Asp Phe Pro Ile Ala Asn Gly Ser Asp Gly Leu Ser Val Pro Cys
435 440 445

Thr Ile Pro Gln Glu Phe Val Thr His Phe Val Asn Glu Gln Ala Pro
450 455 460

Thr Arg Gly Glu Ala Ala Leu Leu His Tyr Val Asp Pro Asp Thr His
465 470 475 480

Arg Asn Leu Gly Glu Phe Lys Leu Tyr Pro Glu Gly Phe Met Thr Cys
485 490 495

Val Pro Asn Ser Ser Gly Ser Gly Pro Gln Thr Leu Pro Ile Asn Gly
500 505 510

Val Phe Thr Phe Ile Ser Trp Val Ser Arg Phe Tyr Gln Leu Lys Pro
515 520 525

Val Gly Thr Thr Gly Pro Val Arg Arg Leu Gly Ile Arg Arg Ser
530 535 540

<210> SEQ ID NO 175
<211> LENGTH: 1617
<212> TYPE: DNA
<213> ORGANISM: Norovirus

<400> SEQUENCE: 175
atgatgatgg ccagcaagga cgctccgagt aacatggacg gcacttcggg cgcggggcag 60
ctggtgcccg aggtcaatgc cgcagaacca cttcctcttg agcccgtcgt tggcgccgcc 120
acagctgtcg caactgcagg ccaagtcaat atgatcgacc cgtggataat gaacaatttc 180
gttcaggcac cagaaggaga attcaccatc tcccccaata acaccccagg ggatattctg 240
tttgacctca ggttaggacc ccacttgaac ccctttctgc ttcatctctc acaaatgtat 300

```
aatggctggg tcgggaatat gcgcgtgcgg gtgatgctag ccggcaatgc tttttctgca    360
ggcaagatta tcatttgctg cgttcctcct ggattcgaat ctcaaaatat cagcattggt    420
caagcaacca tgtttccaca tgtgatcgct gatgttcgcg tcctggaacc cattgaagtt    480
cctctcgacg acgtgagaaa tgttctcttc cacaccaacg agaataggcc gactatgaga    540
cttctgtgta tgctctacac cccattaaga gccgggggag catcctcagg tactgaccca    600
tttgtgattg ccgggcgggt gctcacatgc ccggctccag actttaactt ccttttcttg    660
gtgccaccca gtgttgaaca gaaaaccaga cagctcacca tcccaaatat cccattgaac    720
aatctcgcca acagcagggt gccagcaatg ataaacaaaa tgacagtcag tgctgaccag    780
aaccaggtag tccagtttca gaacggcaga tgcacgcttg agggccaact gcttgggacg    840
accccagtct ccgcgaacca ggtggcccga atccggggta aagtcttcag tacaaactcc    900
ggcactggcc ttaacctcac agaggttgac ggcactccct atcatgcttt tgagtctcca    960
gcccctcttg gctttcccga tataggcaac tgtgactggc acgtttatgc gtttaaagta   1020
aaccagaaca ccggcgatcc tatgtatagg ttggatataa cacaaggtaa ttcattcgcc   1080
ccacacttgg gtagcatcga gttcagttca gagaaccatc cgagtggtga tcagctaggc   1140
acattgacgt ggatcagccc tctgaataac gcatcaagag tggatccctg gaagatccct   1200
acctatgggt ccactctgac agagagcaca aatttggctc cgcccatttt cccacccgga   1260
ttcggcgagg ccatagtgta ctttatgtct gactttccta tcgtcagcgg gaatacagcc   1320
cagattcctt gcacactgcc acaagaattc gtctcatcct ttgtagagca gcaggcacct   1380
attcgaggtg aggccgccct cttgcactac gtggaccctg acacccaccg caatcttggc   1440
gagtttaagc tgtaccctga cgggtttatt acctgtgtac ccaacaccgg cggcggccca   1500
caaaatttgc ccagcaatgg cgtgtttgtc ttttcctctt gggtgtctcg atactaccag   1560
cttaaacctg tcggaactac gggccccgtg cgacgactcg gcgtgaggcg ggtgtga      1617
```

<210> SEQ ID NO 176
<211> LENGTH: 1617
<212> TYPE: DNA
<213> ORGANISM: Artificial Sequence
<220> FEATURE:
<223> OTHER INFORMATION: Nucleic acid sequence of human codon optimized
VP1_GI.7/GA5043/USA/2014_R84S

<400> SEQUENCE: 176

```
atgatgatgg ccagcaagga cgctccgagt aacatggacg gcacttcggg cgcggggcag     60
ctggtgcccg aggtcaatgc cgcagaacca cttcctcttg agcccgtcgt tggcgccgcc    120
acagctgtcg caactgcagg ccaagtcaat atgatcgacc cgtggataat gaacaatttc    180
gttcaggcac cagaaggaga attcaccatc tcccccaata acaccccagg ggatattctg    240
tttgacctca gcttaggacc ccacttgaac cccttttctgc ttcatctctc acaaatgtat   300
aatggctggg tcgggaatat gcgcgtgcgg gtgatgctag ccggcaatgc tttttctgca    360
ggcaagatta tcatttgctg cgttcctcct ggattcgaat ctcaaaatat cagcattggt    420
caagcaacca tgtttccaca tgtgatcgct gatgttcgcg tcctggaacc cattgaagtt    480
cctctcgacg acgtgagaaa tgttctcttc cacaccaacg agaataggcc gactatgaga    540
cttctgtgta tgctctacac cccattaaga gccgggggag catcctcagg tactgaccca    600
tttgtgattg ccgggcgggt gctcacatgc ccggctccag actttaactt ccttttcttg    660
gtgccaccca gtgttgaaca gaaaaccaga cagctcacca tcccaaatat cccattgaac    720
```

```
aatctcgcca acagcagggt gccagcaatg ataaacaaaa tgacagtcag tgctgaccag    780

aaccaggtag tccagtttca gaacggcaga tgcacgcttg agggccaact gcttgggacg    840

accccagtct ccgcgaacca ggtggcccga atccggggta aagtcttcag tacaaactcc    900

ggcactggcc ttaacctcac agaggttgac ggcactccct atcatgcttt tgagtctcca    960

gcccctcttg gctttcccga tataggcaac tgtgactggc acgtttatgc gtttaaagta   1020

aaccagaaca ccggcgatcc tatgtatagg ttggatataa cacaaggtaa ttcattcgcc   1080

ccacacttgg gtagcatcga gttcagttca gagaaccatc cgagtggtga tcagctaggc   1140

acattgacgt ggatcagccc tctgaataac gcatcaagag tggatccctg gaagatccct   1200

acctatgggt ccactctgac agagagcaca aatttggctc cgcccatttt cccacccgga   1260

ttcggcgagg ccatagtgta ctttatgtct gactttccta tcgtcagcgg gaatacagcc   1320

cagattcctt gcacactgcc acaagaattc gtctcatcct ttgtagagca gcaggcacct   1380

attcgaggtg aggccgccct cttgcactac gtggaccctg acacccaccg caatcttggc   1440

gagtttaagc tgtaccctga cgggtttatt acctgtgtac ccaacaccgg cggcggccca   1500

caaaatttgc ccagcaatgg cgtgtttgtc ttttcctctt gggtgtctcg atactaccag   1560

cttaaacctg tcggaactac gggccccgtg cgacgactcg gcgtgaggcg ggtgtga      1617
```

<210> SEQ ID NO 177
<211> LENGTH: 538
<212> TYPE: PRT
<213> ORGANISM: Norovirus

<400> SEQUENCE: 177

```
Met Met Met Ala Ser Lys Asp Ala Pro Ser Asn Met Asp Gly Thr Ser
1               5                   10                  15

Gly Ala Gly Gln Leu Val Pro Glu Val Asn Ala Ala Glu Pro Leu Pro
            20                  25                  30

Leu Glu Pro Val Val Gly Ala Ala Thr Ala Val Ala Thr Ala Gly Gln
        35                  40                  45

Val Asn Met Ile Asp Pro Trp Ile Met Asn Asn Phe Val Gln Ala Pro
    50                  55                  60

Glu Gly Glu Phe Thr Ile Ser Pro Asn Asn Thr Pro Gly Asp Ile Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Val Met
            100                 105                 110

Leu Ala Gly Asn Ala Phe Ser Ala Gly Lys Ile Ile Ile Cys Cys Val
        115                 120                 125

Pro Pro Gly Phe Glu Ser Gln Asn Ile Ser Ile Gly Gln Ala Thr Met
    130                 135                 140

Phe Pro His Val Ile Ala Asp Val Arg Val Leu Glu Pro Ile Glu Val
145                 150                 155                 160

Pro Leu Asp Asp Val Arg Asn Val Leu Phe His Thr Asn Glu Asn Arg
                165                 170                 175

Pro Thr Met Arg Leu Leu Cys Met Leu Tyr Thr Pro Leu Arg Ala Gly
            180                 185                 190

Gly Ala Ser Ser Gly Thr Asp Pro Phe Val Ile Ala Gly Arg Val Leu
        195                 200                 205

Thr Cys Pro Ala Pro Asp Phe Asn Phe Leu Phe Leu Val Pro Pro Ser
    210                 215                 220
```

```
Val Glu Gln Lys Thr Arg Gln Leu Thr Ile Pro Asn Ile Pro Leu Asn
225                 230                 235                 240

Asn Leu Ala Asn Ser Arg Val Pro Ala Met Ile Asn Lys Met Thr Val
                245                 250                 255

Ser Ala Asp Gln Asn Gln Val Val Gln Phe Gln Asn Gly Arg Cys Thr
            260                 265                 270

Leu Glu Gly Gln Leu Leu Gly Thr Thr Pro Val Ser Ala Asn Gln Val
        275                 280                 285

Ala Arg Ile Arg Gly Lys Val Phe Ser Thr Asn Ser Gly Thr Gly Leu
    290                 295                 300

Asn Leu Thr Glu Val Asp Gly Thr Pro Tyr His Ala Phe Glu Ser Pro
305                 310                 315                 320

Ala Pro Leu Gly Phe Pro Asp Ile Gly Asn Cys Asp Trp His Val Tyr
                325                 330                 335

Ala Phe Lys Val Asn Gln Asn Thr Gly Asp Pro Met Tyr Arg Leu Asp
            340                 345                 350

Ile Thr Gln Gly Asn Ser Phe Ala Pro His Leu Gly Ser Ile Glu Phe
        355                 360                 365

Ser Ser Glu Asn His Pro Ser Gly Asp Gln Leu Gly Thr Leu Thr Trp
    370                 375                 380

Ile Ser Pro Leu Asn Asn Ala Ser Arg Val Asp Pro Trp Lys Ile Pro
385                 390                 395                 400

Thr Tyr Gly Ser Thr Leu Thr Glu Ser Thr Asn Leu Ala Pro Pro Ile
                405                 410                 415

Phe Pro Pro Gly Phe Gly Glu Ala Ile Val Tyr Phe Met Ser Asp Phe
            420                 425                 430

Pro Ile Val Ser Gly Asn Thr Ala Gln Ile Pro Cys Thr Leu Pro Gln
        435                 440                 445

Glu Phe Val Ser Ser Phe Val Glu Gln Gln Ala Pro Ile Arg Gly Glu
    450                 455                 460

Ala Ala Leu Leu His Tyr Val Asp Pro Asp Thr His Arg Asn Leu Gly
465                 470                 475                 480

Glu Phe Lys Leu Tyr Pro Asp Gly Phe Ile Thr Cys Val Pro Asn Thr
                485                 490                 495

Gly Gly Gly Pro Gln Asn Leu Pro Ser Asn Gly Val Phe Val Phe Ser
            500                 505                 510

Ser Trp Val Ser Arg Tyr Tyr Gln Leu Lys Pro Val Gly Thr Thr Gly
        515                 520                 525

Pro Val Arg Arg Leu Gly Val Arg Arg Val
    530                 535
```

<210> SEQ ID NO 178
<211> LENGTH: 1617
<212> TYPE: DNA
<213> ORGANISM: Artificial Sequence
<220> FEATURE:
<223> OTHER INFORMATION: Nucleic acid sequence of human codon optimized VP1_GI.7/GA5043/USA/2014_M57I

<400> SEQUENCE: 178

```
atgatgatgg ccagcaagga cgctccgagt aacatggacg gcacttcggg cgcggggcag     60

ctggtgcccg aggtcaatgc cgcagaacca cttcctcttg agcccgtcgt tggcgccgcc    120

acagctgtcg caactgcagg ccaagtcaat atgatcgacc cgtggataat caacaatttc    180

gttcaggcac cagaaggaga attcaccatc tcccccaata acaccccagg ggatattctg    240
```

```
tttgacctca ggttaggacc ccacttgaac ccctttctgc ttcatctctc acaaatgtat    300

aatggctggg tcgggaatat gcgcgtgcgg gtgatgctag ccggcaatgc tttttctgca    360

ggcaagatta tcatttgctg cgttcctcct ggattcgaat ctcaaaatat cagcattggt    420

caagcaacca tgtttccaca tgtgatcgct gatgttcgcg tcctggaacc cattgaagtt    480

cctctcgacg acgtgagaaa tgttctcttc cacaccaacg agaataggcc gactatgaga    540

cttctgtgta tgctctacac cccattaaga gccgggggag catcctcagg tactgaccca    600

tttgtgattg ccgggcgggt gctcacatgc ccggctccag actttaactt ccttttcttg    660

gtgccaccca gtgttgaaca gaaaaccaga cagctcacca tcccaaatat cccattgaac    720

aatctcgcca acagcagggt gccagcaatg ataaacaaaa tgacagtcag tgctgaccag    780

aaccaggtag tccagtttca gaacggcaga tgcacgcttg agggccaact gcttgggacg    840

accccagtct ccgcgaacca ggtggcccga atccggggta aagtcttcag tacaaactcc    900

ggcactggcc ttaacctcac agaggttgac ggcactccct atcatgcttt tgagtctcca    960

gcccctcttg gctttcccga tataggcaac tgtgactggc acgtttatgc gtttaaagta   1020

aaccagaaca ccggcgatcc tatgtatagg ttggatataa cacaaggtaa ttcattcgcc   1080

ccacacttgg gtagcatcga gttcagttca gagaaccatc cgagtggtga tcagctaggc   1140

acattgacgt ggatcagccc tctgaataac gcatcaagag tggatccctg gaagatccct   1200

acctatgggt ccactctgac agagagcaca aatttggctc cgcccatttt cccacccgga   1260

ttcggcgagg ccatagtgta ctttatgtct gactttccta tcgtcagcgg gaatacagcc   1320

cagattcctt gcacactgcc acaagaattc gtctcatcct ttgtagagca gcaggcacct   1380

attcgaggtg aggccgccct cttgcactac gtggaccctg acacccaccg caatcttggc   1440

gagtttaagc tgtaccctga cggtttatt acctgtgtac ccaacaccgg cggcggccca   1500

caaaatttgc ccagcaatgg cgtgtttgtc ttttcctctt gggtgtctcg atactaccag   1560

cttaaacctg tcggaactac gggccccgtg cgacgactcg gcgtgaggcg ggtgtga      1617
```

<210> SEQ ID NO 179
<211> LENGTH: 538
<212> TYPE: PRT
<213> ORGANISM: Norovirus

<400> SEQUENCE: 179

```
Met Met Met Ala Ser Lys Asp Ala Pro Ser Asn Met Asp Gly Thr Ser
1               5                   10                  15

Gly Ala Gly Gln Leu Val Pro Glu Val Asn Ala Ala Glu Pro Leu Pro
            20                  25                  30

Leu Glu Pro Val Val Gly Ala Ala Thr Ala Val Ala Thr Ala Gly Gln
        35                  40                  45

Val Asn Met Ile Asp Pro Trp Ile Ile Asn Asn Phe Val Gln Ala Pro
    50                  55                  60

Glu Gly Glu Phe Thr Ile Ser Pro Asn Asn Thr Pro Gly Asp Ile Leu
65                  70                  75                  80

Phe Asp Leu Arg Leu Gly Pro His Leu Asn Pro Phe Leu Leu His Leu
                85                  90                  95

Ser Gln Met Tyr Asn Gly Trp Val Gly Asn Met Arg Val Arg Val Met
            100                 105                 110

Leu Ala Gly Asn Ala Phe Ser Ala Gly Lys Ile Ile Ile Cys Cys Val
        115                 120                 125
```

```
Pro Pro Gly Phe Glu Ser Gln Asn Ile Ser Ile Gly Gln Ala Thr Met
    130                 135                 140

Phe Pro His Val Ile Ala Asp Val Arg Val Leu Glu Pro Ile Glu Val
145                 150                 155                 160

Pro Leu Asp Asp Val Arg Asn Val Leu Phe His Thr Asn Glu Asn Arg
                165                 170                 175

Pro Thr Met Arg Leu Leu Cys Met Leu Tyr Thr Pro Leu Arg Ala Gly
            180                 185                 190

Gly Ala Ser Ser Gly Thr Asp Pro Phe Val Ile Ala Gly Arg Val Leu
        195                 200                 205

Thr Cys Pro Ala Pro Asp Phe Asn Phe Leu Phe Leu Val Pro Pro Ser
    210                 215                 220

Val Glu Gln Lys Thr Arg Gln Leu Thr Ile Pro Asn Ile Pro Leu Asn
225                 230                 235                 240

Asn Leu Ala Asn Ser Arg Val Pro Ala Met Ile Asn Lys Met Thr Val
                245                 250                 255

Ser Ala Asp Gln Asn Gln Val Val Gln Phe Gln Asn Gly Arg Cys Thr
            260                 265                 270

Leu Glu Gly Gln Leu Leu Gly Thr Thr Pro Val Ser Ala Asn Gln Val
        275                 280                 285

Ala Arg Ile Arg Gly Lys Val Phe Ser Thr Asn Ser Gly Thr Gly Leu
    290                 295                 300

Asn Leu Thr Glu Val Asp Gly Thr Pro Tyr His Ala Phe Glu Ser Pro
305                 310                 315                 320

Ala Pro Leu Gly Phe Pro Asp Ile Gly Asn Cys Asp Trp His Val Tyr
                325                 330                 335

Ala Phe Lys Val Asn Gln Asn Thr Gly Asp Pro Met Tyr Arg Leu Asp
            340                 345                 350

Ile Thr Gln Gly Asn Ser Phe Ala Pro His Leu Gly Ser Ile Glu Phe
        355                 360                 365

Ser Ser Glu Asn His Pro Ser Gly Asp Gln Leu Gly Thr Leu Thr Trp
    370                 375                 380

Ile Ser Pro Leu Asn Asn Ala Ser Arg Val Asp Pro Trp Lys Ile Pro
385                 390                 395                 400

Thr Tyr Gly Ser Thr Leu Thr Glu Ser Thr Asn Leu Ala Pro Pro Ile
                405                 410                 415

Phe Pro Pro Gly Phe Gly Glu Ala Ile Val Tyr Phe Met Ser Asp Phe
            420                 425                 430

Pro Ile Val Ser Gly Asn Thr Ala Gln Ile Pro Cys Thr Leu Pro Gln
        435                 440                 445

Glu Phe Val Ser Ser Phe Val Glu Gln Gln Ala Pro Ile Arg Gly Glu
    450                 455                 460

Ala Ala Leu Leu His Tyr Val Asp Pro Asp Thr His Arg Asn Leu Gly
465                 470                 475                 480

Glu Phe Lys Leu Tyr Pro Asp Gly Phe Ile Thr Cys Val Pro Asn Thr
                485                 490                 495

Gly Gly Gly Pro Gln Asn Leu Pro Ser Asn Gly Val Phe Val Phe Ser
            500                 505                 510

Ser Trp Val Ser Arg Tyr Tyr Gln Leu Lys Pro Val Gly Thr Thr Gly
        515                 520                 525

Pro Val Arg Arg Leu Gly Val Arg Arg Val
    530                 535
```

<210> SEQ ID NO 180
<211> LENGTH: 1617
<212> TYPE: DNA
<213> ORGANISM: Artificial Sequence
<220> FEATURE:
<223> OTHER INFORMATION: Nucleic acid sequence of human codon optimized VP1_GI.7/GA5043/USA/2014_M57I plus sign R84S

<400> SEQUENCE: 180

```
atgatgatgg ccagcaagga cgctccgagt aacatggacg gcacttcggg cgcggggcag     60

ctggtgcccg aggtcaatgc cgcagaacca cttcctcttg agcccgtcgt tggcgccgcc    120

acagctgtcg caactgcagg ccaagtcaat atgatcgacc cgtggataat caacaatttc    180

gttcaggcac cagaaggaga attcaccatc tcccccaata acaccccagg ggatattctg    240

tttgacctca gcttaggacc ccacttgaac ccctttctgc ttcatctctc acaaatgtat    300

aatggctggg tcgggaatat gcgcgtgcgg gtgatgctag ccggcaatgc tttttctgca    360

ggcaagatta tcatttgctg cgttcctcct ggattcgaat ctcaaaatat cagcattggt    420

caagcaacca tgtttccaca tgtgatcgct gatgttcgcg tcctggaacc cattgaagtt    480

cctctcgacg acgtgagaaa tgttctcttc cacaccaacg agaataggcc gactatgaga    540

cttctgtgta tgctctacac cccattaaga gccgggggag catcctcagg tactgaccca    600

tttgtgattg ccgggcgggt gctcacatgc ccggctccag actttaactt ccttttcttg    660

gtgccaccca gtgttgaaca gaaaaccaga cagctcacca tcccaaatat cccattgaac    720

aatctcgcca acagcagggt gccagcaatg ataaacaaaa tgacagtcag tgctgaccag    780

aaccaggtag tccagtttca gaacggcaga tgcacgcttg agggccaact gcttgggacg    840

accccagtct ccgcgaacca ggtggcccga atccggggta aagtcttcag tacaaactcc    900

ggcactggcc ttaacctcac agaggttgac ggcactccct atcatgcttt tgagtctcca    960

gcccctcttg gctttcccga tataggcaac tgtgactggc acgtttatgc gtttaaagta   1020

aaccagaaca ccggcgatcc tatgtatagg ttggatataa cacaaggtaa ttcattcgcc   1080

ccacacttgg gtagcatcga gttcagttca gagaaccatc cgagtggtga tcagctaggc   1140

acattgacgt ggatcagccc tctgaataac gcatcaagag tggatccctg gaagatccct   1200

acctatgggt ccactctgac agagagcaca aatttggctc cgcccatttt cccacccgga   1260

ttcggcgagg ccatagtgta ctttatgtct gactttccta tcgtcagcgg gaatacagcc   1320

cagattcctt gcacactgcc acaagaattc gtctcatcct ttgtagagca gcaggcacct   1380

attcgaggtg aggccgccct cttgcactac gtggaccctg acacccaccg caatcttggc   1440

gagtttaagc tgtaccctga cgggtttatt acctgtgtac ccaacaccgg cggcggccca   1500

caaaatttgc ccagcaatgg cgtgtttgtc ttttcctctt gggtgtctcg atactaccag   1560

cttaaacctg tcggaactac gggccccgtg cgacgactcg gcgtgaggcg ggtgtga      1617
```

<210> SEQ ID NO 181
<211> LENGTH: 538
<212> TYPE: PRT
<213> ORGANISM: Norovirus

<400> SEQUENCE: 181

```
Met Met Met Ala Ser Lys Asp Ala Pro Ser Asn Met Asp Gly Thr Ser
1               5                   10                  15

Gly Ala Gly Gln Leu Val Pro Glu Val Asn Ala Ala Glu Pro Leu Pro
            20                  25                  30

Leu Glu Pro Val Val Gly Ala Ala Thr Ala Val Ala Thr Ala Gly Gln
```

-continued

```
        35                  40                  45

Val Asn Met Ile Asp Pro Trp Ile Ile Asn Asn Phe Val Gln Ala Pro
    50                  55                  60

Glu Gly Glu Phe Thr Ile Ser Pro Asn Asn Thr Pro Gly Asp Ile Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Val Met
            100                 105                 110

Leu Ala Gly Asn Ala Phe Ser Ala Gly Lys Ile Ile Ile Cys Cys Val
        115                 120                 125

Pro Pro Gly Phe Glu Ser Gln Asn Ile Ser Ile Gly Gln Ala Thr Met
    130                 135                 140

Phe Pro His Val Ile Ala Asp Val Arg Val Leu Glu Pro Ile Glu Val
145                 150                 155                 160

Pro Leu Asp Asp Val Arg Asn Val Leu Phe His Thr Asn Glu Asn Arg
                165                 170                 175

Pro Thr Met Arg Leu Leu Cys Met Leu Tyr Thr Pro Leu Arg Ala Gly
            180                 185                 190

Gly Ala Ser Ser Gly Thr Asp Pro Phe Val Ile Ala Gly Arg Val Leu
        195                 200                 205

Thr Cys Pro Ala Pro Asp Phe Asn Phe Leu Phe Leu Val Pro Pro Ser
    210                 215                 220

Val Glu Gln Lys Thr Arg Gln Leu Thr Ile Pro Asn Ile Pro Leu Asn
225                 230                 235                 240

Asn Leu Ala Asn Ser Arg Val Pro Ala Met Ile Asn Lys Met Thr Val
                245                 250                 255

Ser Ala Asp Gln Asn Gln Val Val Gln Phe Gln Asn Gly Arg Cys Thr
            260                 265                 270

Leu Glu Gly Gln Leu Leu Gly Thr Thr Pro Val Ser Ala Asn Gln Val
        275                 280                 285

Ala Arg Ile Arg Gly Lys Val Phe Ser Thr Asn Ser Gly Thr Gly Leu
    290                 295                 300

Asn Leu Thr Glu Val Asp Gly Thr Pro Tyr His Ala Phe Glu Ser Pro
305                 310                 315                 320

Ala Pro Leu Gly Phe Pro Asp Ile Gly Asn Cys Asp Trp His Val Tyr
                325                 330                 335

Ala Phe Lys Val Asn Gln Asn Thr Gly Asp Pro Met Tyr Arg Leu Asp
            340                 345                 350

Ile Thr Gln Gly Asn Ser Phe Ala Pro His Leu Gly Ser Ile Glu Phe
        355                 360                 365

Ser Ser Glu Asn His Pro Ser Gly Asp Gln Leu Gly Thr Leu Thr Trp
    370                 375                 380

Ile Ser Pro Leu Asn Asn Ala Ser Arg Val Asp Pro Trp Lys Ile Pro
385                 390                 395                 400

Thr Tyr Gly Ser Thr Leu Thr Glu Ser Thr Asn Leu Ala Pro Pro Ile
                405                 410                 415

Phe Pro Pro Gly Phe Gly Glu Ala Ile Val Tyr Phe Met Ser Asp Phe
            420                 425                 430

Pro Ile Val Ser Gly Asn Thr Ala Gln Ile Pro Cys Thr Leu Pro Gln
        435                 440                 445

Glu Phe Val Ser Ser Phe Val Glu Gln Gln Ala Pro Ile Arg Gly Glu
    450                 455                 460
```

```
Ala Ala Leu Leu His Tyr Val Asp Pro Asp Thr His Arg Asn Leu Gly
465                 470                 475                 480

Glu Phe Lys Leu Tyr Pro Asp Gly Phe Ile Thr Cys Val Pro Asn Thr
                485                 490                 495

Gly Gly Gly Pro Gln Asn Leu Pro Ser Asn Gly Val Phe Val Phe Ser
            500                 505                 510

Ser Trp Val Ser Arg Tyr Tyr Gln Leu Lys Pro Val Gly Thr Thr Gly
        515                 520                 525

Pro Val Arg Arg Leu Gly Val Arg Arg Val
    530                 535


<210> SEQ ID NO 182
<211> LENGTH: 542
<212> TYPE: PRT
<213> ORGANISM: Norovirus

<400> SEQUENCE: 182

Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
            20                  25                  30

Ala Gly Ala Ala Leu Ala Val Pro Val Thr Gly Gln Thr Asn Ile Ile
        35                  40                  45

Asp Pro Trp Ile Arg Ala Asn Phe Val Gln Ala Pro Asn Gly Glu Phe
    50                  55                  60

Thr Val Ser Pro Arg Asn Ser Pro Gly Glu Val Leu Leu Asn Leu Ser
65                  70                  75                  80

Leu Gly Pro Glu Leu Asn Pro Tyr Leu Leu His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
        275                 280                 285

Glu Val Thr Ala His Leu His Asp Asn Asp His Leu Tyr Asn Val Thr
```

```
    290                 295                 300

Ile Thr Asn Leu Asn Gly Ser Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Ser Gln Arg Asp Lys His Asn Thr Pro Gly His Asn Glu Pro Ala Asn
            340                 345                 350

Arg Ala His Asp Ala Val Val Pro Thr Tyr Thr Ala Gln Tyr Thr Pro
        355                 360                 365

Lys Leu Gly Gln Ile Gln Ile Gly Thr Trp Gln Thr Asp Asp Leu Thr
    370                 375                 380

Val Asn Gln Pro Val Lys Phe Thr Pro Val Gly Leu Asn Asp Thr Asp
385                 390                 395                 400

His Phe Asn Gln Trp Val Val Pro Arg Tyr Ala Gly Ala Leu Asn Leu
                405                 410                 415

Asn Thr Asn Leu Ala Pro Ser Val Ala Pro Val Phe Pro Gly Glu Arg
            420                 425                 430

Leu Leu Phe Phe Arg Ser Tyr Ile Pro Leu Lys Gly Gly Tyr Gly Thr
        435                 440                 445

Pro Ala Ile Asp Cys Leu Leu Pro Gln Glu Trp Val Gln His Phe Tyr
    450                 455                 460

Gln Glu Ala Ala Pro Ser Met Ser Glu Val Ala Leu Val Arg Tyr Ile
465                 470                 475                 480

Asn Pro Asp Thr Gly Arg Ala Leu Phe Glu Ala Lys Leu His Arg Ala
                485                 490                 495

Gly Phe Met Thr Val Ser Ser Asn Thr Ser Ala Pro Val Val Val Pro
            500                 505                 510

Ala Asn Gly Tyr Phe Arg Phe Asp Ser Trp Val Asn Gln Phe Tyr Ser
        515                 520                 525

Leu Ala Pro Met Gly Thr Gly Asn Gly Arg Arg Arg Ile Gln
    530                 535                 540


<210> SEQ ID NO 183
<211> LENGTH: 1629
<212> TYPE: DNA
<213> ORGANISM: Artificial Sequence
<220> FEATURE:
<223> OTHER INFORMATION: Nucleic acid sequence of human codon optimized
      VP1_GII.2_CGMH47_A39V plus sign E80S plus sign A90L

<400> SEQUENCE: 183

atgaagatgg catccaacga cgccgcaccc agcacagacg gagctgccgg attggtaccc     60

gagtctaata acgaggtgat ggccttggag cctgttgcag gggctgccct cgcagtgcct    120

gtgaccgggc agacaaatat catcgatcct tggattagag ctaatttcgt gcaagcccca    180

aatggggagt ttacggtcag ccctagaaat agccctgggg aagtgctcct caatctcagc    240

ctgggaccag aacttaatcc gtacctgctc cacctggccc ggatgtacaa tggatatgca    300

ggagggatgg aggtgcaggt tatgctggct ggcaatgcct ttacagcagg caaactcgtt    360

ttcgcagccg tccctcccca cttcccagtt gaaaatcttt cccctcagca gattaccatg    420

tttccccatg tcatcatcga tgtgcgtacc ctggaacctg tgctgttgcc tttaccagac    480

gtgcggaata atttctttca ctataatcag aaggatgacc caaaaatgcg gatcgttgcg    540

atgctttata ctcccctgcg tagcaatggt agtggggatg acgtttttac agtgagttgt    600

cgggtactaa ctcgcccttc accagacttc gactttacgt acttggtgcc tcccactgtc    660
```

gaaagcaaaa ctaagccatt cacacttccc atcctcaccc tcggagaact ctcgaactcc 720
cgcttccctg tttcaattga tcagatgtac acgtctccaa atgaagtcat ttctgtgcag 780
tgtcagaacg gcaggtgcac cttagacggt gaactgcagg ggacaacgca gttgcaggtc 840
agtggaattt gcgcctttaa gggcgaagtg acagctcacc tccacgacaa cgatcatctc 900
tacaatgtta ctattactaa tctcaatgga agtcctttcg acccctcgga agatattccc 960
gctccactcg gagtacctga ctttcaggga cgcgtcttcg gcgtgatatc acaacgagat 1020
aagcataaca cacccggaca taatgagcca gccaatagag cccacgacgc agtcgttccg 1080
acctatacgg ctcagtacac cccaaagctc ggccagatac aaatcgggac ttggcagacc 1140
gatgacctca ctgtgaatca acctgtgaaa ttcactccag taggtctgaa tgatacagac 1200
cactttaacc agtgggtggt ccctagatac gccggagcct tgaacctaaa cactaacctt 1260
gccccttccg ttgcacctgt gtttccgggg gagcggttgc tcttctttag aagctatatt 1320
cctctgaagg gcgggtatgg tactccagca atcgactgcc tgctacctca ggagtgggtt 1380
caacatttct atcaagaggc cgcacctagt atgagcgagg tggctttggt cagatacatc 1440
aatccagaca caggaagagc actgttcgag gccaagctgc acagagccgg cttcatgacc 1500
gtctcatcca atacatccgc acccgtagta gtccccgcca acgggtactt cagattcgac 1560
agttgggtga atcagtttta ctcgttggcc cccatgggca cagggaacgg tcgccgacgg 1620
atccagtaa 1629

<210> SEQ ID NO 184
<211> LENGTH: 542
<212> TYPE: PRT
<213> ORGANISM: Norovirus

<400> SEQUENCE: 184

Met Lys Met Ala Ser Asn Asp Ala Ala Pro Ser Thr Asp Gly Ala Ala
1 5 10 15

Gly Leu Val Pro Glu Ser Asn Asn Glu Val Met Ala Leu Glu Pro Val
20 25 30

Ala Gly Ala Ala Leu Ala Ala Pro Val Thr Gly Gln Thr Asn Ile Ile
35 40 45

Asp Pro Trp Ile Ile Ala Asn Phe Val Gln Ala Pro Asn Gly Glu Phe
50 55 60

Thr Val Ser Pro Arg Asn Ser Pro Gly Glu Val Leu Leu Asn Leu Ser
65 70 75 80

Leu Gly Pro Glu Leu Asn Pro Tyr Leu Leu His Leu Ala Arg Met Tyr
85 90 95

Asn Gly Tyr Ala Gly Gly Met Glu Val Gln Val Met Leu Ala Gly Asn
100 105 110

Ala Phe Thr Ala Gly Lys Leu Val Phe Ala Ala Val Pro Pro His Phe
115 120 125

Pro Val Glu Asn Leu Ser Pro Gln Gln Ile Thr Met Phe Pro His Val
130 135 140

Ile Ile Asp Val Arg Thr Leu Glu Pro Val Leu Leu Pro Leu Pro Asp
145 150 155 160

Val Arg Asn Asn Phe Phe His Tyr Asn Gln Lys Asp Asp Pro Lys Met
165 170 175

Arg Ile Val Ala Met Leu Tyr Thr Pro Leu Arg Ser Asn Gly Ser Gly
180 185 190

```
Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
        275                 280                 285

Glu Val Thr Ala His Leu His Asp Asn Asp His Leu Tyr Asn Val Thr
    290                 295                 300

Ile Thr Asn Leu Asn Gly Ser Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Ser Gln Arg Asp Lys His Asn Thr Pro Gly His Asn Glu Pro Ala Asn
            340                 345                 350

Arg Ala His Asp Ala Val Val Pro Thr Tyr Thr Ala Gln Tyr Thr Pro
        355                 360                 365

Lys Leu Gly Gln Ile Gln Ile Gly Thr Trp Gln Thr Asp Asp Leu Thr
    370                 375                 380

Val Asn Gln Pro Val Lys Phe Thr Pro Val Gly Leu Asn Asp Thr Asp
385                 390                 395                 400

His Phe Asn Gln Trp Val Val Pro Arg Tyr Ala Gly Ala Leu Asn Leu
                405                 410                 415

Asn Thr Asn Leu Ala Pro Ser Val Ala Pro Val Phe Pro Gly Glu Arg
            420                 425                 430

Leu Leu Phe Phe Arg Ser Tyr Ile Pro Leu Lys Gly Gly Tyr Gly Thr
        435                 440                 445

Pro Ala Ile Asp Cys Leu Leu Pro Gln Glu Trp Val Gln His Phe Tyr
    450                 455                 460

Gln Glu Ala Ala Pro Ser Met Ser Glu Val Ala Leu Val Arg Tyr Ile
465                 470                 475                 480

Asn Pro Asp Thr Gly Arg Ala Leu Phe Glu Ala Lys Leu His Arg Ala
                485                 490                 495

Gly Phe Met Thr Val Ser Ser Asn Thr Ser Ala Pro Val Val Val Pro
            500                 505                 510

Ala Asn Gly Tyr Phe Arg Phe Asp Ser Trp Val Asn Gln Phe Tyr Ser
        515                 520                 525

Leu Ala Pro Met Gly Thr Gly Asn Gly Arg Arg Arg Ile Gln
    530                 535                 540
```

<210> SEQ ID NO 185
<211> LENGTH: 1629
<212> TYPE: DNA
<213> ORGANISM: Artificial Sequence
<220> FEATURE:
<223> OTHER INFORMATION: Nucleic acid sequence of human codon optimized VP1_GII.2_CGMH47_R53I plus sign E80S plus sign A90L

<400> SEQUENCE: 185
atgaagatgg catccaacga cgccgcaccc agcacagacg gagctgccgg attggtaccc 60
gagtctaata acgaggtgat ggccttggag cctgttgcag gggctgccct cgcagctcct 120
gtgaccgggc agacaaatat catcgatcct tggattatcg ctaatttcgt gcaagcccca 180
aatggggagt ttacggtcag ccctagaaat agccctgggg aagtgctcct caatctcagc 240
ctgggaccag aacttaatcc gtacctgctc cacctggccc ggatgtacaa tggatatgca 300
ggagggatgg aggtgcaggt tatgctggct ggcaatgcct ttacagcagg caaactcgtt 360
ttcgcagccg tccctcccca cttcccagtt gaaaatcttt cccctcagca gattaccatg 420
tttccccatg tcatcatcga tgtgcgtacc ctggaacctg tgctgttgcc tttaccagac 480
gtgcggaata atttctttca ctataatcag aaggatgacc caaaaatgcg gatcgttgcg 540
atgctttata ctcccctgcg tagcaatggt agtggggatg acgtttttac agtgagttgt 600
cgggtactaa ctcgcccttc accagacttc gactttacgt acttggtgcc tcccactgtc 660
gaaagcaaaa ctaagccatt cacacttccc atcctcaccc tcggagaact ctcgaactcc 720
cgcttccctg tttcaattga tcagatgtac acgtctccaa atgaagtcat ttctgtgcag 780
tgtcagaacg gcaggtgcac cttagacggt gaactgcagg ggacaacgca gttgcaggtc 840
agtggaattt gcgcctttaa gggcgaagtg acagctcacc tccacgacaa cgatcatctc 900
tacaatgtta ctattactaa tctcaatgga agtcctttcg acccctcgga agatattccc 960
gctccactcg gagtacctga ctttcaggga cgcgtcttcg gcgtgatatc acaacgagat 1020
aagcataaca cacccggaca taatgagcca gccaatagag cccacgacgc agtcgttccg 1080
acctatacgg ctcagtacac cccaaagctc ggccagatac aaatcgggac ttggcagacc 1140
gatgacctca ctgtgaatca acctgtgaaa ttcactccag taggtctgaa tgatacagac 1200
cactttaacc agtgggtggt ccctagatac gccggagcct tgaacctaaa cactaacctt 1260
gccccttccg ttgcacctgt gtttccgggg gagcggttgc tcttctttag aagctatatt 1320
cctctgaagg gcgggtatgg tactccagca atcgactgcc tgctacctca ggagtgggtt 1380
caacatttct atcaagaggc cgcacctagt atgagcgagg tggctttggt cagatacatc 1440
aatccagaca caggaagagc actgttcgag gccaagctgc acagagccgg cttcatgacc 1500
gtctcatcca atacatccgc acccgtagta gtccccgcca acgggtactt cagattcgac 1560
agttgggtga atcagtttta ctcgttggcc cccatgggca cagggaacgg tcgccgacgg 1620
atccagtaa 1629

<210> SEQ ID NO 186
<211> LENGTH: 542
<212> TYPE: PRT
<213> ORGANISM: Norovirus

<400> SEQUENCE: 186

Met Lys Met Ala Ser Asn Asp Ala Ala Pro Ser Thr Asp Gly Ala Ala
1 5 10 15

Gly Leu Val Pro Glu Ser Asn Asn Glu Val Met Ala Leu Glu Pro Val
20 25 30

Ala Gly Ala Ala Leu Ala Val Pro Val Thr Gly Gln Thr Asn Ile Ile
35 40 45

Asp Pro Trp Ile Ile Ala Asn Phe Val Gln Ala Pro Asn Gly Glu Phe
50 55 60

Thr Val Ser Pro Arg Asn Ser Pro Gly Glu Val Leu Leu Asn Leu Ser
65 70 75 80

Leu Gly Pro Glu Leu Asn Pro Tyr Leu Leu His Leu Ala Arg Met Tyr
85 90 95

```
Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
        275                 280                 285

Glu Val Thr Ala His Leu His Asp Asn Asp His Leu Tyr Asn Val Thr
    290                 295                 300

Ile Thr Asn Leu Asn Gly Ser Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Ser Gln Arg Asp Lys His Asn Thr Pro Gly His Asn Glu Pro Ala Asn
            340                 345                 350

Arg Ala His Asp Ala Val Val Pro Thr Tyr Thr Ala Gln Tyr Thr Pro
        355                 360                 365

Lys Leu Gly Gln Ile Gln Ile Gly Thr Trp Gln Thr Asp Asp Leu Thr
    370                 375                 380

Val Asn Gln Pro Val Lys Phe Thr Pro Val Gly Leu Asn Asp Thr Asp
385                 390                 395                 400

His Phe Asn Gln Trp Val Val Pro Arg Tyr Ala Gly Ala Leu Asn Leu
                405                 410                 415

Asn Thr Asn Leu Ala Pro Ser Val Ala Pro Val Phe Pro Gly Glu Arg
            420                 425                 430

Leu Leu Phe Phe Arg Ser Tyr Ile Pro Leu Lys Gly Gly Tyr Gly Thr
        435                 440                 445

Pro Ala Ile Asp Cys Leu Leu Pro Gln Glu Trp Val Gln His Phe Tyr
    450                 455                 460

Gln Glu Ala Ala Pro Ser Met Ser Glu Val Ala Leu Val Arg Tyr Ile
465                 470                 475                 480

Asn Pro Asp Thr Gly Arg Ala Leu Phe Glu Ala Lys Leu His Arg Ala
                485                 490                 495

Gly Phe Met Thr Val Ser Ser Asn Thr Ser Ala Pro Val Val Val Pro
            500                 505                 510
```

```
Ala Asn Gly Tyr Phe Arg Phe Asp Ser Trp Val Asn Gln Phe Tyr Ser
        515                 520                 525

Leu Ala Pro Met Gly Thr Gly Asn Gly Arg Arg Arg Ile Gln
    530                 535                 540
```

<210> SEQ ID NO 187
<211> LENGTH: 1629
<212> TYPE: DNA
<213> ORGANISM: Artificial Sequence
<220> FEATURE:
<223> OTHER INFORMATION: Nucleic acid sequence of human codon optimized VP1_GII.2_CGMH47_A39Vplus sign R53I plus sign E80S plus sign A90L

<400> SEQUENCE: 187

```
atgaagatgg catccaacga cgccgcaccc agcacagacg gagctgccgg attggtaccc     60

gagtctaata acgaggtgat ggccttggag cctgttgcag ggctgccct cgcagtgcct    120

gtgaccgggc agacaaatat catcgatcct tggattatcg ctaatttcgt gcaagcccca    180

aatggggagt ttacggtcag ccctagaaat agccctgggg aagtgctcct caatctcagc    240

ctgggaccag aacttaatcc gtacctgctc cacctggccc ggatgtacaa tggatatgca    300

ggagggatgg aggtgcaggt tatgctggct ggcaatgcct ttacagcagg caaactcgtt    360

ttcgcagccg tccctcccca cttcccagtt gaaaatcttt cccctcagca gattaccatg    420

tttccccatg tcatcatcga tgtgcgtacc ctggaacctg tgctgttgcc tttaccagac    480

gtgcggaata atttctttca ctataatcag aaggatgacc caaaaatgcg gatcgttgcg    540

atgctttata ctcccctgcg tagcaatggt agtggggatg acgtttttac agtgagttgt    600

cgggtactaa ctcgcccttc accagacttc gactttacgt acttggtgcc tcccactgtc    660

gaaagcaaaa ctaagccatt cacacttccc atcctcaccc tcggagaact ctcgaactcc    720

cgcttccctg tttcaattga tcagatgtac acgtctccaa atgaagtcat ttctgtgcag    780

tgtcagaacg gcaggtgcac cttagacggt gaactgcagg ggacaacgca gttgcaggtc    840

agtggaattt gcgcctttaa gggcgaagtg acagctcacc tccacgacaa cgatcatctc    900

tacaatgtta ctattactaa tctcaatgga agtcctttcg acccctcgga agatattccc    960

gctccactcg gagtacctga ctttcaggga cgcgtcttcg gcgtgatatc acaacgagat   1020

aagcataaca cacccggaca taatgagcca gccaatagag cccacgacgc agtcgttccg   1080

acctatacgg ctcagtacac cccaaagctc ggccagatac aaatcgggac ttggcagacc   1140

gatgacctca ctgtgaatca acctgtgaaa ttcactccag taggtctgaa tgatacagac   1200

cactttaacc agtgggtggt ccctagatac gccggagcct tgaacctaaa cactaacctt   1260

gccccttccg ttgcacctgt gtttccgggg gagcggttgc tcttctttag aagctatatt   1320

cctctgaagg gcgggtatgg tactccagca atcgactgcc tgctacctca ggagtgggtt   1380

caacatttct atcaagaggc cgcacctagt atgagcgagg tggctttggt cagatacatc   1440

aatccagaca caggaagagc actgttcgag gccaagctgc acagagccgg cttcatgacc   1500

gtctcatcca atacatccgc acccgtagta gtccccgcca acgggtactt cagattcgac   1560

agttgggtga atcagtttta ctcgttggcc cccatgggca cagggaacgg tcgccgacgg   1620

atccagtaa                                                            1629
```

<210> SEQ ID NO 188
<211> LENGTH: 540
<212> TYPE: PRT
<213> ORGANISM: Norovirus

<400> SEQUENCE: 188

Met Lys Met Ala Ser Ser Asp Ala Asn Pro Ser Asp Gly Ser Ala Ala
1 5 10 15

Asn Leu Val Pro Glu Val Asn Asn Glu Val Met Ala Leu Glu Pro Val
20 25 30

Val Gly Ala Ala Ile Ala Val Pro Val Ala Gly Gln Gln Asn Val Ile
35 40 45

Asp Pro Trp Ile Ile Asn Asn Phe Val Gln Ala Pro Gly Gly Glu Phe
50 55 60

Thr Val Ser Pro Arg Asn Ala Pro Gly Glu Ile Leu Trp Ser Ala Pro
65 70 75 80

Leu Gly Pro Asp Leu Asn Pro Tyr Leu Ser His Leu Ala Arg Met Tyr
85 90 95

Asn Gly Tyr Ala Gly Gly Phe Glu Val Gln Val Ile Leu Ala Gly Asn
100 105 110

Ala Phe Thr Ala Gly Lys Val Ile Phe Ala Ala Val Pro Pro Asn Phe
115 120 125

Pro Thr Glu Gly Leu Ser Pro Ser Gln Val Thr Met Phe Pro His Ile
130 135 140

Val Val Asp Val Arg Gln Leu Glu Pro Val Leu Ile Pro Leu Pro Asp
145 150 155 160

Val Arg Asn Asn Phe Tyr His Tyr Asn Gln Ser Asn Asp Pro Thr Ile
165 170 175

Lys Leu Ile Ala Met Leu Tyr Thr Pro Leu Arg Ala Asn Asn Ala Gly
180 185 190

Asp Asp Val Phe Thr Val Ser Cys Arg Val Leu Thr Arg Pro Ser Pro
195 200 205

Asp Phe Asp Phe Ile Phe Leu Val Pro Pro Thr Val Glu Ser Arg Thr
210 215 220

Lys Pro Phe Ser Val Pro Val Leu Thr Val Glu Glu Met Thr Asn Ser
225 230 235 240

Arg Phe Pro Ile Pro Leu Glu Lys Leu Phe Thr Gly Pro Ser Ser Ala
245 250 255

Phe Val Val Gln Pro Gln Asn Gly Arg Cys Thr Thr Asp Gly Val Leu
260 265 270

Leu Gly Thr Thr Gln Leu Ser Pro Val Asn Ile Cys Thr Phe Arg Gly
275 280 285

Asp Val Thr His Ile Thr Gly Ser Arg Asn Tyr Thr Met Asn Leu Ala
290 295 300

Ser Gln Asn Trp Asn Asp Tyr Asp Pro Thr Glu Glu Ile Pro Ala Pro
305 310 315 320

Leu Gly Thr Pro Asp Phe Val Gly Lys Ile Gln Gly Val Leu Thr Gln
325 330 335

Thr Thr Arg Thr Asp Gly Ser Thr Arg Gly His Lys Ala Thr Val Tyr
340 345 350

Thr Gly Ser Ala Asp Phe Ala Pro Lys Leu Gly Arg Val Gln Phe Glu
355 360 365

Thr Asp Thr Asp Arg Asp Phe Glu Ala Asn Gln Asn Thr Lys Phe Thr
370 375 380

Pro Val Gly Val Ile Gln Asp Gly Gly Thr Thr His Arg Asn Glu Pro
385 390 395 400

Gln Gln Trp Val Leu Pro Ser Tyr Ser Gly Arg Asn Thr His Asn Val

-continued

```
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 189
<211> LENGTH: 1623
<212> TYPE: DNA
<213> ORGANISM: Artificial Sequence
<220> FEATURE:
<223> OTHER INFORMATION: Nucleic acid sequence of human codon optimized
      VP1 GII.4_Syd12_A39V plus sign R53I

<400> SEQUENCE: 189

```
atgaaaatgg cctcgagtga cgctaaccct agtgacggca gcgccgccaa tcttgtgcct     60

gaggttaata atgaggtgat ggccctggag cctgtggtgg gcgcagccat agcagtcccc    120

gtggccggtc agcagaatgt gattgacccg tggataatca acaattttgt ccaagcccct    180

ggtggggagt tcaccgttag cccgagaaat gcgccaggag aaatcctgtg gtcggcccca    240

ttgggacccg atctgaaccc ctatttgtca catctcgctc ggatgtacaa cgggtatgcc    300

ggcggatttg aagtgcaggt gattctggct gggaacgcgt tcactgctgg caaagtgatc    360

tttgcagcgg tgcctcccaa cttccccact gaaggactgt ctccaagcca ggtcacaatg    420

tttccacaca tcgtggtgga cgtacggcag ctagagcctg tcctgattcc cctccctgat    480

gtacgcaata atttctacca ctacaatcaa tccaatgatc cgaccattaa actcatcgcg    540

atgttgtaca cccctctgcg cgctaacaat gctggagacg acgtattcac cgtgtcatgc    600

agagtgctca ccagaccttc accagacttt gactttatct tcttagtgcc ccccactgtt    660

gagagccgaa ccaagccctt tagtgtcccc gtactcacag tcgaggagat gacaaatagc    720

cgctttccaa tcccccttga gaaactgttc acaggacctt cctcggcatt cgtggttcag    780

ccacagaacg gacgctgcac aactgacggc gtgctgctcg gaaccaccca gcttagccct    840

gttaatatct gtacgtttag aggcgacgta actcacataa ctggctcacg gaactatacc    900

atgaatctgg catcacagaa ttggaatgac tacgacccaa ccgaagagat tcccgcacct    960

cttggaaccc ccgactttgt gggaaaaata cagggcgtcc tgacacaaac caccagaacc   1020

gatggctcca cacggggaca caaggcaacc gtctacactg gctctgccga ttttgccccg   1080

aaactgggta gagtgcagtt tgagaccgac actgaccggg actttgaagc caatcagaat   1140

actaagttca cacctgtagg agtgattcag gacgggggca ccactcaccg gaacgagccg   1200

caacaatggg tcctgccctc ttatagcggg aggaatactc ataatgtgca tttggctcct   1260
```

```
gcagtggctc ccacgtttcc cggggaacaa ctgctctttt ttcgttcaac catgcctgga    1320

tgctccggat atcccaatat ggatctcgat tgcctgctcc cacaggaatg ggtgcagtat    1380

ttttatcaag aggccgcacc agcccaatcc gacgtcgcac ttctgcggtt cgtgaatcca    1440

gacacaggcc gcgtgttgtt tgagtgcaaa ttgcacaaat caggatacgt tacagtggct    1500

catactggac agcatgacct ggtgatccca cccaacggat attttaggtt cgactcctgg    1560

gtgaatcagt tttatacatt agcccccatg gggaatggga ctggcagacg cagggctgtc    1620

tga                                                                 1623
```

<210> SEQ ID NO 190
<211> LENGTH: 540
<212> TYPE: PRT
<213> ORGANISM: Norovirus

<400> SEQUENCE: 190

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Val Pro Val Ala Gly Gln Gln Asn Val Ile
        35                  40                  45

Asp Pro Trp Ile Ile Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300
```

```
Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

```
<210> SEQ ID NO 191
<211> LENGTH: 1623
<212> TYPE: DNA
<213> ORGANISM: Artificial Sequence
<220> FEATURE:
<223> OTHER INFORMATION: Nucleic acid sequence of human codon optimized
      VP1 GII.4_Syd12_A39V plus sign R53I plus sign P80S

<400> SEQUENCE: 191

atgaaaatgg cctcgagtga cgctaaccct agtgacggca gcgccgccaa tcttgtgcct      60

gaggttaata atgaggtgat ggccctggag cctgtggtgg gcgcagccat agcagtcccc     120

gtggccggtc agcagaatgt gattgacccg tggataatca acaattttgt ccaagcccct     180

ggtggggagt tcaccgttag cccgagaaat gcgccaggag aaatcctgtg gtcggccagc     240

ttgggacccg atctgaaccc ctatttgtca catctcgctc ggatgtacaa cgggtatgcc     300

ggcggatttg aagtgcaggt gattctggct gggaacgcgt tcactgctgg caaagtgatc     360

tttgcagcgg tgcctcccaa cttccccact gaaggactgt ctccaagcca ggtcacaatg     420

tttccacaca tcgtggtgga cgtacggcag ctagagcctg tcctgattcc cctccctgat     480

gtacgcaata atttctacca ctacaatcaa tccaatgatc cgaccattaa actcatcgcg     540

atgttgtaca cccctctgcg cgctaacaat gctggagacg acgtattcac cgtgtcatgc     600

agagtgctca ccagaccttc accagacttt gactttatct tcttagtgcc ccccactgtt     660

gagagccgaa ccaagccctt tagtgtcccc gtactcacag tcgaggagat gacaaatagc     720
```

```
cgctttccaa tccccttga gaaactgttc acaggacctt cctcggcatt cgtggttcag     780
ccacagaacg gacgctgcac aactgacggc gtgctgctcg gaaccaccca gcttagccct    840
gttaatatct gtacgtttag aggcgacgta actcacataa ctggctcacg gaactatacc    900
atgaatctgg catcacagaa ttggaatgac tacgacccaa ccgaagagat tcccgcacct    960
cttggaaccc ccgactttgt gggaaaaata cagggcgtcc tgacacaaac caccagaacc   1020
gatggctcca cacggggaca caaggcaacc gtctacactg gctctgccga ttttgccccg   1080
aaactgggta gagtgcagtt tgagaccgac actgaccggg actttgaagc caatcagaat   1140
actaagttca cacctgtagg agtgattcag gacgggggca ccactcaccg gaacgagccg   1200
caacaatggg tcctgccctc ttatagcggg aggaatactc ataatgtgca tttggctcct   1260
gcagtggctc ccacgtttcc cggggaacaa ctgctctttt ttcgttcaac catgcctgga   1320
tgctccggat atcccaatat ggatctcgat tgcctgctcc cacaggaatg ggtgcagtat   1380
ttttatcaag aggccgcacc agcccaatcc gacgtcgcac ttctgcggtt cgtgaatcca   1440
gacacaggcc gcgtgttgtt tgagtgcaaa ttgcacaaat caggatacgt tacagtggct   1500
catactggac agcatgacct ggtgatccca cccaacggat attttaggtt cgactcctgg   1560
gtgaatcagt tttatacatt agcccccatg gggaatggga ctggcagacg cagggctgtc   1620
tga                                                                 1623
```

<210> SEQ ID NO 192
<211> LENGTH: 538
<212> TYPE: PRT
<213> ORGANISM: Norovirus

<400> SEQUENCE: 192

```
Met Lys Met Ala Ser Asn Asp Ala Ala Pro Ser Asn Asp Gly Ala Ala
1               5                   10                  15

Gly Leu Val Pro Glu Gly Asn Asn Glu Thr Leu Pro Leu Glu Pro Val
            20                  25                  30

Ala Gly Ala Ala Ile Ala Val Pro Val Thr Gly Gln Asn Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Val Pro Pro Asn Phe
        115                 120                 125

Pro Val Glu Phe Leu Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Thr Phe Phe His Tyr Asn Asn Gln Pro Asn Ser Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205
```

```
Asp Phe Glu Phe Thr Tyr Leu Val Pro Pro Ser Val Glu Ser Lys Thr
    210                 215                 220

Lys Pro Phe Ser Leu Pro Ile Leu Thr Leu Ser Glu Leu Thr Asn Ser
225                 230                 235                 240

Arg Phe Pro Val Pro Ile Asp Ser Leu Phe Thr Ala Gln Asn Asn Val
                245                 250                 255

Leu Gln Val Gln Cys Gln Asn Gly Arg Cys Thr Leu Asp Gly Glu Leu
            260                 265                 270

Gln Gly Thr Thr Gln Leu Leu Pro Ser Gly Ile Cys Ala Phe Arg Gly
        275                 280                 285

Arg Val Thr Ala Glu Thr Asp His Arg Asp Lys Trp His Met Gln Leu
    290                 295                 300

Gln Asn Leu Asn Gly Thr Thr Tyr Asp Pro Thr Asp Asp Val Pro Ala
305                 310                 315                 320

Pro Leu Gly Thr Pro Asp Phe Lys Gly Val Val Phe Gly Val Ala Ser
                325                 330                 335

Gln Arg Asn Val Gly Asn Asp Ala Pro Gly Ser Thr Arg Ala His Glu
            340                 345                 350

Ala Val Ile Ser Thr Tyr Ser Pro Gln Phe Val Pro Lys Leu Gly Ser
        355                 360                 365

Val Asn Phe Arg Ser Asn Asp Asn Asp Phe Gln Leu Gln Pro Thr Lys
    370                 375                 380

Phe Thr Pro Val Gly Ile Asn Asp Asp Gly Asp His Pro Phe Arg Gln
385                 390                 395                 400

Trp Glu Leu Pro Asp Tyr Ser Gly Leu Leu Thr Leu Asn Met Asn Leu
                405                 410                 415

Ala Pro Pro Val Ala Pro Asn Phe Pro Gly Glu Gln Leu Leu Phe Phe
            420                 425                 430

Arg Ser Phe Val Pro Cys Ser Gly Gly Tyr Asn Gln Gly Ile Val Asp
        435                 440                 445

Cys Leu Ile Pro Gln Glu Trp Ile Gln His Phe Tyr Gln Glu Ser Ala
    450                 455                 460

Pro Ser Gln Ser Asp Val Ala Leu Ile Arg Tyr Val Asn Pro Asp Thr
465                 470                 475                 480

Gly Arg Thr Leu Phe Glu Ala Lys Leu His Arg Ser Gly Tyr Ile Thr
                485                 490                 495

Val Ala His Ser Gly Asp Tyr Pro Leu Val Val Pro Ala Asn Gly Tyr
            500                 505                 510

Phe Arg Phe Asp Ser Trp Val Asn Gln Phe Tyr Ser Leu Ala Pro Met
        515                 520                 525

Gly Thr Gly Asn Gly Arg Arg Arg Ala Gln
    530                 535
```

<210> SEQ ID NO 193
<211> LENGTH: 1617
<212> TYPE: DNA
<213> ORGANISM: Artificial Sequence
<220> FEATURE:
<223> OTHER INFORMATION: Nucleic acid sequence of VP1 hCod GII.17 Kawa 2014 A0A077KVU6_A39V

<400> SEQUENCE: 193

```
atgaaaatgg catctaacga cgcagccccc tcaaacgatg gcgctgctgg actcgtgccg      60

gaggggaata atgagacact tccactagag ccggttgcag gcgccgctat agctgtgcca     120
```

```
gtgacagggc agaataatat tatagaccct tggattcgga caaacttcgt gcaggcaccc    180
aacggcgagt ttacagtatc cccccggaac tccccaggtg agatactcct gaatcttgag    240
ctcggccctg acctcaatcc atatctggct catctgagcc gcatgtacaa tggttacgct    300
ggggggggtcg aagtgcaggt cctcctggcc ggaaacgcct ttaccgctgg caaaattctg   360
tttgccgccg ttccaccaaa ctttccagtc gaattcctct ctcccgcgca aataaccatg    420
ctgccacatt tgatcgttga cgtgcggacc ctggagccaa taatgattcc cctgccggat    480
gtgcgtaaca cctttttcca ttataacaat cagccaaact ctcggatgag acttgttgct    540
atgctgtaca cccccctgcg gagcaacggc agtggcgatg atgtgtttac cgtgagttgc    600
agagtcctga cgcgcccaac cccggacttc gagttcacct acctggtgcc cccttctgtg    660
gaatctaaga ccaaaccgtt ttcactgcca atcttaactc tctccgaact gactaacagc    720
cggtttccag tacccataga ttctcttttt accgctcaaa acaacgtact ccaagtccag    780
tgccagaacg gccgctgtac gcttgatggt gagttgcagg ggacaacaca gctactcccc    840
agtggcatct gtgcattccg gggccgcgtg accgctgaga cagaccatcg tgacaaatgg    900
cacatgcaac tccaaaactt aaacgggacc acctacgacc caaccgacga cgtccctgct    960
ccgctaggga ctcctgactt taagggggtg gtgttcggag tggcctctca gcggaatgtt   1020
gggaatgacg cccccggctc tacccgagct cacgaggccg ttatctcaac atatagcccc   1080
caatttgtgc ccaagctcgg atccgttaat tttcgtagta acgacaacga cttccaactg   1140
caaccaacga agtttacgcc agtggggatt aatgatgatg gagaccatcc tttccgccaa   1200
tgggaactac cagattattc tggctgctc accctcaata tgaacctcgc cccacccgtg    1260
gcccctaatt tccccggtga gcagctgctg ttttttcgga gctttgtgcc atgcagtggc   1320
ggatataatc aaggcatcgt agactgcttg attccccaag agtggataca acatttttac   1380
caggaaagtg cgccctccca gtccgatgtg gccctgatac ggtacgttaa ccccgatacc   1440
ggaagaacat tattcgaagc gaaattgcac agatcagggt acattaccgt tgcacattcc   1500
ggcgattatc ccctggtggt tcccgccaac ggttacttta ggttcgatag ttgggtcaac   1560
cagttctatt cactagcccc aatgggcacc ggtaacggca gacgccgggc tcagtag      1617
```

<210> SEQ ID NO 194
<211> LENGTH: 538
<212> TYPE: PRT
<213> ORGANISM: Norovirus

<400> SEQUENCE: 194

```
Met Lys Met Ala Ser Asn Asp Ala Ala Pro Ser Asn Asp Gly Ala Ala
1               5                   10                  15

Gly Leu Val Pro Glu Gly Asn Asn Glu Thr Leu Pro Leu Glu Pro Val
            20                  25                  30

Ala Gly Ala Ala Ile Ala Ala Pro Val Thr Gly Gln Asn Asn Ile Ile
        35                  40                  45

Asp Pro Trp Ile Ile Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110
```

-continued

```
Ala Phe Thr Ala Gly Lys Ile Leu Phe Ala Ala Val Pro Pro Asn Phe
        115                 120                 125

Pro Val Glu Phe Leu Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Thr Phe Phe His Tyr Asn Asn Gln Pro Asn Ser Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Thr Tyr Leu Val Pro Pro Ser Val Glu Ser Lys Thr
    210                 215                 220

Lys Pro Phe Ser Leu Pro Ile Leu Thr Leu Ser Glu Leu Thr Asn Ser
225                 230                 235                 240

Arg Phe Pro Val Pro Ile Asp Ser Leu Phe Thr Ala Gln Asn Asn Val
                245                 250                 255

Leu Gln Val Gln Cys Gln Asn Gly Arg Cys Thr Leu Asp Gly Glu Leu
            260                 265                 270

Gln Gly Thr Thr Gln Leu Leu Pro Ser Gly Ile Cys Ala Phe Arg Gly
        275                 280                 285

Arg Val Thr Ala Glu Thr Asp His Arg Asp Lys Trp His Met Gln Leu
    290                 295                 300

Gln Asn Leu Asn Gly Thr Thr Tyr Asp Pro Thr Asp Asp Val Pro Ala
305                 310                 315                 320

Pro Leu Gly Thr Pro Asp Phe Lys Gly Val Val Phe Gly Val Ala Ser
                325                 330                 335

Gln Arg Asn Val Gly Asn Asp Ala Pro Gly Ser Thr Arg Ala His Glu
            340                 345                 350

Ala Val Ile Ser Thr Tyr Ser Pro Gln Phe Val Pro Lys Leu Gly Ser
        355                 360                 365

Val Asn Phe Arg Ser Asn Asp Asn Asp Phe Gln Leu Gln Pro Thr Lys
    370                 375                 380

Phe Thr Pro Val Gly Ile Asn Asp Asp Gly Asp His Pro Phe Arg Gln
385                 390                 395                 400

Trp Glu Leu Pro Asp Tyr Ser Gly Leu Leu Thr Leu Asn Met Asn Leu
                405                 410                 415

Ala Pro Pro Val Ala Pro Asn Phe Pro Gly Glu Gln Leu Leu Phe Phe
            420                 425                 430

Arg Ser Phe Val Pro Cys Ser Gly Gly Tyr Asn Gln Gly Ile Val Asp
        435                 440                 445

Cys Leu Ile Pro Gln Glu Trp Ile Gln His Phe Tyr Gln Glu Ser Ala
    450                 455                 460

Pro Ser Gln Ser Asp Val Ala Leu Ile Arg Tyr Val Asn Pro Asp Thr
465                 470                 475                 480

Gly Arg Thr Leu Phe Glu Ala Lys Leu His Arg Ser Gly Tyr Ile Thr
                485                 490                 495

Val Ala His Ser Gly Asp Tyr Pro Leu Val Val Pro Ala Asn Gly Tyr
            500                 505                 510

Phe Arg Phe Asp Ser Trp Val Asn Gln Phe Tyr Ser Leu Ala Pro Met
        515                 520                 525

Gly Thr Gly Asn Gly Arg Arg Arg Ala Gln
```

530 535

<210> SEQ ID NO 195
<211> LENGTH: 1617
<212> TYPE: DNA
<213> ORGANISM: Artificial Sequence
<220> FEATURE:
<223> OTHER INFORMATION: Nucleic acid sequence of VP1 hCod GII.17 Kawa 2014 A0A077KVU6_R53I

<400> SEQUENCE: 195
atgaaaatgg catctaacga cgcagccccc tcaaacgatg gcgctgctgg actcgtgccg 60
gaggggaata atgagacact tccactagag ccggttgcag gcgccgctat agctgcccca 120
gtgacagggc agaataatat tatagaccct tggattatca caaacttcgt gcaggcaccc 180
aacggcgagt ttacagtatc cccccggaac tccccaggtg agatactcct gaatcttgag 240
ctcggccctg acctcaatcc atatctggct catctgagcc gcatgtacaa tggttacgct 300 ggggggggtcg aagtgcaggt cctcctggcc ggaaacgcct ttaccgctgg caaaattctg 360
tttgccgccg ttccaccaaa ctttccagtc gaattcctct ctcccgcgca aataaccatg 420
ctgccacatt tgatcgttga cgtgcggacc ctggagccaa taatgattcc cctgccggat 480
gtgcgtaaca ccttttttcca ttataacaat cagccaaact ctcggatgag acttgttgct 540
atgctgtaca ccccccctgcg gagcaacggc agtggcgatg atgtgtttac cgtgagttgc 600
agagtcctga cgcgcccaac cccggacttc gagttcacct acctggtgcc cccttctgtg 660
gaatctaaga ccaaaccgtt ttcactgcca atcttaactc tctccgaact gactaacagc 720
cggtttccag tacccataga ttctcttttt accgctcaaa acaacgtact ccaagtccag 780
tgccagaacg gccgctgtac gcttgatggt gagttgcagg ggacaacaca gctactcccc 840
agtggcatct gtgcattccg gggccgcgtg accgctgaga cagaccatcg tgacaaatgg 900
cacatgcaac tccaaaactt aaacgggacc acctacgacc caaccgacga cgtccctgct 960
ccgctaggga ctcctgactt taagggggtg gtgttcggag tggcctctca gcggaatgtt 1020
gggaatgacg cccccggctc tacccgagct cacgaggccg ttatctcaac atatagcccc 1080
caatttgtgc ccaagctcgg atccgttaat tttcgtagta acgacaacga cttccaactg 1140
caaccaacga agtttacgcc agtggggatt aatgatgatg gagaccatcc tttccgccaa 1200
tgggaactac cagattattc tgggctgctc accctcaata tgaacctcgc cccacccgtg 1260
gcccctaatt tccccggtga gcagctgctg ttttttcgga gctttgtgcc atgcagtggc 1320
ggatataatc aaggcatcgt agactgcttg attccccaag agtggataca acatttttac 1380
caggaaagtg cgccctccca gtccgatgtg gccctgatac ggtacgttaa ccccgatacc 1440
ggaagaacat tattcgaagc gaaattgcac agatcagggt acattaccgt tgcacattcc 1500
ggcgattatc ccctggtggt tcccgccaac ggttacttta ggttcgatag ttgggtcaac 1560
cagttctatt cactagcccc aatgggcacc ggtaacggca gacgccgggc tcagtag 1617

<210> SEQ ID NO 196
<211> LENGTH: 538
<212> TYPE: PRT
<213> ORGANISM: Norovirus

<400> SEQUENCE: 196

Met Lys Met Ala Ser Asn Asp Ala Ala Pro Ser Asn Asp Gly Ala Ala
1 5 10 15

Gly Leu Val Pro Glu Gly Asn Asn Glu Thr Leu Pro Leu Glu Pro Val

```
                20                  25                  30

Ala Gly Ala Ala Ile Ala Ala Pro Val Thr Gly Gln Asn Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Leu His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Val Pro Pro Asn Phe
        115                 120                 125

Pro Val Glu Phe Leu Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Thr Phe Phe His Tyr Asn Asn Gln Pro Asn Ser Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Thr Tyr Leu Val Pro Pro Ser Val Glu Ser Lys Thr
    210                 215                 220

Lys Pro Phe Ser Leu Pro Ile Leu Thr Leu Ser Glu Leu Thr Asn Ser
225                 230                 235                 240

Arg Phe Pro Val Pro Ile Asp Ser Leu Phe Thr Ala Gln Asn Asn Val
                245                 250                 255

Leu Gln Val Gln Cys Gln Asn Gly Arg Cys Thr Leu Asp Gly Glu Leu
            260                 265                 270

Gln Gly Thr Thr Gln Leu Leu Pro Ser Gly Ile Cys Ala Phe Arg Gly
        275                 280                 285

Arg Val Thr Ala Glu Thr Asp His Arg Asp Lys Trp His Met Gln Leu
    290                 295                 300

Gln Asn Leu Asn Gly Thr Thr Tyr Asp Pro Thr Asp Asp Val Pro Ala
305                 310                 315                 320

Pro Leu Gly Thr Pro Asp Phe Lys Gly Val Val Phe Gly Val Ala Ser
                325                 330                 335

Gln Arg Asn Val Gly Asn Asp Ala Pro Gly Ser Thr Arg Ala His Glu
            340                 345                 350

Ala Val Ile Ser Thr Tyr Ser Pro Gln Phe Val Pro Lys Leu Gly Ser
        355                 360                 365

Val Asn Phe Arg Ser Asn Asp Asn Asp Phe Gln Leu Gln Pro Thr Lys
    370                 375                 380

Phe Thr Pro Val Gly Ile Asn Asp Asp Gly Asp His Pro Phe Arg Gln
385                 390                 395                 400

Trp Glu Leu Pro Asp Tyr Ser Gly Leu Leu Thr Leu Asn Met Asn Leu
                405                 410                 415

Ala Pro Pro Val Ala Pro Asn Phe Pro Gly Glu Gln Leu Leu Phe Phe
            420                 425                 430

Arg Ser Phe Val Pro Cys Ser Gly Gly Tyr Asn Gln Gly Ile Val Asp
        435                 440                 445
```

```
Cys Leu Ile Pro Gln Glu Trp Ile Gln His Phe Tyr Gln Glu Ser Ala
    450                 455                 460

Pro Ser Gln Ser Asp Val Ala Leu Ile Arg Tyr Val Asn Pro Asp Thr
465                 470                 475                 480

Gly Arg Thr Leu Phe Glu Ala Lys Leu His Arg Ser Gly Tyr Ile Thr
                485                 490                 495

Val Ala His Ser Gly Asp Tyr Pro Leu Val Val Pro Ala Asn Gly Tyr
            500                 505                 510

Phe Arg Phe Asp Ser Trp Val Asn Gln Phe Tyr Ser Leu Ala Pro Met
        515                 520                 525

Gly Thr Gly Asn Gly Arg Arg Arg Ala Gln
    530                 535


<210> SEQ ID NO 197
<211> LENGTH: 1617
<212> TYPE: DNA
<213> ORGANISM: Artificial Sequence
<220> FEATURE:
<223> OTHER INFORMATION: Nucleic acid sequence of VP1 hCod GII.17 Kawa
      2014 A0A077KVU6_A90L

<400> SEQUENCE: 197

atgaaaatgg catctaacga cgcagccccc tcaaacgatg gcgctgctgg actcgtgccg      60

gaggggaata atgagacact tccactagag ccggttgcag gcgccgctat agctgcccca     120

gtgacagggc agaataatat tatagaccct tggattcgga caaacttcgt gcaggcaccc     180

aacggcgagt ttacagtatc cccccggaac tccccaggtg agatactcct gaatcttgag     240

ctcggccctg acctcaatcc atatctgctg catctgagcc gcatgtacaa tggttacgct     300

gggggggtcg aagtgcaggt cctcctggcc ggaaacgcct ttaccgctgg caaaattctg     360

tttgccgccg ttccaccaaa ctttccagtc gaattcctct ctcccgcgca aataaccatg     420

ctgccacatt tgatcgttga cgtgcggacc ctggagccaa taatgattcc cctgccggat     480

gtgcgtaaca cctttttcca ttataacaat cagccaaact ctcggatgag acttgttgct     540

atgctgtaca cccccctgcg gagcaacggc agtggcgatg atgtgtttac cgtgagttgc     600

agagtcctga cgcgcccaac cccggacttc gagttcacct acctggtgcc cccttctgtg     660

gaatctaaga ccaaaccgtt ttcactgcca atcttaactc tctccgaact gactaacagc     720

cggtttccag tacccataga ttctcttttt accgctcaaa acaacgtact ccaagtccag     780

tgccagaacg gccgctgtac gcttgatggt gagttgcagg ggacaacaca gctactcccc     840

agtggcatct gtgcattccg gggccgcgtg accgctgaga cagaccatcg tgacaaatgg     900

cacatgcaac tccaaaactt aaacgggacc acctacgacc caaccgacga cgtccctgct     960

ccgctaggga ctcctgactt taagggggtg gtgttcggag tggcctctca gcggaatgtt    1020

gggaatgacg cccccggctc tacccgagct cacgaggccg ttatctcaac atatagcccc    1080

caatttgtgc ccaagctcgg atccgttaat tttcgtagta acgacaacga cttccaactg    1140

caaccaacga agtttacgcc agtggggatt aatgatgatg gagaccatcc tttccgccaa    1200

tgggaactac cagattattc tgggctgctc accctcaata tgaacctcgc cccacccgtg    1260

gcccctaatt tccccggtga gcagctgctg ttttttcgga gctttgtgcc atgcagtggc    1320

ggatataatc aaggcatcgt agactgcttg attccccaag agtggataca acatttttac    1380

caggaaagtg cgccctccca gtccgatgtg gccctgatac ggtacgttaa ccccgatacc    1440

ggaagaacat tattcgaagc gaaattgcac agatcagggt acattaccgt tgcacattcc    1500
```

ggcgattatc ccctggtggt tcccgccaac ggttacttta ggttcgatag ttgggtcaac 1560
cagttctatt cactagcccc aatgggcacc ggtaacggca gacgccgggc tcagtag 1617

<210> SEQ ID NO 198
<211> LENGTH: 538
<212> TYPE: PRT
<213> ORGANISM: Norovirus

<400> SEQUENCE: 198

Met Lys Met Ala Ser Asn Asp Ala Ala Pro Ser Asn Asp Gly Ala Ala
1 5 10 15

Gly Leu Val Pro Glu Gly Asn Asn Glu Thr Leu Pro Leu Glu Pro Val
20 25 30

Ala Gly Ala Ala Ile Ala Val Pro Val Thr Gly Gln Asn Asn Ile Ile
35 40 45

Asp Pro Trp Ile Ile Thr Asn Phe Val Gln Ala Pro Asn Gly Glu Phe
50 55 60

Thr Val Ser Pro Arg Asn Ser Pro Gly Glu Ile Leu Leu Asn Leu Glu
65 70 75 80

Leu Gly Pro Asp Leu Asn Pro Tyr Leu Ala His Leu Ser Arg Met Tyr
85 90 95

Asn Gly Tyr Ala Gly Gly Val Glu Val Gln Val Leu Leu Ala Gly Asn
100 105 110

Ala Phe Thr Ala Gly Lys Ile Leu Phe Ala Ala Val Pro Pro Asn Phe
115 120 125

Pro Val Glu Phe Leu Ser Pro Ala Gln Ile Thr Met Leu Pro His Leu
130 135 140

Ile Val Asp Val Arg Thr Leu Glu Pro Ile Met Ile Pro Leu Pro Asp
145 150 155 160

Val Arg Asn Thr Phe Phe His Tyr Asn Asn Gln Pro Asn Ser Arg Met
165 170 175

Arg Leu Val Ala Met Leu Tyr Thr Pro Leu Arg Ser Asn Gly Ser Gly
180 185 190

Asp Asp Val Phe Thr Val Ser Cys Arg Val Leu Thr Arg Pro Thr Pro
195 200 205

Asp Phe Glu Phe Thr Tyr Leu Val Pro Pro Ser Val Glu Ser Lys Thr
210 215 220

Lys Pro Phe Ser Leu Pro Ile Leu Thr Leu Ser Glu Leu Thr Asn Ser
225 230 235 240

Arg Phe Pro Val Pro Ile Asp Ser Leu Phe Thr Ala Gln Asn Asn Val
245 250 255

Leu Gln Val Gln Cys Gln Asn Gly Arg Cys Thr Leu Asp Gly Glu Leu
260 265 270

Gln Gly Thr Thr Gln Leu Leu Pro Ser Gly Ile Cys Ala Phe Arg Gly
275 280 285

Arg Val Thr Ala Glu Thr Asp His Arg Asp Lys Trp His Met Gln Leu
290 295 300

Gln Asn Leu Asn Gly Thr Thr Tyr Asp Pro Thr Asp Asp Val Pro Ala
305 310 315 320

Pro Leu Gly Thr Pro Asp Phe Lys Gly Val Val Phe Gly Val Ala Ser
325 330 335

Gln Arg Asn Val Gly Asn Asp Ala Pro Gly Ser Thr Arg Ala His Glu
340 345 350

-continued

```
Ala Val Ile Ser Thr Tyr Ser Pro Gln Phe Val Pro Lys Leu Gly Ser
        355                 360                 365

Val Asn Phe Arg Ser Asn Asp Asn Asp Phe Gln Leu Gln Pro Thr Lys
    370                 375                 380

Phe Thr Pro Val Gly Ile Asn Asp Asp Gly Asp His Pro Phe Arg Gln
385                 390                 395                 400

Trp Glu Leu Pro Asp Tyr Ser Gly Leu Leu Thr Leu Asn Met Asn Leu
                405                 410                 415

Ala Pro Pro Val Ala Pro Asn Phe Pro Gly Glu Gln Leu Leu Phe Phe
            420                 425                 430

Arg Ser Phe Val Pro Cys Ser Gly Gly Tyr Asn Gln Gly Ile Val Asp
        435                 440                 445

Cys Leu Ile Pro Gln Glu Trp Ile Gln His Phe Tyr Gln Glu Ser Ala
    450                 455                 460

Pro Ser Gln Ser Asp Val Ala Leu Ile Arg Tyr Val Asn Pro Asp Thr
465                 470                 475                 480

Gly Arg Thr Leu Phe Glu Ala Lys Leu His Arg Ser Gly Tyr Ile Thr
                485                 490                 495

Val Ala His Ser Gly Asp Tyr Pro Leu Val Val Pro Ala Asn Gly Tyr
            500                 505                 510

Phe Arg Phe Asp Ser Trp Val Asn Gln Phe Tyr Ser Leu Ala Pro Met
        515                 520                 525

Gly Thr Gly Asn Gly Arg Arg Arg Ala Gln
    530                 535
```

<210> SEQ ID NO 199
<211> LENGTH: 1617
<212> TYPE: DNA
<213> ORGANISM: Artificial Sequence
<220> FEATURE:
<223> OTHER INFORMATION: Nucleic acid sequence of VP1 hCod GII.17 Kawa 2014 A0A077KVU6_A39V+M53I

<400> SEQUENCE: 199

```
atgaaaatgg catctaacga cgcagccccc tcaaacgatg gcgctgctgg actcgtgccg     60
gaggggaata atgagacact tccactagag ccggttgcag gcgccgctat agctgtgcca    120
gtgacagggc agaataatat tatagaccct tggattatca caaacttcgt gcaggcaccc    180
aacggcgagt ttacagtatc cccccggaac tccccaggtg agatactcct gaatcttgag    240
ctcggccctg acctcaatcc atatctggct catctgagcc gcatgtacaa tggttacgct    300
gggggggtcg aagtgcaggt cctcctggcc ggaaacgcct ttaccgctgg caaaattctg    360
tttgccgccg ttccaccaaa ctttccagtc gaattcctct ctcccgcgca aataaccatg    420
ctgccacatt tgatcgttga cgtgcggacc ctggagccaa taatgattcc cctgccggat    480
gtgcgtaaca cctttttcca ttataacaat cagccaaact ctcggatgag acttgttgct    540
atgctgtaca ccccccctgcg gagcaacggc agtggcgatg atgtgtttac cgtgagttgc    600
agagtcctga cgcgcccaac cccggacttc gagttcacct acctggtgcc cccttctgtg    660
gaatctaaga ccaaaccgtt ttcactgcca atcttaactc tctccgaact gactaacagc    720
cggtttccag tacccataga ttctcttttt accgctcaaa acaacgtact ccaagtccag    780
tgccagaacg gccgctgtac gcttgatggt gagttgcagg ggacaacaca gctactcccc    840
agtggcatct gtgcattccg gggccgcgtg accgctgaga cagaccatcg tgacaaatgg    900
cacatgcaac tccaaaactt aaacgggacc acctacgacc caaccgacga cgtccctgct    960
```

-continued ccgctaggga ctcctgactt taagggggtg gtgttcggag tggcctctca gcggaatgtt 1020
gggaatgacg cccccggctc tacccgagct cacgaggccg ttatctcaac atatagcccc 1080
caatttgtgc ccaagctcgg atccgttaat tttcgtagta acgacaacga cttccaactg 1140
caaccaacga agtttacgcc agtggggatt aatgatgatg gagaccatcc tttccgccaa 1200
tgggaactac cagattattc tggctgctc accctcaata tgaacctcgc cccacccgtg 1260
gcccctaatt tccccggtga gcagctgctg ttttttcgga gctttgtgcc atgcagtggc 1320
ggatataatc aaggcatcgt agactgcttg attccccaag agtggataca acatttttac 1380
caggaaagtg cgccctccca gtccgatgtg gccctgatac ggtacgttaa ccccgatacc 1440
ggaagaacat tattcgaagc gaaattgcac agatcagggt acattaccgt tgcacattcc 1500
ggcgattatc ccctggtggt tcccgccaac ggttacttta ggttcgatag ttgggtcaac 1560
cagttctatt cactagcccc aatgggcacc ggtaacggca gacgccgggc tcagtag 1617

<210> SEQ ID NO 200
<211> LENGTH: 538
<212> TYPE: PRT
<213> ORGANISM: Norovirus

<400> SEQUENCE: 200

Met Lys Met Ala Ser Asn Asp Ala Ala Pro Ser Asn Asp Gly Ala Ala
1 5 10 15

Gly Leu Val Pro Glu Gly Asn Asn Glu Thr Leu Pro Leu Glu Pro Val
20 25 30

Ala Gly Ala Ala Ile Ala Ala Pro Val Thr Gly Gln Asn Asn Ile Ile
35 40 45

Asp Pro Trp Ile Arg Thr Asn Phe Val Gln Ala Pro Asn Gly Glu Phe
50 55 60

Thr Val Ser Pro Arg Asn Ser Pro Gly Glu Ile Leu Leu Asn Leu Ser
65 70 75 80

Leu Gly Pro Asp Leu Asn Pro Tyr Leu Leu His Leu Ser Arg Met Tyr
85 90 95

Asn Gly Tyr Ala Gly Gly Val Glu Val Gln Val Leu Leu Ala Gly Asn
100 105 110

Ala Phe Thr Ala Gly Lys Ile Leu Phe Ala Ala Val Pro Pro Asn Phe
115 120 125

Pro Val Glu Phe Leu Ser Pro Ala Gln Ile Thr Met Leu Pro His Leu
130 135 140

Ile Val Asp Val Arg Thr Leu Glu Pro Ile Met Ile Pro Leu Pro Asp
145 150 155 160

Val Arg Asn Thr Phe Phe His Tyr Asn Asn Gln Pro Asn Ser Arg Met
165 170 175

Arg Leu Val Ala Met Leu Tyr Thr Pro Leu Arg Ser Asn Gly Ser Gly
180 185 190

Asp Asp Val Phe Thr Val Ser Cys Arg Val Leu Thr Arg Pro Thr Pro
195 200 205

Asp Phe Glu Phe Thr Tyr Leu Val Pro Pro Ser Val Glu Ser Lys Thr
210 215 220

Lys Pro Phe Ser Leu Pro Ile Leu Thr Leu Ser Glu Leu Thr Asn Ser
225 230 235 240

Arg Phe Pro Val Pro Ile Asp Ser Leu Phe Thr Ala Gln Asn Asn Val
245 250 255

Leu Gln Val Gln Cys Gln Asn Gly Arg Cys Thr Leu Asp Gly Glu Leu

```
            260                 265                 270

Gln Gly Thr Thr Gln Leu Leu Pro Ser Gly Ile Cys Ala Phe Arg Gly
        275                 280                 285

Arg Val Thr Ala Glu Thr Asp His Arg Asp Lys Trp His Met Gln Leu
    290                 295                 300

Gln Asn Leu Asn Gly Thr Thr Tyr Asp Pro Thr Asp Asp Val Pro Ala
305                 310                 315                 320

Pro Leu Gly Thr Pro Asp Phe Lys Gly Val Val Phe Gly Val Ala Ser
                325                 330                 335

Gln Arg Asn Val Gly Asn Asp Ala Pro Gly Ser Thr Arg Ala His Glu
            340                 345                 350

Ala Val Ile Ser Thr Tyr Ser Pro Gln Phe Val Pro Lys Leu Gly Ser
        355                 360                 365

Val Asn Phe Arg Ser Asn Asp Asn Asp Phe Gln Leu Gln Pro Thr Lys
    370                 375                 380

Phe Thr Pro Val Gly Ile Asn Asp Asp Gly Asp His Pro Phe Arg Gln
385                 390                 395                 400

Trp Glu Leu Pro Asp Tyr Ser Gly Leu Leu Thr Leu Asn Met Asn Leu
                405                 410                 415

Ala Pro Pro Val Ala Pro Asn Phe Pro Gly Glu Gln Leu Leu Phe Phe
            420                 425                 430

Arg Ser Phe Val Pro Cys Ser Gly Gly Tyr Asn Gln Gly Ile Val Asp
        435                 440                 445

Cys Leu Ile Pro Gln Glu Trp Ile Gln His Phe Tyr Gln Glu Ser Ala
    450                 455                 460

Pro Ser Gln Ser Asp Val Ala Leu Ile Arg Tyr Val Asn Pro Asp Thr
465                 470                 475                 480

Gly Arg Thr Leu Phe Glu Ala Lys Leu His Arg Ser Gly Tyr Ile Thr
                485                 490                 495

Val Ala His Ser Gly Asp Tyr Pro Leu Val Val Pro Ala Asn Gly Tyr
            500                 505                 510

Phe Arg Phe Asp Ser Trp Val Asn Gln Phe Tyr Ser Leu Ala Pro Met
        515                 520                 525

Gly Thr Gly Asn Gly Arg Arg Arg Ala Gln
    530                 535
```

<210> SEQ ID NO 201
<211> LENGTH: 1617
<212> TYPE: DNA
<213> ORGANISM: Artificial Sequence
<220> FEATURE:
<223> OTHER INFORMATION: Nucleic acid sequence of VP1 hCod GII.17 Kawa 2014 A0A077KVU6_E80S plus sign A90L

<400> SEQUENCE: 201

```
atgaaaatgg catctaacga cgcagccccc tcaaacgatg gcgctgctgg actcgtgccg      60

gaggggaata atgagacact tccactagag ccggttgcag gcgccgctat agctgcccca     120

gtgacagggc agaataatat tatagaccct tggattcgga caaacttcgt gcaggcaccc     180

aacggcgagt ttacagtatc cccccggaac tccccaggtg agatactcct gaatcttagc     240

ctcggccctg acctcaatcc atatctgctg catctgagcc gcatgtacaa tggttacgct     300

ggggggggtcg aagtgcaggt cctcctggcc ggaaacgcct ttaccgctgg caaaattctg     360

tttgccgccg ttccaccaaa ctttccagtc gaattcctct ctcccgcgca aataaccatg     420

ctgccacatt tgatcgttga cgtgcggacc ctggagccaa taatgattcc cctgccggat     480
```

```
gtgcgtaaca ccttttttcca ttataacaat cagccaaact ctcggatgag acttgttgct    540

atgctgtaca cccccctgcg gagcaacggc agtggcgatg atgtgtttac cgtgagttgc    600

agagtcctga cgcgcccaac cccggacttc gagttcacct acctggtgcc cccttctgtg    660

gaatctaaga ccaaaccgtt ttcactgcca atcttaactc tctccgaact gactaacagc    720

cggtttccag tacccataga ttctcttttt accgctcaaa acaacgtact ccaagtccag    780

tgccagaacg gccgctgtac gcttgatggt gagttgcagg ggacaacaca gctactcccc    840

agtggcatct gtgcattccg gggccgcgtg accgctgaga cagaccatcg tgacaaatgg    900

cacatgcaac tccaaaactt aaacgggacc acctacgacc caaccgacga cgtccctgct    960

ccgctaggga ctcctgactt taagggggtg gtgttcggag tggcctctca gcggaatgtt   1020

gggaatgacg cccccggctc tacccgagct cacgaggccg ttatctcaac atatagcccc   1080

caatttgtgc ccaagctcgg atccgttaat tttcgtagta acgacaacga cttccaactg   1140

caaccaacga agtttacgcc agtggggatt aatgatgatg gagaccatcc tttccgccaa   1200

tgggaactac cagattattc tgggctgctc accctcaata tgaacctcgc cccacccgtg   1260

gcccctaatt tccccggtga gcagctgctg ttttttcgga gctttgtgcc atgcagtggc   1320

ggatataatc aaggcatcgt agactgcttg attccccaag agtggataca acatttttac   1380

caggaaagtg cgccctccca gtccgatgtg gccctgatac ggtacgttaa ccccgatacc   1440

ggaagaacat tattcgaagc gaaattgcac agatcagggt acattaccgt tgcacattcc   1500

ggcgattatc cctggtggt tcccgccaac ggttacttta ggttcgatag ttgggtcaac   1560

cagttctatt cactagcccc aatgggcacc ggtaacggca gacgccgggc tcagtag      1617
```

<210> SEQ ID NO 202
<211> LENGTH: 59
<212> TYPE: DNA
<213> ORGANISM: Artificial Sequence
<220> FEATURE:
<223> OTHER INFORMATION: Primer GI.3Lil08(M57I).r

<400> SEQUENCE: 202

```
ctgaacgtaa tttgagatga tccaggggtc gatcatgttt acctgtcctg cggtggcgg      59
```

<210> SEQ ID NO 203
<211> LENGTH: 59
<212> TYPE: DNA
<213> ORGANISM: Artificial Sequence
<220> FEATURE:
<223> OTHER INFORMATION: Primer GI.3Lil08(M57I).c

<400> SEQUENCE: 203

```
gtaaacatga tcgacccctg gatcatctca aattacgttc aggctccaca gggggagtt      59
```

<210> SEQ ID NO 204
<211> LENGTH: 52
<212> TYPE: DNA
<213> ORGANISM: Artificial Sequence
<220> FEATURE:
<223> OTHER INFORMATION: Primer IF-(GI.7USA14)VP1.c

<400> SEQUENCE: 204

```
tcgtgcttcg gcaccagtac aatgatgatg gccagcaagg acgctccgag ta             52
```

<210> SEQ ID NO 205
<211> LENGTH: 49
<212> TYPE: DNA

-continued

<213> ORGANISM: Artificial Sequence
<220> FEATURE:
<223> OTHER INFORMATION: Primer IF-(GI.7USA14)VP1.r

<400> SEQUENCE: 205
actaaagaaa ataggccttc acacccgcct cacgccgagt cgtcgcacg 49

<210> SEQ ID NO 206
<211> LENGTH: 48
<212> TYPE: DNA
<213> ORGANISM: Artificial Sequence
<220> FEATURE:
<223> OTHER INFORMATION: Primer GI.7USA14_VP1(R84S).r

<400> SEQUENCE: 206
agtggggtcc taagctgagg tcaaacagaa tatcccctgg ggtgttat 48

<210> SEQ ID NO 207
<211> LENGTH: 50
<212> TYPE: DNA
<213> ORGANISM: Artificial Sequence
<220> FEATURE:
<223> OTHER INFORMATION: Primer GI.7USA14_VP1(R84S).c

<400> SEQUENCE: 207
tattctgttt gacctcagct taggacccca cttgaacccc tttctgcttc 50

<210> SEQ ID NO 208
<211> LENGTH: 51
<212> TYPE: DNA
<213> ORGANISM: Artificial Sequence
<220> FEATURE:
<223> OTHER INFORMATION: Primer GI.7USA14_VP1(M57I).r

<400> SEQUENCE: 208
aacgaaattg ttgattatcc acgggtcgat catattgact tggcctgcag t 51

<210> SEQ ID NO 209
<211> LENGTH: 48
<212> TYPE: DNA
<213> ORGANISM: Artificial Sequence
<220> FEATURE:
<223> OTHER INFORMATION: Primer GI.7USA14_VP1(M57I).c

<400> SEQUENCE: 209
gatcgacccg tggataatca acaatttcgt tcaggcacca gaaggaga 48

<210> SEQ ID NO 210
<211> LENGTH: 62
<212> TYPE: DNA
<213> ORGANISM: Artificial Sequence
<220> FEATURE:
<223> OTHER INFORMATION: Primer GII.2CGMH11(A39V).r

<400> SEQUENCE: 210
tttgtctgcc cggtcacagg cactgcgagg gcagcccctg caacaggctc caaggccatc 60
ac 62

<210> SEQ ID NO 211
<211> LENGTH: 59
<212> TYPE: DNA
<213> ORGANISM: Artificial Sequence
<220> FEATURE:
<223> OTHER INFORMATION: Primer GII.2CGMH11(A39V).c

<400> SEQUENCE: 211
gttgcagggg ctgccctcgc agtgcctgtg accgggcaga caaatatcat cgatccttg 59

<210> SEQ ID NO 212
<211> LENGTH: 59
<212> TYPE: DNA
<213> ORGANISM: Artificial Sequence
<220> FEATURE:
<223> OTHER INFORMATION: Primer GII.2CGMH11(R53I).r

<400> SEQUENCE: 212
cacgaaatta gcgataatcc aaggatcgat gatatttgtc tgcccggtca caggagctg 59

<210> SEQ ID NO 213
<211> LENGTH: 59
<212> TYPE: DNA
<213> ORGANISM: Artificial Sequence
<220> FEATURE:
<223> OTHER INFORMATION: Primer GII.2CGMH11(R53I).c

<400> SEQUENCE: 213
ggcagacaaa tatcatcgat ccttggatta tcgctaattt cgtgcaagcc ccaaatggg 59

<210> SEQ ID NO 214
<211> LENGTH: 53
<212> TYPE: DNA
<213> ORGANISM: Artificial Sequence
<220> FEATURE:
<223> OTHER INFORMATION: Primer IF-GII17Kaw14VP1.c

<400> SEQUENCE: 214
tcgtgcttcg gcaccagtac aatgaaaatg gcatctaacg acgcagcccc ctc 53

<210> SEQ ID NO 215
<211> LENGTH: 56
<212> TYPE: DNA
<213> ORGANISM: Artificial Sequence
<220> FEATURE:
<223> OTHER INFORMATION: Primer IF-GII17Kaw14VP1.r

<400> SEQUENCE: 215
actaaagaaa ataggcctct actgagcccg gcgtctgccg ttaccggtgc ccattg 56

<210> SEQ ID NO 216
<211> LENGTH: 59
<212> TYPE: DNA
<213> ORGANISM: Artificial Sequence
<220> FEATURE:
<223> OTHER INFORMATION: Primer GII.17Kaw14(A90L).r

<400> SEQUENCE: 216
gcggctcaga tgcagcagat atggattgag gtcagggccg agctcaagat tcaggagta 59

<210> SEQ ID NO 217
<211> LENGTH: 51
<212> TYPE: DNA
<213> ORGANISM: Artificial Sequence
<220> FEATURE:
<223> OTHER INFORMATION: Primer GII.17Kaw14(A90L).c

<400> SEQUENCE: 217
cctgacctca atccatatct gctgcatctg agccgcatgt acaatggtta c 51

<210> SEQ ID NO 218
<211> LENGTH: 59
<212> TYPE: DNA

<213> ORGANISM: Artificial Sequence
<220> FEATURE:
<223> OTHER INFORMATION: Primer GII.17Kaw14(A39V).r

<400> SEQUENCE: 218
attctgccct gtcactggca cagctatagc ggcgcctgca accggctcta gtggaagtg 59

<210> SEQ ID NO 219
<211> LENGTH: 58
<212> TYPE: DNA
<213> ORGANISM: Artificial Sequence
<220> FEATURE:
<223> OTHER INFORMATION: Primer GII.17Kaw14(A39V).c

<400> SEQUENCE: 219
aggcgccgct atagctgtgc cagtgacagg gcagaataat attatagacc cttggatt 58

<210> SEQ ID NO 220
<211> LENGTH: 59
<212> TYPE: DNA
<213> ORGANISM: Artificial Sequence
<220> FEATURE:
<223> OTHER INFORMATION: Primer GII.17Kaw14(R53I).r

<400> SEQUENCE: 220
acgaagtttg tgataatcca agggtctata atattattct gccctgtcac tggggcagc 59

<210> SEQ ID NO 221
<211> LENGTH: 59
<212> TYPE: DNA
<213> ORGANISM: Artificial Sequence
<220> FEATURE:
<223> OTHER INFORMATION: Primer GII.17Kaw14(R53I).c

<400> SEQUENCE: 221
ggcagaataa tattatagac ccttggatta tcacaaactt cgtgcaggca cccaacggc 59

<210> SEQ ID NO 222
<211> LENGTH: 50
<212> TYPE: DNA
<213> ORGANISM: Artificial Sequence
<220> FEATURE:
<223> OTHER INFORMATION: Primer GII.4Syd12(P80A).r

<400> SEQUENCE: 222
atcgggtccc aaggcggccg accacaggat ttctcctggc gcatttctcg 50

<210> SEQ ID NO 223
<211> LENGTH: 50
<212> TYPE: DNA
<213> ORGANISM: Artificial Sequence
<220> FEATURE:
<223> OTHER INFORMATION: Primer GII.4Syd12(P80A).c

<400> SEQUENCE: 223
aatcctgtgg tcggccgcct tgggacccga tctgaacccc tatttgtcac 50

<210> SEQ ID NO 224
<211> LENGTH: 50
<212> TYPE: DNA
<213> ORGANISM: Artificial Sequence
<220> FEATURE:
<223> OTHER INFORMATION: Primer GII.4Syd12(P80N).r

<400> SEQUENCE: 224
atcgggtccc aagttggccg accacaggat ttctcctggc gcatttctcg 50

<210> SEQ ID NO 225
<211> LENGTH: 50
<212> TYPE: DNA
<213> ORGANISM: Artificial Sequence
<220> FEATURE:
<223> OTHER INFORMATION: Primer GII.4Syd12(P80N).c

<400> SEQUENCE: 225
aatcctgtgg tcggccaact tgggacccga tctgaacccc tatttgtcac 50

<210> SEQ ID NO 226
<211> LENGTH: 50
<212> TYPE: DNA
<213> ORGANISM: Artificial Sequence
<220> FEATURE:
<223> OTHER INFORMATION: Primer GII.4Syd12(P80K).r

<400> SEQUENCE: 226
atcgggtccc aacttggccg accacaggat ttctcctggc gcatttctcg 50

<210> SEQ ID NO 227
<211> LENGTH: 50
<212> TYPE: DNA
<213> ORGANISM: Artificial Sequence
<220> FEATURE:
<223> OTHER INFORMATION: Primer GII.4Syd12(P80K).c

<400> SEQUENCE: 227
aatcctgtgg tcggccaagt tgggacccga tctgaacccc tatttgtcac 50

<210> SEQ ID NO 228
<211> LENGTH: 50
<212> TYPE: DNA
<213> ORGANISM: Artificial /Sequence
<220> FEATURE:
<223> OTHER INFORMATION: Primer GII.4Syd12(P80H).r

<400> SEQUENCE: 228
atcgggtccc aagtgggccg accacaggat ttctcctggc gcatttctcg 50

<210> SEQ ID NO 229
<211> LENGTH: 50
<212> TYPE: DNA
<213> ORGANISM: Artificial Sequence
<220> FEATURE:
<223> OTHER INFORMATION: Primer GII.4Syd12(P80H).c

<400> SEQUENCE: 229
aatcctgtgg tcggcccact tgggacccga tctgaacccc tatttgtcac 50

<210> SEQ ID NO 230
<211> LENGTH: 54
<212> TYPE: DNA
<213> ORGANISM: Artificial Sequence
<220> FEATURE:
<223> OTHER INFORMATION: Primer GII.4Syd12(A39I).r

<400> SEQUENCE: 230
gaccggccac ggggattgct atggctgcgc ccaccacagg ctccagggcc atca 54

<210> SEQ ID NO 231
<211> LENGTH: 54
<212> TYPE: DNA
<213> ORGANISM: Artificial Sequence
<220> FEATURE:

<223> OTHER INFORMATION: Primer GII.4Syd12(A39I).c

<400> SEQUENCE: 231
gggcgcagcc atagcaatcc ccgtggccgg tcagcagaat gtgattgacc cgtg 54

<210> SEQ ID NO 232
<211> LENGTH: 54
<212> TYPE: DNA
<213> ORGANISM: Artificial Sequence
<220> FEATURE:
<223> OTHER INFORMATION: Primer GII.4Syd12(A39M).r

<400> SEQUENCE: 232
gaccggccac gggcattgct atggctgcgc ccaccacagg ctccagggcc atca 54

<210> SEQ ID NO 233
<211> LENGTH: 54
<212> TYPE: DNA
<213> ORGANISM: Artificial Sequence
<220> FEATURE:
<223> OTHER INFORMATION: Primer GII.4Syd12(A39M).c

<400> SEQUENCE: 233
gggcgcagcc atagcaatgc ccgtggccgg tcagcagaat gtgattgacc cgtg 54

<210> SEQ ID NO 234
<211> LENGTH: 54
<212> TYPE: DNA
<213> ORGANISM: Artificial Sequence
<220> FEATURE:
<223> OTHER INFORMATION: Primer GII.4Syd12(A39G).r

<400> SEQUENCE: 234
gaccggccac ggggcctgct atggctgcgc ccaccacagg ctccagggcc atca 54

<210> SEQ ID NO 235
<211> LENGTH: 54
<212> TYPE: DNA
<213> ORGANISM: Artificial Sequence
<220> FEATURE:
<223> OTHER INFORMATION: Primer GII.4Syd12(A39G).c

<400> SEQUENCE: 235
gggcgcagcc atagcaggcc ccgtggccgg tcagcagaat gtgattgacc cgtg 54

<210> SEQ ID NO 236
<211> LENGTH: 54
<212> TYPE: DNA
<213> ORGANISM: Artificial Sequence
<220> FEATURE:
<223> OTHER INFORMATION: Primer GII.4Syd12(A39S).r

<400> SEQUENCE: 236
gaccggccac ggggcttgct atggctgcgc ccaccacagg ctccagggcc atca 54

<210> SEQ ID NO 237
<211> LENGTH: 54
<212> TYPE: DNA
<213> ORGANISM: Artificial Sequence
<220> FEATURE:
<223> OTHER INFORMATION: Primer GII.4Syd12(A39S).c

<400> SEQUENCE: 237
gggcgcagcc atagcaagcc ccgtggccgg tcagcagaat gtgattgacc cgtg 54

<210> SEQ ID NO 238
<211> LENGTH: 54
<212> TYPE: DNA
<213> ORGANISM: Artificial Sequence
<220> FEATURE:
<223> OTHER INFORMATION: Primer GII.4Syd12(A39E).r

<400> SEQUENCE: 238
gaccggccac gggctctgct atggctgcgc ccaccacagg ctccagggcc atca 54

<210> SEQ ID NO 239
<211> LENGTH: 49
<212> TYPE: DNA
<213> ORGANISM: Artificial Sequence
<220> FEATURE:
<223> OTHER INFORMATION: Primer GII.4Syd12(A39E).c

<400> SEQUENCE: 239
gggcgcagcc atagcagagc ccgtggccgg tcagcagaat gtgattgac 49

<210> SEQ ID NO 240
<211> LENGTH: 54
<212> TYPE: DNA
<213> ORGANISM: Artificial Sequence
<220> FEATURE:
<223> OTHER INFORMATION: Primer GII.4Syd12(A39D).r

<400> SEQUENCE: 240
gaccggccac ggggtctgct atggctgcgc ccaccacagg ctccagggcc atca 54

<210> SEQ ID NO 241
<211> LENGTH: 54
<212> TYPE: DNA
<213> ORGANISM: Artificial Sequence
<220> FEATURE:
<223> OTHER INFORMATION: Primer GII.4Syd12(A39D).c

<400> SEQUENCE: 241
gggcgcagcc atagcagacc ccgtggccgg tcagcagaat gtgattgacc cgtg 54

<210> SEQ ID NO 242
<211> LENGTH: 54
<212> TYPE: DNA
<213> ORGANISM: Artificial Sequence
<220> FEATURE:
<223> OTHER INFORMATION: Primer GII.4Syd12(A39N).r

<400> SEQUENCE: 242
accggccacg ggtttgcta tggctgcgcc caccacaggc tccagggcca tcac 54

<210> SEQ ID NO 243
<211> LENGTH: 54
<212> TYPE: DNA
<213> ORGANISM: Artificial Sequence
<220> FEATURE:
<223> OTHER INFORMATION: Primer GII.4Syd12(A39N).c

<400> SEQUENCE: 243
gggcgcagcc atagcaaacc ccgtggccgg tcagcagaat gtgattgacc cgtg 54

<210> SEQ ID NO 244
<211> LENGTH: 54
<212> TYPE: DNA
<213> ORGANISM: Artificial Sequence
<220> FEATURE:
<223> OTHER INFORMATION: Primer GII.4Syd12(A39Q).r

<400> SEQUENCE: 244
gaccggccac gggctgtgct atggctgcgc ccaccacagg ctccagggcc atca 54

<210> SEQ ID NO 245
<211> LENGTH: 54
<212> TYPE: DNA
<213> ORGANISM: Artificial Sequence
<220> FEATURE:
<223> OTHER INFORMATION: Primer GII.4Syd12(A39Q).c

<400> SEQUENCE: 245
gggcgcagcc atagcacagc ccgtggccgg tcagcagaat gtgattgacc cgtg 54

<210> SEQ ID NO 246
<211> LENGTH: 54
<212> TYPE: DNA
<213> ORGANISM: Artificial Sequence
<220> FEATURE:
<223> OTHER INFORMATION: Primer GII.4Syd12(A39K).r

<400> SEQUENCE: 246
gaccggccac gggctttgct atggctgcgc ccaccacagg ctccagggcc atca 54

<210> SEQ ID NO 247
<211> LENGTH: 54
<212> TYPE: DNA
<213> ORGANISM: Artificial Sequence
<220> FEATURE:
<223> OTHER INFORMATION: Primer GII.4Syd12(A39K).c

<400> SEQUENCE: 247
gggcgcagcc atagcaaagc ccgtggccgg tcagcagaat gtgattgacc cgtg 54

<210> SEQ ID NO 248
<211> LENGTH: 51
<212> TYPE: DNA
<213> ORGANISM: Artificial Sequence
<220> FEATURE:
<223> OTHER INFORMATION: Primer GII.4Syd12(A39H).r

<400> SEQUENCE: 248
gaccggccac ggggtgtgct atggctgcgc ccaccacagg ctccagggcc a 51

<210> SEQ ID NO 249
<211> LENGTH: 54
<212> TYPE: DNA
<213> ORGANISM: Artificial Sequence
<220> FEATURE:
<223> OTHER INFORMATION: Primer GII.4Syd12(A39H).c

<400> SEQUENCE: 249
gggcgcagcc atagcacacc ccgtggccgg tcagcagaat gtgattgacc cgtg 54

<210> SEQ ID NO 250
<211> LENGTH: 50
<212> TYPE: DNA
<213> ORGANISM: Artificial Sequence
<220> FEATURE:
<223> OTHER INFORMATION: Primer GI.7USA14_VP1(M57L).r

<400> SEQUENCE: 250
gaacgaaatt gttcagtatc cacgggtcga tcatattgac ttggcctgca 50

<210> SEQ ID NO 251
<211> LENGTH: 48

<212> TYPE: DNA
<213> ORGANISM: Artificial Sequence
<220> FEATURE:
<223> OTHER INFORMATION: Primer GI.7USA14_VP1(M57L).c

<400> SEQUENCE: 251
gatcgacccg tggatactga acaatttcgt tcaggcacca gaaggaga 48

<210> SEQ ID NO 252
<211> LENGTH: 52
<212> TYPE: DNA
<213> ORGANISM: Artificial Sequence
<220> FEATURE:
<223> OTHER INFORMATION: Primer GI.7USA14_VP1(M57G).r

<400> SEQUENCE: 252
gaacgaaatt gttgcctatc cacgggtcga tcatattgac ttggcctgca gt 52

<210> SEQ ID NO 253
<211> LENGTH: 48
<212> TYPE: DNA
<213> ORGANISM: Artificial Sequence
<220> FEATURE:
<223> OTHER INFORMATION: Primer GI.7USA14_VP1(M57G).c

<400> SEQUENCE: 253
gatcgacccg tggataggca acaatttcgt tcaggcacca gaaggaga 48

<210> SEQ ID NO 254
<211> LENGTH: 52
<212> TYPE: DNA
<213> ORGANISM: Artificial Sequence
<220> FEATURE:
<223> OTHER INFORMATION: Primer GI.7USA14_VP1(M57S).r

<400> SEQUENCE: 254
gaacgaaatt gttgcttatc cacgggtcga tcatattgac ttggcctgca gt 52

<210> SEQ ID NO 255
<211> LENGTH: 48
<212> TYPE: DNA
<213> ORGANISM: Artificial Sequence
<220> FEATURE:
<223> OTHER INFORMATION: Primer GI.7USA14_VP1(M57S).c

<400> SEQUENCE: 255
gatcgacccg tggataagca acaatttcgt tcaggcacca gaaggaga 48

<210> SEQ ID NO 256
<211> LENGTH: 52
<212> TYPE: DNA
<213> ORGANISM: Artificial Sequence
<220> FEATURE:
<223> OTHER INFORMATION: Primer GI.7USA14_VP1(M57T).r

<400> SEQUENCE: 256
gaacgaaatt gttggttatc cacgggtcga tcatattgac ttggcctgca gt 52

<210> SEQ ID NO 257
<211> LENGTH: 48
<212> TYPE: DNA
<213> ORGANISM: Artificial Sequence
<220> FEATURE:
<223> OTHER INFORMATION: Primer GI.7USA14_VP1(M57T).c

<400> SEQUENCE: 257
gatcgacccg tggataacca acaatttcgt tcaggcacca gaaggaga 48

<210> SEQ ID NO 258
<211> LENGTH: 52
<212> TYPE: DNA
<213> ORGANISM: Artificial Sequence
<220> FEATURE:
<223> OTHER INFORMATION: Primer GI.7USA14_VP1(M57N).r

<400> SEQUENCE: 258
gaacgaaatt gttgtttatc cacgggtcga tcatattgac ttggcctgca gt 52

<210> SEQ ID NO 259
<211> LENGTH: 48
<212> TYPE: DNA
<213> ORGANISM: Artificial Sequence
<220> FEATURE:
<223> OTHER INFORMATION: Primer GI.7USA14_VP1(M57N).c

<400> SEQUENCE: 259
gatcgacccg tggataaaca acaatttcgt tcaggcacca gaaggaga 48

<210> SEQ ID NO 260
<211> LENGTH: 52
<212> TYPE: DNA
<213> ORGANISM: Artificial Sequence
<220> FEATURE:
<223> OTHER INFORMATION: Primer GI.7USA14_VP1(M57Q).r

<400> SEQUENCE: 260
gaacgaaatt gttctgtatc cacgggtcga tcatattgac ttggcctgca gt 52

<210> SEQ ID NO 261
<211> LENGTH: 48
<212> TYPE: DNA
<213> ORGANISM: Artificial Sequence
<220> FEATURE:
<223> OTHER INFORMATION: Primer GI.7USA14_VP1(M57Q).c

<400> SEQUENCE: 261
gatcgacccg tggatacaga acaatttcgt tcaggcacca gaaggaga 48

<210> SEQ ID NO 262
<211> LENGTH: 52
<212> TYPE: DNA
<213> ORGANISM: Artificial Sequence
<220> FEATURE:
<223> OTHER INFORMATION: Primer GI.7USA14_VP1(M57K).r

<400> SEQUENCE: 262
gaacgaaatt gttctttatc cacgggtcga tcatattgac ttggcctgca gt 52

<210> SEQ ID NO 263
<211> LENGTH: 48
<212> TYPE: DNA
<213> ORGANISM: Artificial Sequence
<220> FEATURE:
<223> OTHER INFORMATION: Primer GI.7USA14_VP1(M57K).c

<400> SEQUENCE: 263
gatcgacccg tggataaaga acaatttcgt tcaggcacca gaaggaga 48

<210> SEQ ID NO 264
<211> LENGTH: 52
<212> TYPE: DNA
<213> ORGANISM: Artificial Sequence
<220> FEATURE:
<223> OTHER INFORMATION: Primer GI.7USA14_VP1(M57H).r

<400> SEQUENCE: 264
gaacgaaatt gttgtgtatc cacgggtcga tcatattgac ttggcctgca gt 52

<210> SEQ ID NO 265
<211> LENGTH: 48
<212> TYPE: DNA
<213> ORGANISM: Artificial Sequence
<220> FEATURE:
<223> OTHER INFORMATION: Primer GI.7USA14_VP1(M57H).c

<400> SEQUENCE: 265
gatcgacccg tggatacaca acaatttcgt tcaggcacca gaaggaga 48

<210> SEQ ID NO 266
<211> LENGTH: 54
<212> TYPE: DNA
<213> ORGANISM: Artificial Sequence
<220> FEATURE:
<223> OTHER INFORMATION: Primer GI.3Lil08(S94V).r

<400> SEQUENCE: 266
tctgagccaa gtgcaccaga aacggattca agtgtggtcc tagctgcagg tcaa 54

<210> SEQ ID NO 267
<211> LENGTH: 54
<212> TYPE: DNA
<213> ORGANISM: Artificial Sequence
<220> FEATURE:
<223> OTHER INFORMATION: Primer GI.3Lil08(S94V).c

<400> SEQUENCE: 267
cttgaatccg tttctggtgc acttggctca gatgtataat ggatgggttg gaaa 54

<210> SEQ ID NO 268
<211> LENGTH: 54
<212> TYPE: DNA
<213> ORGANISM: Artificial Sequence
<220> FEATURE:
<223> OTHER INFORMATION: Primer GI.3Lil08(S94I).r

<400> SEQUENCE: 268
tctgagccaa gtggatcaga aacggattca agtgtggtcc tagctgcagg tcaa 54

<210> SEQ ID NO 269
<211> LENGTH: 54
<212> TYPE: DNA
<213> ORGANISM: Artificial Sequence
<220> FEATURE:
<223> OTHER INFORMATION: Primer GI.3Lil08(S94I).c

<400> SEQUENCE: 269
cttgaatccg tttctgatcc acttggctca gatgtataat ggatgggttg gaaa 54

<210> SEQ ID NO 270
<211> LENGTH: 54
<212> TYPE: DNA
<213> ORGANISM: Artificial Sequence
<220> FEATURE:
<223> OTHER INFORMATION: Primer GI.3Lil08(S94M).r

<400> SEQUENCE: 270
tctgagccaa gtgcatcaga aacggattca agtgtggtcc tagctgcagg tcaa 54

<210> SEQ ID NO 271
<211> LENGTH: 54
<212> TYPE: DNA
<213> ORGANISM: Artificial Sequence
<220> FEATURE:
<223> OTHER INFORMATION: Primer GI.3Lil08(S94M).c

<400> SEQUENCE: 271
cttgaatccg tttctgatgc acttggctca gatgtataat ggatgggttg gaaa    54

<210> SEQ ID NO 272
<211> LENGTH: 54
<212> TYPE: DNA
<213> ORGANISM: Artificial Sequence
<220> FEATURE:
<223> OTHER INFORMATION: Primer GI.3Lil08(S94T).r

<400> SEQUENCE: 272
tctgagccaa gtgggtcaga aacggattca agtgtggtcc tagctgcagg tcaa    54

<210> SEQ ID NO 273
<211> LENGTH: 54
<212> TYPE: DNA
<213> ORGANISM: Artificial Sequence
<220> FEATURE:
<223> OTHER INFORMATION: Primer GI.3Lil08(S94T).c

<400> SEQUENCE: 273
cttgaatccg tttctgaccc acttggctca gatgtataat ggatgggttg gaaa    54

<210> SEQ ID NO 274
<211> LENGTH: 54
<212> TYPE: DNA
<213> ORGANISM: Artificial Sequence
<220> FEATURE:
<223> OTHER INFORMATION: Primer GI.3Lil08(S94E).r

<400> SEQUENCE: 274
tctgagccaa gtgctccaga aacggattca agtgtggtcc tagctgcagg tcaa    54

<210> SEQ ID NO 275
<211> LENGTH: 54
<212> TYPE: DNA
<213> ORGANISM: Artificial Sequence
<220> FEATURE:
<223> OTHER INFORMATION: Primer GI.3Lil08(S94E).c

<400> SEQUENCE: 275
cttgaatccg tttctggagc acttggctca gatgtataat ggatgggttg gaaa    54

<210> SEQ ID NO 276
<211> LENGTH: 54
<212> TYPE: DNA
<213> ORGANISM: Artificial Sequence
<220> FEATURE:
<223> OTHER INFORMATION: Primer GI.3Lil08(S94D).r

<400> SEQUENCE: 276
tctgagccaa gtggtccaga aacggattca agtgtggtcc tagctgcagg tcaa    54

<210> SEQ ID NO 277
<211> LENGTH: 54
<212> TYPE: DNA
<213> ORGANISM: Artificial Sequence
<220> FEATURE:
<223> OTHER INFORMATION: Primer GI.3Lil08(S94D).c

<400> SEQUENCE: 277
cttgaatccg tttctggacc acttggctca gatgtataat ggatgggttg gaaa 54

<210> SEQ ID NO 278
<211> LENGTH: 54
<212> TYPE: DNA
<213> ORGANISM: Artificial Sequence
<220> FEATURE:
<223> OTHER INFORMATION: Primer GI.3Lil08(S94N).r

<400> SEQUENCE: 278
tctgagccaa gtggttcaga aacggattca agtgtggtcc tagctgcagg tcaa 54

<210> SEQ ID NO 279
<211> LENGTH: 54
<212> TYPE: DNA
<213> ORGANISM: Artificial Sequence
<220> FEATURE:
<223> OTHER INFORMATION: Primer GI.3Lil08(S94N).c

<400> SEQUENCE: 279
cttgaatccg tttctgaacc acttggctca gatgtataat ggatgggttg gaaa 54

<210> SEQ ID NO 280
<211> LENGTH: 54
<212> TYPE: DNA
<213> ORGANISM: Artificial Sequence
<220> FEATURE:
<223> OTHER INFORMATION: Primer GI.3Lil08(S94Q).r

<400> SEQUENCE: 280
tctgagccaa gtgctgcaga aacggattca agtgtggtcc tagctgcagg tcaa 54

<210> SEQ ID NO 281
<211> LENGTH: 54
<212> TYPE: DNA
<213> ORGANISM: Artificial Sequence
<220> FEATURE:
<223> OTHER INFORMATION: Primer GI.3Lil08(S94Q).c

<400> SEQUENCE: 281
cttgaatccg tttctgcagc acttggctca gatgtataat ggatgggttg gaaa 54

<210> SEQ ID NO 282
<211> LENGTH: 54
<212> TYPE: DNA
<213> ORGANISM: Artificial Sequence
<220> FEATURE:
<223> OTHER INFORMATION: Primer GI.3Lil08(S94K).r

<400> SEQUENCE: 282
tctgagccaa gtgcttcaga aacggattca agtgtggtcc tagctgcagg tcaa 54

<210> SEQ ID NO 283
<211> LENGTH: 54
<212> TYPE: DNA
<213> ORGANISM: Artificial Sequence
<220> FEATURE:
<223> OTHER INFORMATION: Primer GI.3Lil08(S94K).c

<400> SEQUENCE: 283
cttgaatccg tttctgaagc acttggctca gatgtataat ggatgggttg gaaa 54

<210> SEQ ID NO 284

<211> LENGTH: 54
<212> TYPE: DNA
<213> ORGANISM: Artificial Sequence
<220> FEATURE:
<223> OTHER INFORMATION: Primer GI.3Lil08(S94H).r

<400> SEQUENCE: 284
tctgagccaa gtggtgcaga aacggattca agtgtggtcc tagctgcagg tcaa 54

<210> SEQ ID NO 285
<211> LENGTH: 54
<212> TYPE: DNA
<213> ORGANISM: Artificial Sequence
<220> FEATURE:
<223> OTHER INFORMATION: Primer GI.3Lil08(S94H).c

<400> SEQUENCE: 285
cttgaatccg tttctgcacc acttggctca gatgtataat ggatgggttg gaaa 54

<210> SEQ ID NO 286
<211> LENGTH: 540
<212> TYPE: PRT
<213> ORGANISM: Norovirus
<220> FEATURE:
<221> NAME/KEY: MISC_FEATURE
<222> LOCATION: (80)..(80)
<223> OTHER INFORMATION: X may be Ala, Asn, Lys or His

<400> SEQUENCE: 286

Met Lys Met Ala Ser Ser Asp Ala Asn Pro Ser Asp Gly Ser Ala Ala
1 5 10 15

Asn Leu Val Pro Glu Val Asn Asn Glu Val Met Ala Leu Glu Pro Val
20 25 30

Val Gly Ala Ala Ile Ala Ala Pro Val Ala Gly Gln Gln Asn Val Ile
35 40 45

Asp Pro Trp Ile Arg Asn Asn Phe Val Gln Ala Pro Gly Gly Glu Phe
50 55 60

Thr Val Ser Pro Arg Asn Ala Pro Gly Glu Ile Leu Trp Ser Ala Xaa
65 70 75 80

Leu Gly Pro Asp Leu Asn Pro Tyr Leu Ser His Leu Ala Arg Met Tyr
85 90 95

Asn Gly Tyr Ala Gly Gly Phe Glu Val Gln Val Ile Leu Ala Gly Asn
100 105 110

Ala Phe Thr Ala Gly Lys Val Ile Phe Ala Ala Val Pro Pro Asn Phe
115 120 125

Pro Thr Glu Gly Leu Ser Pro Ser Gln Val Thr Met Phe Pro His Ile
130 135 140

Val Val Asp Val Arg Gln Leu Glu Pro Val Leu Ile Pro Leu Pro Asp
145 150 155 160

Val Arg Asn Asn Phe Tyr His Tyr Asn Gln Ser Asn Asp Pro Thr Ile
165 170 175

Lys Leu Ile Ala Met Leu Tyr Thr Pro Leu Arg Ala Asn Asn Ala Gly
180 185 190

Asp Asp Val Phe Thr Val Ser Cys Arg Val Leu Thr Arg Pro Ser Pro
195 200 205

Asp Phe Asp Phe Ile Phe Leu Val Pro Pro Thr Val Glu Ser Arg Thr
210 215 220

Lys Pro Phe Ser Val Pro Val Leu Thr Val Glu Glu Met Thr Asn Ser
225 230 235 240

-continued

```
Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 287
<211> LENGTH: 1623
<212> TYPE: DNA
<213> ORGANISM: Artificial Sequence
<220> FEATURE:
<223> OTHER INFORMATION: Nucleic acid sequence of human codon optimized
VP1 GII.4_Syd12_P80X

<400> SEQUENCE: 287

```
atgaaaatgg cctcgagtga cgctaaccct agtgacggca gcgccgccaa tcttgtgcct      60

gaggttaata atgaggtgat ggccctggag cctgtggtgg gcgcagccat agcagcgccc     120

gtggccggtc agcagaatgt gattgacccg tggatacgca acaattttgt ccaagcccct     180

ggtggggagt tcaccgttag cccgagaaat gcgccaggag aaatcctgtg gtcggccvms     240

ttgggacccg atctgaaccc ctatttgtca catctcgctc ggatgtacaa cgggtatgcc     300

ggcggatttg aagtgcaggt gattctggct gggaacgcgt tcactgctgg caaagtgatc     360
```

```
tttgcagcgg tgcctcccaa cttccccact gaaggactgt ctccaagcca ggtcacaatg    420

tttccacaca tcgtggtgga cgtacggcag ctagagcctg tcctgattcc cctccctgat    480

gtacgcaata atttctacca ctacaatcaa tccaatgatc cgaccattaa actcatcgcg    540

atgttgtaca cccctctgcg cgctaacaat gctggagacg acgtattcac cgtgtcatgc    600

agagtgctca ccagaccttc accagacttt gactttatct tcttagtgcc ccccactgtt    660

gagagccgaa ccaagccctt tagtgtcccc gtactcacag tcgaggagat gacaaatagc    720

cgctttccaa tccccttga gaaactgttc acaggacctt cctcggcatt cgtggttcag    780

ccacagaacg gacgctgcac aactgacggc gtgctgctcg gaaccaccca gcttagccct    840

gttaatatct gtacgtttag aggcgacgta actcacataa ctggctcacg gaactatacc    900

atgaatctgg catcacagaa ttggaatgac tacgacccaa ccgaagagat tcccgcacct    960

cttggaaccc ccgactttgt gggaaaaata cagggcgtcc tgacacaaac caccagaacc   1020

gatggctcca cacggggaca caaggcaacc gtctacactg gctctgccga ttttgccccg   1080

aaactgggta gagtgcagtt tgagaccgac actgaccggg actttgaagc caatcagaat   1140

actaagttca cacctgtagg agtgattcag gacgggggca ccactcaccg gaacgagccg   1200

caacaatggg tcctgccctc ttatagcggg aggaatactc ataatgtgca tttggctcct   1260

gcagtggctc ccacgtttcc cggggaacaa ctgctctttt ttcgttcaac catgcctgga   1320

tgctccggat atcccaatat ggatctcgat tgcctgctcc cacaggaatg ggtgcagtat   1380

ttttatcaag aggccgcacc agcccaatcc gacgtcgcac ttctgcggtt cgtgaatcca   1440

gacacaggcc gcgtgttgtt tgagtgcaaa ttgcacaaat caggatacgt tacagtggct   1500

catactggac agcatgacct ggtgatccca cccaacggat attttaggtt cgactcctgg   1560

gtgaatcagt tttatacatt agccccatg gggaatggga ctggcagacg cagggctgtc    1620

tga                                                                 1623
```

<210> SEQ ID NO 288
<211> LENGTH: 540
<212> TYPE: PRT
<213> ORGANISM: Norovirus
<220> FEATURE:
<221> NAME/KEY: MOD_RES
<222> LOCATION: (39)..(39)
<223> OTHER INFORMATION: X may be Ile, Met, Gly, Ser, Glu, Asp, Asn,
      Gln, Lys or His

<400> SEQUENCE: 288

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Xaa Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110
```

-continued

```
Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
```

530 535 540

<210> SEQ ID NO 289
<211> LENGTH: 1620
<212> TYPE: DNA
<213> ORGANISM: Artificial Sequence
<220> FEATURE:
<223> OTHER INFORMATION: hCod optimize sequence of VP1
GII.4_Syd12_P80S+A39X

<400> SEQUENCE: 289
atgaaaatgg cctcgagtga cgctaaccct agtgacggca gcgccgccaa tcttgtgcct 60
gaggttaata atgaggtgat ggccctggag cctgtggtgg gcgcagccat agcavdsgtg 120
gccggtcagc agaatgtgat tgacccgtgg atacgcaaca attttgtcca agcccctggt 180
ggggagttca ccgttagccc gagaaatgcg ccaggagaaa tcctgtggtc ggccagcttg 240
ggacccgatc tgaaccccta tttgtcacat ctcgctcgga tgtacaacgg gtatgccggc 300
ggatttgaag tgcaggtgat tctggctggg aacgcgttca ctgctggcaa agtgatcttt 360
gcagcggtgc ctcccaactt ccccactgaa ggactgtctc caagccaggt cacaatgttt 420
ccacacatcg tggtggacgt acggcagcta gagcctgtcc tgattcccct ccctgatgta 480
cgcaataatt tctaccacta caatcaatcc aatgatccga ccattaaact catcgcgatg 540
ttgtacaccc ctctgcgcgc taacaatgct ggagacgacg tattcaccgt gtcatgcaga 600
gtgctcacca gaccttcacc agactttgac tttatcttct tagtgccccc cactgttgag 660
agccgaacca agccctttag tgtccccgta ctcacagtcg aggagatgac aaatagccgc 720
tttccaatcc cccttgagaa actgttcaca ggaccttcct cggcattcgt ggttcagcca 780
cagaacggac gctgcacaac tgacggcgtg ctgctcggaa ccacccagct tagccctgtt 840
aatatctgta cgtttagagg cgacgtaact cacataactg gctcacggaa ctataccatg 900
aatctggcat cacagaattg gaatgactac gacccaaccg aagagattcc cgcacctctt 960
ggaacccccg actttgtggg aaaaatacag ggcgtcctga cacaaaccac cagaaccgat 1020
ggctccacac ggggacacaa ggcaaccgtc tacactggct ctgccgattt tgccccgaaa 1080
ctgggtagag tgcagtttga gaccgacact gaccgggact ttgaagccaa tcagaatact 1140
aagttcacac ctgtaggagt gattcaggac gggggcacca ctcaccggaa cgagccgcaa 1200
caatgggtcc tgccctctta tagcgggagg aatactcata atgtgcattt ggctcctgca 1260
gtggctccca cgtttcccgg ggaacaactg ctcttttttc gttcaaccat gcctggatgc 1320
tccggatatc ccaatatgga tctcgattgc ctgctcccac aggaatgggt gcagtatttt 1380
tatcaagagg ccgcaccagc ccaatccgac gtcgcacttc tgcggttcgt gaatccagac 1440
acaggccgcg tgttgtttga gtgcaaattg cacaaatcag gatacgttac agtggctcat 1500
actggacagc atgacctggt gatcccaccc aacggatatt ttaggttcga ctcctgggtg 1560
aatcagtttt atacattagc cccatgggg aatgggactg gcagacgcag ggctgtctga 1620

<210> SEQ ID NO 290
<211> LENGTH: 538
<212> TYPE: PRT
<213> ORGANISM: Norovirus
<220> FEATURE:
<221> NAME/KEY: MOD_RES
<222> LOCATION: (57)..(57)
<223> OTHER INFORMATION: X may be Leu, Gly, Ser, Thr, Asn, Gln, Lys or
His

<400> SEQUENCE: 290

-continued

Met Met Met Ala Ser Lys Asp Ala Pro Ser Asn Met Asp Gly Thr Ser
1 5 10 15

Gly Ala Gly Gln Leu Val Pro Glu Val Asn Ala Ala Glu Pro Leu Pro
20 25 30

Leu Glu Pro Val Val Gly Ala Ala Thr Ala Val Ala Thr Ala Gly Gln
35 40 45

Val Asn Met Ile Asp Pro Trp Ile Xaa Asn Asn Phe Val Gln Ala Pro
50 55 60

Glu Gly Glu Phe Thr Ile Ser Pro Asn Asn Thr Pro Gly Asp Ile Leu
65 70 75 80

Phe Asp Leu Arg Leu Gly Pro His Leu Asn Pro Phe Leu Leu His Leu
85 90 95

Ser Gln Met Tyr Asn Gly Trp Val Gly Asn Met Arg Val Arg Val Met
100 105 110

Leu Ala Gly Asn Ala Phe Ser Ala Gly Lys Ile Ile Ile Cys Cys Val
115 120 125

Pro Pro Gly Phe Glu Ser Gln Asn Ile Ser Ile Gly Gln Ala Thr Met
130 135 140

Phe Pro His Val Ile Ala Asp Val Arg Val Leu Glu Pro Ile Glu Val
145 150 155 160

Pro Leu Asp Asp Val Arg Asn Val Leu Phe His Thr Asn Glu Asn Arg
165 170 175

Pro Thr Met Arg Leu Leu Cys Met Leu Tyr Thr Pro Leu Arg Ala Gly
180 185 190

Gly Ala Ser Ser Gly Thr Asp Pro Phe Val Ile Ala Gly Arg Val Leu
195 200 205

Thr Cys Pro Ala Pro Asp Phe Asn Phe Leu Phe Leu Val Pro Pro Ser
210 215 220

Val Glu Gln Lys Thr Arg Gln Leu Thr Ile Pro Asn Ile Pro Leu Asn
225 230 235 240

Asn Leu Ala Asn Ser Arg Val Pro Ala Met Ile Asn Lys Met Thr Val
245 250 255

Ser Ala Asp Gln Asn Gln Val Val Gln Phe Gln Asn Gly Arg Cys Thr
260 265 270

Leu Glu Gly Gln Leu Leu Gly Thr Thr Pro Val Ser Ala Asn Gln Val
275 280 285

Ala Arg Ile Arg Gly Lys Val Phe Ser Thr Asn Ser Gly Thr Gly Leu
290 295 300

Asn Leu Thr Glu Val Asp Gly Thr Pro Tyr His Ala Phe Glu Ser Pro
305 310 315 320

Ala Pro Leu Gly Phe Pro Asp Ile Gly Asn Cys Asp Trp His Val Tyr
325 330 335

Ala Phe Lys Val Asn Gln Asn Thr Gly Asp Pro Met Tyr Arg Leu Asp
340 345 350

Ile Thr Gln Gly Asn Ser Phe Ala Pro His Leu Gly Ser Ile Glu Phe
355 360 365

Ser Ser Glu Asn His Pro Ser Gly Asp Gln Leu Gly Thr Leu Thr Trp
370 375 380

Ile Ser Pro Leu Asn Asn Ala Ser Arg Val Asp Pro Trp Lys Ile Pro
385 390 395 400

Thr Tyr Gly Ser Thr Leu Thr Glu Ser Thr Asn Leu Ala Pro Pro Ile
405 410 415

-continued

```
Phe Pro Pro Gly Phe Gly Glu Ala Ile Val Tyr Phe Met Ser Asp Phe
            420                 425                 430

Pro Ile Val Ser Gly Asn Thr Ala Gln Ile Pro Cys Thr Leu Pro Gln
        435                 440                 445

Glu Phe Val Ser Ser Phe Val Glu Gln Gln Ala Pro Ile Arg Gly Glu
    450                 455                 460

Ala Ala Leu Leu His Tyr Val Asp Pro Asp Thr His Arg Asn Leu Gly
465                 470                 475                 480

Glu Phe Lys Leu Tyr Pro Asp Gly Phe Ile Thr Cys Val Pro Asn Thr
                485                 490                 495

Gly Gly Gly Pro Gln Asn Leu Pro Ser Asn Gly Val Phe Val Phe Ser
            500                 505                 510

Ser Trp Val Ser Arg Tyr Tyr Gln Leu Lys Pro Val Gly Thr Thr Gly
        515                 520                 525

Pro Val Arg Arg Leu Gly Val Arg Arg Val
    530                 535
```

<210> SEQ ID NO 291
<211> LENGTH: 1614
<212> TYPE: DNA
<213> ORGANISM: Artificial Sequence
<220> FEATURE:
<223> OTHER INFORMATION: Human codon optimized
VP1_GI.7/GA5043/USA/2014_M57x
<220> FEATURE:
<221> NAME/KEY: misc_feature
<222> LOCATION: (170)..(170)
<223> OTHER INFORMATION: n is a, c, g, or t

<400> SEQUENCE: 291

```
atgatgatgg ccagcaagga cgctccgagt aacatggacg gcacttcggg cgcggggcag     60

ctggtgcccg aggtcaatgc cgcagaacca cttcctcttg agcccgtcgt tggcgccgcc    120

acagctgtcg caactgcagg ccaagtcaat atgatcgacc cgtggatavn saatttcgtt    180

caggcaccag aaggagaatt caccatctcc cccaataaca ccccagggga tattctgttt    240

gacctcaggt taggacccca cttgaacccc tttctgcttc atctctcaca aatgtataat    300

ggctgggtcg ggaatatgcg cgtgcgggtg atgctagccg gcaatgcttt ttctgcaggc    360

aagattatca tttgctgcgt tcctcctgga ttcgaatctc aaaatatcag cattggtcaa    420

gcaaccatgt ttccacatgt gatcgctgat gttcgcgtcc tggaacccat tgaagttcct    480

ctcgacgacg tgagaaatgt tctcttccac accaacgaga ataggccgac tatgagactt    540

ctgtgtatgc tctacacccc attaagagcc gggggagcat cctcaggtac tgacccattt    600

gtgattgccg ggcgggtgct cacatgcccg gctccagact ttaacttcct tttcttggtg    660

ccacccagtg ttgaacagaa aaccagacag ctcaccatcc caaatatccc attgaacaat    720

ctcgccaaca gcagggtgcc agcaatgata aacaaaatga cagtcagtgc tgaccagaac    780

caggtagtcc agtttcagaa cggcagatgc acgcttgagg gccaactgct tgggacgacc    840

ccagtctccg cgaaccaggt ggcccgaatc cggggtaaag tcttcagtac aaactccggc    900

actggcctta acctcacaga ggttgacggc actccctatc atgcttttga gtctccagcc    960

cctcttggct ttcccgatat aggcaactgt gactggcacg tttatgcgtt taaagtaaac   1020

cagaacaccg gcgatcctat gtataggttg gatataacac aaggtaattc attcgcccca   1080

cacttgggta gcatcgagtt cagttcagag aaccatccga gtggtgatca gctaggcaca   1140

ttgacgtgga tcagccctct gaataacgca tcaagagtgg atccctggaa gatccctacc   1200
```

-continued

```
tatgggtcca ctctgacaga gagcacaaat ttggctccgc ccattttccc acccggattc   1260

ggcgaggcca tagtgtactt tatgtctgac tttcctatcg tcagcgggaa tacagcccag   1320

attccttgca cactgccaca agaattcgtc tcatcctttg tagagcagca ggcacctatt   1380

cgaggtgagg ccgccctctt gcactacgtg gaccctgaca cccaccgcaa tcttggcgag   1440

tttaagctgt accctgacgg gtttattacc tgtgtaccca acaccggcgg cggcccacaa   1500

aatttgccca gcaatggcgt gtttgtcttt tcctcttggg tgtctcgata ctaccagctt   1560

aaacctgtcg gaactacggg ccccgtgcga cgactcggcg tgaggcgggt gtga         1614


<210> SEQ ID NO 292
<211> LENGTH: 543
<212> TYPE: PRT
<213> ORGANISM: Norovirus
<220> FEATURE:
<221> NAME/KEY: MOD_RES
<222> LOCATION: (94)..(94)
<223> OTHER INFORMATION: X may be Val, Ile, Met, Thr, Glu, Asp, Asn,
      Gln, Lys or His

<400> SEQUENCE: 292

Met Met Met Ala Ser Lys Asp Ala Pro Thr Asn Met Asp Gly Thr Ser
1               5                   10                  15

Gly Ala Gly Gln Leu Val Pro Glu Val Ser Thr Ala Glu Pro Ile Ser
            20                  25                  30

Met Glu Pro Val Ala Gly Ala Ala Thr Ala Ala Ala Thr Ala Gly Gln
        35                  40                  45

Val Asn Met Ile Asp Pro Trp Ile Met Ser Asn Tyr Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Xaa His Leu
                85                  90                  95

Ala Gln Met Tyr Asn Gly Trp Val Gly Asn Met Lys Val Arg Val Leu
            100                 105                 110

Leu Ala Gly Asn Ala Phe Thr Ala Gly Lys Ile Ile Ile Ser Cys Val
        115                 120                 125

Pro Pro Gly Phe Ala Ala Gln Asn Val Ser Ile Ala Gln Ala Thr Met
    130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Asn Asn Asp Ser Thr
                165                 170                 175

Pro Thr Met Arg Leu Ile Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205

Thr Cys Pro Ser Pro Asp Phe Asn Phe Leu Phe Leu Val Pro Pro Asn
    210                 215                 220

Val Glu Gln Lys Thr Lys Pro Phe Ser Val Pro Asn Leu Pro Leu Asn
225                 230                 235                 240

Val Leu Ser Asn Ser Arg Val Pro Ser Leu Ile Lys Ser Met Met Val
                245                 250                 255

Ser Gln Asp His Gly Gln Met Val Gln Phe Gln Asn Gly Arg Val Thr
            260                 265                 270

Leu Asp Gly Gln Leu Gln Gly Thr Thr Pro Thr Ser Ala Ser Gln Leu
```

-continued

```
        275                 280                 285

Cys Lys Ile Arg Gly Thr Val Tyr His Ala Thr Gly Gly Gln Gly Leu
    290                 295                 300

Asn Leu Thr Glu Ile Asp Gly Thr Pro Tyr His Ala Phe Glu Ser Pro
305                 310                 315                 320

Ala Pro Ile Gly Phe Pro Asp Leu Gly Glu Cys Asp Trp His Ile Asn
                325                 330                 335

Ala Ser Pro Ala Asn Ala Phe Thr Asp Gly Ser Ile Ile His Arg Ile
            340                 345                 350

Asp Val Ala Gln Asp Ser Thr Phe Ala Pro His Leu Gly Thr Ile His
        355                 360                 365

Tyr Thr Asn Ala Asp Tyr Asn Ala Asn Val Gly Leu Ile Cys Ser Leu
    370                 375                 380

Glu Trp Leu Ser Pro Pro Ser Gly Gly Ala Pro Lys Val Asn Pro Trp
385                 390                 395                 400

Ala Ile Pro Arg Tyr Gly Ser Thr Leu Thr Glu Ala Ala Gln Leu Ala
                405                 410                 415

Pro Pro Ile Tyr Pro Pro Gly Phe Gly Glu Ala Ile Val Phe Phe Met
            420                 425                 430

Ser Asp Phe Pro Ile Ala Asn Gly Ser Asp Gly Leu Ser Val Pro Cys
        435                 440                 445

Thr Ile Pro Gln Glu Phe Val Thr His Phe Val Asn Glu Gln Ala Pro
    450                 455                 460

Thr Arg Gly Glu Ala Ala Leu Leu His Tyr Val Asp Pro Asp Thr His
465                 470                 475                 480

Arg Asn Leu Gly Glu Phe Lys Leu Tyr Pro Glu Gly Phe Met Thr Cys
                485                 490                 495

Val Pro Asn Ser Ser Gly Ser Gly Pro Gln Thr Leu Pro Ile Asn Gly
            500                 505                 510

Val Phe Thr Phe Ile Ser Trp Val Ser Arg Phe Tyr Gln Leu Lys Pro
        515                 520                 525

Val Gly Thr Thr Gly Pro Val Arg Arg Leu Gly Ile Arg Arg Ser
    530                 535                 540
```

<210> SEQ ID NO 293
<211> LENGTH: 1632
<212> TYPE: DNA
<213> ORGANISM: Artificial Sequence
<220> FEATURE:
<223> OTHER INFORMATION: hCod optimized VP1_GI.3_Lil08_S94x

<400> SEQUENCE: 293

```
atgatgatgg cttccaagga tgctcccaca aacatggatg gaacaagcgg cgcggggcaa      60

cttgtgccgg aggtgtccac ggcggaaccc atttccatgg aacctgtggc cggcgcagcc     120

actgctgccg ccaccgcagg acaggtaaac atgatcgacc cctggatcat gtcaaattac     180

gttcaggctc cacaggggga gtttaccata agcccaaaca acaccccggg tgacatcttg     240

tttgacctgc agctaggacc acacttgaat ccgtttctgv hscacttggc tcagatgtat     300

aatggatggg ttggaaacat gaaggtgcgc gtgctcctgg cgggcaatgc attcacagcc     360

gggaagatta ttatctcttg cgtgccacct ggatttgcag cccagaacgt gtctatcgca     420

caggcaacca tgtttccgca tgtcatcgca gatgtgcgcg tgctagagcc catcgaggtg     480

ccccttgagg acgtgcgcaa cgtcctattc cataacaatg atagcacccc caccatgcgc     540

ttgatatgta tgttatatac tcccctccgc gccagtgggt ccagctccgg gaccgatcct     600
```

```
tttgtgattg ctgggcgggt gttgacttgt cctagccctg acttcaactt ccttttctg      660

gtgcctccaa atgtagaaca gaaaacaaag ccattcagcg tgccaaacct gccccttaac      720

gtgctgtcga attcccgagt gccttccctt attaagtcca tgatggtatc tcaggatcac      780

ggtcaaatgg tgcagtttca gaacggccga gtgacgttag acgggcagct gcagggcaca      840

accccaacca gtgccagtca gctgtgtaag atcagaggca ccgtctacca cgcaactggc      900

ggacaggggc tgaatcttac tgagatcgat ggtaccccct accatgcatt cgagtcacct      960

gcacctattg gatttcccga tcttggggag tgtgattggc atatcaatgc ttcacctgcc     1020

aacgctttca cagacgggtc tattattcat cgcattgacg tagcacagga tagcacattt     1080

gccccgcacc tgggtaccat ccactatacg aacgcagatt acaacgcaaa cgtgggtctt     1140

atctgtagcc tagagtggct atctccgcca agcggtgggg cccctaaagt taacccatgg     1200

gctattcctc ggtacgggtc tacgctgact gaggccgctc agctggcacc ccccatatat     1260

ccaccaggat tcggggaagc cattgttttc tttatgtccg attttccgat agccaacggt     1320

tcagatggcc ttagtgtccc ttgcacgatt ccacaggaat ttgtgacaca cttcgtaaac     1380

gagcaggctc ctactcgggg cgaggctgcc ttgttgcatt acgtagaccc cgatacccat     1440

agaaacctgg gcgaattcaa actctaccct gaaggtttca tgacctgcgt acctaactcc     1500

tccggcagtg gccctcaaac cttgccgatc aacggcgtgt tcacgtttat cagctgggtt     1560

tcacggtttt accaactcaa gcccgtcgga acaactgggc cagttcggag gctcgggatc     1620

agacggagct ag                                                        1632
```

MODIFIED NOROVIRUS VP1 PROTEINS AND VLPS COMPRISING MODIFIED NOROVIRUS VP1 PROTEINS

CROSS REFERENCE TO RELATED APPLICATIONS

This application is a National Stage of International Application No. PCT/CA2018/051530 filed Nov. 30, 2018, claiming priority based on U.S. Patent Application No. 62/593,006 filed Nov. 30, 2017 and U.S. Patent Application No. 62/712,744 filed Jul. 31, 2018.

FIELD OF INVENTION

The present invention relates to modified norovirus VP1 proteins, VLPs comprising modified norovirus VP1 proteins, and methods of producing the same.

BACKGROUND OF THE INVENTION

The global disease burden attributed to norovirus infection is high, being associated with an estimated 20% of all worldwide diarrheal cases and causing over 200,000 deaths annually. Noroviruses are the primary cause of foodborne disease outbreaks in North America and are the causative agent for the majority of healthcare-associated outbreaks amongst the elderly. Norovirus strains are also recognized as being the leading cause of pediatric gastrointestinal illness worldwide.

Noroviruses comprise one of a number of genera of the family Caliciviridae. The human norovirus genome is a single-stranded, positive-sense RNA molecule encoding three open reading frames (ORFs) and capped on its 5' end by a VPg protein. ORF1 encodes six non-structural viral proteins, including VPg, an RNA-dependent RNA polymerase, and a viral protease. ORF2 encodes the major structural capsid protein (VP1). ORF3 encodes a minor capsid protein (VP2).

VP1 is comprised of 2 domains: a shell (S) domain, and a protruding (P) domain. The S domain, for example of GI.1 strains, comprises the first 225 N-terminal amino acids and contains structural elements necessary for capsid assembly and the formation of the viral icosahedron. The P domain comprises the remainder of the VP1 protein and is further comprised of a P1 sub-domain and a P2 sub-domain. The P2 sub-domain is referred to as the hypervariable domain and is thought to play an important role in receptor binding and immune reactivity.

VP1 proteins form dimers via P domain-mediated protein interactions. Dimerization increases the stability of the virion capsid and results in formation of the protrusions extending from the base core of the norovirus particle formed by S domains. When expressed, norovirus VP1 proteins can automatically assemble to form 2 virion structures: a 180-mer capsid structure with T=3 icosahedral symmetry having a 38-40 nm diameter; and a 60-mer capsid structure with T=1 icosahedral symmetry having a 23 nm diameter.

VP2, the minor structural protein, has a molecular weight (MW) of approximately 21-24 kDa. Studies suggest that VP2 is highly basic and located inside the capsid. The function of VP2 is not yet fully understood but it is generally believed to play a role in capsid stability by protecting the virions from disassembly and degradation (Bertolotti-Ciarlet A., Crawford S. E., Hutson A. M., Estes M. K. 2003, J. Virol. 77:11603-11615). VP2 may also have a function during RNA genome packaging. The amount of VP2 minor structural protein in virions is relatively low with 1.5 to 8 copies incorporated into the mature virion. Bertolotti-Ciarlet et. al. (2003) report that in insect and mammalian cells, VLPs composed of VP1/VP2 are more resistant to protease cleavage than those with only VP1, and that expression of VP2 in cis, results in an increase in VP1 protein production. In addition, the presence of the 3'UTR downstream of the ORF2 gene increases the steady-state levels of NV ORF2 mRNA. The greatest increase in VP1 expression was observed when ORF2+ORF3+3'UTR, residing on the same construct and under regulation of one promoter, was expressed. Expression of VP2 in trans did not result in any increase in VP1 expression, indicating that the subgenomic organization of ORF2-ORF2-3'UTR was required for the observed increase in VP1 production.

Noroviruses are classified according to their phylogenetic clustering of the VP1 amino acid sequence. Seven genogroups have been classified to date (GI through GVII) with only genogroups GI, GII, and GIV known to infect humans. Of the 32 specific genotypes currently associated with human infections, GII.4 noroviruses have been responsible for the majority of recent norovirus outbreaks. New strains of GII.4 emerge every two to three years, evolving by a process driven by mutations in epitope determining regions of the hypervariable P2 domain of VP1. This process allows the norovirus to escape humoral immune responses acquired by previous exposure to earlier strains.

While faced with the difficulty of rapidly evolving and genetically diverse norovirus strains, the development of effective norovirus vaccines has been exacerbated by additional challenges. For instance, until recently, human norovirus could not be grown in cell culture and even now, robust cell culture systems for both VLPs and live attenuated noroviruses are lacking.

An additional challenge in vaccine development is that immunity to norovirus infection is strain and genotype specific with minimal cross-immunity conferred against other genogroups. Furthermore, immunity to a norovirus strain is not life-long and is estimated to persist from anywhere between six months and nine years.

Various approaches have been undertaken to develop a suitable vaccine against norovirus infection including the production of recombinant norovirus proteins in insect and plant expression systems.

Huo et al. (*Virus Research,* 2015, 204:1-5) demonstrated that an M27G mutant capsid protein, of norovirus VP1 VLPs produced in insect SF9 cells, resulted in the production of 38 nm and 21 nm VLPs, comprising proteins of 58 kDa and 55 kDa. The 55 kDa protein was a result of degradation or cleavage of the full-length P1 capsid protein as opposed to the translated product of an internal start codon. N-terminal deletion mutants comprising 26 or 38 deleted amino acid residues of the VP1 protein, resulted in the production of 21 nm VLPs. The 26 amino acid deletion mutants produced low numbers of 38 nm VLPs whereas 38 amino acid deletion mutants did not result in formation of 38 nm VLPs.

US 2013/0273105 teaches the production of norovirus formulations comprising antigenic peptides, proteins or VLPs derived from genogroup I (G1), genogroup II (GII), or consensus viral sequences. The norovirus antigens may include variants of the capsid proteins expressed in the VLPs.

US 2015/0023995 provides a vaccine formulation comprising VLPs produced in insect Sf9 cells, the VLPs comprising a composite amino acid sequence derived from at least two viral protein sequences. For Example, a composite GII.4 VP1 VLP, comprising a VP1 sequence from GII.4 Minerva 2006-a, and GII.4 Laurens 2006-b and GII.4 Houston 2002 norovirus strains, is described. Composite sequences derived from GII.1, GII.2 Snow Mountain and GII.3, as well as GI composite sequences derived from Norwalk GI.1, Southampton GI.1, and Chiba GI.1 are also described.

Mason et al. (*Proc Natl Acad Sci U.S.A.,* 1996, 93(11): 5335-40) teach the use of genetically engineered tobacco plants and potato tubers to express GI.1 norovirus VLPs from native VP1 protein. The plant produced norovirus VLPs are morphologically and physically similar to the 38 nm Norwalk VLPs produced in insect cells. Oral administration of purified tobacco-produced Norwalk VLPs from native capsid protein, or potato tubers expressing GU capsid protein induced a humoral immune response in mice and humans (Tacket et al., *J. Infect. Dis.,* 2000, 182(1):302-5).

Huang et al. (*Biotechnol. Bioeng.,* 2009, 103(4):706-14) describe a geminivirus-derived DNA replicon vector for production of GI.1 norovirus VLP in plants. Co-delivery of bean yellow dwarf virus-derived vector and Rep/RepA-supplying vector in *Nicotiana benthamiana* resulted in rapid and robust protein production.

SUMMARY OF THE INVENTION

The present invention relates to modified norovirus proteins, virus like particles (VLPs) comprising modified norovirus proteins, and methods of producing norovirus proteins, and virus like particles (VLPs) comprising modified norovirus proteins.

It is an object of the invention to produce modified norovirus proteins, VLPs comprising modified norovirus proteins, and to produce VLPs comprising modified norovirus proteins in plants.

As described herein, there is provided a recombinant polynucleotide comprising, a nucleotide sequence encoding a modified norovirus VP1 protein, wherein the modified norovirus VP1 protein comprises one or more than one substitution, modification or mutation at:

an amino acid selected from positions in sequence alignment with amino acids 43, 57, 84 and 94 of norovirus VP1 genotype GI.1, a deletion of a peptide fragment in sequence alignment with amino acids 39-46 of norovirus VP1 genotype GI.1, amino acids corresponding to positions 39-46 of norovirus VP1 genotype GI.1, are mutated to the sequence SSTAVATA, or a combination thereof, and the nucleotide sequence is not derived from a genotype GI.1 norovirus VP1.

Also provided is the recombinant polynucleotide as described above, wherein the nucleotide sequence is derived from a norovirus VP1 selected from a group consisting of genotypes GI.2, GI.3. GI.5, GI.7, GII.2, GII.3, GII.4, GII.6, GII.12 and GII.17. For example, which is not to be considered limiting, the nucleotide sequence may be derived from the group comprising of G1.2/Leuven/2003/BEL GI.3/S29/2008/Lilla Edet/Sweden, GI.5/Siklos-HUN5407/2013/HUN, GI.7/USA/2014/GA5043, GII.2/CGMH47/2011/TW; GII.3/Jingzhou/2013402/CHN, GII.4/Sydney/NSW0514/2012/AU, GII.6/Ohio/490/2012/USA, GII.12/HS206/2010/USA, and GII.17_Kawa_2014_A0A077KVU6.

The recombinant polynucleotide described above may comprise specific substitutions, modifications or mutations, independently selected from the following:

a substitution, modification or mutation at the position in sequence alignment with amino acid 43 of VP1 genotype GI.1 to valine, isoleucine, leucine, methionine, threonine, aspartic acid, glutamic acid, asparagine, glutamine, lysine, or histidine;

a substitution, modification or mutation at the position in sequence alignment with amino acid 57 of VP1 genotype GI.1 to isoleucine, leucine, valine, alanine, glycine, serine, threonine, asparagine, glutamine, lysine, or histidine;

a substitution, modification or mutation at the position in sequence alignment with amino acid 84 of VP1 genotype GI.1 to serine, asparagine, cysteine, threonine, alanine, lysine or histidine; and a substitution, modification or mutation at the position in sequence alignment with amino acid 94 of VP1 genotype GI.1 to leucine, isoleucine, methionine, valine, threonine, aspartic acid, glutamic acid, asparagine, glutamine, lysine, or histidine.

Any of the recombinant polynucleotides described above may also be optimized for human codon usage, increased GC content, or a combination thereof.

A modified norovirus VP1 protein encoded by any one of the recombinant polynucleotides described above is also described herein. Furthermore, a VLP comprising the modified norovirus VP1 protein encoded by any one of the recombinant polynucleotides described above, is also disclosed. The VLP comprising the norovirus VP1 protein encoded by any one of the recombinant polynucleotides described above, may further comprise a norovirus VP2 protein.

A method for producing a modified norovirus VP1 in a plant, portion of a plant or plant cell is also provided herein. The modified norovirus VP1 may be encoded by any one of the recombinant polynucleotides described above. The method comprises introducing one or more than one of the recombinant polynucleotide described above into the plant, the portion of the plant or the plant cell, and incubating the plant, the portion of the plant or the plant cell under conditions that permit expression of the one or more than one modified norovirus VP1 protein. The method provided herein may further comprise a step of harvesting the plant, portion of the plant, or the plant cell. Additionally, the method may comprise a step of extracting, purifying, or both extracting and purifying the one or more than one modified norovirus VP1 protein from the plant, the portion of the plant or the plant cell. Furthermore, in the step of introducing, the method may further comprise introducing a second nucleic acid sequence encoding a norovirus VP2 protein into the plant, the portion of the plant, or the plant cell, and in the step of incubating, the conditions permit co-expression and co-production of both the one or more than one modified norovirus VP1 protein and the norovirus VP2 protein in the plant, portion of the plant or the plant cell.

Also described is a method for producing a norovirus virus like particle (VLP) in a plant, portion of a plant or plant cell, wherein the VLP comprises one or more than one of the modified norovirus VP1 proteins encoded by one or more of the recombinant polynucleotides described above. The method comprises introducing one or more than one of the recombinant polynucleotides described above into the plant, the portion of the plant or the plant cell, and incubating the plant, the portion of the plant or the plant cell under conditions that permit expression of the one or more than one modified norovirus VP1 protein, thereby producing the norovirus VLP. The method provided herein may further comprise a step of harvesting the plant, portion of the plant, or the plant cell. Additionally, the method may comprise a step of extracting, purifying, or both extracting and purifying the norovirus VLP from the plant, the portion of the plant or the plant cell. Furthermore, in the step of introducing, the method may further comprise introducing a second nucleic acid sequence encoding a norovirus VP2 protein into the plant, the portion of the plant, or the plant cell, and in the step of incubating, the conditions permit co-expression and co-production of both the modified norovirus VP1 protein and the norovirus VP2 protein in the plant, portion of the plant or the plant cell thereby producing the norovirus VLP. The norovirus VLP produced by the method described herein may have a diameter of about 15 nm to 50 nm. Alternatively, the VLP may have a diameter of about 23 nm (for T=1 icosahedral symmetry) or about 38 nm (for T=3 icosahedral symmetry).

A method of producing an antibody or antibody fragment is provided herein, wherein the method comprises administering one or more than one of the modified norovirus VP1 proteins encoded by one or more than one of the recombinant polynucleotide described above, or the norovirus VLP comprising one or more than one of the modified norovirus VP1 protein, to a subject or a host animal, thereby producing the antibody or the antibody fragment.

Also provided herein is a plant, portion of the plant, or plant cell comprising the recombinant polynucleotide described above, the modified norovirus VP1 encoded by one or more than one of the recombinant polynucleotide, or the norovirus VLP comprising one or more than one the modified norovirus VP1 protein.

A composition for inducing an immune response is also described herein. The composition comprises, an effective dose of one or more than one of the modified norovirus VP1 protein encoded by one or more than one of the recombinant polynucleotide described above, or the norovirus VLP comprising one or more than one of the modified norovirus VP1 protein, and a pharmaceutically acceptable carrier, adjuvant, vehicle or excipient.

The present disclosure also provides a vaccine for inducing an immune response, wherein the vaccine comprises an effective dose of one or more than one of the modified norovirus VP1 proteins encoded by one or more than one of the recombinant polynucleotide described above, or the VLP comprising one or more than one of the modified norovirus VP1 protein.

Multiple strains of Norovirus have been characterized, and norovirus strains may evolve over time. Therefore, the present disclosure is also directed to VP1 and VP2 proteins from norovirus that exhibit from about 30-100% or any amount therebetween, amino acid sequence identity, to the VP1 protein, the VP2 protein, or both the VP1 and the VP2 proteins, of any of the norovirus strains listed in FIGS. 2A and 2B, provided that the VP1 protein can be expressed in a plant, and that the VP1 protein induces immunity to norovirus in a subject, when the VP1 protein is administered to the subject. For example, norovirus strains include strains having 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100%, or any amount therebetween, amino acid sequence identity (sequence similarity; percent identity; percent similarity) to the VP1 protein, the VP2 protein, or both the VP1 and the VP2 proteins, with any of the strains listed in FIGS. 2A and 2B, provided that the VP1 protein can be expressed in a plant, and the VP1 protein induces immunity to norovirus in a subject, when the VP1 protein is administered to the subject.

An antibody or antibody fragment is provided herein, wherein the antibody or antibody fragment is prepared by administering one or more than one of the modified norovirus VP1 encoded by one or more than one of the recombinant polynucleotide described above, or the norovirus VLP comprising one or more than one of the modified norovirus VP1, to a subject or host animal.

Also described herein is a method of inducing immunity to a norovirus infection in a subject, wherein the method comprises administering one or more than one of the modified norovirus VP1 protein encoded by one or more than one of the recombinant polynucleotide described above, or the norovirus VLP comprising one or more than one of the modified norovirus VP1 protein. The one or more than one of the modified norovirus VP1 protein, or the norovirus VLP may be administered to the subject orally, intranasally, intramuscularly, intraperitoneally, intravenously subcutaneously, rectally, or intravaginally.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 2A shows Uniprot and NCBI references for several norovirus VP1 (upper panel) and VP2 (lower panel) proteins. FIG. 2B shows NCBI references for several norovirus VP1 (upper panel) and VP2 (lower panel) nucleic acid sequences.

3760), mut hCod GII.4/Sydney/NSW0514/2012/AU_P80S VP1 (Construct #: 4133), mut hCod GII.4/Sydney/NSW0514/2012/AU_A39V VP1 (Construct #: 4155), mut hCod GII.4/Sydney/NSW0514/2012/AU_P80S+A39V (Construct #: 4165), mut hCod GII.4/Sydney/NSW0514/2012/AU_Δ35-42 VP1 (Construct #: 4158), mut hCod GII.4/Sydney/NSW0514/2012/AU_P80S+Δ35-42 VP1 (Construct #: 4168).

FIG. 12A shows the amino acid sequence of VP1 GI.1 United States Norwalk 1968 (SEQ ID NO:1); FIG. 12B shows the nucleic acid sequence of wild type VP1 GI.1 United States Norwalk 1968 (SEQ ID NO:2); FIG. 12C shows the nucleic acid sequence of hCod VP1 GI.1 United States Norwalk 1968 (SEQ ID NO:3).

FIG. 13A shows the amino acid sequence of VP1 G1.2 Leuven 2003 D2DEL3 (SEQ ID NO:4); FIG. 13B shows the nucleic acid sequence of hCod VP1 G1.2 Leuven 2003 D2DEL3 (SEQ ID NO:5).

FIG. 14A shows the amino acid sequence of VP1 GI.3 LillaEdet 2008 H2DG70 (SEQ ID NO:6); FIG. 14B shows the nucleic acid sequence of hCod GI.3 LillaEdet 2008 H2DG70 (SEQ ID NO:7).

FIG. 15A shows the amino acid sequence of VP1 GI.5 Siklos HUN5407 2013 HUN AHW99832 (SEQ ID NO:12). FIG. 15B shows the nucleic acid sequence of hCod VP1 GI.5 Siklos HUN5407 2013 HUN AHW99832 (SEQ ID NO:33).

FIG. 16A shows the amino acid sequence of GI.7/GA5043/USA/2014 VP1 (SEQ ID NO:101). FIG. 16B shows the nucleic acid sequence of GI.7/GA5043/USA/2014 VP1 (SEQ ID NO:175). FIG. 16C shows the amino acid sequence of VP1 GII.1 Ascension208 2010 USA AFA55174 (SEQ ID NO:13).

FIG. 17A shows the amino acid sequence of VP1 GII.2 CGMH47 2011 TW AGT39206 (SEQ ID NO:14). FIG. 17B shows the nucleic acid sequence of hCod VP1 GII.2 CGMH47 2011 TW AGT39206 (SEQ ID NO:40).

FIG. 18A shows the amino acid sequence of VP1 GII.3 Jingzhou 2013402 CHN AGX01095 (SEQ ID NO:15). FIG. 18B shows the nucleic acid sequence of hCod VP1 GII.3 Jingzhou 2013402 CHN AGX01095 (SEQ ID NO:45).

FIG. 19A shows the amino acid sequence of VP1 GII.4 Sydney NSW0514 2012 (SEQ ID NO:16). FIG. 19B shows the nucleic acid sequence of hCod VP1 GII.4 Sydney NSW0514 2012 (SEQ ID NO: 52). FIG. 19C shows the amino acid sequence of VP1 US96: GII.4 Dresden174 1997 DE AY741811 (SEQ ID NO:27). FIG. 19D shows the amino acid sequence of VP1 FH02: GII.4 FarmingtonHills 2002 US AY502023 (SEQ ID NO:28). FIG. 19E shows the amino acid sequence of VP1 Hnt04:GII.4 Hunter-NSW504D 2004 AU DQ078814 (SEQ ID NO:29). FIG. 19F shows the amino acid sequence of VP1 2006b: GII.4 Shellharbour-NSW696T 2006 AU EF684915 (SEQ ID NO:30). FIG. 19G shows the amino acid sequence of VP1NO09: GII.4 Orange-NSW001P 2008 AU GQ845367 (SEQ ID NO:31).

FIG. 20 shows the amino acid sequence of VP1 GII.5 Alberta 2013 CA ALT54485 (SEQ ID NO:17).

FIG. 21A shows the amino acid sequence of VP1 GII.6 Ohio 2012 M9T020 (SEQ ID NO:20). FIG. 21B shows the nucleic acid sequence of hCod-optimized VP1 GII.6 Ohio 2012 M9T020 (SEQ ID NO:21);

FIG. 22 shows the amino acid sequence of VP1 GII.7 Musa 2010 AII73774 (SEQ ID NO:18).

FIG. 23A shows the amino acid sequence of VP1 GII.12_HS206_2010_USA_AEI29586 (SEQ ID NO:19); FIG. 23B shows the nucleic acid sequence of hCod VP1 GII.12_HS206_2010_USA AEI29586 (SEQ ID NO:87).

FIG. 24A shows the amino acid sequence of VP1 GII.13 VA173 2010 H9AWU4 (SEQ ID NO:22). FIG. 24B shows the nucleic acid sequence of human codon-optimized VP1 GII.13 VA173 2010 H9AWU4 (SEQ ID NO:23).

FIG. 25 shows the amino acid sequence of VP1 GII.14 Saga 2008 JPN ADE28701 (SEQ ID NO:32).

FIG. 26A shows the amino acid sequence of VP1 GII.17 Kawa 2014 A0A077KVU6 (SEQ ID NO:24). FIG. 26B shows the nucleic acid sequence of human codon-optimized VP1 GII.17 Kawa 2014 A0A077KVU6 (SEQ ID NO:25).

FIG. 27 shows the amino acid sequence of VP1 GII.21 Sali 2011 USA AFC89665 (SEQ ID NO:26).

FIG. 28A shows the amino acid sequence of modified VP1 GI.3_Lil08_Q84S (SEQ ID NO:98). FIG. 28B shows the nucleic acid sequence of VP1 GI.3_Lil08_Q84S (SEQ ID NO:167). FIG. 28C shows the amino acid sequence of VP1 GI.3 Lil08_S94L (SEQ ID NO:8). FIG. 28D shows the nucleic acid sequence of hCod VP1 GI.3 Lil08_S94L (SEQ ID NO:9). FIG. 28E shows the amino acid sequence of VP1 GI.3 Lil08_Q84S+S94L (SEQ ID NO:10). FIG. 28F shows the nucleic acid sequence of hCod VP1 GI.3 Lil08_Q84S+S94L (SEQ ID NO:11). FIG. 28G shows the amino acid sequence of VP1 GI.3 Lil08_A43V+S94L (SEQ ID NO:170). FIG. 28H shows the nucleic acid sequence of hCod VP1 GI.3 Lil08_A43V+S94L (SEQ ID NO:169). FIG. 28I shows the amino acid sequence of VP1 GI.3 Lil08_M57I+S94L (SEQ ID NO:172). FIG. 28J shows the nucleic acid sequence of hCod VP1 GI.3 Lil08_M57I+S94L (SEQ ID NO:171). FIG. 28K shows the amino acid sequence of VP1 GI.3 Lil08_A43V+M57I+S94L (SEQ ID NO:174). FIG. 28L shows the nucleic acid sequence of hCod VP1 GI.3 Lil08_A43V+M57I+S94L (SEQ ID NO:173). FIG. 28M shows the amino acid sequence of VP1_GI.3_Lil08_S94<u>X</u> (SEQ ID NO:292); wherein <u>X</u> is selected from V, I M, T, E, D, N, Q, K, or H. FIG. 28N shows the human codon optimized sequence of VP1_GI.3_Lil08_S94X (SEQ ID NO:293); wherein <u>X</u> is selected from a codon encoding V (e.g. <u>XXX</u>=GTG), I (e.g. <u>XXX</u>=ATC), M (e.g. <u>XXX</u>=ATG), T (e.g. <u>XXX</u>=ACC), E (e.g. <u>XXX</u>=GAG), D (e.g. <u>XXX</u>=GAC), N (e.g. <u>XXX</u>=AAC), Q (e.g. <u>XXX</u>=CAG), K (e.g. <u>XXX</u>=AAG), or H (e.g. <u>XXX</u>=CAC).

FIG. 29A shows the amino acid sequence of modified VP1 GI.5 Siklos Q84S (SEQ ID NO:34). FIG. 29B shows the nucleic acid sequence of modified VP1 GI.5 Siklos Q84S (SEQ ID NO:35). FIG. 29C shows the amino acid sequence of VP1 GI.5 Siklos A94L (SEQ ID NO:36). FIG. 29D shows the nucleic acid sequence of hCod VP1 GI.5 Siklos A94L (SEQ ID NO:37). FIG. 29E shows the amino acid sequence of VP1 GI.5 Siklos Q84S+A94L (SEQ ID NO:38). FIG. 29F shows the nucleic acid sequence of hCod VP1 GI.5 Siklos Q84S+A94L (SEQ ID NO:39). FIG. 29G shows the amino acid sequence of modified VP1 GI.7/GA5043/USA/2014_R84S (SEQ ID NO:177). FIG. 29H shows the nucleic acid sequence of modified VP1 hCod GI.7/GA5043/USA/2014_R84S (SEQ ID NO:176). FIG. 29I shows the amino acid sequence of modified VP1 GI.7/GA5043/USA/2014_M57I (SEQ ID NO:179). FIG. 29J shows the nucleic acid sequence of modified VP1 hCod GI.7/GA5043/USA/2014_M57I (SEQ ID NO:178). FIG. 29K shows the amino acid sequence of modified VP1GI.7/GA5043/USA/2014_M57I+R84S (SEQ ID NO:181). FIG. 29L shows the nucleic acid sequence of modified VP1 hCod GI.7/GA5043/USA/2014_M57I+R84S (SEQ ID NO:180). FIG. 29M shows the amino acid sequence of VP1_GI.7/GA5043/USA/2014_M57X (SEQ ID NO:290); wherein <u>X</u> is selected from L, G, S, T, N, Q, K or H. FIG. 29N shows human codon optimized VP1_GI.7/GA5043/USA/2014_M57X (SEQ ID NO:291); wherein <u>X</u> is selected from a codon encoding L (e.g. <u>XXX</u>=CTG), G (e.g. <u>XXX</u>=GGC), S (e.g. <u>XXX</u>=AGC), T (e.g. <u>XXX</u>=ACC), N (e.g. <u>XXX</u>=AAC), Q (e.g. <u>XXX</u>=CAG), K (e.g. <u>XXX</u>=AAG), or H (e.g. <u>XXX</u>=CAC).

FIG. 30A shows the amino acid sequence of VP1 GII.2 CGMH47 E80S (SEQ ID NO:85). FIG. 30B shows the nucleic acid sequence of hCod VP1 GII.2 CGMH47 E80S (SEQ ID NO:86). FIG. 30C shows the amino acid sequence of VP1 GII.2 CGMH47 A90L (SEQ ID NO:41); FIG. 30D shows the nucleic acid sequence of hCod VP1 GII.2 CGMH47 A90L (SEQ ID NO:42). FIG. 30E shows the amino acid sequence of VP1_GII.2_CGMH47_E80S+A90L (SEQ ID NO:43). FIG. 30F shows the nucleic acid sequence of hCod VP1_GII.2_CGMH47_E80S+A90L (SEQ ID NO:44). FIG. 30G shows the amino acid sequence of VP1_GII.2_CGMH47_A39V+E80S+A90L (SEQ ID NO:182). FIG. 30H shows the nucleic acid sequence of hCod VP1_GII.2_CGMH47_A39V+E80S+A90L (SEQ ID NO:183). FIG. 30I shows the amino acid sequence of VP1_GII.2_CGMH47_R53I+E80S+A90L (SEQ ID NO:184). FIG. 30J shows the nucleic acid sequence of hCod VP1_GII.2_CGMH47_R53I+E80S+A90L (SEQ ID NO:185). FIG. 30K shows the amino acid sequence of VP1_GII.2_CGMH47_A39V+R53I+E80S+A90L (SEQ ID NO:186). FIG. 30L shows the nucleic acid sequence of hCod VP1_GII.2_CGMH47_A39V+R53I+E80S+A90L (SEQ ID NO:187).

FIG. 31A shows the amino acid sequence of VP1 GII.3_Jing_E80S (SEQ ID NO:46). FIG. 31B shows the nucleic acid sequence of hCod VP1 GII.3_Jing_E80S (SEQ ID NO:47). FIG. 31C the amino acid sequence of VP1 GII.3_Jing_A90L (SEQ ID NO:48). FIG. 31D shows the nucleic acid sequence of hCod VP1 GII.3_Jing_A90L (SEQ ID NO:49). FIG. 31E the amino acid sequence of VP1 GII.3 Jing_E80S+A90L (SEQ ID NO:50). FIG. 31F shows the nucleic acid sequence of hCod VP1 GII.3_Jing_E80S+A90L (SEQ ID NO:51).

FIG. 32A shows the amino acid sequence of VP1 GII.4 Syd12 A39V (SEQ ID NO:53). FIG. 32B shows the nucleic acid sequence of hCod VP1 GII.4_Syd12_A39V (SEQ ID NO:54). FIG. 32C shows the amino acid sequence of VP1 GII.4_Syd12_V47P (SEQ ID NO:55). FIG. 32D shows the nucleic acid sequence of hCod VP1 GII.4_Syd12_V47P (SEQ ID NO:56). FIG. 32E shows the amino acid sequence of VP1 GII.4_Syd12_R53I (SEQ ID NO:57). FIG. 32F shows the nucleic acid sequence of hCod VP1 GII.4_Syd12_R53I (SEQ ID NO:58). FIG. 32G shows the amino acid sequence of VP1; GII.4_Syd12_P80S (SEQ ID NO:59). FIG. 32H shows the nucleic acid sequence of hCod VP1 GII.4_Syd12_P80S (SEQ ID NO:60). FIG. 32I shows the amino acid sequence of VP1 GII.4_Syd12_S90L (SEQ ID NO:61). FIG. 32J shows the nucleic acid sequence of hCod VP1 GII.4_Syd12_S90L (SEQ ID NO:62). FIG. 32K shows the amino acid sequence of VP1GII.4_Syd12_Δ35-42 (SEQ ID NO:63). FIG. 32L shows the nucleic acid sequence of hCod VP1GII.4_Syd12_Δ35-42 (SEQ ID NO:64). FIG. 32M shows the amino acid sequence of VP1 GII.4_Syd12_SSTAVATA (SEQ ID NO:65). FIG. 32N shows the nucleic acid sequence of hCodVP1 GII.4_Syd12_SSTAVATA (SEQ ID NO:66). FIG. 32O shows the amino acid sequence of VP1GII.4_Syd12_P80S+A39V (SEQ ID NO:67). FIG. 32P shows the nucleic acid sequence of hCod VP1 GII.4_Syd12_P80S+A39V (SEQ ID NO:68). FIG. 32Q shows the amino acid sequence of VP1 GII.4_Syd12_P80S+V47P (SEQ ID NO:69). FIG. 32R shows the nucleic acid sequence of hCod VP1 GII.4_Syd12_P80S+V47P (SEQ ID NO:70). FIG. 32S shows the amino acid sequence of VP1GII.4_Syd12_P80S+R53I (SEQ ID NO:71). FIG. 32T shows the nucleic acid sequence of hCod VP1 GII.4_Syd12_P80S+R53I (SEQ ID NO:72). FIG. 32U shows the amino acid sequence of VP1 GII.4_Syd12_P80S+S90L (SEQ ID NO:73). FIG. 32V shows the nucleic acid sequence of hCod VP1 GII.4_Syd12_P80S+S90L (SEQ ID NO:74). FIG. 32W shows the amino acid sequence of VP1 GII.4_Syd12_P80S+Δ35-42 (SEQ ID NO:75). FIG. 32X shows the nucleic acid sequence of hCod VP1 GII.4_Syd12_P80S+Δ35-42 (SEQ ID NO:76). FIG. 32Y shows the amino acid sequence of VP1 GII.4_Syd12_P80S+SSTAVATA (SEQ ID NO:77). FIG. 32Z shows the nucleic acid sequence of hCod VP1 GII.4_Syd12_P80S+SSTAVATA (SEQ ID NO:78). FIG. 32AA shows the amino acid sequence of VP1 GII.4 Syd12 A39V+R53I (SEQ ID NO:188). FIG. 32BB shows the nucleic acid sequence of hCod VP1 GII.4_Syd12_A39V+R53I (SEQ ID NO:189). FIG. 32CC shows the amino acid sequence of VP1 GII.4 Syd12 A39V+R53I+P80S (SEQ ID NO:190). FIG. 32DD shows the nucleic acid sequence of hCod VP1 GII.4_Syd12_A39V+R53I+P80S (SEQ ID NO:191). FIG. 32EE shows the nucleic acid sequence of human codon optimized VP1 GII.4_Syd12_P80X (SEQ ID NO:287); wherein X is selected from a codon encoding A (e.g. XXX=GCC), N (e.g. XXX=AAC), K (e.g. XXX=AAG), or H (e.g. XXX=CAC). FIG. 32FF shows the amino acid sequence of VP1_GII.4_Syd12_P80X (SEQ ID NO:286); wherein X is selected from A, N, K, or H. FIG. 32GG shows the nucleic acid sequence of human codon optimize sequence of VP1_GII.4_Syd12_P80S+A39X (SEQ ID NO:289); wherein X is selected from a codon encoding I (e.g. XXX=ATC), M (e.g. XXX=ATG), G (e.g. XXX=GGC), S (e.g. XXX=AGC), E (e.g. XXX=GAG), D (e.g. XXX=GAC), N (e.g. XXX=AAC), Q (e.g. XXX=CAG), K (e.g. XXX=AAG), or H (e.g. XXX=CAC). FIG. 32HH show the amino acid sequence of VP1_GII.4_Syd12_P80S+A39X (SEQ ID NO:288); wherein X is selected from I, M, G, S, E, D, N, Q, K, or H.

FIG. 33A shows the amino acid sequence of VP1 GII.6_Ohio_E80S (SEQ ID NO:79). FIG. 33B shows the nucleic acid sequence of hCod VP1 GII.6_Ohio_E80S (SEQ ID NO:80). FIG. 33C shows the amino acid sequence of VP1 GII.6_Ohio_S90L (SEQ ID NO:81). FIG. 33D shows the nucleic acid sequence of hCod VP1 GII.6_Ohio_S90L (SEQ ID NO:82). FIG. 33E shows the amino acid sequence of VP1 GII.6_Ohio_E80S+S90L (SEQ ID NO:83). FIG. 33F shows the nucleic acid sequence of hCod VP1 GII.6_Ohio_E80S+S90L (SEQ ID NO:84).

FIG. 34A shows the amino acid sequence of VP1 GII.12_HS10_E80S (SEQ ID NO:88). FIG. 34B shows the nucleic acid sequence of hCod VP1 GII.12_HS10_E80S (SEQ ID NO:89). FIG. 34C shows the amino acid sequence of VP1 GII.12_HS10_A90L (SEQ ID NO:90). FIG. 34D shows the nucleic acid sequence of hCod VP1 GII.12_HS10_A90L (SEQ ID NO:91). FIG. 34E shows the amino acid sequence of VP1 GII.12_HS10_E80S+A90L (SEQ ID NO:92); FIG. 34F shows the nucleic acid sequence of hCod VP1 GII.12_HS10_E80S+A90L (SEQ ID NO:93). FIG. 34G shows the amino acid sequence of VP1 GII.17 Kawa 2014 A0A077KVU6_A39V (SEQ ID NO:192). FIG. 34H shows the nucleic acid sequence of VP1 hCod GII.17 Kawa 2014 A0A077KVU6_A39V (SEQ ID NO:193). FIG. 34I shows the amino acid sequence of VP1GII.17 Kawa 2014 A0A077KVU6_R53I (SEQ ID NO:194). FIG. 34J shows the nucleic acid sequence of VP1 hCod GII.17 Kawa 2014 A0A077KVU6_R53I (SEQ ID NO:195). FIG. 34K shows the amino acid sequence of VP1GII.17 Kawa 2014 A0A077KVU6_A90L (SEQ ID NO:196). FIG. 34L shows the nucleic acid sequence of VP1 hCod GII.17 Kawa 2014 A0A077KVU6_A90L (SEQ ID NO:197). FIG. 34M shows the amino acid sequence of VP1GII.17 Kawa 2014

A0A077KVU6_A39V+M53I (SEQ ID NO:198). FIG. 34N shows the nucleic acid sequence of VP1 hCod GII.17 Kawa 2014 A0A077KVU6_A39V+M53I (SEQ ID NO:199). FIG. 34O shows the amino acid sequence of VP1GII.17 Kawa 2014 A0A077KVU6_E80S+A90L (SEQ ID NO:200). FIG. 34P shows the nucleic acid sequence of VP1 hCod GII.17 Kawa 2014 A0A077KVU6_E80S+A90L (SEQ ID NO:201);

FIG. 35A shows the amino acid sequence of VP2_GI.1_Norwalk (SEQ ID NO:99). FIG. 35B shows the nucleic acid sequence of human codon optimized VP.2_GI1_Norwalk (SEQ ID NO:100).

FIG. 36A shows the amino acid sequence of VP2_GI.3_Lil08 (SEQ ID NO:94). FIG. 36B shows the nucleic acid sequence of human codon optimized VP2_GI.3_Lil08 (SEQ ID NO:95).

FIG. 37A shows the amino acid sequence of VP2_GII.6_HS10 (SEQ ID NO:96). FIG. 37B shows the nucleic acid sequence of human codon optimized VP2_GII6_HS10 (SEQ ID NO:97).

FIG. 38A shows the cloning vector 1190 from left to right T-DNA (SEQ ID NO:162). FIG. 38B shows the construct 2724 from 2X35S promoter to NOS terminator (SEQ ID NO:163). FIG. 38C shows the cloning vector 3677 from left to right T-DNA (SEQ ID NO:164). FIG. 38D shows the construct 4133 from 2X35S promoter to NOS terminator (SEQ ID NO:165). FIG. 38E shows the construct 4135 from 2X35S promoter to NOS terminator (SEQ ID NO:166).

DETAILED DESCRIPTION

Figure 1A:
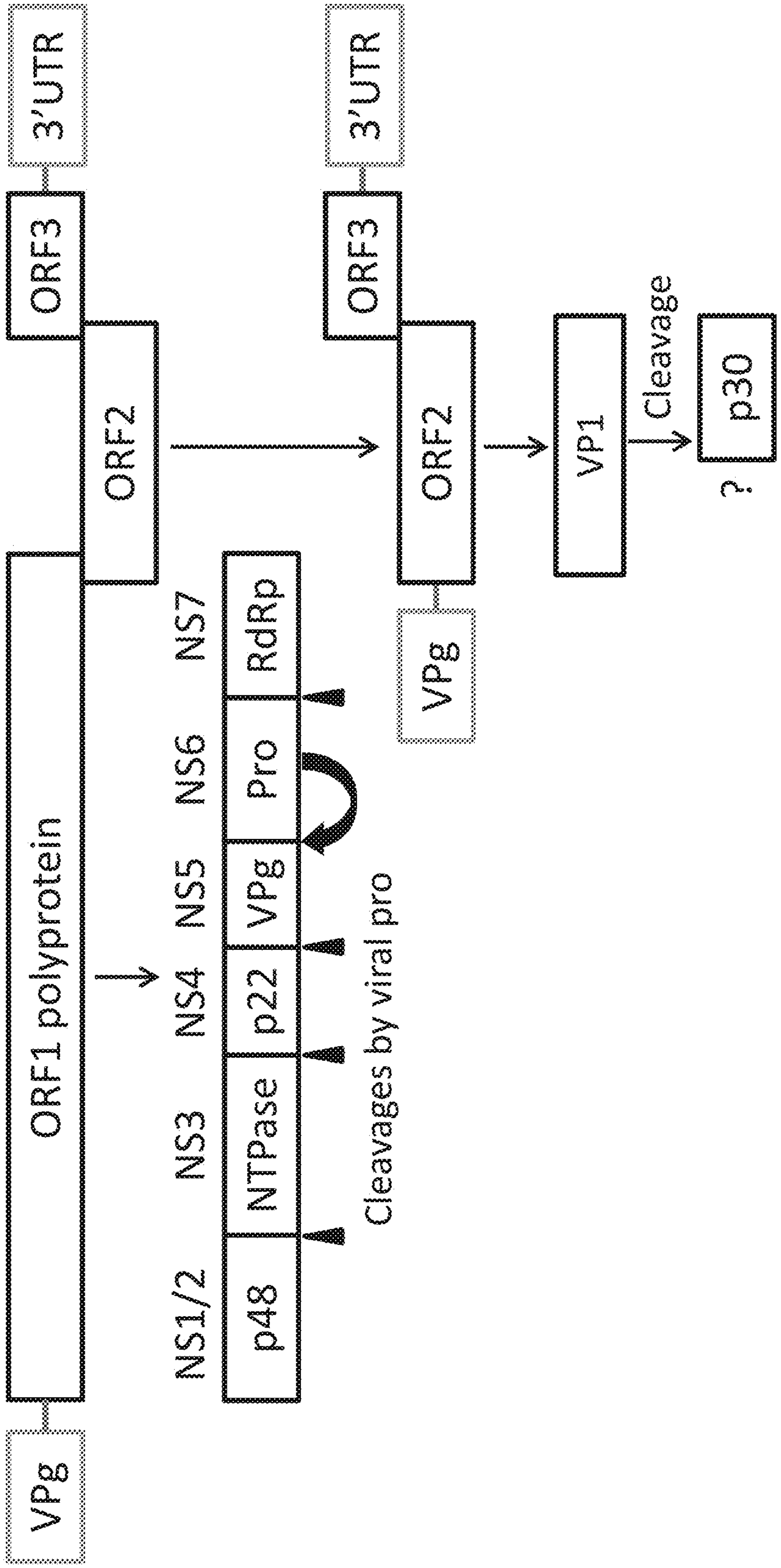
FIG. 1A shows a schematic representation of the linear structure of the norovirus genome and the polyprotein and proteins translated therefrom.

The following description is of a preferred embodiment.

As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments, consist essentially of those elements and/or steps, and in other embodiments consist of those elements and/or steps, whether or not these embodiments are specifically referred to. In addition, the use of the singular includes the plural, and "or" means "and/or" unless otherwise stated. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−10% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

The term "plant", "portion of a plant", "plant portion", "plant matter", "plant biomass", "plant material", plant extract", or "plant leaves", as used herein, may comprise an entire plant, tissue, cells, or any fraction thereof, intracellular plant components, extracellular plant components, liquid or solid extracts of plants, or a combination thereof, that are capable of providing the transcriptional, translational, and post-translational machinery for expression of one or more than one nucleic acids described herein, and/or from which an expressed protein or VLP may be extracted and purified. Plants may include, but are not limited to, agricultural crops including for example canola, *Brassica* spp., maize, *Nicotiana* spp., (tobacco) for example, *Nicotiana benthamiana, Nicotiana rustica, Nicotiana, tabacum, Nicotiana alata, Arabidopsis thaliana*, alfalfa, potato, sweet potato (*Ipomoea batatus*), *ginseng*, pea, oat, rice, soybean, wheat, barley, sunflower, cotton, corn, rye (*Secale cereale*), sorghum (*Sorghum bicolor, Sorghum vulgare*), safflower (*Carthamus tinctorius*).

The term "plant portion", as used herein, refers to any part of the plant including but not limited to leaves, stem, root, flowers, fruits, a plant cell obtained from leaves, stem, root, flowers, fruits, a plant extract obtained from leaves, stem, root, flowers, fruits, or a combination thereof. The term "plant extract", as used herein, refers to a plant-derived product that is obtained following treating a plant, a portion of a plant, a plant cell, or a combination thereof, physically (for example by freezing followed by extraction in a suitable buffer), mechanically (for example by grinding or homogenizing the plant or portion of the plant followed by extraction in a suitable buffer), enzymatically (for example using cell wall degrading enzymes), chemically (for example using one or more chelators or buffers), or a combination thereof. A plant extract may be further processed to remove undesired plant components for example cell wall debris. A plant extract may be obtained to assist in the recovery of one or more components from the plant, portion of the plant or plant cell, for example a protein (including protein complexes, protein surprastructures and/or VLPs), a nucleic acid, a lipid, a carbohydrate, or a combination thereof from the plant, portion of the plant, or plant cell. If the plant extract comprises proteins, then it may be referred to as a protein extract. A protein extract may be a crude plant extract, a partially purified plant or protein extract, or a purified product, that comprises one or more proteins, protein complexes, protein suprastructures, and/or VLPs, from the plant tissue. If desired a protein extract, or a plant extract, may be partially purified using techniques known to one of skill in the art, for example, the extract may be subjected to salt or pH precipitation, centrifugation, gradient density centrifugation, filtration, chromatography, for example, size exclusion chromatography, ion exchange chromatography, affinity chromatography, or a combination thereof. A protein extract may also be purified, using techniques that are known to one of skill in the art.

The term "nucleic acid segment" as used herein refers to a sequence of nucleic acids that encodes a protein of interest. In addition to the sequence of nucleic acids, the nucleic acid segment comprises a regulatory region and a terminator that are operatively linked to the sequence of nucleic acids. The regulatory region may for example comprise a promoter, and optionally, an enhancer element operatively linked to the promoter.

The term "nucleic acid complex" as used herein refers to a combination of two or more than two nucleic acid segments. The two or more than two nucleic acid segments may be present in a single nucleic acid, so that the nucleic acid complex comprises two, or more than two nucleic acid segments, with each nucleic acid segment under the control of a regulatory region and a terminator. Alternatively, the nucleic acid complex may comprise two or more separate nucleic acids, each of the nucleic acids comprising one or more than one nucleic acid segment, where each nucleic acid segment is under the control of a regulatory region and a terminator. For example a nucleic acid complex may comprise one nucleic acid that comprises two nucleic acid segments, a nucleic acid complex may comprise two nucleic acids, each nucleic acid comprising one nucleic acid segment, or a nucleic acid complex may comprise two or more than two nucleic acids, with each nucleic acid comprising one or more than one nucleic acid segment.

The term "vector" or "expression vector", as used herein, refers to a recombinant nucleic acid for transferring exogenous nucleic acid sequences into host cells (e.g. plant cells) and directing expression of the exogenous nucleic acid sequences in the host cells. "Expression cassette" refers to a nucleotide sequence comprising a nucleic acid of interest under the control of, and operably (or operatively) linked to, an appropriate promoter or other regulatory elements for transcription of the nucleic acid of interest in a host cell. As one of skill in the art would appreciate, the expression cassette may comprise a termination (terminator) sequence that is any sequence that is active in the plant host. For example the termination sequence may be derived from the RNA-2 genome segment of a bipartite RNA virus, e.g. a comovirus, the termination sequence may be a NOS terminator, or terminator sequence may be obtained from the 3'UTR of the alfalfa plastocyanin gene.

The constructs of the present disclosure may further comprise a 3' untranslated region (UTR). A 3' untranslated region contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Non-limiting examples of suitable 3'untranslated regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes, the small subunit of the ribulose-1, 5-bisphosphate carboxylase gene (ssRUBISCO; U.S. Pat. No. 4,962,028; which is incorporated herein by reference), the promoter used in regulating plastocyanin expression.

By "regulatory region" "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a nucleotide sequence of interest, this may result in expression of the nucleotide sequence of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element may comprise a basal promoter element, responsible for the initiation of transcription, as well as other regulatory elements that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358). Examples, of potential inducible promoters include, but not limited to, tetracycline-inducible promoter (Gatz, C., 1997, Ann Rev. Plant Physiol. Plant Mol. Biol. 48, 89-108), steroid inducible promoter (Aoyama, T. and Chua, N. H., 1997, Plant J. 2, 397-404) and ethanol-inducible promoter (Salter, M. G., et al, 1998, Plant Journal 16, 127-132; Caddick, M. X., et al, 1998, Nature Biotech. 16, 177-180) cytokinin inducible IB6 and CKI1 genes (Brandstatter, I. and Kieber, J. J., 1998, Plant Cell 10, 1009-1019; Kakimoto, T., 1996, Science 274, 982-985) and the auxin inducible element, DR5 (Ulmasov, T., et al., 1997, Plant Cell 9, 1963-1971).

A constitutive regulatory region directs the expression of a gene throughout the various parts of a plant and continuously throughout plant development. Examples of known constitutive regulatory elements include promoters associated with the CaMV 35S transcript. (p35S; Odell et al., 1985, Nature, 313: 810-812; which is incorporated herein by reference), the rice actin 1 (Zhang et al, 1991, Plant Cell, 3: 1155-1165), actin 2 (An et al., 1996, *Plant J.,* 10: 107-121), or tms 2 (U.S. Pat. No. 5,428,147), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), the tobacco translational initiation factor 4A gene (Mandel et al, 1995 Plant Mol. Biol. 29: 995-1004); the Cassava Vein Mosaic Virus promoter, pCAS, (Verdaguer et al., 1996); the promoter of the small subunit of ribulose biphosphate carboxylase, pRbcS: (Outchkourov et al., 2003), the pUbi (for monocots and dicots).

The term "constitutive" as used herein does not necessarily indicate that a nucleotide sequence under control of the constitutive regulatory region is expressed at the same level in all cell types, but that the sequence is expressed in a wide range of cell types even though variation in abundance is often observed.

The expression constructs as described above may be present in a vector. The vector may comprise border sequences which permit the transfer and integration of the expression cassette into the genome of the organism or host. The construct may be a plant binary vector, for example a binary transformation vector based on pPZP (Hajdukiewicz, et al. 1994). Other example constructs include pBin19 (see Frisch, D. A., L. W. Harris-Haller, et al. 1995, *Plant Molecular Biology* 27: 405-409).

The term "native", "native protein" or "native domain", as used herein, refers to a protein or domain having a primary amino acid sequence identical to wildtype. Native proteins or domains may be encoded by nucleotide sequences having 100% sequence similarity to the wildtype sequence. A native amino acid sequence may also be encoded by a human codon (hCod) optimized nucleotide sequence or a nucleotide sequence comprising an increased GC content when compared to the wild type nucleotide sequence provided that the amino acid sequence encoded by the hCod-nucleotide sequence exhibits 100% sequence identity with the native amino acid sequence.

By a nucleotide sequence that is "human codon optimized" or a "hCod" nucleotide sequence, it is meant the selection of appropriate DNA nucleotides for the synthesis of an oligonucleotide sequence or fragment thereof that approaches the codon usage generally found within an oligonucleotide sequence of a human nucleotide sequence. By "increased GC content" it is meant the selection of appropriate DNA nucleotides for the synthesis of an oligonucleotide sequence or fragment thereof in order to approach codon usage that, when compared to the corresponding native oligonucleotide sequence, comprises an increase of GC content, for example, from about 1 to about 30%, or any amount therebetween, over the length of the coding portion of the oligonucleotide sequence. For example, from about 1, 2, 4, 6, 8, 10, 12, 14, 16, 18, 20, 22, 24, 26, 28, 30%, or any amount therebetween, over the length of the coding portion of the oligonucleotide sequence. As described below, a human codon optimized nucleotide sequence, or a nucleotide sequence comprising an increased GC content (when compared to the wild type nucleotide sequence) exhibits increased expression within a plant, portion of a plant, or a plant cell, when compared to expression of the non-human optimized (or lower GC content) nucleotide sequence.

Norovirus VP1 mutant proteins (also termed modified VP1 protein, or modified norovirus VP1 protein) and methods of producing norovirus VP1 mutant proteins in plants are described herein. Several of the modified norovirus VP1 proteins comprise specific substitutions, modifications or mutations in the S domain of non-GI.1 VP1s, to the corresponding amino acids that are found in GI.1 S domains. It has been observed that in certain norovirus genotypes, mutating specific amino acids to the corresponding amino acids found in GI.1 VP1s, results in similar or improved VP1 and/or VLP characteristics as compared to the wildtype (non-GI.1) VP1 and/or VLP. Examples of improved characteristics of the VP1 and/or VLP include:

- increased VP1 protein yield when expressed in plant cells as compared to the yield of wildtype VP1 of the same genotype that does not comprise the substitution(s), modification(s) or mutation(s);
- increased density of VLPs comprised of the modified VP1 proteins (for example as determined using density gradient separation, and optionally SDS-PAGE and/or Western analysis) as compared to the density of VLPs comprising wildtype VP1 of the same genotype that does not comprise the substitution(s), modification(s) or mutation(s);
- improved integrity, stability, or both integrity and stability, of VLPs that are comprised of the modified VP1 proteins as compared to the integrity, stability or both of VLPs comprising wildtype VP1 of the same genotype that does not comprise the substitution(s), modification(s) or mutation(s);
- increased VLP yield when expressed in plant cells as compared to the wildtype level of VLP production of the same genotype that does not comprise the substitution(s), modification(s) or mutation(s);
- improved accumulation of VLPs that are comprised of the modified VP1 proteins as compared to the accumulation of VLPs comprising wildtype VP1 of the same genotype that does not comprise the substitution(s), modification(s) or mutation(s);
- a greater proportion of VLPs that assemble into 38 nm VLPs as opposed to 23 nm VLPs as compared to the wildtype VP1 of the same genotype that does not comprise the substitution(s), modification(s) or mutation(s); and
- a combination thereof.

For example, the modified norovirus VP1 protein, and methods of producing the modified norovirus VP1 protein, may include a nucleotide sequence encoding a VP1 protein comprising an S domain substitution, mutation, or modification, at any one or more amino acids in sequence alignment with positions 43, 57, 84 and 94 of norovirus VP1 genotype GI.1 (SEQ ID NO:1; see FIG. 2C), or a deletion of a peptide fragment in sequence alignment with amino acids 39 to 46 of norovirus VP1 genotype GI.1 (SEQ ID NO:1), or a combination thereof. The sequence encoding the norovirus VP1 mutant protein may be optimized for human codon usage, for increased GC content, or a combination thereof.

Figures 1, 2C:
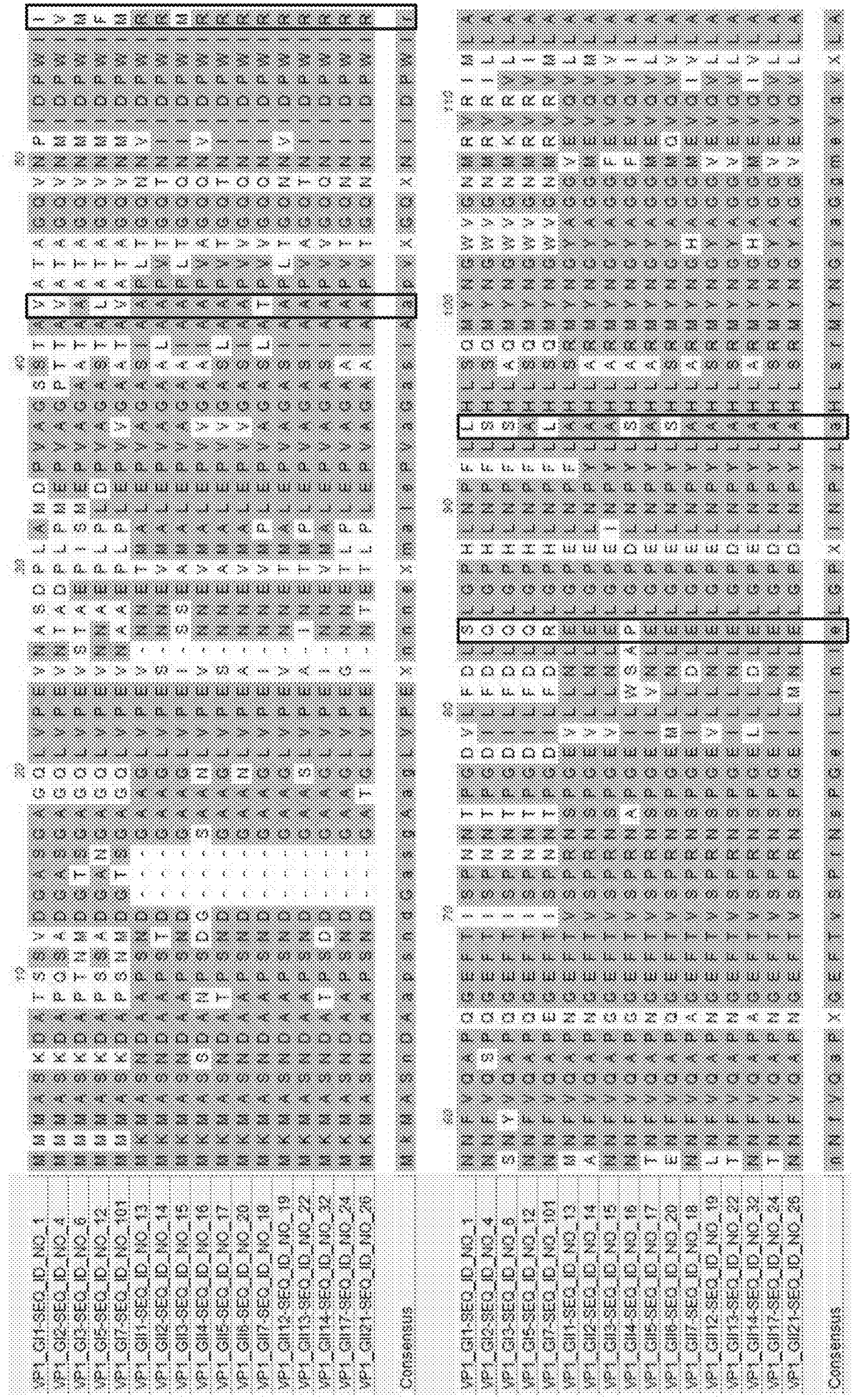
FIG. 2C shows an alignment of several S domains of norovirus VP1 proteins. The norovirus GU sequence (SEQ ID NO:1) is used as a reference sequence to which the other norovirus VP1 sequences (GI.2, SEQ ID NO:4; GI.3, SEQ ID NO:6; GI.5, SEQ ID NO:12; GI.7 SEQ ID NO:101; GII.1. SEQ ID NO:13; GII.2. SEQ ID NO:14; GII.3, SEQ ID NO:15; GII.4, SEQ ID NO:16; GII.5,SEQ ID NO:17; GII.6, SEQ ID NO:20; GII.7,SEQ ID NO:18; GII.12, SEQ ID NO:19; GII.13, SEQ ID NO:22; GII.14, SEQ ID NO:32; GII.17, SEQ ID NO:24; and GII.21, SEQ ID NO:26) are aligned. The VP1 amino acid sequences for the "GII" family of VP1 proteins comprise a 3 amino acid deletion at amino acids 14-16, and a one amino acid deletion at position 26, this results in an alignment offset between the GII VP1 sequences and the GI VP1 sequences by 4 amino acids.
Figures 2, 2C:
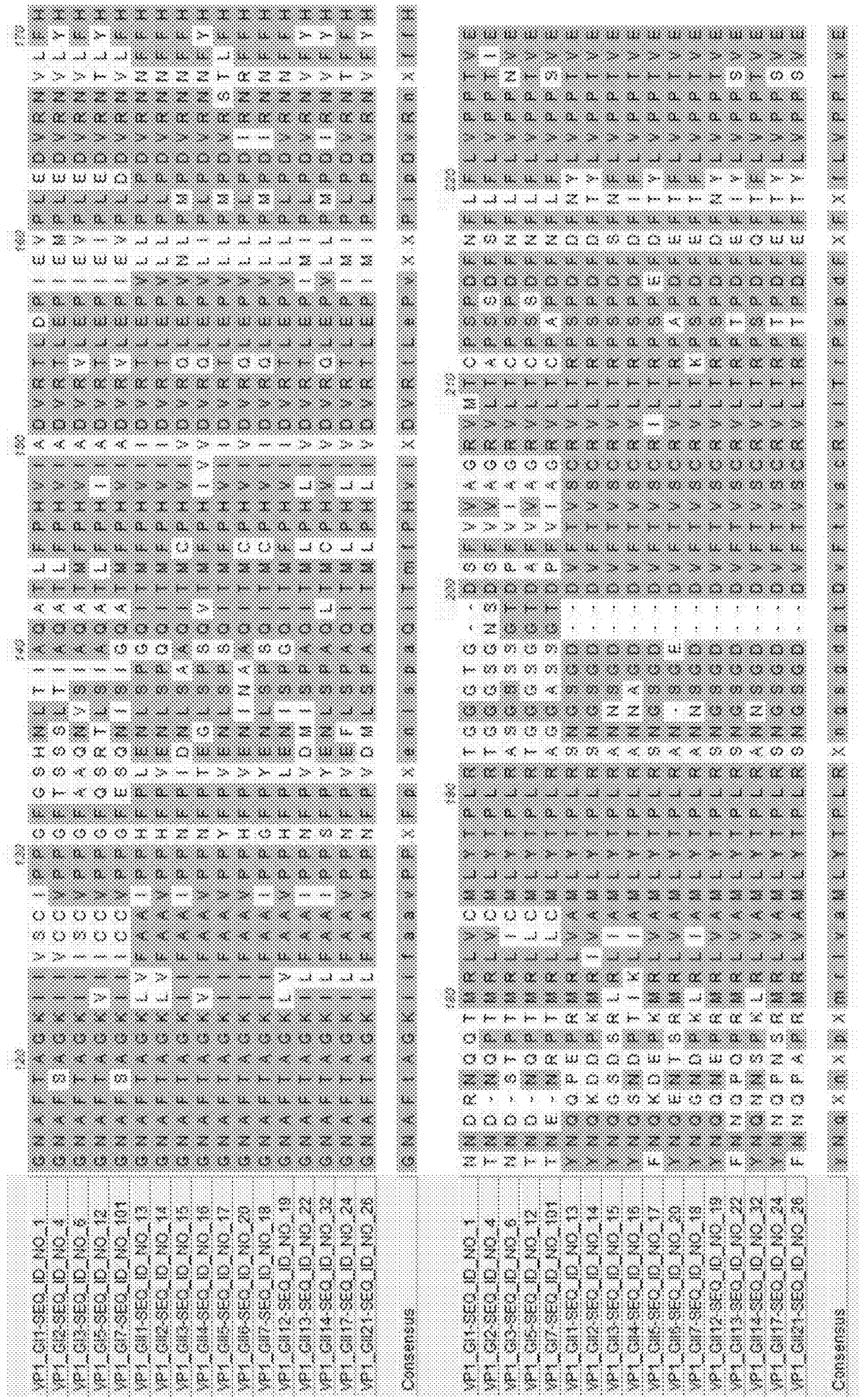

With reference to the sequences shown in FIG. 2C, the norovirus GI.1 sequence (SEQ ID NO:1) is used as a reference sequence against which the other norovirus VP1 sequences may be aligned. The VP1 amino acid sequences for the "GII" family of VP1 proteins comprise a 4 amino acid deletion relative to the GU sequence, comprising a 3 amino acid deletion at positions 14-16, and a one amino acid deletion at position 26. As a result, the alignments between the GII VP1 sequences and the GI VP1 sequences are offset by 3 amino acids after amino acid 13, and 4 amino acids after position 26. For example, amino acid 84 of GI.1, aligns with amino acid 80 of GII.4 (see FIG. 2C). Reference to a substitution, modification or mutation at position 84 (GI.1) and 80 (GII.4) therefore refer to the same aligned amino acids:

| Strain | amino acid alignment. | | | | |
|---|---|---|---|---|---|
| GI: | 39-46 | 43 | 57 | 84 | 94 |
| GII: | 35-42 | 39 | 53 | 80 | 90 |

Also provided herein are methods of increasing production of VLPs comprising modified norovirus VP1 proteins, in plants. For example, a method may involve introducing a nucleic acid encoding a norovirus VP1 mutant protein, as described herein, into the plant, portion of the plant, or plant cell. One or more than one norovirus mutant protein may be expressed in a plant, portion of the plant, or plant cell, in order to produce a VLP comprising one or more than one modified norovirus protein. Alternatively, the method may comprise providing a plant, portion of the plant, or plant cell that comprises the nucleic acid encoding the modified norovirus VP1 protein as described herein, and expressing the nucleic acid encoding the modified norovirus VP1 protein in order to produce a VLP comprising the one or more than one modified norovirus protein.

The methods of producing a VLP comprising a VP1 mutant protein may also comprise a step of co-expressing a nucleic acid sequence encoding a VP2 protein in the plant, portion of the plant, or plant cell.

The term "single construct" or "single constructs", as used herein, refers to nucleic acid vectors comprising a single nucleic acid sequence. The term "dual construct" or "dual constructs", as used herein, refers to a nucleic acid vector comprising two nucleic acid sequences.

By co-expression it is meant the introduction and expression of two or more nucleotide sequences, each of the two or more nucleotide sequences encoding a protein of interest, or a fragment of a protein of interest within a plant, portion of a plant or a plant cell. The two or more nucleotide sequences may be introduced into the plant, portion of the plant or the plant cell within one vector, so that each of the two or more nucleotide sequences is under the control of a separate regulatory region (e.g. comprising a dual construct). Alternatively, the two or more nucleotide sequences may be introduced into the plant, portion of the plant or the plant cell within separate vectors (e.g. comprising single constructs), and each vector comprising appropriate regulatory regions for the expression of the corresponding nucleic acid. For example, two nucleotide sequences, each on a separate vector and introduced into separate *Agrobacterium tumefaciens* hosts, may be co-expressed by mixing suspensions of each *A. tumefaciens* host in a desired volume (for example, an equal volume, or the ratios of each *A. tumefaciens* host may be altered) before vacuum infiltration. In this manner, co-infiltration of multiple *A. tumefaciens* suspensions permits co-expression of multiple transgenes.

The nucleic acid comprising encoding a norovirus VP1 mutant protein as described herein may further comprise sequences that enhance expression of the norovirus VP1 mutant protein in the plant, portion of the plant, or plant cell. Sequences that enhance expression may include, a CPMV enhancer element, or a plant-derived expression enhancer, in operative association with the nucleic acid encoding the norovirus VP1 mutant protein. The sequence encoding the VP1 mutant protein may also be optimized for human codon usage, increased GC content, or a combination thereof. Furthermore, a nucleic acid encoding VP2 may be co-expressed along with the sequence encoding the VP1 mutant protein. The co-expression of a nucleic acid encoding VP2 may lead to an increased yield, increased density, increased integrity, or combination thereof, of VLPs that comprise the one or more than one type of VP1 mutant protein.

The term "CPMV enhancer element", as used herein, refers to a nucleotide sequence encoding the 5'UTR regulating the Cowpea Mosaic Virus (CPMV) RNA2 polypeptide or a modified CPMV sequence as is known in the art. For example, a CPMV enhancer element or a CPMV expression enhancer, includes a nucleotide sequence as described in WO2015/14367; WO2015/103704; WO2007/135480; WO2009/087391; Sainsbury F., and Lomonossoff G. P., (2008, Plant Physiol. 148: pp. 1212-1218), each of which is incorporated herein by reference. A CPMV enhancer sequence can enhance expression of a downstream heterologous open reading frame (ORF) to which they are attached. The CPMV expression enhancer may include CPMV HT, CPMVX (where X=160, 155, 150, 114), for example CPMV 160, CPMVX+(where X=160, 155, 150, 114), for example CPMV 160+, CPMV-HT+, CPMV HT+[WT115], or CPMV HT+[511] (WO2015/143567; WO2015/103704 which are incorporated herein by reference). The CPMV expression enhancer may be used within a plant expression system comprising a regulatory region that is operatively linked with the CPMV expression enhancer sequence and a nucleotide sequence of interest. The term "5'UTR" or "5' untranslated region" or "5' leader sequence" refers to regions of an mRNA that are not translated. The 5'UTR typically begins at the transcription start site and ends just before the translation initiation site or start codon of the coding region. The 5' UTR may modulate the stability and/or translation of an mRNA transcript.

The term "plant-derived expression enhancer", as used herein, refers to a nucleotide sequence obtained from a plant, the nucleotide sequence encoding a 5'UTR. Examples of a plant derived expression enhancer are described in U.S. Provisional Patent Application No. 62/643,053 (Filed Mar. 14, 2018; which is incorporated herein by reference) or in Diamos A. G. et. al. (2016, Front Plt Sci. 7:1-15; which is incorporated herein by reference). The plant-derived expression enhancer may be selected from nbMT78, nbATL75, nbDJ46, nbCHP79, nbEN42, atHSP69, atGRP62, atPK65, atRP46, nb30S72, nbGT61, nbPV55, nbPPI43, nbPM64 (SEQ ID NO:14), and nbH2A86 as described in U.S. 62/643,053). The plant derived expression enhancer may be used within a plant expression system comprising a regulatory region that is operatively linked with the plant-derived expression enhancer sequence and a nucleotide sequence of interest.

The term "5'UTR" or "5' untranslated region" or "5' leader sequence" refers to regions of an mRNA that are not translated. The 5'UTR typically begins at the transcription start site and ends just before the translation initiation site or start codon of the coding region. The 5' UTR may modulate the stability and/or translation of an mRNA transcript.

By "operatively linked" it is meant that the particular sequences interact either directly or indirectly to carry out an intended function, such as mediation or modulation of expression of a nucleic acid sequence. The interaction of operatively linked sequences may, for example, be mediated by proteins that interact with the operatively linked sequences.

When one or more than one type of the modified norovirus VP1 protein is expressed in the plant, portion of the plant or the plant cell, the one or more than one modified VP1 proteins auto-assemble into VLPs. The plant or portion of the plant may be harvested under suitable extraction and purification conditions to maintain the integrity of the VLP, and the VLP comprising the one or more than one type of VP1 mutant (modified) protein may be purified. The one or more than one VP1 mutant protein may also be co-expressed with nucleotide sequence encoding VP2, so that the VLP may comprise both modified VP1 protein and VP2 protein. The present disclosure also provides for the production of one or more than one type of VP1 mutant protein as described herein within a plant, portion of a plant, or plant cell, and the extraction and purification of the one or more than one type of VP1 mutant protein from the plant, the portion of the plant, or the plant cell to produce plant matter, a plant extract, or a protein extract, comprising the modified (mutant) VP1 protein.

Plant matter, a plant extract, or a protein extract comprising the norovirus VP1 mutant protein as described herein is also provided. The plant matter, plant extract, or protein extract may be used to induce immunity to norovirus infection in a subject. Alternatively, the VP1 mutant protein, or the VLP comprising the VP1 mutant protein (and optionally VP2), may be purified or partially purified, and the purified or partially purified preparation may be used to induce immunity to a norovirus infection in a subject.

The present disclosure also provides a composition comprising an effective dose of one or more than one type of modified norovirus VP1 protein, or VLPs comprising one or more than one modified norovirus VP1 protein, and optionally VP2, for inducing an immune response, and a pharmaceutically acceptable carrier, adjuvant, vehicle, or excipient.

Also provided herein are methods of inducing immunity to a norovirus infection in a subject comprising of administering one or more than one type of mutant (modified) norovirus VP1 protein or VLPs comprising one or more than one types of norovirus VP1 mutant proteins to a subject orally, intranasally, intramuscularly, intraperitoneally, intravenously, subcutaneously, rectally, or intravaginally.

The term “norovirus”, as used herein, refers to a non-enveloped viral strain of the genus norovirus of the family Caliciviridae that is characterized as having a single-stranded, positive-sense RNA. The norovirus genome is 7,654 nucleotides in length. The ORF1 encodes a nonstructural polyprotein that is cleaved by viral 3C-like protease into 6 proteins, including an RNA-dependent RNA polymerase. ORF2 and ORF3 encode a major (VP1) and a minor (VP2) capsid protein, respectively (see FIG. 1A).

Norovirus strains as disclosed herein include any known norovirus strain, but also modifications to known norovirus strains that are known to develop on a regular basis over time. For example, norovirus strains may include (as described by their amino acids sequences), but are not limited to Hu/GI.1/United States/Norwalk/1968 (GI.1; SEQ ID NO:1; FIG. 12A), Hu/GI.2/Leuven/2003/BEL (GI.2; SEQ ID NO:4; FIG. 13A), Hu/GI.3/S29/2008/Lilla Edet/Sweden (GI.3; SEQ ID NO:6; FIG. 14A), Hu/GI.5/Siklos/Hun5407/2013/HUN (GI.5; SEQ ID NO:12; FIG. 15A), Hu/GI.7/USA/2014/GA5043 (GI.7; SEQ ID NO:101; FIG. 16A), Hu/GII.1/Ascension208/2010/USA (GII.1; SEQ ID NO:13; FIG. 16B), Hu/GII.2/CGMH47/2011/TW (GII.2; SEQ ID NO: 14; FIG. 17A), Hu/GII.3/Jingzhou/2013402/CHN (GII.3; SEQ ID NO: 15; FIG. 18A), Hu/GII.4/Sydney/NSW0514/2012/AU (GII.4; SEQ ID NO: 16; FIG. 19A), US96/GII.4/Dresden174/1997/DE_AY741811 (SEQ ID NO: 27; FIG. 19C), FH02/GII.4/FarmingtonHills/2002/US_AY502023 (SEQ ID NO: 28; FIG. 19D), Hnt04:GII.4/Hunter-NSW504D/2004/AU_DQ078814 (SEQ ID NO: 29; FIG. 19E), 2006b: GII.4/Shellharbour-NSW696T/2006/AU_EF684915 (SEQ ID NO: 30; FIG. 19F), NO09: GII.4/Orange-NSW001P/2008/AU_GQ845367 (SEQ ID NO: 31; FIG. 19G), Hu/GII.5/AlbertaEI390/2013/CA (GII.5; SEQ ID No:17; FIG. 20), Hu/GII.6/Ohio/490/2012/USA (GII.6; SEQ ID NO: 20; FIG. 21A), GII.7/Musa/2010/A1173774 (GII.7; SEQ ID NO:18; FIG. 22), Hu/GII.12/HS206/2010/USA (GII.12; SEQ ID NO: 19; FIG. 23A), GII.13/VA173/2010/H9AWU4 (GII.13; SEQ ID NO:22; FIG. 24A), GII.14_Saga_2008_JPN_ADE28701 native VP1 (GII.14; SEQ ID NO: 32; FIG. 25), Hu/GII.17/Kawasaki323/2014/JP (GII.17; SEQ ID NO: 24; FIG. 26A), and Hu/GII.21/Salisbury150/2011/USA (GII.21; SEQ ID NO:26; FIG. 27). Norovirus strains are known to readily mutate from year-to-year. Therefore, Norovirus strains also include strains having from about 30-100% or any amount therebetween, amino acid sequence identity, to the VP1 protein, the VP2 protein, or both the VP1 and the VP2 proteins, with any of the above norovirus strains of the strains listed above and in FIGS. 2A and 2B, provided that the VP1 protein can be expressed (i.e. produced) in a plant and that the VP1 protein induces immunity to norovirus in a subject, when the VP1 protein is administered to the subject. For example, norovirus strains also include strains having 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100%, or any amount therebetween, amino acid sequence identity (sequence similarity; percent identity; percent similarity) to the VP1 protein, the VP2 protein, or both the VP1 and the VP2 proteins, with any of the above norovirus strains of the strains listed above and in FIGS. 2A and 2B, provided that the that the VP1 protein can be expressed in a plant and that the VP1 protein induces immunity to norovirus in a subject, when the VP1 protein is administered to the subject. An amino acid sequence identity comparison between the S domain of VP1 proteins of several norovirus strains, which are not to be considered limiting, is shown in FIG. 2C.

The terms “percent similarity”, “sequence similarity”, “percent identity”, or “sequence identity”, when referring to a particular sequence, are used for example as set forth in the University of Wisconsin GCG software program, or by manual alignment and visual inspection (see, e.g., Current Protocols in Molecular Biology, Ausubel et al., eds. 1995 supplement). Methods of alignment of sequences for comparison are well-known in the art. Optimal alignment of sequences for comparison can be conducted, using for example the algorithm of Smith & Waterman, (1981, Adv. Appl. Math. 2:482), by the alignment algorithm of Needleman & Wunsch, (1970, J. Mol. Biol. 48:443), by the search for similarity method of Pearson & Lipman, (1988, Proc. Natl. Acad. Sci. USA 85:2444), by computerized implementations of these algorithms (for example: GAP, BESTFIT, FASTA, and TFASTA in the Wisconsin Genetics Software Package, Genetics Computer Group (GCG), 575 Science Dr., Madison, Wis.).

An example of an algorithm suitable for determining percent sequence identity and sequence similarity are the BLAST and BLAST 2.0 algorithms, which are described in Altschul et al., (1977, Nuc. Acids Res. 25:3389-3402) and Altschul et al., (1990, J. Mol. Biol. 215:403-410), respectively. BLAST and BLAST 2.0 are used, with the parameters described herein, to determine percent sequence identity for the nucleic acids and proteins of the invention. For example the BLASTN program (for nucleotide sequences) may use as defaults a wordlength (W) of 11, an expectation (E) of 10, M=5, N=−4 and a comparison of both strands. For amino acid sequences, the BLASTP program may use as defaults a word length of 3, and expectation (E) of 10, and the BLOSUM62 scoring matrix (see Henikoff & Henikoff, 1989, Proc. Natl. Acad. Sci. USA 89:10915) alignments (B) of 50, expectation (E) of 10, M=5, N=−4, and a comparison of both strands. Software for performing BLAST analyses is publicly available through the National Center for Biotechnology Information (see URL: ncbi.nlm.nih.gov/).

Figure 1B:
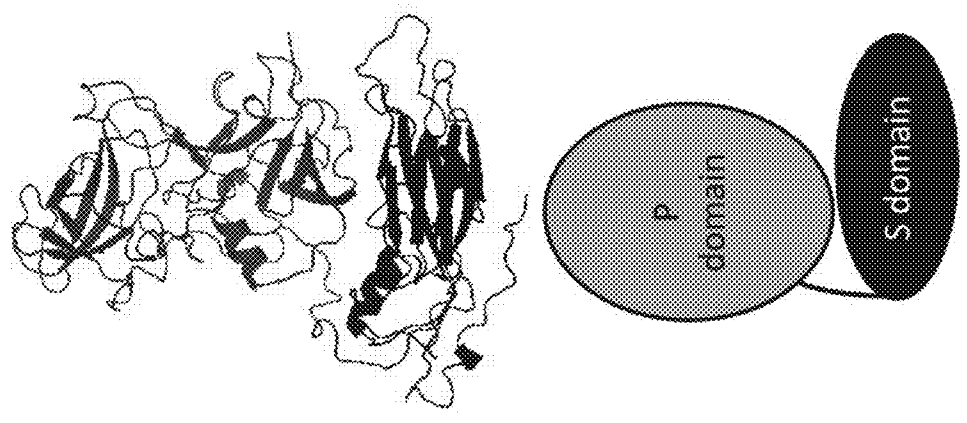
FIG. 1B shows a ribbon diagram representation of the 3-dimensional structure of the norovirus VP1 protein comprising a shell (S) domain, a P1 subdomain (P1), and a P2 subdomain (P2).

The term "VP1", as used herein, refers to the norovirus major capsid protein or polypeptide comprising an amino acid sequence similar to the protein or polypeptide encoded by ORF2 of one or more strains of norovirus as described herein. The major capsid protein folds into two principal domains, a shell (S) domain and a protruding (P) domain (see FIG. 1B). The VP1 protein forms a dimer (FIG. 1C) when incorporated into a virus like particle, or a VLP. The first portion of the N-terminal of VP1 comprise the S domain, with the remainder of the VP1 polypeptide comprising the P domain. For example, in GI.1, the first 225 amino acids of the N-terminal VP1 protein comprise the S domain. When folded, the VP1 assumes a conformation as depicted in FIG. 1B, comprising of a globular S domain (bottom of ribbon structure) and a P domain (top of ribbon structure).

Figure 1C:
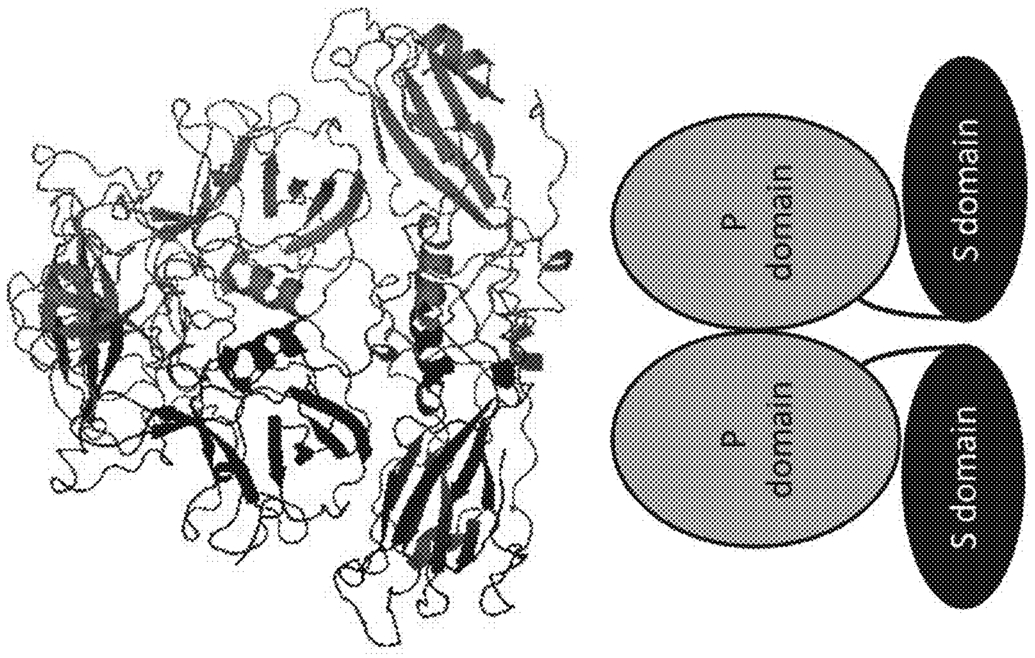
FIG. 1C shows a ribbon diagram representation of the 3-dimensional structure of a norovirus VP1 protein dimer comprising of two S domains (S), two P1 subdomains (P1), and two P2 subdomains (P2).

As shown in FIG. 1C, the VP1 protein dimerizes via P-domain interactions. These interactions stabilize the spontaneous assembly of norovirus capsid molecules.

Methods to produce norovirus VP1 proteins and modified norovirus VP1 proteins in a plant, portion of a plant or a plant cell are described herein that involve introducing the recombinant polynucleotide encoding the norovirus VP1 protein or modified VP1 protein, and incubating the plant, portion of the plant or the plant cell under conditions that permit expression of the norovirus VP1 protein or modified norovirus protein. However, it is also to be understood that norovirus VP1 proteins may be obtained from norovirus VLPs that comprise the VP1 protein, as described in Ausar et al. (Ausar S. F., Foubert T. R, Hudson M. H., Vedvick T. S., Middaugh C. R., 2006, J. Biol. Chem. 281:19478-19488). For example norovirus VLPs comprising norovirus proteins or modified norovirus proteins may dissociate at pH 8 and above, or at temperatures above 55° C., into their VP1 protein constituents, thereby yielding VP1 protein.

The term "virus like particle", "VLP", "virus like particles", or "VLPs", as used herein, refers to a norovirus virus like particle(s) that comprise one or more than one type of norovirus VP1 protein, one or more than one type of VP1 mutant protein, or a combination thereof, and that self-assemble into non-replicating, non-enveloped, non-infectious viral capsid structures lacking all parts of the norovirus genome. For example, the VLP may comprise one type of a modified VP1 protein as described herein, or the VLP may comprise two or more different modified VP1 proteins described herein. Furthermore the VLP may comprise a VP2 protein. VLPs comprising VP1 protein, VP1+VP2 protein, modified VP1 protein, or modified VP1 protein+VP2 protein are of the size from about 15 nm to 50 nm or any amount therebetween, for example 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nm, or any amount therebetween. For example, for T=1 icosahedral symmetry, VLPs may be about 23 nm, or for T=3 icosahedral symmetry, VLPs may be from about 38 to about 40 nm.

As shown in the electron micrographs of FIGS. 3B, 4B, 5C, 5E, 6C, 6E, 7C, 8B, 9B, 9C, 9D, 9G, 10B, 11C and 11D, plant produced VP1 proteins and modified VP1 proteins derived from several norovirus strains self-assemble into VLPs.

Norovirus VP1 Protein Production in Plants

The VP1 protein includes any VP1 protein comprising an amino acid sequence having from about 30 to about 100%, from about 40 to about 100%, from about 50 to about 100%, from about 60 to about 100%, from about 70 to about 100%, from about 80 to about 100%, from about 85 to about 100% from about 90 to about 100%, or from about 95 to about 100% from about 98 to about 100%, or any amount therebetween, sequence identity (which may be also termed sequence similarity) with a VP1 amino acid sequence from a norovirus GI.1 (SEQ ID NO:1; FIG. 12A), GI.2 (SEQ ID NO:4; FIG. 13A), GI.3 (SEQ ID NO:6; FIG. 14A), GI.5 (SEQ ID NO:12; FIG. 15A), Hu/GI.7/USA/2014/GA5043 (GI.7; SEQ ID NO:101; FIG. 16A), GII.1 (SEQ ID NO:13; FIG. 16B), GII.2 (SEQ ID NO:14; FIG. 17A), GII.3 (SEQ ID NO:15; FIG. 18A), GII.4/Sydney (SEQ ID NO:16; FIG. 19A), GII.4/Dresden (SEQ ID NO:27; FIG. 19C), GII.4/FarmingtonHills (SEQ ID NO:28; FIG. 19D), GII.4/Hunter (SEQ ID NO:29; FIG. 19E), GII.4/Shellharbour (SEQ ID NO:30; FIG. 19F), GII.4/Orange (SEQ ID NO:31; FIG. 19G), GII.5 (SEQ ID No:17; FIG. 20), GII.6 (SEQ ID NO:20; FIG. 21A), GII. 7 (SEQ ID NO:18; FIG. 22), GII.12 (SEQ ID NO:19; FIG. 23A), GII.13 (SEQ ID NO:22; FIG. 24A), GII.14/Saga (SEQ ID NO:32; FIG. 25), GII.17 (SEQ ID NO:24; FIG. 26A), GII.21 (SEQ ID NO:26; FIG. 27), provided that the VP1 protein is expressed in a plant and it induces immunity to norovirus when administered to a subject.

The VP1 protein as described herein is modified and comprises an S domain substitution, modification or mutation, at any one or more amino acids in sequence alignment with positions 43, 57, 84 and 94 of norovirus VP1 genotype GI.1 (SEQ ID NO:1; see FIG. 2C), or a deletion of a peptide fragment in sequence alignment with amino acids 39 to 46 of norovirus VP1 genotype GI.1 (SEQ ID NO:1), or a combination thereof. The nucleotide sequence encoding the modified norovirus VP1 protein may be optimized for human codon usage, for increased GC content, or a combination thereof. The modified VP1 protein may be expressed in a plant, portion of a plant, or plant cell.

As shown in FIG. 2C, relative to the hypervariable P domain, the primary amino acid sequence of the norovirus VP1 S domain is well conserved. For example, the VP1 S domain sequences of the norovirus strains shown in FIG. 2C, have sequences ranging from 55.2-98.9% identity to the S domain of GI.1 VP1. For example, nucleic acid sequences described herein may exhibit from about 55 to about 99%, or any amount therebetween sequence identity to the S domain of GU VP1, For example, nucleic acid sequences described herein may exhibit from about 55, 56, 58, 60, 62, 64, 66, 68, 70, 72, 74, 76, 78, 80, 82, 84, 86, 88, 90, 91, 92, 93, 94, 95, 96, 97, 98, 99% or any amount therebetween, sequence identity to the S domain of GI.1 VP1.

As previously shown in U.S. provisional application 62/475,660 (filed Mar. 23, 2017; which is incorporated herein by reference) and PCT/CA2018/050352 (filed Mar. 23, 2018, which is incorporated herein by reference), wild type (also termed native) norovirus VP1 protein may be produced in plants and VLPs comprising the VP1 protein produced. Vacuum infiltration of leaves (from *N. benthamiana*) with *Agrobacterium tumefaciens* comprising expression vectors encoding GI.1 VP1 as a single nucleic acid construct, GU VP2 as a single nucleic acid construct, both GU VP1 and VP2, with VP1 and VP2 nucleic acid sequences introduced in separate vectors ("VP1+VP2"; dual constructs), or on the same vector ("VP1/VP2" or "VP1/VP2/3'UTR"; single nucleic acid constructs) to permit co-expression of the VP1 and/or VP2 sequences and the leaves examined for VP1 and VP2 production. After 6 or 9 days post infiltration (6 DPI and 9 DPI, respectively), total crude protein extracts were prepared from leaf homogenates, separated by SDS-PAGE, and stained with Coomassie Brilliant Blue dye. Leaves infiltrated with expression vectors comprising nucleotide sequences that correspond to wildtype GU ORF2, encoding the VP1 protein, produced low or non-detectable levels of GI.1 VP1 as determined using Coomassie stained gels. In contrast, leaves infiltrated with expression vectors comprising GU VP1 nucleotide sequences that were codon optimized for human expression (hCod), or enriched for GC content when compared to the GC content of the wildtype VP1 nucleic acid sequence, produced increased amounts of GI.1 VP1 protein in Coomassie stained gels. Demonstrating that hCod GI.1 VP1 may be produced in plants when VP1 is expressed on its own.

Furthermore, as described in U.S. provisional application 62/475,660 and PCT/CA2018/050352 (filed Mar. 23, 2017; and Mar. 23, 2018, respectively, both of which are incorporated herein by reference), leaves infiltrated with vectors comprising either wildtype GI.1 VP1 and VP2 or human codon optimized GI.1 VP1 and VP2 produced low levels of GI.1 VP1 protein in Coomassie stained gels, suggesting that expression of VP1 is not enhanced by the presence of VP2 when co-expressed in cis on the same vector, using the same organization as found in the viral genome (using one promoter to control expression). However, when VP1 or human codon optimized VP1 was co-expressed in trans (on a separate construct) along with VP2 or hCod VP2 (hCod VP1+VP2), respectively, an increase in VP1 protein was observed. Each of the VP1 and VP2 nucleic acid segments comprised a regulatory region and a terminator, and the constructs were introduced into the plants as a nucleic acid complex, and this resulted in a corresponding increase in VP1 protein yield.

This observation is in contrast to that observed in insect and mammalian cells (Bertolotti-Ciarlet A., Crawford S. E., Hutson A. M., Estes M. K. 2003, J. Virol. 77:11603-11615), who reported that an increase in VP1 expression was only observed when VP1 and VP2 (or VP1+VP2+3'UTR) resided in cis, and were co-expressed using the same organization as that found in the viral genome, under the control of one promoter and terminator. No increase in VP1 expression was observed by Bertolotti-Ciarlet (2003) in insect or mammalian cells, when VP1 and VP2 were co-expressed in trans.

As described in more detail below, when the modified VP1 proteins, as described herein, are expressed in plants, it is preferred that the ORF3 sequence encoding VP2 is obtained from the same norovirus genotype and strain as that used to obtain the modified VP1 sequence. In the examples provided herein, and unless otherwise stated, the modified VP1 protein and the VP2 protein are obtained from the same norovirus genotype and strain, and the nucleotide sequences encoding the modified VP1 protein and the VP2 protein are co-expressed in the plant using separate expression systems, for example, on separate plasmids, or VP1 and VP2 may be expressed on the same vector but each of the sequences encoding VP1 and VP2 should be under the control of separate promoter and terminator sequences, so that they have a separate expression system.

Figure 3A:
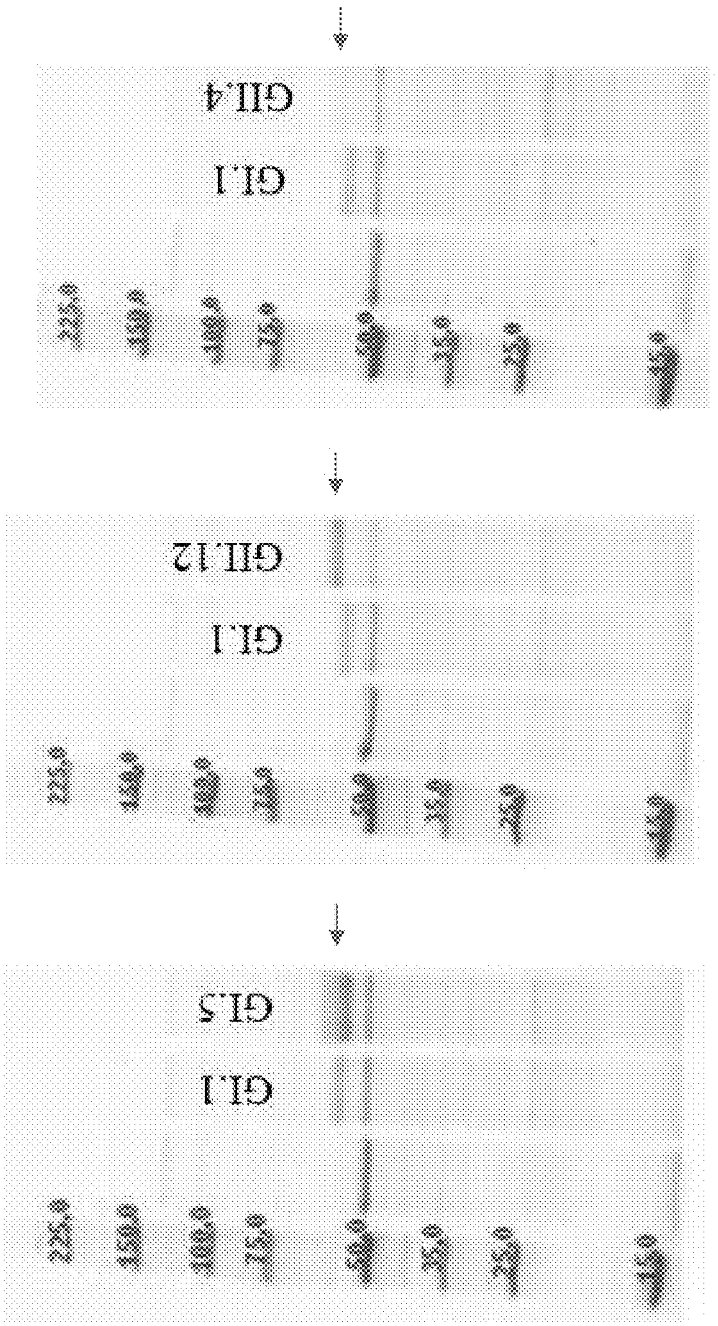
FIG. 3A shows a Coomassie-stained SDS-PAGE of crude protein extracts prepared from agroinfiltrated *Nicotiana benthamiana* leaves, 9 days post infiltration (DPI) with left panel: wild type (wt) human codon-optimized (hCod) GI.1/United States/Norwalk/1968 VP1 (Construct #: 2724; SEQ ID NO:3 (nucleotide); SEQ ID NO: 1 (amino acid)) and hCod GI.5 VP1 (Construct #: 3980; SEQ ID NO:33 (nucleotide); SEQ ID NO:12 (amino acid); center panel: wild type GI.1 and wt hCod GII.12/United States/HS206/2010 VP1 (Construct #: 3995; SEQ ID NO:87 (nucleotide); SEQ ID NO:19 (amino acid)); and right panel: wild type GI.1 and wt hCod GII.4/Sydney/NSW0514/2012 VP1 (Construct #: 3760; SEQ ID NO:52 (nucleotide); SEQ ID NO:16 (amino acid)). Arrow: VP1 norovirus protein. First lane in each of the panels crude protein extracts prepared from mock infiltrated *N. benthamiana* leaves.
Figure 3B:
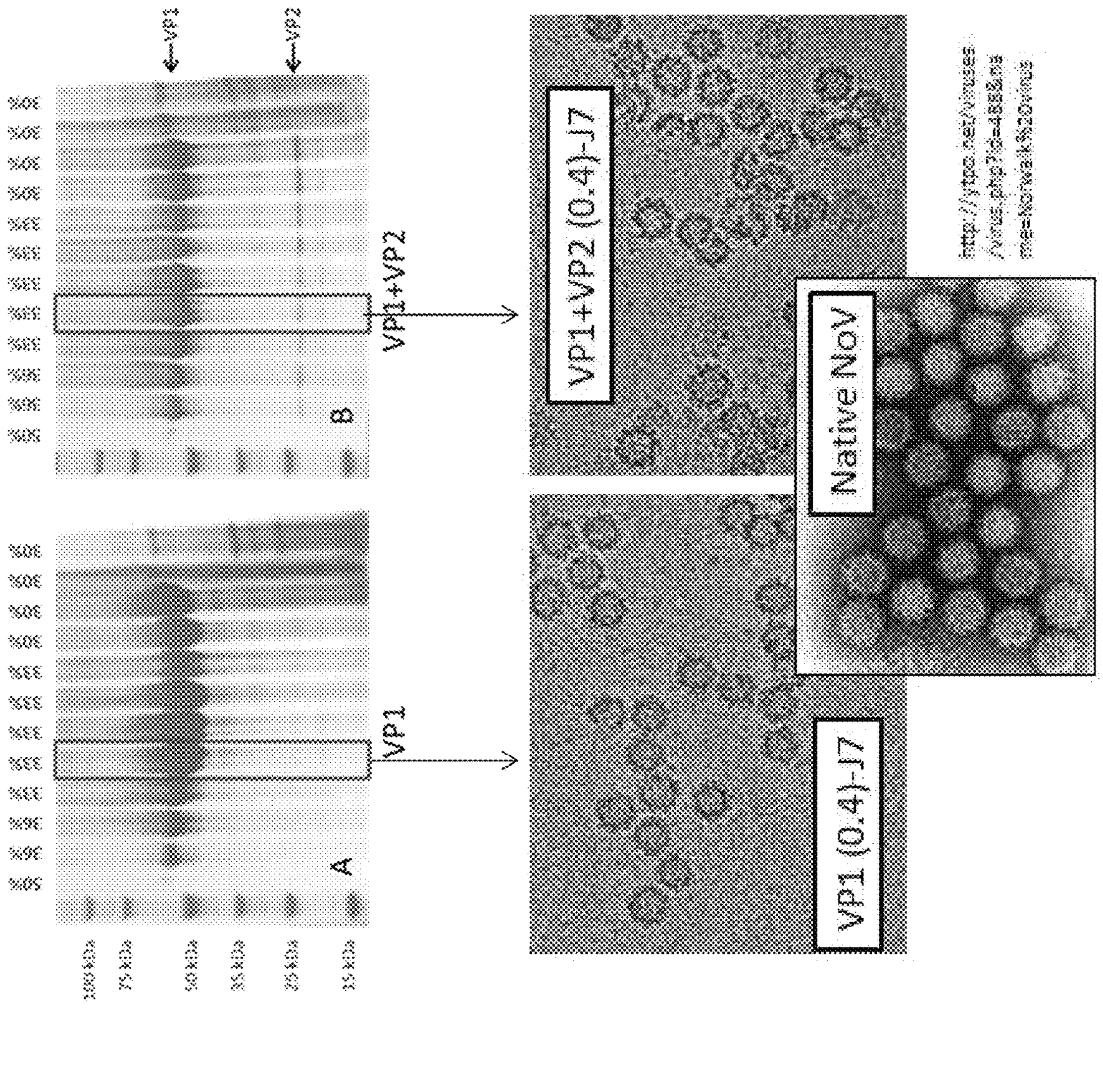
FIG. 3B upper panel shows norovirus protein expression and VLP assembly using Coomassie-stained SDS-PAGE analysis of fractions from an iodixanol density gradient separation of crude protein extracts prepared from *N. benthamiana* leaves expressing wt hCod VP1 GI.1/United States/Norwalk/1968 VP1 (construct #2724), or wt hCod VP1 (construct #2724) and co-expressed with wt hCod VP2 (construct #2725). Lower panel shows electron micrographs of norovirus VLPs purified from 33% iodixanol gradient fractions of VP1 or co-expression of VP1 and VP2 proteins. An electron micrograph of native norovirus VLP is shown for comparison.
Figure 3C:
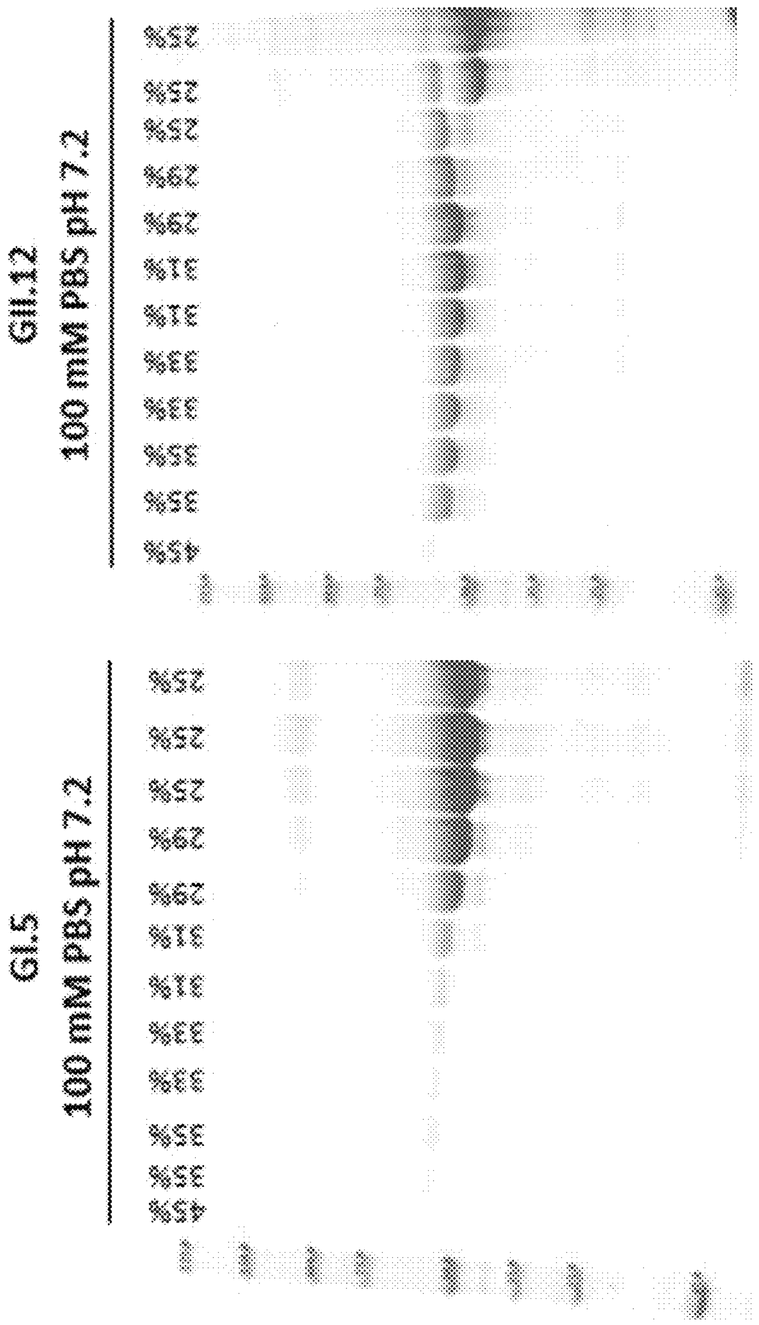
FIG. 3C shows a Coomassie-stained SDS-PAGE analysis of iodixanol density gradient fractions of crude protein extracts prepared from *N. benthamiana* leaves expressing left panel: wt hCod GI.5/Hungary/Siklos/HUN5407/2013 VP1 (Construct #: 3980; SEQ ID NO:33 (nucleotide); SEQ ID NO: 12 (amino acid)); right panel: GII.12/United States/HS206/2010 VP1 (Construct #: 3995; SEQ ID NO:87 (nucleotide); SEQ ID NO: 19 (amino acid).
Figure 4B:
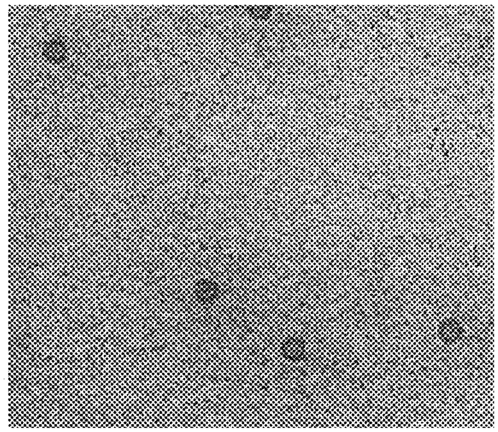
FIG. 4B shows electron micrographs of norovirus VLPs purified from 29-35% iodixanol gradient fractions of VP1.
Figure 4A:
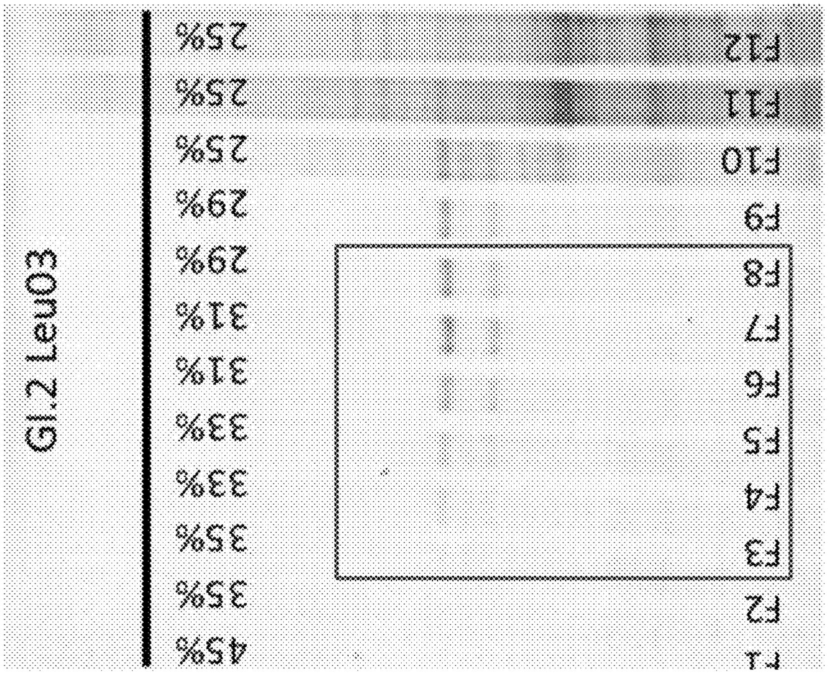
FIG. 4A shows a Coomassie-stained SDS-PAGE analysis of iodixanol density gradient fractions of crude protein extracts prepared from *N. benthamiana* leaves expressing wt hCod GI.2 VP1 (Construct #: 3300; SEQ ID NO:5 (nucleotide); SEQ ID NO:4 (amino acid)).

The yield, or amount of extracted, norovirus VP1 protein and the production of VLPs comprising norovirus VP1 proteins in a plant, differs depending on the genotype of the norovirus VP1 being expressed. For example, as shown in FIG. 3A, the expression of wild type GI.1 VP1, GI.5 VP1, and GII.12 VP1 was robust with good protein yields (determined using SDS PAGE). Furthermore, high density wild type GI.1 VLPs, having well-formed capsids that are predominantly 38 nm in diameter were also produced (FIG. 3B), and high density VLPs were produced from plants expressing wild type GI.5 VLPs, GII.12 VLPs (FIG. 3C) and GI.2 VLPs, (FIG. 4A). In contrast, wild type GII.4 VP1 was poorly expressed in plants (FIG. 3A right hand panel), and low yields of VP1 protein, or non-detectable amounts of VP1 protein (using SDS-PAGE) were observed following expression other wild type VP1 proteins in plants, for example, GII.2 VP1, GII.3 VP1 and GII.6 VP1 (Table 5, Example 3).

Furthermore, expression of native VP1 proteins in plants may result in VLPs characterized as comprising a higher proportion of 23 nm VLPs rather than 38 nm VLPs. For example, expression of wild type GI.3 VP1 results in the production of a significant number of 23 nm VLPs (see FIG. 5C, left hand panel). A greater proportion of 23 nm VLPs also results in the VLPs characterized as being less dense following density gradient centrifugation (see FIG. 5B left hand panel).

The present disclosure provides nucleic acid sequences encoding modified norovirus VP1 proteins, wherein the modified norovirus VP1 comprises one or more than one substitution, modification or mutation at an amino acid selected from a group consisting of amino acids in sequence alignment with amino acids 43, 57, 84 and 94 of norovirus VP1 genotype GI.1 (SEQ ID NO:1) or a deletion of a peptide fragment in sequence alignment with amino acids 39 to 46 of norovirus genotype VP1 GI.1 (SEQ ID NO:1), or a combination thereof. Plant expressing nucleic acid sequences encoding the modified norovirus VP1 protein, and comprising one or more than one substitution, modification or mutation at an amino acid selected from a group consisting of amino acids in sequence alignment with amino acids 43, 57, 84 and 94 of norovirus VP1 genotype GI.1 or a deletion of a peptide fragment in sequence alignment with amino acids 39 to 46 of norovirus genotype VP1 GI.1, or a combination thereof, exhibit similar or improved VP1, and/or VLP characteristics as compared to the wildtype VP1 and/or VLP that does not comprise the one or more than one substitution, modification or mutation.

Examples of improved characteristics of the modified VP1 and/or VLP include,

- increased modified VP1 protein yield (determined for example using Coomassie stained SDS-PAGE and Western analysis) when expressed in plant cells as compared to the wildtype VP1 that does not comprise the one or more than one substitution, modification or mutation. For example, increased yields of modified VP1 protein may range from 1.5 to 50 fold, or any amount there between, over that of the corresponding wild type VP1 yield;
- increased density of VLPs comprising the modified VP1 proteins, for example as determined using iodixanol density gradient separation of protein extracts as compared to density gradient separation of the wildtype VP1 that does not comprise the one or more than one substitution, modification or mutation. For example, VLPs comprising modified VP1 protein may be observed in the same or more dense fractions following density gradient centrifugation;
- improved integrity of VLPs that are comprised of the modified VP1 proteins compared to the wildtype VP1 that does not comprise the one or more than one substitution, modification or mutation. For example, the number of disrupted, or partially assembled, VLPs may be determined using TEM;

increased VLP yield when expressed in plant cells as compared to the wildtype level of VLP production of the same genotype that does not comprise the substitution(s), modification(s) or mutation (s). VLP yield may be determined in washed samples obtained from VLP containing fractions following density gradient centrifugation using TEM. For example, increased yields of VLPs comprising modified VP1 protein may range from 1.5 to 20 fold, or any amount there between, over that of the corresponding yield of VLPs comprising wild type VP1 protein;

improved accumulation of VLPs that are comprised of the modified VP1 proteins as compared to the accumulation of VLPs comprising wildtype VP1 of the same genotype that does not comprise the substitution(s), modification(s) or mutation (s);

a greater proportion of VLPs that assemble into 38 nm VLPs as opposed to 23 nm VLPs, compared to VLPs comprising the wildtype VP1 that does not comprise the one or more than one substitution, modification or mutation (determined using TEM); and a combination of these improved characteristics.

Without wishing to be bound by theory, VLPs that are observed in higher density fractions following density gradient centrifugation, as compared to wildtype norovirus VLPs, indicates that the assembly of the VLPs comprising native VP1 may be less stable when expressed in, and extracted from, plants, than VLPs comprising the modified VP1 protein. The native VLP may therefore be more susceptible to malformed capsid particles and the generation of fragmentation products. As a result, the VLPs comprising modified VP1 protein that are characterized as having increased density may also exhibit greater structural integrity than VLPs produced using the corresponding wildtype VP1.

The nucleic acid sequences described herein may exhibit from about 50% to about 99% sequence similarity with any of the nucleic acid sequences encoding VP1 as identified above and as listed in FIGS. 2A-C, excluding GI. For example, nucleic acid sequences described herein may exhibit from about 50, 52, 54, 56, 58, 60, 62, 64, 66, 68, 70, 72, 74, 76, 78, 80, 82, 84, 86, 88, 90, 91, 92, 93, 94, 95, 96, 97, 98, 99% or any amount therebetween, sequence identity with any of the nucleic acid sequences encoding a norovirus VP1, for example from, Hu/GI.2/Leuven/2003/BEL (GI.2; SEQ ID NO:4; FIG. 12A), Hu/GI.3/S29/2008/Lilla Edet/Sweden (GI.3; SEQ ID NO:6; FIG. 14A), Hu/GI.5/Siklos/Hun5407/2013/HUN (GI.5; SEQ ID NO:12; FIG. 15A), Hu/GI.7/USA/2014/GA5043 (GI.7; SEQ ID NO:101; FIG. 16A), Hu/GII.1/Ascension208/2010/USA (GII.1; SEQ ID NO:13; FIG. 16B), Hu/GII.2/CGMH47/2011/TW (SEQ ID NO:14; FIG. 17A), Hu/GII.3/Jingzhou/2013402/CHN (GII.3; SEQ ID NO: 15; FIG. 18A), Hu/GII.4/Sydney/NSW0514/2012/AU (GII.4; SEQ ID NO: 16; FIG. 19A), US96/GII.4/Dresden174/1997/DE_AY741811 (SEQ ID NO: 27; FIG. 19C), FH02/GII.4/FarmingtonHills/2002/US_AY502023 (SEQ ID NO: 28; FIG. 19D), Hnt04:GII.4/Hunter-NSW504D/2004/AU_DQ078814 (SEQ ID NO: 29; FIG. 19E), 2006b: GII.4/Shellharbour-NSW696T/2006/AU_EF684915 (SEQ ID NO: 30; FIG. 19F), NO09: GII.4/Orange-NSW001P/2008/AU_GQ845367 (SEQ ID NO: 31; FIG. 19G), Hu/GII.5/AlbertaEI390/2013/CA (GII.5; SEQ ID No:17; FIG. 20), Hu/GII.6/Ohio/490/2012/USA (GII.6; SEQ ID NO: 20; FIG. 21A), GII.7/Musa/2010/A1173774 (GII7; SEQ ID NO:18; FIG. 22), Hu/GII.12/HS206/2010/USA (GII.12; SEQ ID NO: 19; FIG. 23A), GII.13/VA173/2010/H9AWU4 (SEQ ID NO:22; FIG. 24A), GII.14_Saga_2008_JPN_ADE28701 native VP1 (SEQ ID NO: 32; FIG. 25), Hu/GII.17/Kawasaki323/2014/JP (GII.17; SEQ ID NO: 24; FIG. 26A), Hu/GII.21/Salisbury150/2011/USA (GII.21; SEQ ID NO:26; FIG. 27), provided that the VP1 protein induces immunity to norovirus in a subject, when the VP1 protein is administered to the subject.

Similarly, the present invention includes amino acid sequences that exhibit from about 30% to about 99% or any amount therebetween, sequence similarity with any of the VP1 sequences for example, Hu/GI.2/Leuven/2003/BEL (GI.2; SEQ ID NO:4; FIG. 12A), Hu/GI.3/S29/2008/Lilla Edet/Sweden (GI.3; SEQ ID NO:6; FIG. 14A), Hu/GI.5/Siklos/Hun5407/2013/HUN (GI.5; SEQ ID NO:12; FIG. 15A), Hu/GI.7/USA/2014/GA5043 (GI.7; SEQ ID NO:101; FIG. 16A), Hu/GII.1/Ascension208/2010/USA (GII.1; SEQ ID NO:13; FIG. 16B), Hu/GII.2/CGMH47/2011/TW (SEQ ID NO:14; FIG. 17A), Hu/GII.3/Jingzhou/2013402/CHN (GII.3; SEQ ID NO: 15; FIG. 18A), Hu/GII.4/Sydney/NSW0514/2012/AU (GII.4; SEQ ID NO: 16; FIG. 19A), US96/GII.4/Dresden174/1997/DE_AY741811 (SEQ ID NO: 27; FIG. 19C), FH02/GII.4/FarmingtonHills/2002/US_AY502023 (SEQ ID NO: 28; FIG. 19D), Hnt04:GII.4/Hunter-NSW504D/2004/AU_DQ078814 (SEQ ID NO: 29; FIG. 19E), 2006b: GII.4/Shellharbour-NSW696T/2006/AU_EF684915 (SEQ ID NO: 30; FIG. 19F), NO09: GII.4/Orange-NSW001P/2008/AU_GQ845367 (SEQ ID NO: 31; FIG. 19G), Hu/GII.5/AlbertaEI390/2013/CA (GII.5; SEQ ID No:17; FIG. 20), Hu/GII.6/Ohio/490/2012/USA (GII.6; SEQ ID NO: 20; FIG. 21A), GII.7/Musa/2010/A1173774 (GII7; SEQ ID NO:18; FIG. 22), Hu/GII.12/HS206/2010/USA (GII.12; SEQ ID NO: 19; FIG. 23A), GII.13/VA173/2010/H9AWU4 (SEQ ID NO:22; FIG. 24A), GII.14_Saga_2008_JPN_ADE28701 native VP1 (SEQ ID NO: 32; FIG. 25), Hu/GII.17/Kawasaki323/2014/JP (GII.17; SEQ ID NO: 24; FIG. 26A), Hu/GII.21/Salisbury150/2011/USA (GII.21; SEQ ID NO:26; FIG. 27), provided that the VP1 protein induces immunity to norovirus when administered to a subject. For example, the amino acid sequences described herein may have from about 30, 32, 34, 36, 38. 40, 42, 44, 46, 48, 50, 52, 54, 56, 58, 60, 62, 64, 66, 68, 70, 72, 74, 76, 78, 80, 82, 84, 86, 88, 90, 91, 92, 93, 94, 95, 96, 97, 98, 99% or any amount therebetween, sequence similarity with any of the VP1 amino acid sequences defined above, provided that the VP1 protein induces immunity to norovirus when administered to a subject.

By "VP1 mutant protein", "mutant VP1 protein", "modified VP1 protein", "modified norovirus VP1 protein" and the like, it is meant, a norovirus VP1 protein comprising one or more than one substitution, mutation, or modification, at positions or amino acids in sequence alignment with amino acids 43, 57, 84 and 94 of norovirus VP1 genotype GI.1 (SEQ ID NO:1; see Table 1 below), or a deletion of a peptide fragment in sequence alignment with amino acids 39 to 46 of norovirus VP1 genotype GI.1 (SEQ ID NO:1), or a combination thereof. The terms "residue", "residue amino acid" and "amino acid" are used interchangeably, and typically refer to an amino acid at a specified position (location) within an amino acid sequence.

TABLE 1

| Listing of Norovirus genotypes (strains) and equivalent amino acid locations of GI and GII strains. | | | | |
|---|---|---|---|---|
| | Position (GI.1 numbering) | | | |
| | 43 | 57 | 64 | 94 |
| Genotype | AA in equivalent position | | | |
| GI.1 | V43 | I57 | S84 | L94 |
| GI.2 | V43 | V57 | Q84 | S94 |
| GI.3 | A43 | M57 | Q84 | S94 |
| GI.5 | L43 | F57 | Q84 | A94 |
| GI.7 | V43 | M57 | R84 | L94 |
| GII.1 | A39 | R53 | E80 | A90 |
| GII.2 | A39 | R53 | E80 | A90 |
| GII.3 | A39 | M53 | E80 | A90 |
| GII.4 | A39 | R53 | P80 | S90 |
| GII.5 | A39 | R53 | E80 | A90 |
| GII.6 | A39 | R53 | E80 | S90 |
| GII.7 | T39 | R53 | E80 | A90 |
| GII.12 | A39 | R53 | E80 | A90 |
| GII.13 | A39 | R53 | E80 | A90 |
| GII.14 | A39 | R53 | E80 | A90 |
| GII.17 | ASS | R53 | E80 | A90 |
| GII.21 | A39 | R53 | E80 | A90 |

As used herein, the term "conserved substitution" or "conservative substitution" refers to the presence of an amino acid residue in the sequence of the GII.4 VP1 protein that is different from, but it is in the same class of amino acid as the described substitution. For example, a nonpolar amino acid may be used to replace a nonpolar amino acid, an aromatic amino acid to replace an aromatic amino acid, a polar-uncharged amino acid to replace a polar-uncharged amino acid, and/or a charged amino acid to replace a charged amino acid). In addition, conservative substitutions can encompass an amino acid having an interfacial hydropathy value of the same sign and generally of similar magnitude as the amino acid that is replacing the corresponding wild type amino acid.

As used herein, the term "nonpolar amino acid" refers to glycine (G, Gly), alanine (A, Ala), valine (V, Val), leucine (L, Leu), isoleucine (I, Ile), and proline (P, Pro); the term "aromatic residue" (or aromatic amino acid) refers to phenylalanine (F, Phe), tyrosine (Y, Tyr), and tryptophan (W, Trp); the term "polar uncharged amino acid" refers to serine (S, Ser), threonine (T, Thr), cysteine (C, Cys), methionine (M, Met), asparagine (N, Asn) and glutamine (Q, Gln); the term "charged amino acid" refers to the negatively charged amino acids aspartic acid (D, Asp) and glutamic acid (E, Glu), as well as the positively charged amino acids lysine (K, Lys), arginine (R, Arg), and histidine (H, His). Other classification of amino acids may be as follows: amino acids with hydrophobic side chain (aliphatic): Alanine (A, Ala), Isoleucine (I, Ile), Leucine (L, Leu), Methionine (M, Met) and Valine (V, Val); amino acids with hydrophobic side chain (aromatic): Phenylalanine (F, Phe), Tryptophan (W, Trp), Tyrosine (Y, Tyr); amino acids with polar neutral side chain: Asparagine (N, Asn), Cysteine (C, Cys), Glutamine (Q, Gln), Serine (S, Ser) and Threonine (T, Thr); amino acids with electrically charged side chains (acidic): Aspartic acid (D, Asp), Glutamic acid (E, Glu); amino acids with electrically charged side chains (basic): Arginine (R, Arg); Histidine (H, His); Lysine (K, Lys), Glycine G, Gly) and Proline (P, Pro).

Conservative amino acid substitutions are likely to have a similar effect on the activity of the resultant modified GII.4 VP1 protein as the original substitution or modification. Further information about conservative substitutions can be found, for example, in Ben Bassat et al. (J. Bacteriol, 169:751-757, 1987), O'Regan et al. (Gene, 77:237-251, 1989), Sahin-Toth et al. (Protein ScL, 3:240-247, 1994), Hochuli et al (Bio/Technology, 6:1321-1325, 1988).

The Blosum matrices are commonly used for determining the relatedness of polypeptide sequences (Henikoff et al., Proc. Natl. Acad. Sci. USA, 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. The following table shows examples of conservative amino acid substitutions: Table 2.

TABLE 2

| Exemplary conservative amino acid substitutions. | | | |
|---|---|---|---|
| Original Residue | Very Highly - Conserved Substitutions | Highly Conserved Substitutions (from the Blosum90 Matrix) | Conserved Substitutions (from the Blosum65 Matrix) |
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Gln | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

For the modifications described herein, the amino acids may be substituted using very high conserved substitutions, highly conserved substitutions or conserved substitutions as outlined in Table 2, as well as aromatic, polar, polar uncharged, polar neutral, or non-polar, negatively charged, positively charged, hydrophobic amino acids as described above.

As described herein, modified VP1 proteins comprising one or more than one substitutions of amino acids at amino acids 43, 57, 84 and 94 (in GI strains, equivalent to amino acids 39, 53, 80 and 90 in GII strains), resulted in an improved characteristic of the modified VP1 protein, or VLP produced using the modified VP1 protein. It is to be understood that the improved characteristic is not limited to substituting the specific amino acid at the specified sites, as one of skill in the art would understand that amino acids with similar properties may be substituted for the amino acids at the identified positions. For example, the modification Q84S, comprises substituting glutamine at position 84 with serine, an amino acid characterized as having a polar neutral side chain. The glutamine at this position may also be substituted with an alternate amino acid characterized as having a polar neutral side chain, for example either asparagine, cysteine, or threonine, i.e. Q84X, where X=S, N, C or T. Similarly, E80S, comprising a substitution of glutamate at position 80 with serine, or P80S (a proline to serine substitution), in addition to substituting the native amino acid with serine, the amino acid at this position may also be substituted with an amino acid having a polar neutral side chain, for example asparagine, cysteine, or threonine, i.e. P80X, where X=S, N, C or T. Furthermore, as described herein additional P80X variants may be used to produce VP1, where X is selected from S, A, N, K or H. In the modifications S94L, S90L, A94L, or A90L, that comprise substituting serine or alanine with leucine (an amino acid characterized as having a hydrophobic side chain), the native amino acid may be substituted using an amino acid characterized as having a hydrophobic side chain, for example either isoleucine, methionine, valine, or in the case of S94X or S90X, an alanine, i.e. S94X (S90X), where X=L, I, M, V or A, or A94X (A90X), where X=L, I, M or V. Furthermore, as described herein additional S94X variants may be used to produce VP1, where X is selected from V, I, M, T, E, D, N, Q, K, or H. The modification A39V that comprises substituting an alanine with valine (an amino acid characterized as having a hydrophobic side chain) at position 39, in addition to valine, native amino acid may also be substituted with an amino acid characterized as having a hydrophobic side chain, for example, isoleucine, leucine, or methionine i.e. A39X, where X=V, I, L or M. Furthermore, as described herein additional A39X variants may be used to produce VP1, where X is selected from I, M, G, S, E, D, N, Q, K, or H. The modification V47P comprising a substitution of valine with proline, may also comprise a substitution of valine with a glycine, i.e. V47X, where X=P or G. The modification R53I that comprises substituting an arginine with isoleucine (an amino acid characterized as having a hydrophobic side chain) at position 53, in addition to isoleucine, arginine may also be substituted with an amino acid characterized as having a hydrophobic side chain, for example, leucine, valine, alanine or methionine i.e. R53X, where X=I, L, V, A or M. The modification M57I that comprises substituting a methionine with isoleucine (an amino acid characterized as having a hydrophobic side chain) at position 57, in addition to isoleucine, methionine may also be substituted with an amino acid characterized as having a hydrophobic side chain, for example, leucine, valine, or alanine i.e. M57X, where X=I, L, V or A. Furthermore, as described herein additional M57X variants may be used to produce VP1, where X is selected from L, G, S, T, N, Q, K, or H.

Examples of VP1 mutant proteins (modified VP1 proteins) include, but are not limited to, the following.

- GI.3_Q84S VP1 (GI.3_Q84X, where X=S, N, C or T VP1): wherein the glutamine corresponding to amino acid 84 of norovirus VP1 genotype GI.1 (SEQ ID NO:1) has been mutated, for example, to serine (GI.3_Q84S; SEQ ID NO:98, FIG. 28A), or a sequence that exhibits from about 80-100% or any amount therebetween, sequence similarity with the amino acid sequence of the GI.3_Q84S VP1 protein. For example, the GI.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.3_Q84S VP1 protein (SEQ ID NO:98, FIG. 28A), provided that the substitution, modification or mutation at the position corresponding to amino acid 84 of norovirus VP1 genotype GI.1 remains an S, N, C or T, for example serine, and provided that the GI.3_Q84X VP1 protein induces immunity to norovirus when administered to a subject. The sequence encoding the GI.3 VP1 may be obtained from any GI.3 strain, for example, but not limited to GI.3/S29/2008/Lilla Edet/Sweden (SEQ ID NO:6 amino acid; SEQ ID NO:7, nucleotide; FIGS. 14A, 14B).
- GI.3_S94X VP1, where X=L, I, A, V, M, T, E, D, N, Q, K, or H, wherein the serine corresponding to amino acid 94 of norovirus VP1 genotype GI.1 (SEQ ID NO:1) has been mutated, for example, to leucine (GI.3_S94L; SEQ ID NO:8, FIG. 28C), valine, isoleucine, methionine, threonine, aspartic acid, glutamic acid, glutamine lysine or histidine (GI.3_S94X , where X=V, I, M, T, E, D, N, Q, K, or H; SEQ ID NO:292, FIG. 28M), or a sequence that exhibits from about 80-100% or any amount therebetween, sequence similarity with the amino acid sequence of the GI.3_S94X VP1 protein, where X=L, V, I, M, T, E, D, N, Q, K, or H. For example, the GI.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.3_S94X VP1 protein, where X=L, V, I, M, T, E, D, N, Q, K, or H VP1 protein (SEQ ID NO:8, FIG. 28C, SEQ ID NO:292; FIG. 28M), provided that the substitution, modification or mutation at the position corresponding to amino acid 94 of norovirus VP1 genotype GI.1 remains an L, V, I, M, T, E, D, N, Q, K, or H, for example leucine, valine, isoleucine, methionine, threonine, aspartic acid, glutamic acid, glutamine lysine or histidine, and provided that the GI.3 S94X VP1 protein induces immunity to norovirus when administered to a subject. The sequence encoding the GI.3 VP1 may be obtained from any GI.3 strain, for example, but not limited to GI.3/S29/2008/Lilla Edet/Sweden (SEQ ID NO:6 amino acid; SEQ ID NO:7, nucleotide; FIGS. 14A, 14B).
- GI.3_A43X+S94x VP1, where X=V, L, I or M, and x=L, I, A, V, M, T, E, D, N, Q, K, or H, wherein the alanine and serine corresponding to amino acids 43 and 94, respectively, of norovirus VP1 genotype GI.1 (SEQ ID NO:1) have been substituted or mutated, for example but not limited to, to valine and leucine, respectively (GI.3_A43V+S94L; SEQ ID NO:170, FIG. 28G), or a sequence that exhibits from about 80-100% or any amount therebetween, sequence similarity with the amino acid sequence of the GI.3_A43V+S94L VP1 protein. For example, the GI.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.3_A43V+S94L VP1 protein (SEQ ID NO:170, FIG. 28G), provided that the substitutions, modifications or mutations at the positions corresponding to amino acids 43 and 94 of norovirus VP1 genotype GI.1 remain a V, L, I or M, for example valine, and an L, I, A, V, M, T, E, D, N, Q, K, or H, for example leucine, respectively, and provided that the GI.3_A43X+S94x VP1 protein induces immunity to norovirus when administered to a subject. The sequence encoding the GI.3 VP1 may be obtained from any GI.3 strain, for example, but not limited to GI.3/S29/2008/Lilla Edet/Sweden (SEQ ID NO:6, amino acid; SEQ ID NO:7, nucleotide; FIGS. 14A, 14B).

GI.3_M57X+S94x VP1, where X=I, V, A, L, G, S, T, N, Q, K, or H and x=L, I, A, V, M, T, E, D, N, Q, K, wherein the methionine and serine corresponding to amino acids 57 and 94, respectively, of norovirus VP1 genotype GI.1 (SEQ ID NO:1) have been mutated, for example, to isoleucine and leucine, respectively (GI.3_M57I+S94L; SEQ ID NO:172, FIG. 28I), or a sequence that exhibits from about 80-100% or any amount therebetween, sequence similarity with the amino acid sequence of the GI.3_M57I+S94L VP1 protein. For example, the GI.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.3_M57I+S94L VP1 protein (SEQ ID NO:172, FIG. 28I), provided that the substitutions, modifications or mutations at the positions corresponding to amino acids 57 and 94 of norovirus VP1 genotype GI.1 remain an I, V, A, L, G, S, T, N, Q, K, or H, for example isoleucine, and an L, I, A, V, M, T, E, D, N, Q, K, for example leucine, respectively, and provided that the GI.3_M57X+S94x VP1 protein induces immunity to norovirus when administered to a subject. The sequence encoding the GI.3 VP1 may be obtained from any GI.3 strain, for example, but not limited to GI.3/S29/2008/Lilla Edet/Sweden (SEQ ID NO:6, amino acid; SEQ ID NO:7, nucleotide; FIGS. 14A, 14B).

GI.3_Q84X+S94x, VP1, where X=S, N, C or T, and x=L, I, A, V, M, T, E, D, N, Q, K, or H, wherein the glutamine and serine corresponding to amino acids 84 and 94, respectively, of norovirus VP1 genotype GI.1 (SEQ ID NO:1) have been mutated, for example, to serine and leucine, respectively (GI.3_Q84S+S94L; SEQ ID NO:10, FIG. 28E), or a sequence that exhibits from about 80-100% or any amount therebetween, sequence similarity with the amino acid sequence of the GI.3_Q84S+S94L VP1 protein. For example, the GI.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.3_Q84S+S94L VP1 protein (SEQ ID NO:10, FIG. 28E), provided that the substitutions, modifications or mutations at the positions corresponding to amino acids 84 and 94 of norovirus VP1 genotype GI.1 remain an S, N, C or T, for example serine, and an L, I, A, V, M, T, E, D, N, Q, K, or H, for example leucine, respectively, and provided that the GI.3_Q84X+S94x VP1 protein induces immunity to norovirus when administered to a subject. The sequence encoding the GI.3 VP1 may be obtained from any GI.3 strain, for example, but not limited to GI.3/S29/2008/Lilla Edet/Sweden (SEQ ID NO:6, amino acid; SEQ ID NO:7, nucleotide; FIGS. 14A, 14B).

GI.3_A43X+M57z+S94x VP1, where X=V, L, I or M, z=I, V, A, L, G, S, T, N, Q, K, or H, and x=L, I, A, V, M, T, E, D, N, Q, K, or H, wherein the alanine, methionine and serine corresponding to amino acids 43, 57 and 94, respectively, of norovirus VP1 genotype GI.1 (SEQ ID NO:1) have been mutated, for example, to valine, isoleucine and leucine, respectively (GI.3_A43V+M57I+S94L; SEQ ID NO:174, FIG. 28K), or a sequence that exhibits from about 80-100% or any amount therebetween, sequence similarity with the amino acid sequence of the GI.3_A43V+M57I+S94L VP1 protein. For example, the GI.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.3_A43V+M57I+S94L VP1 protein (SEQ ID NO:174, FIG. 28K), provided that the substitutions, modifications or mutations at the positions corresponding to amino acids 43, 57 and 94 of norovirus VP1 genotype GI.1 remain a V, L, I or M, for example valine, a I, V, A, L, G, S, T, N, Q, K, or H, for example isoleucine, and L, I, A, V, M, T, E, D, N, Q, K, or H, for example leucine, respectively, and provided that the GI.3_A43X+M57z+S94x VP1 protein induces immunity to norovirus when administered to a subject. The sequence encoding the GI.3 VP1 may be obtained from any GI.3 strain, for example, but not limited to GI.3/S29/2008/Lilla Edet/Sweden (SEQ ID NO:6, amino acid; SEQ ID NO:7, nucleotide; FIGS. 14A, 14B).

GI.5_Q84S VP1 (GI.5_Q84X, where X=S, N, C or T, VP1): wherein the glutamine corresponding to amino acid 84 of norovirus VP1 genotype GI.1 (SEQ ID NO:1) has been mutated, for example, to serine (GI.5_Q84S; SEQ ID NO:34, FIG. 29A), or a sequence that exhibits from about 80-100% or any amount therebetween, sequence similarity with the amino acid sequence of the GI.5_Q84S VP1 protein. For example, the GI.5 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.5_Q84S VP1 protein (SEQ ID NO:34, FIG. 29A), provided that the substitution, modification or mutation at the position corresponding to amino acid 84 of norovirus VP1 genotype GI.1 remains an S, N, C or T, for example serine, and provided that the VP1 protein induces immunity to norovirus when administered to a subject. The sequence encoding the GI.5 VP1 may be obtained from any GI.5 strain, for example, but not limited to GI.5/Siklos/HUN5407/2013/HUN (SEQ ID NO:12, amino acid; FIG. 15A).

GI.5_A94L VP1 (GI.5_A94X, where X=L, I, M or V, VP1): wherein the alanine corresponding to amino acid 94 of norovirus VP1 genotype GI.1 (SEQ ID NO:1) has been mutated, for example, to leucine (GI.5_A94L; SEQ ID NO:36, FIG. 29C), or a sequence that exhibits from about 80-100% or any amount therebetween, sequence similarity with the amino acid sequence of the GI.5_A94L VP1 protein. For example, the GI.5 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.5_A94L VP1 protein (SEQ ID NO:36, FIG. 29C), provided that the substitution, modification or mutation at the position corresponding to amino acid 94 of norovirus VP1 genotype GI.1 remains an L, I, M or V, for example leucine, and provided that the VP1 protein induces immunity to norovirus when administered to a subject. The sequence encoding the GI.5 VP1 may be obtained from any GI.5 strain, for example, but not limited to GI.5/Siklos/HUN5407/2013/HUN (SEQ ID NO:12, amino acid; FIG. 15A).

GI.5_Q84S+A94L VP1 (GI.5_Q84X, where X=S, N, C or T+A94X, where X=L, I, M or V, VP1): wherein the glutamine and alanine corresponding to amino acids 84 and 94, respectively of norovirus VP1 genotype GI.1 (SEQ ID NO:1) have been mutated, for example, to serine and leucine, respectively (GI.5_Q84S+A94L; SEQ ID NO:38, FIG. 29E), or a sequence that exhibits from about 80-100% or any amount therebetween, sequence similarity with the amino acid sequence of the GI.5_Q84S+A94L VP1 protein. For example, the GI.5 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.5_Q84S+A94L VP1 protein (SEQ ID NO:38, FIG. 29E), provided that the substitutions, modifications or mutations at the positions corresponding to amino acids 84 and 94 of norovirus VP1 genotype GI.1 remain an S, N, C or T, for example serine and an L, I, M or V, for example leucine, respectively, and provided that the VP1 protein induces immunity to norovirus when administered to a subject. The sequence encoding the GI.5 VP1 may be obtained from any GI.5 strain, for example, but not limited to GI.5/Siklos/HUN5407/2013/HUN (SEQ ID NO:12, amino acid; FIG. 15A).

GI.7_M57X VP1, where X=I, V, A, L, G, S, T, N, Q, K, or H, wherein the methionine corresponding to amino acid 57 of norovirus VP1 genotype GI.1 (SEQ ID NO:1) has been mutated, for example, to isoleucine (GI.7_M57I; SEQ ID NO:179, FIG. 29I), valine, alanine, leucine, glycine, serine, threonine, asparagine, glutamine, lysine or histidine (GI.7_M57X VP1, where X=I, V, A, L, G, S, T, N, Q, K, or H; SEQ ID NO: 290; FIG. 29M), or a sequence that exhibits from about 80-100% or any amount therebetween, sequence similarity with the amino acid sequence of the GI.7_M57X VP1 protein, where X=I, V, A, L, G, S, T, N, Q, K, or H. For example, the GI.7 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.7_M57X VP1 protein, where X=I, V, A, L, G, S, T, N, Q, K, or H; (SEQ ID NO:179, FIG. 29I; SEQ ID NO:290; FIG. 29M), provided that the substitution, modification or mutation at the position corresponding to amino acid 57 of norovirus VP1 genotype GI.1 remains an I, V, A, L, G, S, T, N, Q, K, or H, for example isoleucine, valine, alanine, leucine, glycine, serine, threonine, asparagine, glutamine, lysine or histidine, and provided that the GI.7_M57X VP1 protein induces immunity to norovirus when administered to a subject. The sequence encoding the GI.7 VP1 may be obtained from any GI.7 strain, for example, but not limited to GI.7/GA5043/USA/2014 (SEQ ID NO:101, amino acid; FIG. 16A).

GI.7_12_84S VP1 (GI.7_R84X, where X=S, N, C, or T, VP1): wherein the arginine corresponding to amino acid 84 of norovirus VP1 genotype GI.1 (SEQ ID NO:1) has been mutated, for example, to serine (GI.7_R84S; SEQ ID NO:177, FIG. 29G), or a sequence that exhibits from about 80-100% or any amount therebetween, sequence similarity with the amino acid sequence of the GI.7_R84S VP1 protein. For example, the GI.7 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.7_R84S VP1 protein (SEQ ID NO:177, FIG. 29G), provided that the substitution, modification or mutation at the position corresponding to amino acid 84 of norovirus VP1 genotype GI.1 remains an S, N, C or T, for example serine, and provided that the VP1 protein induces immunity to norovirus when administered to a subject. The sequence encoding the GI.7 VP1 may be obtained from any GI.7 strain, for example, but not limited to GI.7/GA5043/USA/2014 (SEQ ID NO:101, amino acid; FIG. 16A).

GI.7_M57X+R84x VP1, where X=L, I, A, V, M, T, E, D, N, Q, K, or H, and x=S, N, C, or T, wherein the methionine and arginine, corresponding to amino acids 57 and 84, respectively of norovirus VP1 genotype GI.1 (SEQ ID NO:1) have been mutated, for example, to isoleucine and serine, respectively (GI.7_M57I+R84S; SEQ ID NO:181, FIG. 29K), or a sequence that exhibits from about 80-100% or any amount therebetween, sequence similarity with the amino acid sequence of the GI.7_M57I+R84S VP1 protein. For example, the GI.7 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GI.7_M57I+R84S VP1 protein (SEQ ID NO:181, FIG. 29K), provided that the substitutions, modifications or mutations at the positions corresponding to amino acids 57 and 84 of norovirus VP1 genotype GI.1 remain an L, I, A, V, M, T, E, D, N, Q, K, or H, for example isoleucine, and an S, N, C or T, for example serine, respectively, and provided that the GI.7_M57X+R84x VP1 protein induces immunity to norovirus when administered to a subject. The sequence encoding the GI.7 VP1 may be obtained from any GI.7 strain, for example, but not limited to GI.7/GA5043/USA/2014 (SEQ ID NO:101, amino acid; FIG. 16A).

GII.2_E80S VP1 (GII.2_E80X, where X=S, N, C or T, VP1): wherein the glutamic acid corresponding to amino acid 84 of norovirus VP1 genotype GI.1 (SEQ ID NO:1) has been mutated, for example, to serine (GII.2_E80S; SEQ ID NO:85, FIG. 30A), or a sequence that exhibits from about 80-100% or any amount therebetween, sequence similarity with the amino acid sequence of the GII.2_E80S VP1 protein. For example, the GII.2 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.2_E80S VP1 protein (SEQ ID NO:85, FIG. 30A), provided that the substitution, modification or mutation at the position corresponding to amino acid 84 of norovirus VP1 genotype GI.1 remains an S, N, C or T, for example serine, and provided that the VP1 protein induces immunity to norovirus when administered to a subject. The sequence encoding the GII.2 VP1 may be obtained from any GII.2 strain, for example, but not limited to Hu/GII.2/CGMH47/2011/TW (SEQ ID NO:14, amino acid; FIG. 17A).

GII.2_A90L VP1 (GII.2_A90X, where X=L, I, M or V, VP1): wherein alanine corresponding to amino acid 94 of norovirus VP1 genotype GI.1 (SEQ ID NO:1) has been mutated, for example, to leucine (GII.2_A90L; SEQ ID NO:41, FIG. 30C), or a sequence that exhibits from about 80-100% or any amount therebetween, sequence similarity with the amino acid sequence of the mut GII.2_A90L VP1 protein. For example, the GII.2 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.2_A90L VP1 protein (SEQ ID NO:41, FIG. 30C), provided that the substitution, modification or mutation at the position corresponding to amino acid 94 of norovirus VP1 genotype GI.1 remains an L, I, M or V for example leucine, and provided that the VP1 protein induces immunity to norovirus when administered to a subject. The sequence encoding the GII.2 VP1 may be obtained from any GII.2 strain, for example, but not limited to Hu/GII.2/CGMH47/2011/TW (SEQ ID NO:14, amino acid; FIG. 17A).

GII.2_E80S+A90L VP1 (GII.2_E80X, where X=S, N, C or T+A90X, where X=L, I, M or V, VP1): wherein the glutamic acid and alanine corresponding to amino acids 84 and 94, respectively of norovirus VP1 genotype GI.1 (SEQ ID NO:1) have been mutated, for example, to serine and leucine, respectively (GII.2_E80S+A90L; SEQ ID NO:43, FIG. 30E), or a sequence that exhibits from about 80-100% or any amount therebetween, sequence similarity with the amino acid sequence of the mut GII.2_E80S+A90L VP1 protein. For example, the GII.2 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.2_E80S+A90L VP1 protein (SEQ ID NO:43, FIG. 30E), provided that the substitutions, modifications or mutations at the positions corresponding to amino acids 84 and 94 of norovirus VP1 genotype GI.1 remain an S, N, C or T, for example serine, and an L, I, M or V, for example leucine, respectively, and provided that the VP1 protein induces immunity to norovirus when administered to a subject. The sequence encoding the GII.2 VP1 may be obtained from any GII.2 strain, for example, but not limited to Hu/GII.2/CGMH47/2011/TW (SEQ ID NO:14, amino acid; FIG. 17A).

GII.2_A39V+E80S+A90L VP1 (GII.2_A39X, where X=V, L. I or M+E80X, where X=S, N, C or T+A90X, where X=L, I, M or V, VP1): wherein the alanine, glutamic acid and alanine corresponding to amino acids 43, 84 and 94, respectively of norovirus VP1 genotype GI.1 (SEQ ID NO:1) have been mutated, for example, to valine, serine and leucine, respectively (GII.2_A39V+E80S+A90L; SEQ ID NO:182, FIG. 30G), or a sequence that exhibits from about 80-100% or any amount therebetween, sequence similarity with the amino acid sequence of the GII.2_A39V+E80S+A90L VP1 protein. For example, the GII.2 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.2A39V+E80S+A90L VP1 protein (SEQ ID NO:182, FIG. 30G), provided that the substitutions, modifications or mutations at the positions corresponding to amino acids 43, 84 and 94 of norovirus VP1 genotype GI.1 remain a V, I, L or M, for example valine, an S, N, C or T, for example serine, and an L, I, M or V, for example leucine, respectively, and provided that the VP1 protein induces immunity to norovirus when administered to a subject. The sequence encoding the GII.2 VP1 may be obtained from any GII.2 strain, for example, but not limited to Hu/GII.2/CGMH47/2011/TW (SEQ ID NO:14, amino acid; FIG. 17A).

GII.2 R53I+E80S+A90L VP1 (GII.2_R53X, where X=I, L, M, V or A+E80X, where X=S, N, C or T+A90X, where X=L, I, M or V, VP1): wherein the arginine, glutamic acid and alanine corresponding to amino acids 57, 84 and 94, respectively of norovirus VP1 genotype GI.1 (SEQ ID NO:1) have been mutated, for example, to isoleucine, serine and leucine, respectively (GII.2_M53I+E80S+A90L; SEQ ID NO:184, FIG. 30I), or a sequence that exhibits from about 80-100% or any amount therebetween, sequence similarity with the amino acid sequence of the GII.2_M53I+E80S+A90L VP1 protein. For example, the GII.2 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.2_M53I+E80S+A90L VP1 protein (SEQ ID NO:184, FIG. 30I), provided that the substitutions, modifications or mutations at the positions corresponding to amino acids 57, 84 and 94 of norovirus VP1 genotype GI.1 remain an I, L, M or A, for example isoleucine, an S, N, C or T, for example serine, and an L, I, M or V, for example leucine, respectively, and provided that the VP1 protein induces immunity to norovirus when administered to a subject. The sequence encoding the GII.2 VP1 may be obtained from any GII.2 strain, for example, but not limited to Hu/GII.2/CGMH47/2011/TW (SEQ ID NO:14, amino acid; FIG. 17A).

GII.2 A39V+R53I+E80S+A90L VP1 (GII.2_A39X, where X=V, I, L or, M+R53X, where X=I, L, M, A or V+E80X, where X=S, N, C or T+A90X, where X=L, I, M or V, VP1): wherein the glutamic acid and alanine corresponding to amino acids 43, 57, 84 and 94, respectively of norovirus VP1 genotype GI.1 (SEQ ID NO:1) have been mutated, for example, to valine, isoleucine, serine and leucine, respectively (GII.2_A39V+R53I+E80S+A90L; SEQ ID NO:186, FIG. 30K), or a sequence that exhibits from about 80-100% or any amount therebetween, sequence similarity with the amino acid sequence of the GII.2_A39V+R53I+E80S+A90L VP1 protein. For example, the GII.2 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.2A39V+R53I+E80S+A90L VP1 protein (SEQ ID NO:186, FIG. 30K), provided that the substitutions, modifications or mutations at the positions corresponding to amino acids 43, 57, 84 and 94 of norovirus VP1 genotype GI.1 remain an V, I, L or M, for example valine, an I, L, M, A or V, for example isoleucine, an S, N, C or T, for example serine, and an L, I, M or V, for example leucine, respectively, and provided that the VP1 protein induces immunity to norovirus when administered to a subject. The sequence encoding the GII.2 VP1 may be obtained from any GII.2 strain, for example, but not limited to Hu/GII.2/CGMH47/2011/TW (SEQ ID NO:14, amino acid; FIG. 17A).

GII.3_E80S VP1 (GII.3_E80X, where X=S, N, C or T, VP1): wherein the glutamic acid corresponding to amino acid 84 of norovirus VP1 genotype GI.1 (SEQ ID NO:1) has been mutated, for example, to serine (GII.3_E80S; SEQ ID NO:46, FIG. 31A), or a sequence that exhibits from about 80-100% or any amount therebetween, sequence similarity with the amino acid sequence of the mut GII.3_E80S VP1 protein. For example, the GII.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.3_E80S VP1 protein (SEQ ID NO:46, FIG. 31A), provided that the substitution, modification or mutation at the position corresponding to amino acid 84 of norovirus VP1 genotype GI.1 remains an S, N, C or T, for example serine, and provided that the VP1 protein induces immunity to norovirus when administered to a subject. The sequence encoding the GII.3 VP1 may be obtained from any GII.3 strain, for example, but not limited to GII.3/Jingzhou/2013402/CHN (SEQ ID NO:15, amino acid; FIG. 18A).

GII.3_A90L VP1 (GII.3_A90X, where X=L, I, M or V, VP1): wherein the alanine corresponding to amino acid 94 of norovirus VP1 genotype GI.1 (SEQ ID NO:1) has been mutated, for example, to leucine (GII.3_A90L; SEQ ID NO:48, FIG. 31C), or a sequence that exhibits from about 80-100% or any amount therebetween, sequence similarity with the amino acid sequence of the GII.3_A90L VP1 protein. For example, the GII.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.3_A90L VP1 protein (SEQ ID NO:48, FIG. 31C), provided that the substitution, modification or mutation at the position corresponding to amino acid 94 of norovirus VP1 genotype GI.1 remains an L, I, M or V, for example leucine, and provided that the VP1 protein induces immunity to norovirus when administered to a subject. The sequence encoding the GII.3 VP1 may be obtained from any GII.3 strain, for example, but not limited to GII.3/Jingzhou/2013402/CHN (SEQ ID NO:15, amino acid; FIG. 18A).

GII.3_E80S+A90L VP1 (GII.3_E80X, where X=S, N, C or T+A90X, where X=L, I, M or V, VP1): wherein the glutamic acid and alanine corresponding to amino acids 84 and 94, respectively of norovirus VP1 genotype GI.1 (SEQ ID NO:1) have been mutated, for example, to serine and leucine, respectively (GII.3_E80S+A90L; SEQ ID NO:50, FIG. 31E), or a sequence that exhibits from about 80-100% or any amount therebetween, sequence similarity with the amino acid sequence of the GII.3_E80S+A90L VP1 protein. For example, the GII.3 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.3_E80S+A90L VP1 protein (SEQ ID NO:50, FIG. 31E), provided that the substitutions, modifications or mutations at the positions corresponding to amino acids 84 and 94 of norovirus VP1 genotype GI.1 remain an S, N, C or T, for example serine, and an L, I, M or V, for example leucine, respectively, and provided that the VP1 protein induces immunity to norovirus when administered to a subject. The sequence encoding the GII.3 VP1 may be obtained from any GII.3 strain, for example, but not limited to GII.3/Jingzhou/2013402/CHN (SEQ ID NO:15, amino acid; FIG. 18A).

GII.4_A39X VP1, where X=V, I, L, M, G, S, E, D, N, Q, K, or H, wherein the alanine corresponding to amino acid 43 of norovirus VP1 genotype GI.1 (SEQ ID NO:1) has been mutated, for example, to valine (GII.4_A39V; SEQ ID NO:53, FIG. 32A), isoleucine, leucine, methionine, glycine, serine, aspartic acid, glutamic acid, asparagine, glutamine, lysine, histidine, or a sequence that exhibits from about 80-100% or any amount therebetween, sequence similarity with the amino acid sequence of the GII.4_A39X VP1, where X=V, I, L, M, G, S, E, D, N, Q, K, or H, VP1 protein. For example which is not to be considered limiting, the GII.4 VP1 protein may have from about 0, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_A39V VP1 protein (SEQ ID NO:53, FIG. 32A), provided that the substitution, modification or mutation at the position corresponding to amino acid 43 of norovirus VP1 genotype GI.1 remains a V, I, L, M, G, S, E, D, N, Q, K, or H, for example valine, isoleucine, leucine, methionine, glycine, serine, aspartic acid, glutamic acid, asparagine, glutamine, lysine, or histidine, and provided that the GII.4_A39X VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_V47P VP1 (GII.4_V47X, where X=P or G, VP1): wherein the valine corresponding to amino acid 51 of norovirus VP1 genotype GI.1 (SEQ ID NO:1) has been mutated, for example, to proline (GII.4_V47P; SEQ ID NO:55, FIG. 32C), or a sequence that exhibits from about 80-100% or any amount therebetween, sequence similarity with the amino acid sequence of the GII.4_V47P VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_V47P VP1 protein (SEQ ID NO:55, FIG. 32C), provided that the substitution, modification or mutation at the position corresponding to amino acid 51 of norovirus VP1 genotype GI.1 remains a P or G, for example proline, and provided that the VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_R53I VP1 (GII.4_12531, where X=I, L, V, A or M, VP1): wherein the arginine corresponding to amino acid 57 of norovirus VP1 genotype GI.1 (SEQ ID NO:1) has been mutated, for example, to isoleucine (GII.4_R53I; SEQ ID NO:57, FIG. 32E), or a sequence that exhibits from about 80-100% or any amount therebetween, sequence similarity with the amino acid sequence of the GII.4_R53I VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_R53I VP1 protein (SEQ ID NO:57, FIG. 32E), provided that the substitution, modification or mutation at the position corresponding to amino acid 57 of norovirus VP1 genotype GI.1 remains an I, L, V, A or M, for example isoleucine, and provided that the VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_P80X VP1, where X=S, N, C, T, A, K, or H, wherein the proline corresponding to amino acid 84 of norovirus VP1 genotype GI.1 (SEQ ID NO:1) has been mutated, for example, to serine (GII.4_P80S; SEQ ID NO:59, FIG. 32G), asparagine, cysteine, threonine, alanine, lysine, histidine, or a sequence that exhibits from about 80-100% or any amount therebetween, sequence similarity with the amino acid sequence of the GII.4_P80S VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_P80S VP1 protein (SEQ ID NO:59, FIG. 32G), provided that the substitution, modification or mutation at the position corresponding to amino acid 84 of norovirus VP1 genotype GI.1 remains an S, N, C, T, A, K, or H, for example serine, asparagine, cysteine, threonine, alanine, lysine, or histidine, and provided that the GII.4_P80X VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_S90L VP1 (GII.4_S90X, where X=L, I, M, A or V, VP1): wherein the serine corresponding to amino acid 94 of norovirus VP1 genotype GI.1 (SEQ ID NO:1) has been mutated, for example, to leucine (GII.4_S90L; SEQ ID NO:61, FIG. 32I), or a sequence that exhibits from about 80-100% or any amount therebetween, sequence similarity with the amino acid sequence of the GII.4_S90L VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_S90L VP1 protein (SEQ ID NO:61, FIG. 32I), provided that the substitution, modification or mutation at the position corresponding to amino acid 94 of norovirus VP1 genotype GI.1 remains an L, I, M, A or V, for example leucine, and provided that the VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_Δ35-42 VP1: wherein the amino acids corresponding to positions 39-46 of norovirus VP1 genotype GI.1 (SEQ ID NO:1) have been deleted (GII.4_Δ35-42; SEQ ID NO:63, FIG. 32K), or a sequence that exhibits from about 80-100% or any amount therebetween, sequence similarity with the amino acid sequence of the GII.4_Δ35-42 VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_Δ35-42 VP1 protein (SEQ ID NO:63, FIG. 32K), provided that the amino acids corresponding to positions 39-46 of norovirus VP1 genotype GI.1 (SEQ ID NO:1) remain deleted, and that the VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_SSTAVATA VP1: wherein the amino acids corresponding to positions 39-46 of norovirus VP1 genotype GI.1 (SEQ ID NO:1) have been mutated to the peptide sequence SSTAVATA (SEQ ID NO:168; GII.4_SSTAVATA; SEQ ID NO:65, FIG. 32M), or a sequence that exhibits from about 80-100% or any amount therebetween, sequence similarity with the amino acid sequence of the mut GII.4_SSTAVATA VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_SSTAVATA VP1 protein (SEQ ID NO:65, FIG. 32M), provided that the positions corresponding to amino acids 39-46 of norovirus VP1 genotype GI.1 remain the peptide sequence SSTAVATA, and provided that the VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_A39X+R53x VP1, where X=V, I, L, M, G, S, E, D, N, Q, K, or H, and x=I, L, M, A or V, wherein the alanine and arginine corresponding to amino acids 43 and 57, respectively, of norovirus VP1 genotype GI.1 (SEQ ID NO:1) have been mutated, for example, to valine, isoleucine, leucine, methionine, glycine, serine, aspartic acid, glutamic acid, asparagine, glutamine, lysine or histidine and isoleucine, respectively (e.g. GII.4_A39V+R53I; SEQ ID NO:188, FIG. 32AA), or a sequence that exhibits from about 80-100% or any amount therebetween, sequence similarity with the amino acid sequence of the GII.4_A39V+R53I VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4A39V+R53I VP1 protein (SEQ ID NO:188, FIG. 32AA), provided that the substitutions, modifications or mutations at the positions corresponding to amino acids 43 and 57 of norovirus VP1 genotype GU remain a V, I, L, M, G, S, E, D, N, Q, K, or H, for example valine, isoleucine, leucine, methionine, glycine, serine, aspartic acid, glutamic acid, asparagine, glutamine, lysine or histidine, and an I, L, M, V or A, for example isoleucine, respectively, and provided that the GII.4_A39X+R53x VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_A39X+P80x VP1, where X=V, I, L, M, G, S, E, D, N, Q, K, or H, and x=S, N, C, T, A, K, or H, VP1): wherein the alanine and proline corresponding to amino acids 43 and 84, respectively, of norovirus VP1 genotype GI.1 (SEQ ID NO:1) have been substituted or mutated, for example but not limited to, to valine, isoleucine, leucine, methionine, glycine, serine, aspartic acid, glutamic acid, asparagine, glutamine, lysine, or histidine, and serine, asparagine, cysteine, threonine, alanine, lysine, or histidine, respectively (e.g. GII.4_A39V+P80S; SEQ ID NO:67, FIG. 32O), or a sequence that exhibits from about 80-100% or any amount therebetween, sequence similarity with the amino acid sequence of the GII.4_A39X+P80x VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_A39V+P80S VP1 protein (SEQ ID NO:67, FIG. 32O), provided that the substitutions, modifications or mutations at the positions corresponding to amino acids 43 and 84 of norovirus VP1 genotype GI.1 remain a V, I, L, M, G, S, E, D, N, Q, K, or H, for example valine, isoleucine, leucine, methionine, glycine, serine, aspartic acid, glutamic acid, asparagine, glutamine, lysine, or histidine, and an S, N, C, T, A, K, or H, for example serine, asparagine, cysteine, threonine, alanine, lysine, or histidine, respectively, and provided that the GII.4_A39X+P80x VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_V47P+P80S VP1 (GII.4_V47X, where X=P or G+P80x, where x=S, N, C, T, A, K, or H VP1): wherein the valine and proline corresponding to amino acids 51 and 84, respectively, of norovirus VP1 genotype GI.1 (SEQ ID NO:1) have been substituted or mutated, for example, to proline and serine, asparagine, cysteine, threonine, alanine, lysine, or histidine, respectively (e.g. GII.4_V47P+P80S; SEQ ID NO:69, FIG. 32Q), or a sequence that exhibits from about 80-100% or any amount therebetween, sequence similarity with the amino acid sequence of the GII.4_V47P+P80S VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_V47P+P80S VP1 protein (SEQ ID NO:69, FIG. 32Q), provided that the substitutions, modifications or mutations at the positions corresponding to amino acids 51 and 84 of norovirus VP1 genotype GI.1 remain a P or G, for example proline, and an S, N, C, T, A, K, or H, for example serine, asparagine, cysteine, threonine, alanine, lysine, or histidine, respectively, and provided that the GII.4_V47X+P80x VP1 protein induces immunity to norovirus when administered to a subject. The sequence encoding the GII.4 VP1 may be obtained from any GII.4 strain, for example, but not limited to GII.4/Sydney/NSW0514/2012/(SEQ ID NO:16, amino acid; SEQ ID NO:52, nucleotide; FIGS. 19A and 19B).

GII.4_R53I+P80S VP1 (GII.4_R53X, where X=I, L, V, A or M+P80x, where x=S, N, C, T, A, K, or H, VP1): wherein the arginine and proline corresponding to amino acids 57 and 84, of norovirus VP1 genotype GI.1 (SEQ ID NO:1) have been mutated, for example, to an isoleucine and a serine, asparagine, cysteine, threonine, alanine, lysine, or histidine, respectively (e.g. GII.4_R53I+P80S; SEQ ID NO:71, FIG. 32S), or a sequence that exhibits from about 80-100% or any amount therebetween, sequence similarity with the amino acid sequence of the GII.4_R53I+P80S VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_R53I+P80S VP1 protein (SEQ ID NO:71, FIG. 32S), provided that the substitution, modification or mutation at the position corresponding to amino acids 57 and 84 of norovirus VP1 genotype GI.1 remain an I, L, V, A or M, for example isoleucine, and an S, N, C, T, A, K, or H, for example serine, asparagine, cysteine, threonine, alanine, lysine, histidine, respectively, and provided that the GII.4_R53X+P80x VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_P80S+S90L VP1 (GII.4_P80X, where X=S, N, C, T, A, K, or H+S90x, where x=L, I, M, A or V, VP1): wherein the proline and serine corresponding to amino acids 84 and 94, respectively, of norovirus VP1 genotype GI.1 (SEQ ID NO:1) have been mutated, for example, to serine, asparagine, cysteine, threonine, alanine, lysine, or histidine, and leucine, respectively (e.g. GII.4_P80S+S90L; SEQ ID NO:73, FIG. 32U), or a sequence that exhibits from about 80-100% or any amount therebetween, sequence similarity with the amino acid sequence of the GII.4_P80S+S90L VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_P80S+S90L VP1 protein (SEQ ID NO:73, FIG. 32U), provided that the substitutions, modifications or mutations at the positions corresponding to amino acids 84 and 94 of norovirus VP1 genotype GI.1 remain an S, N, C, T, A, K, or H, for example serine, asparagine, cysteine, threonine, alanine, lysine, or histidine and an L, I, M, A or V, for example leucine, respectively, and provided that the GII.4_P80X+S90x VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_A39X+R53x+P80z VP1, where X=V, I, L, M, G, S, E, D, N, Q, K, or H, where x=I, L, M, A or V, and z=S, N, C, T, A, K, or H, wherein the alanine and arginine corresponding to amino acids 43, 57 and 84, respectively, of norovirus VP1 genotype GI.1 (SEQ ID NO:1) have been substituted or mutated, for example, at position 39, to valine, isoleucine, leucine, methionine, glycine, serine, aspartic acid, glutamic acid, asparagine, glutamine, lysine, or histidine, at portion 53 to isoleucine, and at position 80 to serine, asparagine, cysteine, threonine, alanine, lysine, or histidine, respectively (e.g. GII.4_A39V+R53I+P80S; SEQ ID NO:190, FIG. 32CC), or a sequence that exhibits from about 80-100% or any amount therebetween, sequence similarity with the amino acid sequence of the GII.4_A39V+R53I+P80S VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_A39V+R53I+P80S VP1 protein (SEQ ID NO:190, FIG. 32CC), provided that the substitutions, modifications or mutations at the positions corresponding to amino acids 43, 57 and 84 of norovirus VP1 genotype GI.1 remain a V, I, L, M, G, S, E, D, N, Q, K, or H, for example valine, isoleucine, leucine, methionine, glycine, serine, aspartic acid, glutamic acid, asparagine, glutamine, lysine, or histidine, an I, L, M, V or A, for example isoleucine, and an S, N, C, T, A, K, or H, for example serine, asparagine, cysteine, threonine, alanine, lysine, or histidine, respectively, and provided that the GII.4_A39X+R53x+P80z VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_P80S+Δ35-42 VP1 (GII.4_P80X, where X=S, N, C, T, A, K, or H, +Δ35-42, VP1): wherein the proline corresponding to position 84 of norovirus VP1 genotype GI.1 (SEQ ID NO:1) has been mutated, for example, to serine, asparagine, cysteine, threonine, alanine, lysine, or histidine, and the amino acids corresponding to positions 39-46 of norovirus VP1 genotype GI.1 have been deleted (GII.4_P80S+Δ35-42; SEQ ID NO:75, FIG. 32W), or a sequence that exhibits from about 80-100% or any amount therebetween, sequence similarity with the amino acid sequence of the GII.4_P80S+Δ35-42 VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_P80S+Δ35-42 VP1 protein (SEQ ID NO:75, FIG. 32W), provided that the substitution, modification or mutation at the position corresponding to amino acid 84 of norovirus genotype GI.1 remains an S, N, C, T, A, K, or H, for example serine, asparagine, cysteine, threonine, alanine, lysine, or histidine, and the amino acids corresponding to positions 39-46 of norovirus VP1 genotype GI.1 remain deleted, and that the GII.4_P80X+Δ35-42 VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.4_P80S+SSTAVATA VP1 (GII.4_P80X, where X=S, N, C, T, A, K, or H+SSTAVATA, VP1): wherein the proline corresponding to position 84 of norovirus VP1 genotype GI.1 (SEQ ID NO:1) has been mutated, for example, to serine, asparagine, cysteine, threonine, alanine, lysine, or histidine, and the amino acids corresponding to positions 39-46 of norovirus VP1 genotype GI.1 have been mutated to the peptide sequence SSTAVATA (SEQ ID NO:168; GII.4_P80S+SSTAVATA; SEQ ID NO:77, FIG. 32Y), or a sequence that exhibits from about 80-100% or any amount therebetween, sequence similarity with the amino acid sequence of the mut GII.4_P80S+SSTAVATA VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_P80S+SSTAVATA VP1 protein (SEQ ID NO:77, FIG. 32Y), provided that the position corresponding to amino acid 84 or norovirus VP1 genotype GI.1 remains an S, N, C, T, A, K, or H, for example serine, asparagine, cysteine, threonine, alanine, lysine, or histidine, and the positions corresponding to amino acids 39-46 of norovirus VP1 genotype GI.1 remain the peptide sequence SSTAVATA, and that the GII.4_P80X+SSTAVATA VP1 protein induces immunity to norovirus when administered to a subject. The sequence encoding the GII.4 VP1 may be obtained from any GII.4 strain, for example, but not limited to GII.4/Sydney/NSW0514/2012/AU (SEQ ID NO:16, amino acid; SEQ ID NO:52, nucleotide; FIGS. 19A and 19B).

GII.6_E80S VP1 (GII.6_E80X, where X=S, N, C or T, VP1): wherein the glutamic acid corresponding to amino acid 84 of norovirus VP1 genotype GI.1 (SEQ ID NO:1) has been mutated, for example, to serine (GII.6_E80S; SEQ ID NO:79, FIG. 33A), or a sequence that exhibits from about 80-100% or any amount therebetween, sequence similarity with the amino acid sequence of the GII.6_E80S VP1 protein. For example, the GII.6 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.6_E80S VP1 protein (SEQ ID NO:79, FIG. 33A), provided that the substitution, modification or mutation at the position corresponding to amino acid 84 of norovirus VP1 genotype GI.1 remains an S, N, C or T, for example serine, and provided that the VP1 protein induces immunity to norovirus when administered to a subject. The sequence encoding the GII.6 VP1 may be obtained from any GII.6 strain, for example, but not limited to GII.6/Ohio/490/2012/USA (SEQ ID NO:20, amino acid; SEQ ID NO:21, nucleotide; FIGS. 21A and 21B).

GII.6_S90L VP1 (GII.6_S90X, where X=L, I, M, A or V, VP1): wherein the serine corresponding to amino acid 94 of norovirus VP1 genotype GI.1 (SEQ ID NO:1) has been mutated, for example, to leucine (GII.6_S90L; SEQ ID NO:81, FIG. 33C), or a sequence that exhibits from about 80-100% or any amount therebetween, sequence similarity with the amino acid sequence of the GII.6_S90L VP1 protein. For example, the GII.6 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.6_S90L VP1 protein (SEQ ID NO:81, FIG. 33C), provided that the substitution, modification or mutation at the position corresponding to amino acid 94 of norovirus VP1 genotype GI.1 remains an L, I, M or V, for example leucine, and provided that the VP1 protein induces immunity to norovirus when administered to a subject. The sequence encoding the GII.6 VP1 may be obtained from any GII.6 strain, for example, but not limited to GII.6/Ohio/490/2012/USA (SEQ ID NO:20, amino acid; SEQ ID NO:21, nucleotide; FIGS. 21A and 21B).

GII.6_E80S+S90L VP1 (GII.6_E80X, where X=S, N, C or T+S90X, where X=L, I, M, A or V, VP1): wherein the glutamic acid and serine corresponding to amino acids 84 and 94, respectively of norovirus VP1 genotype GI.1 (SEQ ID NO:1) have been mutated, for example, to serine and leucine, respectively (GII.6_E80S+S90L; SEQ ID NO:83, FIG. 33E), or a sequence that exhibits from about 80-100% or any amount therebetween, sequence similarity with the amino acid sequence of the GII.6_E80S+S90L VP1 protein. For example, the GII.6 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.6_E80S+S90L VP1 protein (SEQ ID NO:83, FIG. 33E), provided that the substitutions, modifications or mutations at the positions corresponding to amino acids 84 and 94 of norovirus VP1 genotype GI.1 remain an S, N, C or T, for example serine, and an L, I, M, A or V, for example leucine, respectively, and provided that the VP1 protein induces immunity to norovirus when administered to a subject. The sequence encoding the GII.6 VP1 may be obtained from any GII.6 strain, for example, but not limited to GII.6/Ohio/490/2012/USA (SEQ ID NO:20, amino acid; SEQ ID NO:21, nucleotide; FIGS. 21A and 21B).

GII.12_E80S VP1 (GII.12_E80X, where X=S, N, C or T, VP1): wherein the glutamic acid corresponding to amino acid 84 of norovirus VP1 genotype GI.1 (SEQ ID NO:1) has been mutated, for example, to serine (GII.12_E80S; SEQ ID NO:88, FIG. 34A), or a sequence that exhibits from about 80-100% or any amount therebetween, sequence similarity with the amino acid sequence of the GII.12_E80S VP1 protein. For example, the GII.12 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.12_E80S VP1 protein (SEQ ID NO:88, FIG. 34A), provided that the substitution, modification or mutation at the position corresponding to amino acid 84 of norovirus VP1 genotype GI.1 remains an S, N, C or T, for example serine, and provided that the VP1 protein induces immunity to norovirus when administered to a subject. The sequence encoding the GII.12 VP1 may be obtained from any GII.12 strain, for example, but not limited to GII.12/HS206/2010/USA (SEQ ID NO:19, amino acid; FIG. 23A).

GII.12_A90L VP1 (GII.12_A90X, where X=L, I, M or V, VP1): wherein the alanine corresponding to amino acid 94 of norovirus VP1 genotype GI.1 (SEQ ID NO:1) has been mutated, for example, to leucine (GII.12_A90L; SEQ ID NO:90, FIG. 34C), or a sequence that exhibits from about 80-100% or any amount therebetween, sequence similarity with the amino acid sequence of the GII.12_A90L VP1 protein. For example, the GII.12 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.12_A90L VP1 protein (SEQ ID NO:90, FIG. 34C), provided that the substitution, modification or mutation at the position corresponding to amino acid 94 of norovirus VP1 genotype GI.1 remains an L, I, M or V, for example leucine, and provided that the VP1 protein induces immunity to norovirus when administered to a subject. The sequence encoding the GII.12 VP1 may be obtained from any GII.12 strain, for example, but not limited to GII.12/HS206/2010/USA (SEQ ID NO:19, amino acid; FIG. 23A).

GII.12_E80S+A90L VP1 (GII.12_E80X, where X=S, N, C or T+A90X, where X=L, I, M or V, VP1): wherein the glutamic acid and alanine corresponding to amino acids 84 and 94, respectively, of norovirus VP1 genotype GI.1 (SEQ ID NO:1) have been mutated, for example, to serine and leucine, respectively (GII.12_E80S+A90L; SEQ ID NO:92, FIG. 34E), or a sequence that exhibits from about 80-100% or any amount therebetween, sequence similarity with the amino acid sequence of the GII.12_E80S+A90L VP1 protein. For example, the GII.12 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.12_E80S+A90L VP1 protein (SEQ ID NO:92, FIG. 34E), provided that the substitutions, modifications or mutations at the positions corresponding to amino acids 84 and 94 of norovirus VP1 genotype GI.1 remain an S, N, C or T, for example serine, and an L, I. M or V, for example leucine, respectively, and provided that the VP1 protein induces immunity to norovirus when administered to a subject. The sequence encoding the GII.12 VP1 may be obtained from any GII.12 strain, for example, but not limited to GII.12/HS206/2010/USA (SEQ ID NO:19, amino acid; FIG. 23A).

GII.17_A39V VP1 (GII.17_A39X, where X=V, I, L or M, VP1): wherein the alanine corresponding to amino acid 43 of norovirus VP1 genotype GI.1 (SEQ ID NO:1) has been mutated, for example, to valine (GII.17_A39V; SEQ ID NO:192, FIG. 34G), or a sequence that exhibits from about 80-100% or any amount therebetween, sequence similarity with the amino acid sequence of the GII.17_A39V VP1 protein. For example, the GII.17 VP1 protein may have from about 0, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.17_A39V VP1 protein (SEQ ID NO:192, FIG. 34G), provided that the substitution, modification or mutation at the position corresponding to amino acid 43 of norovirus VP1 genotype GI.1 remains a V, I, L or M, for example valine, and provided that the VP1 protein induces immunity to norovirus when administered to a subject. The sequence encoding the GII.17 VP1 may be obtained from any GII.17 strain, for example, but not limited to Hu/GII.17/Kawasaki323/2014/JP (SEQ ID NO:24, amino acid; SEQ ID NO:25, nucleotide; FIGS. 26A and 26B).

GII.17 R53I VP1 (GII.17_12531, where X=I, L, V, A or M, VP1): wherein the arginine corresponding to amino acid 57 of norovirus VP1 genotype GI.1 (SEQ ID NO:1) has been mutated, for example, to isoleucine (GII.17_R53I; SEQ ID NO:194, FIG. 34I), or a sequence that exhibits from about 80-100% or any amount therebetween, sequence similarity with the amino acid sequence of the GII.17_R53I VP1 protein. For example, the GII.17 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.17_R53I VP1 protein (SEQ ID NO:194, FIG. 34I), provided that the substitution, modification or mutation at the position corresponding to amino acid 57 of norovirus VP1 genotype GI.1 remains an I, L, V, A or M, for example isoleucine, and provided that the VP1 protein induces immunity to norovirus when administered to a subject. The sequence encoding the GII.17 VP1 may be obtained from any GII.17 strain, for example, but not limited to Hu/GII.17/Kawasaki323/2014/JP (SEQ ID NO:24, amino acid; SEQ ID NO:25, nucleotide; FIGS. 26A and 26B).

GII.17_A90L VP1 (GII.4_A90X, where X=L, I, M or V, VP1): wherein the serine corresponding to amino acid 94 of norovirus VP1 genotype GI.1 (SEQ ID NO:1) has been mutated, for example, to leucine (GII.17_A90L; SEQ ID NO:196, FIG. 34K), or a sequence that exhibits from about 80-100% or any amount therebetween, sequence similarity with the amino acid sequence of the GII.17_A90L VP1 protein. For example, the GII.17 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.17_A90L VP1 protein (SEQ ID NO:196, FIG. 34K), provided that the substitution, modification or mutation at the position corresponding to amino acid 94 of norovirus VP1 genotype GI.1 remains an L, I, M or V, for example leucine, and provided that the VP1 protein induces immunity to norovirus when administered to a subject. The sequence encoding the GII.17 VP1 may be obtained from any GII.17 strain, for example, but not limited to Hu/GII.17/Kawasaki323/2014/JP (SEQ ID NO:24, amino acid; SEQ ID NO:25, nucleotide; FIGS. 26A and 26B).

GII.17_A39V+R53I VP1 (GII.17_A39X, where X=V, I, L or M+R53X, where X=I, L, M, A or V, VP1): wherein the alanine and arginine corresponding to amino acids 43 and 57, respectively, of norovirus VP1 genotype GI.1 (SEQ ID NO:1) have been mutated, for example, to valine and isoleucine, respectively (GII.17_A39V+R53I; SEQ ID NO:198, FIG. 34M), or a sequence that exhibits from about 80-100% or any amount therebetween, sequence similarity with the amino acid sequence of the GII.17_A39V+R53I VP1 protein. For example, the GII.17 VP1 protein may have from about 0, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.17_A39V+R53I VP1 protein (SEQ ID NO:198, FIG. 34M), provided that the substitutions, modifications or mutations at the positions corresponding to amino acid 43 and 57 of norovirus VP1 genotype GI.1 remain a V, I, L or M, for example valine, and an I, L, M, V or A, for example isoleucine, respectively, and provided that the VP1 protein induces immunity to norovirus when administered to a subject. The sequence encoding the GII.17 VP1 may be obtained from any GII.17 strain, for example, but not limited to Hu/GII.17/Kawasaki323/2014/JP (SEQ ID NO:24, amino acid; SEQ ID NO:25, nucleotide; FIGS. 26A and 26B).

GII.17_E80S+A90L VP1 (GII.4_E80X, where X=S, N, C or T+A90X, where X=L, I, M or V, VP1): wherein the glutamic acid and alanine corresponding to amino acids 84 and 94, respectively, of norovirus VP1 genotype GI.1 (SEQ ID NO:1) have been mutated, for example, to serine and leucine, respectively (GII.17_E80S+A90L; SEQ ID NO:200, FIG. 34O), or a sequence that exhibits from about 80-100% or any amount therebetween, sequence similarity with the amino acid sequence of the GII.17_E80S+A90L VP1 protein. For example, the GII.17 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.17_E80S+A90L VP1 protein (SEQ ID NO:200, FIG. 34O), provided that the substitutions, modifications or mutations at the positions corresponding to amino acids 84 and 94 of norovirus VP1 genotype GI.1 remain an S, N, C or T, for example serine, and an L, I, M or V, for example leucine, respectively, and provided that the VP1 protein induces immunity to norovirus when administered to a subject. The sequence encoding the GII.17 VP1 may be obtained from any GII.17 strain, for example, but not limited to Hu/GII.17/Kawasaki323/2014/JP (SEQ ID NO:24, amino acid; SEQ ID NO:25, nucleotide; FIGS. 26A and 26B).

VLP Yield

Figure 5A:
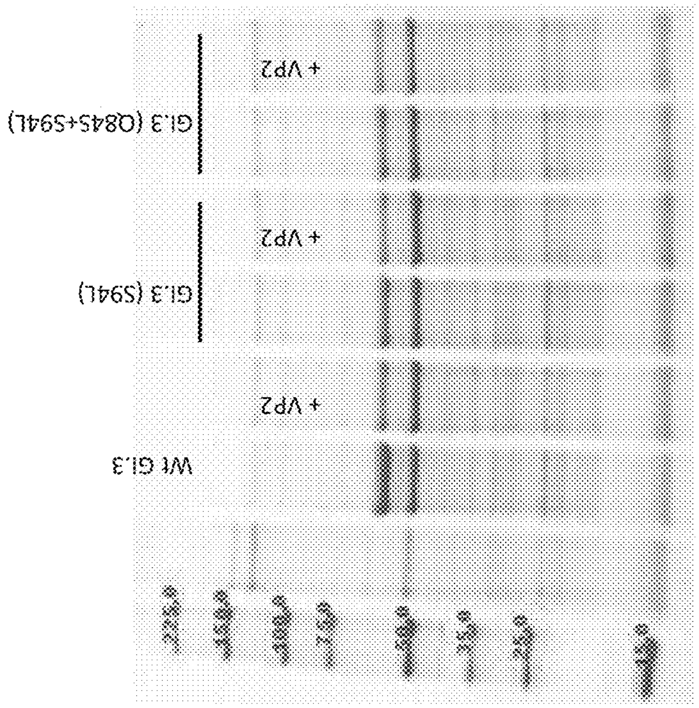
FIG. 5A shows a Coomassie-stained SDS-PAGE of crude protein extracts prepared from agroinfiltrated *N. benthamiana* leaves, 9 days post infiltration (DPI) with wt hCod GI.3/S29/2008/Lila Edet/Sweden VP1 (Construct #: 3979; SEQ ID NO:7 (nucleotide); SEQ ID NO:6 (amino acid)), mut hCod GI.3/S29/2008/Lila Edet/Sweden_S94L VP1 (Construct #: 4141; SEQ ID NO:9 (nucleotide); SEQ ID NO:8 (amino acid)), or mut hCod GI.3/S29/2008/Lila Edet/Sweden_Q84S+S94L VP1 (Construct #: 4142; SEQ ID NO:11 (nucleotide); SEQ ID NO:10 (amino acid)), with and without wt hCod GI.3/S29/2008/Lila Edet/Sweden VP2 (Construct #: 3303; SEQ ID NO:95 (nucleotide); SEQ ID NO:94 (amino acid)). First lane: crude protein extracts prepared from mock infiltrated *N. benthamiana* leaves.
Figure 5B:
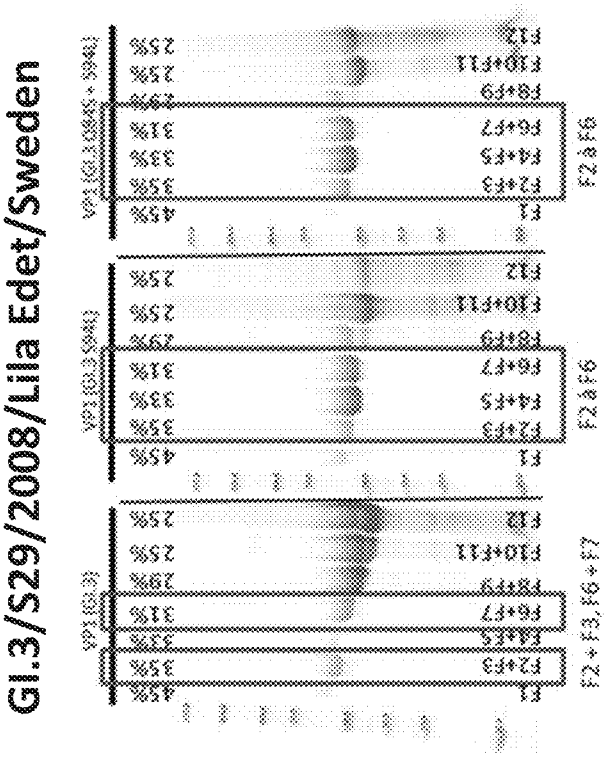
FIG. 5B shows a Coomassie-stained SDS-PAGE analysis of iodixanol density gradient fractions of crude protein extracts prepared from *N. benthamiana* leaves expressing wt hCod GI.3/S29/2008/Lila Edet/Sweden VP1 (Construct #: 3979, left panel), mut hCod GI.3/S29/2008/Lila Edet/Sweden VP1 S94L (Construct #: 4141, middle panel), or mut hCod GI.3/S29/2008/Lila Edet/Sweden VP1_Q84S+S94L (Construct #: 4142, right panel).

An example of an improved characteristic of VP1 may be observed comparing the yields of VLPs comprising GI.3 VP1 protein is shown with reference to FIG. 5B (see Example 3). Expression of modified norovirus VP1 proteins GI.3_S94X , where X=L, V, I, M, T, E, D, N, Q, K, or H (see FIG. 5F), GI.3_M57I+S94L (see FIG. 5D), and GI.3_Q84S+S94L (see FIG. 5B) in plants resulted in similar or higher VLPs yields as compared to the yield of wildtype GI.3 VP1. Furthermore, expression of modified norovirus VP1 proteins GI.7_M57X, where X=I, L, G, S, T, N, Q, K, or H (see FIG. 6F) in plants resulted in similar or higher VLPs yields as compared to the yield of wildtype GI.7 VP1.

An analogous improved characteristic of increased VLP yield is shown with reference to FIGS. 9A-9E, and 9H. VLPs comprising norovirus modified VP1 proteins GII.4_R53I (FIG. 9D), GII.4_P80X, where X=S, A, N, K, or H (FIGS. 9B and 9H), GII.4_P80S+R53I (FIG. 9D), GII.4_P80S+A39X, where X=V, I, M, T, E, D, N, Q, K, or H (FIGS. 9C and 9I), GII.4_P80S+S90L (FIG. 9B), GII.4_P80S+Δ35-42 (FIG. 9C), GII.4_P80S+SSTAVATA (FIG. 9F), and GII.4_A39V+R53I_P80S (FIG. 9G), exhibited enhanced VLP yield in plants, while GII.4_A39V and GII.4_V47P exhibited a slight increase in protein yield, as compared to VLPs comprising wildtype GII.4 VP1.

Figure 10A:
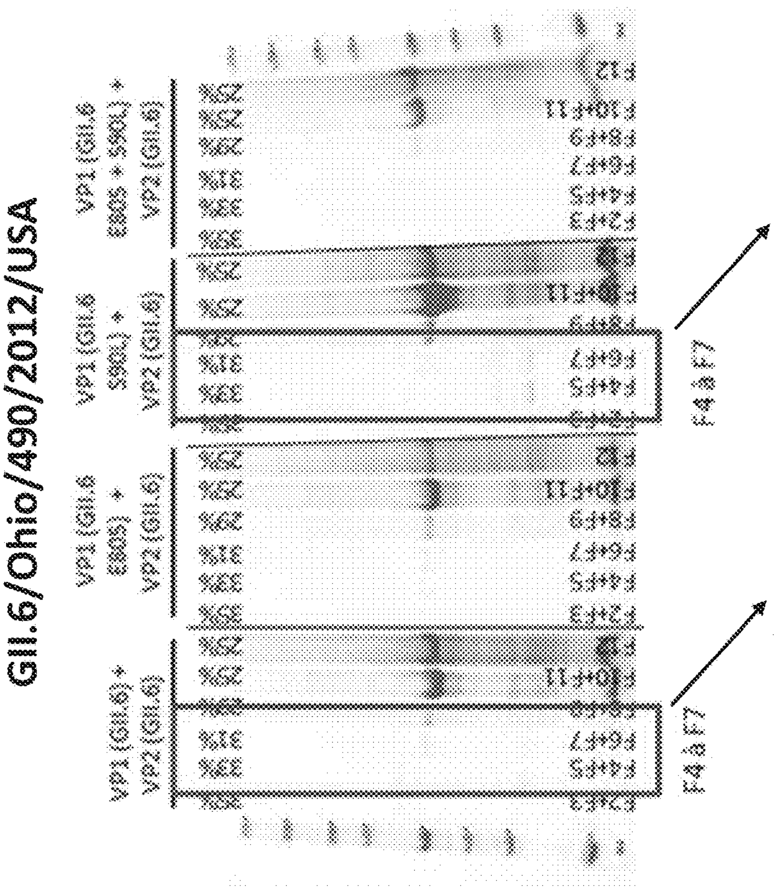
FIG. 10A shows a Coomassie-stained SDS-PAGE analysis of iodixanol density gradient fractions of crude protein extracts prepared from *N. benthamiana* leaves expressing wt hCod GII.6/Ohio/490/2012/USA VP1 (Construct #: 3993; SEQ ID NO:21 (nucleotide); SEQ ID NO: 20 (amino acid)) and wt hCod GII.6/HS245/2010/USA VP2 (Construct #: 3307; SEQ ID NO:97 (nucleotide); SEQ ID NO:96 (amino acid)), mut hCod GII.6/Ohio/490/2012/USA_E80S VP1 (Construct #: 4149; SEQ ID NO:80 (nucleotide); SEQ ID NO:79 (amino acid)) and wt hCod GII.6/HS245/2010/USA VP2 (Construct #: 3307), mut hCod GII.6/Ohio/490/2012/USA_S90L VP1 (Construct #: 4150; SEQ ID NO:82 (nucleotide); SEQ ID NO:81 (amino acid))) and wt hCod GII.6/HS245/2010/USA VP2 (Construct #3307), or mut hCod GII.6/Ohio/490/2012/USA_E80S+S90L VP1 (Construct #: 4151; SEQ ID NO:84 (nucleotide); SEQ ID NO:83 (amino acid)) and wt hCod GII.6/HS245/2010/USA VP2 (Construct #: 3307).
Figure 10B:
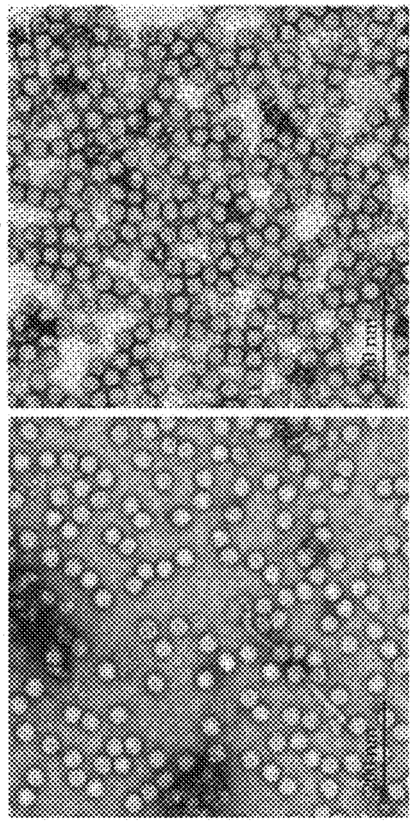
FIG. 10B shows transmission electron micrographs (TEM) of virus like particles (VLPs) purified from 31-35% iodixanol gradient fractions of crude protein extracts prepared from *N. benthamiana* leaves expressing wt hCod GII.6/Ohio/490/2012/USA VP1 (Construct #: 3993) and wt hCod GII.6/HS245/2010/USA VP2 (Construct #: 3307), mut hCod GII.6/Ohio/490/2012/USA_S90L VP1 (Construct #: 4150) and wt hCod GII.6/HS245/2010/USA VP2 (Construct #: 3307). 15,000× magnification; scale bar=200 nm.

Increased VLP yield, compared to wild type was also observed in plant extracts expressing GII.6_S90L VP1 (FIGS. 10A and 10B).

Figure 8A:
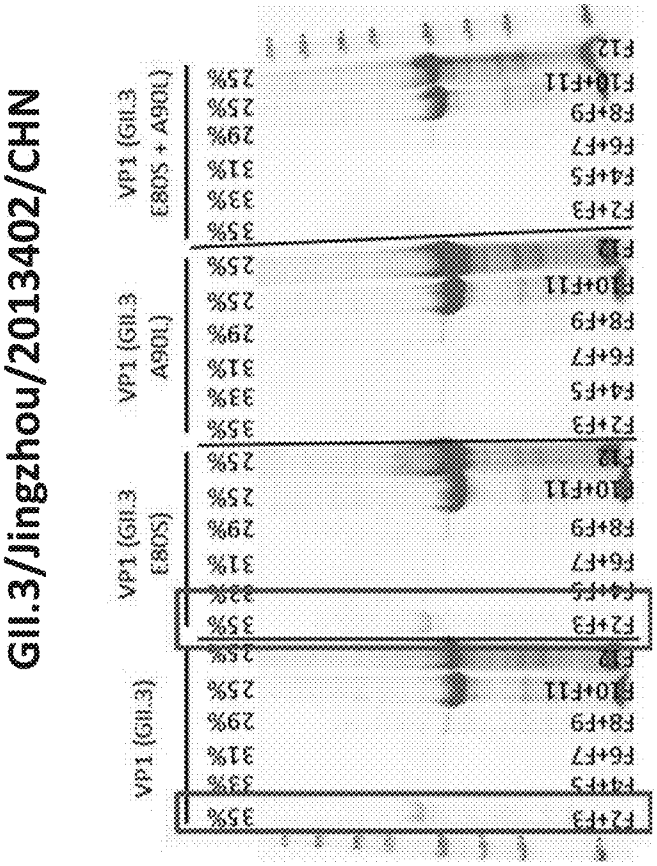
FIG. 8A shows a Coomassie-stained SDS-PAGE analysis of iodixanol density gradient fractions of crude protein extracts prepared from *N. benthamiana* leaves expressing, from left to right, wt hCod GII.3/Jingzhou/2013402/CHN VP1 (Construct #: 3983; SEQ ID NO:45 (nucleotide); SEQ ID NO: 15 (amino acid; first panel)), mut hCod GII.3/Jingzhou/2013402/CHN_E80S VP1 (Construct #: 4146; SEQ ID NO:47 (nucleotide); SEQ ID NO:46 (amino acid; second panel)), mut hCod GII.3/Jingzhou/2013402/CHN_A90L VP1 (Construct #: 4147; SEQ ID NO:49 (nucleotide); SEQ ID NO:48 (amino acid; third panel)), or mut hCod GII.3/Jingzhou/2013402/CHN_E80S+A90L VP1 (Construct #: 4148, SEQ ID NO:51 (nucleotide); SEQ ID NO:50 (amino acid; fourth panel)).

VLPs comprising modified VP1 protein with a substitution of an amino acid at position 84 (GI strains) or position 80 (GII strains, corresponding to, or in alignment with, position 84 of GU VP1) exhibited the same (GI.3_Q84S; GI.5_Q84S, also see FIG. 6B; GII.3_E80S, also see FIG. 8A), or an increased (GI.7_R84S; GI.7_M57I+R84S; also see FIG. 6D; GII.4_P80S also see FIGS. 9B-9F;

GII.12_E80S) VLP yield when compared to the yield of VLPs comprising the corresponding wild type (native) VP1 protein.

Figure 5C:
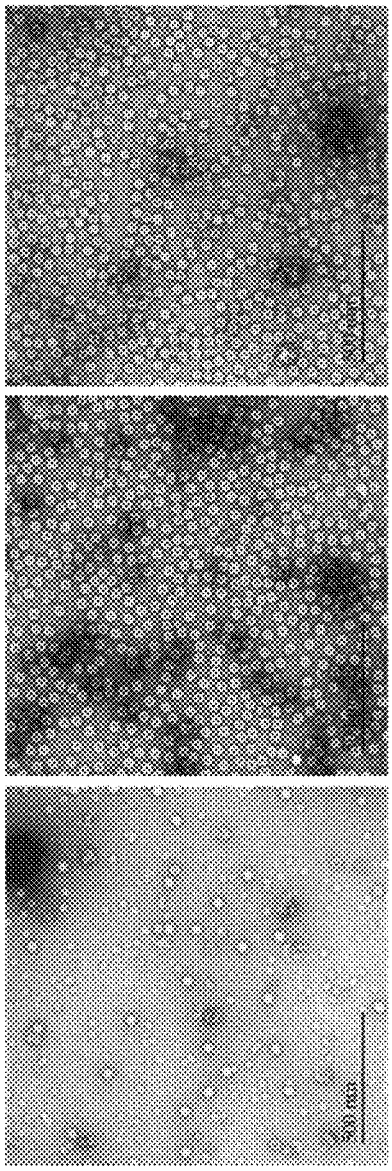
FIG. 5C shows transmission electron micrographs (TEM) of virus like particles (VLPs) purified from 31-35% iodixanol gradient fractions of crude protein extracts prepared from *N. benthamiana* leaves expressing wt hCod GI.3/S29/2008/Lila Edet/Sweden VP1 (Construct #: 3979, left panel; fractions F2+F3, F6+F7 of FIG. 5B), mut hCod GI.3/S29/2008/Lila Edet/Sweden VP1_S94L (Construct #: 4141, middle panel; fractions F2-F6 of FIG. 5B), or mut hCod GI.3/S29/2008/Lila Edet/Sweden VP1_Q84S+S94L (Construct #: 4142, right panel; fractions F2-F6 of FIG. 5B). 15,000× magnification; scale bar=500 nm.
Figure 5D:
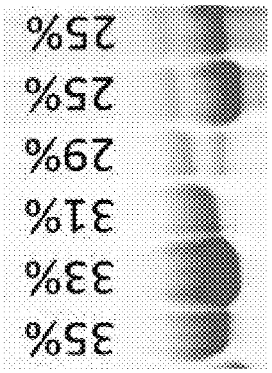
FIG. 5D shows a Coomassie-stained SDS-PAGE of crude protein extracts prepared from agroinfiltrated *N. benthamiana* leaves, 9 days post infiltration (DPI) with mut hCod GI.3/S29/2008/Lila Edet/Sweden_M57I+S94L VP1 (Construct #:4180; SEQ ID NO:171 (nucleotide); SEQ ID NO:172 (amino acid)).
Figure 5E:
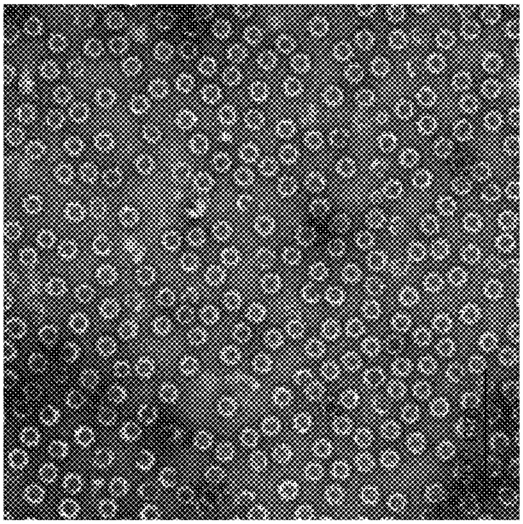
FIG. 5E shows transmission electron micrographs (TEM) of virus like particles (VLPs) purified from 31-35% iodixanol gradient fractions of crude protein extracts prepared from *N. benthamiana* leaves expressing mut hCod GI.3/S29/2008/Lila Edet/Sweden_M57I+S94L VP1 (Construct #: 4180); 15,000× magnification; scale bar=500 nm. FIGURE SF shows the relative yield of VLPs comprising non-native VP1 GI.3 with substitutions at amino acid position 94, compared to the VLP yield of wild-type GI.3 (GI.3 S94; set as "Fold Change" of 1): C #: construct number.
Figure 5F:
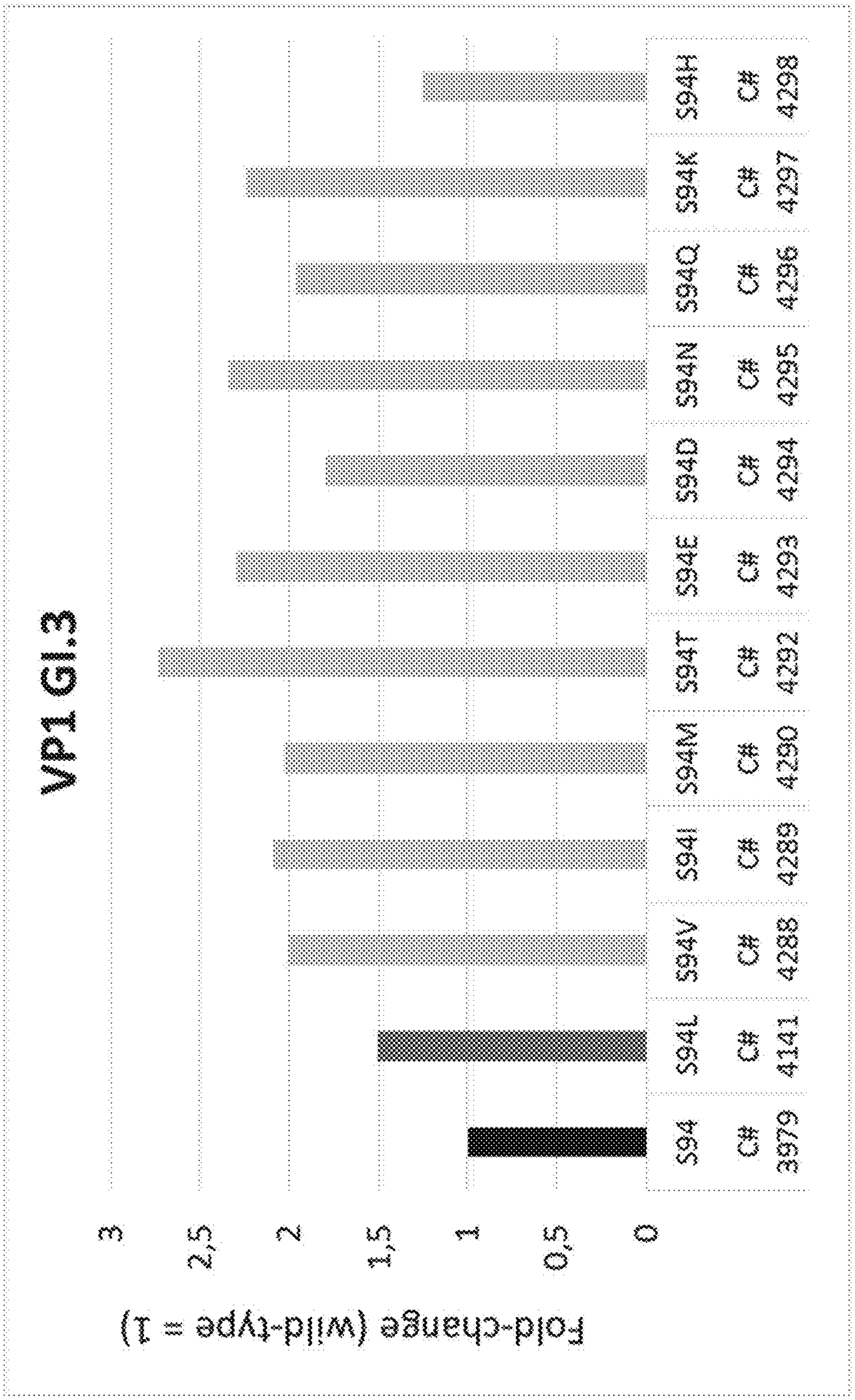

VLPs comprising modified VP1 protein with a substitution of an amino acid at position 94(GI strains) or at position 90 (GII strains, corresponding to, or in alignment with, position 94 of GU VP1) exhibited the same or an increase in VLP yield when compared to the yield of VLPs comprising the corresponding wild type, or native, VP1 protein, for all modified VP1 proteins that were examined (GI.3_S94X, where X=L, V, I, M, T, E, D, N, Q, K, or H (FIGS. 5B and 5F); GI.5_A94L (see FIG. 6B); GII.2_A90L (see FIG. 7B); GII.4_S90L (see FIG. 9B); GII.6_S90L (see FIG. 10A); GII.12_A90L (see FIG. 11B); and GII.17_A90L (see FIG. 11D).

Similarly, VLPs comprising modified VP1 protein with a substitution of an amino acid at positions 84 and 94 (GI strains) or positions 80 and 90 (GII strains, corresponding to, or in alignment with, position 84 and 94 of GU VP1) exhibited an increase in VLP yield when compared to the yield of VLPs comprising the corresponding wild type, or native, VP1 protein, for all modified VP1 proteins that were examined (GI.3_Q84S+S94L, also see FIG. 5B; GI.5_Q84S+A94L, also see FIG. 6B; GII.2_E80S+A90L, also see FIGS. 7B and 7C; GII.4_P80S+S90L, also see FIG. 9B; and GII.12_E80S+A90L, also see FIG. 11B).

Figure 9A:
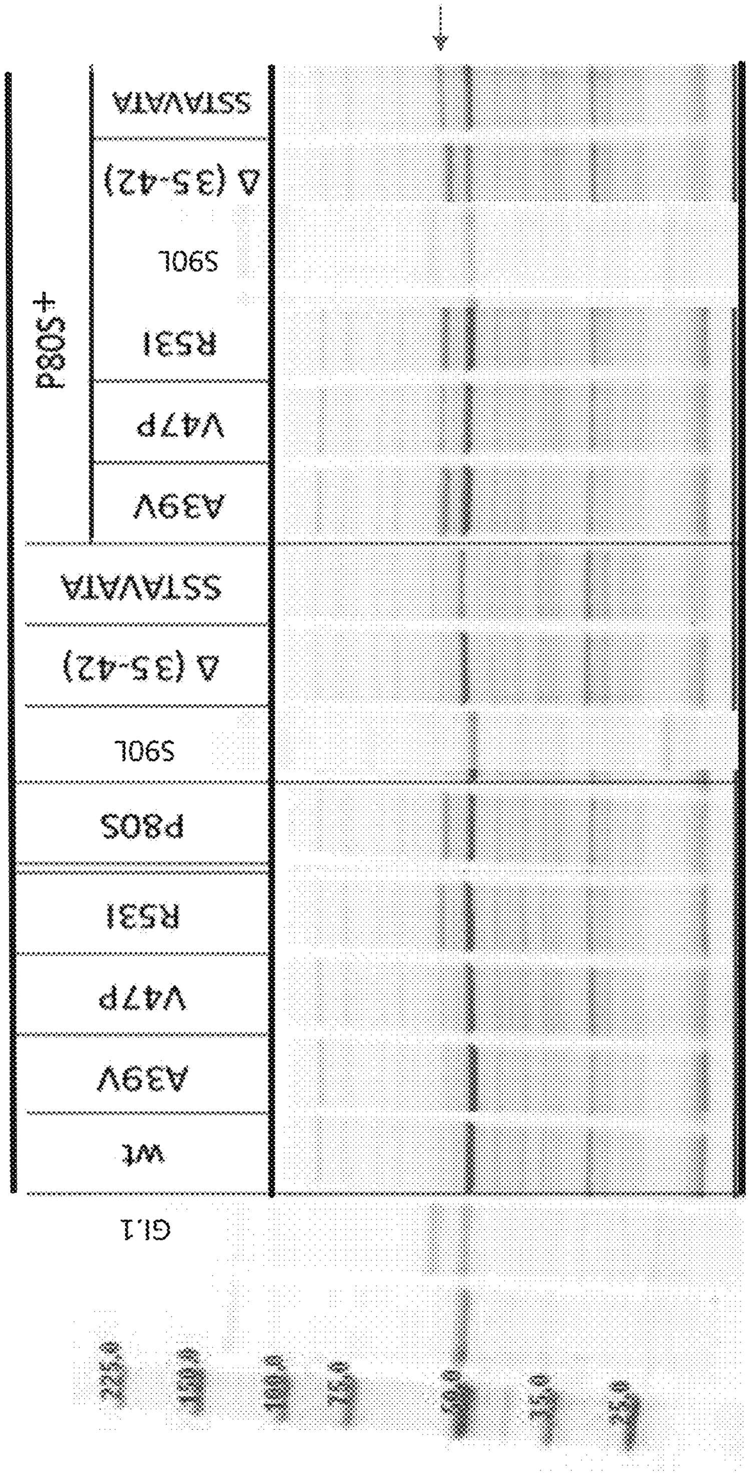
FIG. 9A shows a Coomassie-stained SDS-PAGE of crude protein extracts prepared from agroinfiltrated *N. benthamiana* leaves, 9 days post infiltration (DPI) with wt GI.1/United States/Norwalk/1968 VP1 (Construct #: 2724; SEQ ID NO:3 (nucleotide); SEQ ID NO:1 (amino acid)), wt hCod GII.4/Sydney/NSW0514/2012/AU VP1 (Construct #: 3760; SEQ ID NO:52 (nucleotide); SEQ ID NO:16 (amino acid)), mut hCod GII.4/Sydney/NSW0514/2012/AU_A39V VP1 (Construct #: 4155; SEQ ID NO:54 (nucleotide); SEQ ID NO:53 (amino acid)), mut hCod GII.4/Sydney/NSW0514/2012/AU_V47P VP1 (Construct #: 4156; SEQ ID NO:56 (nucleotide); SEQ ID NO:55 (amino acid)), mut hCod GII.4/Sydney/NSW0514/2012/AU_R53I VP1 (Construct #: 4157; SEQ ID NO:58 (nucleotide); SEQ ID NO:57 (amino acid)), mut hCod GII.4/Sydney/NSW0514/2012/AU_P80S VP1 (Construct #: 4133; SEQ ID NO:60 (nucleotide); SEQ ID NO:59 (amino acid)), mut hCod GII.4/Sydney/NSW0514/2012/AU_S90L VP1 (Construct #: 4134; SEQ ID NO:62 (nucleotide); SEQ ID NO:61 (amino acid)), mut hCod GII.4/Sydney/NSW0514/2012/AU_Δ35-42 VP1 (Construct #: 4158; SEQ ID NO:64 (nucleotide); SEQ ID NO:63 (amino acid)), mut hCod GII.4/Sydney/NSW0514/2012/AU_SSTAVATA VP1 (Construct #: 4159; SEQ ID NO:66 (nucleotide); SEQ ID NO:65 (amino acid)), mut hCod GII.4/Sydney/NSW0514/2012/AU_P80S+A39V (Construct #: 4165; SEQ ID NO:68 (nucleotide); SEQ ID NO:67 (amino acid)), mut hCod GII.4/Sydney/NSW0514/2012/AU_P80S+V47P VP1 (Construct #: 4166; SEQ ID NO:70 (nucleotide); SEQ ID NO:69 (amino acid)), mut hCod GII.4/Sydney/NSW0514/2012/AU_P80S+R53I VP1 (Construct #: 4167; SEQ ID NO:72 (nucleotide); SEQ ID NO:71 (amino acid)), mut hCod GII.4/Sydney/NSW0514/2012/AU_P80S+S90L VP1 (Construct #: 4135; SEQ ID NO:74 (nucleotide); SEQ ID NO:73 (amino acid)), mut hCod GII.4/Sydney/NSW0514/2012/AU_P80S+Δ35-42 VP1 (Construct #: 4168; SEQ ID NO:76 (nucleotide); SEQ ID NO:75 (amino acid)), or mut hCod GII.4/Sydney/NSW0514/2012/AU_P80S+SSTAVATA VP1 (Construct #: 4169; SEQ ID NO:78 (nucleotide); SEQ ID NO:77 (amino acid)). Arrow: VP1 norovirus protein; First lane=crude protein extracts prepared from mock infiltrated *N. benthamiana* leaves.

Additional modifications were also observed to increase VLP yield. These modifications include GI.3_M57I+S94L (FIG. 5D), GI.7_M57I (FIG. 6D), GI.7_M57I+R84S (FIG. 6D), GII.2_A39V+E80S+A90L (FIG. 7C), GII.2_R53I+E80S+A90L (FIG. 7C), GII.4_R53I (FIG. 9D), GII.4_A39V+P80X, where X=S, A, N, K, or H (FIGS. 9C and 9I); GII.4_R53I+P80S (FIG. 9D); GII.4_V47P+P80S (FIG. 9E); GII.4_Δ35-42+P80S (FIG. 9C), and GII.4_A39V+R53I+P80S (FIG. 9G).

Size, Density, Stability and Quality of VLPs

As shown in FIG. 5B, mutant norovirus VP1 proteins GI.3_S94L and GI.3_Q84S+S94L, exhibited the improved characteristic of VLPs having greater densities (determined by Coomassie stained SDS PAGE of iodixanol density gradient fractions of protein extracts), so that the VLPs are observed in fraction 1 (F1) and peaking in fractions F2-F6 as compared to wildtype norovirus GI.3 VP1. These results indicate that the assembly of native GI.3 VLPs may be less stable than GI.3_S94L VLPs and the native GI.3 VLP may be more susceptible to malformed capsid particles and the generation of fragmentation products. As a result, the VLPs comprising GI.3_S94L VP1, GI.3_M57I+S94L and GI.3_Q84S+S94L VP1 exhibit greater structural integrity than wildtype GI.3 VP1. It is also observed that VLPs comprising GI.3_S94L VP1, GI.3_M57I+S94L and GI.3_Q84S+S94L VP1 comprise a greater relative proportion of 38 nm diameter VLPs vs. 23 nm diameter VLPs than wildtype (FIGS. 5C and 5E) as determined using transmission electron micrography (TEM).

Figure 6A:
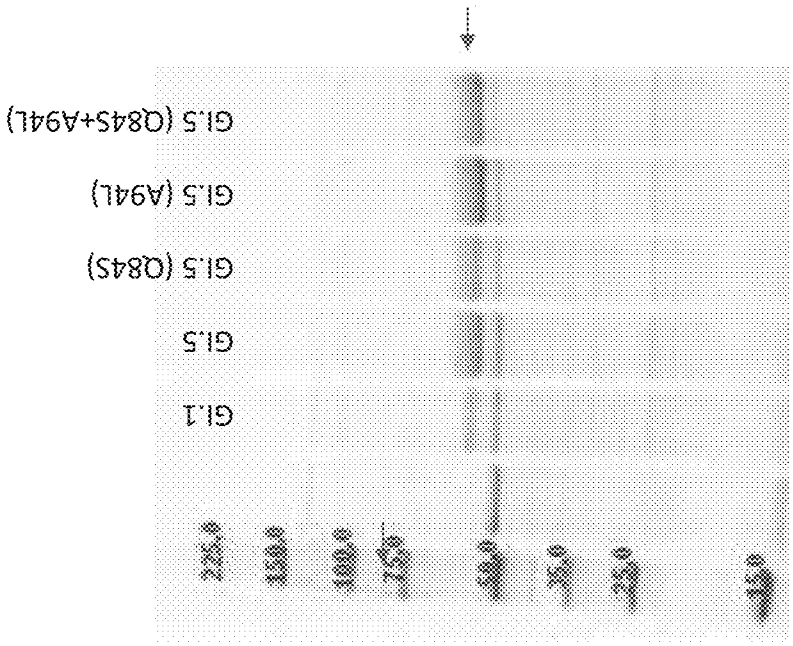
FIG. 6A shows a Coomassie-stained SDS-PAGE of crude protein extracts prepared from agroinfiltrated *N. benthamiana* leaves, 9 days post infiltration (DPI) with wt hCod GI.1/United States/Norwalk/1968 VP1 (Construct #: 2724; SEQ ID NO:3 (nucleotide); SEQ ID NO:1 (amino acid)), wt hCod GI.5/Siklos/HUN5407/2013/HUN VP1 (Construct #: 3980; SEQ ID NO:33 (nucleotide); SEQ ID NO:12 (amino acid)), mut hCod GI.5/Siklos/HUN5407/2013/HUN_Q84S VP1 (Construct #: 4130; SEQ ID NO:35 (nucleotide); SEQ ID NO:34 (amino acid)), mut hCod GI.5/Siklos/HUN5407/2013/HUN_A94L VP1 (Construct #: 4131; SEQ ID NO:37 (nucleotide); SEQ ID NO:36 (amino acid)) or mut hCod GI.5/Siklos/HUN5407/2013/HUN_Q84S+A94L VP1 (Construct #: 4132; SEQ ID NO:39 (nucleotide); SEQ ID NO:38 (amino acid)). Arrow: VP1 norovirus protein; First lane=crude protein extracts prepared from mock infiltrated *N. benthamiana* leaves.
Figures 6B, 6C:
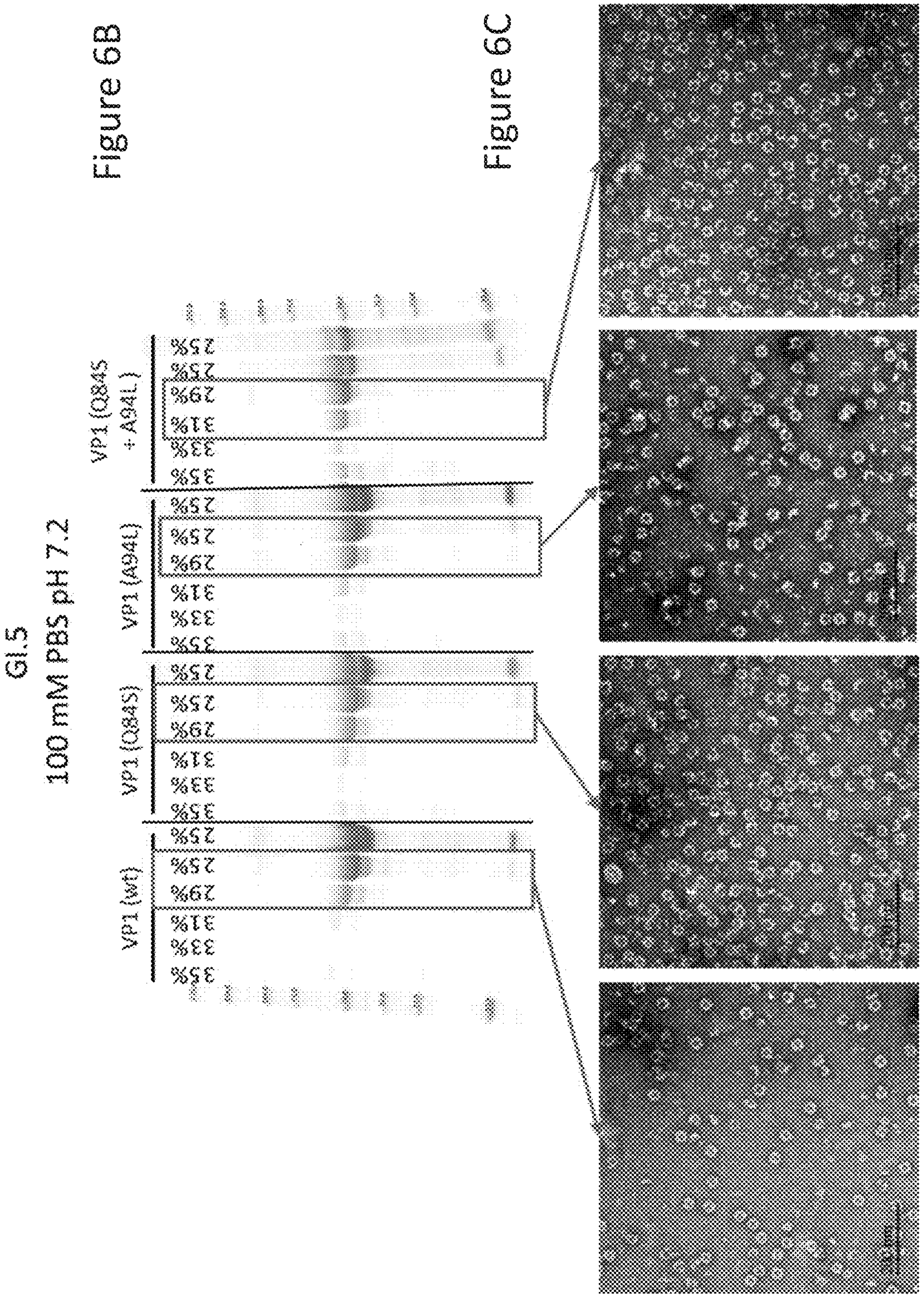
FIG. 6B shows a Coomassie-stained SDS-PAGE analysis of iodixanol density gradient fractions of crude protein extracts prepared from *N. benthamiana* leaves expressing, from left to right, wt hCod GI.5/Siklos/HUN5407/2013/HUN VP1 (Construct #3980), mut hCod GI.5/Siklos/HUN5407/2013/HUN_Q84S VP1 (Construct #: 4130, left panel), mut hCod GI.5/Siklos/HUN5407/2013/HUN_A94L VP1 (Construct #: 4131, middle panel), or mut HCod GI.5/Siklos/HUN5407/2013/HUN_Q84S+A94L VP1 (Construct #: 4132, right panel).
FIG. 6C shows transmission electron micrographs (TEM) of virus like particles (VLPs) purified from 31-35% iodixanol gradient fractions of crude protein extracts prepared from *N. benthamiana* leaves expressing, from left to right, wt hCod GI.5/Siklos/HUN5407/2013/HUN VP1 (Construct #3980), wt hCod GI.5/Siklos/HUN5407/2013/HUN_Q84S VP1 (Construct #: 4130, left panel), mut hCod GI.5/Siklos/HUN5407/2013/HUN_A94L VP1 (Construct #: 4131, middle panel), or mut hCod GI.5/Siklos/HUN5407/2013/HUN_Q84S+A94L VP1 (Construct #: 4132, right panel). 15,000× magnification; scale bar=200 nm.

VLPs comprising of GI.5_Q84S VP1, GI.5_A94L VP1, or GI.5_Q84S+A94L VP1 proteins exhibited an increase in yield, and GI.5_Q84S+A94L VP1 also exhibited greater density, stability and structural integrity (in a manner similar to that described above for VLPs produced using modified GI.3 VP1), as compared to wildtype norovirus GI.5 VP1 (FIG. 6B). As shown in FIG. 6C, the resulting VLPs had fewer damaged VLP particles, and a greater relative proportion of 38 nm diameter particles vs 23 nm diameter VLPs, as compared to wildtype.

Figure 6D:
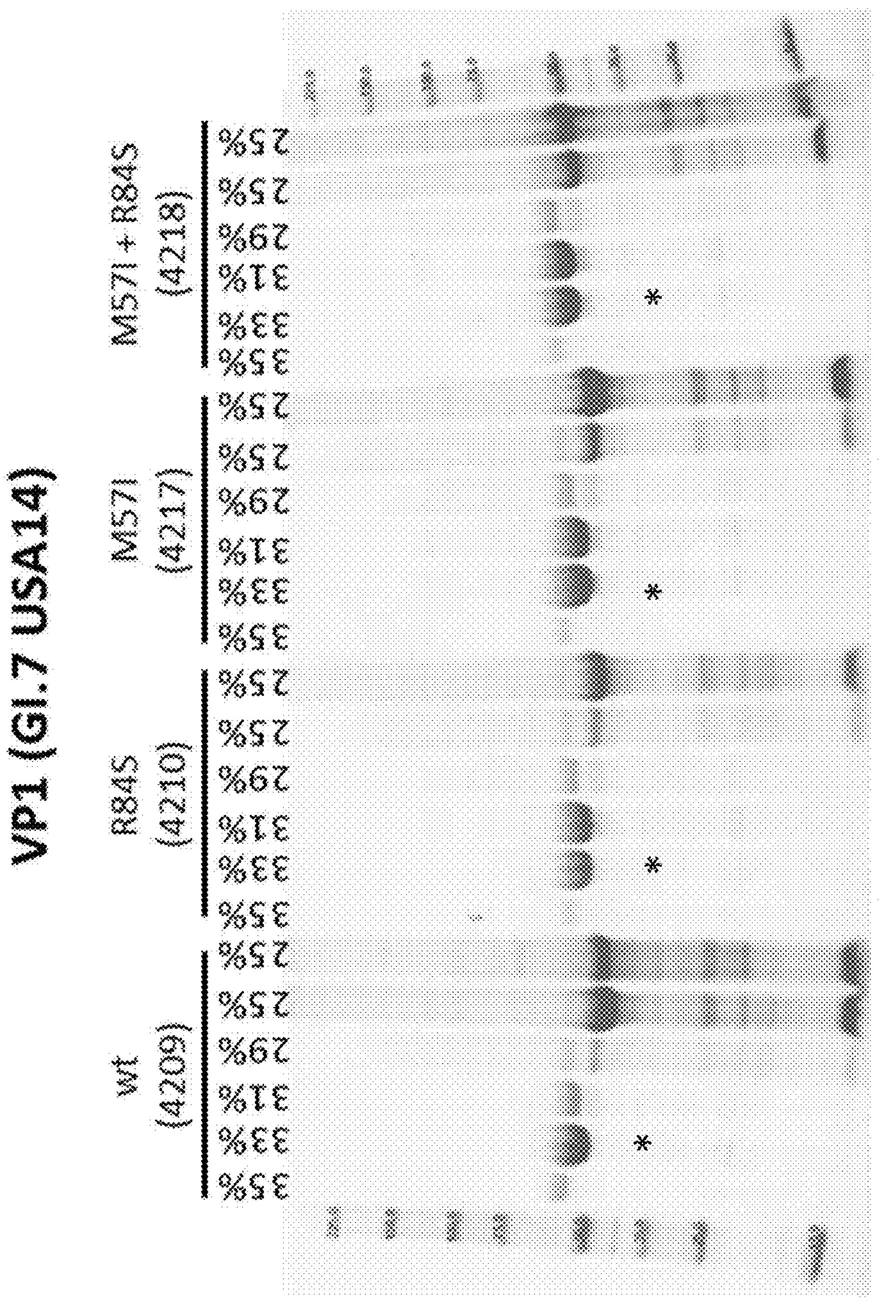
FIG. 6D shows a Coomassie-stained SDS-PAGE analysis of iodixanol density gradient fractions of crude protein extracts prepared from *N. benthamiana* leaves expressing, from left to right, wt hCod GI.7/GA5043/USA/2014 VP1 (Construct #4209; SEQ ID NO:101 (nucleotide); SEQ ID NO:204 (amino acid)), mut hCod GI.7/GA5043/USA/2014_R84S (Construct #4210; SEQ ID NO:176 (nucleotide); SEQ ID NO:177 (amino acid)), mut hCod GI.7/GA5043/USA/2014_M57I (Construct 4217; SEQ ID NO:178 (nucleotide); SEQ ID NO:179 (amino acid)), mut hCod GI.7/GA5043/USA/2014_M57I+R84S Construct #4218; SEQ ID NO:180(nucleotide); SEQ ID NO:181 (amino acid)). * samples obtained for TEM analysis (see FIG. 6E).
Figure 6E:
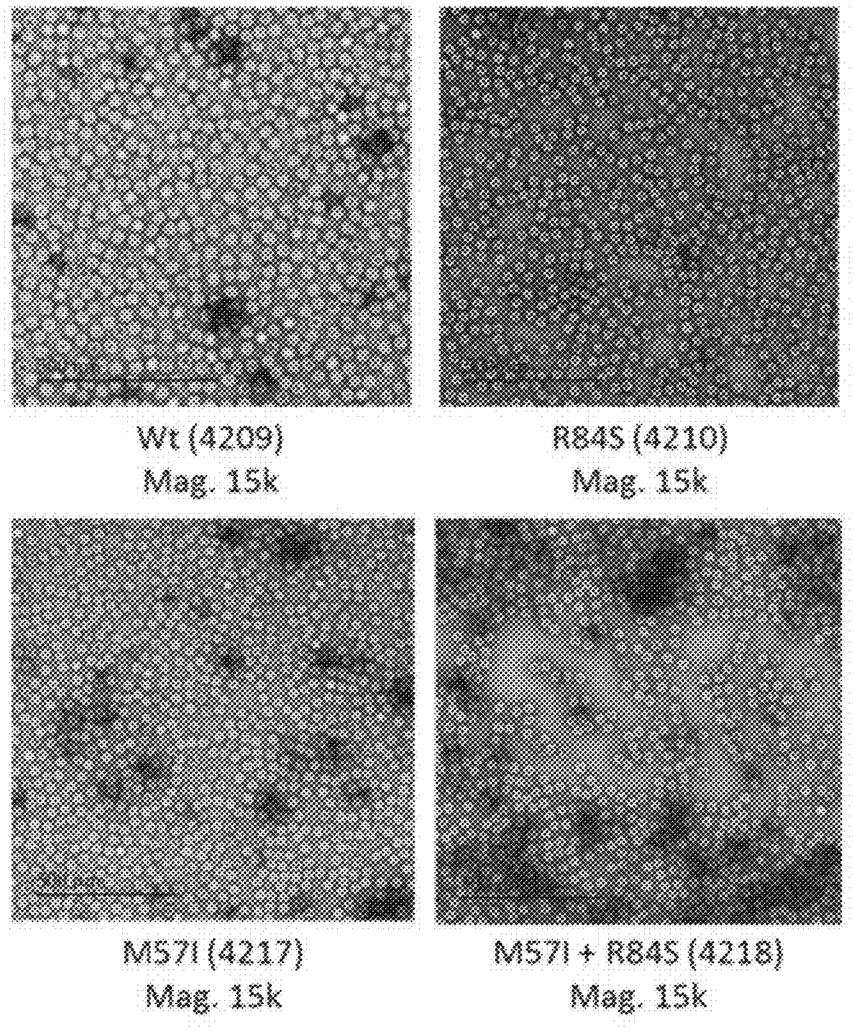
FIG. 6E shows transmission electron micrographs (TEM) of virus like particles (VLPs) purified from 31-35% iodixanol gradient fractions of crude protein extracts prepared from *N. benthamiana* leaves expressing, Top left: wt hCod GI.7/GA5043/USA/2014_VP1 (Construct #4209), Top right: mut hCod GI.7/GA5043/USA/2014_R84S (Construct #4210); Bottom left: mut hCod GI.7/GA5043/USA/2014_M57I (Construct 4217); Bottom Right mut hCod GI.7/GA5043/USA/2014_M57I+R84S Contract #4218). 15,000× magnification; scale bar=500 nm.

VLPs comprising of GI.7_R84S, GI.7_M57I, GI.7_M57I+R84S VP1 proteins were also observed to exhibit the same or greater density as compared to wildtype norovirus GI.7 VP1 (FIG. 6D). As shown in FIG. 6E, the modified VLPs had fewer damaged VLP particles, and a greater relative proportion of 38 nm diameter particles vs 23 nm diameter VLPs, as compared to wildtype.

Figure 7A:
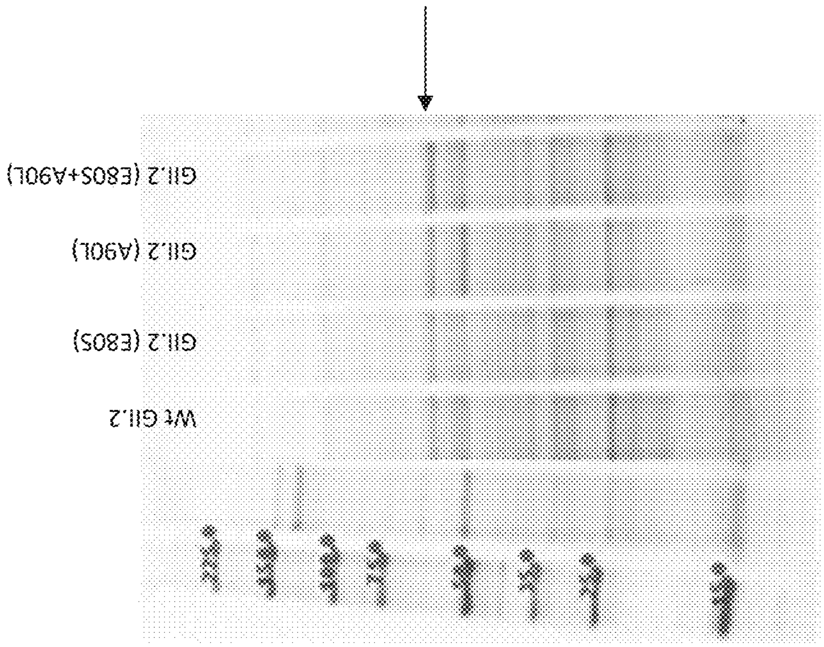
FIG. 7A shows a Coomassie-stained SDS-PAGE of crude protein extracts prepared from agroinfiltrated *N. benthamiana* leaves, 9 days post infiltration (DPI) with wt hCod GII.2/CGMH47/2011/TW VP1 (Construct #: 3982; SEQ ID NO:40 (nucleotide); SEQ ID NO:14 (amino acid)), mut hCod GII.2/CGMH47/2011/TW_E80S VP1 (Construct #: 4143; SEQ ID NO:86 (nucleotide); SEQ ID NO:85 (amino acid)), mut hCod GII.2/CGMH47/2011/TW_A90L VP1 (Construct #: 4144; SEQ ID NO:42 (nucleotide); SEQ ID NO:41 (amino acid)) or mut hCod GII.2/CGMH47/2011/TW_E80S+A90L VP1 (Construct #: 4145; SEQ ID NO:44 (nucleotide); SEQ ID NO:43 (amino acid)). Arrow: VP1 norovirus protein; First lane=crude protein extracts prepared from mock infiltrated *N. benthamiana* leaves.
Figure 7B:
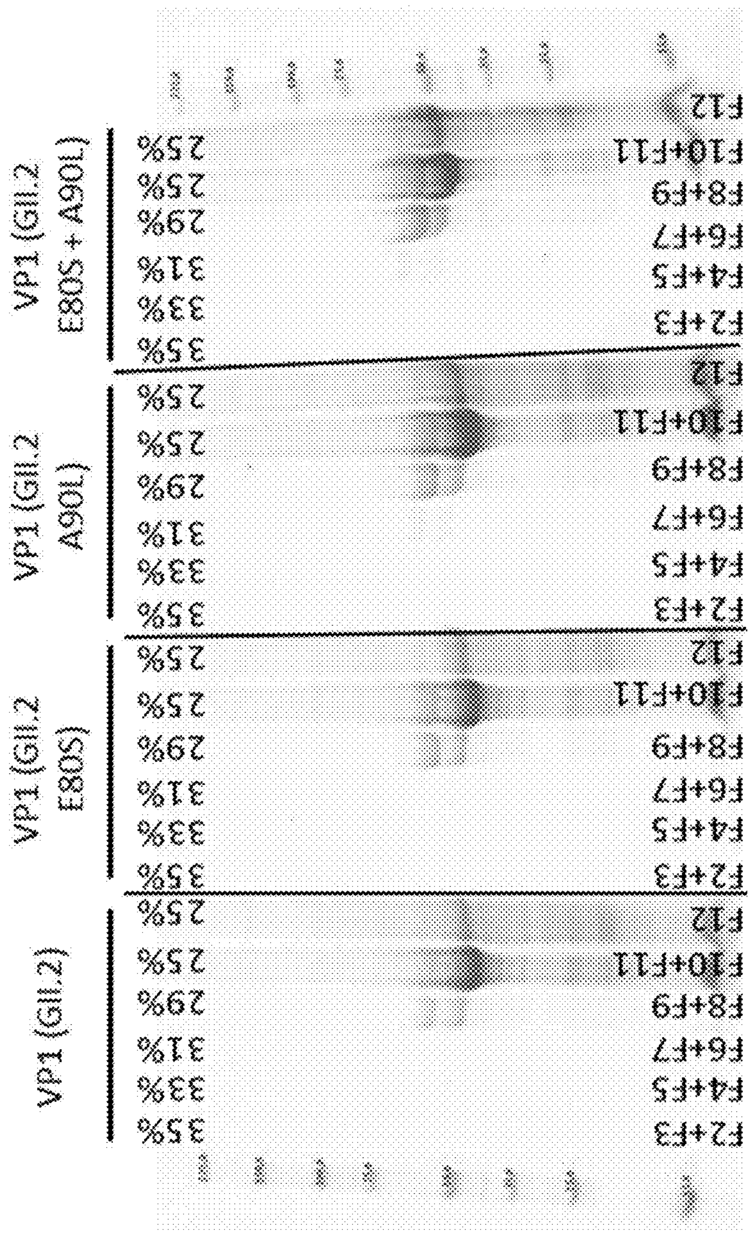
FIG. 7B shows a Coomassie-stained SDS-PAGE analysis of iodixanol density gradient fractions of crude protein extracts prepared from *N. benthamiana* leaves expressing, from left to right, wt hCod GII.2/CGMH47/2011/TW VP1 (Construct #3982), mut hCod GII.2/CGMH47/2011/TW_E80S VP1 (Construct #4143), mut hCod GII.2/CGMH47/2011/TW_A90L (Construct #: 4144), or mut hCod GII.2/CGMH47/2011/TW_E80S+A90L VP1 (Construct #: 4145).
Figure 7C:
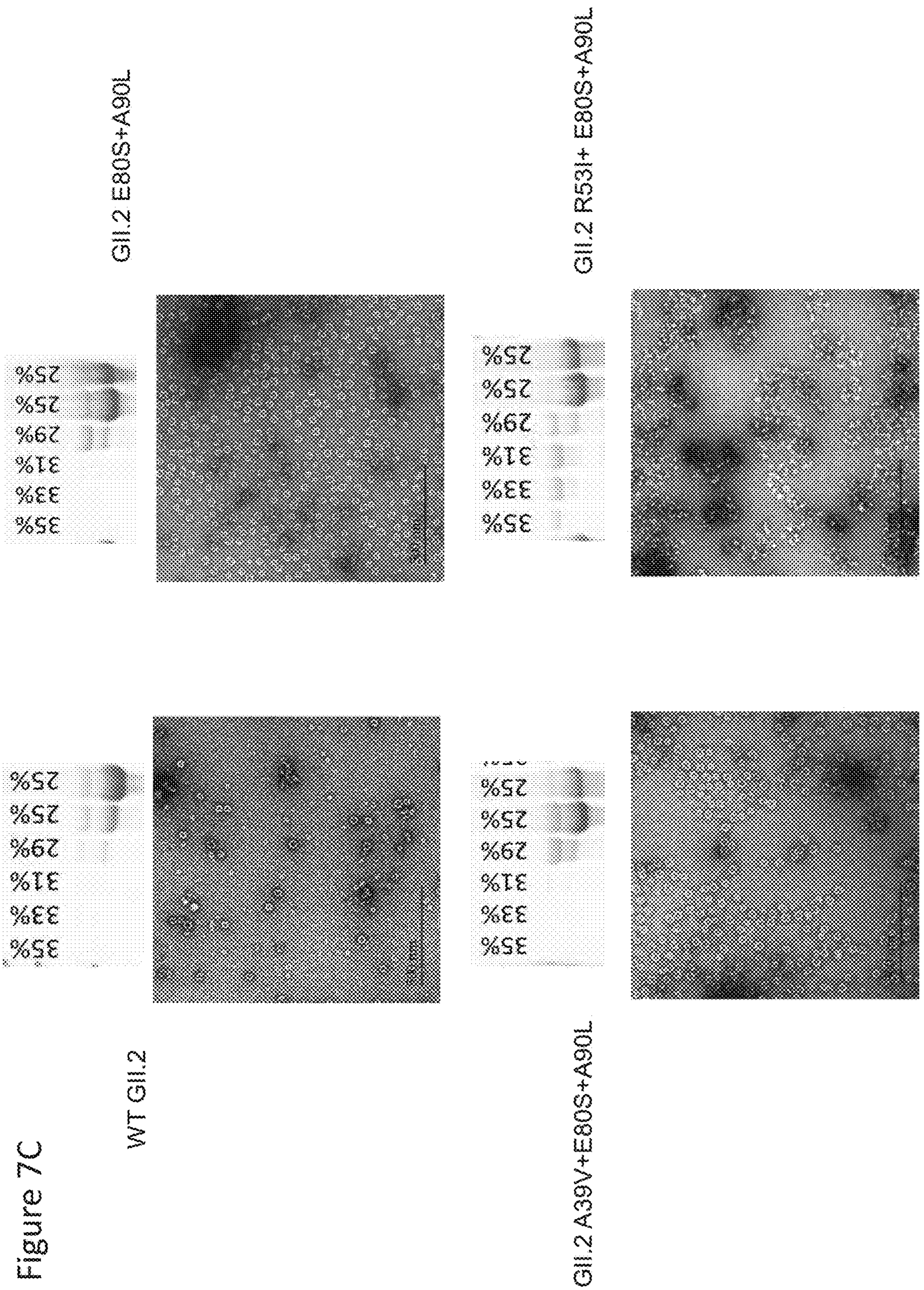
FIG. 7C shows Coomassie-stained SDS-PAGE analysis of iodixanol density gradient fractions of crude protein extracts prepared from *N. benthamiana* leaves (upper part of each panel), and transmission electron micrographs (TEM) of virus like particles (VLPs) purified from 29-35% iodixanol gradient fractions of crude protein extracts prepared from *N. benthamiana* leaves (lower part of each panel), expressing: Top Left Panel: wt hCod GII.2/CGMH47/2011/TW VP1 (Construct #3982), Top Right panel mut hCod GII.2/CGMH47/2011/TW_E80S+A90L VP1 (Construct #4145); Bottom Left Panel: mut hCod GII.2/CGMH47/2011/TW_A39V+E80S+A90L VP1 (Construct #4182; SEQ ID NO:183 (nucleotide); SEQ ID NO:182 (amino acid)); Bottom Right Panel: mut hCod GII.2/CGMH47/2011/TW_M53I+E80S+A90L VP1 (Construct #4183 SEQ ID NO:185 (nucleotide); SEQ ID NO:184 (amino acid)); 15,000× magnification; scale bar=500 nm.

VLPs comprising of GII.2_E80S+A90L, GII.2_A39V+E80S+A90L VP1 proteins exhibited greater density, stability and structural integrity (in a manner similar to that described above) as compared to wildtype norovirus GII.2 VP1 (FIG. 7C). As shown in FIG. 7C, the modified VLPs had fewer damaged VLP particles, and a greater relative proportion of 38 nm diameter particles vs 23 nm diameter VLPs, as compared to wildtype.

Figure 8B:
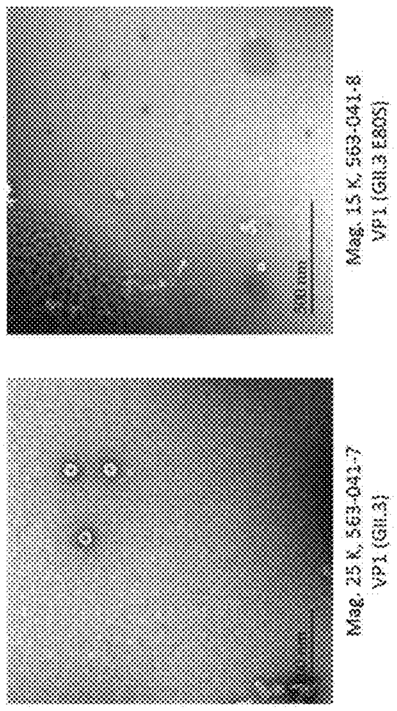
FIG. 8B shows transmission electron micrographs (TEM) of virus like particles (VLPs) purified from 31-35% iodixanol gradient fractions of crude protein extracts prepared from *N. benthamiana* leaves expressing wt hCod GII.3/Jingzhou/2013402/CHN VP1 (Construct #3983, first panel), or mut hCod GII.3/Jingzhou/2013402/CHN_E80S VP1 (Construct #: 4146, second panel). 15,000× magnification; scale bar=500 nm.

Expression of GII.3_E80S in plants, resulted in VLPs of 38 nm diameter particles (FIG. 8B). However, yields of VP1 protein (determined via SDS-PAGE) remained low.

Figure 9B:
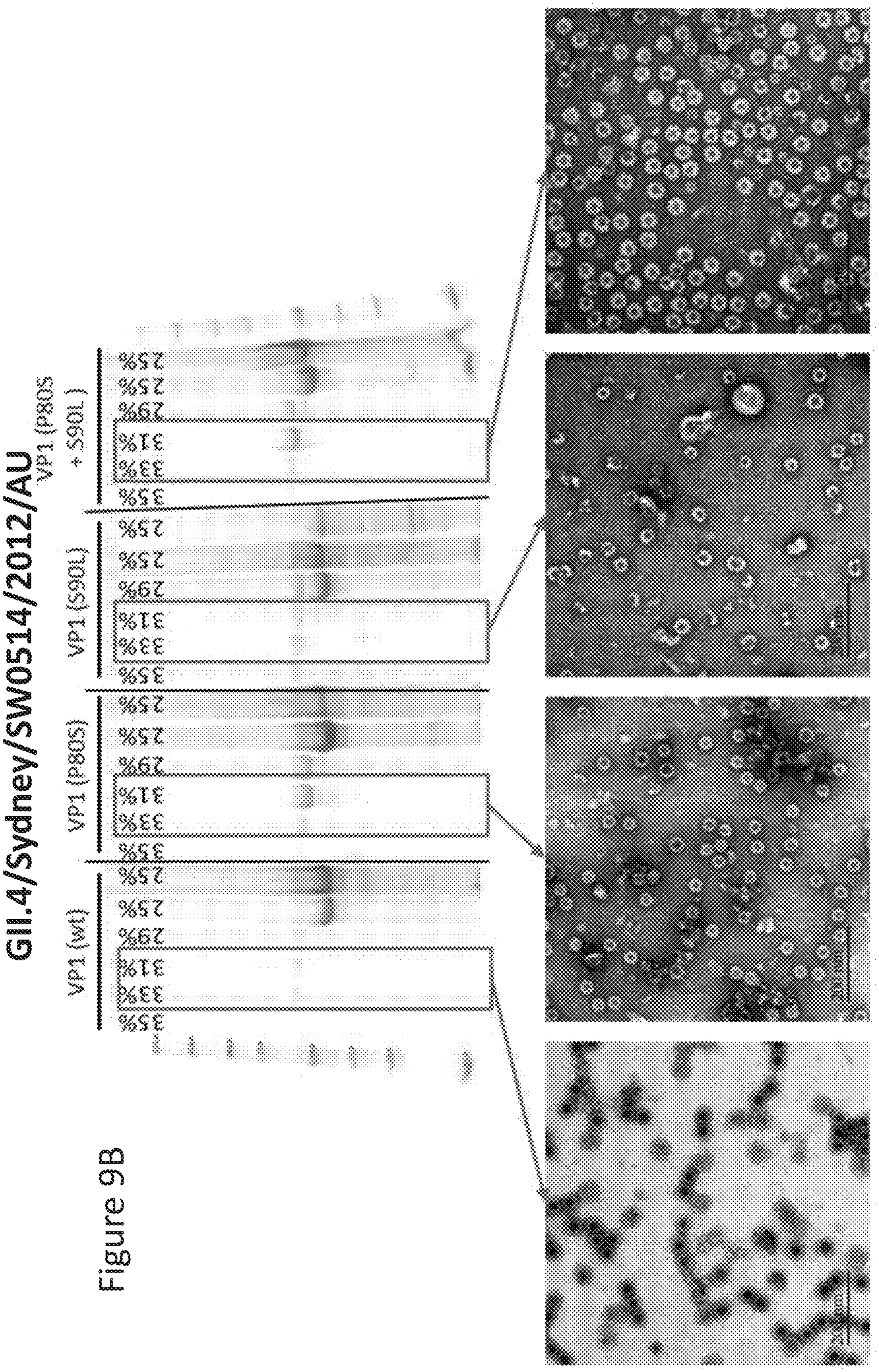
FIG. 9B shows a Coomassie-stained SDS-PAGE analysis (upper panel) and transmission electron micrographs (TEM; lower panel; 15,000× magnification; scale bar=200 nm) of virus like particles (VLPs) purified from iodixanol density gradient fractions of crude protein extracts prepared from *N. benthamiana* leaves expressing wt hCod GII.4/Sydney/NSW0514/2012/AU VP1 (Construct #: 3760), mut hCod GII.4/Sydney/NSW0514/2012/AU_P80S VP1 (Construct #: 4133), mut hCod GII.4/Sydney/NSW0514/2012/AU_S90L VP1 (Construct #: 4134), GII.4/Sydney/NSW0514/2012/AU_P80S+S90L VP1 (Construct #: 4135).
Figure 9C:
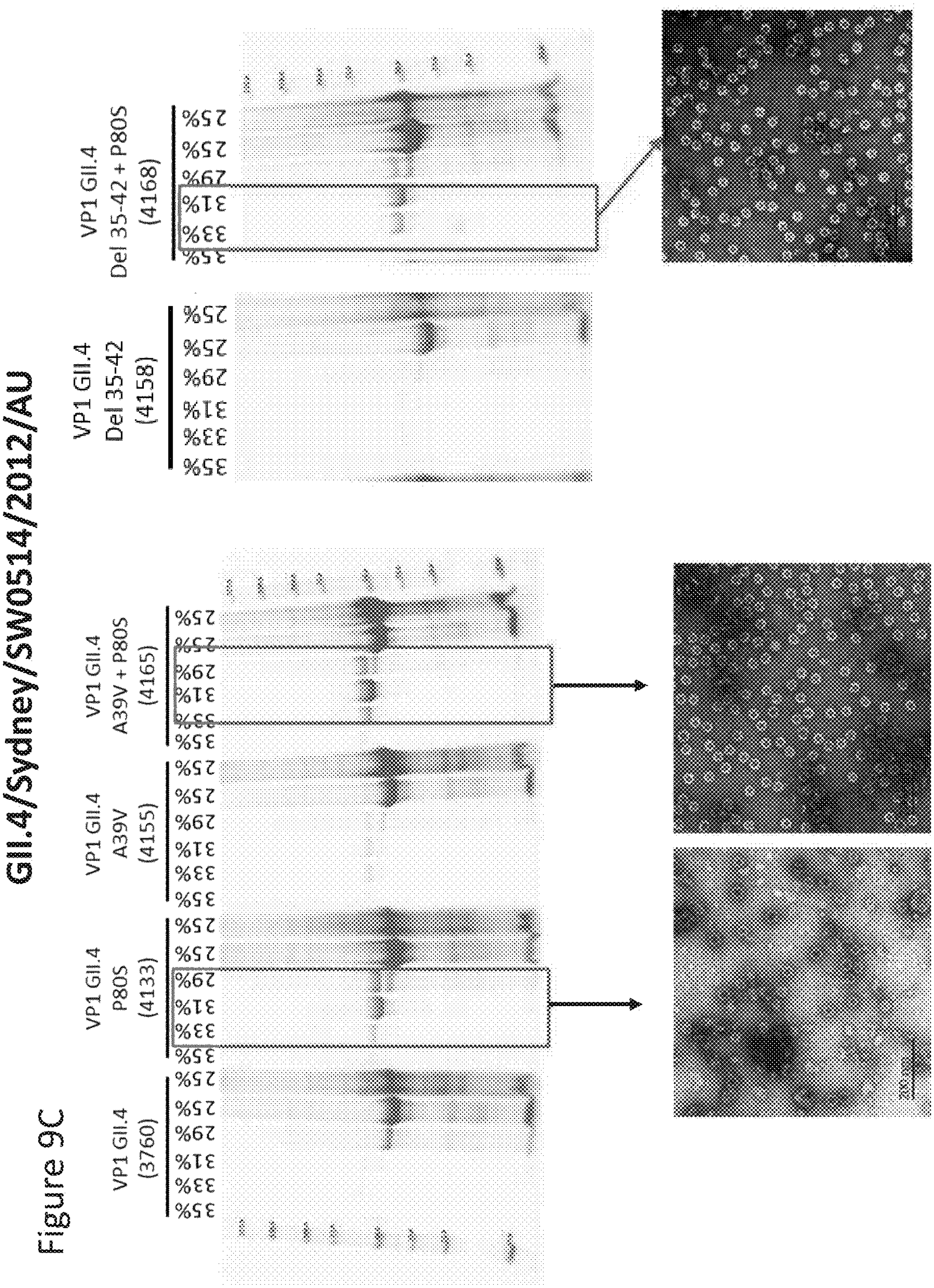
FIG. 9C shows a Coomassie-stained SDS-PAGE analysis (upper panel) and transmission electron micrographs (TEM; lower panel; 15,000× magnification; scale bar=200 nm) of virus like particles (VLPs) purified from iodixanol density gradient fractions of crude protein extracts prepared from *N. benthamiana* leaves expressing wt hCod GII.4/Sydney/NSW0514/2012/AU VP1 (Construct #.
Figure 9D:
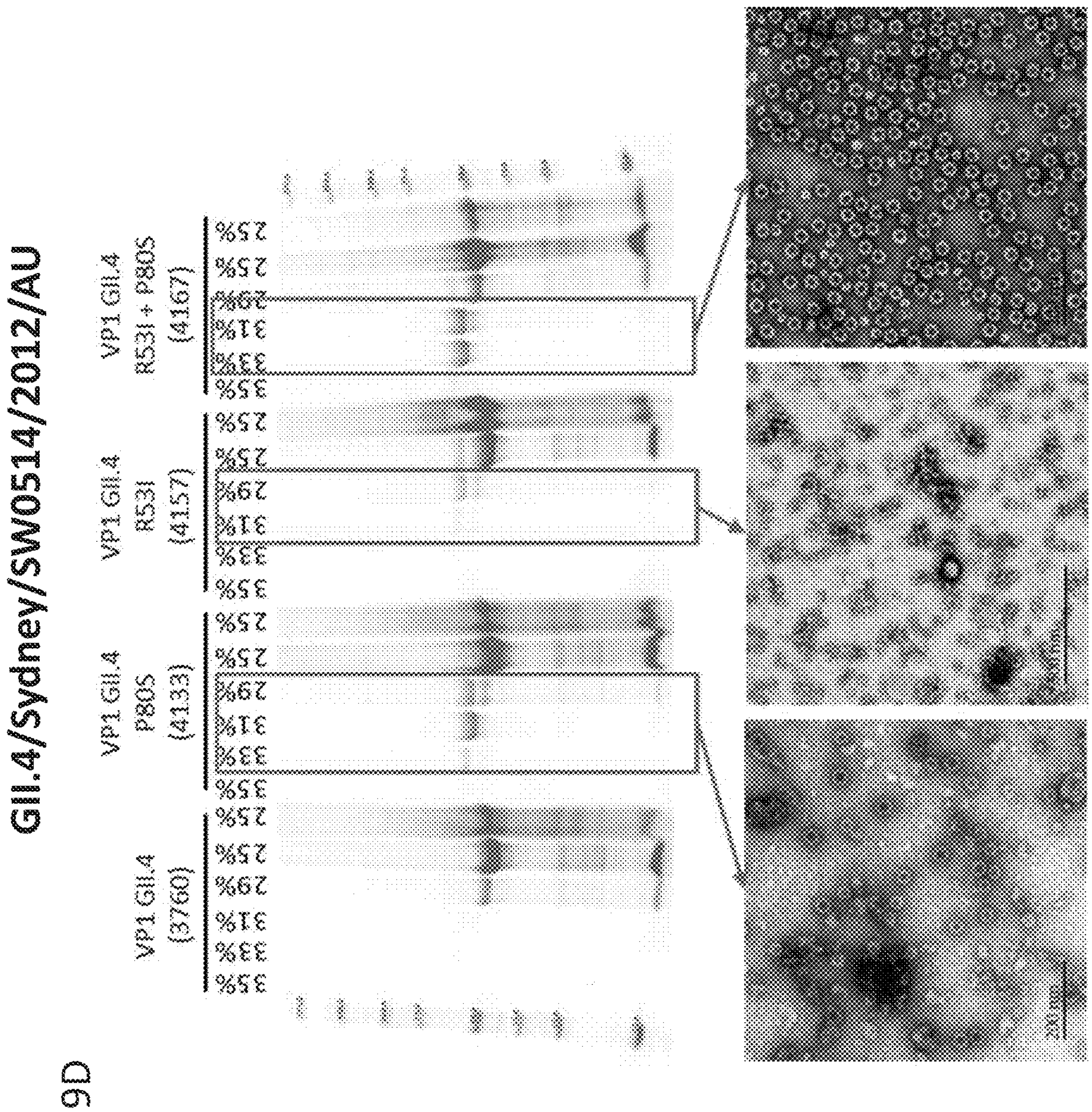
FIG. 9D shows a Coomassie-stained SDS-PAGE analysis (upper panel) and transmission electron micrographs (TEM; lower panel; 15,000× magnification; scale bar=200 nm) of virus like particles (VLPs) purified from iodixanol density gradient fractions of crude protein extracts prepared from *N. benthamiana* leaves expressing wt hCod GII.4/Sydney/NSW0514/2012/AU VP1 (Construct #: 3760), mut hCod GII.4/Sydney/NSW0514/2012/AU_P80S VP1 (Construct #: 4133), mut hCod GII.4/Sydney/NSW0514/2012/AU_R53I VP1 (Construct #: 4157), mut hCod GII.4/Sydney/NSW0514/2012/AU_R53I+P80S VP1 (Construct #: 4167).
Figure 9E:
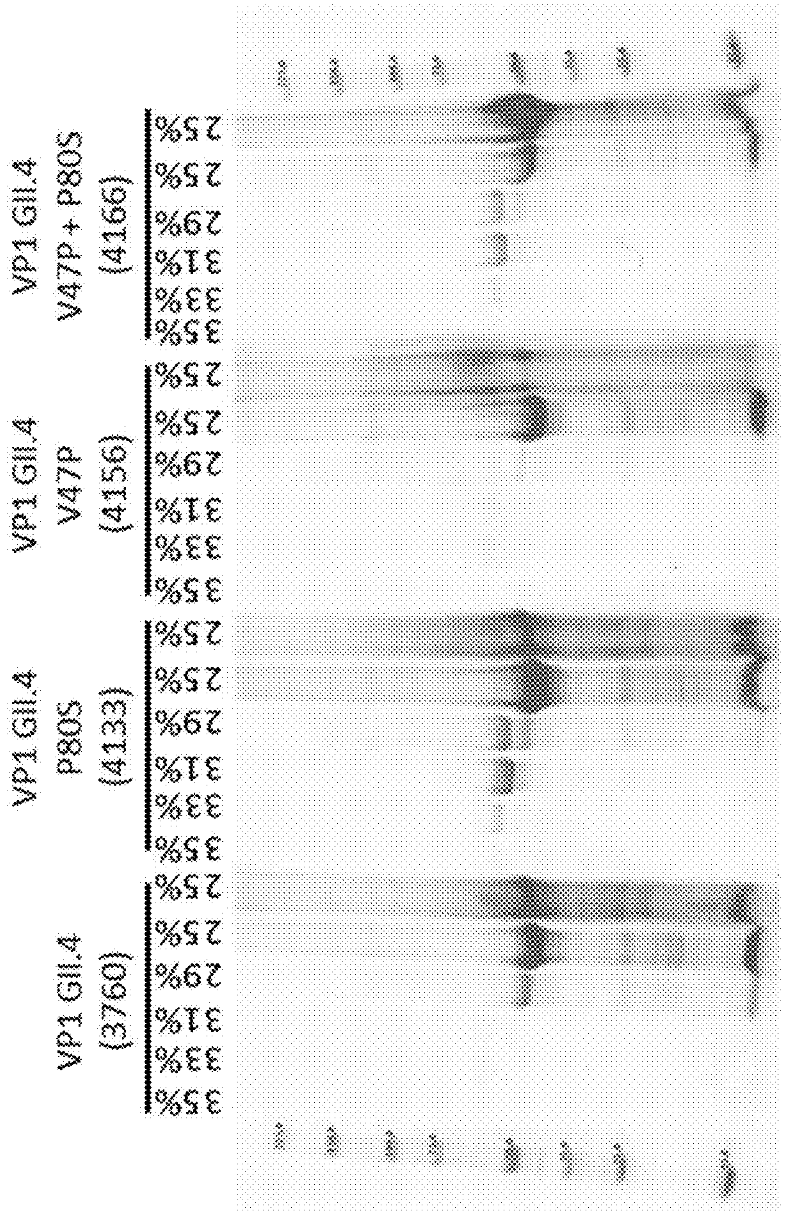
FIG. 9E shows a Coomassie-stained SDS-PAGE analysis of virus like particles (VLPs) purified from iodixanol density gradient fractions of crude protein extracts prepared from *N. benthamiana* leaves expressing wt hCod GII.4/Sydney/NSW0514/2012/AU VP1 (Construct #: 3760), mut hCod GII.4/Sydney/NSW0514/2012/AU_P80S VP1 (Construct #: 4133), mut hCod GII.4/Sydney/NSW0514/2012/AU_V47P VP1 (Construct #: 4156, mut hCod GII.4/Sydney/NSW0514/2012/AU_P80S+V47P VP1 (Construct #: 4166).
Figure 9F:
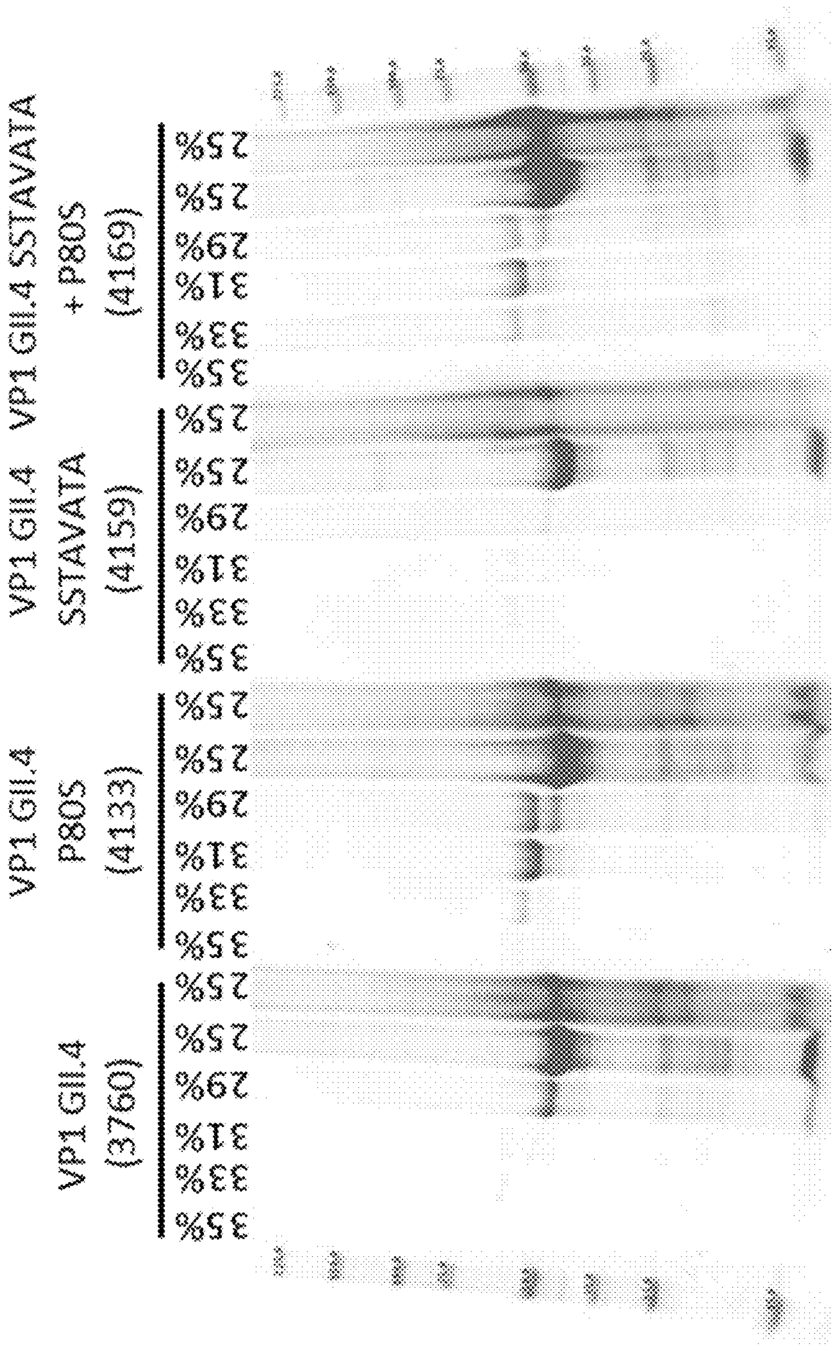
FIG. 9F shows a Coomassie-stained SDS-PAGE analysis of virus like particles (VLPs) purified from iodixanol density gradient fractions of crude protein extracts prepared from *N. benthamiana* leaves expressing wt hCod GII.4/Sydney/NSW0514/2012/AU VP1 (Construct #: 3760), mut hCod GII.4/Sydney/NSW0514/2012/AU_P80S VP1 (Construct #: 4133), mut hCod GII.4/Sydney/NSW0514/2012/AU_SSTAVATA VP1 (Construct #: 4159), mut hCod GII.4/Sydney/NSW0514/2012/AU_SSTAVATA+P80S VP1 (Construct #: 4169).
Figure 9G:
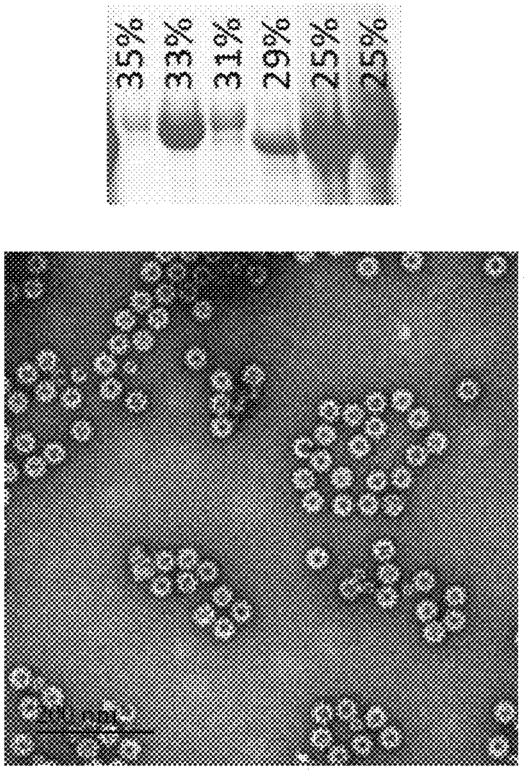
FIG. 9G shows Coomassie-stained SDS-PAGE analysis of iodixanol density gradient fractions of crude protein extracts prepared from *N. benthamiana* leaves (upper panel), and transmission electron micrographs (TEM) of virus like particles (VLPs) purified from 31-35% iodixanol gradient fractions of crude protein extracts prepared from *N. benthamiana* leaves (lower panel), expressing: Left Panel: mut hCod GII.4/Sydney/NSW0514/2012/AU_R53I+P80S VP1 (Construct #4167); Right panel mut hCod GII.4/Sydney/NSW0514/2012/AU_A39V+R53I+P80S VP1 (Construct #4186; SEQ ID NO:191 (nucleotide); SEQ ID NO:190 (amino acid)); 15,000× magnification; scale bar=500 nm.

As shown in FIGS. 9B, 9C, 9D and 9G, modified VP1 proteins, GII.4_A39V, GII.4_V47P, GII.4_R53I, GII.4_P80S, GII.4_S90L, GII.4_A39V+P80S, GII.4_R53I+P80S, GII.4_P80S+S90L, GII.4_P80S+Δ35-42 and GII.4_A39V+R53I+P80S all exhibited VLPs having greater densities, stability, and structural integrity than VLPs comprising wildtype GII.4 VP1 protein. Further, the VLPs comprising GII.4_A39V+P80S, GII.4_R53I+P80S, GII.4_P80S+S90L, GII.4_P80S+Δ35-42, and GII.4_A39V+R53I+P80S all had improved viral capsid integrity and fewer damaged particles as seen by TEM (FIGS. 9B, 9C, 9D and 9E). VLPs comprising GII.4_A39V+P80S and GII.4_P80S+Δ35-42 were also observed to have a greater proportion of 38 nm diameter particles vs 23 nm diameter particles as compared to wildtype GII.4 VLPs (FIGS. 9B and 9C). VLPs were also produced from GII.4_V47P; GII.4_V47P+P80S, GII.4_SSTAVATA; GII.4_P80S+SSTAVATA (FIGS. 9E and 9F).

As shown in FIGS. 10A and 10B, expression of modified norovirus VP1 protein GII.6_S90L produced 38 nm diameter VLPs, determined using transmission electron micrography (TEM).

VLPs comprising GII.12_E80S, GII.12_A90L and GII.12_E80S+A90L, also exhibited the improved characteristic of having a greater density of 38 nm diameter VLPs than VLPs comprising wildtype GII.12 VP1 (FIG. 11C) as determined using transmission electron micrography (TEM).

VLPs comprising GII.17_A39V, GII.17_A90L, and GII.17_R53I, also exhibited the improved characteristic of having a greater density of 38 nm diameter VLPs than VLPs comprising wildtype GII.17 VP1 (FIG. 11D) as determined using transmission electron micrography (TEM).

Induction of Immunity Against Norovirus Infection

An "immune response" generally refers to a response of the adaptive immune system of a subject. The adaptive immune system generally comprises a humoral response, and a cell-mediated response. The humoral response is the aspect of immunity that is mediated by secreted antibodies, produced in the cells of the B lymphocyte lineage (B cell). Secreted antibodies bind to antigens on the surfaces of invading microbes (such as viruses or bacteria), which flags them for destruction. Humoral immunity is used generally to refer to antibody production and the processes that accompany it, as well as the effector functions of antibodies, including Th2 cell activation and cytokine production, memory cell generation, opsonin promotion of phagocytosis, pathogen elimination and the like. The terms "modulate" or "modulation" or the like refer to an increase or decrease in a particular response or parameter, as determined by any of several assays generally known or used, some of which are exemplified herein.

A cell-mediated response is an immune response that does not involve antibodies but rather involves the activation of macrophages, natural killer cells (NK), antigen-specific cytotoxic T-lymphocytes, and the release of various cytokines in response to an antigen. Cell-mediated immunity is used generally to refer to some Th cell activation, Tc cell activation and T-cell mediated responses. Cell mediated immunity may be of particular importance in responding to viral infections.

For example, the induction of antigen specific CD8 positive T lymphocytes may be measured using an ELISPOT assay; stimulation of CD4 positive T-lymphocytes may be measured using a proliferation assay. Anti-norovirus antibody titres may be quantified using an ELISA assay; isotypes of antigen-specific or cross reactive antibodies may also be measured using anti-isotype antibodies (e.g. anti-IgG, IgA, IgE or IgM). Methods and techniques for performing such assays are well-known in the art.

Cytokine presence or levels may also be quantified. For example a T-helper cell response (Th1/Th2) will be characterized by the measurement of IFN-γ and IL-4 secreting cells using by ELISA (e.g. BD Biosciences OptEIA kits). Peripheral blood mononuclear cells (PBMC) or splenocytes obtained from a subject may be cultured, and the supernatant analyzed. T lymphocytes may also be quantified by fluorescence-activated cell sorting (FACS), using marker specific fluorescent labels and methods as are known in the art.

A microneutralization assay may also be conducted to characterize an immune response in a subject, see for example the methods of Rowe et al., 1973. Virus neutralization titers may be quantified in a number of ways, including: enumeration of lysis plaques (plaque assay) following crystal violent fixation/coloration of cells; microscopic observation of cell lysis in in vitro culture; and 2) ELISA and spectrophotometric detection of norovirus.

The term "epitope" or "epitopes", as used herein, refers to a structural part of an antigen to which an antibody specifically binds.

Figure 3D:
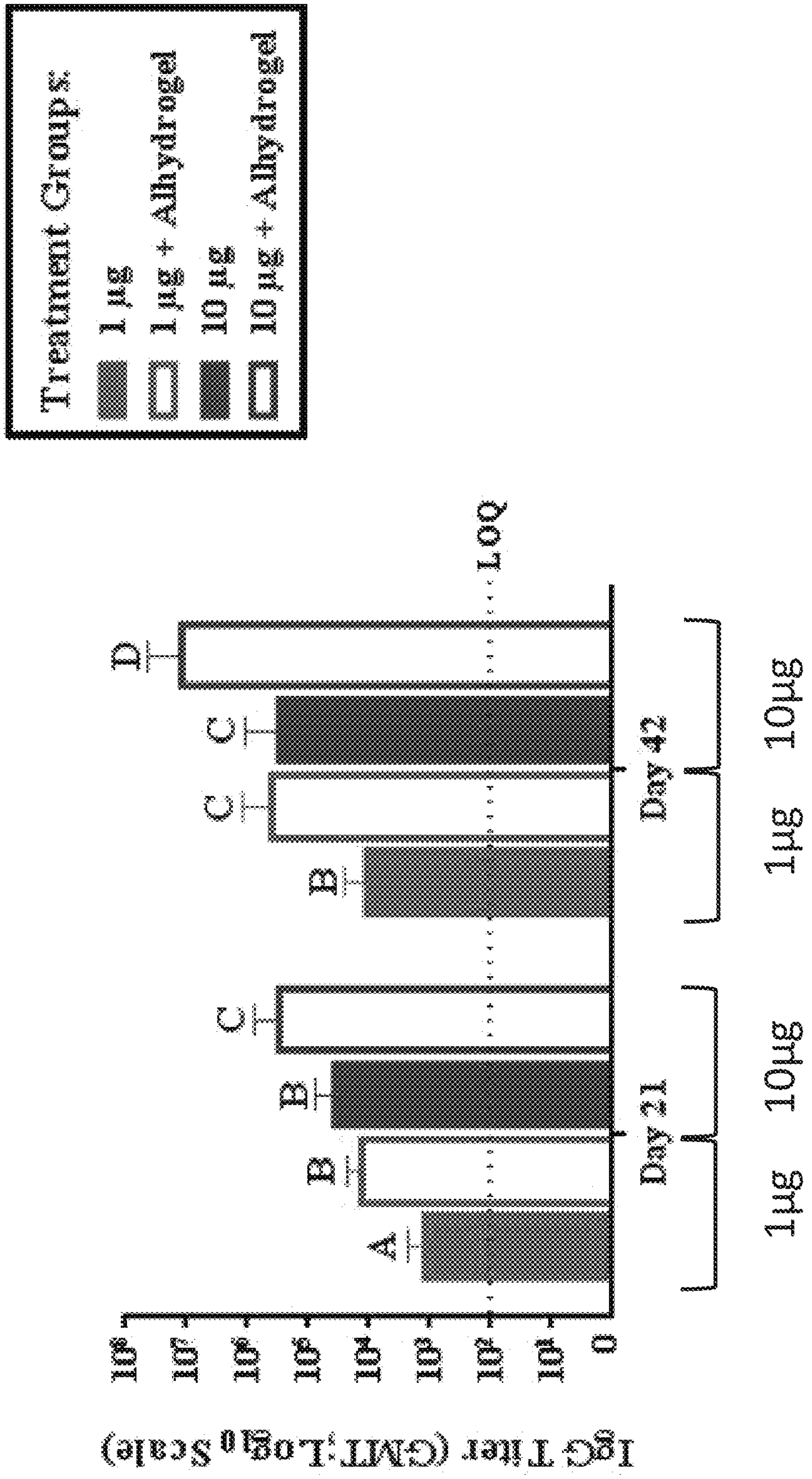
FIG. 3D shows GI.1 VLP-specific total IgG titers measured in serum samples from animals after IM immunization with one dose (Day 21) and two doses (Day 42) of 1 µg or 10 µg of each formulation. Total IgG titers were measured by ELISA using GI.1 VLP-coated plates (LOQ=100). Total IgG titers per treatment group (n=8 animals/group) are represented by geometric mean titer (GMT) with a 95% confidence interval. Same letter (A, B, C, D): no significant difference detected between treatment groups ($p>0.05$).

Immune response to plant produced wild type Norovirus native GI.1 (SEQ ID NO:1) VLP administration were performed using BALB/c mice (Example 4). Plant-produced modified VP1 proteins, or VLPs comprising modified VP1 proteins, for example, produced using GI.3_Q84S (construct 4140; SEQ ID NO:167), GI.3_S94L (construct 4141; SEQ ID NO:9), GI.3_A43V+S94L (construct 4179; SEQ ID NO:169), GI.3_M57I+S94L (construct 4180; SEQ ID NO:171), GI.3_P84S+S94L (construct 4142; SEQ ID NO:11), GI.3_A43V+M57I+S94L (construct 4181; SEQ ID NO:173), GI.5_Q84S (construct 4130; SEQ ID NO:35), GI.5_A94L (construct 4131; SEQ ID NO:37), GI.5_Q84S+A94L (construct 4132; SEQ ID NO:39), GI.7_R84S (construct 4210; SEQ ID NO:176), GI.7_M57I (construct 4217; SEQ ID NO:178), GI.7_M57I+R84S (construct 4218; SEQ ID NO:180), GII.2_E80S (construct 4143; SEQ ID NO:86), GII.2_A90L (construct 4144; SEQ ID NO:42), GII.2_Q80S+A90L (construct 4145; SEQ ID NO:44), GII.2_A39V+Q80S+A90L (construct 4182; SEQ ID NO:183), GII.2_R53I+Q80S+A90L (construct 4183; SEQ ID NO:185), GII.2_A39V+R53I+Q80S+A90L (construct 4184; SEQ ID NO:187), GII.3_E80S (construct 4146; SEQ ID NO:47), GII.3_A90L (construct 4147; SEQ ID NO:49), GII.3_E80S+A90L (construct 4148; SEQ ID NO:51), GII.4_A39V (construct 4155; SEQ ID NO:54), GII.4_V47P (construct 4156; SEQ ID NO:56), GII.4_R53I (construct 4157; SEQ ID NO:58), GII.4_P80S (construct 4133; SEQ ID NO:60), GII.4_S90L (construct 4134; SEQ ID NO:62), GII.4_Δ35-42 (construct 4158; SEQ ID NO:64), GII.4_SSTAVATA (construct 4159; SEQ ID NO:66). GII.4_A39V+R53I (construct 4185; SEQ ID NO:189), GII.4A39V+P80S (construct 4165; SEQ ID NO:68), GII.4_V47P+P80S (construct 4166; SEQ ID NO:70), GII.4_R53I+P80S (construct 4167; SEQ ID NO:72), GII.4_P80S+S90L (construct 4135; SEQ ID NO:74), GII.4_Δ35-42+P80S (construct 4168; SEQ ID NO:76), GII.4_P80S+SSTAVATA (construct 4169; SEQ ID NO:78), GII.4_A39V+R53I+P80S (construct 4186; SEQ ID NO:191), GII.6_E80S (construct 4149; SEQ ID NO:80), GII.6_S90L (construct 4150; SEQ ID NO:82), GII.6_E80S+S90L (construct 4151; SEQ ID NO:84), GII.12_E80S (construct 4136; SEQ ID NO:89), GII.12_A90L (construct 4137; SEQ ID NO:91), GII.12_E80S+A90L (construct 4138; SEQ ID NO:93), GII.17_A39V (construct 4234; SEQ ID NO:193), GII.17_R53I (construct 4235; SEQ ID NO:195), GII.17_A90L (construct 4232; SEQ ID NO:197), GII.17_A39V+R53I (construct 4236; SEQ ID NO:199), GII.17_E80S+A90L (construct 4233; SEQ ID NO:201), or a combination thereof, may also administered to mice. Serum samples from blood collected from animals were analyzed by ELISA for GI.1 VLP-specific total IgG and IgA antibodies using GI.1 VLP-coated plates. With reference to FIG. 3D, mice immunized with plant norovirus native VP1 VLPs from GU genotype exhibit GI.1 VLP-specific IgG antibody titers in sera for each treatment group. The IgG titer levels induced by each treatment were statistically higher than the titers quantified for the placebo group ($p<0.05$). IgG titer level increased in a dose-dependent manner (significant difference detected between the 1 μg and 10 μg treatments formulated with or without Alhydrogel; $p<0.05$). A significant increase of IgG titer level was also detected for each treatment group between Days 21 and 42 ($p<0.05$). These results collectively demonstrate the ability of plant produced Norovirus native VP1 VLPs to elicit a robust immune response in mice.

Therefore, there is provided herein a method of producing an antibody or antibody fragment comprising, administering a modified norovirus VP1 protein, or a norovirus VLP comprising one or more than one modified VP1 protein to a subject, or a host animal, thereby producing the antibody or the antibody fragment. The modified norovirus VP1 protein (either a GI VP1 protein or GII VP1 protein), comprising one or more than one substitution, modification or mutation at: an amino acid residue selected from positions in sequence alignment with amino acids 43, 57, 84 and 94 of norovirus VP1 genotype GI.1 (SEQ ID NO:1); a deletion of a peptide fragment in sequence alignment with amino acids 39 to 46 of norovirus VP1 genotype GI.1 (SEQ ID NO:1); amino acids corresponding to amino acid residues 39-46 of norovirus VP1 genotype GI.1 are mutated to the sequence SSTAVATA, or a combination thereof, and the nucleotide sequence is not derived from a genotype GI.1 norovirus VP1. The VLP may further comprise a norovirus VP2 protein.

There is also provided a composition for inducing an immune response comprising, an effective dose of the VLP comprising the modified norovirus VP1 protein, and a pharmaceutically acceptable carrier, adjuvant, vehicle or excipient.

Plant Expression

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology,* 2d Ed. (1988); and Miki and Iyer, *Fundamentals of Gene Transfer in Plants*. In *Plant Metabolism,* 2d Ed. D T. Dennis, D H Turpin, D D Lefebrvre, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (1991*, Gene* 100: 247-250), Scheid et al. (1991*, Mol. Gen. Genet.* 228: 104-112), Guerche et al. (1987*, Plant Science* 52: 111-116), Neuhause et al. (1987*, Theor. Appl Genet.* 75: 30-36), Klein et al. (2987*, Nature* 327: 70-73); Freeman et al. (1984*, Plant Cell Physiol.* 29: 1353), Howell et al. (1980*, Science* 208: 1265), Horsch et al. (1985*, Science* 227: 1229-1231), DeBlock et al. (1989*, Plant Physiology* 91: 694-701), Methods for Plant Molecular Biology (Weissbach and Weissbach, eds., Academic Press Inc., 1988), Methods in Plant Molecular Biology (Schuler and Zielinski, eds., Academic Press Inc., 1989), WO 92/09696, WO 94/00583, EP 331083, EP 175966, Liu and Lomonossoff (2002*, J Virol Meth,* 105:343-348), EP 290395; WO 8706614; U.S. Pat. Nos. 4,945,050; 5,036,006; and 5,100,792, U.S. patent application Ser. No. 08/438,666, filed May 10, 1995, and Ser. No. 07/951,715, filed Sep. 25, 1992, (all of which are hereby incorporated by reference).

Transient expression methods may be used to express the constructs of the present invention (see D'Aoust et al., 2009*, Methods in molecular biology*, Vol 483, pages 41-50; Liu and Lomonossoff, 2002*, Journal of Virological Methods,* 105:343-348; which is incorporated herein by reference). Alternatively, a vacuum-based transient expression method, as described by Kapila et al. (1997*, Plant Sci.* 122, 101-108; which is incorporated herein by reference), or WO 00/063400, WO 00/037663 (which are incorporated herein by reference) may be used. These methods may include, for example, but are not limited to, a method of Agro-inoculation or Agro-infiltration, syringe infiltration, however, other transient methods may also be used as noted above. With Agro-inoculation, Agro-infiltration, or syringe infiltration, a mixture of Agrobacteria comprising the desired nucleic acid enter the intercellular spaces of a tissue, for example the leaves, aerial portion of the plant (including stem, leaves and flower), other portion of the plant (stem, root, flower), or the whole plant. After crossing the epidermis the Agrobacteria infect and transfer t-DNA copies into the cells. The t-DNA is episomally transcribed and the mRNA translated, leading to the production of the protein of interest in infected cells, however, the passage of t-DNA inside the nucleus is transient.

Also considered part of this invention are transgenic plants, plant cells or seeds containing the gene construct of the present invention that may be used as a platform plant suitable for transient protein expression described herein. Methods of regenerating whole plants from plant cells are also known in the art (for example see Guerineau and Mullineaux (1993, Plant transformation and expression vectors. In: Plant Molecular Biology Labfax (Croy RRD ed) Oxford, BIOS Scientific Publishers, pp 121-148). In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue culture. Methods for stable transformation, and regeneration of these organisms are established in the art and known to one of skill in the art. Available techniques are reviewed in Vasil et al. (Cell Culture and Somatic Cell Genetics of Plants, Vol I, II and III, Laboratory Procedures and Their Applications, Academic Press, 1984), and Weissbach and Weissbach (Methods for Plant Molecular Biology, Academic Press, 1989). The method of obtaining transformed and regenerated plants is not critical to the present invention.

If plants, plant portions or plant cells are to be transformed or co-transformed by two or more nucleic acid constructs, the nucleic acid construct may be introduced into the *Agrobacterium* in a single transfection event so that the nucleic acids are pooled, and the bacterial cells transfected. Alternatively, the constructs may be introduced serially. In this case, a first construct is introduced into the *Agrobacterium* as described, the cells are grown under selective conditions (e.g. in the presence of an antibiotic) where only the singly transformed bacteria can grow. Following this first selection step, a second nucleic acid construct is introduced into the *Agrobacterium* as described, and the cells are grown under doubly-selective conditions, where only the doubly-transformed bacteria can grow. The doubly-transformed bacteria may then be used to transform a plant, plant portion or plant cell as described herein, or may be subjected to a further transformation step to accommodate a third nucleic acid construct.

Alternatively, if plants, plant portions, or plant cells are to be transformed or co-transformed by two or more nucleic acid constructs, the nucleic acid construct may be introduced into the plant by co-infiltrating a mixture of *Agrobacterium* cells with the plant, plant portion, or plant cell, each *Agrobacterium* cell may comprise one or more constructs to be introduced within the plant. In order to vary the relative expression levels within the plant, plant portion or plant cell, of a nucleotide sequence of interest within a construct, during the step of infiltration, the concentration of the various Agrobacteria populations comprising the desired constructs may be varied.

Therefore, there is provided herein, a plant, a portion of a plant, a plant cell, or a plant extract, comprising, one or more than one modified norovirus VP1 protein, or a norovirus VLP comprising one or more than one modified VP1 protein. The one or more than one modified norovirus VP1 protein comprising one or more than one substitution, modification or mutation at a position selected from amino acid residues in sequence alignment with amino acids 43, 57, 84 and 94 of norovirus VP1 genotype GU (SEQ ID NO:1); a deletion of a peptide fragment in sequence alignment with amino acids 39 to 46 of norovirus VP1 genotype GI.1 (SEQ ID NO:1); or a combination thereof, and the nucleotide sequence is not derived from a genotype GI.1 norovirus VP1. The VLP may further comprise a norovirus VP2 protein.

Also provided herein is a plant, portion of a plant, a plant cell, or a plant extract comprising, a polynucleotide sequence encoding one or more than one modified norovirus VP1 protein. The one or more than one modified norovirus VP1 protein comprising one or more than one substitution, modification or mutation at a position selected from amino acid residues in sequence alignment with amino acids 43, 57, 84 and 94 of norovirus VP1 genotype GI.1 (SEQ ID NO:1); a deletion of a peptide fragment in sequence alignment with amino acids 39 to 46 of norovirus VP1 genotype GI.1 (SEQ ID NO:1); or a combination thereof, and the nucleotide sequence is not derived from a genotype GI.1 norovirus VP1.

A list of the Norovirus strains and constructs is provided in Table 3.

TABLE 3

Norovirus strains and constructs.

| Trivial Name | Norovirus Strain | SEQ ID NO: | SEQ FIG. # | Const # | Const. FIG. # |
|---|---|---|---|---|---|
| VP1 GI.1 | | | | | |
| Wt GI.1 (aa) | Hu/GI.1/United States/Norwalk/1968 | 1 | 12A | — | |
| Wt Gl.1 (na) | Hu/GI.1/United States/Norwalk/1968 | 2 | 12B | — | |
| Wt Gl.1 hCod (na) | Hu/GI.1/United States/Norwalk/1968 | 3 | 12C | 2724 | 39A |
| VP1 GI.2 | | | | | |
| Wt GI.2 (aa) | Hu/GI.2/Leuven/2003/BEL | 4 | 13A | — | |
| Wt GI.2 hCod (na) | Hu/GI.2/Leuven/2003/BEL | 5 | 13B | 3300 | 39B |
| VP1 GI.3 | | | | | |
| Wt GI.3 (aa) | Hu/GI.3/S29/2008/Lilla Edet/Sweden | 6 | 14A | — | |
| Wt GI.3 hCod (na) | Hu/GI.3/S29/2008/Lilla Edet/Sweden | 7 | 14B | 3979 | 39C |
| Mut GI.3__Q84S (aa) | Hu/GI.3/S29/2008/Lilla Edet/Sweden | 98 | 28A | | |
| Mut GI.3__Q84S hCod (na) | Hu/GI.3/S29/2008/Lilla Edet/Sweden | 167 | 28B | 4140 | 40A |
| Mut GI.3__S94L (aa) | Hu/GI.3/S29/2008/Lilla Edet/Sweden | 8 | 28C | — | |
| Mut GI.3__S94L hCod (na) | Hu/GI.3/S29/2008/Lilla Edet/Sweden | 9 | 28D | 4141 | 40B |
| Mut GI.3__S94V (aa) | Hu/GI.3/S29/2008/Lilla Edet/Sweden | 292 | 28M | — | |
| Mut GI.3__S94V hCod (na) | Hu/GI.3/S29/2008/Lilla Edet/Sweden | 293 | 28N | 4288 | 52 |
| Mut GI.3__S94I (aa) | Hu/GI.3/S29/2008/Lilla Edet/Sweden | 292 | 28M | — | |
| Mut GI.3__S94I hCod (na) | Hu/GI.3/S29/2008/Lilla Edet/Sweden | 293 | 28N | 4289 | 52 |
| Mut GI.3__S94M (aa) | Hu/GI.3/S29/2008/Lilla Edet/Sweden | 292 | 28M | — | |
| Mut GI.3__S94M hCod (na) | Hu/GI.3/S29/2008/Lilla Edet/Sweden | 293 | 28N | 4290 | 52 |
| Mut GI.3__S94T (aa) | Hu/GI.3/S29/2008/Lilla Edet/Sweden | 292 | 28M | — | |
| Mut GI.3__S94T hCod (na) | Hu/GI.3/S29/2008/Lilla Edet/Sweden | 293 | 28N | 4292 | 52 |
| Mut GI.3__S94E (aa) | Hu/GI.3/S29/2008/Lilla Edet/Sweden | 292 | 28M | — | |
| Mut GI.3__S94E hCod (na) | Hu/GI.3/S29/2008/Lilla Edet/Sweden | 293 | 28N | 4293 | 52 |
| Mut GI.3__S94D (aa) | Hu/GI.3/S29/2008/Lilla Edet/Sweden | 292 | 28M | — | |
| Mut GI.3__S94D hCod (na) | Hu/GI.3/S29/2008/Lilla Edet/Sweden | 293 | 28N | 4294 | 52 |
| Mut GI.3__S94N (aa) | Hu/GI.3/S29/2008/Lilla Edet/Sweden | 292 | 28M | — | |
| Mut GI.3__S94N hCod (na) | Hu/GI.3/S29/2008/Lilla Edet/Sweden | 293 | 28N | 4295 | 52 |
| Mut GI.3__S94Q (aa) | Hu/GI.3/S29/2008/Lilla Edet/Sweden | 292 | 28M | — | |
| Mut GI.3__S94Q hCod (na) | Hu/GI.3/S29/2008/Lilla Edet/Sweden | 293 | 28N | 4296 | 52 |
| Mut GI.3__S94K (aa) | Hu/GI.3/S29/2008/Lilla Edet/Sweden | 292 | 28M | — | |
| Mut GI.3__S94K hCod (na) | Hu/GI.3/S29/2008/Lilla Edet/Sweden | 293 | 28N | 4297 | 52 |
| Mut GI.3__S94H (aa) | Hu/GI.3/S29/2008/Lilla Edet/Sweden | 292 | 28M | — | |
| Mut GI.3__S94H hCod (na) | Hu/GI.3/S29/2008/Lilla Edet/Sweden | 293 | 28N | 4298 | 52 |
| Mut GI.3__A43V + S94L (na) | Hu/GI.3/S29/2008/Lilla Edet/Sweden | 169 | 28H | 4179 | 40D |
| Mut GI.3__A43V + S94L (aa) | Hu/GI.3/S29/2008/Lilla Edet/Sweden | 170 | 28G | — | |
| Mut GI.3__M57I + S94L (na) | Hu/GI.3/S29/2008/Lilla Edet/Sweden | 171 | 28J | 4180 | 40E |
| Mut GI.3__M57I + S94L (aa) | Hu/GI.3/S29/2008/Lilla Edet/Sweden | 172 | 28I | — | |
| Mut GI.3__A43V + M57I + S94L (na) | Hu/GI.3/S29/2008/Lilla Edet/Sweden | 173 | 28L | 4181 | 40F |
| Mut GI.3__A43V + M57I + S94L (aa) | Hu/GI.3/S29/2008/Lilla Edet/Sweden | 174 | 28K | — | |
| Mut GI.3__Q84S + S94L (aa) | Hu/GI.3/S29/2008/Lilla Edet/Sweden | 10 | 28E | — | |
| Mut GI.3__Q84S + S94L hCod (na) | Hu/GI.3/S29/2008/Lilla Edet/Sweden | 11 | 28F | 4142 | 40C |
| VP1 Gi.5 | | | | | |
| Wt GI.5 (aa) | Hu/GI.5/Siklos/HUN5407/2013/HUN | 12 | 15A | — | |
| Wt GI.5 hCod (na) | Hu/GI.5/Siklos/HUN5407/2013/HUN | 33 | 15B | 3980 | 41A |
| Mut GI.5__Q84S (aa) | Hu/GI.5/Siklos/HUN5407/2013/HUN | 34 | 29A | — | |
| Mut GI.5__Q84S (na) | Hu/GI.5/Siklos/HUN5407/2013/HUN | 35 | 29B | 4130 | 41B |
| Mut GI.5__ A94L (aa) | Hu/GI.5/Siklos/HUN5407/2013/HUN | 36 | 29C | — | |
| Mut GI.5__A94L hCod (na) | Hu/GI.5/Siklos/HUN5407/2013/HUN | 37 | 29D | 4131 | 41C |
| Mut GI.5__Q84S + A94L (aa) | Hu/GI.5/Siklos/HUN5407/2013/HUN | 38 | 29E | — | |
| Mut GI.5__Q84S + A94L hCod (na) | Hu/GI.5/Siklos/HUN5407/2013/HUN | 39 | 29F | 4132 | 41D |
| VP1 GI.7 | | | | | |
| Wt GI.7 (na) | Hu/GI.7/USA/2014/GA5043 | 175 | 16B | — | |
| Wt GI.7 (aa) | Hu/GI.7/USA/2014/GA5043 | 101 | 16A | — | |
| Mut GI.7__R84S (na) | Hu/GI.7/USA/2014/GA5043 | 176 | 29H | 4210 | 41E |
| Mut GI.7__R84S (aa) | Hu/GI.7/USA/2014/GA5043 | 177 | 29G | — | |
| Mut GI.7__M57I (na) | Hu/GI.7/USA/2014/GA5043 | 178 | 29J | 4217 | 41F |
| Mut GI.7__M57I (aa) | Hu/GI.7/USA/2014/GA5043 | 179 | 29I | — | — |
| Mut GI.7__M57L (na) | Hu/GI.7/USA/2014/GA5043 | 291 | 29N | 4266 | 51 |

TABLE 3-continued

| Norovirus strains and constructs. | | | | | |
|---|---|---|---|---|---|
| Mut GI.7_M57L (aa) | Hu/GI.7/USA/2014/GA5043 | 290 | 29M | — | |
| Mut GI.7_M57G (na) | Hu/GI.7/USA/2014/GA5043 | 291 | 29N | 4268 | 51 |
| Mut GI.7_M57G (aa) | Hu/GI.7/USA/2014/GA5043 | 290 | 29M | — | |
| Mut GI.7_M57S (na) | Hu/GI.7/USA/2014/GA5043 | 291 | 29N | 4269 | 51 |
| Mut GI.7_M57S (aa) | Hu/GI.7/USA/2014/GA5043 | 290 | 29M | — | |
| Mut GI.7_M57T (na) | Hu/GI.7/USA/2014/GA5043 | 291 | 29N | 4270 | 51 |
| Mut GI.7_M57T (aa) | Hu/GI.7/USA/2014/GA5043 | 290 | 29M | — | |
| Mut GI.7_M57N (na) | Hu/GI.7/USA/2014/GA5043 | 291 | 29N | 4273 | 51 |
| Mut GI.7_M57N (aa) | Hu/GI.7/USA/2014/GA5043 | 290 | 29M | — | |
| Mut GI.7_M57Q (na) | Hu/GI.7/USA/2014/GA5043 | 291 | 29N | 4274 | 51 |
| Mut GI.7_M57Q (aa) | Hu/GI.7/USA/2014/GA5043 | 290 | 29M | — | |
| Mut GI.7_M57K (na) | Hu/GI.7/USA/2014/GA5043 | 291 | 29N | 4275 | 51 |
| Mut GI.7_M57K (aa) | Hu/GI.7/USA/2014/GA5043 | 290 | 29M | — | |
| Mut GI.7_M57H (na) | Hu/GI.7/USA/2014/GA5043 | 291 | 29N | 4276 | 51 |
| Mut GI.7_M57H (aa) | Hu/GI.7/USA/2014/GA5043 | 290 | 29M | — | |
| Mut GI.7_M57I + R84S (na) | Hu/GI.7/USA/2014/GA5043 | 180 | 29L | 4218 | 41G |
| Mut GI.7_M57I + R84S (aa) | Hu/GI.7/USA/2014/GA5043 | 181 | 29K | | |
| VP1 GII.1 | | | | | |
| Wt GII.1 (aa) | GII.I_Ascension208/2010/ USA_AFA55174 | 13 | 16C | — | |
| VP1 GII.2 | | | | | |
| Wt GII.2 (aa) | Hu/GII.2/CGMH47/2011/TW | 14 | 17A | — | |
| Wt GII.2 hCod (na) | Hu/GII.2/CGMH47/2011/TW | 40 | 17B | 3982 | 42A |
| Mut GII.2_E80S (aa) | Hu/GII.2/CGMH47/2011/TW | 85 | 30A | — | |
| Mut GII.2_E80S (aa) | Hu/GII.2/CGMH47/2011/TW | 86 | 30B | 4143 | 42B |
| Mut GII.2_A90L (aa) | Hu/GII.2/CGMH47/2011/TW | 41 | 30C | — | |
| Mut GII.2_A90L hCod (na) | Hu/GII.2/CGMH47/2011/TW | 42 | 30D | 4144 | 42C |
| Mut GII.2_E80S + A90L (aa) | Hu/GII.2/CGMH47/2011/TW | 43 | 30E | — | |
| Mut GII.2_E80S + A90L hCod (na) | Hu/GII.2/CGMH47/2011/TW | 44 | 30F | 4145 | 42D |
| Mut GII.2_A39V + E80S + A90L (aa) | Hu/GII.2/CGMH47/2011/TW | 182 | 30G | — | |
| Mut GII.2_A39V + E80S + A90L hCod (na) | Hu/GII.2/CGMH47/2011/TW | 183 | 30H | 4182 | 42E |
| Mut GII.2_R53I + E80S + A90L (aa) | Hu/GII.2/CGMH47/2011/TW | 184 | 30I | — | |
| Mut GII.2_R53I + E80S + A90L hCod (na) | Hu/GII.2/CGMH47/2011/TW | 185 | 30J | 4183 | 42F |
| Mut GII.2_A39V + R53I + E80S + A90L (aa) | Hu/GII.2/CGMH47/2011/TW | 186 | 30K | — | |
| Mut GII.2_A39V + R53I + E80S + A90L hCod (na) | Hu/GII.2/CGMH47/2011/TW | 187 | 30L | 4184 | 42G |
| VP1 GII.3 | | | | | |
| Wt GII.3 (aa) | Hu/GII.3/Jingzhou/2013402/CHN | 15 | 18A | — | |
| Wt GII.3 hCod (na) | Hu/GII.3/Jingzhou/2013402/CHN | 45 | 18B | 3983 | 43A |
| Mut GII.3_E80S (aa) | Hu/GII.3/Jingzhou/2013402/CHN | 46 | 31A | — | |
| Mut GII.3_E80S hCod (na) | Hu/GII.3/Jingzhou/2013402/CHN | 47 | 31B | 4146 | 43B |
| Mut GII.3_A90L (aa) | Hu/GII.3/Jingzhou/2013402/CHN | 48 | 31C | — | |
| Mut GII.3_A90L hCod (na) | Hu/GII.3/Jingzhou/2013402/CHN | 49 | 31D | 4147 | 43C |
| Mut GII.3_E80S + A90L (aa) | Hu/GII.3/Jingzhou/2013402/CHN | 50 | 31E | — | |
| Mut GII.3_E80S + A90L hCod (na) | Hu/GII.3/Jingzhou/2013402/CHN | 51 | 31F | 4148 | 43D |
| VP1 GII.4 | | | | | |
| Wt GII.4 (aa) | Hu/GII.4/Sydney/NSW0514/2012/AU | 16 | 19A | — | |
| Wt GII.4 hCod (na) | Hu/GII.4/Sydney/NSW0514/2012/AU | 52 | 19B | 3760 | 44A |
| Mut GII.4_A39V (aa) | Hu/GII.4/Sydney/NSW0514/2012/AU | 53 | 32A | — | |
| Mut GII.4_A39V hCod (na) | Hu/GII.4/Sydney/NSW0514/2012/AU | 54 | 32B | 4155 | 44B |
| Mut GII.4_V47P (aa) | Hu/GII.4/Sydney/NSW0514/2012/AU | 55 | 32C | — | |
| Mut GII.4_V47P hCod (na) | Hu/GII.4/Sydney/NSW0514/2012/AU | 56 | 32D | 4156 | 44C |
| Mut GII.4_R53I (aa) | Hu/GII.4/Sydney/NSW0514/2012/AU | 57 | 32E | — | |
| Mut GII.4_R53I hCod (na) | Hu/GII.4/Sydney/NSW0514/2012/AU | 58 | 32F | 4157 | 44D |
| Mut GII.4_P80S (aa) | Hu/GII.4/Sydney/NSW0514/2012/AU | 59 | 32G | — | |
| Mut GII.4_P80S hCod (na) | Hu/GII.4/Sydney/NSW0514/2012/AU | 60 | 32H | 4133 | 44E |
| Mut GII.4_P80A (aa) | Hu/GII.4/Sydney/NSW0514/2012/AU | 287 | 32FF | — | |
| Mut GII.4_P80A hCod (na) | Hu/GII.4/Sydney/NSW0514/2012/AU | 286 | 32EE | 4281 | 50A |
| Mut GII.4_P80N (aa) | Hu/GII.4/Sydney/NSW0514/2012/AU | 287 | 32FF | — | |
| Mut GII.4_P80N hCod (na) | Hu/GII.4/Sydney/NSW0514/2012/AU | 286 | 32EE | 4285 | 50A |
| Mut GII.4_P80K (aa) | Hu/GII.4/Sydney/NSW0514/2012/AU | 287 | 32FF | — | |
| Mut GII.4_P80K hCod (na) | Hu/GII.4/Sydney/NSW0514/2012/AU | 286 | 32EE | 4286 | 50A |
| Mut GII.4_P80H (aa) | Hu/GII.4/Sydney/NSW0514/2012/AU | 287 | 32FF | — | |
| Mut GII.4_P80H hCod (na) | Hu/GII.4/Sydney/NSW0514/2012/AU | 286 | 32EE | 4287 | 50A |
| Mut GII.4_S90L (aa) | Hu/GII.4/Sydney/NSW0514/2012/AU | 61 | 32I | — | |
| Mut GII.4_S90L hCod (na) | Hu/GII.4/Sydney/NSW0514/2012/AU | 62 | 32J | 4134 | 44F |
| Mut GII.4_Δ35-42 (aa) | Hu/GII.4/Sydney/NSW0514/2012/AU | 63 | 32K | — | |

TABLE 3-continued

Norovirus strains and constructs.

| | | | | | |
|---|---|---|---|---|---|
| Mut GII.4_Δ35-42 hCod (na) | Hu/GII.4/Sydney/NSW0514/2012/AU | 64 | 32L | 4158 | 44G |
| Mut GII.4_SSTAVATA (aa) | Hu/GII.4/Sydney/NSW0514/2012/AU | 65 | 32M | — | |
| Mut GII.4_SSTAVATA hCod (na) | Hu/GII.4/Sydney/NSW0514/2012/AU | 66 | 32N | 4159 | 44H |
| Mut GII.4_A39V + R53I (aa) | Hu/GII.4/Sydney/NSW0514/2012/AU | 188 | 32AA | — | |
| Mut GII.4_A39V + R53I hCod (na) | Hu/GII.4/Sydney/NSW0514/2012/AU | 189 | 32BB | 4185 | 44O |
| Mut GII.4_A39V + P80S (aa) | Hu/GII.4/Sydney/NSW0514/2012/AU | 67 | 32O | — | |
| Mut GII.4_A39V + P80S hCod (na) | Hu/GII.4/Sydney/NSW0514/2012/AU | 68 | 32P | 4165 | 44I |
| Mut GII.4_A39I + P80S (aa) | Hu/GII.4/Sydney/NSW0514/2012/AU | 288 | 32HH | — | |
| Mut GII.4_A39I + P80S hCod (na) | Hu/GII.4/Sydney/NSW0514/2012/AU | 289 | 32GG | 4256 | 50B |
| Mut GII.4_A39M + P80S (aa) | Hu/GII.4/Sydney/NSW0514/2012/AU | 288 | 32HH | — | |
| Mut GII.4_A39M + P80S hCod (na) | Hu/GII.4/Sydney/NSW0514/2012/AU | 289 | 32GG | 4257 | 50B |
| Mut GII.4_A39G + P80S (aa) | Hu/GII.4/Sydney/NSW0514/2012/AU | 288 | 32HH | — | |
| Mut GII.4_A39G + P80S hCod (na) | Hu/GII.4/Sydney/NSW0514/2012/AU | 289 | 32GG | 4258 | 50B |
| Mut GII.4_A39S + P80S (aa) | Hu/GII.4/Sydney/NSW0514/2012/AU | 288 | 32HH | — | |
| Mut GII.4_A39S + P80S hCod (na) | Hu/GII.4/Sydney/NSW0514/2012/AU | 289 | 32GG | 4259 | 50B |
| Mut GII.4_A39E + P80S (aa) | Hu/GII.4/Sydney/NSW0514/2012/AU | 288 | 32HH | — | |
| Mut GII.4_A39E + P80S hCod (na) | Hu/GII.4/Sydney/NSW0514/2012/AU | 289 | 32GG | 4260 | 50B |
| Mut GII.4_A39D + P80S (aa) | Hu/GII.4/Sydney/NSW0514/2012/AU | 288 | 32HH | — | |
| Mut GII.4_A39D + P80S hCod (na) | Hu/GII.4/Sydney/NSW0514/2012/AU | 289 | 32GG | 4261 | 50B |
| Mut GII.4_A39N + P80S (aa) | Hu/GII.4/Sydney/NSW0514/2012/AU | 288 | 32HH | — | |
| Mut GII.4_A39N + P80S hCod (na) | Hu/GII.4/Sydney/NSW0514/2012/AU | 289 | 32GG | 4262 | 50B |
| Mut GII.4_A39Q + P80S (aa) | Hu/GII.4/Sydney/NSW0514/2012/AU | 288 | 32HH | — | |
| Mut GII.4_A39Q + P80S hCod (na) | Hu/GII.4/Sydney/NSW0514/2012/AU | 289 | 32GG | 4263 | 50B |
| Mut GII.4_A39K + P80S (aa) | Hu/GII.4/Sydney/NSW0514/2012/AU | 288 | 32HH | — | |
| Mut GII.4_A39K + P80S hCod (na) | Hu/GII.4/Sydney/NSW0514/2012/AU | 289 | 32GG | 4264 | 50B |
| Mut GII.4_A39H + P80S (aa) | Hu/GII.4/Sydney/NSW0514/2012/AU | 288 | 32HH | — | |
| Mut GII.4_A39H + P80S hCod (na) | Hu/GII.4/Sydney/NSW0514/2012/AU | 289 | 32GG | 4265 | 50B |
| Mut GII.4_V47P + P80S (aa) | Hu/GII.4/Sydney/NSW0514/2012/AU | 69 | 32Q | — | |
| Mut GII.4_V47P + P80S hCod (na) | Hu/GII.4/Sydney/NSW0514/2012/AU | 70 | 32R | 4166 | 44J |
| Mut GII.4_R53I + P80S (aa) | Hu/GII.4/Sydney/NSW0514/2012/AU | 71 | 32S | — | |
| Mut GII.4_R53I + P80S hCod (na) | Hu/GII.4/Sydney/NSW0514/2012/AU | 72 | 32T | 4167 | 44K |
| Mut GII.4_P80S + S90L (aa) | Hu/GII.4/Sydney/NSW0514/2012/AU | 73 | 32U | — | |
| Mut GII.4_P80S + S90L hCod (na) | Hu/GII.4/Sydney/NSW0514/2012/AU | 74 | 32V | 4135 | 44L |
| Mut GII.4_P80S + Δ35-42 (aa) | Hu/GII.4/Sydney/NSW0514/2012/AU | 75 | 32W | — | |
| Mut GII.4_P805 + Δ35-42 hCod (na) | Hu/GII.4/Sydney/NSW0514/2012/AU | 76 | 32X | 4168 | 44M |
| Mut GII.4_P80S + SSTAVATA (aa) | Hu/GII.4/Sydney/NSW0514/2012/AU | 77 | 32Y | — | |
| Mut GII.4_P80S + SSTAVATA hCod (na) | Hu/GII.4/Sydney/NSW0514/2012/AU | 78 | 32Z | 4169 | 44N |
| Mut GII.4_A39V + R53I + P80S(aa) | Hu/GII.4/Sydney/NSW0514/2012/AU | 190 | 32CC | — | |
| Mut GII.4_A39V + R53I + P80ShCod (na) | Hu/GII.4/Sydney/NSW0514/2012/AU | 191 | 32DD | 4186 | 44P |
| Wt GII.4 (aa) | US96/GII.4/Dresden174/ 1997/DE_AY741811 | 27 | 19C | — | |
| Wt GII.4 (aa) | FH02/GII.4/FarmingtonHills/ 2002/US_AY502023 | 28 | 19D | — | |
| Wt GII.4 (aa) | Hnt04: GII.4/Hunter- NSW504D/2004/AU_DQ078814 | 29 | 19E | — | |
| Wt GII.4 (aa) | 2006b: GII.4/Shellharbour- NSW696T/2006/AU_EF684915 | 30 | 19F | — | |
| Wt GII.4 (aa) | NO09/GII.4/Orange- NSW001P/2008/AU_GQ845367 | 31 | 19G | — | |
| VP1 GII.5 | | | | | |
| Wt GII.5 (aa) | GII.5_Alberta/2013/CA_ALT54485 | 17 | 20 | — | |
| VP1 GII.6 | | | | | |
| Wt GII.6 (aa) | Hu/GII.6/Ohio/490/2012/USA | 20 | 21A | — | |
| Wt GII.6 hCod (na) | Hu/GII.6/Ohio/490/2012/USA | 21 | 21B | 3993 | 45A |
| Mut GII.6_E80S (aa) | Hu/GII.6/Ohio/490/2012/USA | 79 | 33A | — | |
| Mut GII.6_E80S hCod (na) | Hu/GII.6/Ohio/490/2012/USA | 80 | 33B | 4149 | 45B |
| Mut GII.6_S90L (aa) | Hu/GII.6/Ohio/490/2012/USA | 81 | 33C | — | |
| Mut GII.6_S90L hCod (na) | Hu/GII.6/Ohio/490/2012/USA | 82 | 33D | 4150 | 45C |
| Mut GII.6_E80S + S90L (aa) | Hu/GII.6/Ohio/490/2012/USA | 83 | 33E | — | |
| Mut GII.6_E80S + S90L hCod (na) | Hu/GII.6/Ohio/490/2012/USA | 84 | 33F | 4151 | 45D |
| VP1 GII.7 | | | | | |
| Wt GII.7 (aa) | GII.7_Musa_2010_AII73774 | 18 | 22 | — | |
| VP1 GII.12 | | | | | |
| Wt GII.12 (aa) | GII.12_HS206_2010_USA_AEI29586 | 19 | 23A | — | |
| Wt GII.12 hCod (na) | GII.12_HS206_2010_USA_AEI29586 | 87 | 23B | 3995 | 46A |
| Mut GII.12_E80S (aa) | GII.12_HS206_2010_USA_AEI29586 | 88 | 34A | — | |
| Mut GII.12_E8OS hCod (na) | GII.12_HS206_2010_USA_AEI29586 | 89 | 34B | 4136 | 46B |
| Mut GII.12_A90L (aa) | GII.12_HS206_2010_USA_AEI29586 | 90 | 34C | — | |
| Mut GII.12_A90L hCod (na) | GII.12_HS206_2010_USA_AEI29586 | 91 | 34D | 4137 | 46C |
| Mut GII.12_E80S + A90L (aa) | GII.12_HS206_2010_USA_AEI29586 | 92 | 34E | — | |
| Mut GII.12_E80S + A90L hCod (na) | GII.12_HS206_2010_USA_AEI29586 | 93 | 34F | 4138 | 46D |
| VP1 GII.13 | | | | | |
| Wt GII.13 (aa) | GII.13_VA173_2010_H9AWU4 | 22 | 24A | — | |
| Wt GII.13 hCod (na) | GII.13_VA173_2010_H9AWU4 | 23 | 24B | — | |
| VP1 GII.14 | | | | | |
| Wt GII.14 (aa) | GII.l4_Saga/2008/JPN/_ADE28701 | 32 | 25 | — | |
| VP1 GII.17 | | | | | |

TABLE 3-continued

| Norovirus strains and constructs. | | | | | |
|---|---|---|---|---|---|
| Wt GII.17 (aa) | GII.17_Kawa_2014_A0A077KVU6 | 24 | 26A | — | |
| Wt GII.17 hCod (na) | GII.17_Kawa_2014_A0A077KVU6 | 25 | 26B | — | |
| Mut GII.17_A39V (aa) | GII.17_Kawa_2014_A0A077KVU6 | 192 | 34G | — | |
| Mut GII.17_A39V hCod (na) | GII.17_Kawa_2014_A0A077KVU6 | 193 | 34H | 4234 | 46E |
| Mut GII.17_R53I (aa) | GII.17_Kawa_2014_A0A077KVU6 | 194 | 34I | — | |
| Mut GII.17_R53I hCod (na) | GII.17_Kawa_2014_A0A077KVU6 | 195 | 34J | 4235 | 46F |
| Mut GII.17_A90L (aa) | GII.17_Kawa_2014_A0A077KVU6 | 196 | 34K | — | |
| Mut GII.17_A90L hCod (na) | GII.17_Kawa_2014_A0A077KVU6 | 197 | 34L | 4232 | 46G |
| Mut GII.17_A39V + R53I (aa) | GII.17_Kawa_2014_A0A077KVU6 | 198 | 34M | — | |
| Mut GII.17_A39V + R53I hCod (na) | GII.17_Kawa_2014_A0A077KVU6 | 199 | 34N | 4236 | 46H |
| Mut GII.17_E80S + A90L (aa) | GII.17_Kawa_2014_A0A077KVU6 | 200 | 340 | — | |
| Mut GII.17_ E80S + A90L hCod (na) | GII.17_Kawa_2014_A0A077KVU6 | 201 | 34P | 4233 | 46I |
| VP1 GII.21 | | | | | |
| Wt GII.21 (aa) | GII.21_Sali_2011_USA_AFC89665 | 26 | 27 | — | |
| VP2 | | | | | |
| Wt GI.1 (aa) | Hu/GI.1/United States/Norwalk/1968 | 99 | 35A | — | |
| Wt GI.1 hCod (na) | Hu/GI.1/United States/Norwalk/1968 | 100 | 35B | 2725 | 47A |
| Wt GI.3 (aa) | GI.3/S29/2008/Lila Edet/Sweden | 94 | 36A | — | |
| Wt GI.3 hCod (na) | GI.3/S29/2008/Lila Edet/Sweden | 95 | 36B | 3303 | 47B |
| Wt GII.6 (aa) | GII.6 HS245/2010/USA | 96 | 37A | — | |
| Wt GII.6 hCod (na) | GII.6 HS245/2010/USA | 97 | 37B | 3307 | 47C |

| Construct | SEQ ID NO: | SEQ FIG. # | Const # | Const. FIG. # |
|---|---|---|---|---|
| Cloning vector 1190 from left to right T-DNA | 162 | 38A | 1190 | 48 |
| Construct 2724 from 2X35S promoter to NOS terminator | 163 | 38B | 2724 | |
| Cloning vector 3677 from left to right T-DNA | 164 | 38C | 3677 | 49 |
| Construct 4133 from 2X35S promoter to NOS terminator | 165 | 38D | 4133 | |
| Construct 4135 from 2X35S promoter to NOS terminator | 166 | 38E | 4135 | |

The present invention will be further illustrated in the following examples.

Example 1: Norovirus VP1 Constructs

The candidate sequences for VP1 and VP2 are available in Genbank (see FIGS. 2A and 2B). Non-limiting examples of these sequences are:

Hu/GI.2/Leuven/2003/BEL (GI.2; SEQ ID NO:4; FIG. 13A);

Hu/GI.3/S29/2008/Lilla Edet/Sweden (GI.3; SEQ ID NO:6; FIG. 14A);

Hu/GI.5/Siklos/Hun5407/2013/HUN (GI.5; SEQ ID NO:12; FIG. 15A);

Hu/GI.7/USA/2014/GA5043 (GI.7, SEQ ID NO:101, FIG. 16A)

Hu/GII.1/Ascension208/2010/USA (GII.1; SEQ ID NO:13; FIG. 16C);

Hu/GII.2/CGMH47/2011/TW (GII.2; SEQ ID NO:14; FIG. 17A);

Hu/GII.3/Jingzhou/2013402/CHN (GII.3; SEQ ID NO:15; FIG. 18A);

Hu/GII.4/Sydney/NSW0514/2012/AU (GII.4; SEQ ID NO:16; FIG. 19A);

US96/GII.4/Dresden174/1997/DE_AY741811 (GII.4; SEQ ID NO:27; FIG. 19C);

FH02/GII.4/FarmingtonHills/2002/US_AY502023 (GII.4; SEQ ID NO:28; FIG. 19D);

Hnt04:GII.4/Hunter-NSW504D/2004/AU_DQ078814 (GII.4; SEQ ID NO:29; FIG. 19E);

2006b: GII.4/Shellharbour-NSW696T/2006/AU_EF684915 (GII.4; SEQ ID NO:30; FIG. 19F);

NO09: GII.4/Orange-NSW001P/2008/AU_GQ845367 (GII.4; SEQ ID NO:31; FIG. 19G);

GII.14_Saga_2008_JPN_ADE28701 native VP1 (GII.14; SEQ ID NO:32; FIG. 25);

Hu/GII.5/AlbertaEI390/2013/CA (GII.5; SEQ ID No:17; FIG. 20);

Hu/GII.6/Ohio/490/2012/USA (GII.6; SEQ ID NO: 20; FIG. 21A);

G11.7/Musa/2010/A1173774 (GII.7; SEQ ID NO:18; FIG. 22);

Hu/GII.12/HS206/2010/USA (GII.12; SEQ ID NO:19; FIG. 23A);

GII.13/VA173/2010/H9AWU4 (GII.13; SEQ ID NO:22; FIG. 24A);

Hu/GII.17/Kawasaki323/2014/JP (GII.17; SEQ ID NO:24; FIG. 26A);

Hu/GII.21/Salisbury150/2011/USA (GII.21; SEQ ID NO:26; FIG. 27).

The primers listed in Table 4 were used to prepare the constructs described below.

TABLE 4

| primers used to prepare constructs defined herein. | | |
|---|---|---|
| Primer | Sequence | SEQ ID NO |
| IF-NoV(US68)VP1(ORF1)(hCod).c | TCGTGCTTCGGCACCAGTACAATGATGATGGCTAGTAAAGATGCGACCT | 102 |
| IF-NoV(US68)VP1(ORF1)(hCod).r | ACTAAAGAAAATAGGCCTTTATCTCCGCAGACCGAGGCGTCCGCGGGCAGAA | 103 |

TABLE 4 -continued

| primers used to prepare constructs defined herein. | | |
|---|---|---|
| Primer | Sequence | SEQ ID NO |
| IF-GI3Lil08VP1.c | TCGTGCTTCGGCACCAGTACAATGATGATGGCTTCC AAGGATGCTCCCA | 104 |
| IF-GI3Lil08VP1.r | ACTAAAGAAAATAGGCCTCTAGCTCCGTCTGATCCC GAGCCTCCGAACT | 105 |
| VP1_GI.3Lil08(S94L).r | CTGAGCCAAGTGGAGCAGAAACGGATTCAAGTGTGG TCCTAGCTGCAGGTCAAACAAGA | 106 |
| VP1_GI.3Lil08(S94L).c | AGGACCACACTTGAATCCGTTTCTGCTCCACTTGGC TCAGATGTATAATGGATGGG | 107 |
| VP1_GI.3Lil08(Q84S).r | GTGTGGTCCTAGGCTCAGGTCAAACAAGATGTCACC CGGGGTGTTGTTTGGGCTTAT | 108 |
| VP1_GI.3Lil08(Q84S).c | GGTGACATCTTGTTTGACCTGAGCCTAGGACCACAC TTGAATCCGTTT | 109 |
| IF-GI3Lil08VP2.c | TCGTGCTTCGGCACCAGTACAATGGCTCAGGCAATC TTCGGCGCAATC | 110 |
| IF-GI3Lil08VP2.r | ACTAAAGAAAATAGGCCTTCACTTCCTCATGTTTGC GAACAGGGGAAGC | 111 |
| IF-(160)GI.5_Sikl13_VP1.c | TCGTGCTTCGGCACCAGTACAATGATGATGGCCTCC AAAGACGCTCCT | 112 |
| IF-GI.5_Sikl13_VP1.r | ACTAAAGAAAATAGGCCTTCAGCGCCGCACGCCAAG GCGCCCCCGGGCAGATG | 113 |
| GI.5(hCod)(Q84S).r | GATGAGGGCCTAAGCTCAGGTCGAACAGAATATCCC CTGGTGTGTTGTTAG | 114 |
| GI.5(hCod)(Q84S).c | TATTCTGTTCGACCTGAGCTTAGGCCCTCATCTCAA CCCCTTCTTGGCCCA | 115 |
| GI.5(hCod)(A94L).r | ATCTGGCTCAGGTGGAGCAAGAAGGGGTTGAGATGA GGGCCTAACTGCAG | 116 |
| GI.5(hCod)(A94L).c | TCTCAACCCCTTCTTGCTCCACCTGAGCCAGATGTA CAATGGCTGGGTGGG | 117 |
| IF-(160)GII.2_CGMH11_VP1.c | TCGTGCTTGGGCACCAGTACAATGAAGATGGCATCC AACGACGCCGCACCCAGC | 118 |
| IF-GII.2_CGMH11_VP1.r | ACTAAAGAAAATAGGCCTTTACTGGATCCGTCGGCG ACCGTTCCCTGTGCCCA | 119 |
| VP1_GII.2CGMH11(E80S).r | TTCTGGTCCCAGGCTGAGATTGAGGAGCACTTCCCC AGGGCTATTTCTAGGGCTGACCG | 120 |
| VP1_GII.2CGMH11(E80S).c | GGAAGTGCTCCTCAATCTCAGCCTGGGACCAGAACT TAATCCGTACCT | 121 |
| VP1_GII.2CGMH11(A90L).r | TCCGGGCCAGGTGGAGCAGGTACGGATTAAGTTCTG GTCCCAGCTCGAGATTGAGGAGC | 122 |
| VP1_GII.2CGMH11(A90L).c | GGGACCAGAACTTAATCCGTACCTGCTCCACCTGGC CCGGATGTACAATGGATATGCAG | 123 |
| IF-(160)GII.3_Jing13_VP1.c | TCGTGCTTCGGCACCAGTACAATGAAAATGGCTTCC AACGATGCAGCACCCT | 124 |
| IF-GII.3_Jing13_VP1.r | ACTAAAGAAAATAGGCCTTTACTGGATCCGCCGTCT GCCATTGCCTGTAC | 125 |
| VP1_GII.3Jing13(E80S).r | ATTTCAGGGCCCAGGCTCAAATTCAAGAGAACCTCC CCGGGGGAGTTTCGAGGAGAGAC | 126 |
| VP1_GII.3Jing13(E80S).c | GGAGGTTCTCTTGAATTTGAGCCTGGGCCCTGAAAT TAATCCTTATCT | 127 |
| VP1_GII.3Jing13(A90L).r | ATTCGGGCTAGATGGAGCAGATAAGGATTAATTTCA GGGCCCAGTTCCAAATTCAAGAG | 128 |

TABLE 4 -continued primers used to prepare constructs defined herein.

| Primer | Sequence | SEQ ID NO |
|---|---|---|
| VP1_GII.3Jing13(A90L).c | GGGCCCTGAAATTAATCCTTATCTGCTCCATCTAGC CCGAATGTACAACGGCTACG | 129 |
| IF-GII.4Syd12VP1.c | TCGTGCTTCGGCACCAGTACAATGAAAATGGCCTCG AGTGACGCTAACC | 130 |
| IF-GII.4Syd12VP1.r | ACTAAAGAAAATAGGCCTTCAGACAGCCCTGCGTCT GCCAGTCCCATT | 131 |
| VP1_GII.4Syd12(A39V).r | GACCGGCCACGGGGACTGCTATGGCTGCGCCCACCA CAGGCTCCAGGGCCATCA | 132 |
| VP1_GII.4Syd12(A39V).c | GGGCGCAGCCATAGCAGTCCCCGTGGCCGGTCAGCA GAATGTGATTGACCCGTG | 133 |
| VP1_GII.4Syd12(V47P).r | CGTATCCACGGGTCAATGGGATTCTGCTGACCGGCC ACGGGCGCTGCTATG | 134 |
| VP1_GII.4Syd12(V47P).c | GGCCGGTCAGCAGAATCCCATTGACCCGTGGATACG CAACAATTTTGTCCAAG | 135 |
| VP1_GII.4Syd12(R53I).r | TGGACAAAATTGTTGATTATCGACGGGTCAATCACA TTCTGCTGACCG | 136 |
| VP1_GII.4Syd12(R53I).c | GATTGACCCGTGGATAATCAACAATTTTGTCCAAGC CCCTGGTGGGGAGT | 137 |
| GII.4(P80S).r | GATCGGGTCCCAAGCTGGCCGACCACAGGATTTCTC CTGGCGCATTTCTC | 138 |
| GII.4(P80S).c | AATCCTGTGGTCGGCCAGCTTGGGACCCGATCTGAA CCCCTATTTGTCAC | 139 |
| GII.4(S90L).r | ATCCGAGCGAGATGCAGCAAATAGGGGTTCAGATCG GGTCCCAATGGGGCCGACCA | 140 |
| GII.4(S90L).c | TCTGAACCCCTATTTGCTGCATCTCGCTCGGATGTA CAACGGGTATGC | 141 |
| VP1_GII.4Syd12(Del(35-42)).r | CACATTCTGCTGACCGCCCACCACAGGCTCCAGGGC CATCACCTCATTAT | 142 |
| VP1_GII.4Syd12(Del(35-42)).c | GGAGCCTGTGGTGGGCGGTCAGCAGAATGTGATTGA CCCGTGGATACG | 143 |
| VP1_GII.4Syd12(SSTAVATA).r | CTGACCGGCTGTAGCGACGGCGGTGGAGCTGCCCAC CACAGGCTCCAGGGCCATCACCTC | 144 |
| VP1_GII.4Syd12(SSTAVATA).c | TGTGGTGGGCAGCTCCACCGCCGTCGCTACAGCCGG TCAGCAGAATGTGATTGACCCGTG | 145 |
| IF-GII.6Ohi12VP1.c | TCGTGCTTCGGCACCAGTACAATGAAGATGGCAAGC AACGACGCAGCTC | 146 |
| IF-GII.6Ohi12VP1.r | ACTAAAGAAAATAGGCCTTCACTGATCCCGGCGTCG CCCCTGGCCTGTCCCCAT | 147 |
| IF-GII.6HS10VP2.c | TCGTGCTTCGGCACCAGTACAATGGCCTCCGCATTT CTAGCTGGATTGGCC | 148 |
| IF-GII.6HS10VP2.r | ACTAAAGAAAATAGGCCTCTAAACTTGTGATTCTCC CCGTCGCCTGGGGTGTG | 149 |
| VP1_GII.6Ohi12(E80S).r | AGTTCAGGGCCGAGGCTCAGATTGAGCAGCATCTCG CCCGGGGAGTTCCGGGGGGAGAC | 150 |
| VP1_GII.6Ohi12(E80S).c | CGAGATGCTGCTCAATCTGAGCCTCGGCCCTGAACT AAACCCTTATCT | 151 |
| VP1_GII.6Ohi12(S90L).r | ATCCGTGAAAGGTGGAGCAGATAAGGGTTTAGTTCA GGGCCGAGTTCCAGATTGAGCAG | 152 |
| VP1_GII.6Ohi12(S90L).c | CCCTGAACTAAACCCTTATCTGCTCCACCTTTCACG GATGTACAATGGCTACGCAGGAG | 153 |

TABLE 4 -continued primers used to prepare constructs defined herein.

| Primer | Sequence | SEQ ID NO |
|---|---|---|
| IF-(160)GII.12_HS10_VP1.c | TCGTGCTTCGGCACCAGTACAATGAAGATGGCGTCT AATGATGCTGCTCCTT | 154 |
| IF-GII.12_HS10_VP1.r | ACTAAAGAAAATAGGCCTTTACTGCACACGCCTCCT CCCATTTCCTGTTCCCAT | 155 |
| GII.12(E80S).r | AGTTCTGGTCCTAAGCTCAAATTCAATAACACTTCG CCGGGGGAGTTT | 156 |
| GII.12(E80S).C | AGTGTTATTGAATTTGAGCTTAGGACCAGAACTCAA CCCCTATCTGGCA | 157 |
| GII.12(A90L).r | ATCCGAGACAGATGGAGCAGATAGGGGTTGAGTTCT GGTCCTAATTCCAA | 158 |
| GII.12(A90L).c | ACTCAACCCCTATCTGCTCCATCTGTCTCGGATGTA CAACGGCTATGCGGGCGGAGT | 159 |
| IF-NoV(US68)VP2(ORF3)(hCod).c | TCGTGCTTCGGCACCAGTACAATGGCTCAGGCCATT ATTGGCGCCAT | 160 |
| IF-NoV(US68)VP2(ORF3)(hCod).r | ACTAAAGAAAATAGGCCTTCAGCGGCGGTTGTTAGC GAACAGAGGAAGTC | 161 |
| GI.3Lil08(M57I).r | CTGAACGTAATTTGAGATGATCCAGGGGTCGATCAT GTTTACCTGTCCTGCGGTGGCGG | 202 |
| GI.3Lil08(M57I).c | GTAAACATGATCGACCCCTGGATCATCTCAAATTAC GTTCAGGGTCCACAGGGGGAGTT | 203 |
| IF-(GI.7USA14)VP1.c | TCGTGCTTCGGCACCAGTACAATGATGATGGCCAGC AAGGACGCTCCGAGTA | 204 |
| IF-(GI.7USA14)VP1.r | ACTAAAGAAAATAGGCCTTCACACCCGCCTCACGCC GAGTCGTCGCACG | 205 |
| GI.7USA14_VP1(R84S).r | AGTGGGGTCCTAAGCTGAGGTCAAACAGAATATCCC CTGGGGTGTTAT | 206 |
| GI.7USA14_VP1(R84S).c | TATTCTGTTTGACCTCAGCTTAGGACCCCACTTGAA CCCCTTTCTGCTTC | 207 |
| GI.7USA14_VP1(M57I).r | AACGAAATTGTTGATTATCCACGGGTCGATCATATT GACTTGGCCTGCAGT | 208 |
| GI.7USA14_VP1(M57I).c | GATCGACCCGTGGATAATCAACAATTTCGTTCAGGC ACCAGAAGGAGA | 209 |
| GII.2CGMH11(A39V).r | TTTGTCTGCCCGGTCACAGGCACTGCGAGGGCAGCC CCTGCAACAGGCTCCAAGGCCATCAC | 210 |
| GII.2CGMH11(A39V).c | GTTGCAGGGGCTGCCCTCGCAGTGCCTGTGACCGGG CAGACAAATATCATCGATCCTTG | 211 |
| GII.2CGMH11(R53I).r | CACGAAATTAGCGATAATCCAAGGATCGATGATATT TGTCTGCCCGGTCACAGGAGCTG | 212 |
| GII.2CGMH11(R53I).c | GGCAGACAAATATCATCGATCCTTGGATTATCGCTA ATTTCGTGCAAGCCCCAAATGGG | 213 |
| IF-GII17Kaw14VP1.c | TCGTGCTTCGGCACCAGTACAATGAAAATGGCATCT AACGACGCAGCCCCCTC | 214 |
| IF-GII17Kaw14VP1.r | ACTAAAGAAAATAGGCCTCTACTGAGCCCGGCGTCT GCCGTTACCGGTGCCCATTG | 215 |
| GII.17Kaw14(A90L).r | GCGGCTCAGATGCAGCAGATATGGATTGAGGTCAGG GCCGAGCTCAAGATTCAGGAGTA | 216 |
| GII.17Kaw14(A90L).c | CCTGACCTCAATCCATATCTGCTGCATCTGAGCCGC ATGTACAATGGTTAC | 217 |
| GII.17Kaw14(A39V).r | ATTCTGCCCTGTCACTGGCACAGCTATAGCGGCGCC TGCAACCGGCTCTAGTGGAAGTG | 218 |

TABLE 4 -continued primers used to prepare constructs defined herein.

| Primer | Sequence | SEQ ID NO |
|---|---|---|
| GII.17Kaw14(A39V).c | AGGCGCCGCTATAGCTGTGCCAGTGACAGGGCAGAA TAATATTATAGACCCTTGGATT | 219 |
| GII.17Kaw14(R53I).r | ACGAAGTTTGTGATAATCCAAGGGTCTATAATATTA TTCTGCCCTGTCACTGGGGCAGC | 220 |
| GII.17Kaw14(R53I).c | GGCAGAATAATATTATAGACCCTTGGATTATCACAA ACTTCGTGCAGGCACCCAACGGC | 221 |
| GII.4Syd12(P80A).r | ATCGGGTCCCAAGGCGGCCGACCACAGGATTTCTCC TGGCGCATTTCTCG | 222 |
| GII.4Syd12(P80A).c | AATCCTGTGGTCGGCCGCCTTGGGACCCGATCTGAA CCCCTATTTGTCAC | 223 |
| GII.4Syd12(P80N).r | ATCGGGTCGCAAGTTGGCCGACCACAGGATTTCTCC TGGCGCATTTCTCG | 224 |
| GII.4Syd12(P80N).c | AATCCTGTGGTCGGCCAACTTGGGACCCGATCTGAA CCCCTATTTGTCAC | 225 |
| GII.4Syd12(P80K).r | ATCGGGTCCCAACTTGGCCGACCACAGGATTTCTCC TGGCGCATTTCTCG | 226 |
| GII.4Syd12(P80K).c | AATCCTGTGGTCGGCCAAGTTGGGACCCGATCTGAA CCCCTATTTGTCAC | 227 |
| GII.4Syd12(P80H).r | ATCGGGTCCCAAGTGGGCCGACCACAGGATTTCTCC TGGCGCATTTCTCG | 228 |
| GII.4Syd12(P80H).c | AATCCTGTGGTCGGCCCACTTGGGACCCGATCTGAA CCCCTATTTGTCAC | 229 |
| GII.4Syd12(A39I).r | GACCGGCCACGGGGATTGCTATGGCTGCGCCCACCA CAGGCTCCAGGGCCATCA | 230 |
| GII.4Syd12(A39I).c | GGGCGCAGCCATAGCAATCCCCGTGGCCGGTCAGCA GAATGTGATTGACCCGTG | 231 |
| GII.4Syd12(A39M).r | GACCGGCCACGGGCATTGCTATGGCTGCGCCCACCA CAGGCTCCAGGGCCATCA | 232 |
| GII.4Syd12(A39M).c | GGGCGCAGCCATAGCAATGCCCGTGGCCGGTCAGCA GAATGTGATTGACCCGTG | 233 |
| GII.4Syd12(A39G).r | GACCGGCCACGGGGCCTGCTATGGCTGCGCCCACCA CAGGCTCCAGGGCCATCA | 234 |
| GII.4Syd12(A39G).c | GGGCGCAGCCATAGCAGGCCCCGTGGCCGGTCAGCA GAATGTGATTGACCCGTG | 235 |
| GII.4Syd12(A39S).r | GACCGGCCACGGGGCTTGCTATGGCTGCGCCCACCA CAGGCTCCAGGGCCATCA | 236 |
| GII.4Syd12(A39S).c | GGGCGCAGCCATAGCAAGCCCCGTGGCCGGTCAGCA GAATGTGATTGACCCGTG | 237 |
| GII.4Syd12(A39E).r | GACCGGCCACGGGCTCTGCTATGGCTGCGCCCACCA CAGGCTCCAGGGCCATCA | 238 |
| GII.4Syd12(A39E).c | GGGCGCAGCCATAGCAGAGCCCGTGGCCGGTCAGCA GAATGTGATTGAC | 239 |
| GII.4Syd12(A39D).r | GACCGGCCACGGGGTCTGCTATGGCTGCGCCCACCA CAGGCTCCAGGGCCATCA | 240 |
| GII.4Syd12(A39D).c | GGGCGCAGCCATAGCAGACCCCGTGGCCGGTCAGCA GAATGTGATTGACCCGTG | 241 |
| GII.4Syd12(A39N).r | ACCGGCCACGGGGTTTGCTATGGCTGCGCCCACCAC AGGCTCCAGGGCCATCAC | 242 |
| GII.4Syd12(A39N).c | GGGCGCAGCCATAGCAAACCCCGTGGCCGGTCAGCA GAATGTGATTGACCCGTG | 243 |

TABLE 4 -continued primers used to prepare constructs defined herein.

| Primer | Sequence | SEQ ID NO |
|---|---|---|
| GII.4Syd12(A39Q).r | GACCGGCCACGGGCTGTGCTATGGCTGCGCCCACCA CAGGCTCCAGGGCCATCA | 244 |
| GII.4Syd12(A39Q).c | GGGCGCAGCCATAGCACAGCCCGTGGCCGGTCAGCA GAATGTGATTGACCCGTG | 245 |
| GII.4Syd12(A39K).r | GACCGGCCACGGGCTTTGCTATGGCTGCGCCCACCA CAGGCTCCAGGGCCATCA | 246 |
| GII.4Syd12(A39K).c | GGGCGCAGCCATAGCAAAGCCCGTGGCCGGTCAGCA GAATGTGATTGACCCGTG | 247 |
| GII.4Syd12(A39H).r | GACCGGCCACGGGGTGTGCTATGGCTGCGCCCACCA CAGGCTCCAGGGCCA | 248 |
| GII.4Syd12(A39H).c | GGGCGCAGCCATAGCACACCCCGTGGCCGGTCAGCA GAATGTGATTGACCCGTG | 249 |
| GI.7USA14(M57L).r | GAACGAAATTGTTCAGTATCCACGGGTCGATCATAT TGACTTGGCCTGCA | 250 |
| GI.7USA14(M57L).c | GATCGACCCGTGGATACTGAACAATTTCGTTCAGGC ACCAGAAGGAGA | 251 |
| GI.7USA14(M57G).r | GAACGAAATTGTTGCCTATCCACGGGTCGATCATAT TGACTTGGCCTGCAGT | 252 |
| GI.7USA14(M57G).c | GATCGACCCGTGGATAGGCAACAATTTCGTTCAGGC ACCAGAAGGAGA | 253 |
| GI.7USA14(MS7S).r | GAACGAAATTGTTGCTTATCCACGGGTCGATCATAT TGACTTGGCCTGCAGT | 254 |
| GI.7USA14(M57S).c | GATCGACCCGTGGATAAGCAACAATTTCGTTCAGGC ACCAGAAGGAGA | 255 |
| GI.7USA14(M57T).r | GAACGAAATTGTTGGTTATCCACGGGTCGATCATAT TGACTTGGCCTGCAGT | 256 |
| GI.7USA14(M57T).c | GATCGACCCGTGGATAACCAACAATTTCGTTCAGGC ACCAGAAGGAGA | 257 |
| GI.7USA14(M57N).r | GAACGAAATTGTTGTTTATCCACGGGTCGATCATAT TGACTTGGCCTGCAGT | 258 |
| GI.7USA14(M57N).c | GATCGACCCGTGGATAAACAACAATTTCGTTCAGGC ACCAGAAGGAGA | 259 |
| GI.7USA14(M57Q).r | GAACGAAATTGTTCTGTATCCACGGGTCGATCATAT TGACTTGGCCTGCAGT | 260 |
| GI.7USA14(M57Q).c | GATCGACCCGTGGATACAGAACAATTTCGTTCAGGC ACCAGAAGGAGA | 261 |
| GI.7USA14(M57K).r | GAACGAAATTGTTCTTTATCCACGGGTCGATCATAT TGACTTGGCCTGCAGT | 262 |
| GI.7USA14(M57K).C | GATCGACCCGTGGATAAAGAACAATTTCGTTCAGGC ACCAGAAGGAGA | 263 |
| GI.7USA14(M57H).r | GAACGAAATTGTTGTGTATCCACGGGTCGATCATAT TGACTTGGCCTGCAGT | 264 |
| GI.7USA14(M57H).c | GATCGACCCGTGGATACACAACAATTTCGTTCAGGC ACCAGAAGGAGA | 265 |
| GI.3Lil08(S94V).r | TCTGAGCCAAGTGCACCAGAAACGGATTCAAGTGTG GTCCTAGCTGCAGGTCAA | 266 |
| GI.3Lil08(S94V).c | CTTGAATCCGTTTCTGGTGCACTTGGCTCAGATGTA TAATGGATGGGTTGGAAA | 267 |
| GI.3Lil08(S94I).r | TCTGAGCCAAGTGGATCAGAAACGGATTCAAGTGTG GTCCTAGCTGCAGGTCAA | 268 |

TABLE 4 -continued primers used to prepare constructs defined herein.

| Primer | Sequence | SEQ ID NO |
|---|---|---|
| GI.3Lil08(S94I).c | CTTGAATCCGTTTCTGATCCACTTGGCTCAGATGTA TAATGGATGGGTTGGAAA | 269 |
| GI.3Lil08(S94M).r | TCTGAGCCAAGTGCATCAGAAACGGATTCAAGTGTG GTCCTAGCTGCAGGTCAA | 270 |
| GI.3Lil08(S94M).c | CTTGAATCCGTTTCTGATGCACTTGGCTCAGATGTA TAATGGATGGGTTGGAAA | 271 |
| GI.3Lil08(S94T).r | TCTGAGCCAAGTGGGTCAGAAACGGATTCAAGTGTG GTCCTAGCTGCAGGTCAA | 272 |
| GI.3Lil08(S94T).c | CTTGAATCCGTTTCTGACCCACTTGGCTCAGATGTA TAATGGATGGGTTGGAAA | 273 |
| GI.3Lil08(S94E).r | TCTGAGCCAAGTGCTCCAGAAACGGATTCAAGTGTG GTCCTAGCTGCAGGTCAA | 274 |
| GI.3Lil08(S94E).c | CTTGAATCCGTTTCTGGAGCACTTGGCTCAGATGTA TAATGGATGGGTTGGAAA | 275 |
| GI.3Lil08(S94D).r | TCTGAGCCAAGTGGTCCAGAAACGGATTCAAGTGTG GTCCTAGCTGCAGGTCAA | 276 |
| GI.3Lil08(S94D).c | CTTGAATCCGTTTCTGGACCACTTGGCTCAGATGTA TAATGGATGGGTTGGAAA | 277 |
| GI.3Lil08(S94N).r | TCTGAGCCAAGTGGTTCAGAAACGGATTCAAGTGTG GTCCTAGCTGCAGGTCAA | 278 |
| GI.3Lil08(S94N).c | CTTGAATCCGTTTCTGAACCACTTGGCTCAGATGTA TAATGGATGGGTTGGAAA | 279 |
| GI.3Lil08(S94Q).r | TCTGAGCCAAGTGCTGCAGAAACGGATTCAAGTGTG GTCCTAGCTGCAGGTCAA | 280 |
| GI.3Lil08(S94Q).c | CTTGAATCCGTTTCTGCAGCACTTGGCTCAGATGTA TAATGGATGGGTTGGAAA | 281 |
| GI.3Lil08(S94K).r | TCTGAGCCAAGTGCTTCAGAAACGGATTCAAGTGTG GTCCTAGCTGCAGGTCAA | 282 |
| GI.3Lil08(S94K).c | CTTGAATCCGTTTCTGAAGCACTTGGCTCAGATGTA TAATGGATGGGTTGGAAA | 283 |
| GI.3Lil08(S94H).r | TCTGAGCCAAGTGGTGCAGAAACGGATTCAAGTGTG GTCCTAGCTGCAGGTCAA | 284 |
| GI.3Lil08(S94H).c | CTTGAATCCGTTTCTGCACCACTTGGCTCAGATGTA TAATGGATGGGTTGGAAA | 285 |

WT GI.1 Norovirus VP1: A2X35S/CPMV 160/Wt VP1 GI.1/NOS (Construct Number 2724)

Figure 39A:
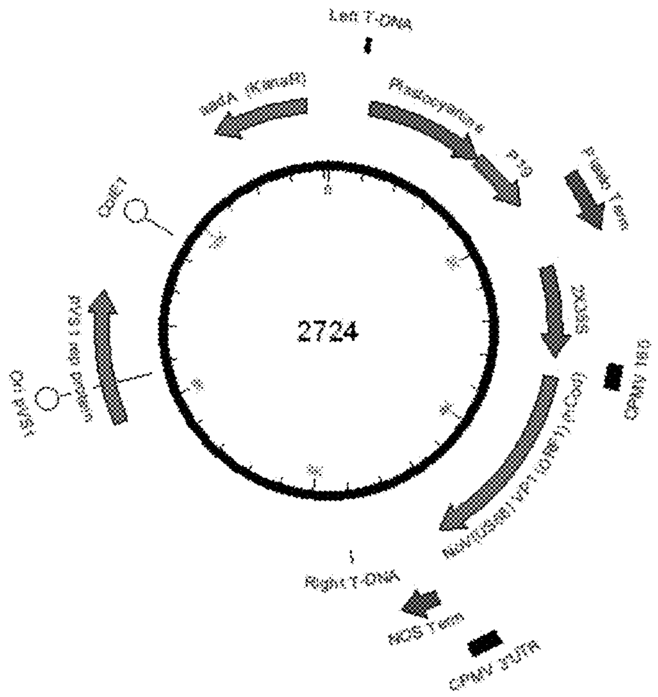
FIG. 39A shows a schematic representation of construct 2724 (VP1 Wt GI.1 hCod).
Figure 39B:
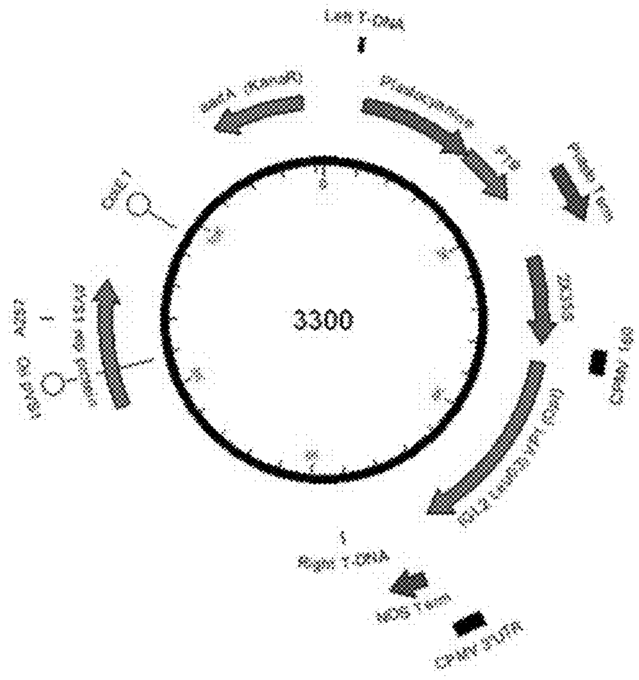
FIG. 39B shows a schematic representation of construct 3300 (VP1 Wt GI.2 hCod).
Figure 39C:
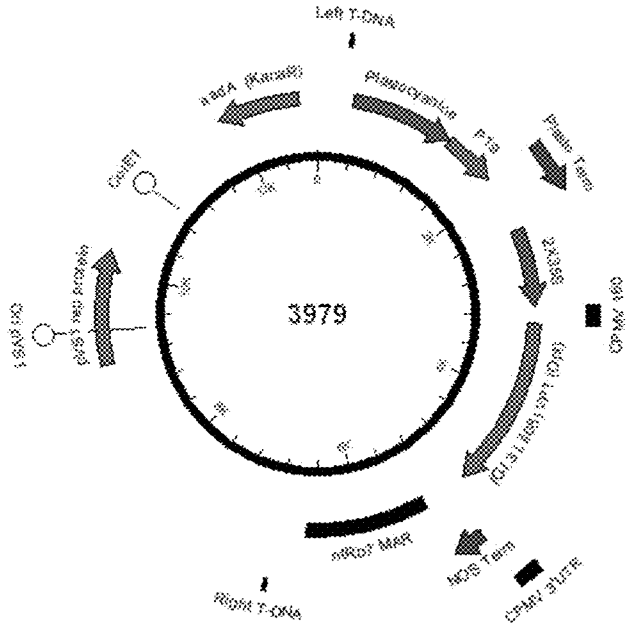
FIG. 39C shows a schematic representation of construct 3979 (VP1 Wt GI.3 hCod).
Figure 40A:
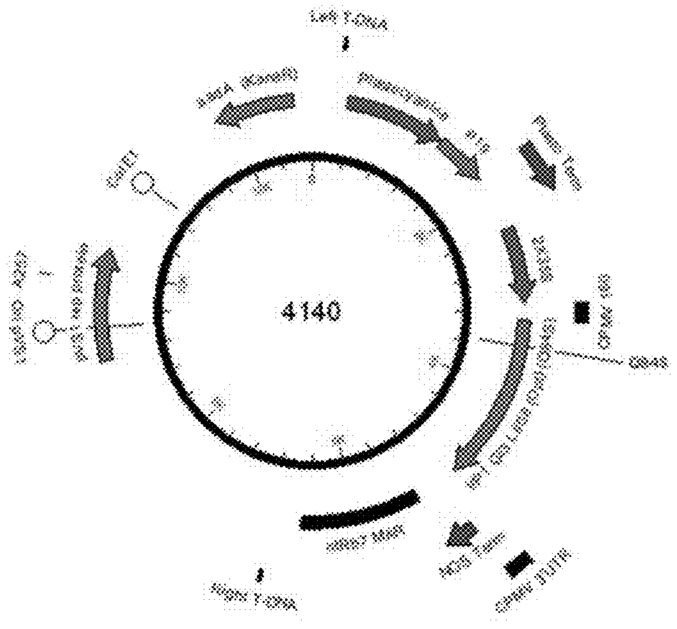
FIG. 40A shows a schematic representation of construct 4140 (VP1 GI.3_Q84S hCod).
Figure 40B:
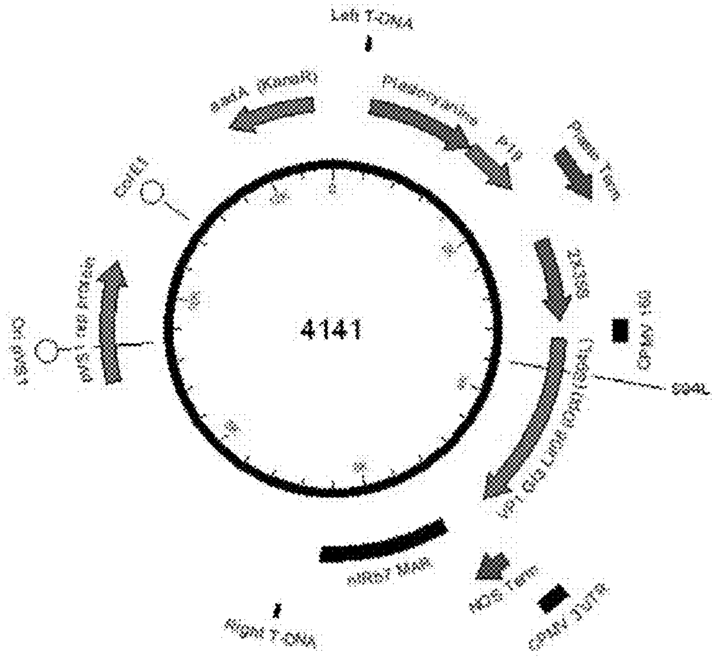
FIG. 40B shows a schematic representation of construct 4141 (VP1 GI.3_S94L hCod).
Figure 40C:
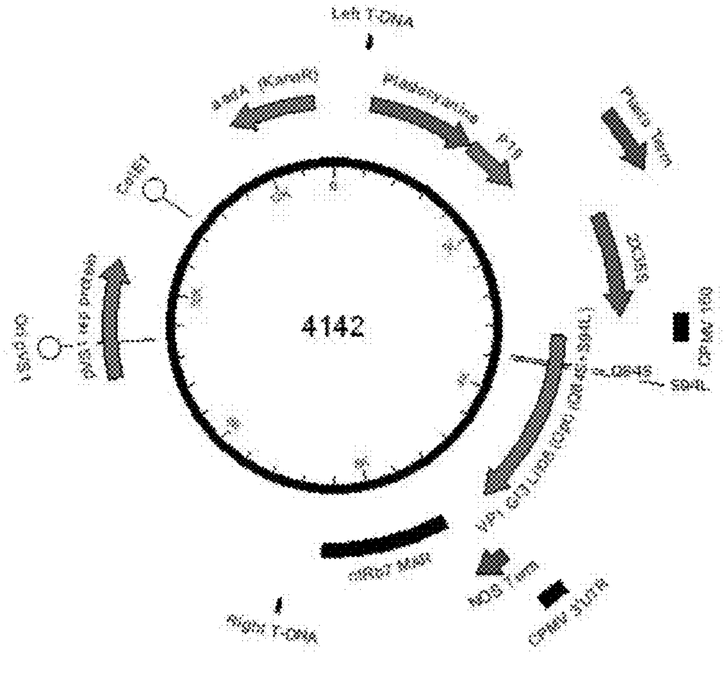
FIG. 40C shows a schematic representation of construct 4142 (VP1 GI.3_P84S+S94L hCod).
Figure 40D:
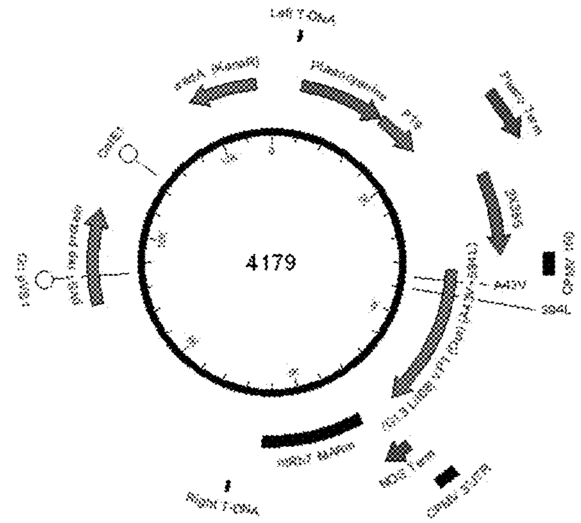
FIG. 40D shows a schematic representation of construct 4179 (VP1 GI.3_A43V+S94L hCod).
Figure 40E:
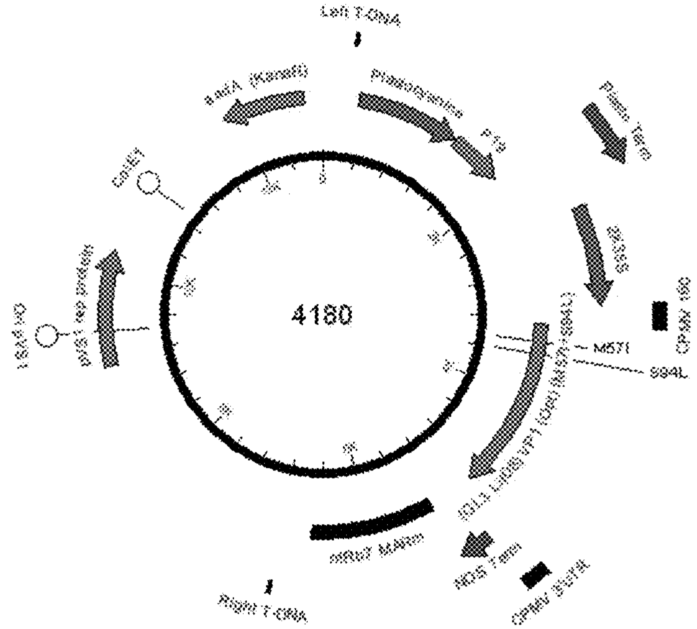
FIG. 40E shows a schematic representation of construct 4180 (VP1 GI.3_M57I+S94L hCod).
Figure 40F:
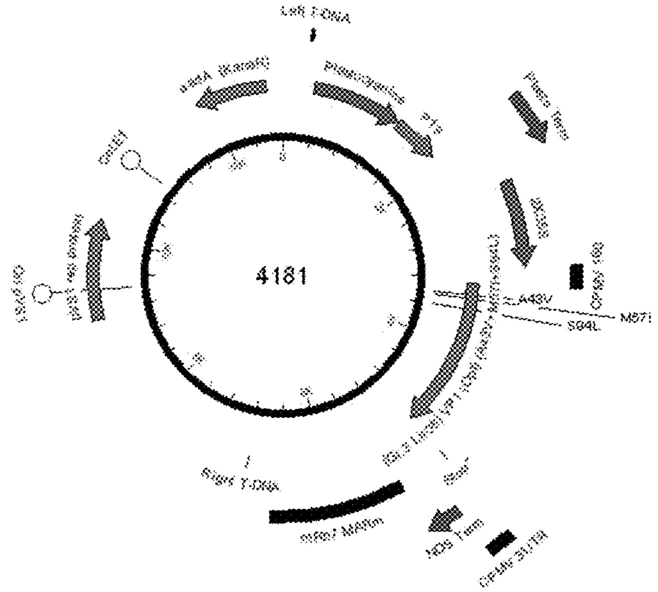
FIG. 40F shows a schematic representation of construct 4181 (VP1 GI.3_A43V+M57I+S94L hCod).
Figure 41A:
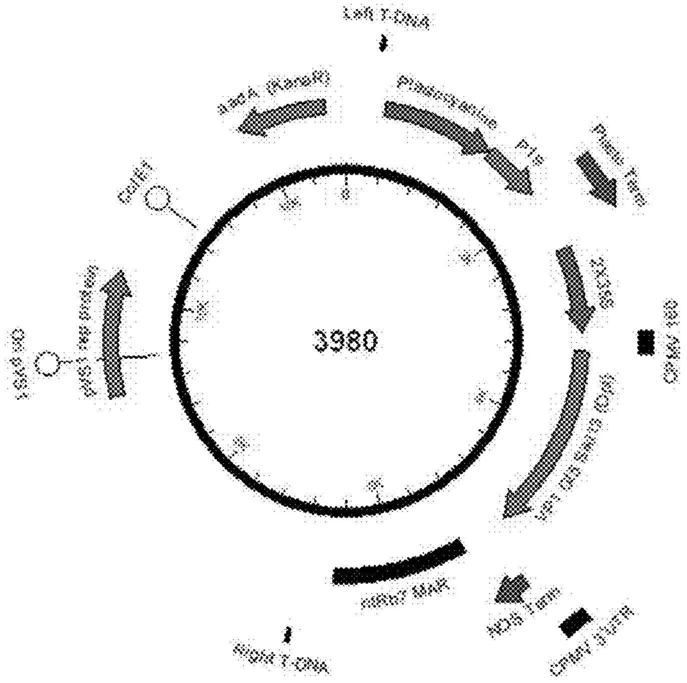
FIG. 41A shows a schematic representation of construct 3980 (VP1 Wt GI.5 hCod (Wt GI.5 hCod).
Figure 41B:
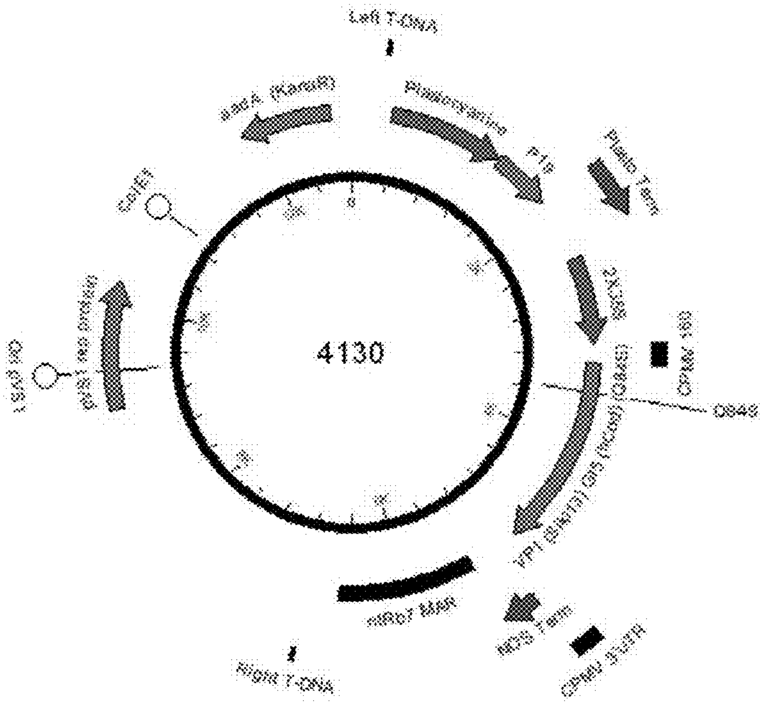
FIG. 41B shows a schematic representation of construct 4130 (VP1 GI.5_Q84S).
Figure 41C:
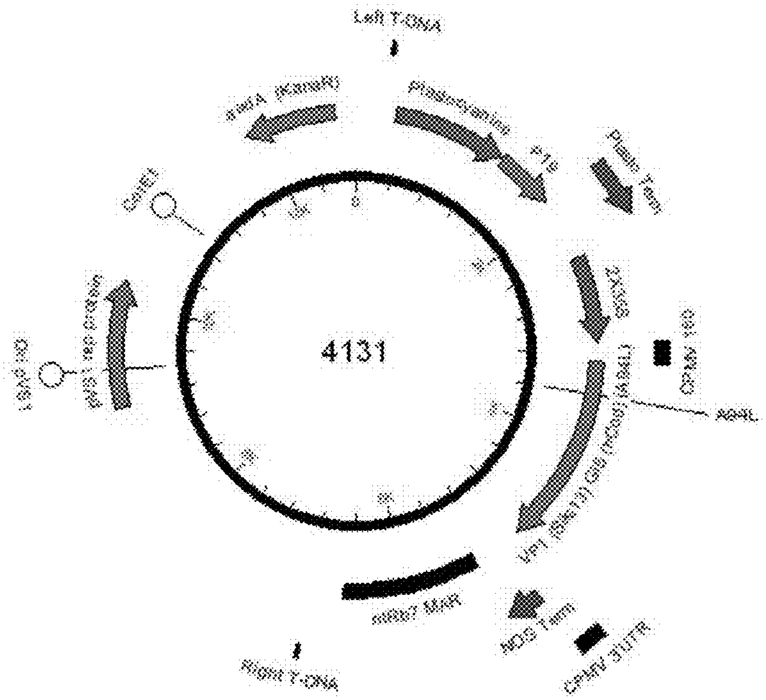
FIG. 41C shows a schematic representation of construct 4131 (VP1 GI.5_A94L hCod).
Figure 41D:
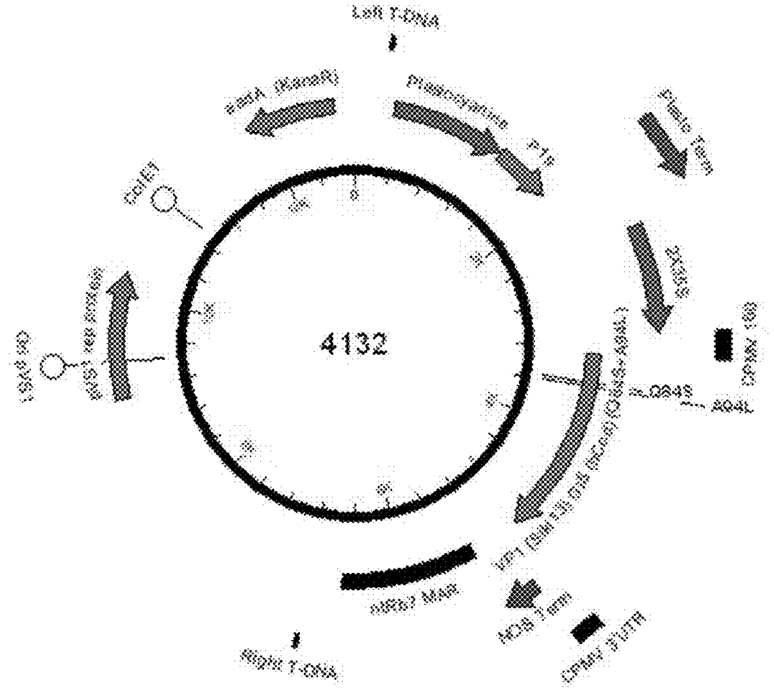
FIG. 41D shows a schematic representation of construct 4132 (VP1 GI.5_Q84S+A94L hCod).
Figure 41E:
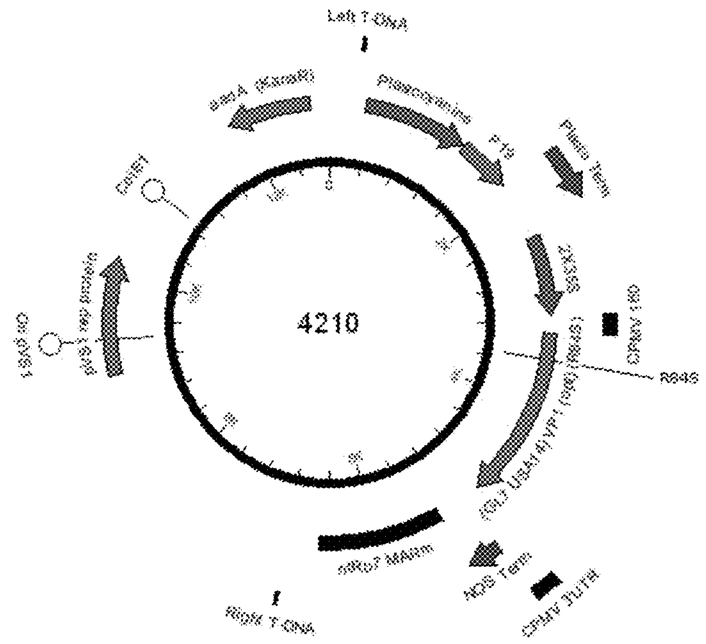
FIG. 41E shows a schematic representation of construct 4210 (VP1 GI.7_R84S hCod).
Figure 41F:
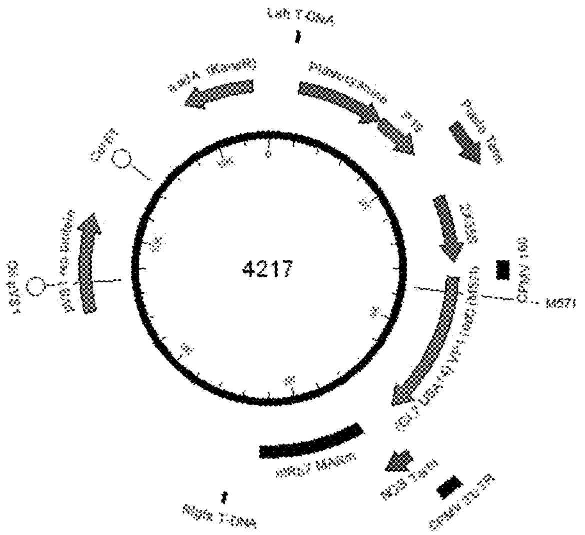
FIG. 41F shows a schematic representation of construct 4217 (VP1 GI.7_M57I hCod).
Figure 41G:
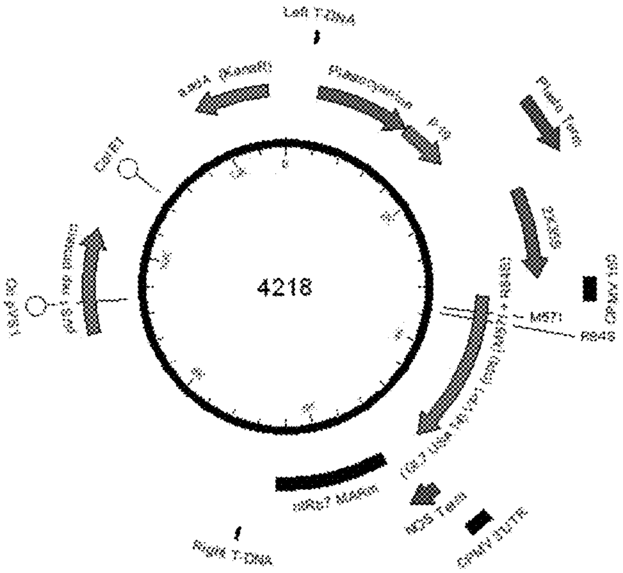
FIG. 41G shows a schematic representation of construct 4218 (VP1 GI.7_M57I+R84S hCod).
Figure 42A:
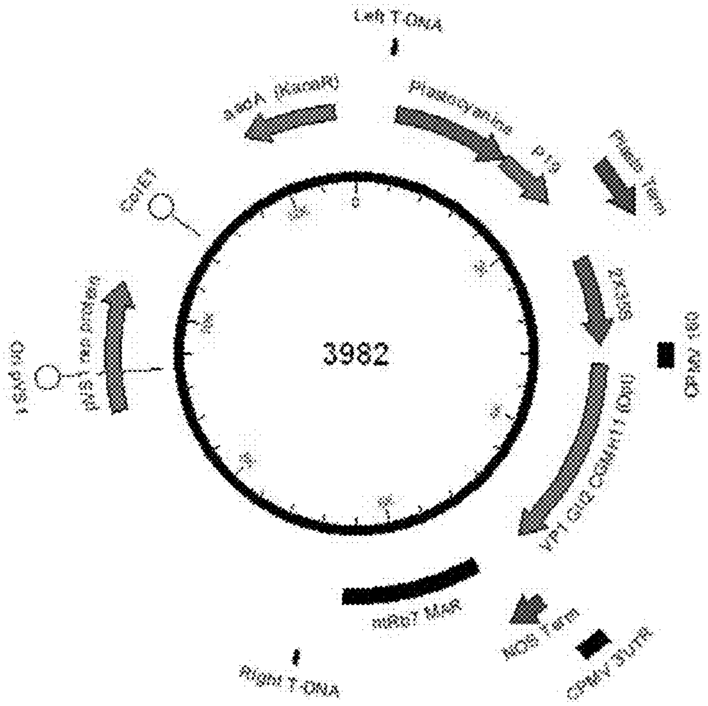
FIG. 42A shows a schematic representation of construct 3982 (Wt VP1 GII.2 hCod).
Figure 42B:
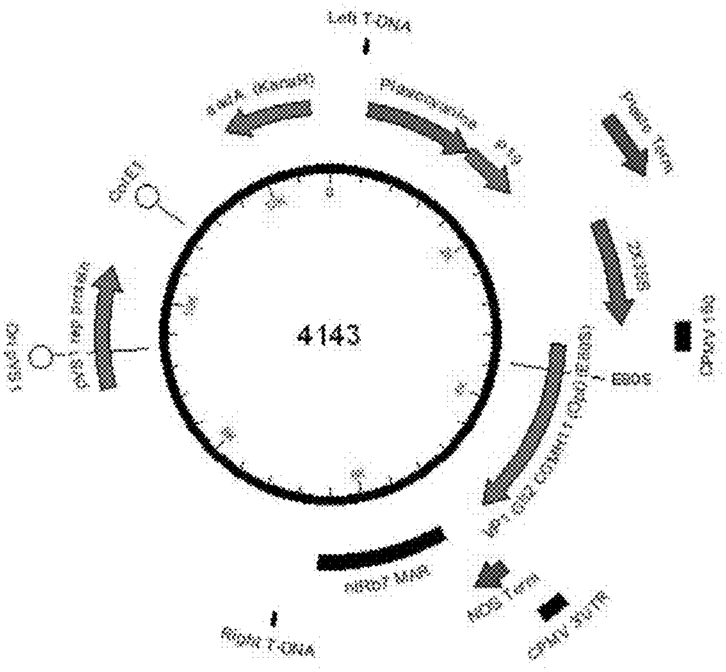
FIG. 42B shows a schematic representation of construct 4143 (VP1 GII.2_E80S).
Figure 42C:
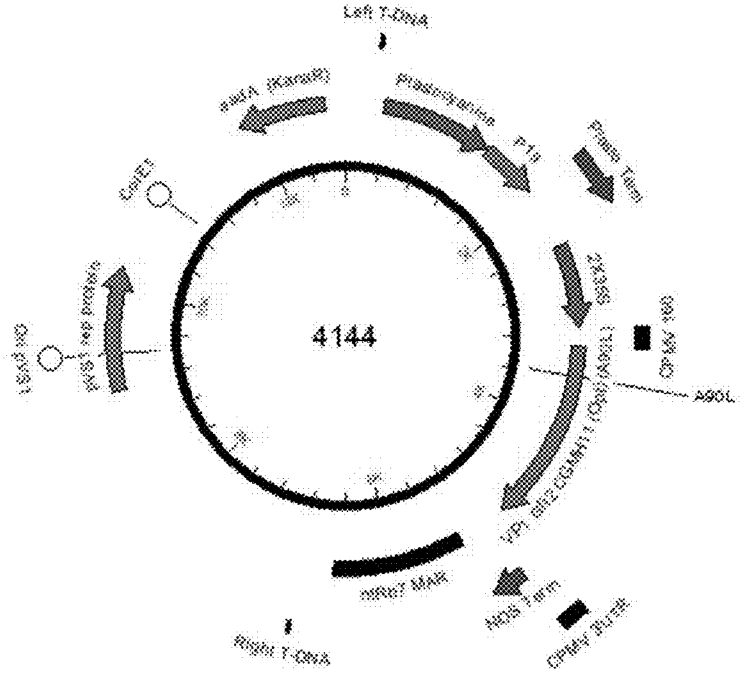
FIG. 42C shows a schematic representation of construct 4144 (VP1 GII.2_A90L hCod).
Figure 42D:
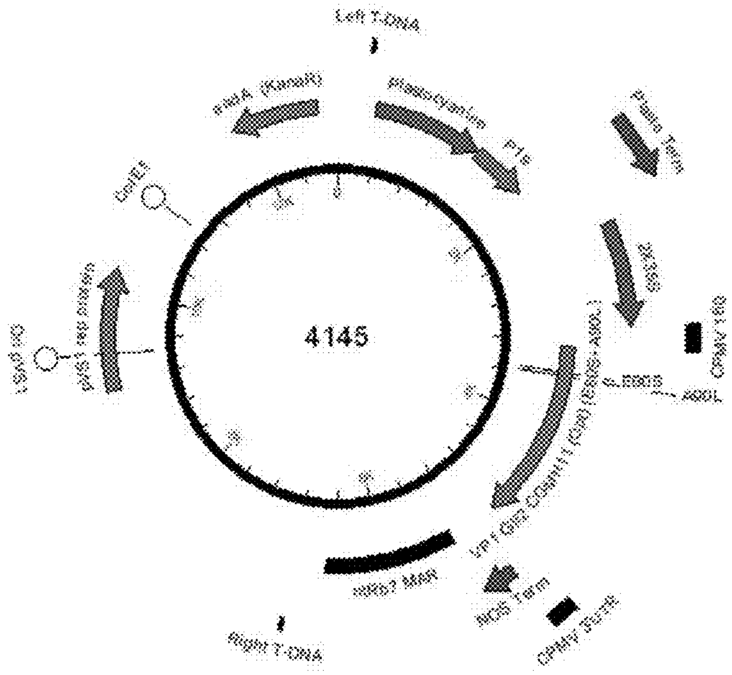
FIG. 42D shows a schematic representation of construct 4145 (VP1 GII.2_E80S+A90L hCod).
Figure 42E:
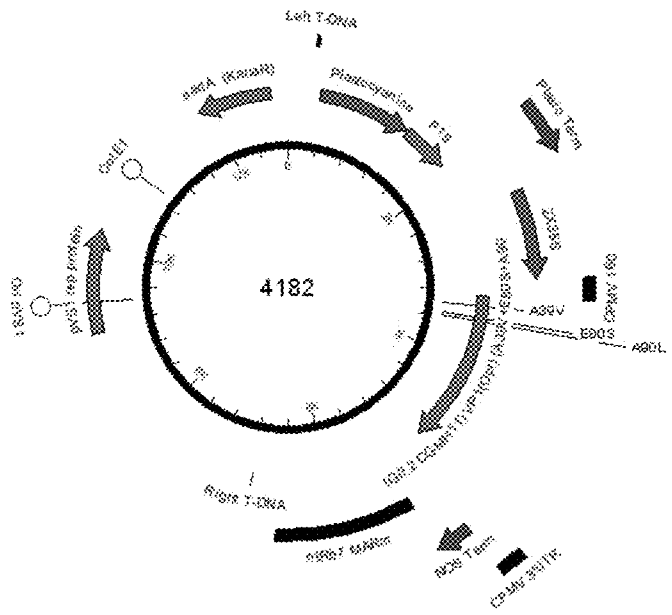
FIG. 42E shows a schematic representation of construct 4182 (VP1 GII.2_A39V+E80S+A90L hCod).
Figure 42F:
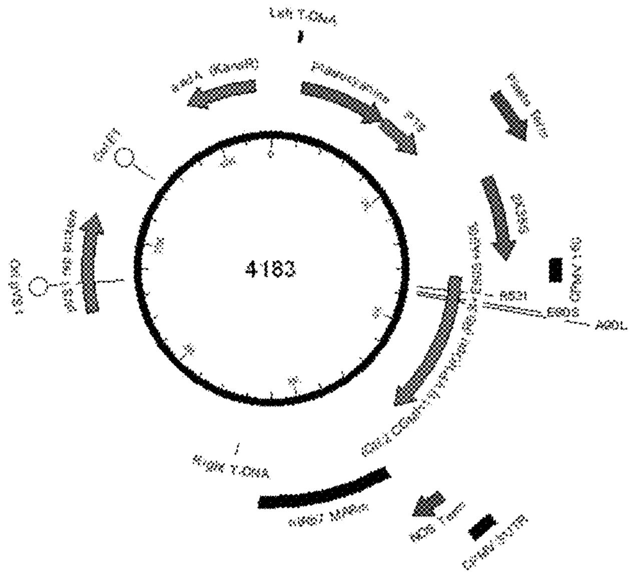
FIG. 42F shows a schematic representation of construct 4183 (VP1 GII.2_R53I+E80S+A90L hCod).
Figure 42G:
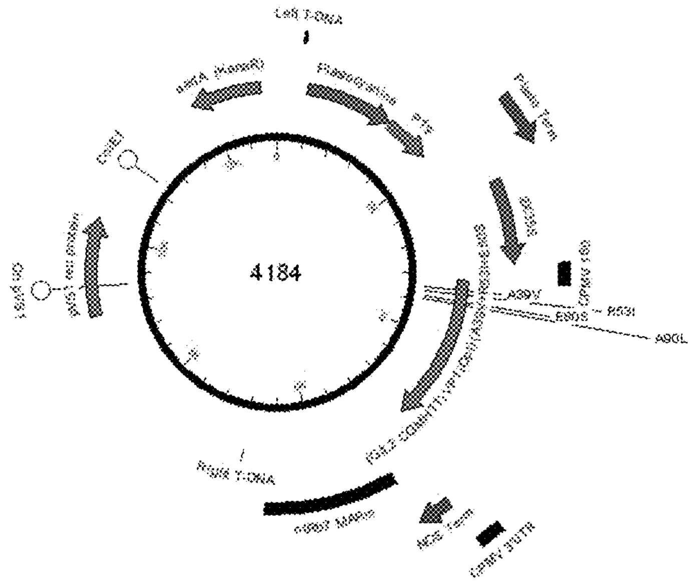
FIG. 42G shows a schematic representation of construct 4184 (VP1 GII.2_A39V+R53I+E80S+A90L hCod).
Figure 43A:
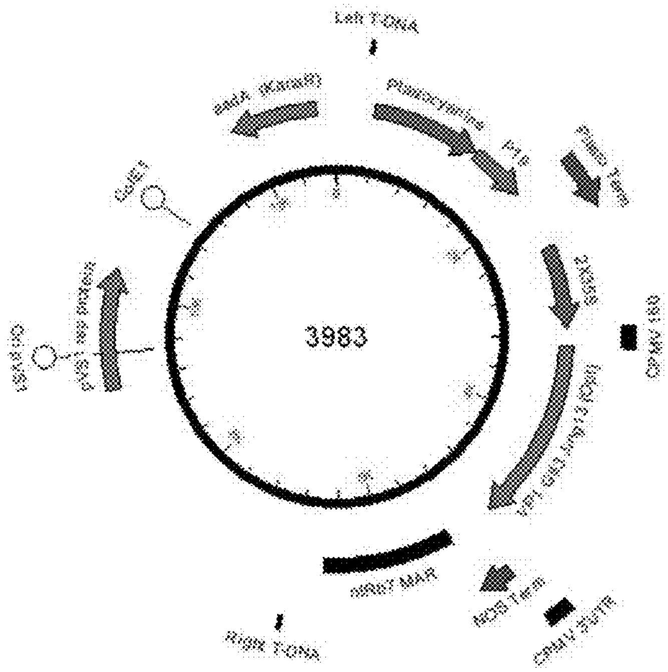
FIG. 43A shows a schematic representation of construct 3983 (Wt VP1 GII.3 hCod).
Figure 43B:
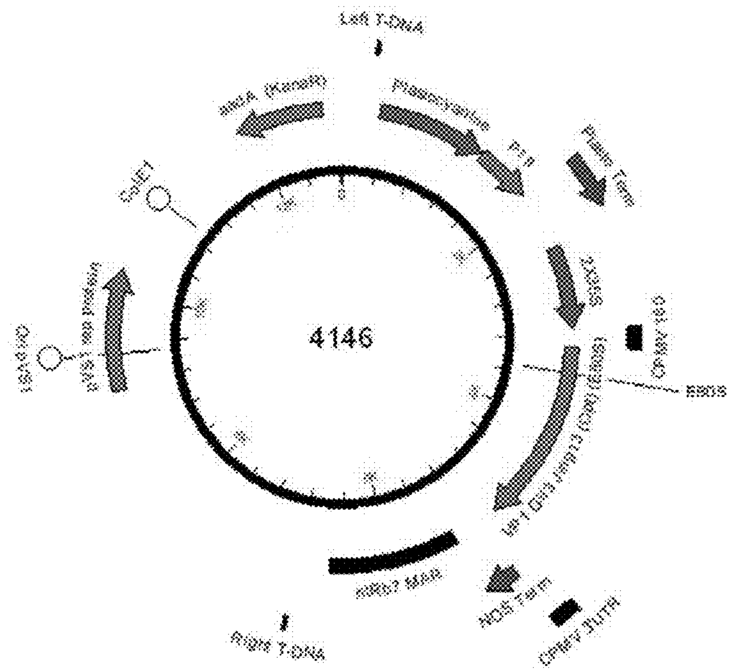
FIG. 43B shows a schematic representation of construct 4146 (VP1 GII.3_E80S hCod).
Figure 43C:
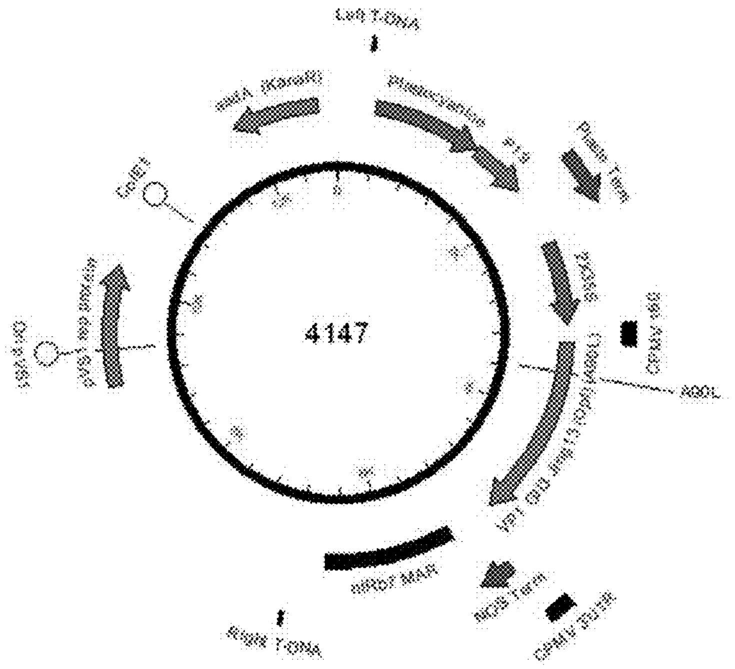
FIG. 43C shows a schematic representation of construct 4147 (VP1 GII.3_A90L hCod).
Figure 43D:
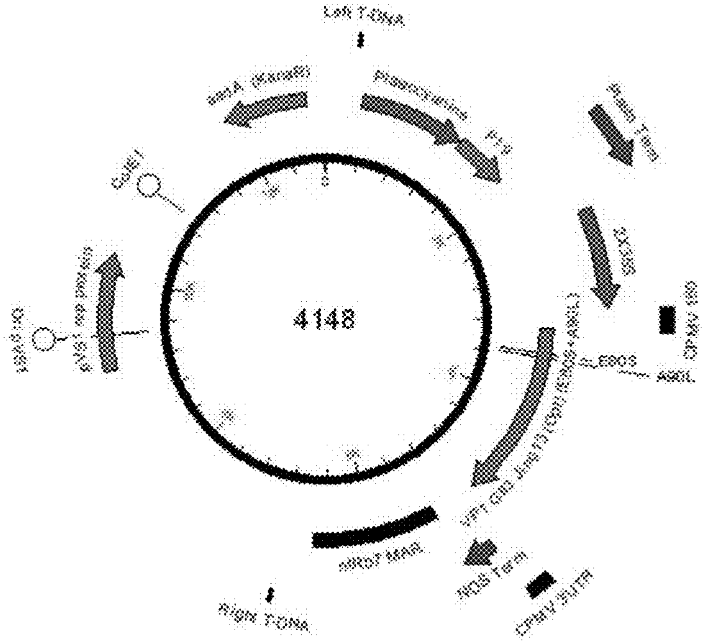
FIG. 43D shows a schematic representation of construct 4148 (VP1 GII.3_E80S+A90L).
Figure 48:
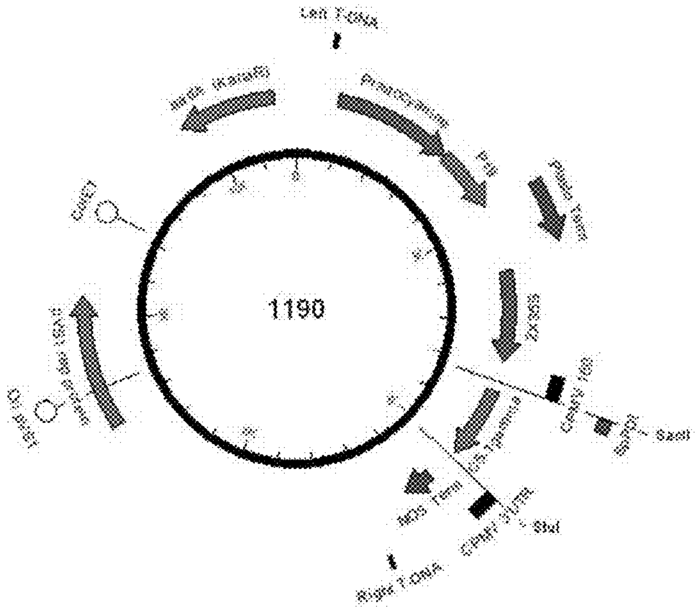
FIG. 48 shows a schematic representation of construct 1190 (Cloning vector 1190).

A human codon-optimized sequence encoding VP1 from Norovirus strain GI.1/Norwalk/1968/US was cloned into 2X35S/CPMV 160/NOS expression system using the following PCR-based method. A fragment containing the GU VP1 coding sequence was amplified using primers IF-NoV (US68)VP1(ORF2)(hCod).c (SEQ ID NO:102) and IF-NoV (US68)VP1(ORF2)(hCod).r (SEQ ID NO:103), using human codon-optimized GI.1 VP1 gene sequence (SEQ ID NO:3) as template. For sequence optimization, GI.1/Norwalk/1968/US VP1 protein sequence (Genbank accession number NP 056821) was backtranslated and optimized for human codon usage, GC content and mRNA structure. The PCR product was cloned in 2X35S/CPMV 160/NOS expression system using In-Fusion cloning system (Clontech, Mountain View, Calif.). Construct number 1190 (SEQ ID NO:162; FIGS. 38A and 48) was digested with SacII and StuI restriction enzyme and the linearized plasmid was used for the In-Fusion assembly reaction. Construct number 1190 is an acceptor plasmid intended for "In Fusion" cloning of genes of interest in a 2X35S/CPMV 160/NOS-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO:162. The resulting construct was given number 2724 (FIG. 38B; SEQ ID NO: 163). The amino acid sequence of native VP1 from Norovirus strain GI.1/Norwalk/1968/US is presented in SEQ ID NO: 1. A representation of plasmid 2724 is presented in FIG. 39A.

2X35S/CPMV 160/GII.4_P80S (hCod)/NOS+MAR (Construct Number 4133)

Figure 44A:
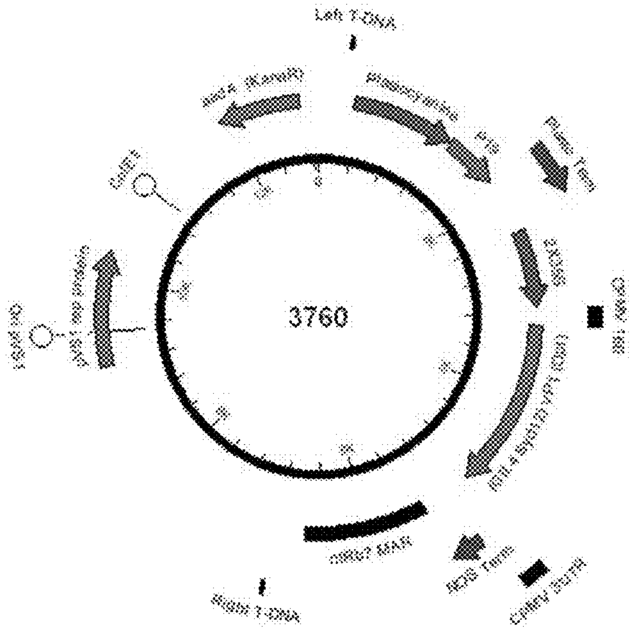
FIG. 44A shows a schematic representation of construct 3760 (Wt VP1 GII.4 hCod).
Figure 44B:
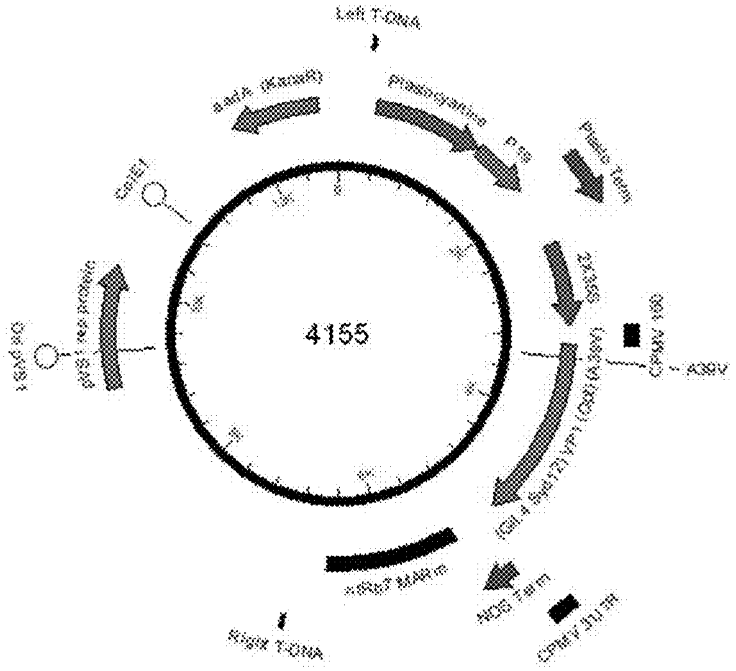
FIG. 44B shows a schematic representation of construct 4155 (VP1 GII.4_A39V hCod).
Figure 44C:
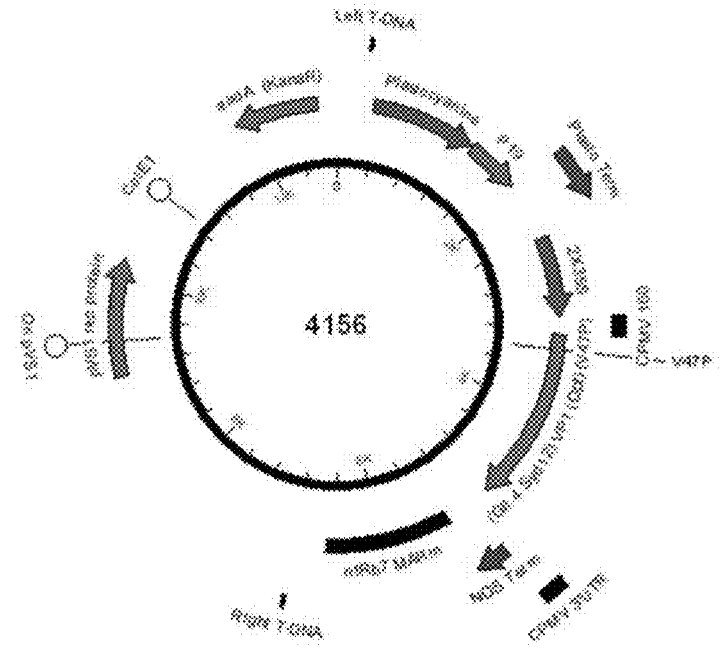
FIG. 44C shows a schematic representation of construct 4156 (VP1 GII.4_V47P hCod).
Figure 44D:
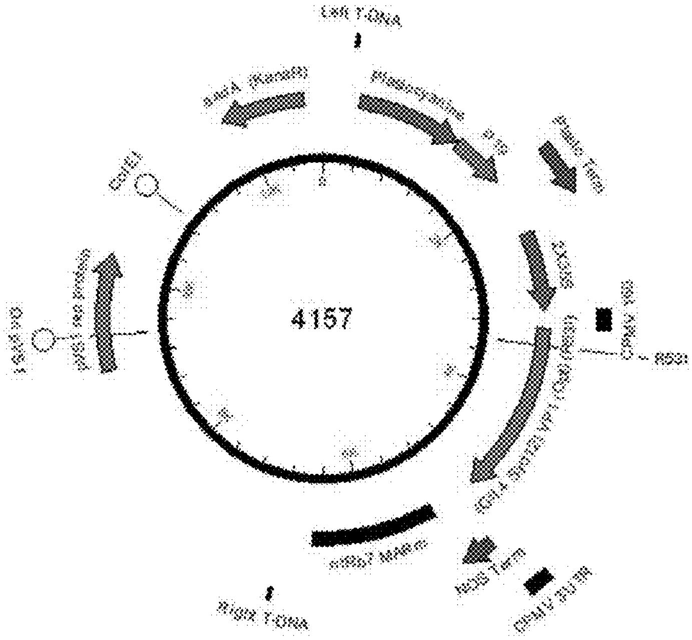
FIG. 44D shows a schematic representation of construct 4157 (VP1 GII.4_R53I hCod).
Figure 44E:
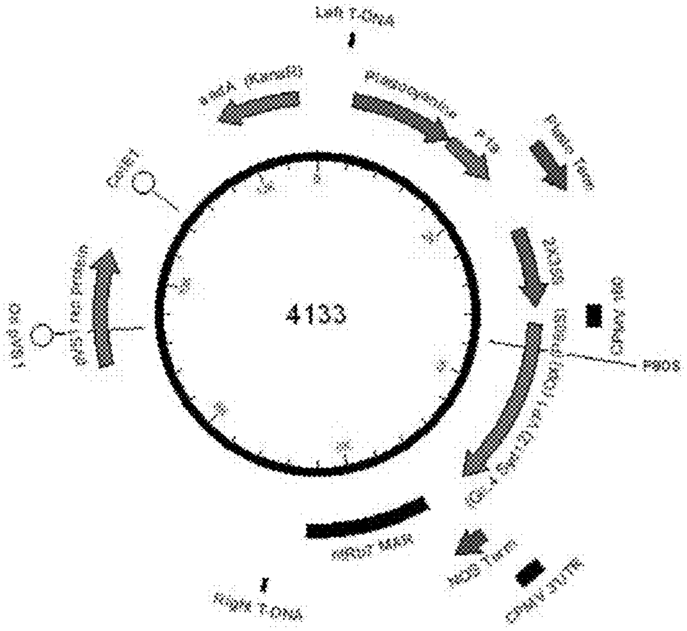
FIG. 44E shows a schematic representation of construct 4133 (VP1 GII.4_P80S hCod).
Figure 44F:
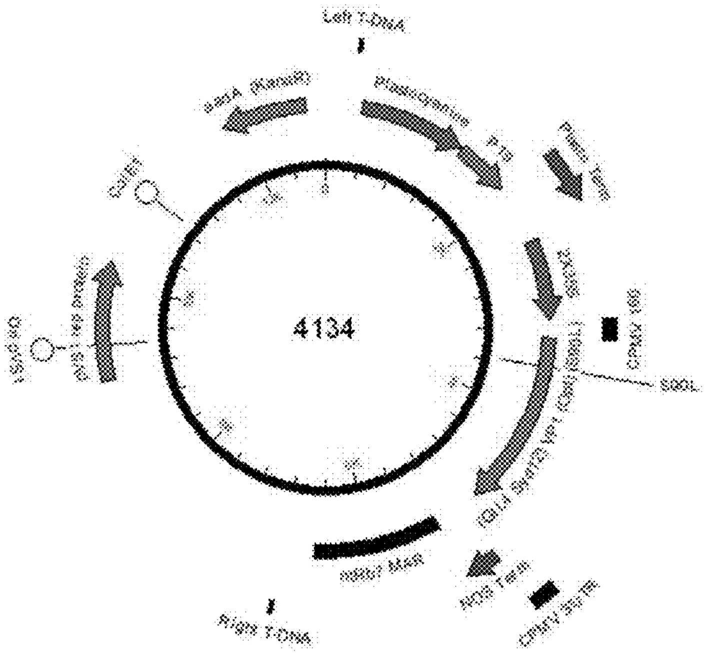
FIG. 44F shows a schematic representation of construct 4134 (VP1 GII.4_S90L hCod).
Figure 44G:
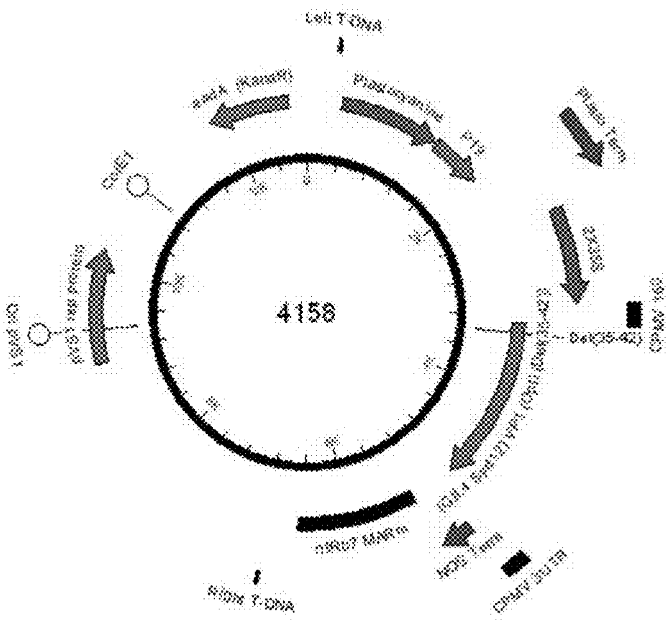
FIG. 44G shows a schematic representation of construct 4158 (VP1 GII.4_Δ35-42 hCod).
Figure 44H:
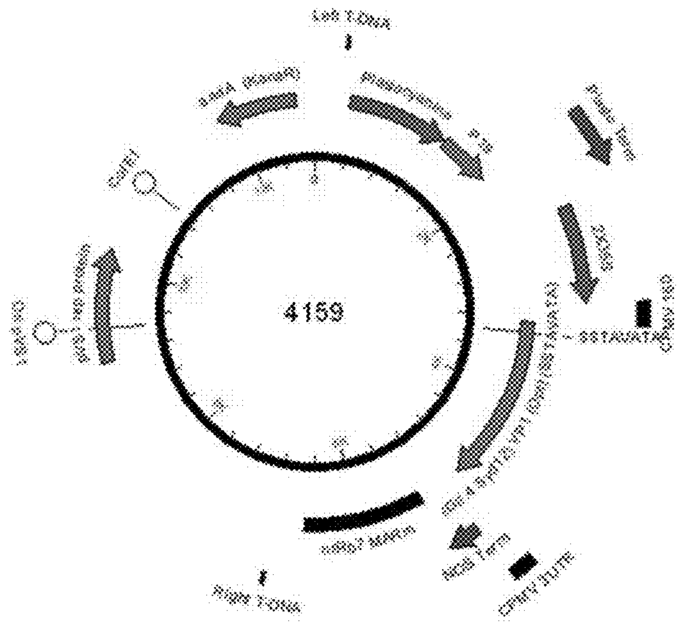
FIG. 44H shows a schematic representation of construct 4159 (VP1 GII.4_SSTAVATA hCod).
Figure 44I:
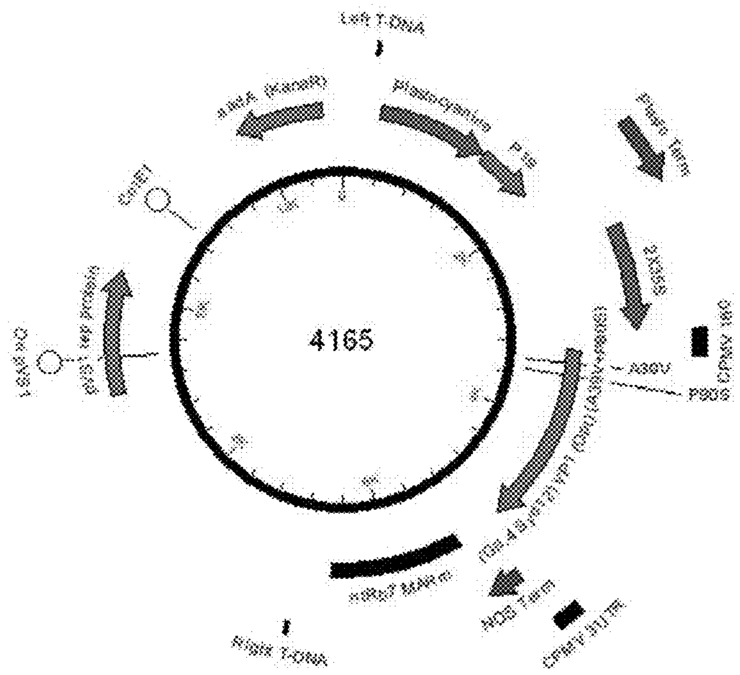
FIG. 44I shows a schematic representation of construct 4165 (VP1 GII.4_A39V+P80S hCod).
Figure 44J:
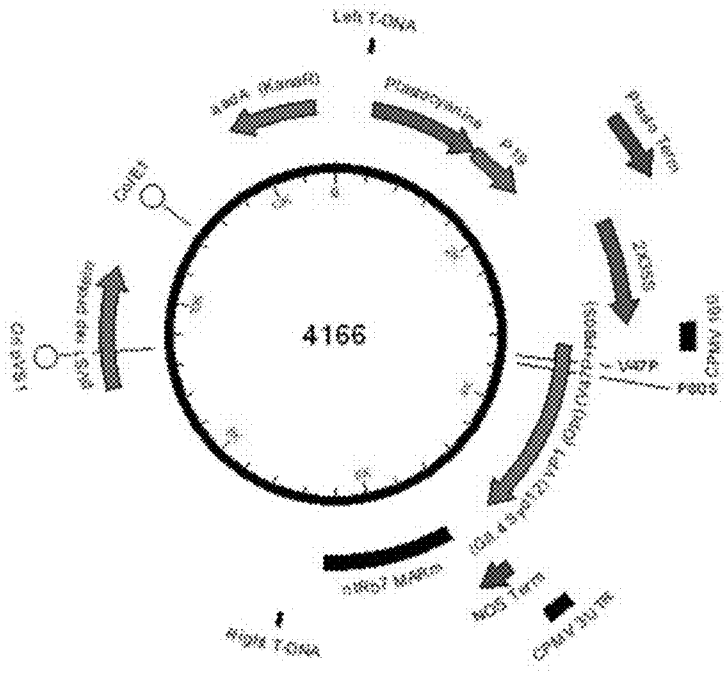
FIG. 44J shows a schematic representation of construct 4166 (VP1 GII.4_V47P+P80S hCod).
Figure 44K:
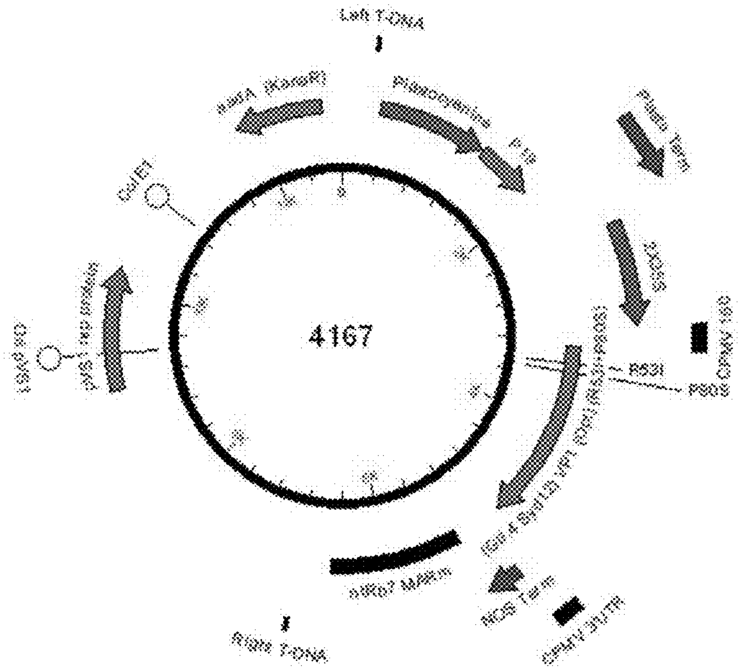
FIG. 44K shows a schematic representation of construct 4167 (VP1 GII.4_R53I+P80S hCod).
Figure 49:
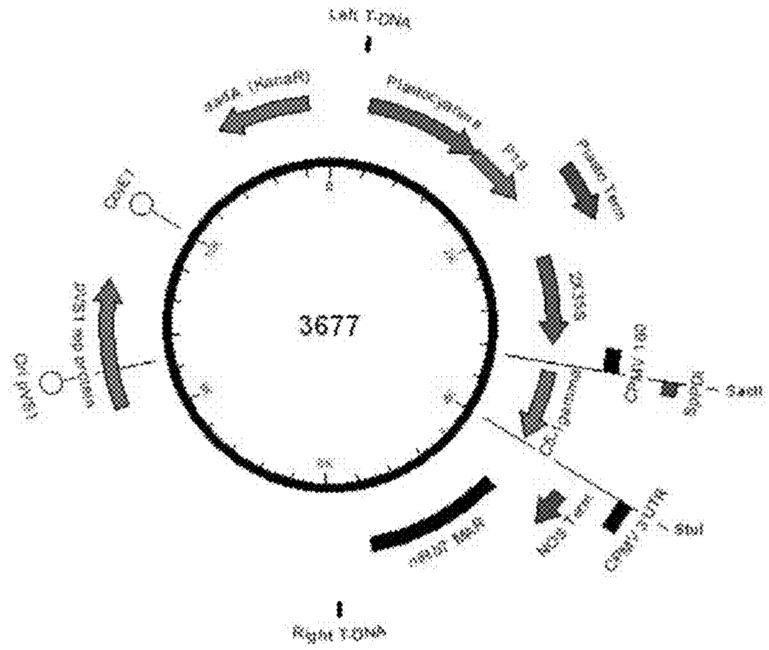
FIG. 49 shows a schematic representation of construct 3677 (Cloning vector 3677).
Figure 50A:
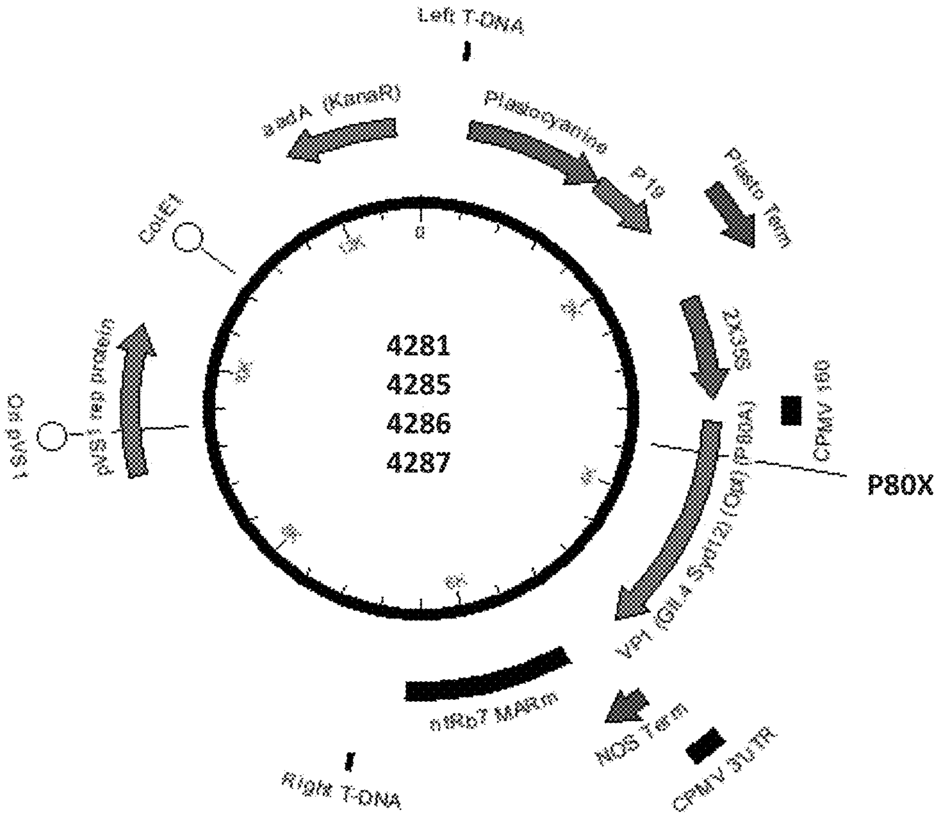
FIG. 50A shows a schematic representation of GII.4 P80X constructs (cloning vectors), wherein X is selected from: A (construct 4281); N (construct 4285); K (construct 4286); or H (construct 4287).
Figure 50B:
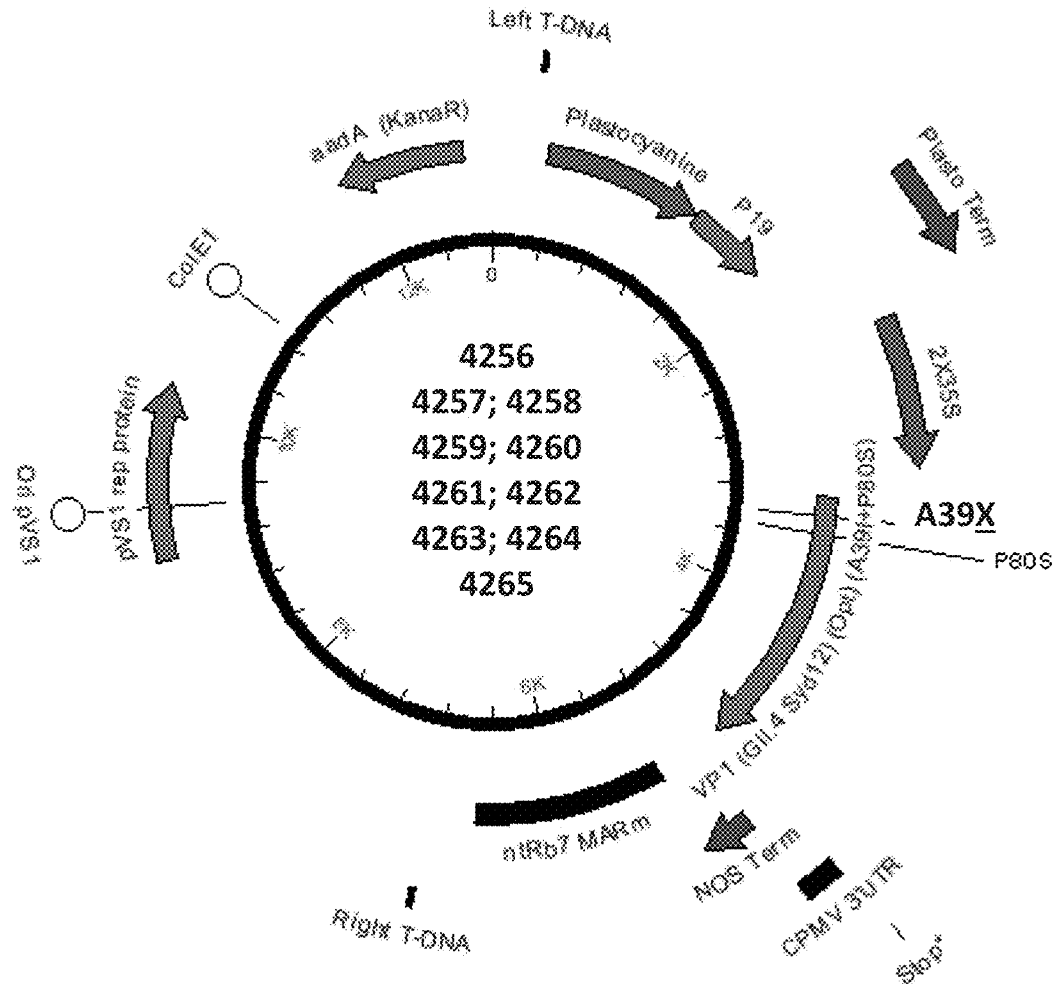
FIG. 50B shows a schematic representation of GII.4 P80s+A39X constructs (cloning vectors), wherein X is selected from I (construct 4256); M (construct 4257); G (construct 4258); S (construct 4259); E (construct 4260); D (construct 4261); N (construct 4262); Q (construct 4263); construct K (4264); or H (construct 4265).
Figure 51:
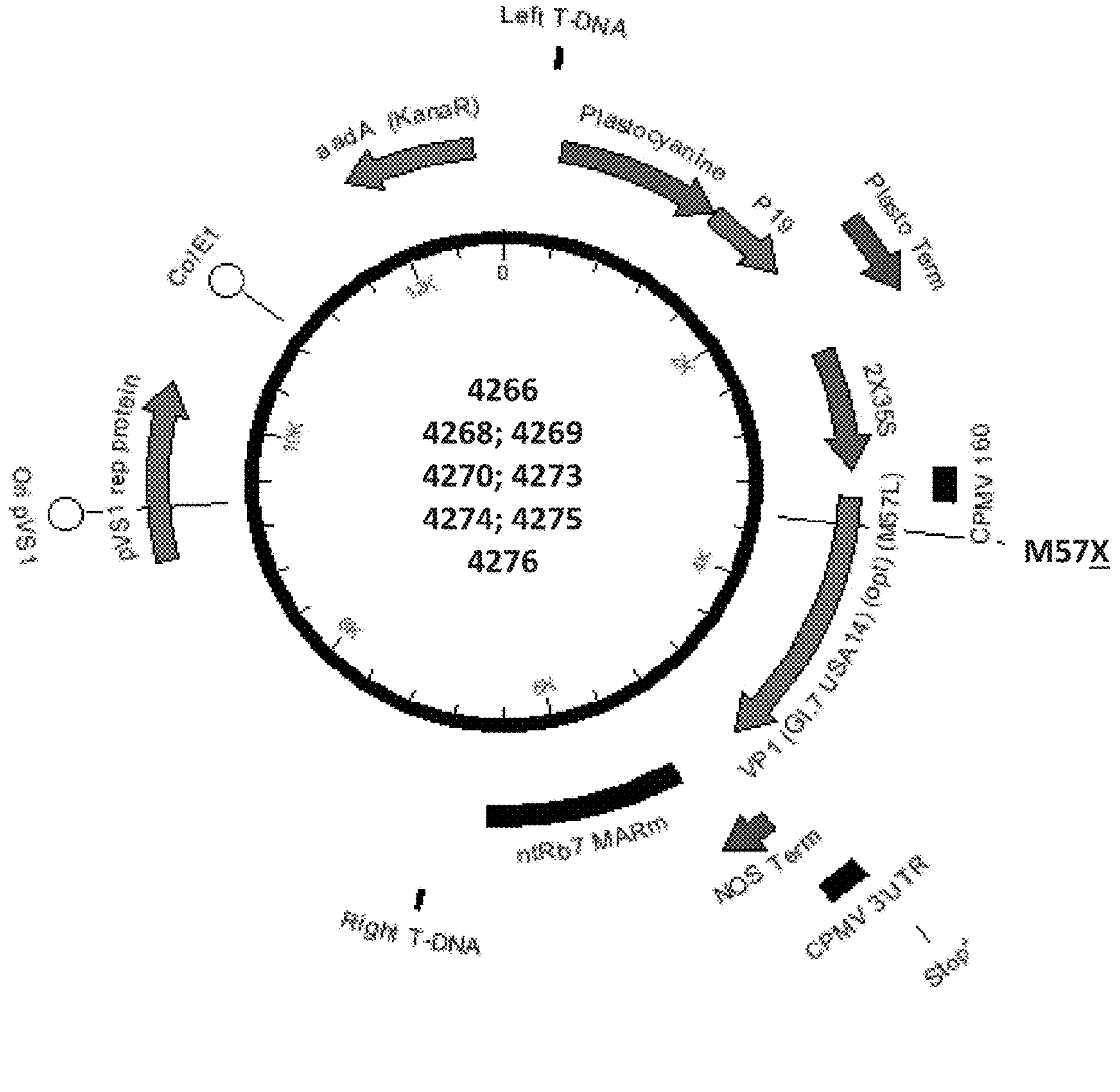
FIG. 51 shows a schematic representation of GI.7 M57X constructs (cloning vectors), wherein X is selected from: L (construct 4266); G (construct 4268); S (construct 4269); T (construct 4270; N (construct 4273); Q (construct 4274); K (construct 4275); or H (construct 4276).
Figure 52:
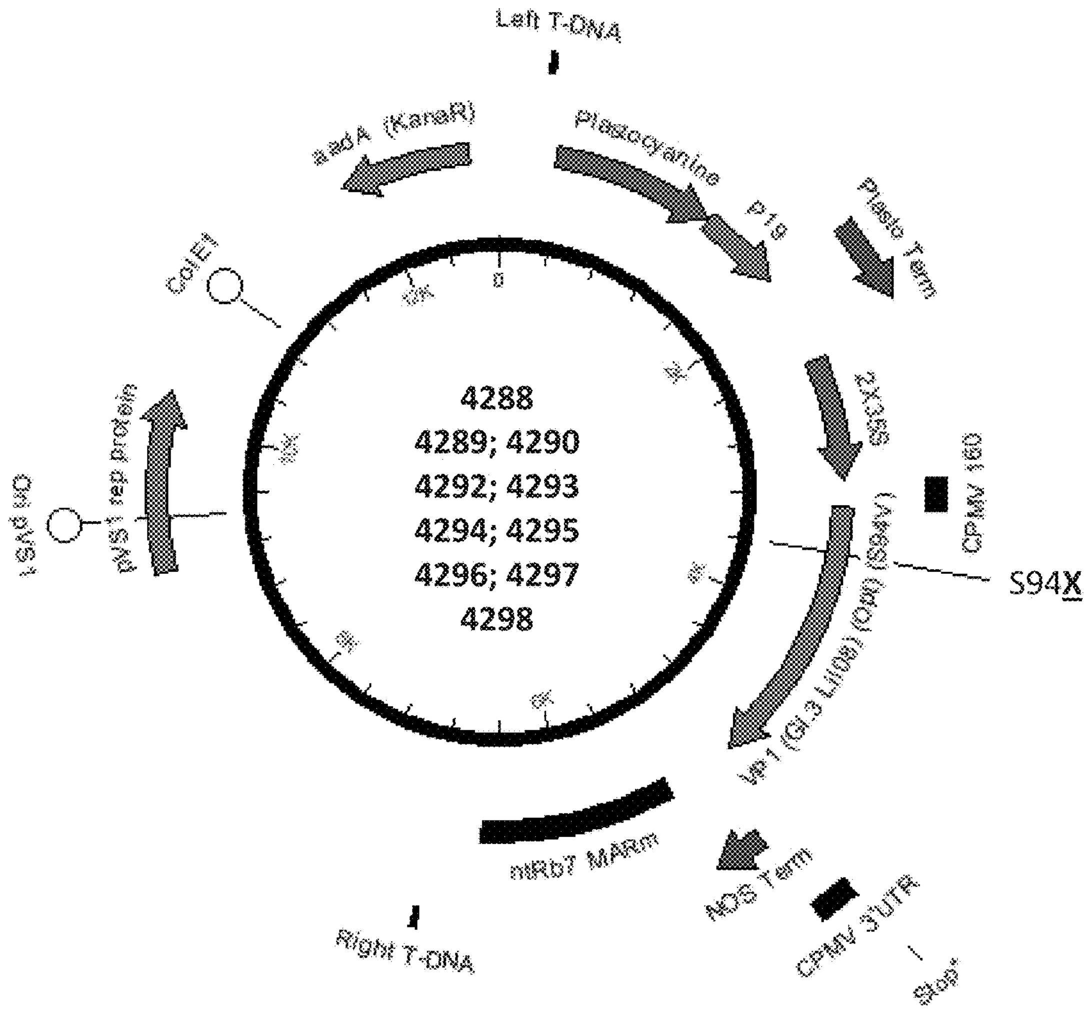
FIG. 52 shows a schematic representation of GI.3 S94X constructs (cloning vectors), wherein X is selected from: V (construct 4288); I (construct 4289); M (construct 4290); T (construct 4292); E (construct 4293); D (construct 4294); N (construct 4295); Q (construct 4296); K (construct 4297); or H (construct 4298).

A human codon-optimized sequence encoding VP1 from GII.4/Sydney/NSW0514/2012/AU comprising the P80S substitution in the S domain was cloned into 2X35S/CPMV 160/NOS+MAR expression system using the following PCR-based method. In a first round of PCR, a fragment containing the S domain with the mutated P80S amino acid was amplified using primers IF-GII.4Syd12VP1.c (SEQ ID NO:130) and GII.4(P80S).r (SEQ ID NO:138), using human codon-optimized GII.4 VP1 gene sequence (SEQ ID NO:52) as template. A second fragment containing the P80S substitution with the remaining of the S and P domain was amplified using GII.4(P80S).c (SEQ ID NO:139) and IF-GII.4Syd12VP1.r (SEQ ID NO:131), using human codon-optimized GII.4 VP1 gene sequence (SEQ ID NO:52) as template. For sequence optimization, GII.4/Sydney/NSW0514/2012/AU VP1 protein sequence (Genbank accession number AFV08795) was backtranslated and optimized for human codon usage, GC content and mRNA structure. The PCR products from both amplifications were then mixed and used as template for a second round of amplification using IF-GII.4Syd12VP1.c (SEQ ID NO:130) and IF-GII.4Syd12VP1s (SEQ ID NO:131) as primers. The final PCR product was cloned in 2X35S/CPMV 160/NOS+MAR expression system using In-Fusion cloning system (Clontech, Mountain View, Calif.). Construct number 3677 (SEQ ID NO:164; FIGS. 38C and 49) was digested with SacII and StuI restriction enzyme and the linearized plasmid was used for the In-Fusion assembly reaction. Construct number 3677 is an acceptor plasmid intended for “In Fusion” cloning of genes of interest in a 2X35S/CPMV 160/NOS+MAR-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO:164. The resulting construct was given number 4133 (FIG. 38D; SEQ ID NO:165). The amino acid sequence of mutated GII.4_P80S is presented in SEQ ID NO:59. A representation of plasmid 4133 is presented in FIG. 44E.

2X35S/CPMV 160/GII.4_P80S+S90L (hCod)/NOS+MAR (Construct number 4135)

Figure 44L:
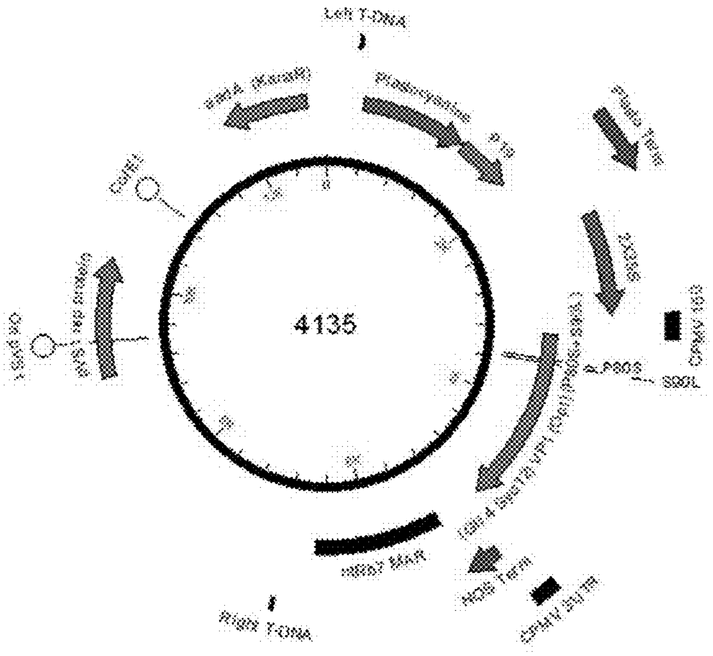
FIG. 44L shows a schematic representation of construct 4135 (VP1 GII.4_P80S+S90L hCod).
Figure 44M:
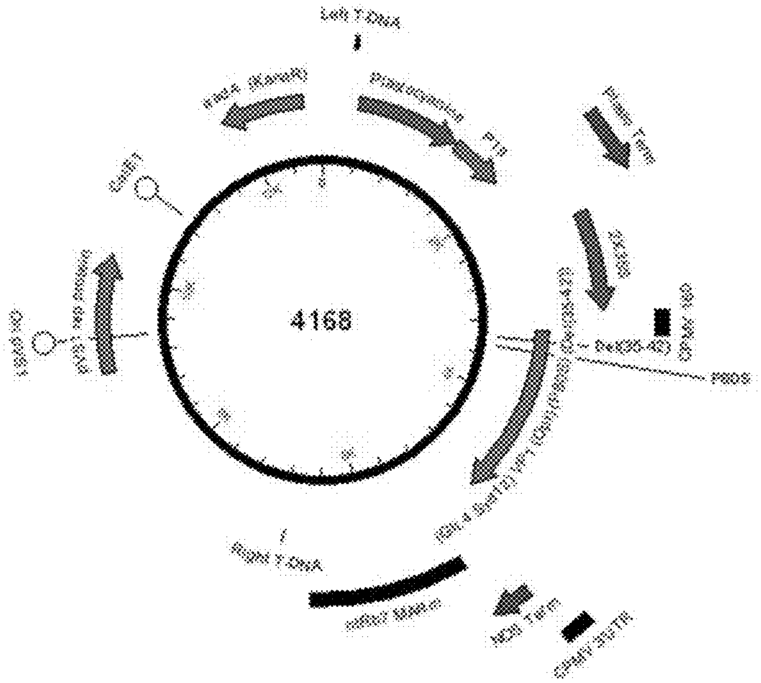
FIG. 44M shows a schematic representation of construct 4168 (GII.4_P80S+Δ35-42 hCod).
Figure 44N:
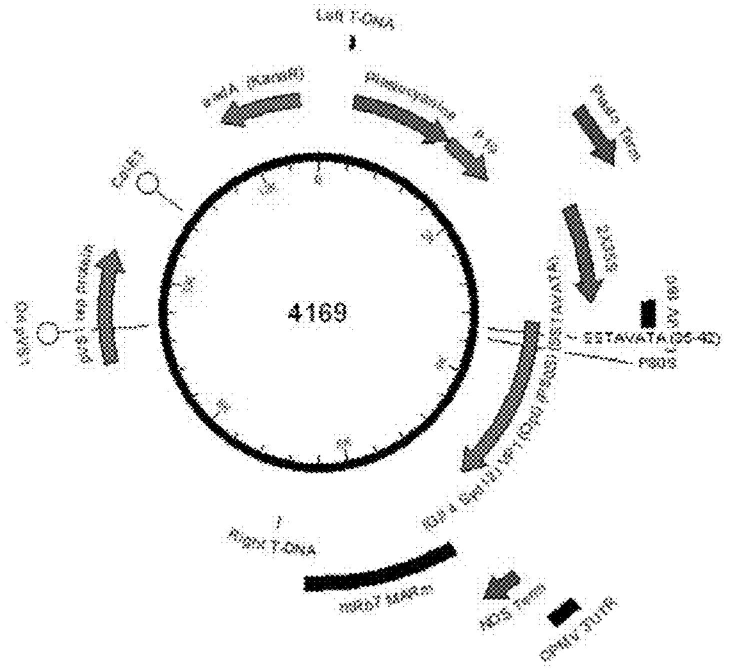
FIG. 44N shows a schematic representation of construct 4169 (VP1 GII.4_P80S+SSTAVATA hCod).
Figure 44O:
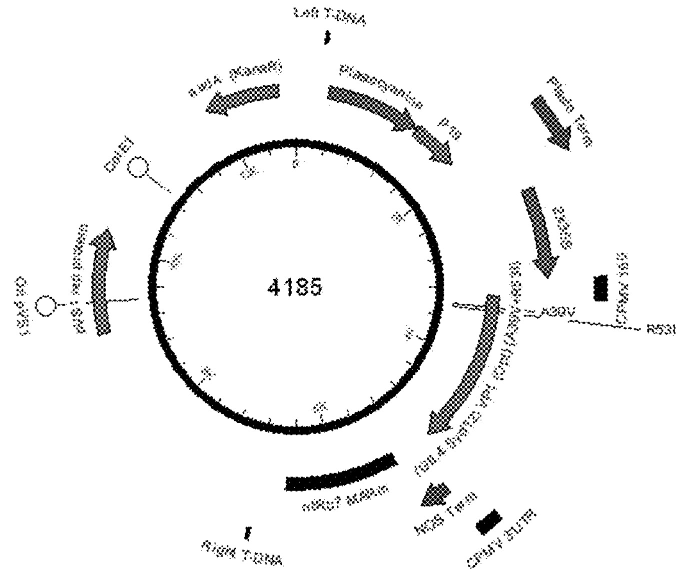
FIG. 44O shows a schematic representation of construct 4185 (VP1 GII.4_A39V+R53I hCod).
Figure 44P:
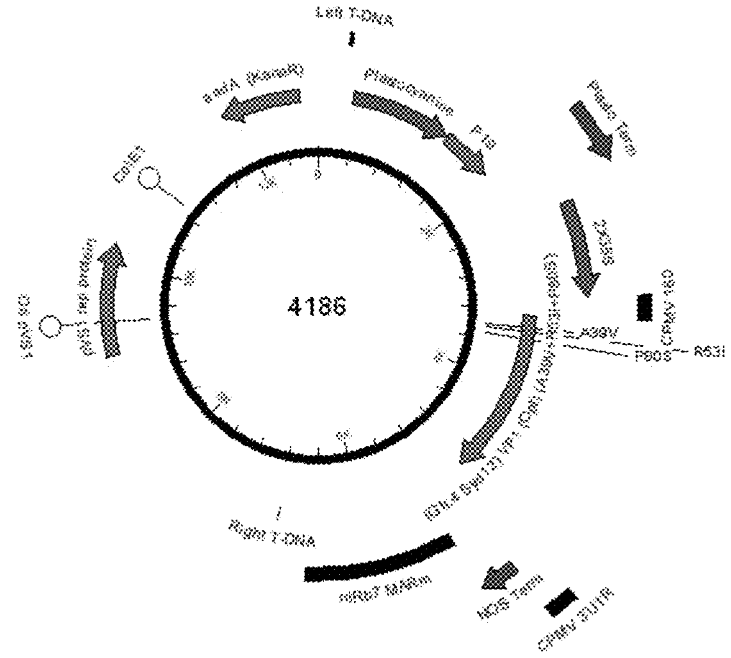
FIG. 44P shows a schematic representation of construct 4186 (VP1 GII.4_A39V+R53I+P80S hCod).
Figure 45A:
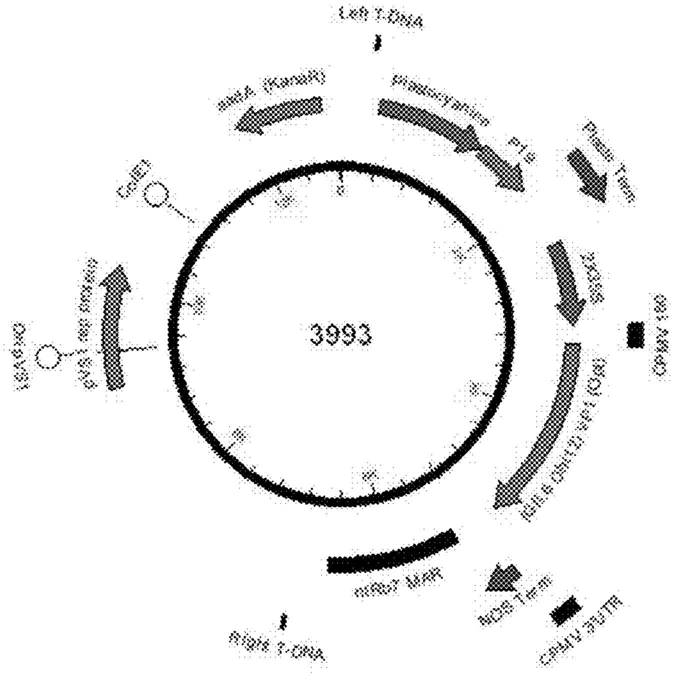
FIG. 45A shows a schematic representation of construct 3993 (Wt VP1 GII.6 hCod).
Figure 45B:
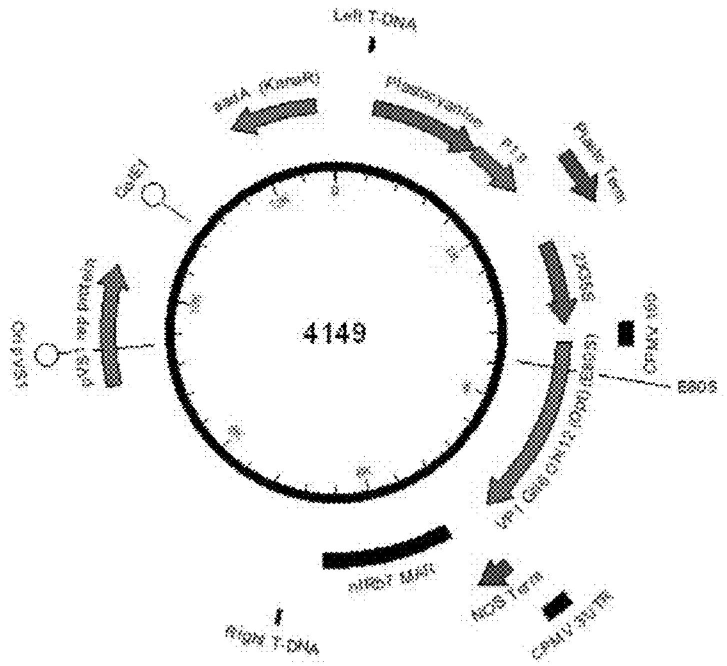
FIG. 45B shows a schematic representation of construct 4149 (VP1 GII.6_E80S hCod).
Figure 45C:
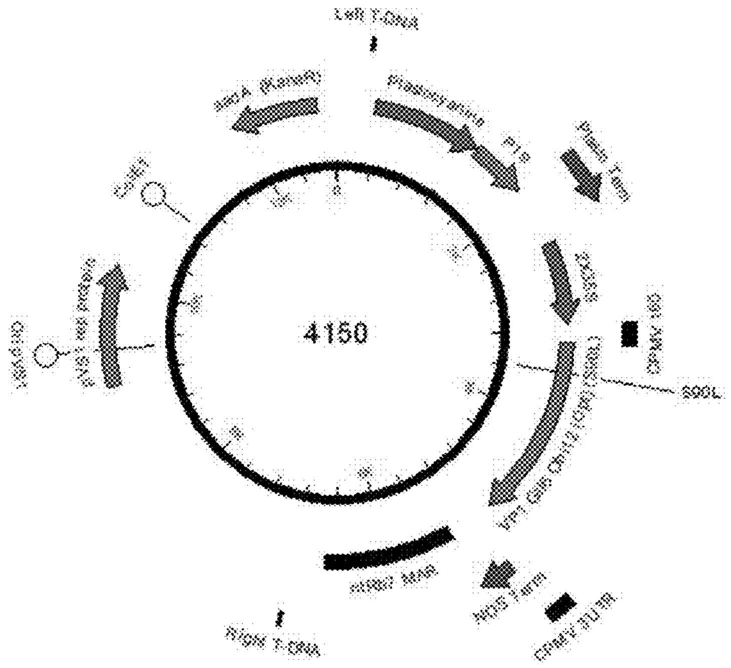
FIG. 45C shows a schematic representation of construct 4150 (VP1 GII.6_S90L hCod).
Figure 45D:
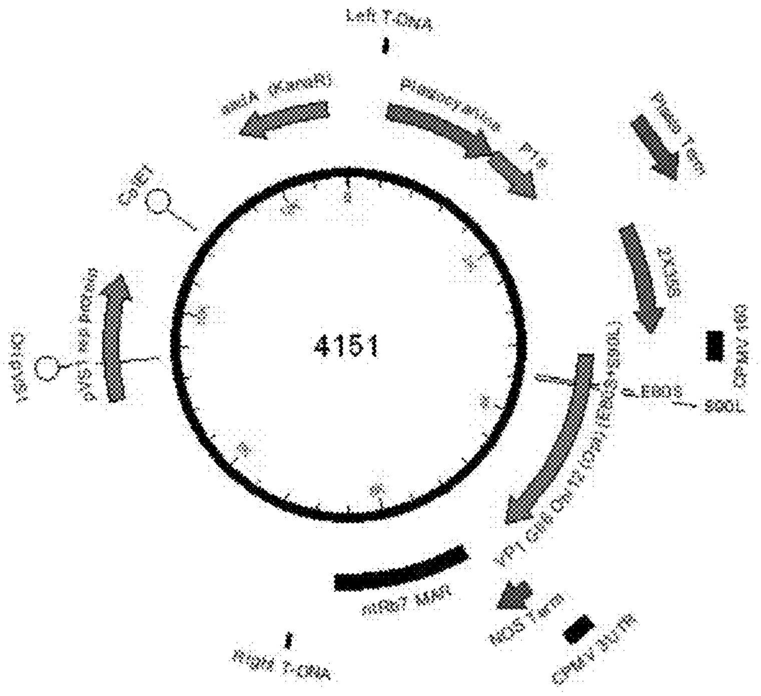
FIG. 45D shows a schematic representation of construct 4151 (VP1 GII.6_E80S+S90L).
Figure 46A:
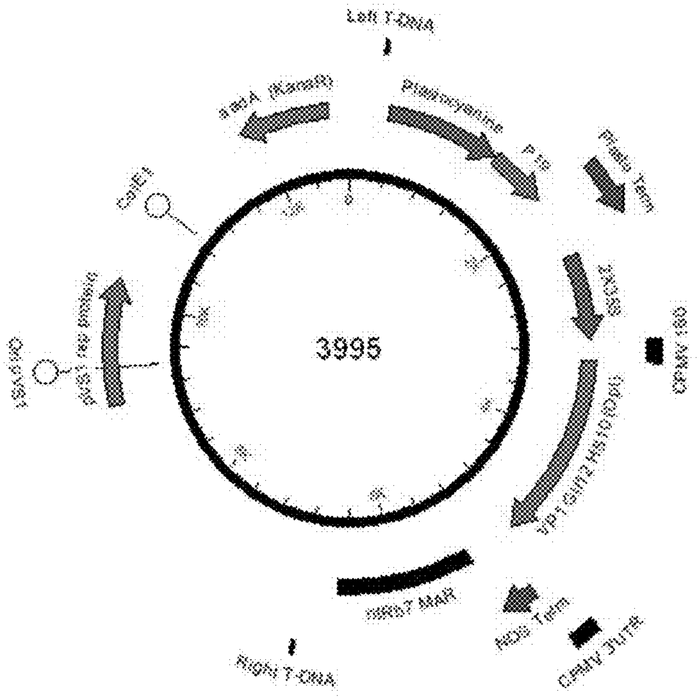
FIG. 46A shows a schematic representation of construct 3995 (Wt VP1 GII.12 hCod).
Figure 46B:
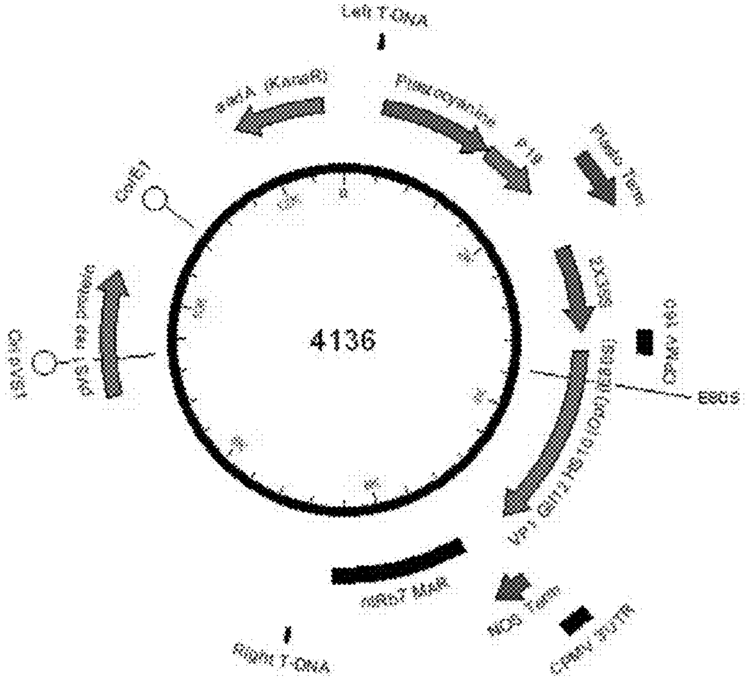
FIG. 46B shows a schematic representation of construct 4136 (VP1 GII.12_E80S hCod.
Figure 46C:
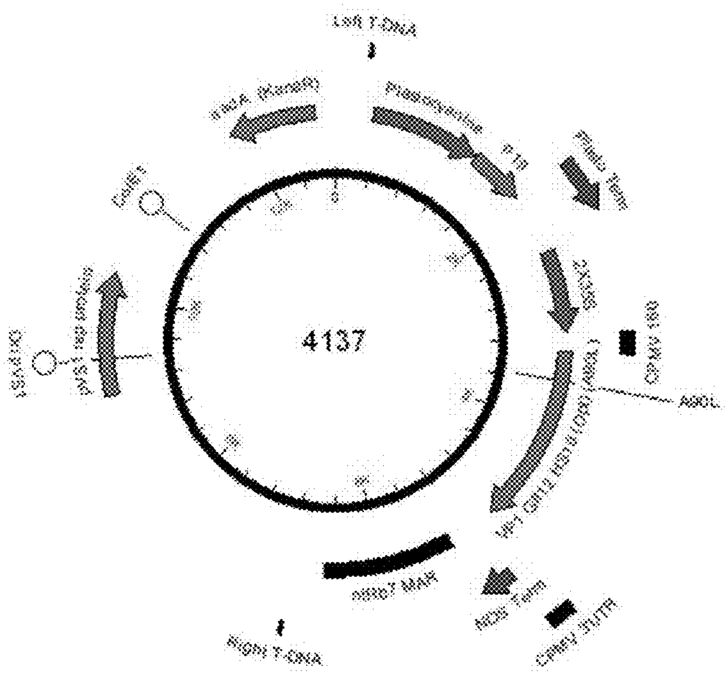
FIG. 46C shows a schematic representation of construct 4137 (VP1 GII.12_A90L hCod).
Figure 46D:
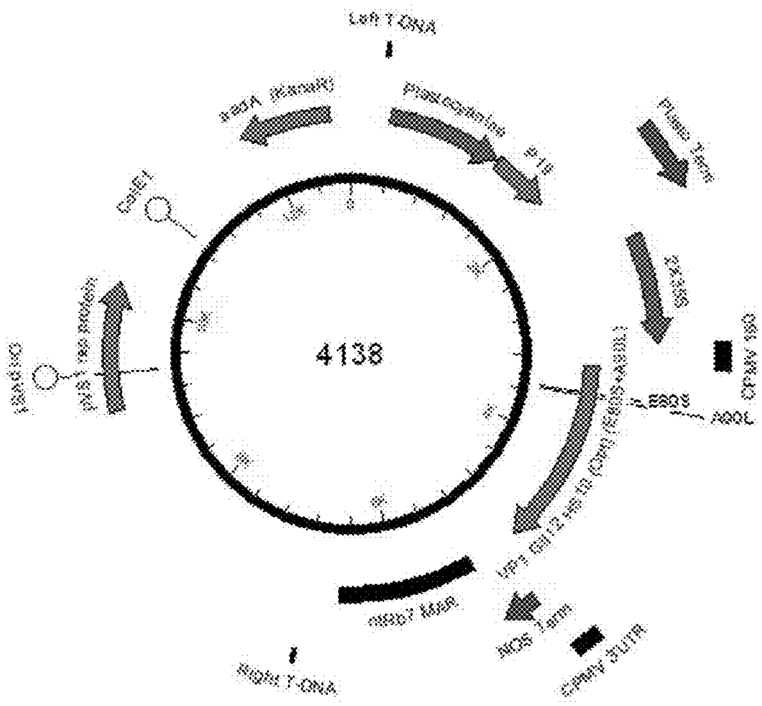
FIG. 46D shows a schematic representation of construct 4138 (VP1 GII.12_E80S+A90L).
Figure 46E:
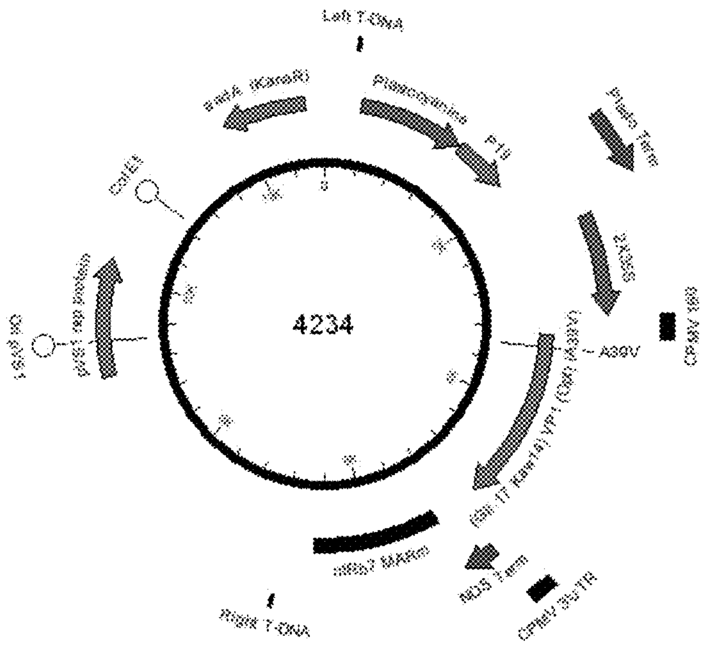
FIG. 46E shows a schematic representation of construct 4234 (VP1 GII.17_A39V).
Figure 46F:
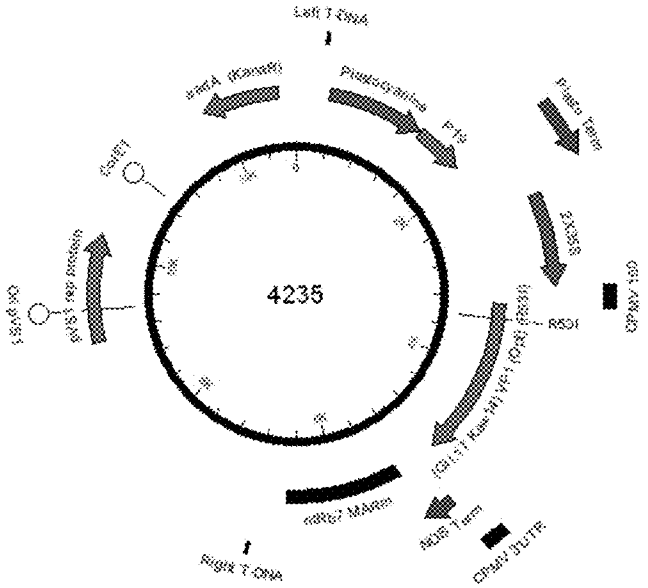
FIG. 46F shows a schematic representation of construct 4235 (VP1 GII.17_R53I).
Figure 46G:
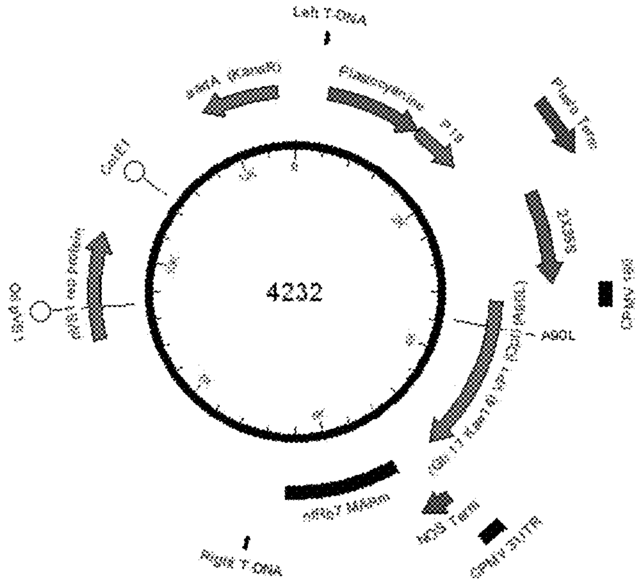
FIG. 46G shows a schematic representation of construct 4232 (VP1 GII.17_A90L).
Figure 46H:
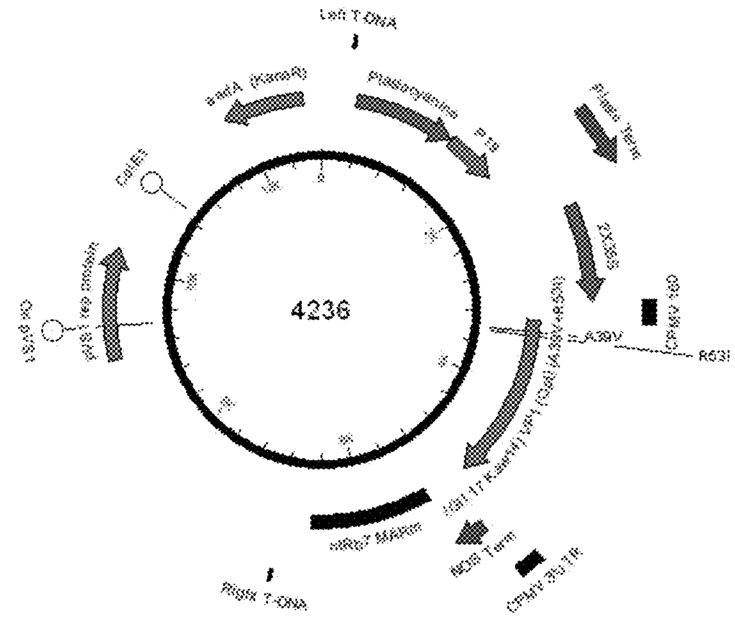
FIG. 46H shows a schematic representation of construct 4236 (VP1 GII.17_A39V+R53I).
Figure 46I:
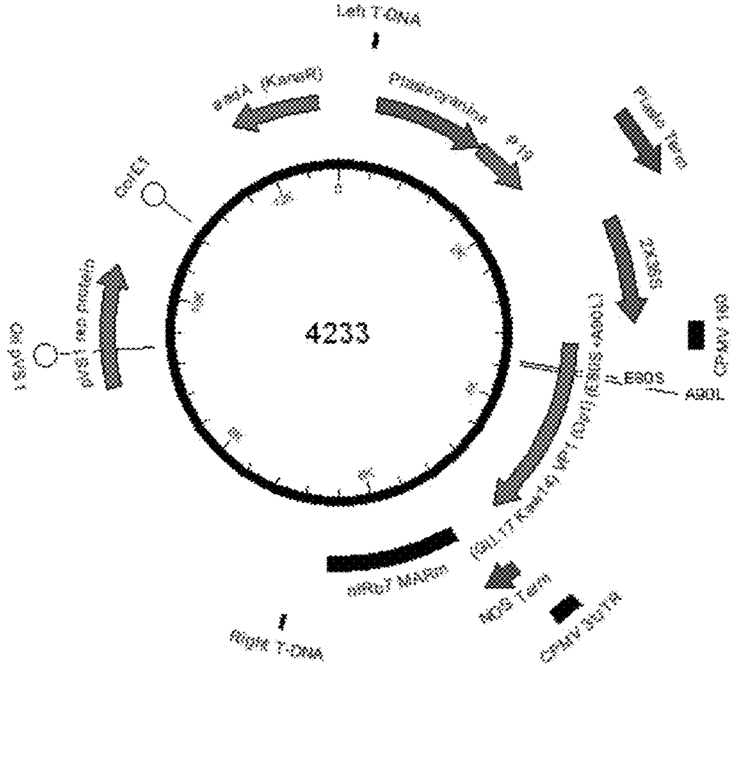
FIG. 46I shows a schematic representation of construct 4233 (VP1 GII.17_E80S+A90L).
Figure 47A:
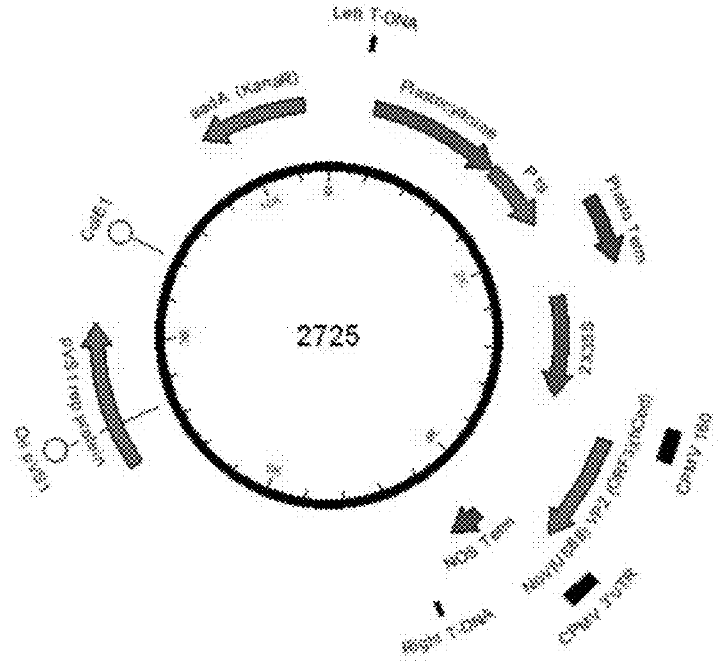
FIG. 47A shows a schematic representation of construct 2725 (Wt VP2 GI.1).
Figure 47B:
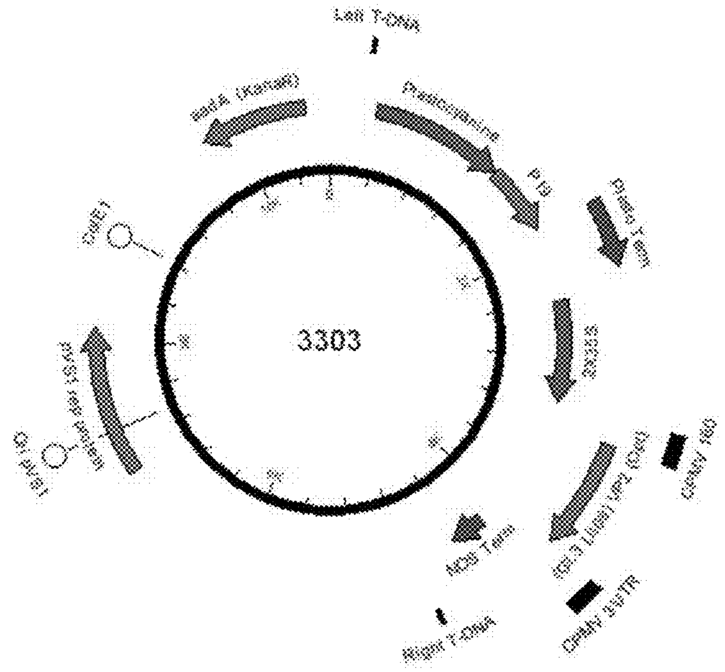
FIG. 47B shows a schematic representation of construct 3303 (Wt VP2 GI.3 hCod).
Figure 47C:
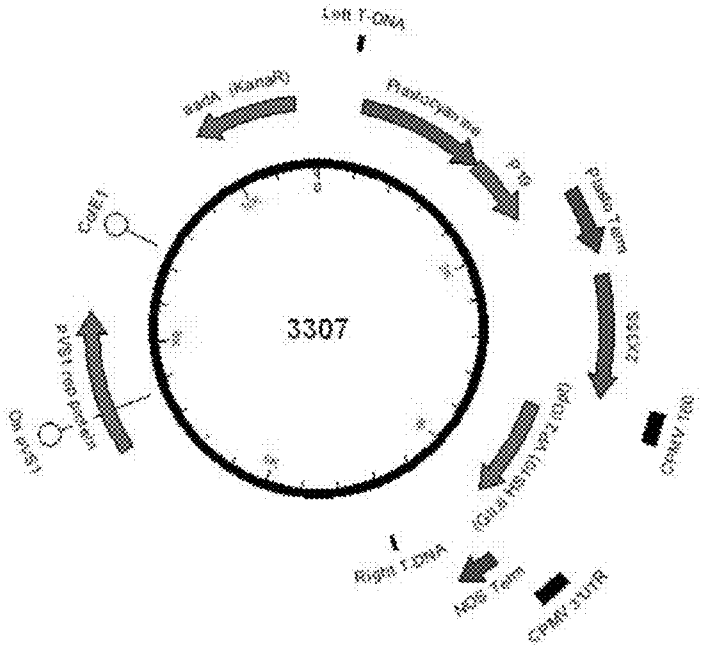
FIG. 47C shows a schematic representation of construct 3307 (Wt VP2 GII.6).

A human codon-optimized sequence encoding VP1 from GII.4/Sydney/NSW0514/2012/AU comprising the P80S and the S90L substitutions in the S domain was cloned into 2X35S/CPMV 160/NOS+MAR expression system using the following PCR-based method. In a first round of PCR, a fragment containing the S domain with the mutated P80S and S90L amino acids was amplified using primers IF-GII.4Syd12VP1.c (SEQ ID NO:130) and GII.4(S90L).r (SEQ ID NO:140), using human codon-optimized GII.4_P80S VP1 gene sequence (SEQ ID NO:60) as template. A second fragment containing the S90L substitution with the remaining of the S and P domain was amplified using GII.4(S90L).c (SEQ ID NO:141) and IF-GII.4Syd12VP1.r (SEQ ID NO:131), using human codon-optimized GII.4_P80S VP1 gene sequence (SEQ ID NO:60) as template. For sequence optimization, GII.4/Sydney/NSW0514/2012/AU VP1 protein sequence (Genbank accession number AFV08795) was backtranslated and optimized for human codon usage, GC content and mRNA structure. The PCR products from both amplifications were then mixed and used as template for a second round of amplification using IF-GII.4Syd12VP1.c (SEQ ID NO:130) and IF-GII.4Syd12VP1s (SEQ ID NO:131) as primers. The final PCR product was cloned in 2X35S/CPMV 160/NOS+MAR expression system using In-Fusion cloning system (Clontech, Mountain View, Calif.). Construct number 3677 (SEQ ID NO:164; FIGS. 38C and 49) was digested with SacII and StuI restriction enzyme and the linearized plasmid was used for the In-Fusion assembly reaction. Construct number 3677 is an acceptor plasmid intended for “In Fusion” cloning of genes of interest in a 2X35S/CPMV 160/NOS+MAR-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO:164. The resulting construct was given number 4135 (SEQ ID NO:166). The amino acid sequence of mutated GII.4_P80S+S90L is presented in SEQ ID NO:73. A representation of plasmid 4135 is presented in FIG. 44L.

A summary of the wildtype and mutated VP1 and VP2 proteins, primers, templates and products is provided in Tables 3 and 4. The VP1 proteins with single, double, triple, and quadruple modifications, substitutions, or mutations were constructed using the same methods as described above, with reference to construct #4133 for single modification and #4135 for the double, triple, and quadruple modifications. VP2 proteins are assembled using essentially the same method as that described for construct #2724.

Example 2: Methods

*Agrobacterium tumefaciens* Transfection

*Agrobacterium tumefaciens* strain AGL1 was transfected by electroporation with the native norovirus VP1, native norovirus VP2, or norovirus VP1 mutant protein expression vectors using the methods described by D'Aoust et al., 2008 (*Plant Biotech. J.* 6:930-40). Transfected *Agrobacterium* were grown in YEB medium supplemented with 10 mM 2-(N-morpholino)ethanesulfonic acid (MES), 20 μM acetosyringone, 50 μg/ml kanamycin and 25 μg/ml of carbenicillin pH5.6 to an $OD_{600}$ between 0.6 and 1.6. *Agrobacterium* suspensions were centrifuged before use and resuspended in infiltration medium (10 mM $MgCl_2$ and 10 mM MES pH 5.6).

Preparation of Plant Biomass, Inoculum and Agroinfiltration

*N. benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions Agrobacteria transfected with each native norovirus VP1, native norovirus VP2, or norovirus VP1 mutant expression vector were grown in a YEB medium supplemented with 10 mM 2-(N-morpholino)ethanesulfonic acid (MES), 20 μM acetosyringone, 50 μg/ml kanamycin and 25 μg/ml of carbenicillin pH5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6) and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Plants were returned to the greenhouse for a 6 or 9 day incubation period until harvest.

Leaf Harvest and Total Protein Extraction

Following incubation, the aerial part of plants was harvested, frozen at −80° C. and crushed into pieces. Total soluble proteins were extracted by homogenizing (Polytron) each sample of frozen-crushed plant material in 2 volumes of cold 100 mM phosphate buffer pH 7.2+150 mM NaCl, 0.4 μg/ml Metabisulfite and 1 mM phenylmethanesulfonyl fluoride. After homogenization, the slurries were centrifuged at 10,000 g for 10 min at 4° C. and these clarified crude extracts (supernatant) kept for analyses.

The total protein content of clarified crude extracts was determined by the Bradford assay (Bio-Rad, Hercules, Calif.) using bovine serum albumin as the reference standard. Proteins were separated by SDS-PAGE under reducing conditions using Criterion™ TGX Stain-Free™ precast gels (Bio-Rad Laboratories, Hercules, Calif.). Proteins were visualized by staining the gels with Coomassie Brilliant Blue. Alternatively, proteins were visualized with Gel Doc™ EZ imaging system (Bio-Rad Laboratories, Hercules, Calif.) and electrotransferred onto polyvinylene difluoride (PVDF) membranes (Roche Diagnostics Corporation, Indianapolis, Ind.) for immunodetection. Prior to immunoblotting, the membranes were blocked with 5% skim milk and 0.1% Tween-20 in Tris-buffered saline (TBS-T) for 16-18 h at 4° C.

Protein Analysis and Immunoblotting

Immunoblotting was performed with a first incubation with a primary mAb 242P antibody specific to VP1 from GI and GII genotypes, diluted 1/500 in 2% skim milk in TBS-Tween 20 0.1%. Peroxydase-conjugated goat anti-mouse (Jackson Immunoresearch, cat #115-035-146) diluted 1/10000 was used as secondary antibody for chemiluminescence detection, diluted in 2% skim milk in TBS-Tween 20 0.1% Immunoreactive complexes were detected by chemiluminescence using luminol as the substrate (Roche Diagnostics Corporation). Horseradish peroxidase-enzyme conjugation of human IgG antibody was carried out by using the EZ-Link Plus® Activated Peroxidase conjugation kit (Pierce, Rockford, Ill.).

Analysis of VLP Formation/Iodixanol Gradients

Proteins were extracted from frozen biomass by mechanical extraction in a blender with 2 volumes of extraction buffer (100 mM phosphate buffer pH 7.2+150 mM NaCl). The slurry was filtered through a large pore nylon filter to remove large debris and centrifuged 5000 g for 5 min at 4° C. The supernatant was collected and centrifuged again at 5000 g for 30 min (4° C.) to remove additional debris. The supernatant is then loaded on a discontinuous iodixanol density gradient. Analytical density gradient centrifugation was performed as follows: 38 ml tubes containing discontinuous iodixanol density gradient in acetate buffer (1 ml at 45%, 2 ml at 35%, 2 ml at 33%, 2 ml at 31%, 2 ml at 29% and 5 ml at 25% of iodixanol) were prepared and overlaid with 25 ml of the extracts containing the virus-like particles. The gradients were centrifuged at 175 000 g for 4 hours (4° C.). After centrifugation, 1 ml fractions were collected from the bottom to the top and fractions were analyzed by SDS-PAGE combined with protein staining or Western blot.

Electron Microscopy

Following centrifugation of partially clarified plant extracts on discontinuous iodixanol density gradients, as described above, fractions (1 ml/fraction) containing the samples are pooled, mixed with 100 mM PBS pH 7.2+150 mM NaCl buffer to completely fill the tube and centrifuged 120 minutes at 100000 g. The pellets were re-suspended in 300-1000 μl of buffer depending of the VP1 quantity.

Carbon-coated copper grids with a 200 nm mesh size are made hydrophilic by placing the carbon side face up on a Whatman paper in a petri dish and incubated overnight at 4° C. 20 μl of pooled fractions from density gradient centrifugation to be observed by transmission electron microscopy (TEM) are deposited on a Parafilm and grids were floated with the carbon side facing down and incubated at room temperature for 5 minutes. Grids are then washed 4 times on 20 μl water droplet and the excess water from the last wash is drained by touching a Whatman paper with the side of the grid. Grids are then incubated 1 minute on a 20 μl droplet of 2% uranyl acetate in water. Grids are allowed to dry 5 minutes on a Whatman paper. Observation was performed under transmission electron microscopy at magnifications ranging from 10,000× to 150,000×.

Example 3: VP1 Protein and VLP Production in Plants

*N. benthamiana* leaves were, vacuum infiltrated, as described in Example 2, with *Agrobacterium tumefaciens* comprising expression vectors encoding wildtype norovirus VP1s or mutant norovirus VP1 constructs to permit expression of the VP1 sequences, and the leaves examined for VP1 protein and/or VLP production. After 9 days post infiltration (DPI), total crude protein extracts were prepared from leaf homogenates were separated by SDS-PAGE, and stained with Coomassie (VP1 production), or separated using discontinuous iodixanol density gradients as described in Example 2, above (VLP production). Fractions from the density gradients were examined using Coomassie-stained SDS-PAGE. Norovirus VP1 proteins appear at an approximate 55-60 kDa band. The occurrence of the VP1 protein within a fraction of the density gradients is indicative of the fraction(s) to which the VLPs equilibrate during density gradient centrifugation. The yield of VLPs obtained from peak fractions after density gradient centrifugation was also determined.

The yield, or amount of extracted, wild type norovirus VP1 protein from plants differs depending on the genotype of the norovirus VP1 being expressed. Wild type GI.1 VP1, GI.5 VP1, and GII.12 VP1 exhibit readily detectable protein yields as determined using SDS PAGE (FIG. 3A). In contrast, wild type GII.4 VP1 was poorly expressed in plants (FIG. 3A right hand panel), and low yields of VP1 protein, or non-detectable amounts of VP1 protein (using SDS-PAGE) were also observed following expression, for example, wild type GII.2 VP1, GII.3 VP1 and GII.6 VP1 (Table 5).

Table 5: VP1 yields (determined in crude extracts) of several wildtype (native) norovirus strains produced in plants.

TABLE 5

VP1 yields (determined in crude extracts) of several wildtype (native) norovirus strains produced in plants.

| Genotype | Strain | Native Max yields |
|---|---|---|
| GI.1 | GI.1/US/68 | +++++ |
| GI.3 | 529/2008/Lilla Edet/Sweeden | +++ |
| GII.2 | CGMH47/2011/TW | ++ |
| GII.3 | Jingzhou/2013402/CHN | − |
| GII.6 | Ohio/490/2012/USA | +/− |

GI.3 VLPs and VLPs Comprising Modified GI.3 VP1 Proteins

Norovirus GI.3 VP1 constructs having a glutamine to serine substitution at position 84 (Q84S) resulted in similar yield than the wildtype GI.3 VP1, while norovirus GI.3 VP1 constructs having a serine to leucine substitution at position 94 (S94L), or combination of substitutions including the S94L substitution, exhibited a greater yield of VLP comprising the VP1 protein, of a 1.9 to 3.8 fold increase (S94L), a 4.2 fold increase (A43V+S94L), a 1.8 fold increase (Q84S+S94L), and a 10.2 fold increase (A34V+M57I+Q84S+S94L) as compared to VLPs comprising wild type GI.3 VP1. Furthermore, constructs having a serine to leucine, valine, isoleucine, methionine, threonine, glutamic acid, aspartic acid, asparagine, glutamine, lysine, or histidine substitution at position 94 (GI.3_S94X, where X=L, V, I, M, T, E, D, N, Q, K, or H), exhibited a greater yield, from about 1.2 to about 2.75 fold, compared to VLPs comprising the wild type GI.3 VP1 protein (FIG. 5F).

As shown in FIGS. 5B and 5D, expression of norovirus GI.3 constructs having, a serine to leucine substitution at position 94 (S94L), or a combination including a glutamine to serine substitution at position 84 (Q84S) and a serine to leucine substitution at position 94 (Q84S+S94L), or methionine to isoleucine substitution at position 57 (M57I+S94L), resulted in a shift of VLPs into higher density fractions (F2-F6; 31-35% iodixanol), as compared to VLPs comprising wildtype GI.3 VP1, which predominantly separated into lower density fractions (F8-F11; 25-29% iodixanol).

VLPs comprised of modified GI.3 VP1 proteins having a S94L substitution, a combination of Q84S+S94L, or a combination of M57I+S94L, had fewer damaged viral particles and a greater proportion of 38 nm particles, over 23 nm particles, when compared to wildtype GI.3 VLPs (FIGS. 5C and 5E).

GI.5 VLPs and VLPs Comprising Modified GI.5 VP1 Proteins

Norovirus GI.5 VP1 constructs having a serine to proline substitution at position 84 (Q84S), an alanine to leucine substitution at position 94 (A94L), or a combination of these substitutions (Q84S+A94L), exhibited a similar yield of VP1 protein in plant extracts when compared to the yield of wild type GI.5 VP1 protein expressed in plants (FIG. 6A). After gradient purification, centrifugation and resuspension, Norovirus GI.5 construct having an alanine to leucine substitution at position 94 (A94L) exhibited a greater yield, 1.5 fold increase, when compared to the wildtype GI.5 VP1.

As shown in FIG. 6B, a GI.5 VP1 construct having a glutamine to serine substitution at position 84 in combination with an alanine to leucine substitution at position 94 (Q84S+A94L), resulted in VP1 proteins that exhibited a shift to higher density iodixianol fractions (29-31%) as compared to wildtype GI.5 VP1 (predominantly found in 25-29% iodixanol fractions). The VLP preparations also comprised fewer damaged viral particles when compared to wildtype GI.5 VLPs (FIG. 6C).

GI.7 VLPs and VLPs Comprising Modified GI.7 VP1 Proteins

Figure 6F:
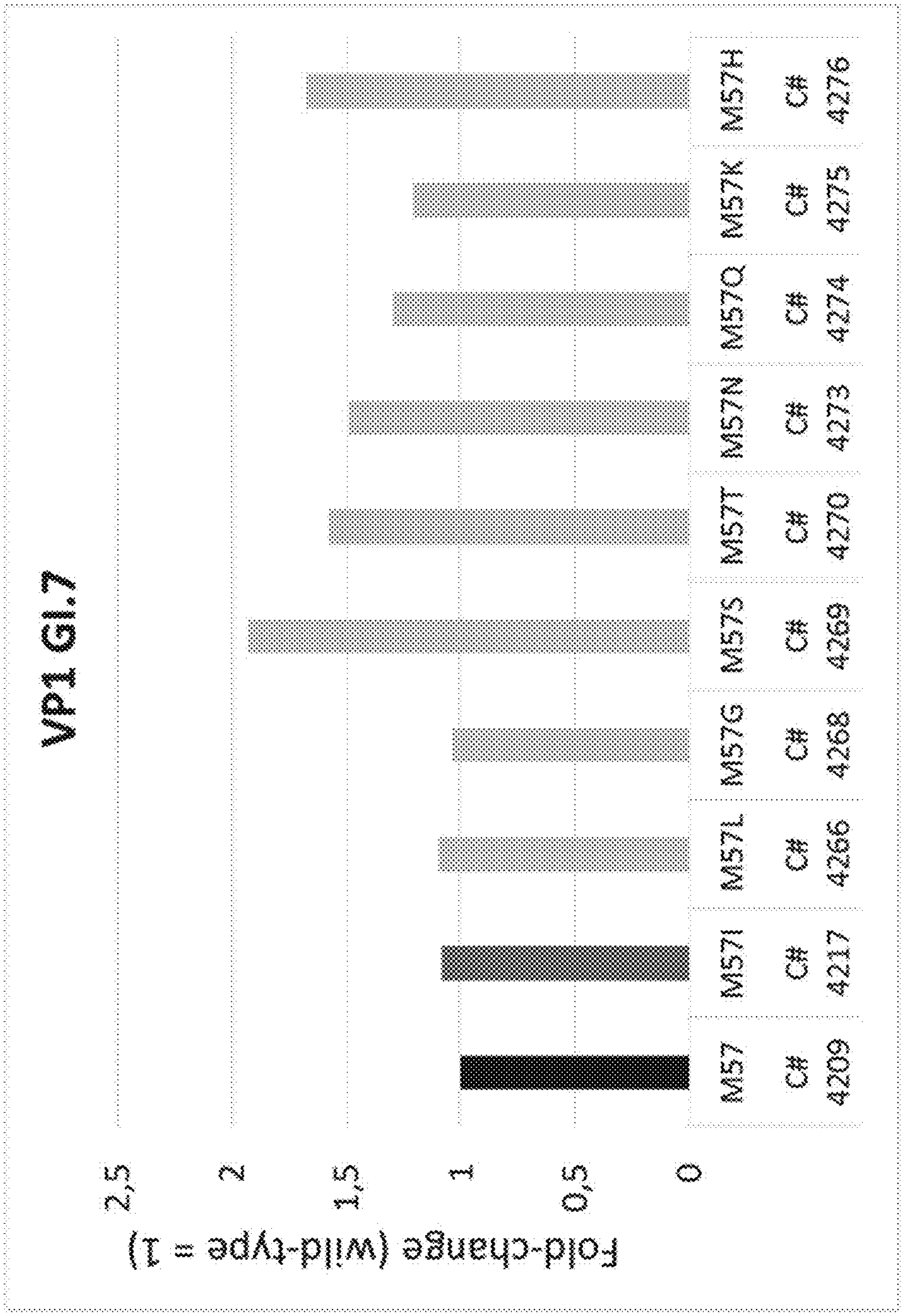
FIG. 6F shows the relative yield of VLPs comprising non-native VP1 GI.7 with substitutions at amino acid position 57, compared to the VLP yield of wild-type GI.7 (GI.7 M57; set as "Fold Change" of 1): C #: construct number.

Norovirus GI.7 VP1 constructs having an arginine to serine substitution at position 84 (R84S), a methionine to isoleucine substitution at position 57 (M57I), or a combination of these substitutions (M57I+R84S), exhibited an increased yield of VP1 protein after gradient purification, centrifugation and resuspension, when compared to the wildtype GI.7 VP1. Furthermore, GI.7 constructs having a methionine to isoleucine, leucine, glycine, serine, threonine, asparagine, glutamine, lysine, or histidine substitution at position 57 (GI.7_M57X, where X=I, L, G, S, T, N, Q, K, or H), exhibited a greater yield, from about 1.1 to about 1.95 fold, VLPs comprising the wild type GI.7 VP1 protein (FIG. 6F).

As shown in FIG. 6D, a GI.7 VP1 construct having the M57I, R84S or M57I+R84S substitutions resulted in VP1 proteins that exhibited a shift to higher density iodixianol fractions (31-35%) as compared to wildtype GI.7 VP1. The GI.7 VLP preparations having the M57I, R84S or M57I+R84S substitutions also comprised the same or fewer damaged viral particles when compared to wildtype GI.7 VLPs (FIG. 6E).

GII.2 VLPs and VLPs Comprising Modified GII.2 VP1 Proteins

Expression of modified norovirus VP1 proteins GII.2_A90L and GII.2_E80S+A90L in plants resulted in higher VP1 protein yield as compared to the yield of wildtype GII.2 VP1 (see FIG. 7A).

Norovirus GII.2 VP1 constructs having a glutamate to serine substitution at position 84 and an alanine to leucine substitution at position 90 (E84S+A90L), an alanine to valine substitution at position 39, a glutamate to serine substitution at position 84, and an alanine to leucine substitution at position 90 (A39S+E84S+A90L), an arginine to isoleucine substitution at position 53, a glutamate to serine substitution at position 84, and an alanine to leucine substitution at position 90 (R53I+E84S+A90L), an alanine to valine substitution at position 39, an arginine to isoleucine substitution at position 53, a glutamate to serine substitution at position 84, and an alanine to leucine substitution at position 90 (A39V+R53I+E84S+A90L), all exhibited an increased yield of VP1 protein after gradient purification, centrifugation and resuspension, when compared to the wildtype GII.2 VP1.

Expression of a GII.2 VP1 constructs having a glutamic acid to serine substitution at position 80 (E80S), an alanine to leucine substitution at position 90 (A90L), or a glutamic acid to serine substitution at position 80 and an alanine to leucine substitution at positions 80 and 90 (E80S+A90L) resulted in similar production of VLPs as that of the wildtype GII.2 (FIG. 7B). The GII.2 VLP preparations having the E80S+A90L, or A39V+E80S+A90L substitution s also comprised the same or fewer damaged viral particles when compared to wildtype GII.2 VLPs (FIG. 7C).

GII.3 VLPs and VLPs Comprising Modified GII.3 VP1 Proteins

Norovirus GII.3 VP1 constructs having a replacement of glutamic acid with serine at position 80 (E80S) exhibited a similar yield of VP1 protein in plant extracts, when compared to the yield of wild type GII.3 VP1 protein expressed in plants. The yields of VLPs comprising either wild type of modified VP1 protein were generally low.

Expression of a GII.3 VP1 constructs having a glutamic acid to serine substitution at position 80 (E80S) resulted in similar production of VLPs that resided in similar density iodixanol fractions (35%) as that of the wildtype GII.3 (FIG. 8B).

GII.4 VLPs and VLPs Comprising Modified GII.4 VP1 Proteins

Figure 9H:
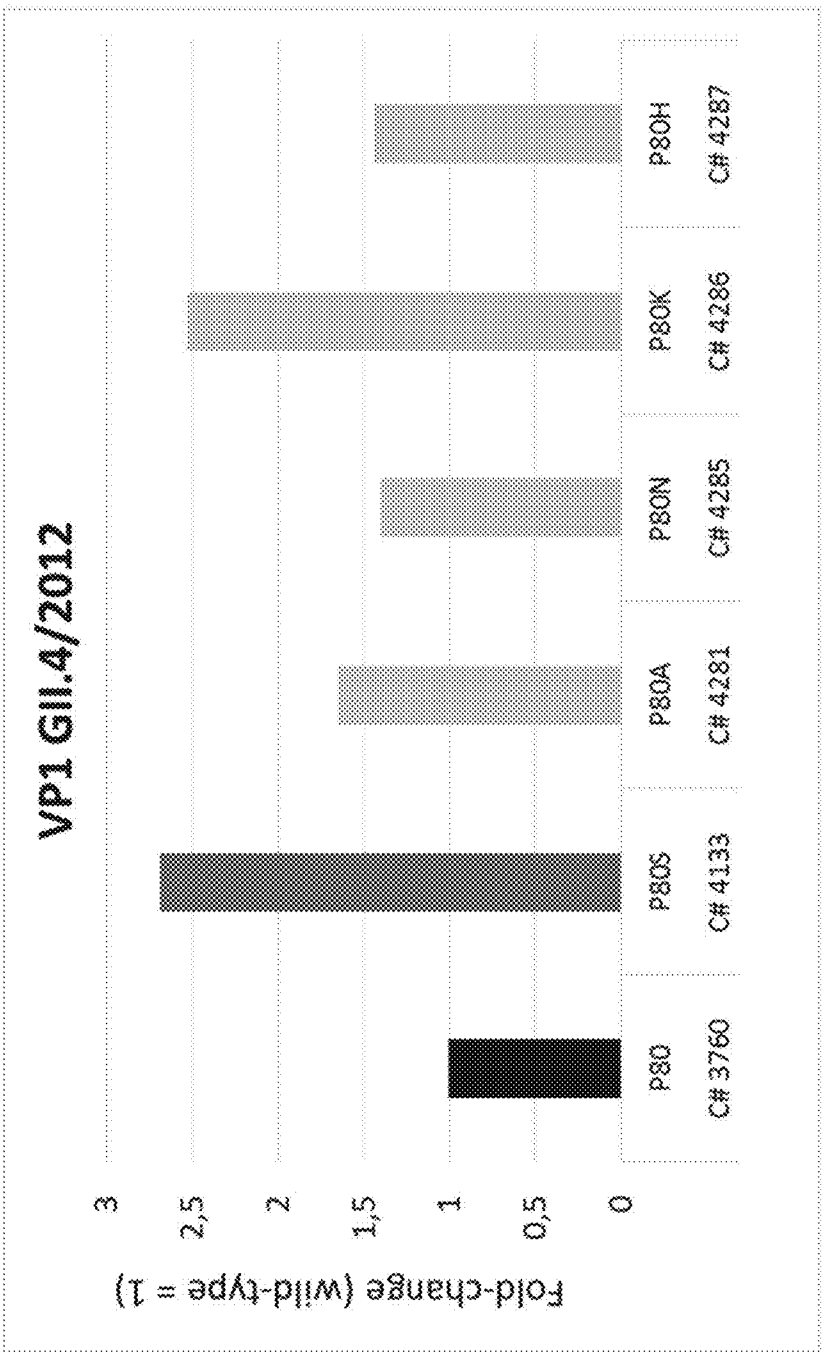
FIG. 9H shows the relative yield of VLPs comprising non-native VP1 GII.4/2012 with substitutions at amino acid position 80, compared to the VLP yield of wild-type (native) GII.4/2012 (GII.4/2012 P80 set as "Fold Change" of 1; C #: construct number.
Figure 9I:
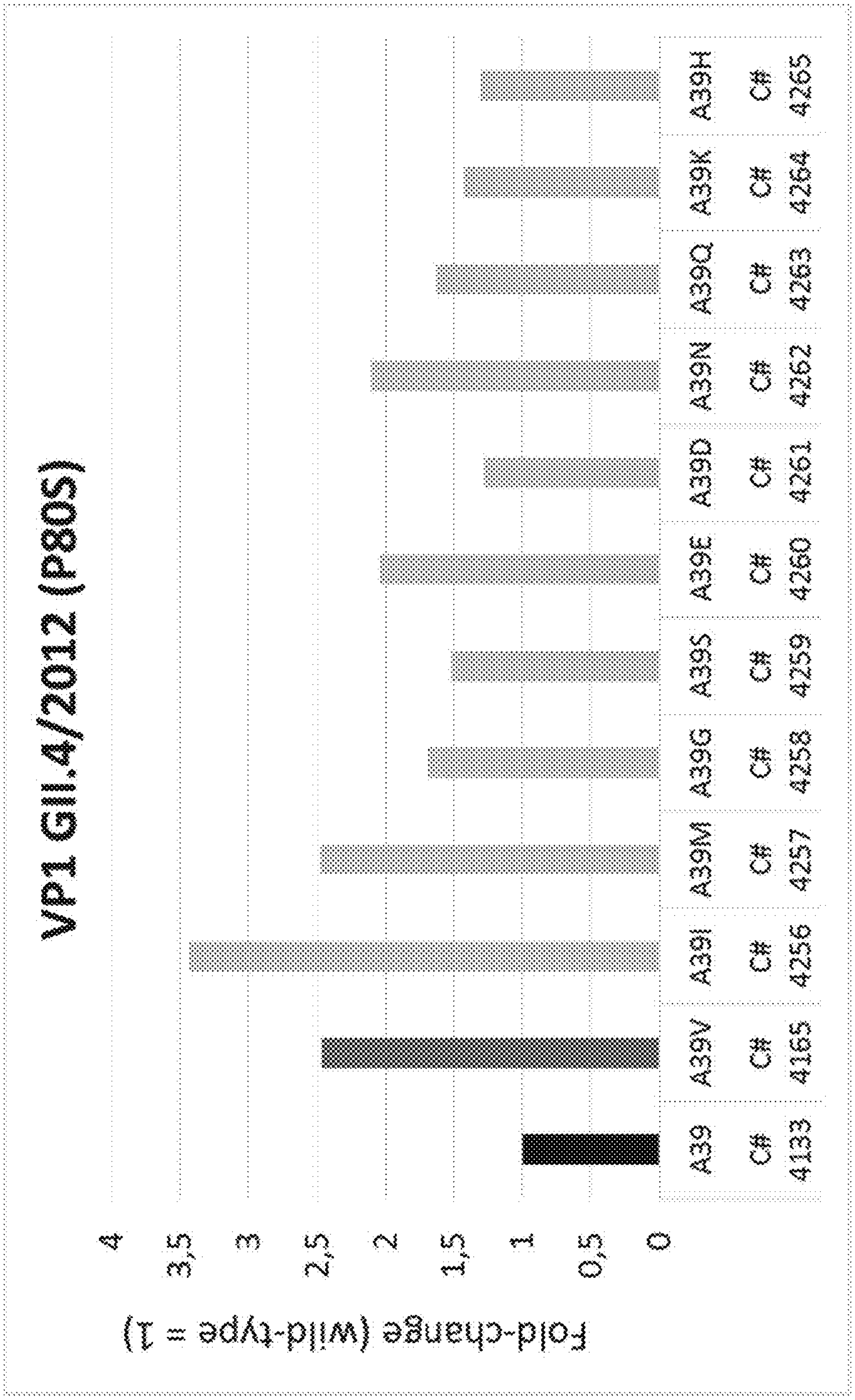
FIG. 9I shows the relative yield of VLPs comprising VP1 GII.4/2012 (P80S) with an additional substitution at amino acid position 39, compared to the VLP yield of GII.4/2012 (P80S) comprising A39. GII.4/2012 (P80S) A39 set as "Fold Change" of 1; C #: construct number.

With reference to FIGS. 9A, 9H and 9I, norovirus GII.4 VP1 constructs having: an arginine to isoleucine substitution at position 53 (R53I); a proline to serine, alanine, asparagine, lysine, or histidine substitution at position 80 (P80X, where X=S, A, N, K, or H); a serine to leucine substitution at position 90 (S90L); an alanine to valine, isoleucine, methionine, threonine, aspartic acid, glutamic acid, asparagine, glutamine, lysine, or histidine substitution at position 39 (A39X, where X=V, I, M, T, E, D, N, Q, K, or H) in combination with a proline to serine substitution at position 80 (A39V+P80S); an arginine to isoleucine substitution at position 53 in combination with a proline to serine substitution at position 80 (R53I+P80S); a serine to leucine substitution at position 90 in combination with a proline to serine substitution at position 80 (P80S+S90L); and a deletion of positions 35 to 42 (Δ35-42) in combination with a proline to serine substitution at position 80 (Δ35-42+P80S), resulted in higher VP1 protein yields following extraction for plants, as compared to VP1 yields using wildtype GI.4.

For each of the tested modified GII.4 VP1 proteins, the VLP yield, comprising the various modified GII.4 VP1 proteins, was greater than that of VLPs comprising wild type GII.4 VP1 protein. A ten-fold increase in VLP yield was observed in VLPs comprising GII.4_A39V VP1; from about a 1.4 to about a 2.7 fold increase in VLP yield was observed in VLPs comprising GII.4_P80X, where X=S, A, N, K, H, an over 8-fold increase in VLP yield was observed in VLPs comprising either GII.4_S90L VP1, or GII.4_Δ35-42+P80S VP1; a 14-fold increase in VLP yield was observed in VLPs comprising GII.4_P80S+P90L VP1; from about 1.3 to about 3.4 fold increase in VLP yield was observed in VLPs comprising GII.4_A39X+P80S VP1, where X=V, I, M, T, E, D, N, Q, K, or H, GII.4_R53I+P80S (21 fold increase), or GII.4_A39V+P80S+A90L VP1 (38.5 fold increase); a five-fold increase in VLP yield was observed in VLPs comprising GII.4_A39V+R53I VP1; a four-fold increase in VLP yield was observed in VLPs comprising GII.4_V47P+P80S VP1; and a 1.5-fold increase in VLP yield was observed in VLPs comprising GII.4_R53I VP1.

Results of VLPs comprising modified GII.4 proteins are shown in FIGS. 9B-9D and 9G. Constructs comprising GII.4 VP1 having: a proline to serine substitution at position 80 (P80S; FIG. 9B, 9C, 9D); a serine to leucine substitution at position 90 (S90L; FIG. 9B); an alanine to valine substitution at position 39 in combination with a proline to serine substitution at position 80 (A39V+P80S; FIG. 9C); an arginine to isoleucine substitution at position 53 in combination with a proline to serine substitution at position 80 (R53I+P80S; FIG. 9D); a proline to serine substitution at position 80 in combination with a serine to leucine substitution at position 90 (P80S+S90L; FIG. 9B); a proline to serine substitution at position 80 in combination with a deletion of positions 35-42 (P80S+Δ35-42; FIG. 9C), and an alanine to valine substitution at position 39, in combination with a proline to serine substitution at position 80 and a serine to leucine substitution at position 90 (GII.4_A39V+P80S+A90L; FIG. 9G), resulted in the production of VLPs that reside in higher density iodixanol fractions (29-33%).

VLPs comprising GII.4 VP1 proteins having: a P80S substitution in combination with an S90L substitution (P80S+S90L; FIG. 9B); an A39V substitution in combination with a P80S substitution (A39V+P80S; FIG. 9C); a P80S substitution in combination with a deletion of positions 35-42 (Δ35-42+P80S; FIG. 9C); an R53I substitution in combination with a P80S substitution (R53I+P80S; FIG. 9D); and an alanine to valine substitution at position 39, in combination with a proline to serine substitution at position 80 and a serine to leucine substitution at position 90 (GII.4_A39V+P80S+A90L; FIG. 9G), had fewer damaged viral particles and/or a greater ratio of 38 nm particles:23 nm particles, as compared to wildtype GII.4 VLPs.

GII.6 VLPs and VLPs Comprising Modified GII.6 VP1 Proteins

Increased VLP yield of over 2.2 fold, compared to wild type, (determined following gradient purification, centrifugation and resuspension) was also observed in plant extracts expressing GII.6_S90L VP1.

GII.12 VLPs and VLPs Comprising Modified GII.12 VP1 Proteins

Figure 11A:
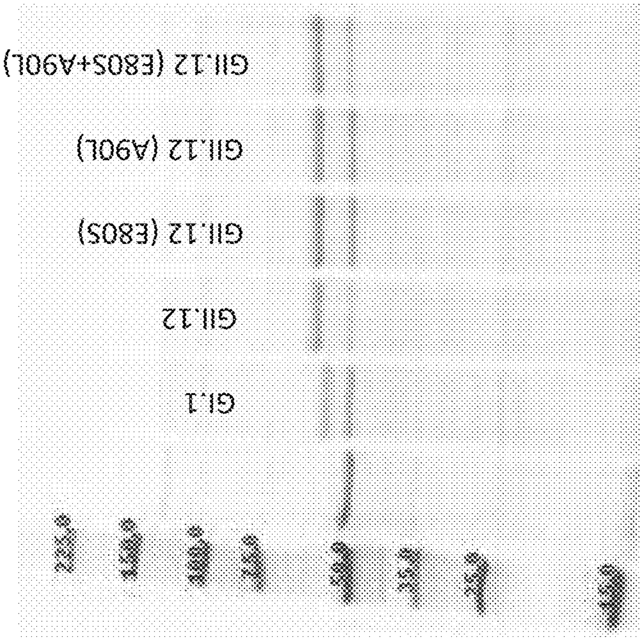
FIG. 11A shows a Coomassie-stained SDS-PAGE of crude protein extracts prepared from agroinfiltrated *N. benthamiana* leaves, 9 days post infiltration (DPI) with wt hCod GI.1/United States/Norwalk/1968 VP1 (Construct #: 2724; SEQ ID NO:3 (nucleotide); SEQ ID NO: 1 (amino acid)), wt hCod GII.12/HS206/2010/USA VP1 (Construct #: 3995; SEQ ID NO:87 (nucleotide); SEQ ID NO:19 (amino acid)), mut hCod GII.12/1-15206/2010/USA_E80S VP1 (Construct #: 4136; SEQ ID NO:89 (nucleotide); SEQ ID NO:88 (amino acid)), mut hCod GII.12/HS206/2010/USA_A90L VP1 (Construct #: 4137; SEQ ID NO:91 (nucleotide); SEQ ID NO:90 (amino acid)), or mut hCod GII.12/HS206/2010/USA_E80S+A90L VP1 (Construct #: 4138; SEQ ID NO:93 (nucleotide); SEQ ID NO:92 (amino acid)). First lane=crude protein extracts prepared from mock infiltrated *N. benthamiana* leaves.
Figures 11B, 11C:
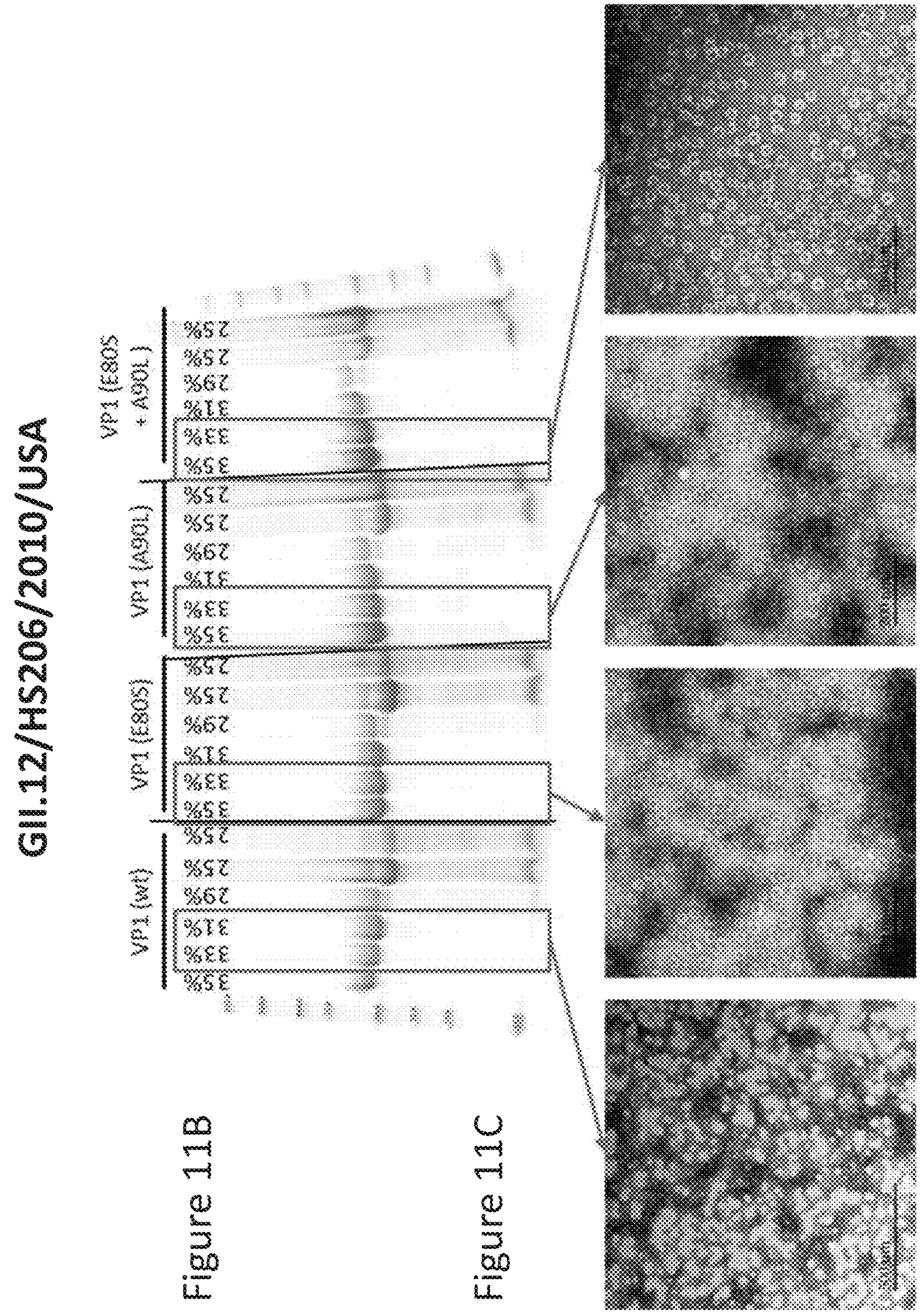
FIG. 11B shows a Coomassie-stained SDS-PAGE analysis of iodixanol density gradient fractions of crude protein extracts prepared from *N. benthamiana* leaves expressing wt GII.12/HS206/2010/USA VP1 (Construct #: 3995), GII.12/HS206/2010/USA_E80S VP1 (Construct #: 4136), GII.12/HS206/2010/USA_A90L VP1 (Construct #: 4137), or GII.12/HS206/2010/USA_E80S+A90L VP1 (Construct #: 4138).
FIG. 11C shows transmission electron micrographs (TEM) of virus like particles (VLPs) purified from 31-35% iodixanol gradient fractions of crude protein extracts prepared from *N. benthamiana* leaves expressing wt GII.12/HS206/2010/USA VP1 (Construct #: 3995, first panel GII.12/HS206/2010/USA_P80S VP1 (Construct #: 4136, second panel), GII.12/HS206/2010/USA_S90L VP1 (Construct #: 4137, third panel), or GII.12/HS206/2010/USA_P80S+S90L VP1 (Construct #: 4138, fourth panel).15,000× magnification; scale bar=500 nm.
Figure 11D:
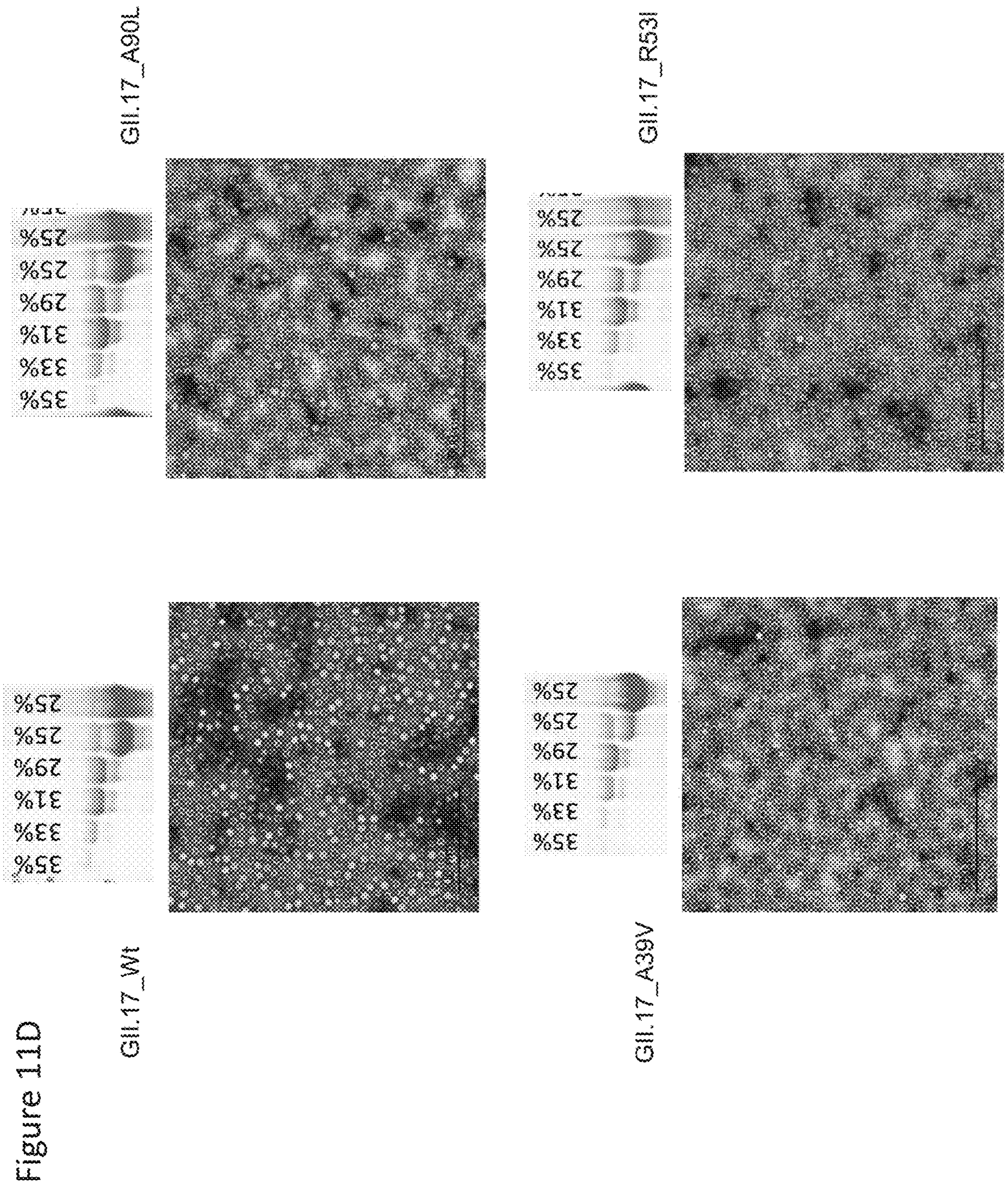
FIG. 11D shows Coomassie-stained SDS-PAGE analysis of iodixanol density gradient fractions of crude protein extracts prepared from *N. benthamiana* leaves (upper part of each panel), and transmission electron micrographs (TEM) of virus like particles (VLPs) purified from 31-35% iodixanol gradient fractions of crude protein extracts prepared from *N. benthamiana* leaves (lower part of each panel), expressing: Top Left Panel: wt hCod GII.17 Kawa 2014 A0A077KVU6VP1 (Construct #3998; SEQ ID NO:25 (nucleotide); SEQ ID NO:24 (amino acid)), Top Right panel mut hCod GII.17 Kawa 2014 A0A077KVU6_A90L VP1 (Construct #4232; SEQ ID NO:197 (nucleotide); SEQ ID NO:196 (amino acid)); Bottom Left Panel: mut hCod GII.17 Kawa 2014 A0A077KVU6_A39V VP1 (Construct #4234; SEQ ID NO:193 (nucleotide); SEQ ID NO:192 (amino acid)); Bottom Right Panel: mut hCod GII.17 Kawa 2014 A0A077KVU6_R53I VP1 (Construct #4235; SEQ ID NO:195 (nucleotide); SEQ ID NO:194 (amino acid)); 15,000× magnification; scale bar=500 nm.

The yield of modified GII.12, for example, GII.12 comprising a glutamic to serine substitution at position 80 (E80S), an arginine to leucine substitution at position 90 (A90L), or a combination of these substitutions (E80S+A90L) resulted in an increase of about 1.2-1.4 fold compared to wild type, (determined following gradient purification, centrifugation and resuspension; FIG. 11A).

GII.12 constructs having: a glutamic acid to serine substitution at position 80 (E80S); an alanine to leucine substitution at position 90 (A90L); and a combination thereof (E80S+A90L), resulted in the expression of GII.12 VP1 protein that resided in higher density iodixanol fractions (33-35%) as compared to wildtype GII.12 VP1 (31-33%).

GII.17 VLPs and VLPs Comprising Modified GII.17 VP1 Proteins

The yield of modified GII.17, for example, GII.17 comprising an alanine to valine substitution at position 39 (A39V), a arginine to isoleucine substitution at position 53 (R53I), or an alanine to leucine substitution at position 90 (A90L) resulted in an increase of about 1.1-3.4 fold compared to wild type, (determined following gradient purification, centrifugation and resuspension).

GII.17 constructs having: an alanine to valine substitution at position 39 (A39V), a arginine to isoleucine substitution at position 53 (R53I), or an alanine to leucine substitution at position 90 (A90L), resulted in the expression of GII.17 VP1 protein that resided in higher density iodixanol fractions (33-35%) as compared to wildtype GII.12 VP1 (31-33%).

Collectively, the above described results demonstrate that protein components from the high density iodixanol gradient fractions demonstrate that Norovirus VP1 proteins, and modified Norovirus VP1 proteins, were found to self-assemble into VLPs in plants. The isolated VLPs comprised of mutant VP1 proteins exhibited a structural conformation similar to that of wildtype norovirus virion particles.

Example 4: Immune Response Using VP1

Studies on the immune response to Norovirus native GI.1 (SEQ ID NO:1) VLP administration were performed with 6-8 week old female BALB/c mice (Charles River Laboratories). Thirty seven mice were randomly divided into four groups of eight animals for Norovirus VLP vaccine and a group of five animals for placebo. All groups were injected using intramuscular immunization. All groups were immunized in a two-dose regimen, the boost immunization being administered 3 weeks following the first immunization.

For intramuscular administration in hind legs, two groups (eight animals) of unanaesthetized mice were immunized with the plant-made VLP native VP1 from Norovirus GI.1 genotype vaccine (1 or 10 μg). Placebo group (five animals) was immunized using the same route and regimen as the candidate vaccine using vaccine buffer (PBS at pH 6.0).

To measure the potential benefit of adjuvant, two groups of animals (8 animals) were immunized by intramuscular administration in hind legs on unanaesthetized mice with 1 or 10 μg plant-made VLP Norovirus vaccine plus one volume Alhydrogel 2% (alum, Cedarlane Laboratories Ltd., Burlington, Ontario, Canada). All groups were immunized according to a prime-boost regimen with the boost immunization performed 3 weeks following the first immunization.

Mice were evaluated through clinical observations during the in-life period as followed: daily monitoring for mortality and clinical signs, weekly detailed examinations, injection site observations and body weight measurements. All animals were under observation and sacrificed on Day 42 for gross examination. Blood was collected from all animals prior to dosing on Day 0, on Days 21 and 42 (21 days after each immunization). Samples were processed to isolate the serum for specific antibody response analyses.

Serum samples from blood collected on Days 21 and 42 from all animals were analyzed individually by ELISA for GI.1 VLP-specific total IgG and IgA antibodies using GI.1 VLP-coated plates. Pre-immune serum samples (Day 0—prior dosing) collected from all animals were pooled by treatment group and each pool was analyzed to insure that they were negative (or below the cut-off value of the analytical test).

Descriptive statistics were performed using GraphPad Prism software (Version 6.05; GraphPad Software, La Jolla, Calif., USA). Antibody titers measured for each group were reported as geometric mean titer (GMT) with 95% confidence intervals (CI). Half of the value of the limit of detection was attributed to antibody titers below the limit of detection of the method specific to the tested antibodies. Therefore, in this study, an animal was considered to be a positive responder if its GMT value for a determined condition was equal or above the limit of detection of the method (LOQ=100). Statistical comparisons between IgG titers of treatment groups were performed using one-way ANOVA followed by a Tukey's test on log 10-transformed data. A comparison between the placebo group and each treatment group was also performed using oneway ANOVA followed by a post hoc Dunnett's test on log 10-transformed data.

The GI.1 VLP-specific total IgG titers that were measured in serum samples from all animals after IM immunization with one dose (Day 21) and two doses (Day 42) of 1 μg or 10 μg of each formulation. Total IgG titers were measured by ELISA using GI.1 VLP-coated plates (LOQ=100). The results are present in FIG. 3D. Total IgG titers per treatment group (n=8 animals/group) are represented by geometric mean titer (GMT) with a 95% confidence interval. Statistical comparisons between IgG titers of treatment groups were performed using one-way ANOVA followed by a Tukey's test on log 10-transformed data. A comparison between the placebo group and each treatment group was also performed using one-way ANOVA followed by a post-hoc Dunnett's test on log 10-transformed data. Significant differences were annotated as letters in FIG. 3D (the same letter indicates that no significant difference was detected between treatment groups; p>0.05).

In a similar manner plant-produced modified VP1 proteins, as described herein, including for example: produced using GI.3_Q84S (construct 4140; SEQ ID NO:167), GI.3_S94L (construct 4141; SEQ ID NO:9), GI.3_A43V+S94L (construct 4179; SEQ ID NO:169), GI.3_M57I+S94L (construct 4180; SEQ ID NO:171), GI.3P84S+S94L (construct 4142; SEQ ID NO:11), GI.3_A43V+M57I+S94L (construct 4181; SEQ ID NO:173), GI.5_Q84S (construct 4130; SEQ ID NO:35), GI.5_A94E (construct 4131; SEQ ID NO:37), GI.5_Q84S+A94L (construct 4132; SEQ ID NO:39), GI.7_R84S (construct 4210; SEQ ID NO:176), GI.7_M57I (construct 4217; SEQ ID NO:178), GI.7_M57I+R84S (construct 4218; SEQ ID NO:180), GII.2_E80S (construct 4143; SEQ ID NO:86), GII.2_A90L (construct 4144; SEQ ID NO:42), GII.2_E80S+A90L (construct 4145; SEQ ID NO:44), GII.2_A39V+E80S+A90L (construct 4182; SEQ ID NO:183), GII.2_R53I+E80S+A90L (construct 4183; SEQ ID NO:185), GII.2_A39V+R53I+E80S+A90L (construct 4184; SEQ ID NO:187), GII.3_E80S (construct 4146; SEQ ID NO:47), GII.3_A90L (construct 4147; SEQ ID NO:49), GII.3_E80S+A90L (construct 4148; SEQ ID NO:51), GII.4_A39V (construct 4155; SEQ ID NO:54), GII.4_V47P (construct 4156; SEQ ID NO:56), GII.4_R53I (construct 4157; SEQ ID NO:58), GII.4_P80S (construct 4133; SEQ ID NO:60), GII.4_S90L (construct 4134; SEQ ID NO:62), GII.4_Δ35-42 (construct 4158; SEQ ID NO:64), GII.4_SSTAVATA (construct 4159; SEQ ID NO:66). GII.4_A39V+R53I (construct 4185; SEQ ID NO:189), GII.4A39V+P80S (construct 4165; SEQ ID NO:68), GII.4_V47P+P80S (construct 4166; SEQ ID NO:70), GII.4_R53I+P80S (construct 4167; SEQ ID NO:72), GII.4_P80S+S90L (construct 4135; SEQ ID NO:74), GII.4_Δ35-42+P80S (construct 4168; SEQ ID NO:76), GII.4_P80S+SSTAVATA (construct 4169; SEQ ID NO:78), GII.4_A39V+R53I+P80S (construct 4186; SEQ ID NO:191), GII.6_E80S (construct 4149; SEQ ID NO:80), GII.6_S90L (construct 4150; SEQ ID NO:82), GII.6_E80S+S90L (construct 4151; SEQ ID NO:84), GII.12_E80S (construct 4136; SEQ ID NO:89), GII.12_A90L (construct 4137; SEQ ID NO:91), GII.12_E80S+A90L (construct 4138; SEQ ID NO:93), GII.17_A39V (construct 4234; SEQ ID NO:193), GII.17_R53I (construct 4235; SEQ ID NO:195), GII.17_A90L (construct 4232; SEQ ID NO:197), GII.17_A39V+R53I (construct 4236; SEQ ID NO:199), GII.17_E80S+A90L (construct 4233; SEQ ID NO:201), or a combination thereof, may be administered to mice following the same protocol as described in this example.

Mouse Immune Response to Norovirus Native VP1 VLPs

As demonstrated in FIG. 3D, mice immunized with plant-made Norovirus native VP1 VLPs from GU genotype had shown GI.1 VLP-specific IgG antibody titers in sera and were detected for each treatment group on Days 21 and 42. IgG titer levels that were induced by each treatment on Days 21 and 42 were statistically higher than the titers quantified for the placebo group (p<0.05). On each day, IgG titer level increased in a dose-dependent manner as demonstrated by the significant differences detected between the 1 μg and 10 μg treatments formulated with Alhydrogel or not (p<0.05) and the addition of Alhydrogel to the NoV VLP vaccine enhanced significantly the induced immune response at doses of 1 μg and 10 μg (p<0.05). A significant increase of IgG titer level was also detected for each treatment group between Days 21 and 42 (p<0.05). These results collectively demonstrate the ability of plant produced Norovirus native VP1 VLPs to elicit a robust immune response in mice.

Similar results may also be observed with the administration of VLPs comprising modified VP1 proteins, including for example: produced using GI.3_Q84S (construct 4140; SEQ ID NO:167), GI.3_S94L (construct 4141; SEQ ID NO:9), GI.3_A43V+S94L (construct 4179; SEQ ID NO:169), GI.3_M57I+S94L (construct 4180; SEQ ID NO:171), GI.3P84S+S94L (construct 4142; SEQ ID NO:11), GI.3_A43V+M57I+S94L (construct 4181; SEQ ID NO:173), GI.5_Q84S (construct 4130; SEQ ID NO:35), GI.5_A94L (construct 4131; SEQ ID NO:37), GI.5_Q84S+A94L (construct 4132; SEQ ID NO:39), GI.7_R84S (construct 4210; SEQ ID NO:176), GI.7_M57I (construct 4217; SEQ ID NO:178), GI.7_M57I+R84S (construct 4218; SEQ ID NO:180), GII.2_E80S (construct 4143; SEQ ID NO:86), GII.2_A90L (construct 4144; SEQ ID NO:42), GII.2_E80S+A90L (construct 4145; SEQ ID NO:44), GII.2_A39V+E80S+A90L (construct 4182; SEQ ID NO:183), GII.2_R53I+E80S+A90L (construct 4183; SEQ ID NO:185), GII.2_A39V+R53I+E80S+A90L (construct 4184; SEQ ID NO:187), GII.3_E80S (construct 4146; SEQ ID NO:47), GII.3_A90L (construct 4147; SEQ ID NO:49), GII.3_E80S+A90L (construct 4148; SEQ ID NO:51), GII.4_A39V (construct 4155; SEQ ID NO:54), GII.4_V47P (construct 4156; SEQ ID NO:56), GII.4_R53I (construct 4157; SEQ ID NO:58), GII.4_P80S (construct 4133; SEQ ID NO:60), GII.4_S90L (construct 4134; SEQ ID NO:62), GII.4_Δ35-42 (construct 4158; SEQ ID NO:64), GII.4_SSTAVATA (construct 4159; SEQ ID NO:66). GII.4_A39V+R53I (construct 4185; SEQ ID NO:189), GII.4A39V+P80S (construct 4165; SEQ ID NO:68), GII.4_V47P+P80S (construct 4166; SEQ ID NO:70), GII.4_R53I+P80S (construct 4167; SEQ ID NO:72), GII.4_P80S+S90L (construct 4135; SEQ ID NO:74), GII.4_Δ35-42+P80S (construct 4168; SEQ ID NO:76), GII.4_P80S+SSTAVATA (construct 4169; SEQ ID NO:78), GII.4_A39V+R53I+P80S (construct 4186; SEQ ID NO:191), GII.6_E80S (construct 4149; SEQ ID NO:80), GII.6_S90L (construct 4150; SEQ ID NO:82), GII.6_E80S+S90L (construct 4151; SEQ ID NO:84), GII.12_E80S (construct 4136; SEQ ID NO:89), GII.12_A90L (construct 4137; SEQ ID NO:91), GII.12_E80S+A90L (construct 4138; SEQ ID NO:93), GII.17_A39V (construct 4234; SEQ ID NO:193), GII.17_R53I (construct 4235; SEQ ID NO:195), GII.17_A90L (construct 4232; SEQ ID NO:197), GII.17_A39V+R53I (construct 4236; SEQ ID NO:199), GII.17_E80S+A90L (construct 4233; SEQ ID NO:201), or a combination thereof, following the same protocol as described in this example.

All citations are hereby incorporated by reference.

The present invention has been described with regard to one or more embodiments. However, it will be apparent to persons skilled in the art that a number of variations and modifications can be made to the described subject matter. The scope of the claims should not be limited by the preferred embodiments set forth in the examples, but should be given the broadest interpretation consistent with the description as a whole.

The invention claimed is:

1. A modified norovirus VP1 protein comprising an amino acid sequence of a wild type norovirus VP1 protein and comprising,
one or more than one amino acid substitution in the amino acid sequence of the wild type norovirus VP1, wherein the one or more than one amino acid substitution consists of one or more than one amino acid substitution at a position selected from amino acids in sequence alignment with amino acids 43, 57, 84 and 94 of reference sequence SEQ ID NO:1, and
the wild type norovirus VP1 protein is not a GI.1 genotype.

2. The modified norovirus VP1 protein of claim 1, wherein the wild type norovirus VP1 is selected from a group consisting of genotypes GI.3, GI.5, GI.7, GII.2, GII.3, GII.4, GII.6, GII.12 and GII.17.

3. The modified norovirus VP1 protein of claim 1,
wherein the one or more than one substitution at the position in sequence alignment with amino acid 43 is to valine, isoleucine, leucine, methionine, threonine, aspartic acid, glutamic acid, asparagine, glutamine, lysine, or histidine;
wherein the one or more than one substitution at the position in sequence alignment with amino acid 57 is to isoleucine, leucine, valine, alanine, glycine, serine, threonine, asparagine, glutamine, lysine, or histidine;
wherein the one or more than one substitution at the position in sequence alignment with amino acid 84 is to serine, asparagine, cysteine, threonine, alanine, lysine or histidine; or
wherein the one or more than one substitution at the position in sequence alignment with amino acid 94 is to leucine, isoleucine, methionine, valine, threonine, aspartic acid, glutamic acid, asparagine, glutamine, lysine, or histidine.

4. A recombinant polynucleotide encoding the modified norovirus VP1 protein of claim 1.

5. A virus-like particle (VLP) comprising the norovirus VP1 of claim 1.

6. The VLP of claim 5, further comprising a norovirus VP2 protein.

7. A method of producing a norovirus VP1 protein, or a VLP comprising the norovirus VP1 protein, in a plant, portion of a plant or a plant cell, the method comprising:
introducing the recombinant polynucleotide of claim 4; and
incubating the plant, portion of the plant or the plant cell under conditions that permit expression of the norovirus VP1 protein.

8. The method of claim 7, wherein the method further comprises a step of harvesting the plant, portion of the plant, or the plant cell.

9. The method of claim 7, wherein in the step of introducing, a second polynucleotide encoding a norovirus VP2 protein is introduced into the plant, the portion of the plant or the plant cell, and in the step of incubating, the conditions permit co-expression and co-production of both the norovirus VP1 protein and the norovirus VP2 protein in the plant, portion of the plant, or the plant cell.

10. The method of claim 8, wherein the method further comprises a step of:
extracting, purifying, or both extracting and purifying the norovirus VP1 protein, or
extracting, purifying or both extracting and purifying the virus-like particle (VLP) from the plant, the portion of the plant or the plant cell, wherein the VLP comprises the norovirus VP1 protein.

11. A norovirus virus like particle (VLP) produced by the method of claim 7.

12. A method of producing an antibody or antibody fragment comprising, administering the norovirus VP1 protein of claim 1 to a subject, or a host animal, thereby producing the antibody or the antibody fragment.

13. A method of producing an antibody or an antibody fragment comprising, administering the VLP of claim 5 to a subject, or a host animal, thereby producing the antibody or the antibody fragment.

14. A plant, portion of the plant, or plant cell comprising the norovirus VP1 protein of claim 1.

15. A plant, portion of the plant, or plant cell comprising the VLP of claim 5.

16. A plant, portion of the plant, or plant cell comprising the recombinant polynucleotide of claim 4.

17. A composition for inducing an immune response comprising, an effective dose of the norovirus VP1 protein of claim 1, and a pharmaceutically acceptable carrier, adjuvant, vehicle or excipient.

18. A composition for inducing an immune response comprising, an effective dose of the VLP of claim 5, and a pharmaceutically acceptable carrier, adjuvant, vehicle or excipient.

19. A vaccine comprising an effective dose of the norovirus VP1 protein of claim 1, for inducing an immune response.

20. A vaccine comprising an effective dose of the VLP of claim 5, for inducing an immune response.

21. A method for inducing immunity to a norovirus infection in a subject, the method comprising administering the VLP of claim 5 to the subject.

22. The method of claim 21, wherein the VLP is administered to the subject orally intranasally, intramuscularly, intraperitoneally, intravenously, subcutaneously, rectally, or intravaginally.

* * * * *